(12) United States Patent
Harwig et al.

(10) Patent No.: US 11,420,962 B2
(45) Date of Patent: *Aug. 23, 2022

(54) INDENE DERIVATIVES USEFUL IN TREATING PAIN AND INFLAMMATION

(71) Applicant: TARO PHARMACEUTICALS INC., Brampton (CA)

(72) Inventors: Curtis Harwig, Vancouver (CA); Jeremy D. Pettigrew, Vancouver (CA); Jennifer Cross, Vancouver (CA); Jeyaprakashnarayanan Seenisamy, Vancouver (CA); Mahesh Narayan Keregadde, Vancouver (CA); Samir Satish Kher, Vancouver (CA)

(73) Assignee: TARO PHARMACEUTICALS INC., Brampton (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/045,626

(22) PCT Filed: Apr. 5, 2019

(86) PCT No.: PCT/US2019/026092
§ 371 (c)(1),
(2) Date: Oct. 6, 2020

(87) PCT Pub. No.: WO2019/195751
PCT Pub. Date: Oct. 10, 2019

(65) Prior Publication Data
US 2021/0155615 A1    May 27, 2021

Related U.S. Application Data

(60) Provisional application No. 62/654,202, filed on Apr. 6, 2018.

(51) Int. Cl.
| | | |
|---|---|---|
| C07D 263/56 | (2006.01) |
| C07D 231/54 | (2006.01) |
| C07D 239/74 | (2006.01) |
| C07D 241/42 | (2006.01) |
| C07D 261/20 | (2006.01) |
| C07D 209/08 | (2006.01) |
| C07D 277/64 | (2006.01) |
| C07D 285/14 | (2006.01) |
| A61K 31/437 | (2006.01) |
| A61P 29/00 | (2006.01) |
| C07D 413/06 | (2006.01) |
| C07D 239/84 | (2006.01) |
| C07D 401/08 | (2006.01) |
| C07D 403/04 | (2006.01) |
| C07D 403/08 | (2006.01) |
| C07D 405/12 | (2006.01) |

(52) U.S. Cl.
CPC ............ C07D 413/06 (2013.01); A61P 29/00 (2018.01); C07D 209/08 (2013.01); C07D 231/54 (2013.01); C07D 239/74 (2013.01); C07D 239/84 (2013.01); C07D 241/42 (2013.01); C07D 261/20 (2013.01); C07D 263/56 (2013.01); C07D 401/08 (2013.01); C07D 403/04 (2013.01); C07D 403/08 (2013.01); C07D 405/12 (2013.01)

(58) Field of Classification Search
CPC .. C07D 263/56; C07D 231/54; C07D 239/74; C07D 241/42; C07D 261/20; C07D 209/08; C07D 277/64; C07D 285/14; A61K 31/437; A61P 29/00
See application file for complete search history.

(56) References Cited

FOREIGN PATENT DOCUMENTS

| | | |
|---|---|---|
| WO | WO 2004/092100 A1 | 10/2004 |
| WO | WO 2014/158654 A1 | 10/2014 |

OTHER PUBLICATIONS

Jun. 7, 2022, Indian Examination Report issued for related IN Application No. 202017048050.

*Primary Examiner* — Bruck Kifle
(74) *Attorney, Agent, or Firm* — Paratus Law Group, PLLC

(57) ABSTRACT

Compounds of formula (I) wherein, $R^1$, $R^2$, $R^3$, $R^{4a}$, R4b and $R^5$ are described herein, or a stereoisomer, enantiomer or tautomer thereof or mixtures thereof, or a pharmaceutically acceptable salt or solvate thereof, are described herein, as well as other compounds. These compounds are useful in treating inflammation and/or pain. Compositions comprising a compound of the invention are also disclosed, as are methods of using the compounds to treat inflammation and/or pain.

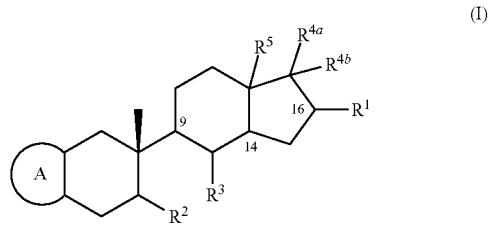

(I)

58 Claims, No Drawings

INDENE DERIVATIVES USEFUL IN TREATING PAIN AND INFLAMMATION

CROSS REFERENCE TO PRIOR APPLICATION

This application is a National Stage Patent Application of PCT International Patent Application No. PCT/US2019/026092 (filed on Apr. 5, 2019) under 35 U.S.C. § 371, which claims priority to U.S. Provisional Patent Application No. 62/654,202 (filed on Apr. 6, 2018), which are all hereby incorporated by reference in their entirety.

FIELD OF THE INVENTION

The present invention is generally directed to indene derivatives which are useful in treating pain and inflammation, as well as to compositions and methods related to the same.

BACKGROUND OF THE INVENTION

Tissue injury results in the initiation of a complex cascade of cellular events which result in redness, swelling, heat and pain at the site of insult. This inflammatory response is the normal mechanism by which the body contains and removes pathogens and repairs tissue damage. These classic and acute signs of inflammation are in large part attributable to the influx and accumulation of activated leukocytes and the subsequent release of mediators such as histamine, leukotrienes, substance P, prostaglandins, cytokines, reactive oxygen species and proteases. Activated immune cells and their proinflammatory products can also induce sensitization of peripheral nociceptors, contributing to the development of both acute and chronic inflammatory pain.

Normal inflammation is a tightly controlled, temporary, process, involving many different cell types, and is ultimately followed by a resolution phase featuring the expression of anti-inflammatory mediators and involving cell subsets that coordinate the tissue repair process. Inflammatory disease occurs when this normal cycle of activation/repair goes awry, resulting in a chronic state of immune cell activation and misdirection of the immune response towards host tissue. Inflammatory pain is also a protective response, designed to shield the injured tissue from further damage, but under conditions of uncontrolled inflammation, the multi-faceted interplay between the immune and nervous systems can drive the establishment of chronic pain and create a host of pathologies which are difficult to manage, creating a large personal and economic burden on society.

One of the key signaling pathways involved in the initiation and propagation of immune cell activation is the phosphoinositide-3-kinase (PI3K) pathway. In response to extracellular signals, phosphoinositide 3-kinase (PI3K) becomes activated and phosphorylates phosphatidylinositol-4,5-bisphosphate (PI-4,5-P2) within the plasma membrane to generate phosphatidylinositol-3,4,5-trisphosphate (PIP3). PIP3 then initiates a cascade of downstream signaling pathways by interacting with pleckstrin homology (PH) domain-containing proteins, such as protein kinase B (PKB, also known as Akt), that regulate cellular activation, function, proliferation and/or survival, depending on the cell type and stimulus (Deane et al., *Annu Rev Immunol* 22, 563-598, 2004). Cellular levels of PIP5 are normally tightly regulated by PI3K, the inositol 5-phosphatases SHIP1 (SH2 domain-containing inositol phosphatase), SHIP2, and by the inositol 3-phosphatase PTEN.

To date, a number of small molecule SHIP1 modulators have been disclosed, including sesquiterpene compounds such as pelorol. Other reported SHIP1 modulators include the compounds described in U.S. Pat. Nos. 8,765,994, 7,601,874, 9,000,050, 9,540,353, and 9,765,085 U.S. Published Patent Application No. 2017/0253596.

Pain is another critical component of a body's defense system. In general, pain is a basic bodily sensation induced by a noxious stimulus, received by nerve endings (nociceptive receptors) and characterized by physical discomfort (such as pricking, throbbing, or aching), and typically leads to evasive action (i.e., removing oneself from the source of the stimulus). Pain is typically classified into two main categories: acute and chronic pain.

Acute or nociceptive pain is part of a rapid warning relay instructing the motor neurons of the central nervous system to minimize detected physical harm. It is mediated by nociceptors, which are free nerve endings that terminate just below the skin, in tendons, joints, and in body organs. They serve to detect cutaneous pain, somatic pain and visceral pain. Nociception can be associated with nerve damage caused by trauma, diseases such as diabetes, shingles, irritable bowel syndrome, late stage cancer or the toxic effects of chemotherapy.

Chronic pain is typically classified into two types: inflammatory nociceptive pain and neuropathic pain. Inflammatory nociceptive pain is associated with tissue damage and the resulting inflammatory process.

Neuropathic pain is produced by damage to and/or inflammation of the neurons in the peripheral and central nervous systems and involves sensitization of these systems.

One of the challenges for researchers is that chronic pain may involve a mix of both inflammatory and neuropathic components. In inflammatory nociceptive pain, inflammation may cause damage to the neurons and produce neuropathic pain. Likewise, neuronal injury may cause an inflammatory reaction (neurogenic inflammation) that contributes to inflammatory pain.

While significant strides have been made in the field of anti-inflammatory agents and analgesics, there remains a need for effective small molecule for the treatment of inflammation and/or pain. There is also a need for pharmaceutical compositions containing such compounds, as well as for methods relating to the use thereof to treat diseases, disorders or conditions that would benefit from such treatment. The present invention fulfills these needs, and provides other related advantages.

SUMMARY OF THE INVENTION

The present invention is generally directed to compounds which are useful in treating inflammation and/or pain, pharmaceutical compositions comprising the compounds and methods of using the compounds and the pharmaceutical compositions of the invention for the treatment of inflammation and/or pain.

Accordingly, in one aspect, this invention is directed to compounds of formula (I):

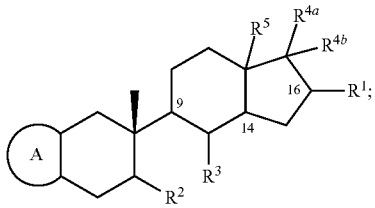

wherein
Ⓐ is an optionally substituted fused N-heteroaryl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ and $R^{4b}$ are each independently selected from hydrogen, alkyl or alkenyl;
or $R^{4a}$ is hydrogen, alkyl or alkenyl and $R^{4b}$ is a direct bond to the carbon to which $R^1$ is attached;
or $R^{4a}$ and $R^{4b}$ together form alkylidene;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two $R^8$'s, together with the nitrogen to which they are attached, form an optionally substituted N-heterocyclyl or an optionally substituted N-heteroaryl;
or a stereoisomer, enantiomer or tautomer thereof or mixtures thereof, or a pharmaceutically acceptable salt or solvate thereof.

In another aspect, this invention is directed to compositions comprising a pharmaceutically acceptable excipient, carrier and/or diluent and a compound of formula (I), or a stereoisomer, enantiomer or tautomer thereof or mixtures thereof; or a pharmaceutically acceptable salt or solvate thereof.

In another aspect, this invention is directed to methods for treating inflammation and/or pain in a mammal comprising administering an effective amount of a compound of formula (I), or a stereoisomer, enantiomer or tautomer thereof or mixtures thereof; or a pharmaceutically acceptable salt or solvate thereof, as set forth above, to the mammal in need thereof.

In another aspect, this invention is directed to methods for treating inflammation and/or pain in a mammal comprising administering a composition comprising an effective amount of a compound of formula (I), or a stereoisomer, enantiomer or tautomer thereof or mixtures thereof; or a pharmaceutically acceptable salt or solvate thereof, as set forth above, to the mammal in need thereof.

In another aspect, this invention is directed to methods of preparing compounds of formula (I), or stereoisomers, enantiomers or tautomers thereof or mixtures thereof; or pharmaceutically acceptable salts or solvates thereof.

In another aspect, this invention is directed to the use of the compounds of the invention, as set forth above, or a stereoisomer, enantiomer or tautomer thereof or mixtures thereof, or a pharmaceutically acceptable salt or solvate thereof, or the use of a pharmaceutical composition comprising a pharmaceutically acceptable excipient and a compound of the invention, as set forth above, or a stereoisomer, enantiomer or tautomer thereof or mixtures thereof, or a pharmaceutically acceptable salt or solvate thereof, in the preparation of a medicament for the treatment of inflammation and/or pain.

These aspects and embodiments thereof are described in more detail below. To this end, various references are set forth herein which describe in more detail certain background information, procedures, compounds and/or compositions, and are each hereby incorporated by reference in their entirety.

DETAILED DESCRIPTION OF THE INVENTION

Definitions

As used in the specification and appended claims, unless specified to the contrary, the following terms have the meaning indicated:

"Oxo" refers to =O.
"Cyano" refers to —CN.
"Nitro" refers to —$NO_2$.
"Alkyl" refers to a straight or branched hydrocarbon chain radical consisting solely of carbon and hydrogen atoms, containing no unsaturation, having from one to twelve carbon atoms, preferably one to ten carbon atoms, more preferably one to eight carbon atoms, most preferably one to six carbon atoms and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, 6-methylheptan-2-yl, 5-ethyl-6-methylheptan-2-yl and the like. When specifically stated in the specification, an alkyl group may be optionally substituted by one of the following groups: alkyl, halo, haloalkyl, cyano, nitro, aryl, cycloalkyl, heterocyclyl, heteroaryl, oxo, trimethylsilanyl, —$OR^{20}$, —OC(O)—$R^{20}$, —$N(R^2)_2$, —C(O)$R^{20}$, —C(O)O$R^{20}$, —C(O)N($R^2$)$_2$, —N($R^{20}$)C(O)O$R^{22}$, —N($R^2$)C(O)$R^{22}$, —N($R^{20}$)S(O)$_p R^{22}$ (where p is 1 to 2), —S(O)$_p$O$R^{22}$ (where p is 1 to 2), —S(O)$_t R^{22}$ (where t is 0 to 2), and —S(O)$_p$N($R^{20}$)$_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl. For purposes of this invention, the alkyl group for $R^{4a}$ and $R^{4b}$ is defined as having one to ten carbons and the alkyl group for $R^5$ is defined as having one to three carbons.

"Alkenyl" refers to a straight or branched hydrocarbon chain radical group consisting solely of carbon and hydrogen atoms, containing at least one double bond, having from two to twelve carbon atoms, preferably one to eight carbon atoms and which is attached to the rest of the molecule by a single bond, e.g., ethenyl, prop-1-enyl, but-1-enyl, pent-1-enyl, penta-1,4-dienyl, and the like. When specifically stated in the specification, an alkenyl group may be optionally substituted by one of the following groups: alkyl, halo, haloalkyl, cyano, nitro, aryl, cycloalkyl, heterocyclyl, heteroaryl, oxo, trimethylsilanyl, —$OR^{20}$, —OC(O)—$R^{20}$, —N($R^2$)$_2$, —C(O)$R^{20}$, —C(O)O$R^{20}$, —C(O)N($R^{20}$)$_2$, —N($R^{20}$)C(O)O$R^{22}$, —N($R^{20}$)C(O)$R^{22}$, —N($R^{20}$)S(O)$_p R^{22}$ (where p is 1 to 2), —S(O)$_p$O$R^{22}$ (where p is 1 to 2), —S(O)$_t R^{22}$ (where t is 0 to 2), and —S(O)$_p$N($R^{20}$)$_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, e.g., —$CH_2$—, —$CH_2$—$CH_2$—, —$CH_2$—$CH_2$—$CH_2$—, and the like. The alkylene chain is attached to the rest of the molecule through a single bond and to the radical group through a single bond. The radical group can be attached to any carbon in the alkylene chain. When specifically stated in the specification, an alkylene chain may be optionally substituted by one of the following groups: alkyl, alkenyl, halo, cyano, nitro, aryl, cycloalkyl, heterocyclyl, heteroaryl, oxo, trimethylsilanyl, —$OR^{20}$, —$OC(O)$—$R^{22}$, —$N(R^{20})_2$, —$C(O)R^{20}$, —$C(O)OR^{20}$, —$C(O)N(R^2)_2$, —$N(R^{20})C(O)OR^{22}$, —$N(R^{20})C(O)R^{22}$; —$N(R^{20})S(O)_pR^{22}$ (where p is 1 to 2), —$S(O)_pOR^{22}$ (where p is 1 to 2), —$S(O)_tR^{22}$ (where t is 0 to 2), and —$S(O)_pN(R^{20})_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Alkylidene" refers to a straight or branched hydrocarbon radical group consisting solely of carbon and hydrogen, containing at least one double bond, having from one to seven carbon atoms, and that is attached to the rest of the molecule through a double bond, e.g., methylene, ethylidene, propylidene, and the like. When specifically stated in the specification, an alkylidene radical may be optionally substituted by one of the following groups: alkyl, halo, haloalkyl, cyano, nitro, aryl, cycloalkyl, heterocyclyl, heteroaryl, oxo, trimethylsilanyl, —$OR^{20}$—$OC(O)$—$R^{20}$, —$N(R^{20})_2$, —$C(O)R^{20}$, —$C(O)OR^{20}$, —$C(O)N(R^{20})_2$, —$N(R^{20})C(O)OR^{22}$, —$N(R^{20})C(O)R^{22}$, —$N(R^{20})S(O)_pR^{22}$ (where p is 1 to 2), —$S(O)OR^{22}$ (where p is 1 to 2), —$S(O)R^{22}$ (where t is 0 to 2), and —$S(O)_pN(R^{20})_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. When specifically stated in the specification, an aryl group may be optionally substituted by one or more substituents independently selected from the group consisting of alkyl, alkenyl, halo, haloalkyl, cyano, nitro, aryl, aralkyl, cycloalkyl, cycloalkylalkyl, heterocyclyl, heterocyclylalkyl, heteroaryl, heteroarylalkyl, —$R^{21}$—$OR^{20}$, —$R^{21}$—$OC(O)$—$R^{20}$, —$R^{21}$—$N(R^{20})_2$, —$R^{21}$—$C(O)R^{20}$, —$R^2$—$C(O)OR^{20}$, —$R^{21}$—$C(O)N(R^2)_2$, —$R^{21}$—$N(R^{20})C(O)OR^{22}$, —$R^2$—$N(R^{20})C(O)R^{22}$, —$R^2$—$N(R^{20})S(O)_pR^{22}$ (where p is 1 to 2), —$R^{21}$—$N=C(OR^{20})R^{20}$, —$R^{21}S(O)_pOR^{22}$ (where p is 1 to 2), —$R^{21}$—$S(O)_tR^{22}$ (where t is 0 to 2), and —$R^{21}$—$S(O)_pN(R^{20})_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Aralkyl" refers to a radical of the formula —$R_b$—$R_c$ where $R_b$ is an alkylene chain as defined above and $R_c$ is one or more aryl radicals as defined above, for example, benzyl, diphenylmethyl and the like. When specifically stated in the specification, the alkylene chain part of the aralkyl radical may be optionally substituted as described above for an optionally substituted alkylene chain. When specifically stated in the specification, the aryl part of the aralkyl radical may be optionally substituted as described above for an optionally substituted aryl group.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptly, and cyclooctyl. Polycyclic radicals include, for example, adamantyl, norbornyl, decalinyl, and the like. When specifically stated in the specification, a cycloalkyl group may be optionally substituted by one or more substituents independently selected from the group consisting of alkyl, halo, haloalkyl, cyano, nitro, oxo, aryl, aralkyl, cycloalkyl, cycloalkylalkyl, heterocyclyl, heterocyclylalkyl, heteroaryl, heteroarylalkyl, —$R^{21}$—$OR^{20}$, —$R^{21}$—$OC(O)$—$R^{20}$, —$R^{21}$—$N(R^{20})_2$—$R^1$—$C(O)R^{20}$, —$R^{21}$—$C(O)OR^{20}$, —$R^{21}$—$C(O)N(R^{20})_2$, —$R^{21}$—$N(R^{20})$ $C(O)OR^{22}$, —$R^{21}$—$N(R^{20})C(O)R^{22}$, —$R^{21}$—$N(R^{20})S(O)_p$ $R^{22}$ (where p is 1 to 2), —$R^{21}$—$N=C(OR^{20})R^{20}$, —$R^{21}$—$S(O)OR^{22}$ (where p is 1 to 2), —$R^{21}$—$S(O)_tR^{22}$ (where t is 0 to 2), and $R^{21}$—$S(O)_pN(R^{20})_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Cycloalkylalkyl" refers to a radical of the formula —$R_bR_g$ where $R_b$ is an alkylene chain as defined above and $R_g$ is a cycloalkyl radical as defined above. When specifically stated in the specification, the alkylene chain and/or the cycloalkyl radical may be optionally substituted as defined above for optionally substituted alkylene chain and optionally substituted cycloalkyl.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

"Heterocyclyl" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include spiro, fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, dioxinyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, 1,2,4-thiadiazol-5(4H)-ylidene, tetrahydrofuryl, trioxanyl, trithianyl, triazinanyl, tetrahydropyranyl, thiomorpholinyl, thiamorpholinyl, 1-oxo-thiomorpholinyl, and 1,1-dioxo-thiomorpholinyl. When specifically stated in the specification, a heterocyclyl group may be optionally substituted by one or more substituents selected from the group consisting of alkyl, alkenyl, halo, haloalkyl, cyano, oxo, thioxo, nitro, aryl, aralkyl, cycloalkyl, cycloalkylalkyl, optionally substituted heterocyclyl, optionally substituted heterocyclylalkyl, optionally substituted heteroaryl, optionally substituted heteroarylalkyl, —$R^{21}R^{20}$, —$R^{21}$—OC(O)—$R^{20}$, a $R^{21}$—N($R^{20}$)$_2$, —$R^{21}$—C(O)$R^{20}$. —$R^{21}$—C(O)O$R^{20}$, —$R^{21}$—C(O)N($R^{20}$)$_2$, —$R^{21}$—N($R^{20}$)C(O)O$R^{22}$, —$R^{21}$—N($R^{20}$)C(O)O$R^{22}$, —$R^{21}$—N($R^{20}$)S(O)$_p$$R^{22}$ (where p is 1 to 2), —$R^{21}$—N═C(O$R^{20}$)$R^{20}$, —$R^{21}$—S(O)$_p$O$R^{22}$ (where p is 1 to 2), —$R^{21}$—S(O)$_t$$R^{22}$ (where t is 0 to 2), and —$R^{21}$—S(O)$_p$N($R^{20}$)$_2$ (where p is 1 to 2) where each $R^{20}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain and each $R^{22}$ is alkyl, alkenyl, haloalkyl, cycloalkyl, cycloalkylalkyl, aryl, aralkyl, heterocyclyl, heterocyclylalkyl, heteroaryl or heteroarylalkyl, and where the optional substituents on the heterocyclyl, heterocyclylalkyl, heteroaryl and heteroarylalkyl substitutents are selected from alkyl, halo or haloalkyl.

"N-heterocyclyl" refers to a heterocyclyl radical as defined above containing at least one nitrogen. The point of attachment of the N-heterocyclyl to the rest of the molecule can be through a nitrogen atom or a carbon atom in the N-heterocyclyl. When specifically stated in the specification, an N-heterocyclyl radical may be optionally substituted as described above for an optionally substituted heterocyclyl radical.

"Heterocyclylalkyl" refers to a radical of the formula —$R_bR_h$ where $R_b$ is an alkylene chain as defined above and $R_h$ is a heterocyclyl radical as defined above, and if the heterocyclyl is a nitrogen-containing heterocyclyl, the heterocyclyl may be attached to the alkyl radical at the nitrogen atom. When specifically stated in the specification, the alkylene chain of the heterocyclylalkyl radical may be optionally substituted as defined above for an optionally substituted alkylene chain. When specifically stated in the specification, the heterocyclyl part of the heterocyclylalkyl radical may be optionally substituted as defined above for an optionally substituted heterocyclyl group.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; and the nitrogen atom may be optionally quaternized. Examples include, but are not limited to, azepinyl, acridinyl, benzimidazolyl, benzo[d]imidazolyl, benzimidazopyrimidinyl, benzo[4,5]imidazo[1,2-a]pyrimidinyl, benzthiazolyl, benzindolyl, benzodioxolyl, benzofuranyl, benzooxazolyl, benzothiazolyl, benzo[d]isoxazolyl, benzothiadiazolyl, benzo[b][1,4]dioxepinyl, 1,4-benzodioxanyl, benzonaphthofuranyl, benzoxazolyl, benzodioxolyl, benzodioxinyl, benzpyranyl, benzopyranonyl, benzofuranyl, benzofuranonyl, benzothienyl (benzthiophenyl), benzotriazolyl, benzo[4,6]imidazo[1,2-a]pyridinyl, benzoxazolinonyl, benzimidazolthionyl, carbazolyl, cinnolinyl, dibenzofuranyl, dibenzothiophenyl, furanyl, furanonyl, isothiazolyl, imidazo[1,2-a]pyridinyl, imidazo[1,2-a]pyrimidinyl, imidazo[1,2-a]pyrazinyl, imidazo[1,5-a]pyrazinyl, imidazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, pteridinonyl, purinyl, pyrrolyl, pyrazolyl, pyridinyl, pyridinonyl, pyrazinyl, pyrimidinyl, pryrimidinonyl, pyridazinyl, pyrido[2,3-d]pyrimidinonyl, pyrazolo[1,5-a]pyrimidinyl, quinazolinyl, quinazolinonyl, quinoxalinyl, quinoxalinonyl, quinolinyl, isoquinolinyl, tetrahydroquinolinyl, thiazolyl, thiadiazolyl, thieno[3,2-d]pyrimidin-4-onyl, thieno[2,3-d]pyrimidin-4-onyl, triazolyl, tetrazolyl, triazinyl, and thiophenyl (i.e. thienyl). When specifically stated in the specification, a heteroaryl group may be optionally substituted by one or more substituents selected from the group consisting of alkyl, alkenyl, halo, haloalkyl, cyano, oxo, thioxo, nitro, thioxo, aryl, aralkyl, cycloalkyl, cycloalkylalkyl, heterocyclyl, heterocyclylalkyl, heteroaryl, heteroarylalkyl, —$R^{21}$—O$R^{20}$, —$R^{21}$—OC(O)—$R^{20}$, —$R^{21}$—N($R^{20}$)$_2$, —$R^{21}$—C(O)$R^{20}$, —$R^{21}$—C(O)O$R^{20}$, —$R^{21}$—C(O)N($R^{20}$)$_2$, —$R^{21}$—N($R^{20}$)C(O)O$R^{22}$, $R^{21}$— N($R^{20}$)C(O)O$R^{22}$, —$R^{21}$—N($R^{20}$)S(O)$_p$$R^{22}$ (where p is 1 to 2), —$R^{21}$—N═C(O$R^{20}$)$R^{20}$, —$R^{21}$—S(O)$_p$O$R^{22}$ (where p is 1 to 2), —$R^{21}$—S(O)$_t$$R^{22}$ (where t is 0 to 2), and —$R^{21}$—S(O)$_p$N($R^{20}$)$_2$ (where p is 1 to 2) where each $R^{20}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; and each $R^{22}$ is alkyl, alkenyl, haloalkyl, cycloalkyl, cycloalkylalkyl, aryl, aralkyl, heterocyclyl, heterocyclylalkyl, heteroaryl or heteroarylalkyl.

"N-heteroaryl" refers to a heteroaryl radical as defined above containing at least one nitrogen. The point of attachment of the V-heteroaryl to the rest of the molecule can be through a nitrogen atom or a carbon atom in the N-heteroaryl. When specifically stated in the specification, an N-heteroaryl radical may be optionally substituted as described above for an optionally substituted heteroaryl radical.

"Heteroarylalkyl" refers to a radical of the formula —$R_bR_i$ where $R_b$ is an alkylene chain as defined above and $R_i$ is a heteroaryl radical as defined above. When specifically stated in the specification, the heteroaryl part of the heteroarylalkyl radical may be optionally substituted as defined above for an optionally substituted heteroaryl group. When specifically stated in the specification, the alkylene chain part of the heteroarylalkyl radical may be optionally substituted as defined above for an optionally substituted alkylene chain.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets, (e.g., cats, dogs, swine, cattle, sheep, goats, horses, rabbits), and non-domestic animals such as wildlife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution ("unsubstituted"). When a functional group is described as "optionally substituted," and in turn, substitutents on the functional group are also "optionally substituted" and so on, for the purposes of this invention, such iterations are limited to five, preferably such iterations are limited to two.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfnic acid, capric acid, caproic acid, caprylic acid, carbonic acid, cinnamic acid, citric acid, cyclamic acid, dodecylsulfuric acid, ethane-1,2-disulfonic acid, ethane-sulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent. Furthermore, some of the crystalline forms of the compounds of the invention may exist as polymorphs, which are included in the present invention.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Therapeutically effective amount" refers to that amount of a compound of the invention which, when administered to a mammal, preferably a human, is sufficient to effect treatment, as defined below, of inflammation and/or pain in the mammal, preferably a human. The amount of a compound of the invention which constitutes a "therapeutically effective amount" will vary depending on the compound, the inflammation and/or pain and its severity, the manner of administration, and the age of the mammal to be treated, but can be determined routinely by one of ordinary skill in the art having regard to his own knowledge and to this disclosure.

"Treating" or "treatment" as used herein covers the treatment of inflammation and/or pain in a mammal, preferably a human, having the inflammation and/or pain, and includes:

(a) preventing the inflammation and/or pain from occurring in a mammal, in particular, when such mammal is predisposed to the condition but has not yet been diagnosed as having it;
(b) inhibiting the inflammation and/or pain, i.e., arresting its development;
(c) relieving (or ameliorating) the inflammation and/or pain, i.e., causing regression of the inflammation and/or pain; or
(d) relieving (or ameliorating) the symptoms resulting from the inflammation and/or pain, e.g., relieving inflammation and/or pain without addressing the underlying disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts or solvates thereof, may contain one or more asymmetric centres and may thus give rise to enantiomers, diastereomers, and other stereoisomeric forms that may be defined, in terms of absolute stereochemistry, as (R)- or (S)- or, as (D)- or (L)- for amino acids. Compounds of the invention may also possess axial chirality which may result in atropisomers. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallisation. Conventional techniques for the preparation/isolation of individual enantiomers include chiral synthesis from a suitable optically pure precursor or resolution of the racemate (or the racemate of a salt or derivative) using, for example, chiral high-pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes enantiomers, which refers to two stereoisomers whose molecules are nonsuperimposeable mirror images of one another. See, for example, Smith, M. B. and J. March, *March's Advanced Organic Chemistry: Reactions, Mechanisms, and Structure*, 6th edition (Wiley, 2007), for a detailed description of the structure and properties of enantiomers and stereoisomers.

A "tautomer" refers to a proton shift from one atom of a molecule to another atom of the same molecule. The present invention includes tautomers of any said compounds.

Certain carbons are identified by numerals in the formulae of the compounds of the invention. For purposes herein, the carbon at numeral 14 in formula (I) is indicated herein as C14 and the carbon at numeral 16 is indicated herein as C16, and so forth. These numerals may or may not be the same as the locants in the compound names given herein.

When a substituent is indicated as being substituted, such as —R$^6$—OR$^7$ or —R$^6$—N(R$^8$)$_2$, it is understood that the substituent may be substituted by the indicated substituent at any carbon in the substituent. Thus, for example, when the R$^6$ in the —R$^6$—OR$^7$ substituent is an alkylene chain, the —OR$^7$ group in the —R$^6$—OR$^7$ group can be on any carbon in the R alkylene chain.

The chemical naming protocol and structure diagrams used herein are a modified form of the I.U.P.A.C. nomenclature system, using ChemDraw Ultra Version 12.0 software program, wherein the compounds of the invention are named herein as derivatives of a central core structure. For complex chemical names employed herein, a substituent group is named before the group to which it attaches. For example, cyclopropylethyl comprises an ethyl backbone with cyclopropyl substituent. In chemical structure diagrams, all bonds are identified, except for some carbon atoms, which are assumed to be bonded to sufficient hydrogen atoms to complete the valency.

Thus, for example, a compound of formula (I) wherein Ⓐ is a fused pyrazolyl, R$^1$ is hydrogen, R$^2$ is —CH$_2$OH, R$^3$ is 1H-benzo[d]imidazol-1-yl)methyl, R$^{4a}$ and R$^{4b}$ together form methylene and R$^5$ is methyl, i.e., a compound of the following structure:

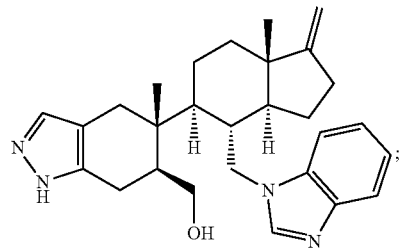 [SMILES: C=C1CC[C@H]2[C@H](Cn3cnc4ccccc43)[C@@H]([C@@]3(C)Cc4cn[nH]c4C[C@@H]3CO)CC[C@]12C]

is named herein as ((5R,6S)-5-((3aS,4R,5S,7aS)-4-((1H-benzo[d]imidazol-1-yl)methyl)-7a-methyl-1-methyleneoctahydro-1H-inden-5-yl)-5-methyl-4,5,6,7-tetrahydro-1-indazol-6-yl)methanol.

Embodiments of the Invention

Of the various aspects of the invention set forth above in the Summary of the Invention, certain embodiments are preferred.

Of the compounds of formula (I), or a stereoisomer, enantiomer or tautomer thereof or mixtures thereof, or a pharmaceutically acceptable salt or solvate thereof, as described above in the Summary of the Invention, a first embodiment are compounds of formula (I) wherein:
Ⓐ is a fused 5-membered N-heteroaryl optionally substituted by one or more substitutents selected from alkyl, haloalkyl, —C(O)OR$^7$, —N(R$^3$)$_2$, —C(O)N(R$^3$)$_2$, cycloalkyl, aryl, aralkyl or heteroaryl;
R$^1$ is hydrogen or —R$^6$—OR$^7$;
R$^2$ is —R$^6$—OR$^7$ or —R$^6$—N(R$^8$)$_2$;
R$^3$ is —R$^6$—OR$^7$ or —R$^6$—N(R$^8$)$_2$;
R$^{4a}$ and R$^{4b}$ are each independently selected from hydrogen, alkyl or alkenyl;
or R$^{4a}$ is hydrogen, alkyl or alkenyl and R$^{4b}$ is a direct bond to the carbon to which R$^1$ is attached;
or R$^{4a}$ and R$^{4b}$ together form alkylidene;
R$^5$ is alkyl or R$^5$ is a direct bond to the carbon at C14;
each R$^6$ is independently selected from a direct bond or a straight or branched alkylene chain;
each R$^7$ is independently selected from hydrogen or alkyl; and each R⁸ is independently selected from hydrogen, alkyl or optionally substituted heteroarylalkyl, or two R⁸'s, together with the nitrogen to which they are attached, form an optionally substituted N-heterocyclyl or an optionally substituted N-heteroaryl.

Of this first embodiment, an embodiment are compounds of formula (I) wherein:

Ⓐ is selected from optionally substituted pyrazolyl, optionally substituted oxazolyl, optionally substituted isoxazolyl, optionally substituted pyrrolyl, optionally substituted thiazolyl, or optionally substituted thiadiazolyl;

R¹ is hydrogen or —R⁶—OR⁷:
R² is —R⁶—OR⁷ or —R⁶—N(R⁸)₂;
R³ is —R⁶—OR⁷ or —R⁶—N(R⁸)₂;
R⁴ᵃ and R⁴ᵇ are each independently selected from hydrogen, alkyl or alkenyl;
or R⁴ᵃ is hydrogen, alkyl or alkenyl and R⁴ᵇ is a direct bond to the carbon to which R¹ is attached;
or R⁴ᵃ and R⁴ᵇ together form alkylidene;
R⁵ is alkyl or R⁵ is a direct bond to the carbon at C14;
each R⁶ is independently selected from a direct bond or a straight or branched alkylene chain;
each R⁷ is independently selected from hydrogen or alkyl; and
each R⁸ is independently selected from hydrogen, alkyl or optionally substituted heteroarylalkyl,
or two R⁸'s, together with the nitrogen to which they are attached, form an optionally substituted N-heterocyclyl or an optionally substituted N-heteroaryl.

Of this embodiment, a first embodiment are compounds of formula (I) wherein:

Ⓐ is optionally substituted pyrazolyl;
R¹ is hydrogen or —R⁶—OR⁷;
R² is —R⁶—OR⁷ or —R⁶—N(R⁸)₂;
R³ is —R⁶—OR⁷ or —R⁶—N(R⁸)₂;
R⁴ᵃ and R⁴ᵇ are each independently selected from hydrogen, alkyl or alkenyl;
or R⁴ᵃ is hydrogen, alkyl or alkenyl and R⁴ᵇ is a direct bond to the carbon to which R¹ is attached;
or R⁴ᵃ and R⁴ᵇ together form alkylidene;
R⁵ is alkyl or R⁵ is a direct bond to the carbon at C14;
each R⁶ is independently selected from a direct bond or a straight or branched alkylene chain;
each R⁷ is independently selected from hydrogen or alkyl; and
each R⁸ is independently selected from hydrogen, alkyl or optionally substituted heteroarylalkyl,
or two R⁸'s, together with the nitrogen to which they are attached, form an optionally substituted N-heterocyclyl or an optionally substituted N-heteroaryl.

Of this first embodiment, a first embodiment are compounds of formula (I) wherein:

Ⓐ is optionally substituted pyrazolyl;
R¹ is hydrogen or —R⁶—OR⁷;
R² is —R⁶—OR⁷ or —R⁶—N(R⁸)₂;
R³ is —R⁶—OR⁷ or —R⁶—N(R⁸)₂;
R⁴ᵃ and R⁴ᵇ are each independently selected from hydrogen, alkyl or alkenyl;
R⁵ is alkyl or R⁵ is a direct bond to the carbon at C14;
each R⁶ is independently selected from a direct bond or a straight or branched alkylene chain;
each R⁷ is independently selected from hydrogen or alkyl; and
each R⁸ is independently selected from hydrogen, alkyl or optionally substituted heteroarylalkyl,
or two R⁸'s, together with the nitrogen to which they are attached, form an optionally substituted N-heterocyclyl or an optionally substituted N-heteroaryl.

Of this embodiment, an embodiment is a compound of formula (I), or a stereoisomer, enantiomer or tautomer thereof or mixtures thereof, or a pharmaceutically acceptable salt or solvate thereof, selected from:

((5R,6S)-5-((1S,3aS,4S,5S,7aR)-4-(aminomethyl)-1-ethyl-7a-methyloctahydro-1H-inden-5-yl)-5-methyl-4,5,6,7-tetrahydro-1H-indazol-6-yl)methanol;

((5R,6S)-5-((4R,5S)-4-(hydroxymethyl)-1,1-dimethyl-2,3,4,5,6,7-hexahydro-1H-inden-5-yl)-5-methyl-4,5,6,7-tetrahydro-1H-indazol-6-yl)methanol;

((5R,6S)-5-((1S,3aS,4S,5S,7aR)-4-(hydroxymethyl)-1,7a-dimethyloctahydro-1H-inden-5-yl)-5-methyl-4,5,6,7-tetrahydro-1H-indazol-6-yl)methanol;

((5R,6S)-5-((4R,5S)-4-(aminomethyl)-1,1-dimethyl-2,3,4,5,6,7-hexahydro-1H-inden-5-yl)-5-methyl-4,5,67-tetrahydro-1H-indazol-6-yl)methanol;

((5R,6S)-5-((1S,3aS,4S,5S,7aR)-4-(aminomethyl)-1,7a-dimethyloctahydro-1H-inden-5-yl)-5-methyl-4,5,6,7-tetrahydro-1H-indazol-6-yl)methanol;

((3aS,4S,5S,7aS)-5-((5R,6S)-6-(hydroxymethyl)-5-methyl-4,5,6,7-tetrahydro-1H-indazol-5-yl)-7a-methyloctahydro-1H-inden-4-yl)methanol;

(2R,4R,5S)-4-(hydroxymethyl)-5-((5R,6S)-6-(hydroxymethyl)-5-methyl-4,5,6,7-tetrahydro-1H-indazol-5-yl)-1,1-dimethyl-2,3,4,5,6,7-hexahydro-1H-inden-2-ol;

((5R,6S)-5-((3aS,4S,5S,7aS)-4-(aminomethyl)-7a-methyloctahydro-1H-inden-5-yl)-5-methyl-4,5,6,7-tetrahydro-1H-indazol-6-yl)methanol;

((5R,6S)-5-((1R,3aS,4S,5S,7aR)-4-(aminomethyl)-7a-methyl-1-((R)-6-methylheptan-2-yl)octahydro-1H-inden-5-yl)-5-methyl-4,5,6,7-tetrahydro-1H-indazol-6-yl)methanol;

((5R,6S)-5-((1R,3aS,4S,5S,7aR)-4-((((2,2-difluorobenzo[d][1,3]dioxol-5-yl)methyl)amino)methyl)-7a-methyl-1-((R)-6-methylheptan-2-yl)octahydro-1H-inden-5-yl)-5-methyl-4,5,6,7-tetrahydro-1H-indazol-6-yl)methanol;

((5R,6S)-5-((1R,3aS,4S,5S,7aS)-4-(aminomethyl)-7a-methyl-1-(prop-1-en-2-yl)octahydro-1H-inden-5-yl)-5-methyl-4,5,6,7-tetrahydro-1H-indazol-6-yl)methanol;

((1R,3aS,4S,5S,7aR)-5-((5R,6S)-6-(aminomethyl)-5-methyl-4,5,6,7-tetrahydro-1H-indazol-5-yl)-7a-methyl-1-((R)-6-methylheptan-2-yl)octahydro-1H-inden-4-yl)methanamine;

((1R,3aS,4S,5S,7aR)-5-((5R,6S)-6-(hydroxymethyl)-5-methyl-4,5,6,7-tetrahydro-1H-indazol-5-yl)-7a-methyl-1-((R)-6-methylheptan-2-yl)octahydro-1H-inden-4-yl)methanol;

((1R,3aS,4S,5S,7aS)-5-((5R,6S)-6-(hydroxymethyl)-5-methyl-4,5,6,7-tetrahydro-1H-indazol-5-yl)-7a-methyl-1-(prop-1-en-2-yl)octahydro-1H-inden-4-yl)methanol;

((5R,6S)-5-((1S,3aS,4S,5S,7aR)-1,7a-dimethyl-4-((methylamino)methyl)octahydro-1H-inden-5-yl)-5-methyl-4,5,6,7-tetrahydro-1H-indazol-6-yl)methanol;

((5R,6S)-5-((1S,3aS,4S,5S,7aR)-4-(aminomethyl)-1,7a-dimethyloctahydro-1H-inden-5-yl)-5-methyl-2-phenyl-4,5,6,7-tetrahydro-2H-indazol-6-yl)methanol;

((5R,6S)-5-((1S,3aS,4S,5S,7aR)-4-(aminomethyl)-1,7a-dimethyloctahydro-1H-inden-5-yl)-5-methyl-1-phenyl-4,5,6,7-tetrahydro-1H-indazol-6-yl)methanol;

((5R,6S)-5-((1S,3aS,4S,5S,7aR)-4-(aminomethyl)-1,7a-dimethyloctahydro-1H-inden-5-yl)-1-cyclohexyl-5-methyl-4,5,6,7-tetrahydro-1H-indazol-6-yl)methanol;

((5R,6S)-5-((1S,3aS,4S,5S,7aR)-4-(aminomethyl)-1,7a-dimethyloctahydro-1H-inden-5-yl)-5-methyl-1-(pyridin-2-yl)-4,5,6,7-tetrahydro-1H-indazol-6-yl)methanol;
((5R,6S)-5-((1S,3aS,4S,5S,7aR)-4-(aminomethyl)-1,7a-dimethyloctahydro-1H-inden-5-yl)-5-methyl-2-(pyridin-2-yl)-4,5,6,7-tetrahydro-2H-indazol-6-yl)methanol;
((5R,6S)-5-((1S,3aS,4S,5S,7aR)-4-(aminomethyl)-1,7a-dimethyloctahydro-1H-inden-5-yl)-2-(tert-butyl)-5-methyl-4,5,6,7-tetrahydro-2H-indazol-6-yl)methanol;
((5R,6S)-5-((1S,3aS,4S,5S,7aR)-4-(aminomethyl)-1,7a-dimethyloctahydro-1H-inden-5-yl)-1-(tert-butyl)-5-methyl-4,5,6,7-tetrahydro-1H-indazol-6-yl)methanol;
((5R,6S)-5-((1S,3aS,4S,5S,7aR)-4-(aminomethyl)-1,7a-dimethyloctahydro-1H-inden-5-yl)-5-methyl-1-neopentyl-4,5,6,7-tetrahydro-1H-indazol-6-yl)methanol; or
((5R,6S)-5-((1S,3aS,4S,5S,7aR)-4-(aminomethyl)-1,7a-dimethyloctahydro-1H-inden-5-yl)-5-methyl-2-neopentyl-4,5,6,7-tetrahydro-2H-indazol-6-yl)methanol.

Of this first embodiment, a second embodiment are compounds of formula (I) wherein:
Ⓐ is optionally substituted pyrazolyl;
$R^1$ is hydrogen or —$R^6$—$OR^7$;
$R^2$ is —$R^6$—$OR^7$ or —$R^6$—$N(R^8)_2$;
$R^3$ is —$R^3$—$OR^7$ or —$R^6$—$N(R^8)_2$;
$R^{4a}$ is hydrogen, alkyl or alkenyl and $R^{4b}$ is a direct bond to the carbon to which $R^1$ is attached;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two $R^8$'s, together with the nitrogen to which they are attached, form an optionally substituted N-heterocyclyl or an optionally substituted N-heteroaryl.

Of this embodiment, an embodiment is a compound of formula (I), or a stereoisomer, enantiomer or tautomer thereof or mixtures thereof, or a pharmaceutically acceptable salt or solvate thereof, selected from:
((5R,6S)-5-((3aR,6S,7R,7aS)-7-(hydroxymethyl)-3a-methyl-3a,4,5,6,7,7a-hexahydro-1H-inden-6-yl)-5-methyl-4,5,6,7-tetrahydro-1H-indazol-6-yl)methanol;
((5R,6S)-5-((3aR,6S,7R,7aS)-7-(aminomethyl)-3a-methyl-3a,4,5,6,7,7a-hexahydro-1H-inden-6-yl)-5-methyl-4,5,6,7-tetrahydro-1H-indazol-6-yl)methanol; or
((5R,6S)-5-((3aS,6S,7R,7aS)-7-(aminomethyl)-3,3a-dimethyl-3a,4,5,6,7,7a-hexahydro-1H-inden-6-yl)-5-methyl-4,5,6,7-tetrahydro-1H-indazol-6-yl)methanol.

Of this first embodiment, a third embodiment are compounds of formula (I) wherein:
Ⓐ is optionally substituted pyrazolyl;
$R^1$ is hydrogen or —$R^6$—$OR^7$;
$R^2$ is —$R^6$—$OR^7$ or —$R^6$—$N(R^8)_2$;
$R^3$ is —$R^3$—$OR^7$ or —$R^6$—$N(R^8)_2$;
$R^{4a}$ and $R^{4b}$ together form alkylidene;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two $R^8$'s, together with the nitrogen to which they are attached, form an optionally substituted N-heterocyclyl or an optionally substituted N-heteroaryl.

Of this embodiment, an embodiment is a compound of formula (I), or a stereoisomer, enantiomer or tautomer thereof or mixtures thereof, or a pharmaceutically acceptable salt or solvate thereof, selected from:
((5R,6S)-5-((3aS,4R,5S,7aS)-4-(aminomethyl)-7a-methyl-1-methyleneoctahydro-1H-inden-5-yl)-5-methyl-4,5,6,7-tetrahydro-1H-indazol-6-yl)methanol;
((5R,6S)-5-((3aS,4R,5S,7aS)-4-(aminomethyl)-7a-methyl-1-methyleneoctahydro-1H-inden-5-yl)-5-methyl-1-phenyl-4,5,6,7-tetrahydro-1H-indazol-6-yl)methanol;
(5R,6S)-6-(hydroxymethyl)-5-((3aS,4R,5S,7aS)-4-(hydroxymethyl)-7a-methyl-1-methyleneoctahydro-1H-inden-5-yl)-5-methyl-4,5,6,7-tetrahydro-1H-indazole-3-carboxylic acid;
(5R,6S)-6-(hydroxymethyl)-5-((3aS,4R,5S,7aS)-4-(hydroxymethyl)-7a-methyl-1-methyleneoctahydro-1H-inden-5-yl)-5-methyl-4,5,6,7-tetrahydro-1H-indazole-3-carboxamide;
((5R,6S)-6-(hydroxymethyl)-5-((3aS,4R,5S,7aS)-4-(hydroxymethyl)-7a-methyl-1-methyleneoctahydro-1H-inden-5-yl)-5-methyl-4,5,6,7-tetrahydro-1H-indazol-3-yl)(piperidin-1-yl)methanone;
((5R,6S)-6-(hydroxymethyl)-5-((3aS,4R,5S,7aS)-4-(hydroxymethyl)-7a-methyl-1-methyleneoctahydro-1H-inden-5-yl)-5-methyl-4,5,6,7-tetrahydro-1H-indazol-3-yl)(morpholino)methanone;
(2R,3aS,4R,5S,7aS)-4-(hydroxymethyl)-5-((5R,6S)-6-(hydroxymethyl)-5-methyl-4,5,6,7-tetrahydro-1H-indazol-5-yl)-7a-methyl-1-methyleneoctahydro-1H-inden-2-ol;
(2S,3aS,4R,5S,7aS)-4-(hydroxymethyl)-5-((5R,6S)-6-(hydroxymethyl)-5-methyl-4,5,6,7-tetrahydro-1H-indazol-5-yl)-7a-methyl-1-methyleneoctahydro-1H-inden-2-ol;
((5R,6S)-5-((3aS,4R,5S,7aS)-4-((((2,2-difluorobenzo[d][1,3]dioxol-5-yl)methyl)amino)methyl)-7a-methyl-1-methyleneoctahydro-1H-inden-5-yl)-5-methyl-4,5,6,7-tetrahydro-1H-indazol-6-yl)methanol;
((5R,6S)-5-((3aS,4R,5S,7aS)-4-(aminomethyl)-7a-methyl-1-methyleneoctahydro-1H-inden-5-yl)-3,5-dimethyl-4,5,6,7-tetrahydro-1H-indazol-6-yl)methanol;
((5R,6S)-5-((3aS,4R,5S,7aS)-4-(aminomethyl)-7a-methyl-1-methyleneoctahydro-1H-inden-5-yl)-5-methyl-3-(trifluoromethyl)-4,5,6,7-tetrahydro-1H-indazol-6-yl)methanol;
((5R,6S)-5-((3aS,4R,5S,7aS)-4-(aminomethyl)-7a-methyl-1-methyleneoctahydro-1H-inden-5-yl)-3-(difluoromethyl)-5-methyl-4,5,6,7-tetrahydro-1H-indazol-6-yl)methanol;
((5R,6S)-5-methyl-5-((3aS,4R,5S,7aS)-7a-methyl-1-methylene-4-(morpholinomethyl)octahydro-1H-inden-5-yl)-4,5,6,7-tetrahydro-1H-indazol-6-yl)methanol;
((5R,6S)-5-methyl-5-((3aS,4R,5S,7aS)-7a-methyl-1-methylene-4-((4-methylpiperazin-1-yl)methyl)octahydro-1H-inden-5-yl)-4,5,6,7-tetrahydro-1H-indazol-6-yl)methanol;
((5R,6S)-5-((3aS,4R,5S,7aS)-4-((1H-imidazol-1-yl)methyl)-7a-methyl-1-methyleneoctahydro-1H-inden-5-yl)-5-methyl-4,5,6,7-tetrahydro-1H-indazol-6-yl)methanol;
((5R,6S)-5-((3aS,4R,5S,7aS)-4-((1H-pyrazol-1-yl)methy)-7a-methy-1-methyleneoctahydro-1H-inden-5-yl)-5-methyl-4,5,6,7-tetrahydro-1H-indazol-6-yl)methanol;
((3aS,4R,5S,7aS)-5-((5R,6S)-6-(aminomethyl)-5-methyl-4,5,6,7-tetrahydro-1H-indazol-5-yl)-7a-methyl-1-methyleneoctahydro-1H-inden-4-yl)methanamine;
((5R,6S)-5-((3aS,4R,5S,7aS)-4-((1H-indol-1-yl)methyl)-7a-methyl-1-methyleneoctahydro-1H-inden-5-yl)-5-methyl-4,5,6,7-tetrahydro-1H-indazol-6-yl)methanol;

((5R,6S)-5-(((3aS,4R,5S,7aS)-4-((6-amino-9H-purin-9-yl)methyl)-7a-methyl-1-methyleneoctahydro-1H-inden-5-yl)-5-methyl-4,5,6,7-tetrahydro-1H-indazol-6-yl)methanol;

((5R,6S)-5-(((3aS,4R,5S,7aS)-4-((1H-benz[d]imidazol-1-yl)methyl)-7a-methyl-1-methyleneoctahydro-1H-inden-5-yl)-5-methyl-4,5,6,7-tetrahydro-1H-indazol-6-yl)methanol;

((5R,6S)-5-methyl-5-((3aS,4R,5S,7aS)-7a-methyl-1-methylene-4-(thiomorpholinomethyl)octahydro-1H-inden-5-yl)-4,5,6,7-tetrahydro-1H-indazol-6-yl)methanol;

((5R,6S)-5-methyl-5-((3aS,4R,5S,7aS)-7a-methyl-1-methylene-4-(piperidin-1-ylmethyl)octahydro-1H-inden-5-yl)-4,5,6,7-tetrahydro-1H-indazol-6-yl)methanol;

(3aR,4R,5R,7aS)-7a-methyl-5-((5S,6S)-5-methyl-6-(morpholinomethyl)-4,5,6,7-tetrahydro-1H-indazol-5-yl)-1-methyleneoctahydro-1H-inden-4-ol;

((5R,6S)-5-((3aS,4R,5S,7aS)-4-(aminomethyl)-1-ethylidene-7a-methyloctahydro-1H-inden-5-yl)-5-methyl-4,5,6,7-tetrahydro-1H-indazol-6-yl)methanol;

((5R,6S)-5-((3aS,4R,5S,7aS,E)-1-ethylidene-4-(hydroxymethyl)-7a-methyloctahydro-1H-inden-5-yl)-5-methyl-4,5,6,7-tetrahydro-1H-indazol-6-yl)methanol;

((5R,6S)-5-methyl-5-((3aS,4R,5S,7aS)-7a-methyl-4-((methylamino)methyl)-1-methyleneoctahydro-1H-inden-5-yl)-4,5,6,7-tetrahydro-1H-indazol-6-yl)methanol;

((5R,6S)-5-((3aS,4R,5S,7aS)-4-((dimethylamino)methyl)-7a-methyl-1-methyleneoctahydro-1H-inden-5-yl)-5-methyl-4,5,6,7-tetrahydro-1H-indazol-6-yl)methanol;

((3aS,4R,5S,7aS)-7a-methyl-5-((5R,6S)-5-methyl-6-(piperidin-1-ylmethyl)-4,5,6,7-tetrahydro-1H-indazol-5-yl)-1-methyleneoctahydro-1H-inden-4-yl)methanol;

((3aS,4R,5S,7aS)-7a-methyl-5-((5R,6S)-5-methyl-6-(morpholinomethyl)-4,5,6,7-tetrahydro-1H-indazol-5-yl)-1-methyleneoctahydro-1H-inden-4-yl)methanol;

((3aS,4R,5S,7aS)-7a-methyl-5-((5R,6S)-5-methyl-6-(thiomorpholinomethyl)-4,5,6,7-tetrahydro-1H-indazol-5-yl)-1-methyleneoctahydro-1H-inden-4-yl)methanol;

((3aS,4R,5S,7aS)-7a-methyl-5-((5R,6S)-5-methyl-6-((4-methylpiperazin-1-yl)methyl)-4,5,6,7-tetrahydro-1H-indazol-5-yl)-1-methyleneoctahydro-1H-inden-4-yl)methanol;

((3aS,4R,5S,7aS)-7a-methyl-5-((5R,6S)-5-methyl-6-(piperidin-1-ylmethyl)-4,5,6,7-tetrahydro-1H-indazol-5-yl)-1-methyleneoctahydro-1H-inden-4-yl)methanamine;

((3aS,4R,5S,7aS)-7a-methyl-5-((5R,6S)-5-methyl-6-(morpholinomethyl)-4,5,6,7-tetrahydro-1H-indazol-5-yl)-1-methyleneoctahydro-1H-inden-4-yl)methanamine;

((3aS,4R,5S,7aS)-7a-methyl-5-((5R,6S)-5-methyl-6-(thiomorpholinomethyl)-4,5,6,7-tetrahydro-1H-indazol-5-yl)-1-methyleneoctahydro-1H-inden-4-yl)methanamine;

((3aS,4R,5S,7aS)-7a-methyl-5-((5R,6S)-5-methyl-6-((4-methylpiperazin-1-yl)methyl)-4,5,6,7-tetrahydro-1H-indazol-5-yl)-1-methyleneoctahydro-1H-inden-4-yl)methanamine;

((5R,6S)-5-((3aS,4R,5S,7aS)-4-(aminomethyl)-7a-methyl-1-methyleneoctahydro-1H-inden-5-yl)-2-(tert-butyl)-5-methyl-4,5,6,7-tetrahydro-2H-indazol-6-yl)methanol;

((5R,6S)-5-((3aS,4R,5S,7aS)-4-(aminomethyl)-7a-methyl-1-methyleneoctahydro-1H-inden-5-yl)-1-(tert-butyl)-5-methyl-4,5,6,7-tetrahydro-1H-indazol-6-yl)methanol;

((5R,6S)-5-((3aS,4R,5S,7aS)-4-(aminomethyl)-7a-methyl-1-methyleneoctahydro-1H-inden-5-yl)-2,5-dimethyl-4,5,6,7-tetrahydro-2H-indazol-6-yl)methanol;

((5R,6S)-5-((3aS,4R,5S,7aS)-4-(aminomethyl)-7a-methyl-1-methyleneoctahydro-1H-inden-5-yl)-1-cyclohexyl-5-methyl-4,5,6,7-tetrahydro-1H-indazol-6-yl)methanol;

((5R,6S)-5-((3aS,4R,5S,7aS)-4-(aminomethyl)-7a-methyl-1-methyleneoctahydro-1H-inden-5-yl)-5-methyl-2-(pyridin-2-yl)-4,5,6,7-tetrahydro-2H-indazol-6-yl)methanol;

((5R,6S)-5-((3aS,4R,5S,7aS)-4-(aminomethyl)-7a-methyl-1-methyleneoctahydro-1H-inden-5-yl)-2-benzyl-5-methyl-4,5,6,7-tetrahydro-2H-indazol-6-yl)methanol;

((5R,6S)-5-((3aS,4R,5S,7aS)-4-(aminomethyl)-7a-methyl-1-methyleneoctahydro-1H-inden-5-yl)-5-methyl-1-(pyridin-3-yl)-4,5,6,7-tetrahydro-1H-indazol-6-yl)methanol;

((5R,6S)-5-((3aS,4R,5S,7aS)-4-(aminomethyl)-7a-methyl-1-methyleneoctahydro-1H-inden-5-yl)-5-methyl-1-neopentyl-4,5,6,7-tetrahydro-1H-indazol-6-yl)methanol;

((5R,6S)-5-((3aS,4R,5S,7aS)-4-(aminomethyl)-7a-methyl-1-methyleneoctahydro-1H-inden-5-yl)-5-methyl-2-neopentyl-4,5,6,7-tetrahydro-2H-indazol-6-yl)methanol;

((3aS,4R,5S,7aS)-5-((5R,6S)-6-(aminomethyl)-5-methyl-4,5,6,7-tetrahydro-1H-indazol-5-yl)-7a-methyl-1-methyleneoctahydro-1H-inden-4-yl)methanol;

(3aR,4R,5R,7aS)-7a-methyl-5-((5S,6S)-5-methyl-6-((4-methylpiperazin-1-yl)methyl)-4,5,6,7-tetrahydro-1H-indazol-5-yl)-1-methyleneoctahydro-1H-inden-4-ol;

((5R,6S)-5-((3aS,4R,5S,7aS)-4-(aminomethyl)-7a-methyl-1-methyleneoctahydro-1H-inden-5-yl)-5-methyl-2-phenyl-4,5,6,7-tetrahydro-2H-indazol-6-yl)methanol;

((5R,6S)-5-((3aS,4R,5S,7aS)-4-(aminomethyl)-7a-methyl-1-methyleneoctahydro-1H-inden-5-yl)-5-methyl-1-(pyridin-2-yl)-4,5,6,7-tetrahydro-1H-indazol-6-yl)methanol;

((5R,6S)-5-((3aS,4R,5S,7aS)-4-(aminomethyl)-7a-methyl-1-methyleneoctahydro-1H-inden-5-yl)-1,5-dimethyl-4,5,6,7-tetrahydro-1H-indazol-6-yl)methanol;

((5R,6S)-5-((3aS,4R,5S,7aS)-4-(aminomethyl)-7a-methyl-1-methyleneoctahydro-1H-inden-5-yl)-2-cyclohexyl-5-methyl-4,5,6,7-tetrahydro-2H-indazol-6-yl)methanol;

((5R,6S)-5-((3aS,4R,5S,7aS)-4-(aminomethyl)-7a-methyl-1-methyleneoctahydro-1H-inden-5-yl)-1-benzyl-5-methyl-4,5,6,7-tetrahydro-1H-indazol-6-yl)methanol; or ((5R,6S)-5-((3aS,4R,5S,7aS)-4-(aminomethyl)-7a-methyl-1-methyleneoctahydro-1H-inden-5-yl)-5-methyl-2-(pyridin-3-yl)-4,5,6,7-tetrahydro-2H-indazol-6-yl)methanol;

(3aR,4R,5R,7aS)-5-((5S,6S)-6-(hydroxymethyl)-5-methyl-2-(pyridin-2-yl)-4,5,6,7-tetrahydro-2H-indazol-5-yl)-7a-methyl-1-methyleneoctahydro-1H-inden-4-ol;

(3aR,4R,5R,7aS)-5-((S,6S)-6-(hydroxymethyl)-5-methyl-2-(pyrazin-2-yl)-4,5,6,7-tetrahydro-2H-indazol-5-yl)-7a-methyl-1-methyleneoctahydro-1H-inden-4-ol; or (3aR,4R,5R,7aS)-5-((5S,6S)-6-(hydroxymethyl)-5-methyl-2-(pyrimidin-2-yl)-4,5,6,7-tetrahydro-2H-indazol-5-yl)-7a-methyl-1-methyleneoctahydro-1H-inden-4-ol.

Of this embodiment, a second embodiment are compounds of formula (I) wherein:

Ⓐ is optionally substituted isoxazolyl;
$R^1$ is hydrogen or —$R^6$—$OR^7$;
$R^2$ is —$R^6$—$OR^7$ or —$R^6$—$N(R^8)_2$,
$R^3$ is —$R^6$—$OR^7$ or —$R^6$—$N(R^8)_2$;
$R^{4a}$ and $R^{4b}$ are each independently selected from hydrogen, alkyl or alkenyl;
or $R^{4a}$ is hydrogen, alkyl or alkenyl and $R^{4b}$ is a direct bond to the carbon to which $R^1$ is attached;
or $R^{4a}$ and $R^{4b}$ together form alkylidene;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl, or two R⁸'s, together with the nitrogen to which they are attached, form an optionally substituted N-heterocyclyl or an optionally substituted N-heteroaryl.

Of this second embodiment, a first embodiment are compounds of formula (I) wherein:
(A) is optionally substituted isoxazolyl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ and $R^{4b}$ are each independently selected from hydrogen, alkyl or alkenyl;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two $R^8$'s, together with the nitrogen to which they are attached, form an optionally substituted N-heterocyclyl or an optionally substituted N-heteroaryl.

Of this embodiment, an embodiment is a compound of formula (I), or a stereoisomer, enantiomer or tautomer thereof or mixtures thereof, or a pharmaceutically acceptable salt or solvate thereof, selected from:
((5R,6S)-5-((4R,5S)-4-(aminomethyl)-1,1-dimethyl-2,3,4,5,6,7-hexahydro-1H-inden-5-yl)-5-methyl-4,5,6,7-tetrahydrobenzo[d]isoxazol-6-yl)methanol; or
((1R,3aS,4S,5S,7aR)-5-((5R,6S)-6-(hydroxymethyl)-5-methyl-4,5,6,7-tetrahydrobenzo[d]isoxazol-5-yl)-7a-methyl-1-((R)-6-methylheptan-2-yl)octahydro-1H-inden-4-yl)methanol.

Of this second embodiment, a second embodiment are compounds of formula (I) wherein:
(A) is optionally substituted isoxazolyl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ is hydrogen, alkyl or alkenyl and $R^{4b}$ is a direct bond to the carbon to which $R^1$ is attached;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two $R^8$'s, together with the nitrogen to which they are attached, form an optionally substituted N-heterocyclyl or an optionally substituted N-heteroaryl.

Of this embodiment, an embodiment is a compound of formula (I), or a stereoisomer, enantiomer or tautomer thereof or mixtures thereof, or a pharmaceutically acceptable salt or solvate thereof, selected from:
((5R,6S)-5-((3aS,6S,7R,7aS)-7-(aminomethyl)-3,3a-dimethyl-3a,4,5,6,7,7a-hexahydro-1H-inden-6-yl)-5-methyl-4,5,6,7-tetrahydrobenzo[d]isoxazol-6-yl)methanol.

Of this second embodiment, a third embodiment are compounds of formula (I) wherein:
(A) is optionally substituted isoxazolyl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ and $R^{4b}$ together form alkylidene;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two $R^8$'s, together with the nitrogen to which they are attached, form an optionally substituted N-heterocyclyl or an optionally substituted N-heteroaryl.

Of this embodiment, an embodiment is a compound of formula (I), or a stereoisomer, enantiomer or tautomer thereof or mixtures thereof, or a pharmaceutically acceptable salt or solvate thereof, selected from:
((5R,6S)-5-((3aS,4R,5S,7aS)-4-(aminomethyl)-7a-methyl-1-methyleneoctahydro-1H-inden-5-yl)-5-methyl-4,5,6,7-tetrahydrobenzo[c]isoxazol-6-yl)methanol.

Of this embodiment, a third embodiment are compounds of formula (I) wherein:
(A) is optionally substituted pyrrolyl;
$R^1$ is hydrogen or —$R^6$—$OR^7$;
$R^2$ is —$R^6$—$OR^7$ or —$R^6$—$N(R^8)_2$;
R is —$R^6$—$OR^7$ or —$R^6$—$N(R^8)_2$;
$R^{4a}$ and $R^{4b}$ are each independently selected from hydrogen, alkyl or alkenyl;
or $R^{4a}$ is hydrogen, alkyl or alkenyl and $R^{4b}$ is a direct bond to the carbon to which $R^1$ is attached;
or $R^{4a}$ and $R^{4b}$ together form alkylidene;
$R^6$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two $R^8$'s, together with the nitrogen to which they are attached, form an optionally substituted N-heterocyclyl or an optionally substituted N-heteroaryl.

Of this third embodiment, a first embodiment are compounds of formula (I) wherein:
(A) is optionally substituted pyrrolyl;
$R^1$ is hydrogen or —$R^5$—$OR^7$;
$R^2$ is —$R^6$—$OR^7$ or —$R^6$—$N(R^8)_2$;
$R^3$ is —$R^6$—$OR^7$ or $R^6$—$N(R^8)_2$;
$R^{4a}$ and $R^{4b}$ are each independently selected from hydrogen, alkyl or alkenyl;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two $R^8$'s, together with the nitrogen to which they are attached, form an optionally substituted N-heterocyclyl or an optionally substituted N-heteroaryl.

Of this third embodiment, a second embodiment are compounds of formula (I) wherein:
(A) is optionally substituted pyrrolyl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ is hydrogen, alkyl or alkenyl and $R^{4b}$ is a direct bond to the carbon to which $R^1$ is attached;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and each R⁸ is independently selected from hydrogen, alkyl or optionally substituted heteroarylalkyl,
or two R⁸'s, together with the nitrogen to which they are attached, form an optionally substituted N-heterocyclyl or an optionally substituted N-heteroaryl.

Of this third embodiment, a third embodiment are compounds of formula (I) wherein:
Ⓐ is optionally substituted pyrrolyl;
R¹ is hydrogen or —R⁶—OR:
R² is —R⁶—OR⁷ or —R⁶—N(R⁸)₂;
R³ is —R⁶—OR⁷ or —R⁶—N(R⁸)₂;
R⁴ᵃ and R⁴ᵇ together form alkylidene;
R⁵ is alkyl or R⁵ is a direct bond to the carbon at C14;
each R⁶ is independently selected from a direct bond or a straight or branched alkylene chain;
each R⁷ is independently selected from hydrogen or alkyl; and
each R⁸ is independently selected from hydrogen, alkyl or optionally substituted heteroarylalkyl,
or two R⁸'s, together with the nitrogen to which they are attached, form an optionally substituted N-heterocyclyl or an optionally substituted N-heteroaryl.

Of this embodiment, an embodiment is a compound of formula (I), or a stereoisomer, enantiomer or tautomer thereof or mixtures thereof, or a pharmaceutically acceptable salt or solvate thereof, selected from:
((5R,6S)-5-((3aS,4R,5S,7aS)-4-(aminomethyl)-7a-methyl-1-methyleneoctahydro-1H-inden-5-yl)-5-methyl-4,5,6,7-tetrahydro-1H-indol-6-yl)methanol.

Of this embodiment, a fourth embodiment are compounds of formula (I) wherein:
Ⓐ is optionally substituted thiazolyl;
R¹ is hydrogen or —R⁶—OR⁷;
R² is —R⁶—OR⁷ or —R⁶—N(R⁸)₂;
R³ is —R⁶—OR⁷ or —R⁶—N(R⁸)₂;
R⁴ᵃ and R⁴ᵇ are each independently selected from hydrogen, alkyl or alkenyl;
or R⁴ᵃ is hydrogen, alkyl or alkenyl and R⁴ᵇ is a direct bond to the carbon to which R¹ is attached;
or R⁴ᵃ and R⁴ᵇ together form alkylidene;
R⁵ is alkyl or R⁵ is a direct bond to the carbon at C14;
each R⁶ is independently selected from a direct bond or a straight or branched alkylene chain;
each R⁷ is independently selected from hydrogen or alkyl; and
each R⁸ is independently selected from hydrogen, alkyl or optionally substituted heteroarylalkyl,
or two R⁸'s, together with the nitrogen to which they are attached, form an optionally substituted N-heterocyclyl or an optionally substituted N-heteroaryl.

Of this fourth embodiment, a first embodiment are compounds of formula (I) wherein:
Ⓐ is optionally substituted thiazolyl;
R¹ is hydrogen or —R⁶—OR⁷;
R² is —R⁶—OR⁷ or —R⁶—N(R⁸)₂;
R³ is —R⁶—OR⁷ or —R⁶—N(R⁸)₂;
R⁴ᵃ and R⁴ᵇ are each independently selected from hydrogen, alkyl or alkenyl;
R⁵ is alkyl or R⁵ is a direct bond to the carbon at C14:
each R⁶ is independently selected from a direct bond or a straight or branched alkylene chain;
each R⁷ is independently selected from hydrogen or alkyl; and
each R⁸ is independently selected from hydrogen, alkyl or optionally substituted heteroarylalkyl,
or two R⁸'s, together with the nitrogen to which they are attached, form an optionally substituted N-heterocyclyl or an optionally substituted N-heteroaryl.

Of this embodiment, an embodiment is a compound of formula (I), or a stereoisomer, enantiomer or tautomer thereof or mixtures thereof, or a pharmaceutically acceptable salt or solvate thereof, selected from:
((1R,3aS,4S,5S,7aR)-5-((5S,6R)-2-amino-5-(hydroxymethyl)-6-methyl-4,5,6,7-tetrahydrobenzo[d]thiazol-6-yl)-7a-methyl-1-((R)-6-methylheptan-2-yl)octahydro-1H-inden-4-yl)methanol; or
((5S,6R)-2-amino-6-((1R,3aS,4S,5S,7aR)-4-(aminomethyl)-7a-methyl-1-((R)-6-methylheptan-2-yl)octahydro-1H-inden-5-yl)-6-methyl-4,5,6,7-tetrahydrobenzo[d]thiazol-5-yl)methanol.

Of this fourth embodiment, a second embodiment are compounds of formula (I) wherein:
Ⓐ is optionally substituted thiazolyl;
R¹ is hydrogen or —R⁶—OR¹;
R² is —R⁶—OR⁷ or —R⁶—N(R⁸)₂;
R³ is —R⁶—OR⁷ or —R⁶—N(R⁸)₂;
R⁴ᵃ is hydrogen, alkyl or alkenyl and R⁴ᵇ is a direct bond to the carbon to which R¹ is attached;
R⁵ is alkyl or R⁵ is a direct bond to the carbon at C14:
each R⁶ is independently selected from a direct bond or a straight or branched alkylene chain;
each R⁷ is independently selected from hydrogen or alkyl; and
each R⁸ is independently selected from hydrogen, alkyl or optionally substituted heteroarylalkyl,
or two R⁸'s, together with the nitrogen to which they are attached, form an optionally substituted N-heterocyclyl or an optionally substituted N-heteroaryl.

Of this fourth embodiment, a third embodiment are compounds of formula (I) wherein:
Ⓐ is optionally substituted thiazolyl;
R¹ is hydrogen or —R⁶—OR⁷;
R² is —R⁶—OR⁷ or —R⁶—N(R⁸)₂;
R³ is —R⁶—OR⁷ or —R⁶—N(R⁸)₂;
R⁴ᵃ and R⁴ᵇ together form alkylidene;
R⁵ is alkyl or R⁵ is a direct bond to the carbon at C14;
each R⁶ is independently selected from a direct bond or a straight or branched alkylene chain;
each R⁷ is independently selected from hydrogen or alkyl; and
each R⁸ is independently selected from hydrogen, alkyl or optionally substituted heteroarylalkyl,
or two R⁸'s, together with the nitrogen to which they are attached, form an optionally substituted N-heterocyclyl or an optionally substituted N-heteroaryl.

Of this embodiment, an embodiment is a compound of formula (I), or a stereoisomer, enantiomer or tautomer thereof or mixtures thereof, or a pharmaceutically acceptable salt or solvate thereof, selected from:
((5S,6R)-6-((3aS,4R,5S,7aS)-4-(aminomethyl)-7a-methyl-1-methyleneoctahydro-1H-inden-5-yl)-2,6-dimethyl-4,5,6,7-tetrahydrobenzo[d]thiazol-5-yl)methanol; or
((5S,6R)-2-amino-6-((3aS,4R,5S,7aS)-4-(aminomethyl)-7a-methyl-1-methyleneoctahydro-1H-inden-5-yl)-6-methyl-4,5,6,7-tetrahydrobenzo[d]thiazol-6-yl)methanol.

Of this embodiment, a fifth embodiment are compounds of formula (I) wherein:
Ⓐ is optionally substituted thiadiazolyl;
R¹ is hydrogen or —R⁶—OR⁷:
R² is —R⁶—OR⁷ or —R⁶—N(R⁸)₂;
R³ is —R⁶—OR⁷ or —R⁶—N(R⁸)₂;

$R^{4a}$ and $R^{4b}$ are each independently selected from hydrogen, alkyl or alkenyl;

or $R^{4a}$ is hydrogen, alkyl or alkenyl and $R^{4b}$ is a direct bond to the carbon to which $R^1$ is attached;

or $R^{4a}$ and $R^{4b}$ together form alkylidene;

$R^5$ is alkyl or $R^5$ is a direct bond to the carbon at C14;

each $R^6$ is independently selected from a direct bond or a straight or branched alkylene chain;

each $R^7$ is independently selected from hydrogen or alkyl; and each $R^8$ is independently selected from hydrogen, alkyl or optionally substituted heteroarylalkyl, or two $R^8$'s, together with the nitrogen to which they are attached, form an optionally substituted N-heterocyclyl or an optionally substituted N-heteroaryl.

Of this fifth embodiment, a first embodiment are compounds of formula (I) wherein:

Ⓐ is optionally substituted thiadiazolyl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ and $R^{4b}$ are each independently selected from hydrogen, alkyl or alkenyl;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two $R^8$'s, together with the nitrogen to which they are attached, form an optionally substituted N-heterocyclyl or an optionally substituted N-heteroaryl.

Of this embodiment, an embodiment is a compound of formula (I), or a stereoisomer, enantiomer or tautomer thereof or mixtures thereof, or a pharmaceutically acceptable salt or solvate thereof, selected from:

((1R,3aS,4S,5S,7aR)-5-((5S,6R)-5-(hydroxymethyl)-6-methyl-4,5,6,7-tetrahydrobenzo[d][1,2,3]thiadiazol-6-yl)-7a-methyl-1-((R)-6-methylheptan-2-yl)octahydro-1H-inden-4-yl)methanol; or ((5S,6R)-6-((1R,3aS,4S,5S,7aR)-4-(aminomethyl)-7a-methyl-1-((R)-6-methylheptan-2-yl)octahydro-1H-inden-5-yl)-6-methyl-4,5,6,7-tetrahydrobenzo[d][1,2,3]thiadiazol-5-yl)methanol.

Of this fifth embodiment, a second embodiment are compounds of formula (I) wherein:

Ⓐ is optionally substituted thiadiazolyl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ is hydrogen, alkyl or alkenyl and $R^{4b}$ is a direct bond to the carbon to which $R^1$ is attached;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two $R^8$'s, together with the nitrogen to which they are attached, form an optionally substituted N-heterocyclyl or an optionally substituted N-heteroaryl.

Of this fifth embodiment, a third embodiment are compounds of formula (I) wherein:
Ⓐ is optionally substituted thiadiazolyl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ and $R^{4b}$ together form alkylidene;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two $R^8$'s, together with the nitrogen to which they are attached, form an optionally substituted N-heterocyclyl or an optionally substituted N-heteroaryl.

Of this embodiment, a sixth embodiment are compounds of formula (I) wherein:
Ⓐ is optionally substituted oxazolyl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ and $R^{4b}$ are each independently selected from hydrogen, alkyl or alkenyl;
or $R^{4a}$ is hydrogen, alkyl or alkenyl and $R^{4b}$ is a direct bond to the carbon to which $R^1$ is attached;
or $R^{4a}$ and $R^{4b}$ together form alkylidene;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two $R^8$'s, together with the nitrogen to which they are attached, form an optionally substituted N-heterocyclyl or an optionally substituted N-heteroaryl.

Of this sixth embodiment, a first embodiment are compounds of formula (I) wherein:
Ⓐ is optionally substituted oxazolyl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ and $R^{4b}$ are each independently selected from hydrogen, alkyl or alkenyl;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two $R^6$'s, together with the nitrogen to which they are attached, form an optionally substituted N-heterocyclyl or an optionally substituted N-heteroaryl.

Of this sixth embodiment, a second embodiment are compounds of formula (I) wherein:
Ⓐ is optionally substituted oxazolyl;
$R^1$ is hydrogen or —$R^5$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ is hydrogen, alkyl or alkenyl and $R^{4b}$ is a direct bond to the carbon to which $R^1$ is attached;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl, or two R⁸'s, together with the nitrogen to which they are attached, form an optionally substituted N-heterocyclyl or an optionally substituted N-heteroaryl.

Of this sixth embodiment, a third embodiment are compounds of formula (I) wherein:

Ⓐ is optionally substituted oxazolyl;
$R^1$ is hydrogen or —$R^6$—$OR^7$;
$R^2$ is —$R^6$—$OR^7$ or, —$R^6$—$N(R^8)_2$;
$R^3$ is —$R^6$—$OR^7$ or —$R^6$—$N(R^8)_2$;
$R^{4a}$ and $R^{4b}$ together form alkylidene;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two R⁸'s, together with the nitrogen to which they are attached, form an optionally substituted N-heterocyclyl or an optionally substituted N-heteroaryl.

Of this embodiment, an embodiment is a compound of formula (I), or a stereoisomer, enantiomer or tautomer thereof or mixtures thereof, or a pharmaceutically acceptable salt or solvate thereof, selected from:
((3aS,4R,5S,7aS)-5-((5R,6S)-6-(hydroxymethyl)-2,5-dimethyl-4,5,6,7-tetrahydrobenzo[d]oxazol-5-yl)-7a-methyl-1-methyleneoctahydro-1H-inden-4-yl)methanol; or
((5R,6S)-5-((3aS,4R,5S,7aS)-4-(aminomethyl)-7a-methyl-1-methyleneoctahydro-1H-inden-5-yl)-2,5-dimethyl-4,5,6,7-tetrahydrobenzo[d]oxazol-6-yl)methanol.

Of the compounds of formula (I), or a stereoisomer, enantiomer or tautomer thereof or mixtures thereof, or a pharmaceutically acceptable salt or solvate thereof, as described above in the Summary of the Invention, a second embodiment are compounds of formula (I) wherein:

Ⓐ is fused 6-membered N-heteroaryl optionally substituted by one or more substitutents selected from alkyl, haloalkyl, —C(O)OR, —N(R⁷)₂, —C(O)N(R⁸)₂, cycloalkyl, aryl, aralkyl or heteroaryl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ and $R^{4b}$ are each independently selected from hydrogen, alkyl or alkenyl;
or $R^{4a}$ is hydrogen, alkyl or alkenyl and $R^{4b}$ is a direct bond to the carbon to which $R^1$ is attached;
or $R^{4a}$ and $R^{4b}$ together form alkylidene;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two R⁸'s, together with the nitrogen to which they are attached, form an optionally substituted N-heterocyclyl or an optionally substituted N-heteroaryl.

Of this second embodiment, an embodiment are compounds of formula (I) wherein:

Ⓐ is selected from optionally substituted pyrazinyl or optionally substituted pyrimidinyl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ and $R^{4b}$ are each independently selected from hydrogen, alkyl or alkenyl;
or $R^{4a}$ is hydrogen, alkyl or alkenyl and $R^{4b}$ is a direct bond to the carbon to which $R^1$ is attached;
or $R^{4a}$ and $R^{4b}$ together form alkylidene;
$R^5$ is alkyl or $R^5$ is a direct bond to the carbon at C14:
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two R⁸'s, together with the nitrogen to which they are attached, form an optionally substituted N-heterocyclyl or an optionally substituted N-heteroaryl.

Of this embodiment, a first embodiment are the compounds of formula (I) wherein:

Ⓐ is optionally substituted pyrazinyl;
$R^1$ is hydrogen or —$R^6$—$OR^7$;
$R^2$ is —$R^6$—$OR^7$ or, —$R^6$—$N(R^8)_2$;
$R^3$ is —$R^6$—$OR^7$ or —$R^6$—$N(R^8)_2$;
$R^{4a}$ and $R^{4b}$ are each independently selected from hydrogen, alkyl or alkenyl;
or $R^{4a}$ is hydrogen, alkyl or alkenyl and $R^{4b}$ is a direct bond to the carbon to which $R^1$ is attached;
or $R^{4a}$ and $R^{4b}$ together form alkylidene;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two R⁸'s, together with the nitrogen to which they are attached, form an optionally substituted N-heterocyclyl or an optionally substituted N-heteroaryl.

Of this first embodiment, a first embodiment are compounds of formula (I) wherein:

Ⓐ is optionally substituted pyrazinyl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ and $R^{4b}$ are each independently selected from hydrogen, alkyl or alkenyl;
$R^5$ is alkyl or $R^5$ is a direct bond to the carbon at C14:
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two R⁸'s, together with the nitrogen to which they are attached, form an optionally substituted N-heterocyclyl or an optionally substituted N-heteroaryl.

Of this embodiment, an embodiment is a compound of formula (I), or a stereoisomer, enantiomer or tautomer thereof or mixtures thereof, or a pharmaceutically acceptable salt or solvate thereof, selected from:
((1R,3aS,4S,5S,7aR)-5-((6R,7S)-7-(hydroxymethyl)-6-methyl-5,6,7,8-tetrahydroquinoxalin-6-yl)-7a-methyl-1-((R)-6-methylheptan-2-yl)octahydro-1H-inden-4-yl)methanol; or
((6S,7R)-7-((1R,3aS,4S,5S,7aR)-4-(aminomethyl)-7a-methyl-1-((R)-6-methylheptan-2-yl)octahydro-1H-inden-5-yl)-7-methyl-5,6,7,8-tetrahydroquinoxalin-6-yl)methanol.

Of this first embodiment, a second embodiment are compounds of formula (I) wherein:
Ⓐ is optionally substituted pyrazinyl;
$R^1$ is hydrogen or —$R^6$—$OR^1$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ is hydrogen, alkyl or alkenyl and $R^4$ is a direct bond to the carbon to which $R^1$ is attached;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two $R^8$'s, together with the nitrogen to which they are attached, form an optionally substituted N-heterocyclyl or an optionally substituted N-heteroaryl.

Of this first embodiment, a third embodiment are compounds of formula (I) wherein:
Ⓐ is optionally substituted pyrazinyl;
$R^1$ is hydrogen or —$R^6$—$OR^7$;
$R^2$ is —$R^3$—$OR^7$ or —$R^6$—$N(R^8)_2$;
$R^3$ is —$R^6$—$OR^7$ or —$R^6$—$N(R^8)_2$;
$R^{4a}$ and $R^{4b}$ together form alkylidene;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two $R^8$'s, together with the nitrogen to which they are attached, form an optionally substituted N-heterocyclyl or an optionally substituted N-heteroaryl.

Of this embodiment, an embodiment is a compound of formula (I), or a stereoisomer, enantiomer or tautomer thereof or mixtures thereof, or a pharmaceutically acceptable salt or solvate thereof, selected from:
((3aS,4R,5S,7aS)-5-((6R,7S)-7-(hydroxymethyl)-6-methyl-5,6,7,8-tetrahydroquinoxalin-6-yl)-7a-methyl-1-methyleneoctahydro-1H-inden-4-yl)methanol; or
((6S,7R)-7-((3aS,4R,5S,7aS)-4-(aminomethyl)-7a-methyl-1-methyleneoctahydro-1H-inden-5-yl)-7-methyl-5,6,7,8-tetrahydroquinoxalin-6-yl)methanol.

Of this embodiment, a second embodiment are the compounds of formula (I) wherein:
Ⓐ is optionally substituted pyrimidinyl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ and $R^{4b}$ are each independently selected from hydrogen, alkyl or alkenyl;
or $R^{4a}$ is hydrogen, alkyl or alkenyl and $R^{4b}$ is a direct bond to the carbon to which $R^1$ is attached;
or $R^{4a}$ and $R^{4b}$ together form alkylidene;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two $R^8$'s, together with the nitrogen to which they are attached, form an optionally substituted N-heterocyclyl or an optionally substituted N-heteroaryl.

Of this second embodiment, a first embodiment are compounds of formula (I) wherein:
Ⓐ is optionally substituted pyrimidinyl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ and $R^{4b}$ are each independently selected from hydrogen, alkyl or alkenyl;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two $R^8$'s, together with the nitrogen to which they are attached, form an optionally substituted N-heterocyclyl or an optionally substituted N-heteroaryl.

Of this embodiment, an embodiment is a compound of formula (I), or a stereoisomer, enantiomer or tautomer thereof or mixtures thereof, or a pharmaceutically acceptable salt or solvate thereof, selected from:
((6R,7S)-2-amino-6-((1R,3aS,4S,5S,7aR)-4-(hydroxymethyl)-7a-methyl-1-((R)-6-methylheptan-2-yl)octahydro-1H-inden-5-yl)-6-methyl-5,6,7,8-tetrahydroquinazolin-7-yl)methanol;
((6R,7S)-2-amino-6-((1R,3aS,4S,5S,7aR)-4-(aminomethyl)-7a-methyl-1-((R)-6-methylheptan-2-yl)octahydro-1H-inden-5-yl)-6-methyl-5,6,7,8-tetrahydroquinazolin-7-yl)methanol;
((1R,3aS,4S,5S,7aR)-5-((6R,7S)-7-(hydroxymethyl)-2,6-dimethyl-5,6,7,8-tetrahydroquinazolin-6-yl)-7a-methyl-1-((R)-6-methylheptan-2-yl)octahydro-1H-inden-4-yl)methanol;
((6R,7S)-6-((1R,3aS,4S,5S,7aR)-4-(aminomethyl)-7a-methyl-1-((R)-6-methylheptan-2-yl)octahydro-1H-inden-5-yl)-2,6-dimethyl-5,6,7,8-tetrahydroquinazolin-7-yl)methanol;
((1R,3aS,4S,5S,7aR)-5-((6R,7S)-7-(hydroxymethyl)-6-methyl-5,6,7,8-tetrahydroquinazolin-6-yl)-7a-methyl-1-((R)-6-methylheptan-2-yl)octahydro-1H-inden-4-yl)methanol; or
((6R,7S)-6-((1R,3aS,4S,5S,7aR)-4-(aminomethyl)-7a-methyl-1-((R)-6-methylheptan-2-yl)octahydro-1H-inden-5-yl)-6-methyl-5,6,7,8-tetrahydroquinazolin-7-yl)methanol.

Of this second embodiment, a second embodiment are compounds of formula (I) wherein:
Ⓐ is optionally substituted pyrimidinyl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ is hydrogen, alkyl or alkenyl and $R^{4b}$ is a direct bond to the carbon to which $R^1$ is attached;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two $R^8$'s, together with the nitrogen to which they are attached, form an optionally substituted N-heterocyclyl or an optionally substituted N-heteroaryl.

Of this second embodiment, a third embodiment are compounds of formula (I) wherein:

Ⓐ is optionally substituted pyrimidinyl;
$R^1$ is hydrogen or —$R^6$—$OR^7$;
$R^2$ is —$R^6$—$OR^7$ or —$R^6$—$N(R^8)_2$,
$R^3$ is —$R^6$—$OR^7$ or —$R^6$—$N(R^8)_2$;
$R^{4a}$ and $R^{4b}$ together form alkylidene;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two $R^8$'s, together with the nitrogen to which they are attached, form an optionally substituted N-heterocyclyl or an optionally substituted N-heteroaryl.

Of this embodiment, an embodiment is a compound of formula (I), or a stereoisomer, enantiomer or tautomer thereof or mixtures thereof, or a pharmaceutically acceptable salt or solvate thereof, selected from:

((6R,7S)-2-amino-6-((3aS,4R,5S,7aS)-4-(aminomethyl)-7a-methyl-1-methyleneoctahydro-1H-inden-5-yl)-6-methyl-5,6,7,8-tetrahydroquinazolin-7-yl)methanol;

((6R,7S)-6-((3aS,4R,5S,7aS)-4-(aminomethyl)-7a-methyl-1-methyleneoctahydro-1H-inden-5-yl)-2,6-dimethyl-5,6,7,8-tetrahydroquinazolin-7-yl)methanol;

((6R,7S)-6-((3aS,4R,5S,7aS)-4-(aminomethyl)-7a-methyl-1-methyleneoctahydro-1H-inden-5-yl)-6-methyl-5,6,7,8-tetrahydroquinazolin-7-yl)methanol;

((6R,7S)-2-amino-6-((3aS,4R,5S,7aS)-4-(hydroxymethyl)-7a-methyl-1-methyleneoctahydro-1H-inden-5-yl)-6-methyl-5,6,7,8-tetrahydroquinazolin-7-yl)methanol;

((3aS,4R,5S,7aS)-5-((6R,7S)-7-(hydroxymethyl)-2,6-dimethyl-5,6,7,8-tetrahydroquinazolin-6-yl)-7a-methyl-1-methyleneoctahydro-1H-inden-4-yl)methanol; or ((3aS,4R,5S,7aS)-5-((6R,7S)-7-(hydroxymethyl)-6-methyl-5,6,7,8-tetrahydroquinazolin-6-yl)-7a-methyl-1-methyleneoctahydro-1H-inden-4-yl)methanol.

Of the compounds of formula (I), or a stereoisomer, enantiomer or tautomer thereof or mixtures thereof, or a pharmaceutically acceptable salt or solvate thereof, as described above in the Summary of the Invention, a third embodiment are compounds of formula (I) wherein:

Ⓐ is an optionally substituted fused 13-membered N-heteroaryl;
$R^1$ is hydrogen or —$R^6$—$OR^7$;
$R^2$ is —$R^6$—$OR^7$ or —$R^6$—$N(R^8)_2$,
$R^3$ is —$R^6$—$OR^7$ or —$R^6$—$N(R^8)_2$;
$R^{4a}$ and $R^{4b}$ are each independently selected from hydrogen, alkyl or alkenyl;
or $R^{4a}$ is hydrogen, alkyl or alkenyl and $R^{4b}$ is a direct bond to the carbon to which $R^1$ is attached;
or $R^{4a}$ and $R^{4b}$ together form alkylidene;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two $R^8$'s, together with the nitrogen to which they are attached, form an optionally substituted N-heterocyclyl or an optionally substituted N-heteroaryl.

Of this third embodiment, an embodiment are compounds of formula (I) wherein:

Ⓐ is optionally substituted benzo[4,5]imidazo[1,2-a]pyrimidinyl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ and $R^{4b}$ are each independently selected from hydrogen, alkyl or alkenyl;
or $R^{4a}$ is hydrogen, alkyl or alkenyl and $R^{4b}$ is a direct bond to the carbon to which $R^1$ is attached;
or $R^{4a}$ and $R^{4b}$ together form alkylidene;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two $R^8$'s, together with the nitrogen to which they are attached, form an optionally substituted N-heterocyclyl or an optionally substituted N-heteroaryl.

Of this embodiment, an embodiment are the compounds of formula (I) wherein:

Ⓐ is optionally substituted benzo[4,5]imidazo[1,2-a]pyrimidinyl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ and $R^{4b}$ together form alkylidene;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two $R^8$'s, together with the nitrogen to which they are attached, form an optionally substituted N-heterocyclyl or an optionally substituted N-heteroaryl.

Of this embodiment, an embodiment is a compound of formula (I), or a stereoisomer, enantiomer or tautomer thereof or mixtures thereof, or a pharmaceutically acceptable salt or solvate thereof, selected from:

((3aS,4R,5S,7aS)-5-((2R,3S)-3-(hydroxymethyl)-2-methyl-1,2,3,4-tetrahydrobenzo[4,5]imidazo[2,1-b]quinazolin-2-yl)-7a-methyl-1-methyleneoctahydro-1H-inden-4-yl) methanol; or ((2R,3S)-2-((3aS,4R,5S,7aS)-4-(aminomethyl)-7a-methyl-1-methyleneoctahydro-1H-inden-5-yl)-2-methyl-1,2,3,4-tetrahydrobenzo[4,5]imidazo[2,1-b]quinazolin-3-yl) methanol.

In an embodiment of the invention Ⓐ is an unsubstituted fused N-heteroaryl.

In another embodiment of the invention Ⓐ is a fused N-heteroaryl substituted by alkyl, haloalkyl, —C(O)$OR^7$, —N($R^8$)$_2$, —C(O)N($R^8$)$_2$, unsubstituted cycloalkyl, unsubstituted aryl (preferably unsubstituted phenyl), unsubstituted aralkyl (preferably unsubstituted benzyl) or unsubstituted heteroaryl, where $R^7$ and $R^8$ are as described above in the Summary of the Invention.

It is understood that any embodiment of the compounds of the invention, as set forth above, and any specific substituent set forth herein for a particular R group in the compounds of the invention, as set forth above, may be independently combined with other embodiments and/or substituents of compounds of the invention to form embodiments of the inventions not specifically set forth above. In addition, in the event that a list of substituents is listed for any particular R group in a particular embodiment and/or claim, it is understood that each individual substituent may be deleted from the particular embodiment and/or claim and that the remaining list of substituents will be considered to be within the scope of the invention.

Another embodiment of the invention are methods for treating inflammation in the presence or absence of pain in a mammal in need thereof is where the inflammation is an autoimmune disease, disorder or condition, an inflammatory disease, disorder or condition, or a neoplastic or cell proliferative disease, disorder or condition.

Another embodiment of the methods for treating inflammation in the presence or absence of pain in a mammal in need thereof is where the inflammation is an autoimmune disease, disorder or condition selected from idiopathic pulmonary fibrosis, an inflammatory bowel disease, rheumatoid arthritis, osteoarthritis, Still's Disease, Sjógren's Syndrome, systemic lupus erythematosus, multiple sclerosis, psoriasis and systemic sclerosis.

Another embodiment of the methods for treating inflammation in the presence or absence of pain in a mammal in need thereof is where the inflammation is an inflammatory bowel disease selected from Crohn's Disease and ulcerative colitis.

Another embodiment of the methods for treating inflammation in the presence or absence of pain in a mammal in need thereof is where the inflammation is an inflammatory disease, disorder or condition selected from acute respiratory distress syndrome, allergic rhinitis, Alzheimer's Disease, asthma, an ocular inflammatory disease, atopic dermatitis, bladder pain syndrome/interstitial cystitis, chronic prostatitis/chronic pelvic pain syndrome (CP/CPPS), chronic obstructive pulmonary disease (COPD) including emphysematous, bronchitic, and alpa 1 anti-trypsin deficiency related COPD; dermal contact hypersensitivy, eczema, eosiniphilic gastrointestinal disorder, fibromyalgia, gout, hepatic fibrosis, irritable bowl syndrome, ischemic reperfusion disease, kidney fibrosis, pancreatitis, Parkisons Disease, post operative inflammation, a seronegative spondyloarthropathy, and vasculitis.

Another embodiment of the methods for treating inflammation in the presence or absence of pain in a mammal in need thereof is where the inflammation is an ocular inflammatory disease selected from allergic conjunctivitis, dry eye, and uveitis.

Another embodiment of the methods for treating inflammation in the presence or absence of pain in a mammal in need thereof is where the inflammation is a seronegative spondyloarthropathy selected from anklyosing spondylitis, psoriatic arthritis, and Reiter's Syndrome.

Another embodiment of the methods for treating inflammation in the presence or absence of pain in a mammal in need thereof is where the inflammation is vasculitis selected from Wegener's Granulomatosis, polyarteritis nodosa, leucocytoclastic vasculitis, Churg-Strauss Syndrome, cryoglobulinemic vasculitis, and giant cell arteritis.

Another embodiment of the methods for treating inflammation in the presence or absence of pain in a mammal in need thereof is where the inflammation is a neoplastic or cell proliferative disease, disorder or condition selected from acute myelogenous leukemia, chronic myelogenous leukemia, acute lymphocytic leukemia, chronic lymphocytic leukemia, basophilic leukemia, cutaneous T-cell lymphoma, Sezary Syndrome, Hodgkin's Disease, Non-Hodgkin's Lymphoma, multiple myeloma, hypereosinophilic syndromes, mastocytosis and thrombocythemia.

Another embodiment of the methods for treating pain in a mammal in need thereof is where the pain is acute pain, chronic pain, inflammatory pain, nociceptive pain, inflammatory nociceptive pain, neuropathic pain and any combinations thereof.

Another embodiment of the methods for treating pain in a mammal in need thereof is where the pain is in the absence or presence of inflammation.

Another embodiment of the invention is a method of using the compounds of the invention as standards or controls in in vitro or in vivo assays in determining the efficacy of test compounds in treating inflammation and/or pain.

In another embodiment of the invention, the compounds of the invention are isotopically-labeled by having one or more atoms therein replaced by an atom having a different atomic mass or mass number. Such isotopically-labeled (i.e., radiolabelled) compounds of the invention are considered to be within the scope of this invention. Examples of isotopes that can be incorporated into the compounds of the invention include isotopes of hydrogen, carbon, nitrogen, oxygen, phosphorous, sulfur, fluorine, chlorine, and iodine, such as, but not limited to, $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These isotopically-labeled compounds would be useful to help determine or measure the effectiveness of the compounds, by characterizing, for example, the site or mode of action for the modulation, or binding affinity to pharmacologically important site of action for the modulation. Certain isotopically-labeled compounds of the invention, for example, those incorporating a radioactive isotope, are useful in drug and/or substrate tissue distribution studies. The radioactive isotopes tritium, i.e. $^{3}H$, and carbon-14, i.e., $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of the invention can generally be prepared by conventional techniques known to those skilled in the art or by processes analogous to those described in the Synthetic Examples as set out below using an appropriate isotopically-labeled reagent in place of the non-labeled reagent previously employed.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising contacting a compound of this invention with a mammal for a period of time sufficient to yield a metabolic product thereof. Such products are typically are identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

In other embodiments, preferred stereochemistry of the compounds of formula (I) is shown below:

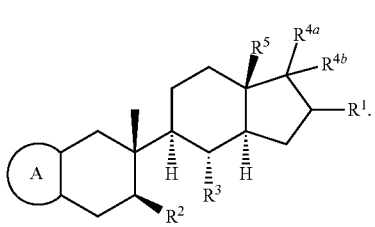

Specific embodiments of the compounds of the invention are described in more detail below in the Preparation of the Compounds of the Invention.

Utility and Testing of the Compounds of the Invention

Compounds and compositions of the invention are useful in treating inflammation and/or pain. In particular, the compounds and compositions of the invention may be used to treat inflammation in the absence of pain, inflammation in the presence of pain or pain in the absence of inflammation, preferably pain in the absence of visible inflammation.

Without being bound to any theory, and for the sole purpose of this invention, the term "inflammation" is intended to include, but not limited to, an autoimmune disease, disorder or condition, an inflammatory disease, disorder or condition, or a neoplastic or cell proliferative disease, disorder or condition; idiopathic pulmonary fibrosis, an inflammatory bowel disease, rheumatoid arthritis, osteoarthritis, Still's Disease, Sjögren's Syndrome, systemic lupus erythematosus, multiple sclerosis, psoriasis and systemic sclerosis; Crohn's Disease or ulcerative colitis; acute respiratory distress syndrome, allergic rhinitis, Alzheimer's Disease, asthma, an ocular inflammatory disease, atopic dermatitis, bladder pain syndrome/interstitial cystitis, chronic prostatitis/chronic pelvic pain syndrome (CP/CPPS), chronic obstructive pulmonary disease (COPD) including emphysematous, bronchitic, and alpa 1 anti-trypsin deficiency related COPD; dermal contact hypersensitivity, eczema, eosiniphilic gastrointestinal disorder, fibromyalgia, gout, hepatic fibrosis, irritable bowel syndrome, ischemic reperfusion disease, kidney fibrosis, pancreatitis, Parkinson's Disease, postoperative inflammation, a sero-negative spondyloarthropathy or vasculitis; allergic conjunctivitis, dry eye or uveitis; ankylosing spondylitis, psoriatic arthritis or Reiter's Syndrome; vasculitis selected from Wegener's Granulomatosis, polyarteritis *nodosa*, leucocytoclastic vasculitis, Churg-Strauss Syndrome, cryoglobulinemic vasculitis or giant cell arteritis; a neoplastic or cell proliferative disease, disorder or condition selected from acute myelogenous leukemia, chronic myelogenous leukemia, acute lymphocytic leukemia, chronic lymphocytic leukemia, basophilic leukemia, cutaneous T-cell lymphoma, Sezary Syndrome, Hodgkin's Disease, Non-Hodgkin's Lymphoma, multiple myeloma, hypereosinophilic syndromes, mastocytosis and thrombocythemia.

For the sole purpose of this invention, the term "pain" is intended to include acute pain, chronic pain, inflammatory pain, nociceptive pain, inflammatory nociceptive pain, neuropathic pain and any combinations thereof. The types of pain intended to be treated by the compounds of the invention include, but are not limited to, pain associated with any of the above disclosed inflammatory diseases, disorders and conditions, burn pain, chronic bone pain, low back pain, neck pain, abdominal pain, somatic pain, visceral pain, myofascial pain, dental pain, cancer pain, chemotherapy pain, temporomandibular joint pain, trauma pain, surgical pain, post-surgical pain, labor pain, bladder pain, musculoskeletal pain, peripherally mediated pain, centrally mediated pain, headache pain, migraine pain, phantom limb pain, peripheral nerve injury pain, post-herpetic pain, non-cardiac chest pain, irritable bowel syndrome pain, fibromyalgia and combinations thereof.

The effectiveness of the compounds of the invention in treating inflammation and/or pain may be determined by any number of known in vitro and in vivo assays, including the assays set forth below in Biological Examples 1-15 For example, the compounds of the invention may be tested in the following in vitro assays:

A. Rat or human dorsal root ganglion excitability assay (see, e.g., Young, G. T., et al., *Mol. Ther.* 22, 1530-43 (2014), and Tams, D., et al., *Nature Methods* 14 (2017)):

This assay measures the effect of electrical field stimulation on the excitability of rat or human dorsal root ganglionic cells. Compounds which demonstrate the ability to decrease the excitability response of a cell when tested in this assay may be useful in treating neuropathic pain.

B. T-cell proliferation and cytokine release assay:

This assay measures the inflammatory response.

C. Metabolism (microsomal stability) (see, e.g., Chiba, M, et al., *AAPS J.* 2009 11(2) 262):

This assay measures a compound's stability against microsomal metabolism, which is a primary metabolic pathway: Compounds tested in this assay which are relatively more stable than others may be more effective in treating inflammation or pain.

Furthermore, the general value of the compounds of the of the invention in treating inflammation and pain may be established in industry standard animal models for demonstrating the efficacy of compounds in treating inflammation and pain. Examples of these animal models are as follows:

A. Mouse LPS challenge (see, e.g., Kabir, K. et al., *Shock*, 2002, 17(4), 300-3): This is a well-known animal model for inflammation.

B. Mouse formalin pain (see, e.g., Le Bars, D. et al., *Pharmacol. Rev.* 2001, 53(4), 597-652):

This is a well-known model of inflammatory and neuropathic pain.

C. Rat TNBS Colitis (see, e.g., Antoniou, E., et al., *Ann Med Surg* (Lond), 2016, 11, 9-15):

This is a model for inflammatory colitis and measures inflammatory response.

D. Rat CYP Cystitis (see, e.g., Golubeva, A. V., et al., *Physiol. Rev.*, 2014, 2(3), e00260 and Keay, S., et al., BMC Urol, 2012, 12, 17):

This is a cyclophosphamide-induced cystitis model which measures the effect on visceral/abdominal/pelvic pain. This is directly supportive of use of the compounds for treating nociceptive pain.

E. Rat Ketamine cystitis (see, e.g., Jang, M.-Y., et al., *Urological Science*, 28(3), 123-7, 2017):

This is a urogenital (upper and lower) model for pain.

F. Rat Chronic Prostatitis/Chronic Pelvic Pain (see, e.g., Radhakrishnan, R. and Nallu, R. S., 2009, *Inflammopharmacology*, 17:23-28):

This is a model for assessing a compounds ability to treat prostatitis and prostate inflammatory pain.

G. Rat MIA-induced osteoarthritis (see, e.g., Guingamp, C., et al., *Arthritis and Rheumatism*, 40(9), 1997, 1670-9):

This is a model for chronic nociceptive joint pain, which has both an inflammatory component and a nociceptive component.

H. Rat Carrageenan-induced hyperalgesia and paw edema (see, e.g., Morris, C. J., *Methods Mo. Biol.*, 2003, 225, 115-21): This is an inflammatory response model. It measures both inflammatory and pain responses.

I. Rat Complete Freund's Adjuvant model of inflammatory pain (see, e.g., Fehrenbacher, J. C., et al., *Curr. Protoc. Pharmacol.*, 2012 March, Chapter 5, Unit 5.4):
This is well-known model for inflammatory pain, particularly in the joints.

J. Rat Spinal nerve ligation model of neuropathic pain (see, e.g., Chung, J. M., et al., *Methods in Molecular Medicine,* 2004, 99, 35-45):
This is a model for neuropathic pain.

K. Mouse Bleomycin Lung Fibrosis Model (see, e.g., Moore, B. B., et al., *Am J Respir Cell Mol Biol,* 2013, 49(2), 167-79):
This is an inflammatory response model.

Pharmaceutical Compositions of the Invention and Administration

For the purposes of administration, the compounds of the present invention may be formulated as pharmaceutical compositions. Pharmaceutical compositions comprise one or more compounds of this invention in combination with a pharmaceutically acceptable carrier and/or diluent. The compound is present in the composition in an amount which is effective to treat inflammation and/or pain, and preferably with acceptable toxicity to the patient. Typically, the pharmaceutical compositions of the present invention may include a compound in an amount from 0.1 mg to 250 mg per dosage depending upon the route of administration, and more typically from 1 mg to 60 mg. Appropriate concentrations and dosages can be readily determined by one skilled in the art.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a compound of this invention, diluents, dispersing and surface active agents, binders, and lubricants. One skilled in this art may further formulate the compounds in an appropriate manner, and in accordance with accepted practices, such as those disclosed in *Remington's Pharmaceutical Sciences* (Mack Pub. Co., N.J. current edition).

In another embodiment, the present invention provides a method for treating inflammation and/or pain generally and, more specifically, to treating the diseases, disorders and conditions as discussed above. Such methods include administering of a compound of the present invention to a mammal, preferably a human, in an amount sufficient to treat the inflammation and/or pain. In this context, "treat" includes prophylactic administration. Such methods include systemic administration of a compound of the invention, preferably in the form of a pharmaceutical composition as discussed above. As used herein, systemic administration includes oral and parenteral methods of administration. For oral administration, suitable pharmaceutical compositions include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parenteral administration, the compounds of the present invention can be prepared in aqueous injection solutions which may contain buffers, antioxidants, bacteriostats, and other additives commonly employed in such solutions.

Preparation of the Compounds of the Invention

The following Reaction Schemes illustrate methods to make compounds of the present invention, i.e., compounds of formula (I), as set forth above in the Summary of the Invention.

The compounds of the present invention may be prepared by known organic synthesis techniques, including the methods described in more detail in the Examples. In general, the compounds of formula (I) may be made by the following Reaction Schemes, wherein all substituents are as defined above in the Summary of the Invention unless indicated otherwise. Although not generally depicted in the following schemes, one skilled in the art will understand that appropriate protecting group strategies may be useful in preparing compounds of formula (I). Protecting group methodology is well known to those skilled in the art (see, for example, Greene, T. W. and Wuts, P. G. M. *Greene's Protective Groups in Organic Synthesis* (latest edition). In particular, suitable protecting groups for an oxygen atom ("oxygen protecting groups") include, but are not limited to, acetyl, trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for a nitrogen atom ("nitrogen protecting groups") include, but are not limited to, benzhydryl (diphenylmethyl), t-butxycarbonyl, benzyloxycarbonyl, trifluoroacetate, and the like.

It is also understood that one skilled in the art would be able to make the compounds of the invention by similar methods, by methods known to one skilled in the art, or by methods similar to the methods disclosed in U.S. Pat. Nos. 6,635,629, 7,601,874, and 9,765,085 and U.S. Published Patent Application No. 2017/0253596. It is also understood that one skilled in the art would be able to make in a similar manner as described below other compounds of the invention not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Smith, M. B. and J. March, *March's Advanced Organic Chemistry: Reactions, Mechanisms, and Structure,* 6th edition (Wiley, 2007)) or prepared as described herein. Certain starting materials, or their salts thereof, may be prepared according to the methods disclosed in U.S. Pat. Nos. 6,635,629, 7,601,874 and 9,765,085 and U.S. Published Patent Application No. 2017/0253596, the relevant disclosures therein are incorporated in reference herein, or by methods known to one skilled in the art.

It is also understood that in the following description, combinations of substituents and/or variables of the depicted formulae are permissible only if such contributions result in stable compounds.

It will also be appreciated by those skilled in the art, although protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

When a compound of the invention is depicted in the General Reaction Schemes below without stereochemistry, it is understood that one skilled in the art would readily recognize that such compounds could also be prepared in an optically pure form by utilizing methods known to one skilled in the art, such as the use of stereoselective reagents, chiral starting materials and phase transfer catalysts.

Abbreviations

The following abbreviations may be used herein in the following General Reaction Schemes and in the Synthetic Examples. If an abbreviation is not included below, it is understood to have its accepted meaning in the field to which it pertains:

Ac for acetyl;
$Ac_2O$ for acetic anhydride;
ACN for acetonitrile
AcOH for acetic acid;
BALF for Bronchoalveolar lavage fluid;
Boc for tert-butoxycarbonyl;
$(Boc)_2O$ for di-tert-butyl dicarbonate;
n-BuLi for n-butyl lithium;
t-BuOH for tert-butyl alcohol;
CFA for Complete Freund's Adjuvant;
CP/CPPS for chronic prostatitis/chronic pelvic pain syndrome;
DCE for dichloroethane;
DCM for dichloromethane;
DMAP for 4-dimethylaminopyridine;
DMF for N,N-dimethylformamide;
DMP for Dess-Martin periodinane;
DMSO for dimethyl sulfoxide;
DRG for Dorsal root ganglion;
EFS for Electrical field stimulation;
ELISA for enzyme-linked immunosorbent assay;
ELSD for Evaporative Light Scattering Detection;
Eq for equivalents;
Et for ethyl;
EtOAc for ethyl acetate
$EtOCHO$ or $HCO_2Et$ for ethyl formate;
EtOH for ethanol;
Fluo 8-AM for Bis(acetoxymethyl) 2,2'-((4-(6-(acetoxymethoxy)-3-oxo-3H-xanthen-9-yl)-2-(2-(bis(2-acetoxymethoxy)-2-oxoethyl)amino)phenoxy)ethoxy)phenyl) azanediyl)diacetate;
h for hours;
$H_2/Pd/C$ or Pd/C for hydrogen on palladium on charcoal;
HPLC for high-pressure liquid chromatography;
HATU for 1-[bis(dimethylamino)methylene]-1H-1,2,3-triazolo[4,5-b]pyridinium 3-oxide hexafluorophosphate;
IP for intraperitoneal;
$KO^tBu$ or KtBuO for potassium tert-butoxide;
LCMS or LC/MS for liquid chromatography-mass spectrometry;
$LiAlH_4$ or LAH for lithium aluminum hydride;
$LiOH.H_2O$ for lithium hydroxide monohydrate;
LPS for lipopolysaccharide;
m-CPBA or MCPBA for meta-chloroperoxybenzoic acid;
m or min for minutes;
NBS for N-bromosuccinimide;
MeOH for methanol;
$p-MePhSO_2NHNH_2$ for p-toluenesulphonyl hydrazide;
$MeP(OPh_3)I$ for methyl(triphenoxy)phosphonium iodide;
MIA for monosodium iodoacetate;
$MnOAc_3$ for manganese (III) acetate;
$MnOAc_3.2H_2O$ for manganese (III) acetate dihydrate;
MRM for multiple reaction monitoring;
MS for Mass spectrometry;
MsCl for mesyl chloride;
NADPH for nicotinamide adenine dinucleotide phosphate;
NaOMe for sodium methoxide;
$NaBH(OAc)_3$ or $Na(OAc)_3BH$ for sodium triacetoxyborohydride;
$NH_4OAc$ for ammonium acetate;
NMO for N-methylmorpholine N-oxide;
NMR for nuclear magnetic resonance;
$pTsNHNH_2$ for para-toluenesulfonyl hydrazide;
Pd/C for palladium metal on charcoal;
Pet ether for petroleum ether;
Ph for phenyl;
$PhI(OAc)_2$ for (diacetoxyiodo)benzene;
$PPh_3$ for triphenylphosphine;
$PPH_3CH_2CHBr$ for ethyltriphenylphosphonium bromide;
$POCl_3$ for phosphoryl chloride;
PTSA or $PTSA.H_2O$ for para-toluenesulfonic acid/para-toluenesulfonic acid monohydrate;
Pyr or Py for pyridine;
RB for round bottom
RT for room temperature;
s for seconds;
SBTH for sodium triacetoxyborohydride;
TBAF for tetrabutylammonium fluoride:
TBDPS for tert-butyldiphenylsilyl;
TBDPSCl for tert-butyldiphenylsilyl chloride;
TBHP for tert-butyl hydroperoxide;
TBS or TBDMS for tert-butyldimethylsilyl;
TBSCl or TBDMSCl for tert-butyldimethylsilyl chloride;
TEA for triethylamine;
TEMPO for (2,2,6,6-tetramethylpiperidin-1-yl)oxy or (2,2,6,6-tetramethylpiperidin-1-yl)oxidanyl;
TFA for trifluoroacetic acid;
TFAA for trifluoroacetic anhydride;
THF for tetrahydrofuran;
TLC for thin layer chromatography;
TMSOTf for trimethylsilyl triflate;
TNBS for 2,4,6-trinitrobenzenesulfonic acid;
TPAP for tetrapropylammonium perruthenate;
$t_R$ for retention time;
TTX for tetrodotoxin:
UHPLC for ultra high-pressure liquid chromatography;
UV for ultraviolet; and
Ts for tosyl (p-toluenesulphonyl).

The following General Methods and Procedures were used to prepare, separate or characterize individual compounds of the invention. It will be appreciated that in the following general methods, reagent levels and relative amounts or reagents/intermediates can be changed to suit particular compounds to be synthesized, up or down by up to 50% without significant change in expected results.

1 General LC/MS Analytical Methods

| Method # | Column Details | A | B | Flow rate (ml/min) | | T1 | T2 | T3 | T4 | T5 |
|---|---|---|---|---|---|---|---|---|---|---|
| Ia | A | 0.1% TFA in water | 0.1% TFA in ACN | 1.5 | Time % B | 0 10 | 2.5 95 | 4.5 95 | 4.6 10 | 6 10 |

-continued

| Method # | Column Details | A | B | Flow rate (ml/min) | | T1 | T2 | T3 | T4 | T5 |
|---|---|---|---|---|---|---|---|---|---|---|
| 1b | B | | | 2 | Time | 0 | 8 | 8.1 | 8.5 | 10 |
| | | | | | % B | 5 | 100 | 100 | 5 | 5 |
| 1c | B | 0.1% TFA in water:ACN (95:5) | 0.1% TFA in ACN | 1.5 | Time | 0 | 2.5 | 4 | 4.5 | 6 |
| | | | | | % B | 5 | 95 | 95 | 5 | 5 |
| 1d | C | 0.1% formic in water:ACN (95:5) | ACN | 1.5 | Time | 0 | 2.5 | 4 | 4.5 | 6 |
| | | | | | % B | 5 | 65 | 95 | 5 | 5 |
| 1e | B | 10 mM NH$_4$HCO$_3$ in water | ACN | 2 | Time | 0 | 4 | 5 | 5.5 | 6.5 |
| | | | | | % B | 10 | 95 | 95 | 10 | 10 |
| 1f | A | 0.1% formic acid in water | ACN | 1.5 | Time | 0 | 3 | 5 | 5.5 | 6 |
| | | | | | % B | 50 | 95 | 95 | 50 | 50 |
| 1g | B | 10 mM NH$_4$HCO$_3$ in water | ACN | 1 | Time | 0 | 8 | 8.1 | 8.5 | 10 |
| | | | | | % B | 5 | 100 | 100 | 5 | 5 |
| 1h | B | 10 mM NH$_4$HCO$_3$ in water | ACN | 1.2 | Time | 0 | 2.5 | 5.0 | 5.5 | 7 |
| | | | | | % B | 50 | 95 | 95 | 50 | 50 |
| 1i | D | ACN | 0.1% formic acid in water | 1.5 | Time | 0 | 2.5 | 4.5 | 4.6 | 6 |
| | | | | | % B | 10 | 95 | 95 | 10 | 10 |
| 1j | E | 10 mM NH$_4$HCO$_3$ in water | ACN | 1.2 | Time | 0 | 2.5 | 5.0 | 5.5 | 7 |
| | | | | | % B | 50 | 95 | 95 | 50 | 50 |
| 1k | E | 10 mM NH$_4$HCO$_3$ in water | ACN | 1.2 | Time | 0 | 3.5 | 4.5 | 5.0 | 6 |
| | | | | | % B | 10 | 95 | 95 | 10 | 10 |
| 1l | B | 0.1% TFA in water:ACN (95:5) | 0.1% TFA in ACN | 1.8 | Time | 0 | 2.5 | 7.0 | 7.1 | 8 |
| | | | | | % B | 80 | 98 | 98 | 80 | 80 |

Column details:
A: Atlantis dC18 (50 × 4.6 mm, 5 μm),
B: XBridge C8 (50 × 4.6 mm, 3.5 μm),
C: Zorbax XDB C18 (50 × 4.6 mm, 3.5 μm),
D: Zorbax C18 (50 × 4.6 mm, 5 μm),
E: Zorbax Extend C18 (50 × 4.6 mm, 5 μm).

2. General HPLC Analytical Methods

| Method # | Column Details | A | B | Flow rate (ml/min) | | T1 | T2 | T3 | T4 | T5 |
|---|---|---|---|---|---|---|---|---|---|---|
| 2a | B | 0.1% TFA in water | 0.1% TFA in ACN | 2 | Time | 0 | 8 | 8.1 | 8.5 | 10 |
| | | | | | % B | 5 | 100 | 100 | 5 | 5 |
| 2b | F | 10 mM NH$_4$HCO$_3$ in water | ACN | 1 | Time | 0 | 15 | 20 | 26 | 30 |
| | | | | | % B | 10 | 100 | 100 | 10 | 10 |
| 2c | A | 0.1% TFA in water | 0.1% TFA in ACN | 1.5 | Time | 0 | 8 | 8.1 | 8.5 | 10 |
| | | | | | % B | 5 | 100 | 100 | 5 | 5 |
| 2d | G | 0.1% TFA in water | ACN | 1 | Time | 0 | 15 | 20 | 26 | 30 |
| | | | | | % B | 10 | 100 | 100 | 10 | 10 |
| 2e | B | 10 mM NH$_4$HCO$_3$ in water | ACN | 1 | Time | 0 | 8 | 8.1 | 8.5 | 10 |
| | | | | | % B | 5 | 100 | 100 | 5 | 5 |

Columm details:
A: Atlantis dC18 (50 × 4.6 mm, 5 μm),
B: XBridge C8 (50 × 4.6 mm, 3.5 μm),
C: Zorbax XDB C18 (50 × 4.6 mm, 3.5 μm),
F: Phenomenex Gemini C18 (150 × 4.6 mm, 3.0 μm),
G: Atlantis dC18 (250 × 4.6 mm, 5 μm).

3. General Preparative HPLC Methods

| Method # | Column Details | A | B | Flow rate (ml/min) |
|---|---|---|---|---|
| 3a | H | 0.1% TFA in water | 0.1% TFA in ACN | 15 |
| 3b | H | 0.1% formic acid in water:ACN (95:5) | ACN | 15 |
| 3c | I | 10 mM NH$_4$OAc in water | ACN | 22 |
| 3d | I | Water | ACN | 22 |
| 3e | H | 0.1% TFA in water | ACN | 15 |

Column details: H: Sunfire C18 (19 × 150 mm, 5 μm), I: YMC-triart C18 (30 × 250 mm, 5 μm).

General Procedure A

Acetylation with Ac$_2$O

To a stirred solution of the alcohol (1 equivalent) in pyridine at 0° C. were added DMAP (0.05 equivalent) and Ac$_2$O (1 equivalent) and the resultant solution was stirred at ambient temperature. In a standard workup, the mixture was concentrated under reduced pressure, diluted with EtOAc and washed consecutively with water and brine. The combined organic extracts were dried (Na$_2$SO$_4$ or MgSO$_4$), filtered and concentrated under reduced pressure. The crude material was purified by flash column chromatography on silica gel.

General Procedure B

TBS Protection of Alcohols

To a stirred solution of the alcohol (1 equivalent) in DMF at ambient temperature was added imidazole (2 equivalents) followed by TBSCl (1 equivalent) at 0° C. The resulting mixture was stirred at ambient temperature. In a standard workup, the mixture was concentrated under reduced pressure, diluted with CH$_2$Cl$_2$ and washed consecutively with water and brine. The combined organic extracts were dried (Na$_2$SO$_4$ or MgSO$_4$), filtered and concentrated under reduced pressure. The crude material was purified by flash column chromatography on silica gel.

General Procedure C

Allylic Oxidation with TBHP/Cat

1. Option Using Copper(I)Iodide
   To a stirred solution of the alkene (1 equivalent) in CH$_2$Cl$_2$:ACN (1:1) at 0° C. were added TBHP in decane (5 equivalents) and copper(I)iodide (0.1 equivalent) and the resultant mixture was stirred at ambient temperature for 12 hours. In a standard workup, the mixture was concentrated under reduced pressure, diluted with EtOAc and washed consecutively with water and brine. The combined organic extracts were dried (Na$_2$SO$_4$ or MgSO$_4$), filtered and concentrated under reduced pressure. The crude material was purified by flash column chromatography on silica gel.
2. Option Using Manganese(III)Acetate Dihydrate:
   To a stirred solution of the alkene (1 equivalent) in CH$_2$Cl$_2$:ACN:EtOAc (1:1:1) at room temperature were added TBHPin decane (5.2 equivalents) and 4 Å molecular sieves, the resultant mixture was stirred at room temperature for 0.5 hours. At this point, was added Mn(OAc)$_3$.2H$_2$O (0.1 equivalent) and stirring was continued overnight at ambient temperature. In a standard workup, the mixture was filtered through a bed of CELITE® and the filtrate was concentrated under reduced pressure. The crude material was purified by flash column chromatography on silica gel.
3. Option Using Selenium Dioxide:
   To a stirred solution of the alkene (1 equivalent) in CH$_2$Cl$_2$ at 0° C. were added TBHP in decane (5 equivalents) and SeO$_2$ (0.5 equivalent) and the resultant mixture was stirred at ambient temperature for 12 hours. In a standard workup, the mixture was diluted with CH$_2$Cl$_2$ and washed consecutively with water and brine. The combined organic extracts were dried (Na$_2$SO$_4$ or MgSO$_4$), filtered and concentrated under reduced pressure. The crude material was purified by flash column chromatography on silica gel.

General Procedure D

Hydroboration Sequence

To a stirred solution of the ketone (1 equivalent) in THF at 0° C. was added Borane in THF (1 M, 2.23 equivalents). The resulting mixture was stirred at same temperature for 12 hours. The mixture was quenched with dropwise addition of purified chilled water and stirred for 15 minutes. To the resulting mixture was added sodium perborate tetrahydrate at ambient temperature and stirred for 3 hours. In a standard workup, the mixture was diluted with EtOAc and washed consecutively with water and brine. The combined organic extracts were dried (Na$_2$SO$_4$ or MgSO$_4$), filtered and concentrated under reduced pressure. The crude material was purified by flash column chromatography on silica gel.

General Procedure E

Ketal/Acetal Deprotection with AcOH

The Ketal/Acetal protected moiety (1 equivalent) was dissolved in 80% aqueous AcOH. The resulting mixture was heated to 65° C. and stirred for 1 hour. In a standard workup, the mixture was concentrated under reduced pressure and diluted with saturated aqueous NaHCO$_3$. The aqueous was extracted with CH$_2$Cl$_2$. The combined organic extracts were washed with brine, dried (Na$_2$SO$_4$ or MgSO$_4$, filtered and concentrated under reduced pressure. The crude material was purified by flash column chromatography on silica gel.

General Procedure F

NaIO$_4$ Diol Cleavage

To a stirred solution of the alcohol (1 equivalent) in THF and water (2:1) at ambient temperature was added NaIO$_4$ (2 equivalents). The resulting mixture was stirred at room temperature for 1 hour. In a standard workup, the mixture was diluted with EtOAc and washed consecutively with water and brine. The combined organic extracts were dried (Na$_2$SO$_4$ or MgSO$_4$), filtered and concentrated under reduced pressure. The crude material was purified by flash column chromatography on silica gel.

General Procedure G

NaBH$_4$ Reduction of Carbonyls

To a stirred solution of the carbonyl compound (1 equivalent) in MeOH at room temperature was added NaBH$_4$ (2 equivalents). The resulting mixture was stirred at ambient temperature 4 hours. In a standard workup, the mixture was concentrated under reduced pressure and diluted with EtOAc and washed consecutively with saturated aqueous NaHCO$_3$ and brine. The combined organic extracts were dried (Na$_2$SO$_4$ or MgSO$_4$), filtered and concentrated under reduced pressure. The crude material was purified by flash column chromatography on silica gel.

General Procedure H

Acetonide Formation with 2,2-Dimethoxypropane

To a stirred solution of the diol (1 equivalent) in 2,2-dimethoxypropane at 0° C. was added camphorsulphonic acid (0.1 equivalent). The resulting mixture was stirred at ambient temperature 2-4 hours. In a standard workup, the mixture was concentrated under reduced pressure and diluted with EtOAc and washed consecutively with saturated aqueous $NaHCO_3$ and brine. The combined organic extracts were dried ($Na_2SO_4$ or $MgSO_4$), filtered and concentrated under reduced pressure. The crude material was purified by flash column chromatography on silica gel.

General Procedure I

Wittig Reaction

To a stirred solution of methyltrphenylphosphonium bromide (Wittig reagent, 3 equivalents) in THF at 0° C. was added potassium tert-butoxide (2.9 equivalents) and the mixture was stirred at ambient temperature for 2 hours. To the resultant solution was added ketone (1 equivalent) in THF at room temperature and stirred overnight. In a standard workup, the mixture was diluted with EtOAc and washed consecutively with saturated aqueous $NaHCO_3$ and brine. The combined organic extracts were dried ($Na_2SO_4$ or $MgSO_4$), filtered and concentrated under reduced pressure. The crude material was purified by flash column chromatography on silica gel.

General Procedure J

Mesylate Formation

To a stirred solution of the alcohol (1 equivalent) in pyridine at 0° C. was added (MsCl (2 equivalents). The resulting mixture was stirred at ambient temperature for 1 hour. In a standard workup, the mixture was concentrated under reduced pressure and diluted with EtOAc and washed consecutively with water and brine. The combined organic extracts were dried ($Na_2SO_4$ or $MgSO_4$), filtered and concentrated under reduced pressure. The crude material was purified by flash column chromatography on silica gel.

General Procedure K

Azide Introduction

To a stirred solution of the mesylate (1 equivalent) in DMF at ambient temperature was added sodium azide (3 equivalents). The resulting mixture was stirred at 80° C. for 8 hours. In a standard workup, the mixture was concentrated under reduced pressure and diluted with EtOAc and washed consecutively with water and brine. The combined organic extracts were dried ($Na_2SO_4$ or $MgSO_4$), filtered and concentrated under reduced pressure. The crude material was purified by flash column chromatography on silica gel.

General Procedure L $K_2CO_3$ Deprotection of Esters/TFA Amides

To the stirred solution of the ester/TFA-protected amide (1 equivalent) in MeOH at ambient temperature was added $K_2CO_3$ (2 equivalents) and few drops of water. The resulting mixture was heated to reflux for 2 hours. In a standard workup, the mixture was concentrated under reduced pressure and diluted with EtOAc and washed consecutively with water and brine. The combined organic extracts were dried ($Na_2SO_4$ or $MgSO_4$), filtered and concentrated under reduced pressure. The crude material was purified by flash column chromatography on silica gel.

General Procedure M

TPAP/NMO Oxidation

To a stirred solution of the alcohol (1 equivalent) in $CH_2Cl_2$ at 0° C. were added NMO $H_2O$ (2 equivalents), 4 Å molecular sieves and TPAP (0.1 equivalents). The resulting mixture was stirred at ambient temperature for 2 hours. In a standard workup, the mixture was diluted with $CH_2Cl_2$ and filtered through a bed of CELITE® and the filtrate was concentrated under reduced pressure. The crude material was purified by flash column chromatography on silica gel.

General Procedure N

Dess-Martin Periodinane Oxidation

To a stirred solution of the alcohol (1 equivalent) in $CH_2Cl_2$ at 0° C. was added Dess-Martin periodinane (2 equivalents). The resulting mixture was stirred at ambient temperature for 2 hours. In a standard workup, the mixture was diluted with $CH_2Cl_2$ and washed consecutively with saturated aqueous $NaHCO_3$ and brine. The combined organic extracts were dried ($Na_2SO_4$ or $MgSO_4$), filtered and concentrated under reduced pressure. The crude material was purified by flash column chromatography on silica gel.

General Procedure O

Knoevenagel Condensation

To a stirred solution of the sodium hydride (60% dispersion in mineral oil, 4 equivalents) in THF at 0° C. was added the ketone in THF (1 equivalent) dropwise. The resulting mixture was stirred at same temperature for 2 hours. To the resulting mixture was added ethyl formate (6 equivalents) at 0° C. and stirred at ambient temperature for 8 hours. In a standard workup, the mixture was quenched with a saturated aqueous solution of $NH_4Cl$ and the aqueous layer extracted with EtOAc. The combined organic extracts were washed with brine, dried ($Na_2SO_4$ or $MgSO_4$), filtered and concentrated under reduced pressure. The crude material was purified by flash column chromatography on silica gel.

Alternative conditions for the Knoevenagel condensation include the following: To a stirred solution of the ketone in toluene at 0° C. were added sodium methoxide solution (25% wt. in MeCOH, 15-3 equivalents) and ethyl formate (5-6 equivalents) dropwise and the resultant solution stirred at ambient temperature for 16 hours. In a standard workup, the mixture was concentrated under reduced pressure and diluted with chilled water. The aqueous layer was extracted with EtOAc, washed with brine and the organic layer dried ($Na_2SO_4$ or $MgSO_4$), filtered, concentrated and purified by silica gel chromatography, if required.

General Procedure P

Hydrazine Condensation to Form Pyrazoles

To a stirred solution of the ketone (1 equivalent) in EtOH at ambient temperature was added hydrazine hydrate (2 equivalents) dropwise. The resulting mixture was heated to 70° C. and stirred for 2 hours. In a standard workup, the mixture was concentrated under reduced pressure and diluted with EtOAc and washed consecutively with water and brine. The combined organic extracts were dried ($Na_2SO_4$ or $MgSO_4$), filtered and concentrated under reduced pressure. The crude material was purified by flash column chromatography on silica gel.

General Procedure Q

TBS Deprotection with TBAF

The TBS silyl ether (1 equivalent) was dissolved in THF and (TBAF (1 M in THF, 2 equivalents) was added at ambient temperature. The mixture was heated to 65° C. and stirred for 2 hours. In a standard workup, the mixture was diluted with EtOAc and washed consecutively with water and brine. The combined organic extracts were dried ($Na_2SO_4$ or $MgSO_4$), filtered and concentrated under reduced pressure. The crude material was purified by flash column chromatography on silica gel.

General Procedure R

Azide Reduction with $PPh_3$

To a stirred solution of the azide (1 equivalent) in THF and water (9:1) at ambient temperature was added $PPh_3$ (2 equivalents). The mixture was heated to 60° C. and stirred for 4 hours. In a standard workup, the mixture was diluted with EtOAc and washed consecutively with water and brine. The combined organic extracts were dried ($Na_2SO_4$ or $MgSO_4$), filtered and concentrated under reduced pressure. The crude material was purified by flash column chromatography on silica gel.

General Procedure S

Reduction with Lithium Aluminum Hydride

To a stirred solution of the azide (1 equivalent) in tetrahydrofuran at 0° C. was added LAH (1 M in THF, 2 equivalents) dropwise. The mixture was stirred at room temperature for 4 hours. In a standard workup, the mixture was quenched with saturated solution of $Na_2SO_4$ and filtered through a bed of CELITE®, the aqueous was extracted with EtOAc. The combined organic extracts were washed with brine, dried ($Na_2SO_4$ or $MgSO_4$), filtered and concentrated under reduced pressure. The crude material was purified by flash column chromatography on silica gel.

General Procedure T

Pd-Catalyzed Hydrogenation of Double Bonds

To a stirred solution of the alkene (1 equivalent) in ethyl acetate at room temperature was added 10% Pd/C (~5-10% of alkene weight) under a nitrogen atmosphere. The mixture was stirred at ambient temperature for 2-4 hours under 1 hydrogen atmosphere using a balloon. In a standard workup, the mixture was filtered through a bed of CELITE® and filtrate was concentrated under reduced pressure. The crude material was purified by flash column chromatography on silica gel.

General Procedure U

Reductive Amination (Using Amine Precursor)

To the stirred solution of the amine (1 equivalent) in MeOH at room temperature was added the carbonyl compound (1.2 equivalents) and the mixture was heated to reflux for 4 hours. The resulting mixture was cooled to room temperature and $NaBH_4$ (1.5 equivalents) was added. The resultant solution was stirred at ambient temperature for 2 hours. In a standard workup, the mixture was concentrated under reduced pressure and diluted with a saturated aqueous solution of $NaHCO_3$. The aqueous was extracted with EtOAc and the combined organic extracts were washed with brine, dried ($Na_2SO_4$ or $MgSO_4$), filtered and concentrated under reduced pressure. The crude material was purified by flash column chromatography on silica gel.

General Procedure V

Reductive Amination (Using Aldehyde Precursor)

To the stirred solution of the aldehyde/ketone (1 equivalent) in MeOH and 1,2-DCE(1:3) at ambient temperature were added the amine (5 equivalents), 4 Å molecular sieves and the mixture was heated to reflux for 12 hours. The resulting mixture was cooled to ambient temperature and SBTH (2 equivalents) was added. The resultant solution was stirred at ambient temperature for 2 hours. In a standard workup, the mixture was concentrated under reduced pressure and diluted with a saturated aqueous solution of $NaHCO_3$. The aqueous was extracted with EtOAc and the combined organic extracts were washed with brine, dried ($Na_2SO_4$ or $MgSO_4$, filtered and concentrated under reduced pressure. The crude material was purified by flash column chromatography on silica gel.

General Procedure W

Double bond isomerization/methyl group migration with HCl

To the solution of amine (1 equivalent) in MeOH (5 volumes) at ambient temperature was added 4M HCl in dioxane (5 volumes) and the resulting solution was heated to 80° C. for 2-4 hours. In a standard workup, the mixture was concentrated under reduced pressure and neutralized with saturated solution of $NaHCO_3$. The aqueous was extracted with $CH_2Cl_2$ and the combined organic extracts were washed with brine, dried ($Na_2SO_4$ or $MgSO_4$), filtered and concentrated under reduced pressure. The crude material was purified by flash column chromatography on silica gel.

General Reaction Schemes

The following General Reaction Schemes illustrate methods to make compounds of formula (I), or stereoisomers, enantiomers or tautomers thereof or mixtures thereof, or pharmaceutically acceptable salts or solvates thereof, as set forth above in the Summary of the Invention.

General Reaction Scheme 1

Compounds of formula (I-1) are compounds of formula (I), as described above in the Summary of the Invention, and may be prepared according the following General Reaction Scheme 1 wherein $R^1$, $R^{4a}$, $R^{4b}$ and $R^5$ are as described above in the Summary of the Invention, $R^{10}$ is hydrogen, alkyl, or haloalkyl, $Pg^1$ is an oxygen protecting group, such as acetyl, $Pg^2$ is an oxygen protecting group such as tert-butyldimethylsilyl or tert-butyldiphenylsilyl, and X is halo, preferably chloro:

GENERAL REACTION SCHEME 1

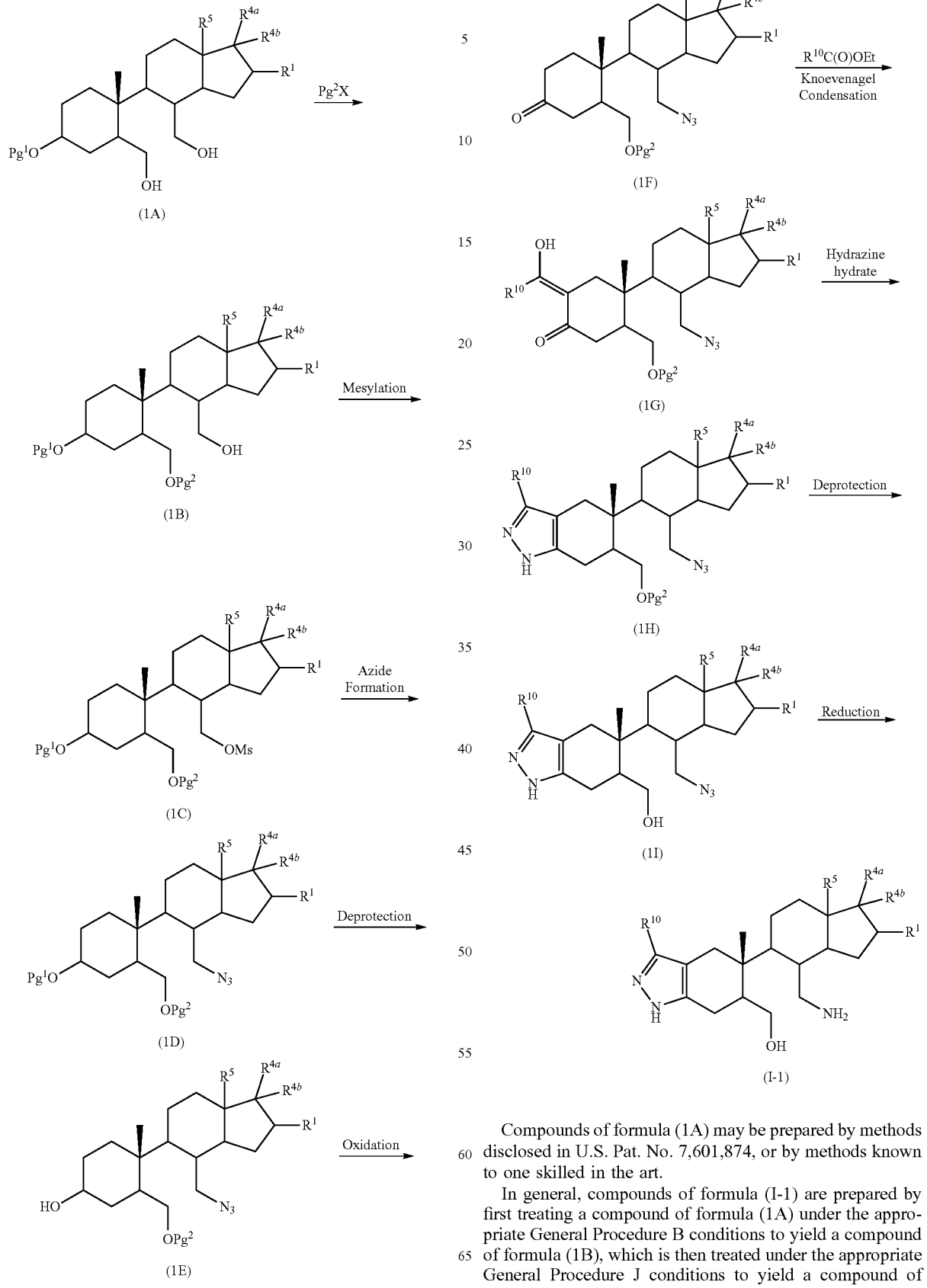

Compounds of formula (1A) may be prepared by methods disclosed in U.S. Pat. No. 7,601,874, or by methods known to one skilled in the art.

In general, compounds of formula (I-1) are prepared by first treating a compound of formula (1A) under the appropriate General Procedure B conditions to yield a compound of formula (1B), which is then treated under the appropriate General Procedure J conditions to yield a compound of formula (1C), which is then treated under the appropriate General Procedure K conditions to yield a compound of formula (1D), which is then treated under the appropriate General Procedure L conditions to yield a compound of formula (1E), which is then treated under the appropriate General Procedure M conditions to yield a compound of formula (1F), which is then treated under the appropriate General Procedure O conditions to yield a compound of formula (1G), which is then treated under the appropriate General Procedure P conditions to yield a compound of formula (1H), which is then treated under the appropriate General Procedure Q conditions to yield a compound of formula (1I), which is then treated under the appropriate General Procedure R conditions or the appropriate General Procedure S conditions to yield a compound of formula (I-1).

Alternatively, the unsubstituted hydrazine utilized in General Procedure P may be replaced with an appropriately substituted hydrazine to prepare compounds of formula (I-1) wherein the fused pyrazolyl ring is substituted accordingly.

An embodiment of General Reaction Scheme 1 is described in more detail below in Synthetic Example 1. Additional embodiments are described in more detail below in Synthetic Examples 8 and 13.

General Reaction Scheme 2

Compounds of formula (I-2) are compounds of formula (I), as described above in the Summary of the Invention, and may be prepared according the following General Reaction Scheme 2 wherein Ⓐ is as described in the Summary of the Invention, R is hydrogen, $R^2$ and $R^3$ are each as described above in the Summary of the Invention and $R^5$ is methyl:

GENERAL REACTION SCHEME 2

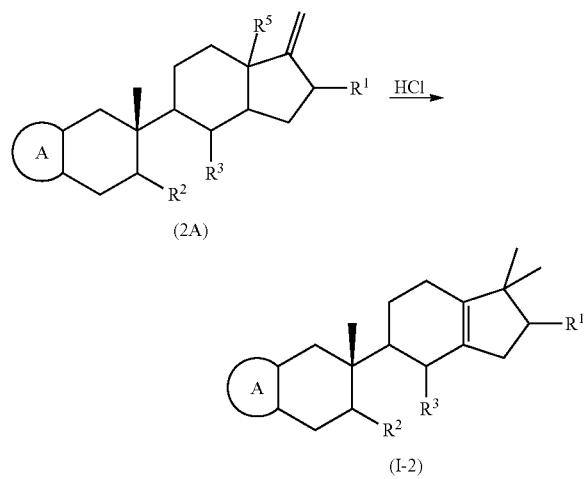

Compounds of formula (2A) are compounds of formula (I) as prepared herein or by methods known to one skilled in the art.

In general, compounds of formula (I-2) are prepared by treating a compound of formula (2A) under the appropriate General Procedure W conditions to yield a compound of formula (I-2).

Embodiments of Reaction Scheme 2 are disclosed in detail below in Synthetic Examples 2 and 4.

General Reaction Scheme 3

Compounds of formula (I-3) are compounds of formula (I), as described above in the Summary of the Invention, and may be prepared according the following General Reaction Scheme 3 wherein Ⓐ, $R^1$, $R^2$, $R^{4a}$, $R^{4b}$ and $R^5$ are each as described above in the Summary of the Invention:

GENERAL REACTION SCHEME 3

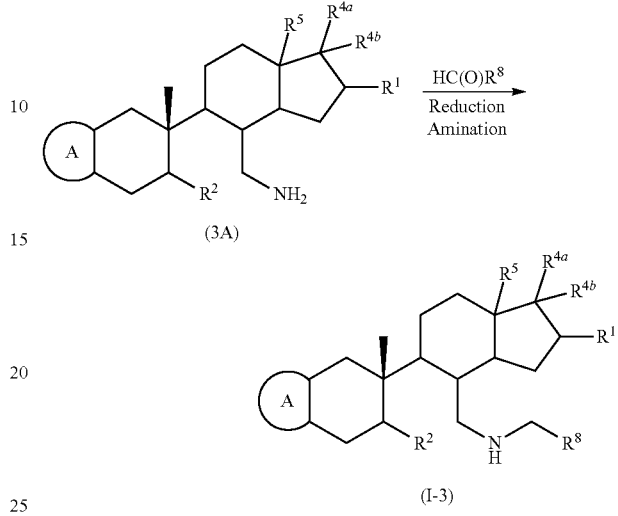

Compounds of formula (3A) are compounds of formula (I) as prepared herein or can be prepared by methods known to one skilled in the art.

In general, compounds of formula (I-3) are prepared by first treating a compound of formula (3A) under the appropriate General Procedure U conditions to yield a compound of formula (I-3).

Embodiments of Reaction Scheme 3 are described in detail below in Synthetic Examples 3 and 7.

General Reaction Scheme 4

Compounds of formula (I-4) are compounds of formula (I), as described above in the Summary of the Invention, and may be prepared according the following General Reaction Scheme 4 wherein Ⓐ, $R^1$, $R^2$, $R^3$ and $R^5$ are each as described above in the Summary of the Invention:

GENERAL REACTION SCHEME 4

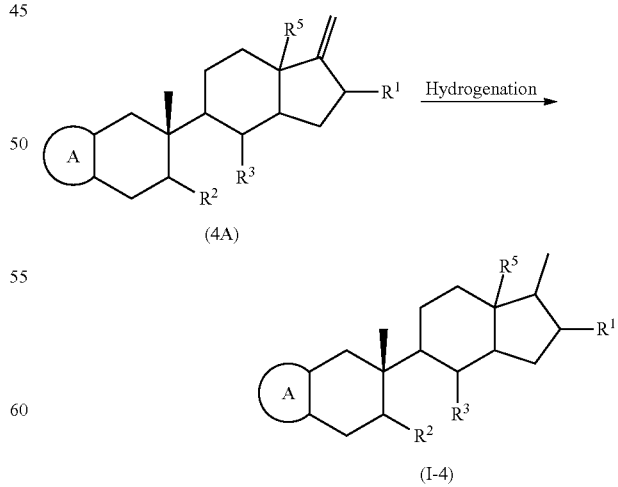

Compounds of formula (4A) may be prepared by methods disclosed in U.S. Pat. No. 9,765,085, or by the methods disclosed herein.

In general, compounds of formula (I-4) are prepared by treating a compound of formula (4A) under the appropriate General Procedure T conditions to yield a compound of formula (I-4).

An embodiment of General Reaction Scheme 4 is described in more detail below in Synthetic Example 5.

General Reaction Scheme 5

Compounds of formula (I-5) are compounds of formula (I), as described above in the Summary of the Invention, and may be prepared according the following General Reaction Scheme 5 wherein $R^1$, $R^{4a}$, $R^{4b}$ and $R^5$ are each as described above in the Summary of the Invention, $Pg^1$ and $Pg^2$ are each an oxygen protecting group, such as tert-butyldimethylsilyl or tert-butyldiphenylsilyl, and each X is halo, preferably chloro:

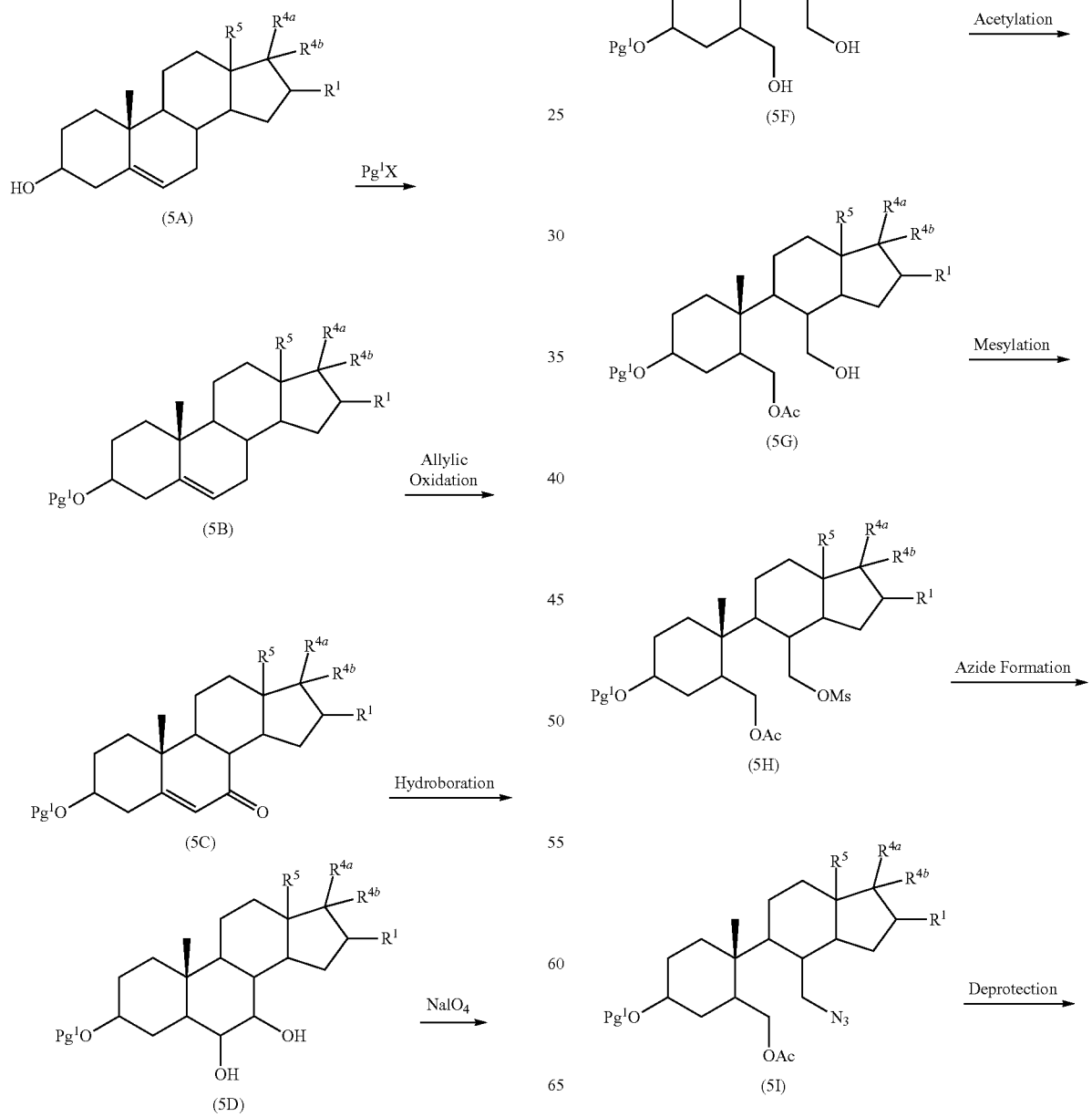

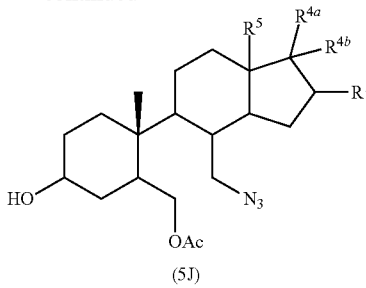

(5J)

Compound of formula (5J) —Oxidation→

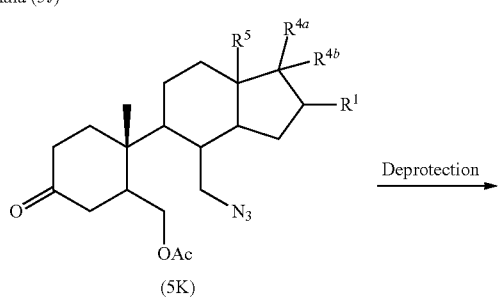

(5K)

Deprotection →

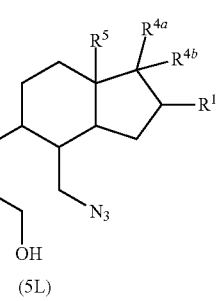

(5L)

Pg²X →

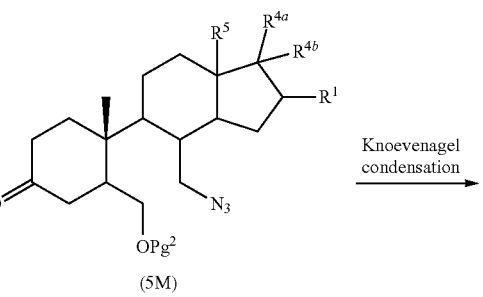

(5M)

Knoevenagel condensation →

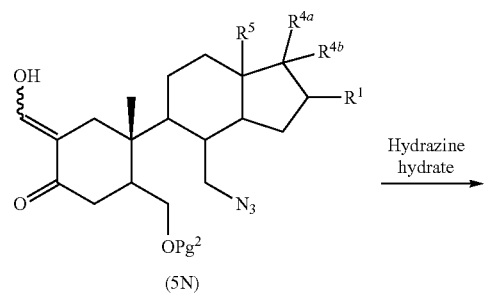

(5N)

Hydrazine hydrate →

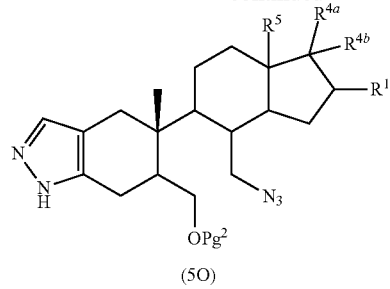

(5O)

Deprotection →

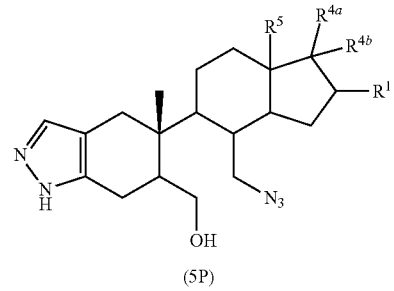

(5P)

Reduction →

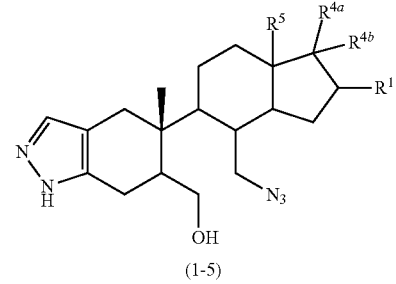

(1-5)

Compounds of formula (5A), such as cholesterol, are commercially available or can be prepared according to methods known to one skilled in the art.

In general, compounds of formula (I-5) are prepared by first treating a compound of formula (5A) with $Pg^1X$ under the appropriate General Procedure B conditions to yield a compound of formula (5B), which is then treated under appropriate General Procedure C conditions to yield a compound of formula (5C), which is then treated under appropriate General Procedure D conditions to yield a compound of formula (5D), which is then treated under appropriate General Procedure F conditions to yield a compound of formula (5E), which is then treated under appropriate General Procedure G conditions to yield a compound of formula (5F), which is then treated under appropriate General Procedure A conditions to yield a compound of formula (5G), which is then treated under appropriate General Procedure J conditions to yield a compound of formula (5H), which is then treated under appropriate General Procedure K conditions to yield a compound of formula (5I), which is then treated under appropriate General Procedure Q conditions to yield a compound of formula (5J), which is then treated under appropriate General Procedure M conditions to yield a compound of formula (5K), which is then treated under appropriate General Procedure L conditions to yield a compound of formula (5L), which is then treated under appropriate General Procedure B conditions to yield a compound of formula (5M), which is then treated under appropriate General Procedure O conditions to yield a compound of formula (5N), which is then treated under appropriate General Procedure P conditions to yield a compound of formula (5O), which is then treated under appropriate General Procedure Q conditions to yield a compound of formula (5P), which is then treated under appropriate General Procedure R conditions or appropriate General Procedure S conditions to yield a compound of formula (I-5).

An embodiment of General Reaction Scheme 5 is described in more detail below in Synthetic Example 6.

General Reaction Scheme 6

Compounds of formula (I-6) and formula (I-6a) are compounds of formula (I), as described above in the Summary of the Invention, and may be prepared according the following General Reaction Scheme 6 wherein $R^1$ and $R^5$ are each as described above in the Summary of the Invention, $Pg^1$ is an oxygen protecting group, such as tert-butyldimethylsilyl or tert-butyldiphenylsilyl, and X is halo, preferably chloro:

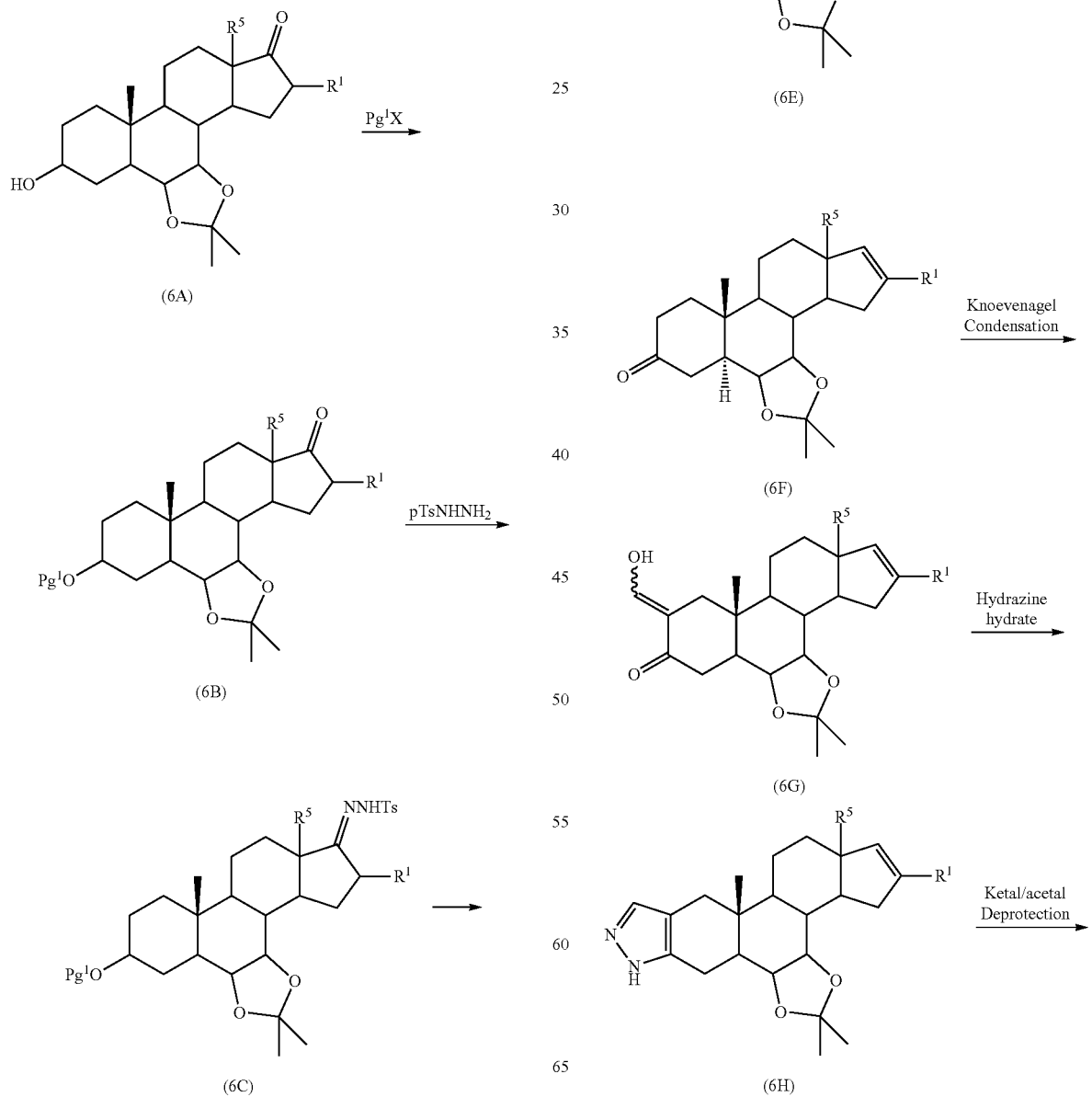

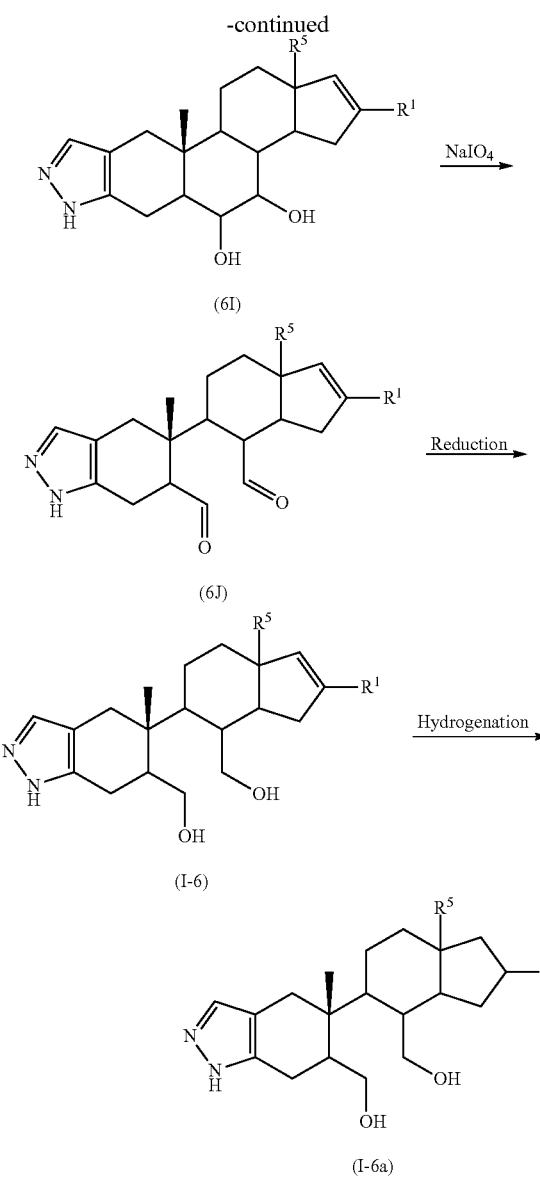

(6I)

(6J)

(I-6)

(I-6a)

Compounds of formula (6A) may be prepared according to the methods disclosed in U.S. Pat. No. 6,046,185, or by methods known to one skilled in the art.

In general, compounds of formula (I-6) are prepared by first treating a compound of formula (6A) under the appropriate General Procedure B conditions to yield a compound of formula (6B), which is then treated with p-toluenesulfonyl hydrazide under the appropriate conditions to yield a compound of formula (6C), which is then treated under the appropriate basic conditions (e.g., organolithium reagent such as n-butyllithium) conditions to yield a compound of formula (6D), which is then treated under the appropriate General Procedure Q conditions to yield a compound of formula (6E), which is then treated under the appropriate General Procedure N conditions to yield a compound of formula (6F), which is then treated under the appropriate General Procedure O conditions to yield a compound of formula (6G), which is then treated under the appropriate General Procedure P conditions to yield a compound of formula (6H), which is then treated under the appropriate General Procedure E conditions to yield a compound of formula (6I), which is then treated under the appropriate General Procedure F conditions to yield a compound of formula (6J), which is then treated under the appropriate General Procedure G conditions to yield a compound of formula (I-6), which is then treated under appropriate General Procedure T conditions to yield a compound of formula (I-7).

Embodiments of General Reaction Scheme 6 are described in more detail below in Synthetic Examples 9 and 10.

General Reaction Scheme 7

Compounds of formula (I-7) are compounds of formula (I), as described above in the Summary of the Invention, and may be prepared according the following General Reaction Scheme 7 wherein $R^1$ and $R^5$ are each as described above in the Summary of the Invention:

GENERAL REACTION SCHEME 7

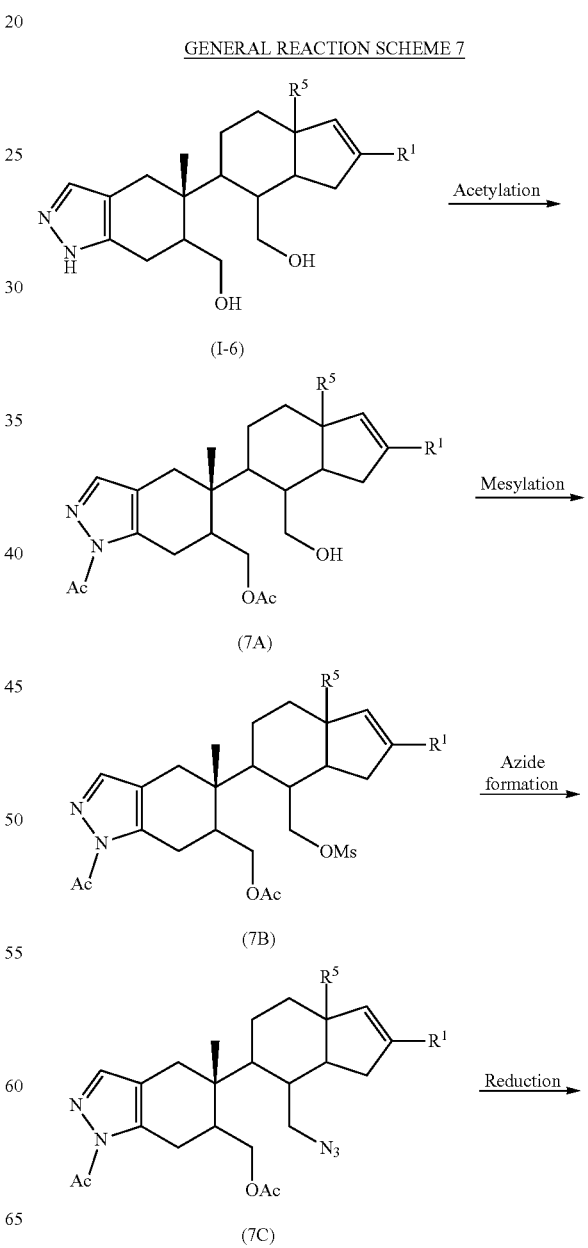

(I-6)

(7A)

(7B)

(7C)

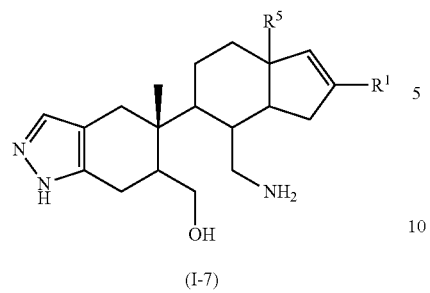

(I-7)

Compounds of formula (I-6) may be prepared as described herein.

In general, compounds of formula (I-7) are prepared by first treating a compound of formula (I-6) under the appropriate General Procedure A conditions to yield a compound of formula (7A), which is then treated under the appropriate General Procedure J conditions to yield a compound of formula (7B), which is then treated under the appropriate General Procedure K conditions to yield a compound of formula (7C), which is then treated under the appropriate General Procedure S conditions to yield a compound of formula (I-7).

An embodiment of General Reaction Scheme 7 is described in more detail below in Synthetic Example 11.

General Reaction Scheme 8

Compounds of formula (I-8) are compounds of formula (I), as described above in the Summary of the Invention, and may be prepared according the following General Reaction Scheme 8 wherein $R^1$ and $R^5$ are each as described above in the Summary of the Invention, $Pg^1$ is an oxygen protecting group, such as ter-butyldimethylsilyl or tert-butyldiphenylsilyl, X is halo, preferably chloro and $Pg^3$ is a nitrogen protecting group, such as tert-butoxycarbonyl:

GENERAL REACTION SCHEME 8

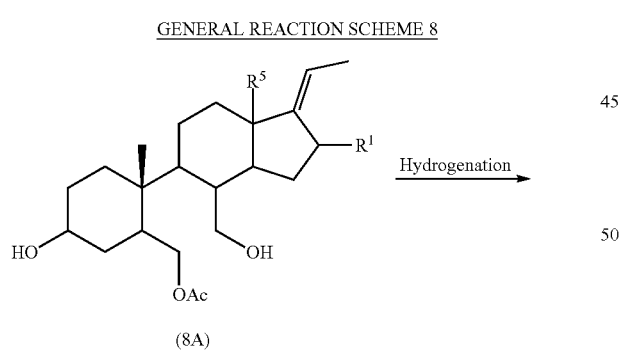

(8A)

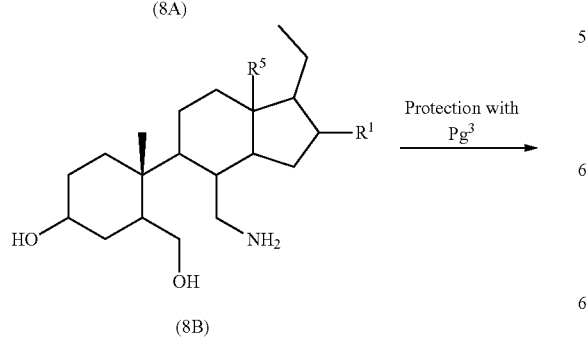

(8B)

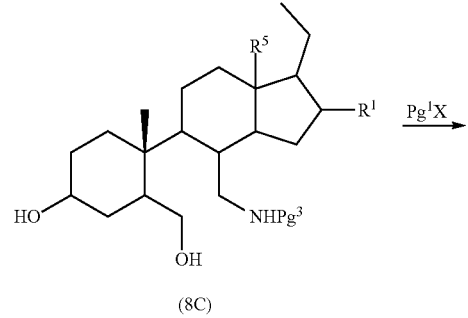

(8C)

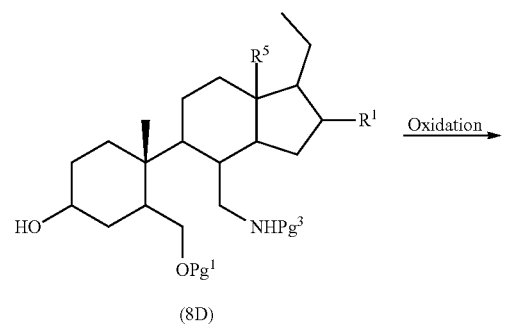

(8D)

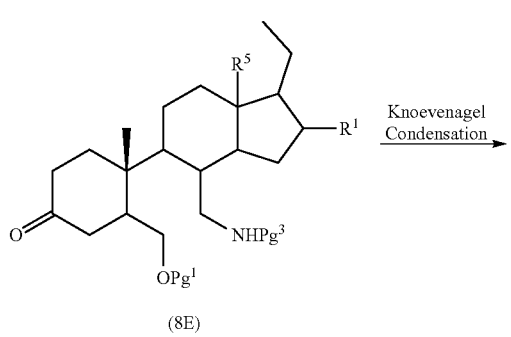

(8E)

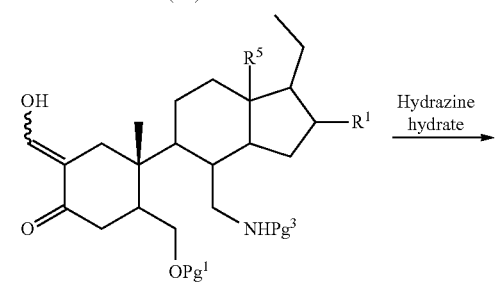

(8F)

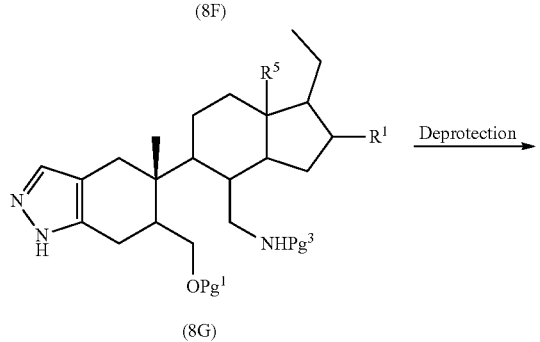

(8G)

61

-continued

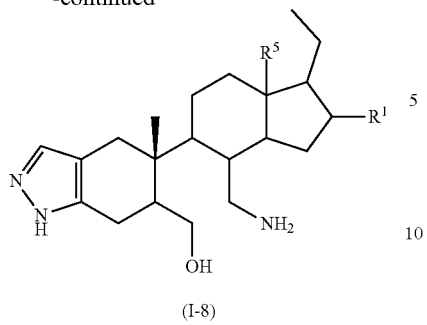

(I-8)

Compounds of formula (6A) may be prepared according to the methods disclosed in U.S. Pat. No. 7,601,874, or by methods known to one skilled in the art.

In general, compounds of formula (I-8) are prepared by first treating a compound of formula (8A) under the appropriate General Procedure T conditions to yield a compound of formula (8B), which is then treated under standard amine protecting conditions to yield a compound of formula (C), which is then treated under the appropriate General Procedure B conditions to yield a compound of formula (8D), which is then treated under the appropriate General Procedure N conditions to yield a compound of formula (8E), which is then treated under the appropriate General Procedure O conditions to yield a compound of formula (8F), which is then treated under the appropriate General Procedure P conditions to yield a compound of formula (8G), which is then treated under standard acidic deprotecting condition to yield a compound of formula (I-8).

An embodiment of General Reaction Scheme 8 is described in more detail below in Synthetic Example 12.

General Reaction Scheme 9

Compounds of formula (I-9) are compounds of formula (I), as described above in the Summary of the Invention, and may be prepared according the following General Reaction Scheme 9 wherein $R^1$ and $R^5$ are each as described above in the Summary of the Invention, $Pg^1$ is an oxygen protecting group, such as ter-butyldimethylsilyl or tert-butyldiphenylsilyl, X is halo, preferably chloro and $Pg^3$ is a nitrogen protecting group, such as trifluoroacetate:

GENERAL REACTION SCHEME 9

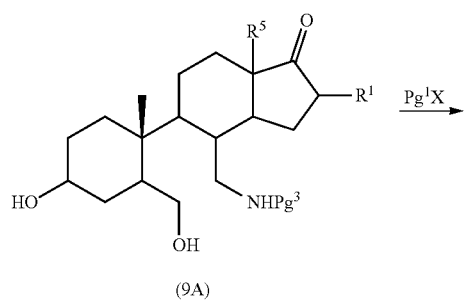

(9A)

62

-continued

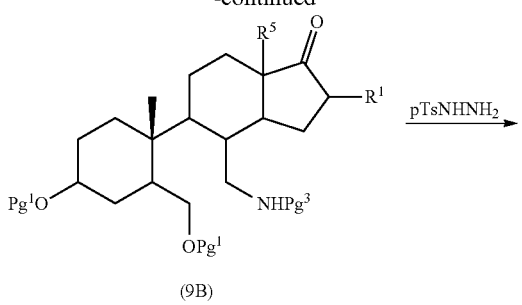

(9B)

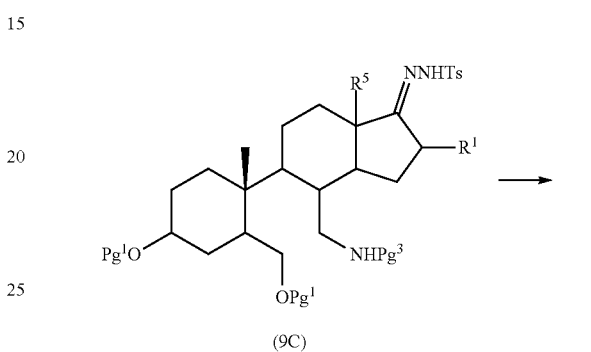

(9C)

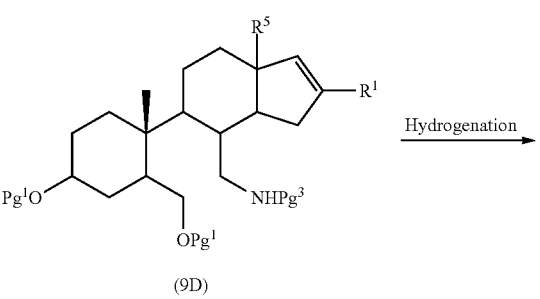

(9D)

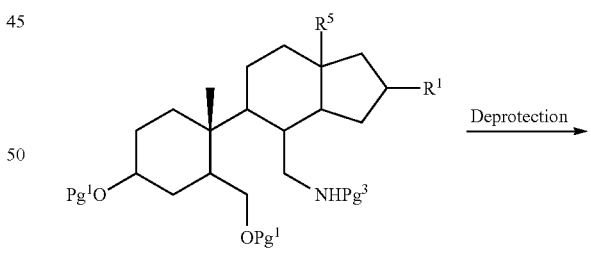

(9E)

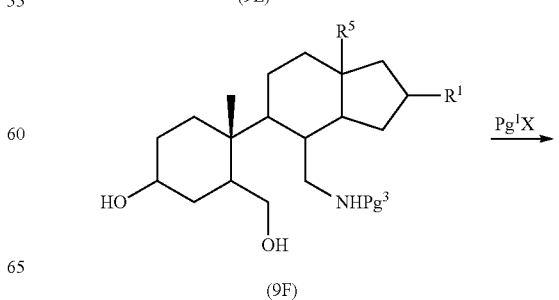

(9F)

63

-continued

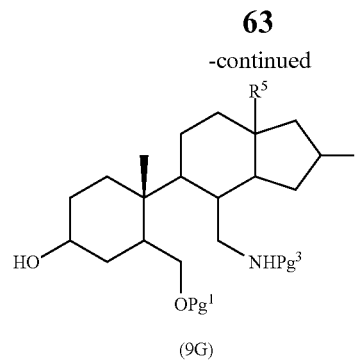

(9G)

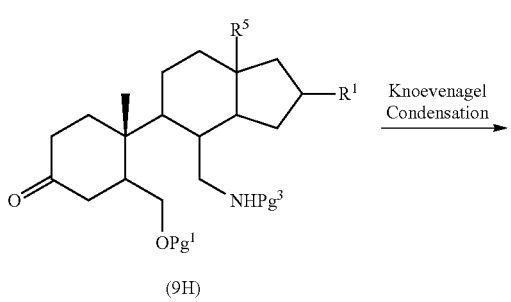

(9H)

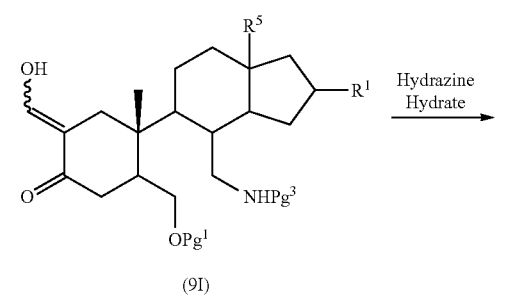

(9I)

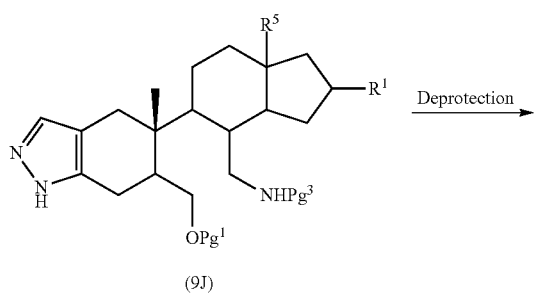

(9J)

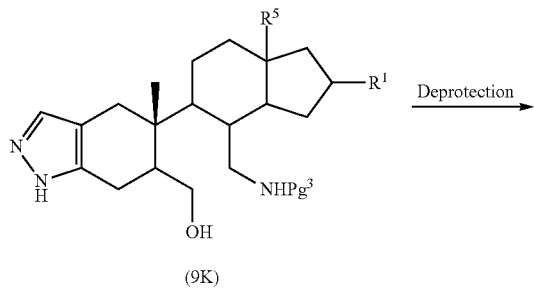

(9K)

64

-continued

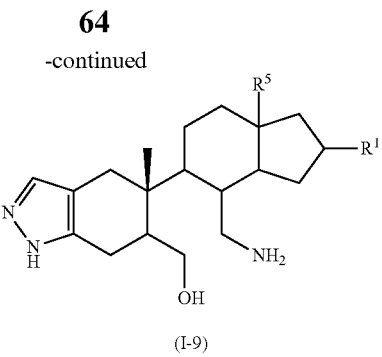

(I-9)

Compounds of formula (9A) may be prepared by methods disclosed herein or can be prepared according to methods known to one skilled in the art.

In general, compounds of formula (I-9) are prepared by first treating a compound of formula (9A) under the appropriate General Procedure B conditions to yield a compound of formula (9B), which is then treated with p-toluenesulfonyl hydrazide under the appropriate conditions to yield a compound of formula (9C), which is then treated under the appropriate basic conditions (e.g., organolithium reagent such as n-butyllithium) conditions to yield a compound of formula (9), which is then treated under appropriate General Procedure T conditions to yield a compound of formula (9E), which is then treated under appropriate General Procedure Q conditions to yield a compound of formula (9F), which is then treated under appropriate General Procedure B conditions to yield a compound of formula (9G), which is then treated under appropriate General Procedure M conditions to yield a compound of formula (9H), which is then treated under appropriate General Procedure O conditions to yield a compound of formula (9I), which is then treated under appropriate General Procedure P conditions to yield a compound of formula (9E), which is then treated under appropriate General Procedure Q conditions to yield a compound of formula (9K), which is then treated under appropriate General Procedure L conditions to yield a compound of formula (I-9).

An embodiment of General Reaction Scheme 9 is described in more detail below in Synthetic Example 14.

General Reaction Scheme 10

Compounds of formula (I-10) are compounds of formula (I), as described above in the Summary of the Invention, and may be prepared according the following General Reaction Scheme 10 wherein Ⓐ, $R^1$ and $R^5$ are each as described above in the Summary of the Invention:

GENERAL REACTION SCHEME 10

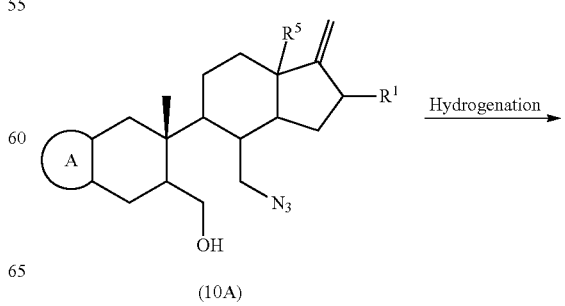

(10A)

-continued

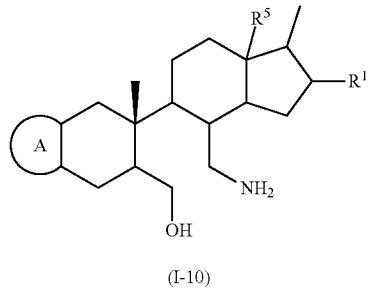

(I-10)

Compound of formula (10A) may be prepared by methods disclosed herein or can be prepared according to methods known to one skilled in the art.

In general, compounds of formula (I-10) are prepared by treating a compound of formula (10A) under the appropriate General Procedure T conditions to yield a compound of formula (I-10).

An embodiment of General Reaction Scheme 10 is described in more detail below in Synthetic Example 15.

General Reaction Scheme 11

Compounds of formula (I-11) are compounds of formula (I), as described above in the Summary of the Invention, and may be prepared according the following General Reaction Scheme 11 wherein $R^1$, $R^{4a}$, $R^{4b}$ and $R^5$ are as described above in the Summary of the Invention, $Pg^1$ is an oxygen protecting group, such as acetyl, $Pg^2$ is an oxygen protecting group such as tert-butyldimethylsilyl or tert-butyldiphenylsilyl, and X is halo, preferably chloro:

GENERAL REACTION SCHEME 11

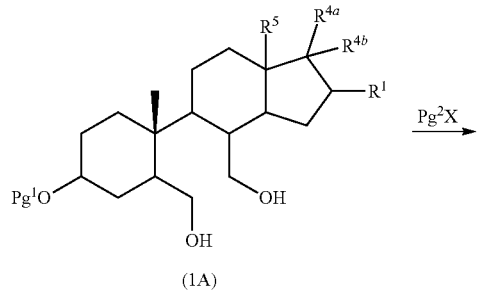

(1A)

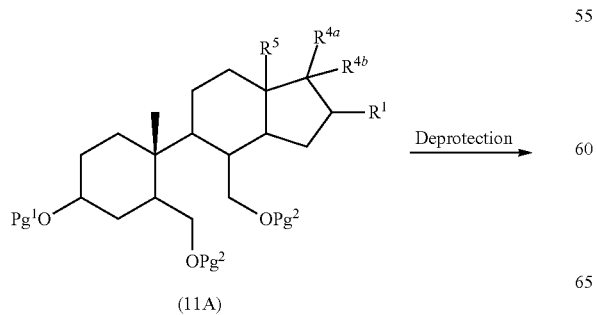

(11A)

-continued

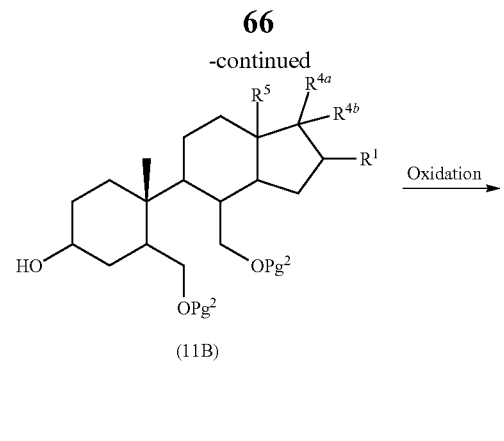

(11B)

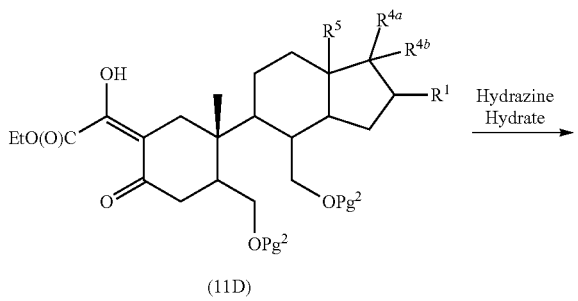

(11C)

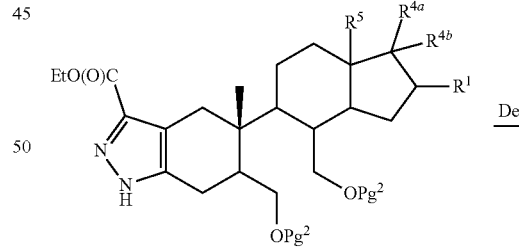

(11D)

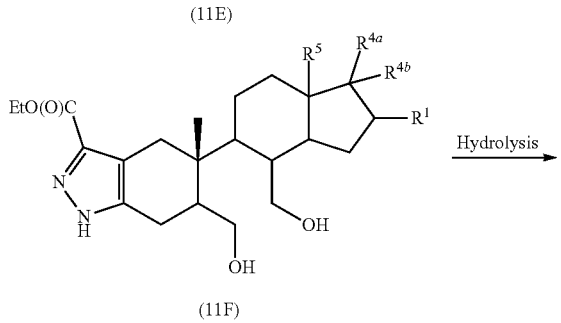

(11E)

(11F)

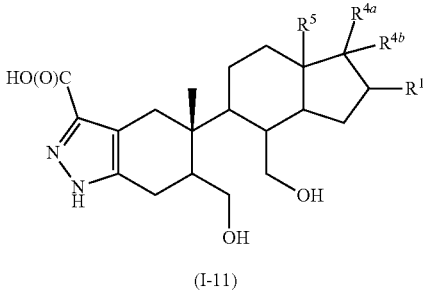

(I-11)

Compounds of formula (1A) may be prepared according to the methods disclosed herein or by methods known to one skilled in the art.

In general, compounds of formula (I-11) are prepared by first treating a compound of formula (1A) under the appropriate General Procedure B conditions to yield a compound of formula (11A), which is then treated under the appropriate General Procedure L conditions to yield a compound of formula (11B), which is then treated under the appropriate General Procedure N conditions to yield a compound of formula (11C), which is then treated under the appropriate condensation conditions with diethyl oxalate to yield a compound of formula (11D), which is then treated under the appropriate General Procedure P conditions to yield a compound of formula (11E), which is then treated under the appropriate General Procedure Q conditions to yield a compound of formula (11F), which is then treated under the appropriate hydrolysis conditions to yield a compound of formula (I-11).

An embodiment of General Reaction Scheme 11 is described in more detail below in Synthetic Example 16.

General Reaction Scheme 12 Compounds of formula (I-12) are compounds of formula (I), as described above in the Summary of the Invention, and may be prepared according the following General Reaction Scheme 12 wherein $R^1$, $R^{4a}$, $R^{4b}$, $R^5$ and $R^8$ are each as described above in the Summary of the Invention:

GENERAL REACTION SCHEME 12

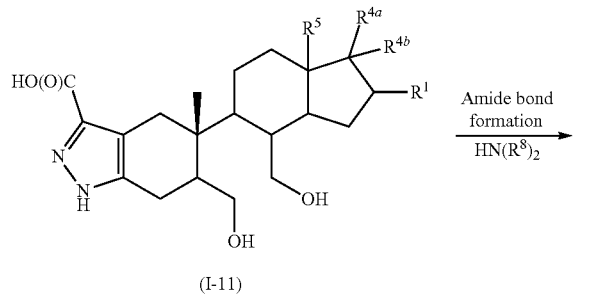

Compounds of formula (I-11) may be prepared by methods disclosed herein or can be prepared according to methods known to one skilled in the art.

In general, compounds of formula (I-12) are prepared by first treating a compound of formula (I-11) under standard amide bond formation conditions using $HN(R^8)_2$ as the amine to form a compound of formula (I-12).

An embodiment of General Reaction Scheme 12 is described in more detail below in Synthetic Example 17.

General Reaction Scheme 13

Compounds of formula (I-13) are compounds of formula (I), as described above in the Summary of the Invention, and may be prepared according the following General Reaction Scheme 13 wherein Ⓐ, $R^1$, $R^{4a}$, $R^{4b}$, $R^5$ and $R^8$ are each as described above in the Summary of the Invention:

GENERAL REACTION SCHEME 13

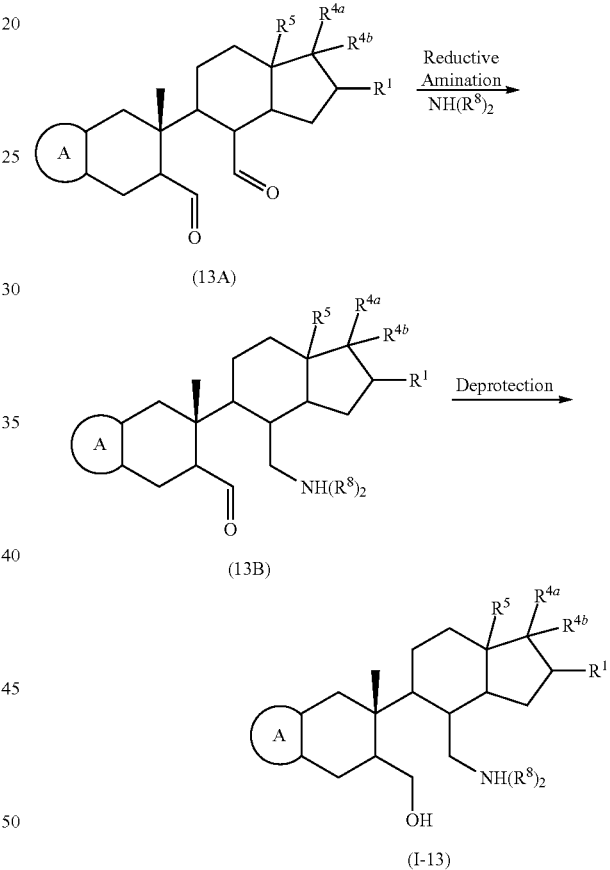

Compounds of formula (13A) may be prepared by methods disclosed in U.S. Pat. No. 9,765,085 or by methods known to one skilled in the art.

In general, compounds of formula (I-13) are prepared by first treating a compound of formula (13A) under the appropriate General Procedure V conditions to yield a compound of formula (13B), which is then treated under the appropriate General Procedure G conditions to yield a compound of formula (I-13).

An embodiment of General Reaction Scheme 13 is described in more detail below in Synthetic Example 18.

General Reaction Scheme 14

Compounds of formula (I-14) are compounds of formula (I), as described above in the Summary of the Invention, and may be prepared according the following General Reaction Scheme 14 wherein $R^1$, $R^{4a}$, $R^{4b}$, $R^5$ and $R^8$ are as described above in the Summary of the Invention, $Pg^1$ is an oxygen protecting group such as tert-butyldimethylsilyl or tert-butyldiphenylsilyl, and X is halo, preferably chloro:

Compounds of formula (14A) may be prepared by methods disclosed in U.S. Pat. No. 7,601,874, or by methods disclosed herein or known to one skilled in the art.

In general, compounds of formula (I-14) are prepared by first treating a compound of formula (14A) under the appropriate General Procedure B conditions to yield a compound of formula (14B), which is then treated under the appropriate General Procedure J conditions to yield a compound of formula (14C), which is then treated with $HN(R^8)_2$ under the appropriate substitution conditions to yield a compound of formula (14D), which is then treated under the appropriate General Procedure Q conditions to yield a compound of formula (I-14), An embodiment of General Reaction Scheme 14 is described in more detail below in Synthetic Example 19.

General Reaction Scheme 15

Compounds of formula (I-15a) and formula (I-15b) are compounds of formula (I), as described above in the Summary of the Invention, and may be prepared according the following General Reaction Scheme 15 wherein $R^1$, $R^{4a}$, $R^{4b}$ and $R^5$ are as described above in the Summary of the Invention and $Pg^1$ is an oxygen protecting group such as tert-butyldimethylsilyl or tert-butyldiphenylsilyl:

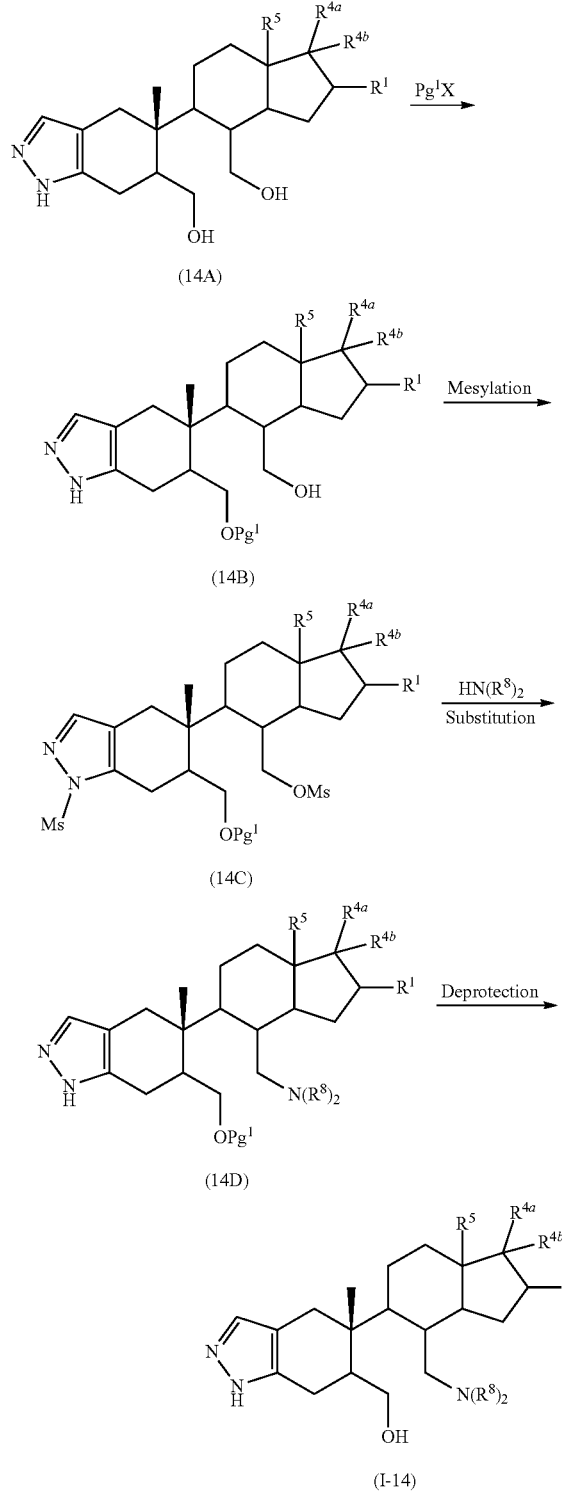

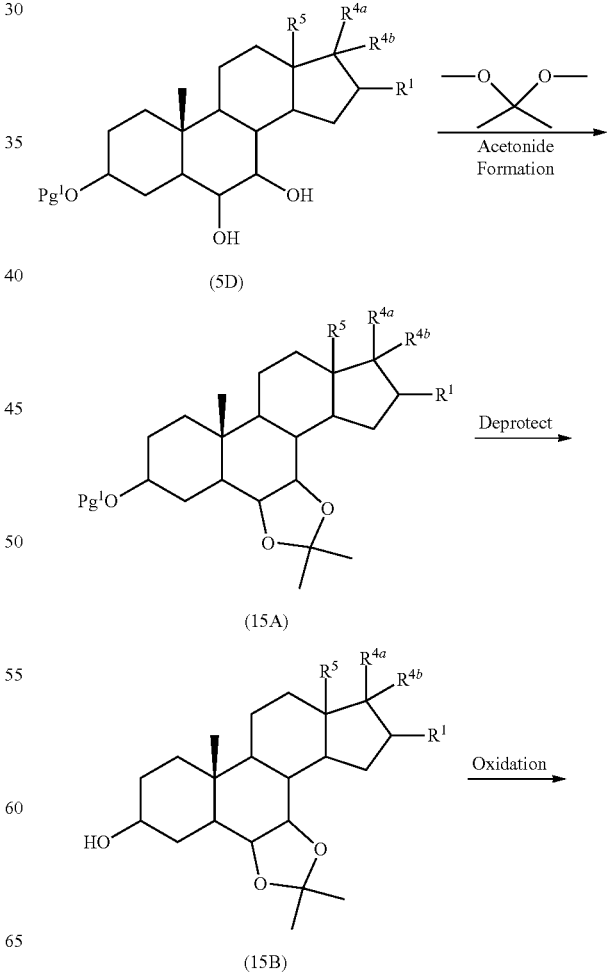

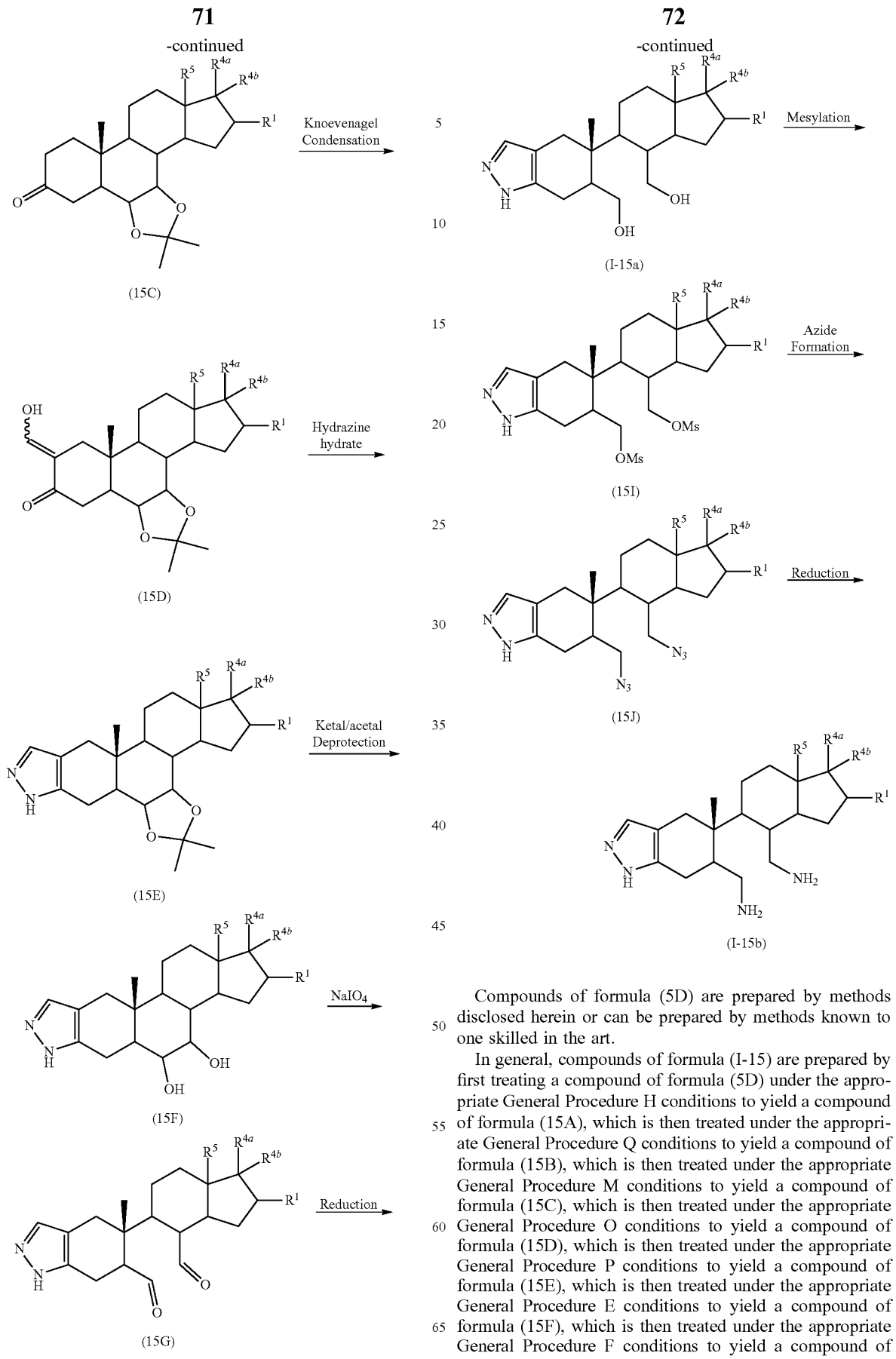

Compounds of formula (5D) are prepared by methods disclosed herein or can be prepared by methods known to one skilled in the art.

In general, compounds of formula (I-15) are prepared by first treating a compound of formula (5D) under the appropriate General Procedure H conditions to yield a compound of formula (15A), which is then treated under the appropriate General Procedure Q conditions to yield a compound of formula (15B), which is then treated under the appropriate General Procedure M conditions to yield a compound of formula (15C), which is then treated under the appropriate General Procedure O conditions to yield a compound of formula (15D), which is then treated under the appropriate General Procedure P conditions to yield a compound of formula (15E), which is then treated under the appropriate General Procedure E conditions to yield a compound of formula (15F), which is then treated under the appropriate General Procedure F conditions to yield a compound of formula (15G), which is then treated under the appropriate General Procedure G conditions to yield a compound of formula (I-15a), which is then treated under the appropriate General Procedure J conditions to yield a compound of formula (15I), which is then treated under the appropriate General Procedure K conditions to yield a compound of formula (15J), which is then treated under the appropriate General Procedure S conditions to yield a compound of formula (I-15b).

Embodiments of General Reaction Scheme 15 are described in more detail below in Synthetic Examples 20 and 27.

General Reaction Scheme 16

Compounds of formula (I-16) are compounds of formula (I), as described above in the Summary of the Invention, and may be prepared according the following General Reaction Scheme 16 wherein $R^1$, $R^{4a}$, $R^{4b}$ and $R^5$ are as described above in the Summary of the Invention:

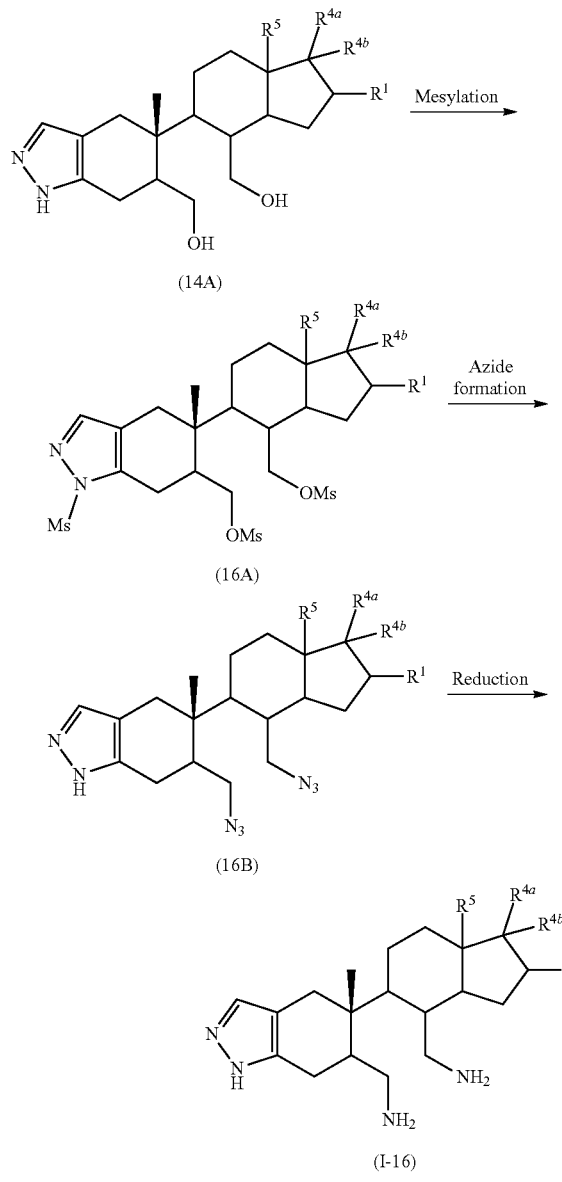

Compounds of formula (14A) may be prepared by methods disclosed in U.S. Pat. No. 7,601,874, or by methods disclosed herein or known to one skilled in the art.

In general, compounds of formula (I-14) are prepared by first treating a compound of formula (14A) under the appropriate General Procedure J conditions to yield a compound of formula (16A), which is then treated under the appropriate General Procedure K conditions to yield a compound of formula (16B), which is then treated under the appropriate General Procedure S conditions to yield a compound of formula (I-16).

An embodiment of General Reaction Scheme 16 is described in more detail below in Synthetic Example 21.

General Reaction Scheme 17

Compounds of formula (I-17) are compounds of formula (I), as described above in the Summary of the Invention, and may be prepared according the following General Reaction Scheme 17 wherein $R^1$, $R^{4a}$, $R^{4b}$ and $R^5$ are as described above in the Summary of the Invention, $Pg^1$ is an oxygen protecting group such as tert-butyldimethylsilyl or tert-butyldiphenylsilyl, and X is halo, preferably chloro:

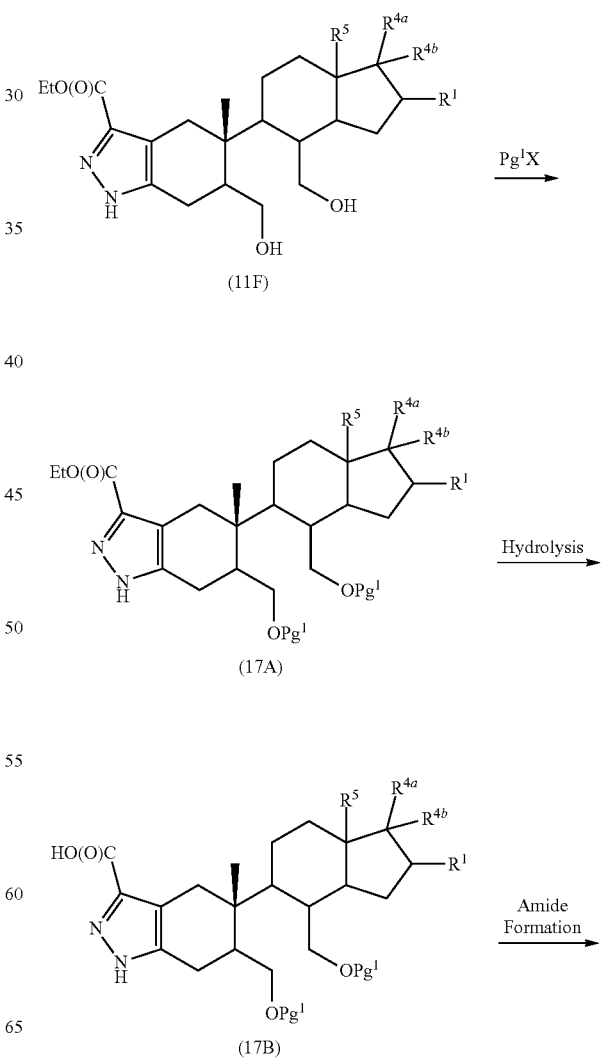

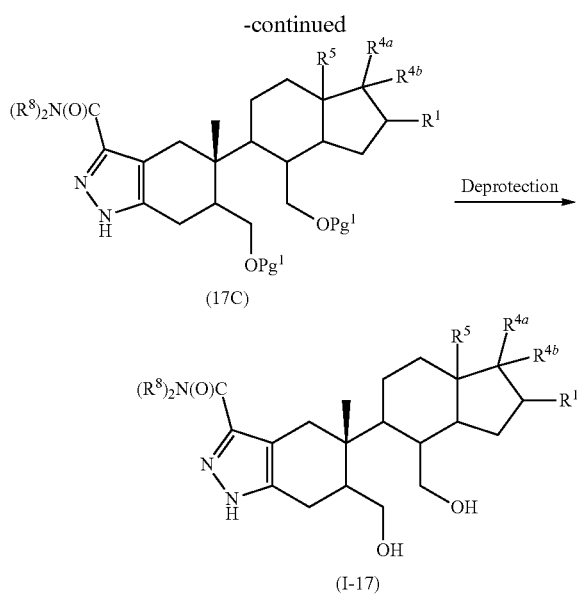

Compounds of formula (11F) are prepared by methods disclosed herein.

In general, compounds of formula (I-17) are prepared by first treating a compound of formula (11F) under the appropriate General Procedures B conditions to yield a compound of formula (17A), which is then treated under the appropriate hydrolysis conditions to yield a compound of formula (17B), which is then treated under the appropriate amide formation conditions to yield a compound of formula (17C), which is then treated under the appropriate General Procedure Q conditions to yield a compound of formula (I-17).

An embodiment of General Reaction Scheme 17 is described in more detail below in Synthetic Example 22.

General Reaction Scheme 18

Compounds of formula (I-18) are compounds of formula (I), as described above in the Summary of the Invention, and may be prepared according the following General Reaction Scheme 18 wherein $R^1$ is hydrogen, $R^{4a}$, $R^{4b}$ and $R^5$ are as described above in the Summary of the Invention:

GENERAL REACTION SCHEME 18

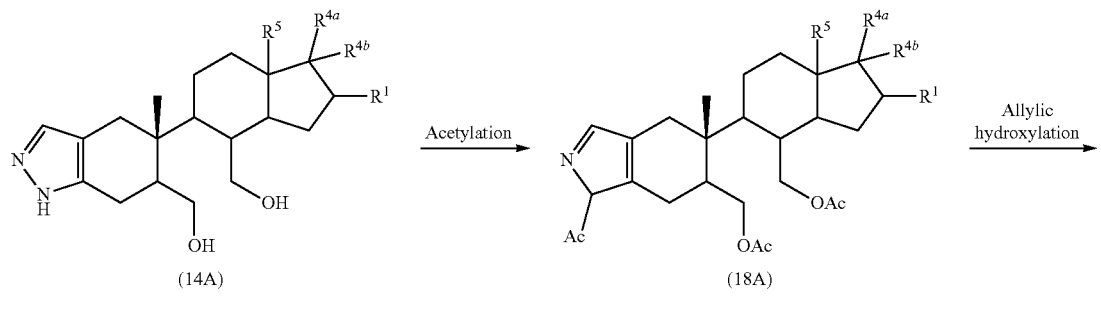

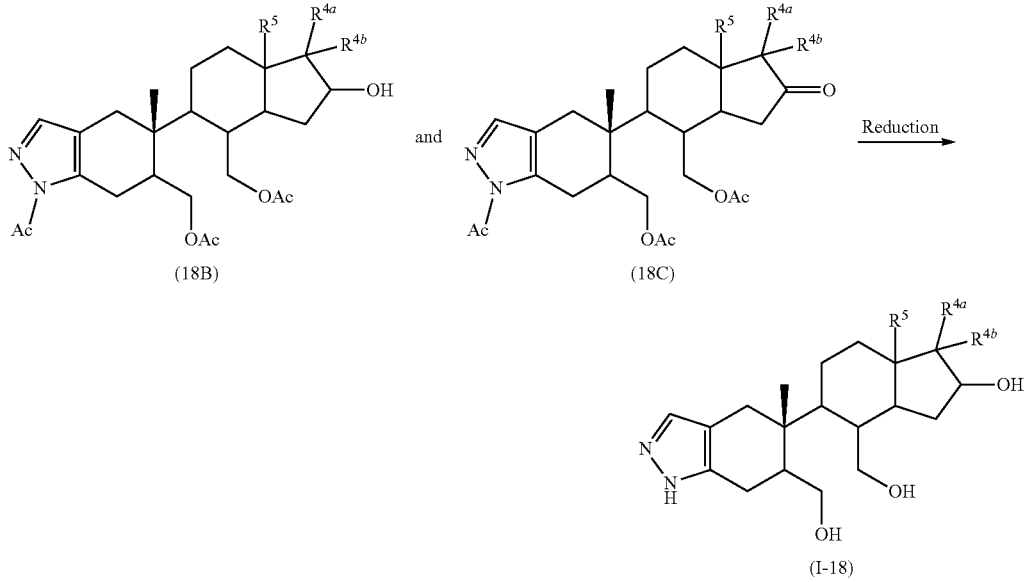

Compounds of formula (14A) are prepared by methods disclosed herein.

In general, compounds of formula (I-18) are prepared by first treating a compound of formula (14A) under the appropriate General Procedure A conditions to yield a compound of formula (18A), which is then treated under the appropriate allylic hydroxylation conditions to yield a mixture of a compound of formula (18B) and a compound of formula (18C). The mixture is then treated under the appropriate General Procedure S conditions to yield a compound of formula (I-18).

Alternatively, the compound of formula (18B) and (18C) were isolated and the compound of formula (18B) is treated under the appropriate General Procedure N conditions to yield a compound formula (18C), which is then treated under General Procedure S conditions to yield a compound of formula (I-18)

Embodiments of General Reaction Scheme 18 is described in more detail below in Synthetic Examples 23 and 29.

General Reaction Scheme 19

Compounds of formula (I-19) are compounds of formula (I), as described above in the Summary of the Invention, and may be prepared according the following General Reaction Scheme 19 wherein $R^1$ is hydrogen, $R^5$ is alkyl, $R^{4a}$ is alkyl, alkenyl, optionally substituted aryl or optionally substituted heteroaryl, $R^{4b}$ is alkyl and $Pg^1$ is an oxygen protecting group, such as tert-butyldimethylsilyl or tert-butyldiphenylsilyl:

GENERAL REACTION SCHEME 19

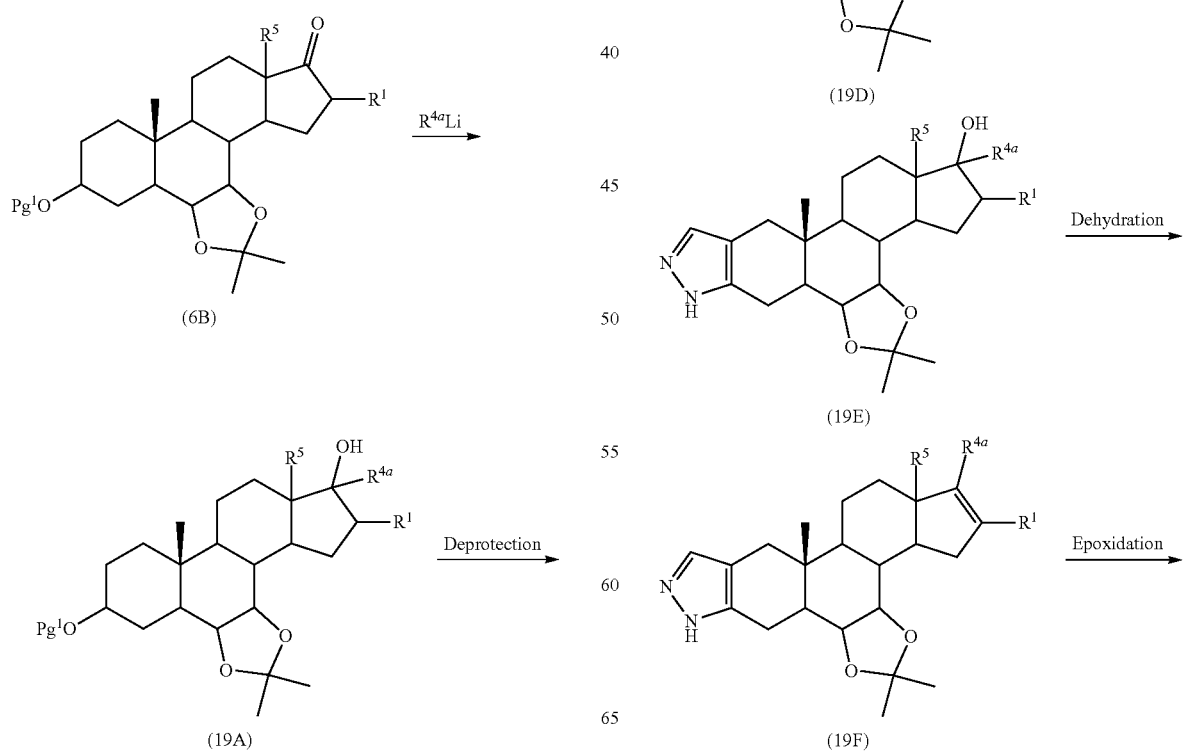
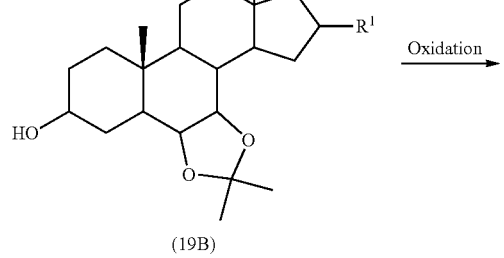
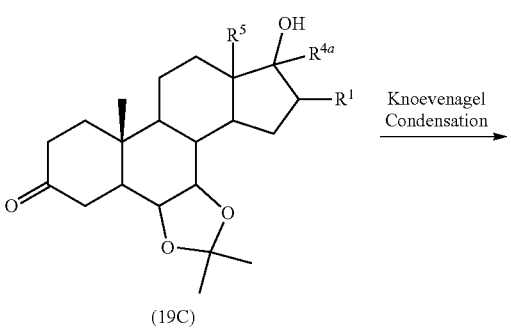
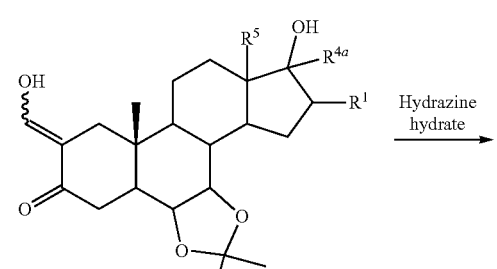
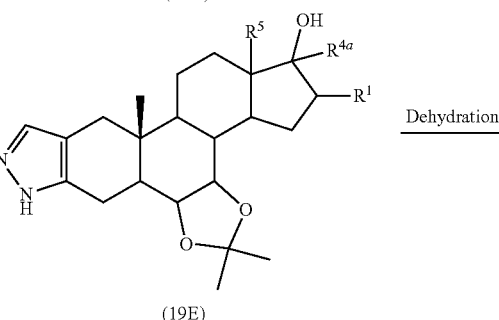
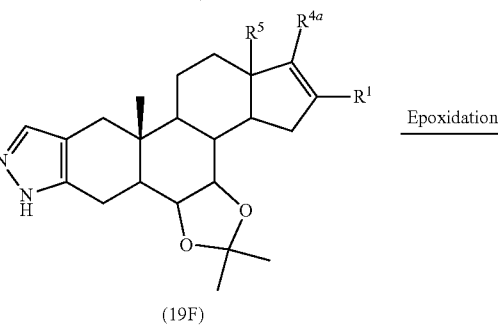

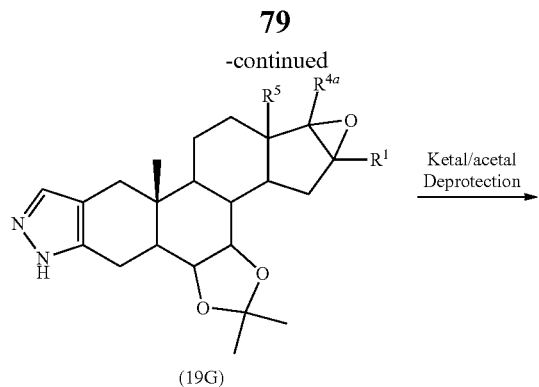

(19G)

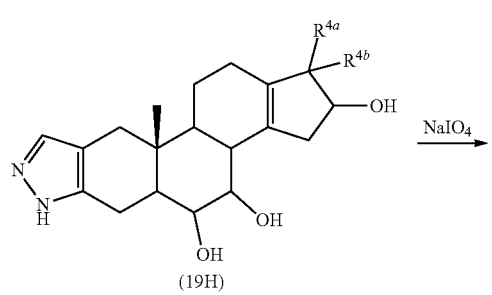

(19H)

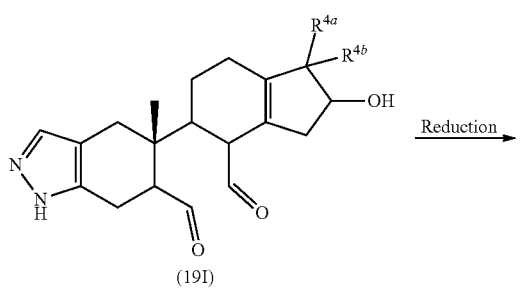

(19I)

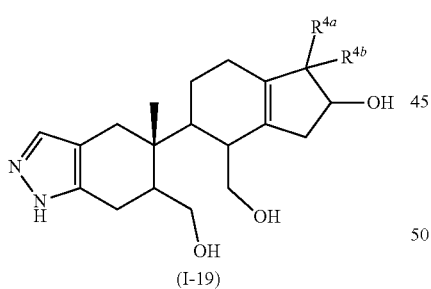

(I-19)

Compounds of formula (6B) are prepared by methods disclosed herein or by methods known to one skilled in the art.

In general, compounds of formula (I-19) are prepared by nucleophilic addition to a compound of formula (6) with $R^{4a}$Li under standard reduction conditions to yield a compound of formula (19A), which is then treated under appropriate General Procedure Q conditions to yield a compound of formula (19B), which is then treated under appropriate General Procedure N conditions to yield a compound of formula (19C), which is then treated under appropriate General Procedure O conditions to yield a compound of formula (19D), which is then treated under appropriate General Procedure P conditions to yield a compound of formula (19E), which is then treated under appropriate dehydration conditions to yield a compound of formula (19F), which is then treated under appropriate epoxidation conditions to yield a compound of formula (19G), which is then treated under appropriate General Procedure E conditions to yield a compound of formula (19H), which is then treated under appropriate General Procedure F conditions to yield a compound of formula (19I), which is then treated under appropriate General Procedure G conditions to yield a compound of formula (I-19).

An embodiment of General Reaction Scheme 19 is described in more detail below in Synthetic Example 24.

General Reaction Scheme 20

Compounds of formula (I-20) are compounds of formula (I), as described above in the Summary of the Invention, and may be prepared according the following General Reaction Scheme 20 wherein $R^1$ is as described in the Summary of the Invention, $R^5$ is alkyl, and $Pg^1$ is an oxygen protecting group, such as tert-butyldimethylsilyl or tert-butyldiphenylsilyl:

GENERAL REACTION SCHEME 20

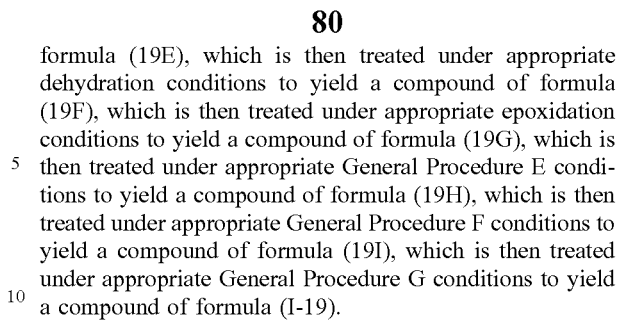

(6B)

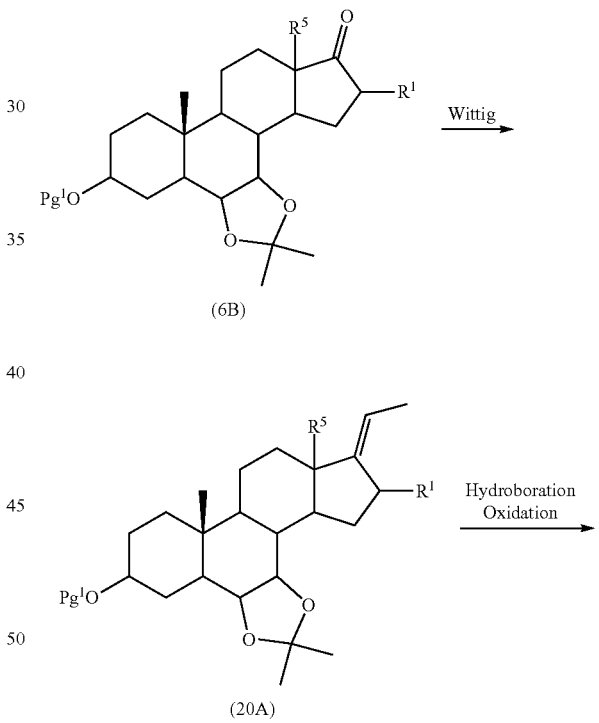

(20A)

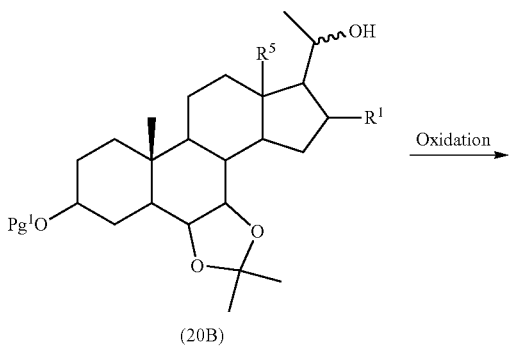

(20B)

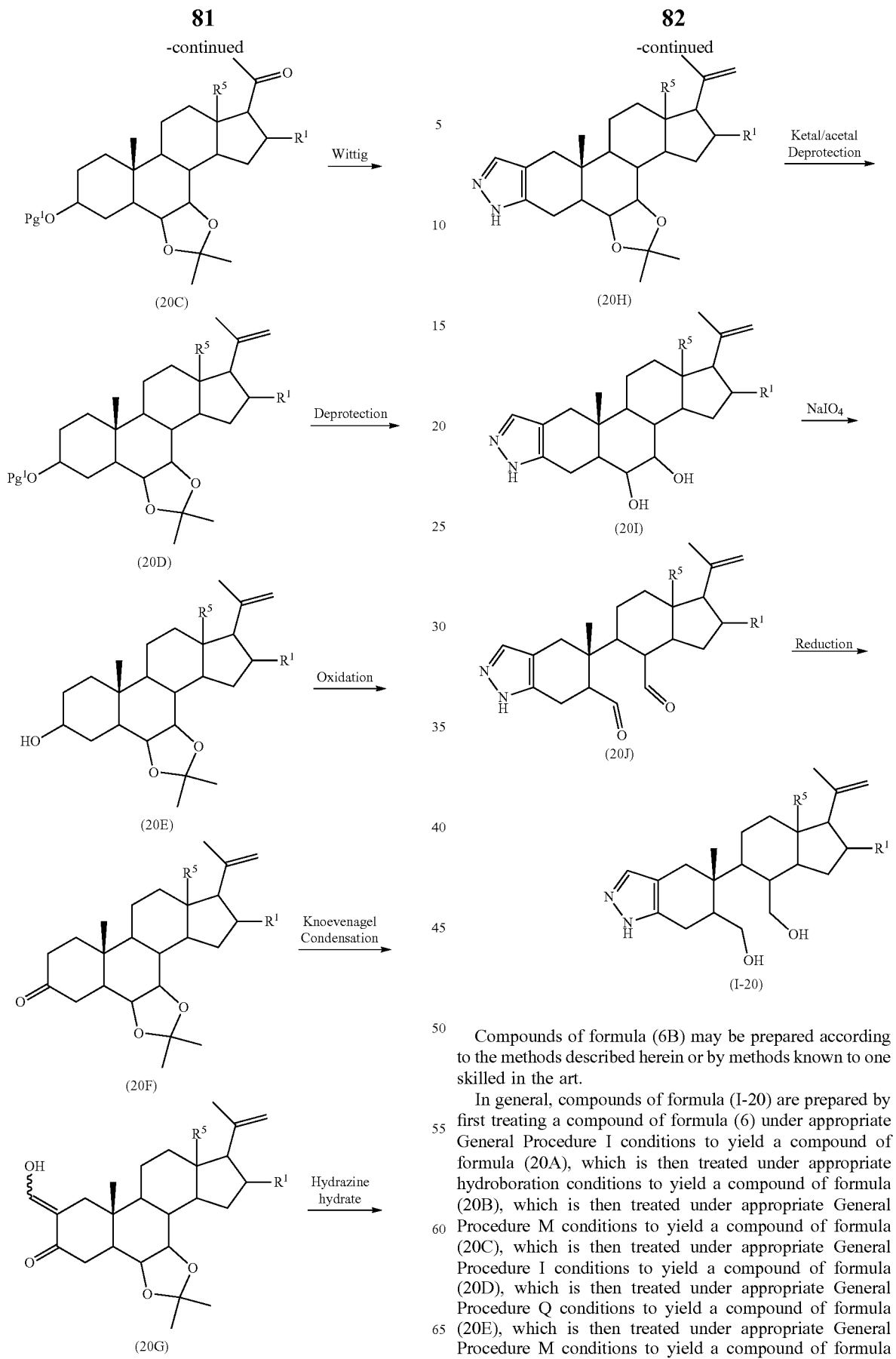

Compounds of formula (6B) may be prepared according to the methods described herein or by methods known to one skilled in the art.

In general, compounds of formula (I-20) are prepared by first treating a compound of formula (6) under appropriate General Procedure I conditions to yield a compound of formula (20A), which is then treated under appropriate hydroboration conditions to yield a compound of formula (20B), which is then treated under appropriate General Procedure M conditions to yield a compound of formula (20C), which is then treated under appropriate General Procedure I conditions to yield a compound of formula (20D), which is then treated under appropriate General Procedure Q conditions to yield a compound of formula (20E), which is then treated under appropriate General Procedure M conditions to yield a compound of formula (20F), which is then treated under appropriate General Procedure O conditions to yield a compound of formula (20G), which is then treated under appropriate General Procedure P conditions to yield a compound of formula (20H), which is then treated under appropriate General Procedure E conditions to yield a compound of formula (20I), which is then treated under appropriate General Procedure F conditions to yield a compound of formula (20J), which is then treated under appropriate General Procedure G conditions to yield a compound of formula (I-20).

An embodiment of General Reaction Scheme 20 is described in more detail below in Synthetic Example 25.

General Reaction Scheme 21

Compounds of formula (I-21) are compounds of formula (I), as described above in the Summary of the Invention, and may be prepared according the following General Reaction Scheme 21 wherein Ⓐ, $R^1$, $R^{4a}$, $R^{4b}$ and $R^5$ are as described above in the Summary of the Invention, $Pg^1$ is an oxygen protecting group such as tert-butyldimethylsilyl or tert-butyldiphenylsilyl, and X is halo, preferably chloro:

GENERAL REACTION SCHEME 21

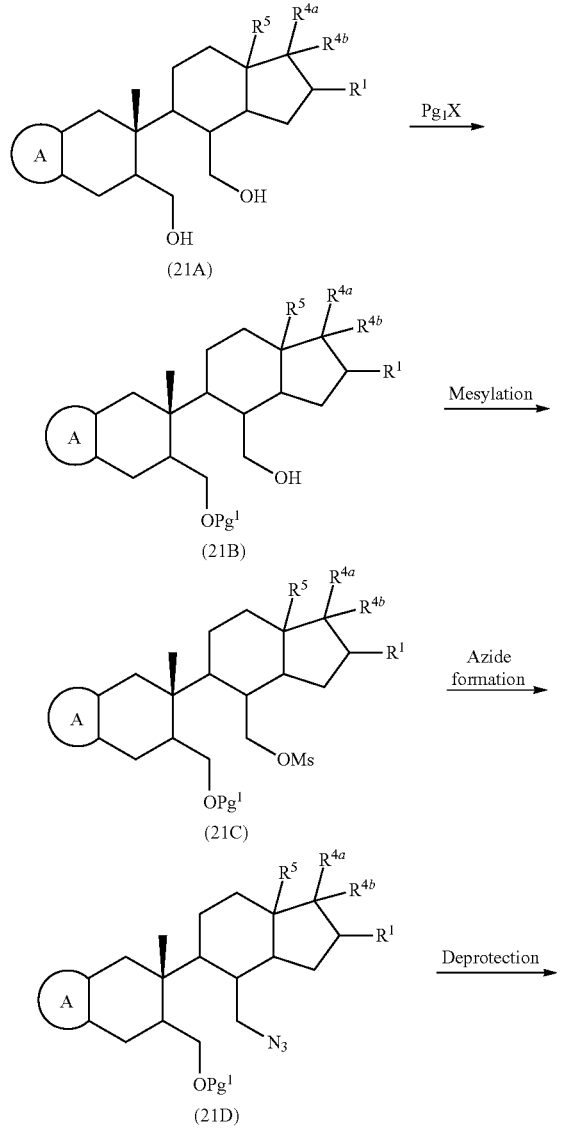

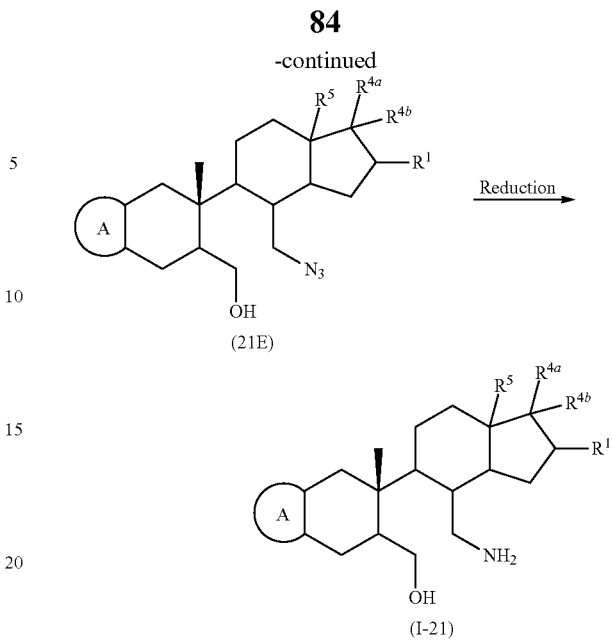

Compounds of formula (21A) may be prepared accordingly to methods disclosed herein.

In general, compounds of formula (I-21) are prepared by first treating a compound of formula (21A) under the appropriate General Procedure B conditions to yield a compound of formula (21B), which is then treated under the appropriate General Procedure J conditions to yield a compound of formula (21C), which is then treated under the appropriate General Procedure K conditions to yield a compound of formula (21D), which is then treated under the appropriate General Procedure Q conditions to yield a compound of formula (21E), which is then treated under the appropriate General Procedure R conditions or under the appropriate General Procedure S conditions to yield a compound of formula (I-21).

Embodiments of General Reaction Scheme 21 are described in more detail below in Synthetic Examples 26, 28, 38 and 40.

General Reaction Scheme 22

Compounds of formula (I-22) are compounds of formula (I), as described above in the Summary of the Invention, and may be prepared according the following General Reaction Scheme 22 wherein Ⓐ, $R^1$ and $R^5$ are as described above in the Summary of the Invention:

GENERAL REACTION SCHEME 22

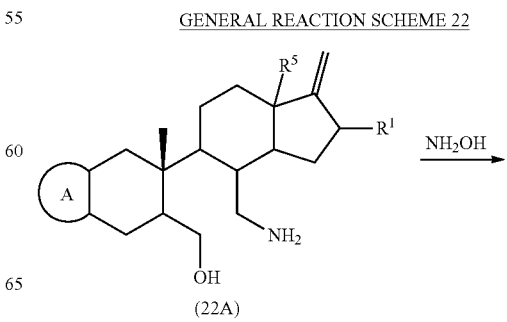

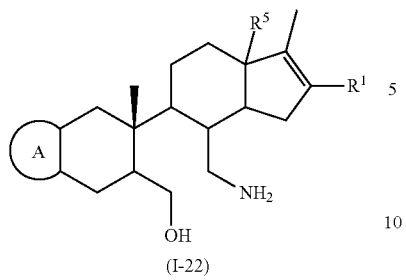

(I-22)

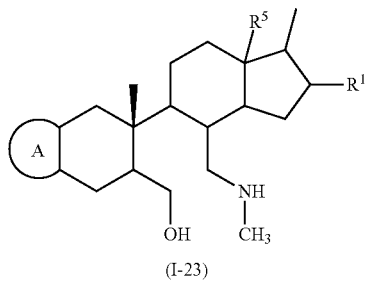

(I-23)

Compounds of formula (22A) can be prepared by methods disclosed herein.

In general, compounds of formula (I-22) are prepared by treating a compound of formula (22A) with hydroxylamine under standard condensation conditions to form a compound of formula (I-22).

An embodiment of General Reaction Scheme 22 is described in more detail below in Synthetic Example 30.

General Reaction Scheme 23

Compounds of formula (I-23) are compounds of formula (I), as described above in the Summary of the Invention, and may be prepared according the following General Reaction Scheme 23 wherein Ⓐ, $R^1$ and $R^5$ are as described above in the Summary of the Invention, $R^9$ is alkyl and X is halo, preferably chloro:

Compounds of formula (22A) can be prepared by methods disclosed herein.

In general, compounds of formula (I-23) are prepared by first treating a compound of formula (22A) with $XC(O)OR^9$ under appropriate carbamoylation conditions to yield a compound of formula (23A), which is then treated under standard reduction conditions to yield a compound of formula (23B), which is then treated under appropriate General Procedure T conditions to yield a compound of formula (I-23).

An embodiment of General Reaction Scheme 23 is described in more detail below in Synthetic Example 31.

General Reaction Scheme 24

Compounds of formula (I-24) are compounds of formula (I), as described above in the Summary of the Invention, and may be prepared according the following General Reaction Scheme 24 wherein Ⓐ, $R^1$ and $R^5$ are as described above in the Summary of the Invention and $R^{8a}$ is hydrogen or alkyl:

GENERAL REACTION SCHEME 23

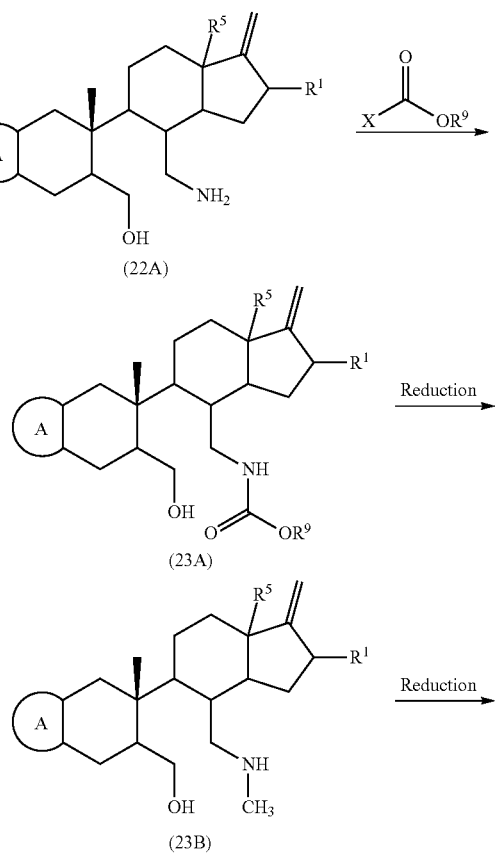

GENERAL REACTION SCHEME 24

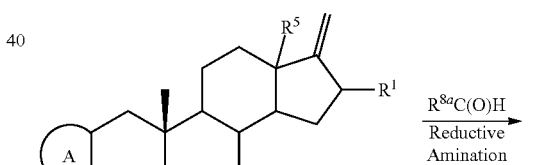

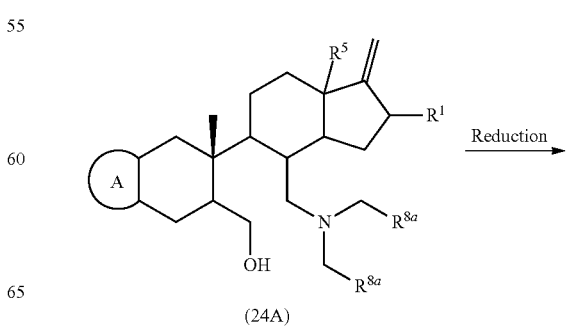

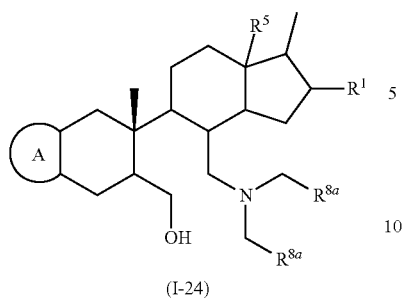

(I-24)

Compounds of formula (22A) can be prepared by methods disclosed herein.

In general, compounds of formula (I-24) are prepared by first treating a compound of formula (22A) under the appropriate General Procedure U conditions to yield a compound of formula (24A), which is then treated under appropriate General Procedure T conditions to yield a compound of formula (I-24).

An embodiment of General Reaction Scheme 24 is described in more detail below in Synthetic Example 32.

General Reaction Scheme 25

Compounds of formula (I-25) are compounds of formula (I), as described above in the Summary of the Invention, and may be prepared according the following General Reaction Scheme 25 wherein Ⓐ, $R^1$, $R^{4a}$, $R^{4b}$, $R^5$ and Rare as described above in the Summary of the Invention and $Pg^1$ is an oxygen protecting group such as tert-butyldimethylsilyl or tert-butyldiphenylsilyl:

GENERAL REACTION SCHEME 25

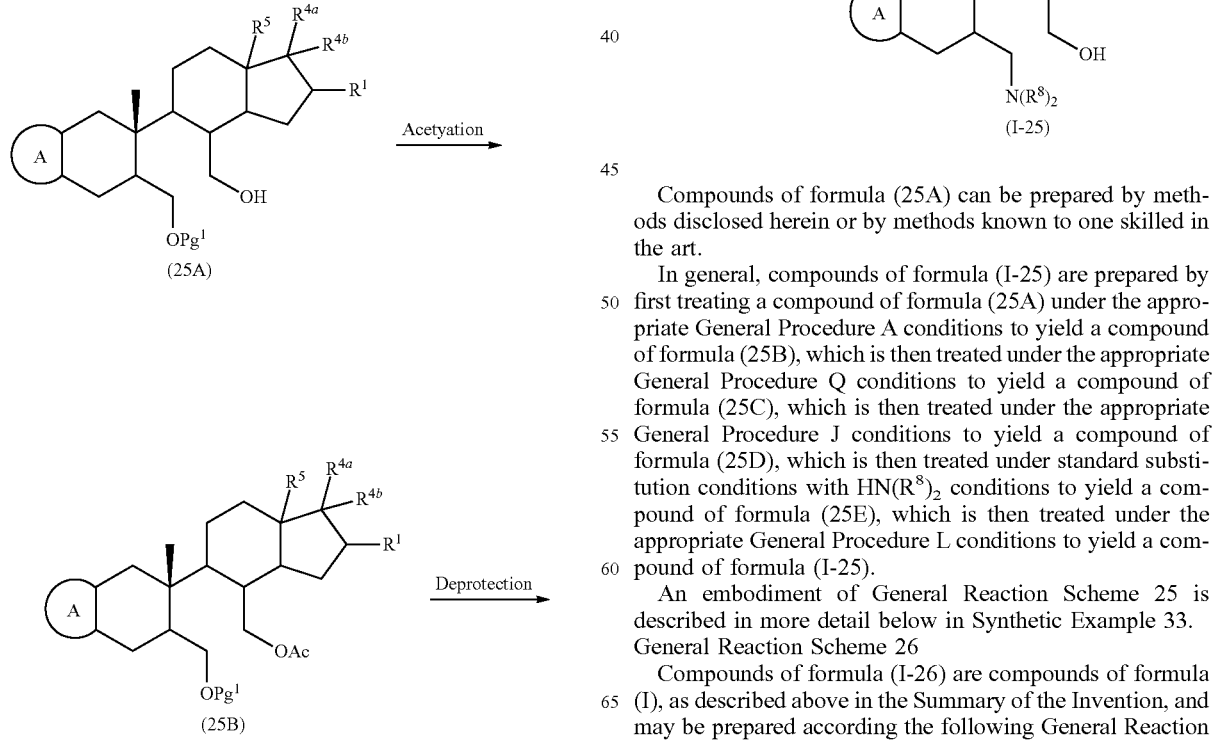

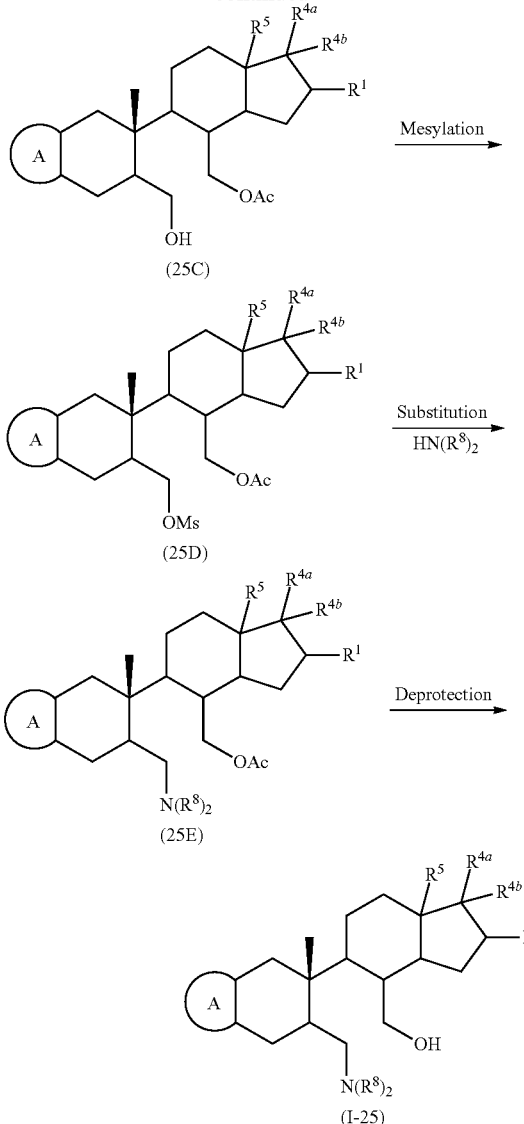

Compounds of formula (25A) can be prepared by methods disclosed herein or by methods known to one skilled in the art.

In general, compounds of formula (I-25) are prepared by first treating a compound of formula (25A) under the appropriate General Procedure A conditions to yield a compound of formula (25B), which is then treated under the appropriate General Procedure Q conditions to yield a compound of formula (25C), which is then treated under the appropriate General Procedure J conditions to yield a compound of formula (25D), which is then treated under standard substitution conditions with $HN(R^8)_2$ conditions to yield a compound of formula (25E), which is then treated under the appropriate General Procedure L conditions to yield a compound of formula (I-25).

An embodiment of General Reaction Scheme 25 is described in more detail below in Synthetic Example 33.

General Reaction Scheme 26

Compounds of formula (I-26) are compounds of formula (I), as described above in the Summary of the Invention, and may be prepared according the following General Reaction Scheme 26 wherein Ⓐ, $R^1$, $R^{4a}$, $R^{4b}$, $R^5$ and $R^8$ are as described above in the Summary of the Invention and $Pg^1$ is an oxygen protecting group such as tert-butyldimethylsilyl or tert-butyldiphenylsilyl:

may be prepared according the following General Reaction Scheme 27 wherein $R^1$, $R^{4a}$, $R^4$ and $R^5$ are as described above in the Summary of the Invention and $Pg^1$ is an oxygen protecting group such as tert-butyldimethylsilyl or tert-butyldiphenylsilyl:

GENERAL REACTION SCHEME 26

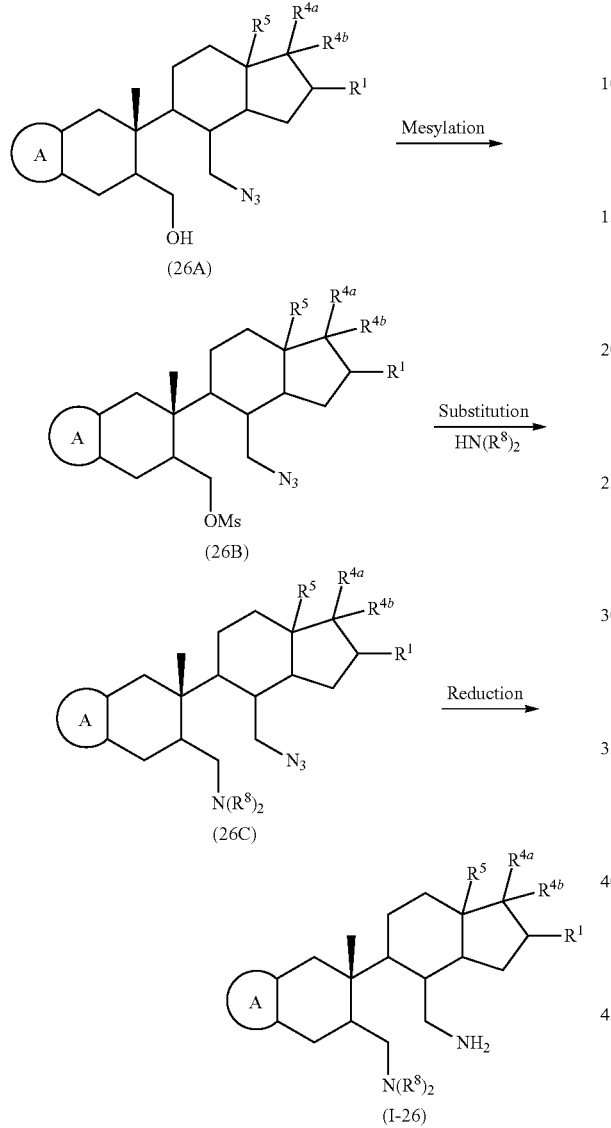

GENERAL REACTION SCHEME 27

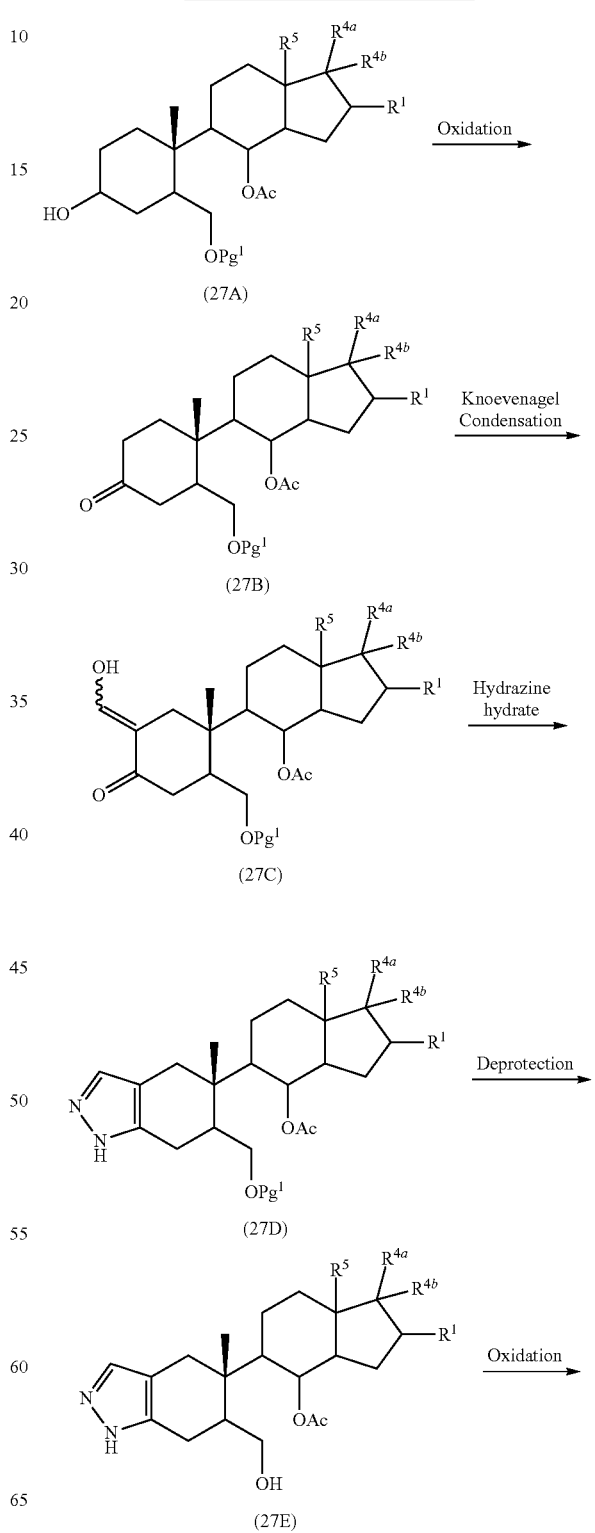

Compounds of formula (26A) can be prepared by methods disclosed herein or by methods known to one skilled in the art.

In general, compounds of formula (I-26) are prepared by first treating a compound of formula (26A) under the appropriate General Procedure J conditions to yield a compound of formula (26B), which is then treated under standard substitution conditions with $HN(R^8)_2$ conditions to yield a compound of formula (26C), which is then treated under the appropriate General Procedure R conditions or General Procedure S conditions to yield a compound of formula (I-26).

An embodiment of General Reaction Scheme 26 is described in more detail below in Synthetic Example 34.

General Reaction Scheme 27

Compounds of formula (I-27) are compounds of formula (I), as described above in the Summary of the Invention, and

91

-continued

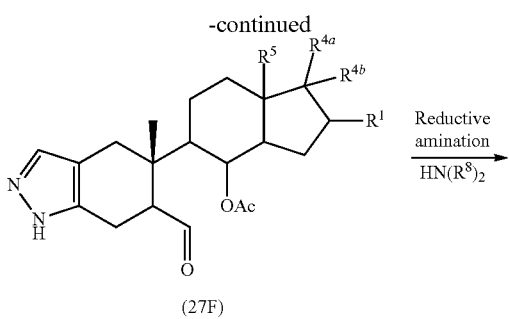

(27F)

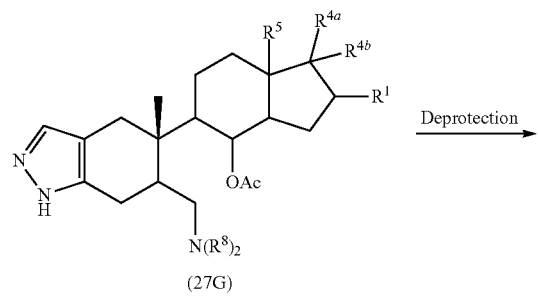

(27G)

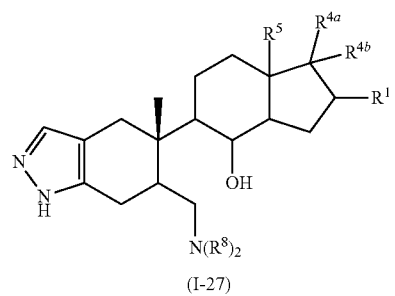

(I-27)

Compounds of formula (27A) can be prepared by the methods disclosed in U.S. Pat. No. 7,601,874, or by methods known to one skilled in the art.

In general, compounds of formula (I-27) are prepared by first treating a compound of formula (27A) under the appropriate General Procedure M conditions to yield a compound of formula (27B), which is then treated under the appropriate General Procedure O conditions to yield a compound of formula (27C), which is then treated under the appropriate General Procedure P conditions to yield a compound of formula (27D), which is then treated under the appropriate General Procedure Q conditions to yield a compound of formula (27E), which is then treated under the appropriate oxidation conditions to yield a compound of formula (27F), which is then treated under the appropriate reductive amination conditions with $HN(R^8)_2$ to yield a compound of formula (27G), which is then treated under the appropriate General Procedure L conditions to yield a compound of formula (I-27).

An embodiment of General Reaction Scheme 27 is described in more detail below in Synthetic Example 35.

General Reaction Scheme 28

Compounds of formula (I-28) are compounds of formula (I), as described above in the Summary of the Invention, and may be prepared according the following General Reaction Scheme 28 wherein $R^1$, $R^{4a}$, $R^{4b}$ and $R^5$ are as described above in the Summary of the Invention, $Pg^1$ and $Pg^2$ are each independently such as tert-butyldimethylsilyl or tert-butyldiphenylsilyl and X is halo, preferably chloro:

GENERAL REACTION SCHEME 28

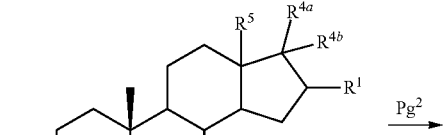

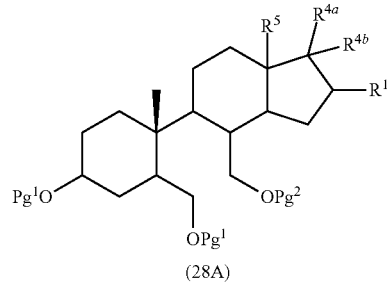

(1B)

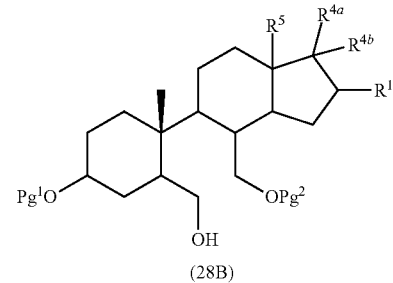

(28A)

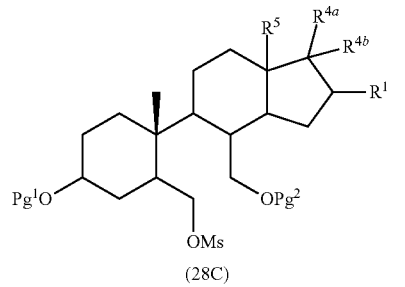

(28B)

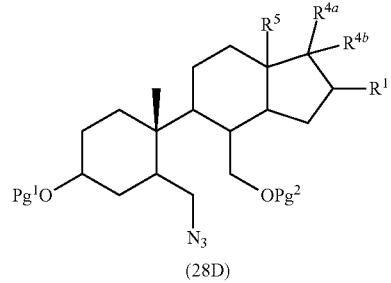

(28C)

(28D)

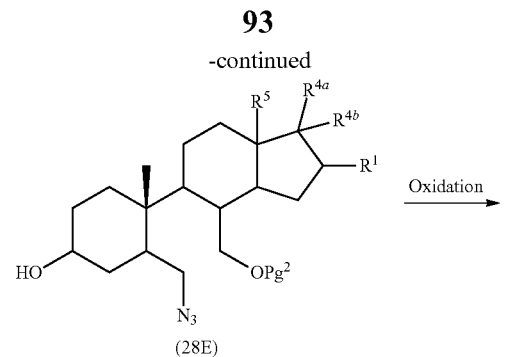

(28E)

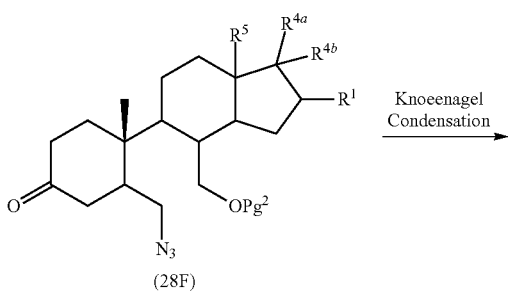

(28F)

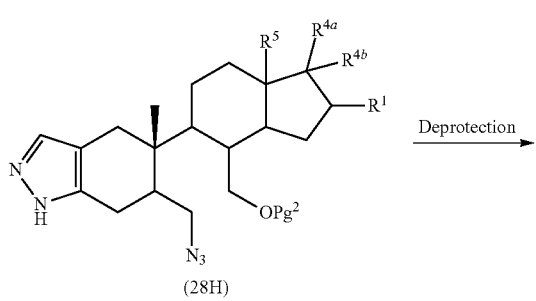

(28G)

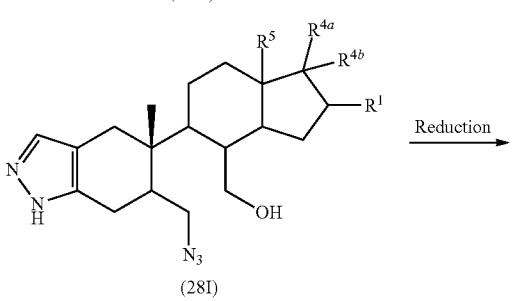

(28H)

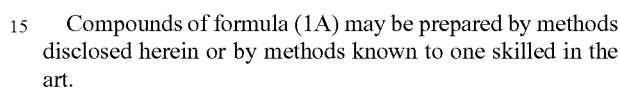

Oxidation

Knoeenagel Condensation

Hydrazine hydrate

Deprotection

Reduction

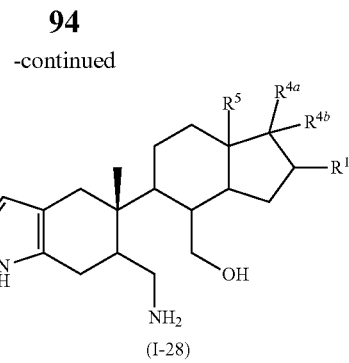

(I-28)

Compounds of formula (1A) may be prepared by methods disclosed herein or by methods known to one skilled in the art.

In general, compounds of formula (I-28) are prepared by first treating a compound of formula (1A) under the appropriate General Procedure B conditions to yield a compound of formula (28A), which is then treated under standard deprotection conditions to yield a compound of formula (28B), which is then treated under the appropriate General Procedure J conditions to yield a compound of formula (28C), which is then treated under the appropriate General Procedure K conditions to yield a compound of formula (28D), which is then treated under the appropriate General Procedure L conditions to yield a compound of formula (28E), which is then treated under the appropriate General Procedure M conditions to yield a compound of formula (28F), which is then treated under the appropriate General Procedure O conditions to yield a compound of formula (28G), which is then treated under the appropriate General Procedure P conditions to yield a compound of formula (28H), which is then treated under the appropriate General Procedure Q conditions to yield a compound of formula (28I), which is then treated under the appropriate General Procedure T conditions to yield a compound of formula (I-28).

An embodiment of General Reaction Scheme 28 is described in more detail below in Synthetic Example 36.

General Reaction Scheme 29

Compounds of formula (I-29) are compounds of formula (I), as described above in the Summary of the Invention, and may be prepared according the following General Reaction Scheme 29 wherein $R^1$, $R^4$, $R^{4b}$ and $R^5$ are as described above in the Summary of the Invention:

GENERAL REACTION SCHEME 29

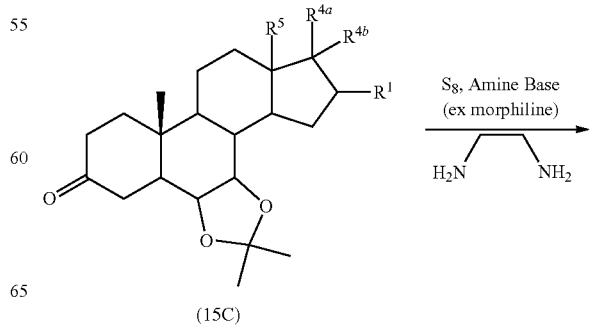

(15C)

$S_8$, Amine Base (ex morphiline)

-continued

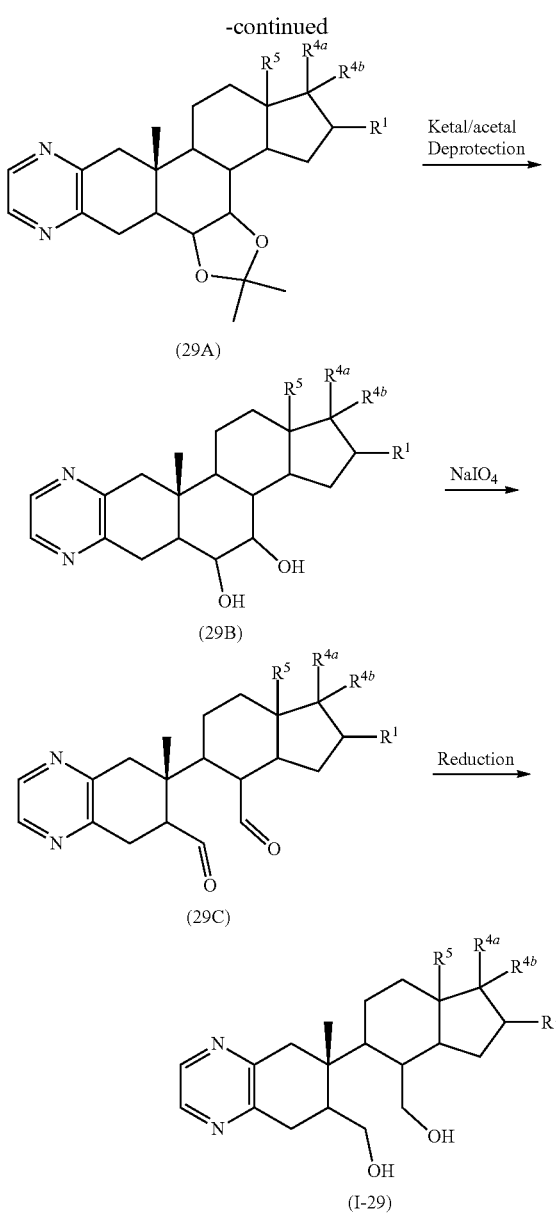

(29A)

(29B)

(29C)

(I-29)

Compounds of formula (15C) may be prepared by method disclosed herein or by methods known to one skilled in the art.

In general, compounds of formula (I-29) are prepared by first treating a compound of formula (15C) with 1,2-ethanediamine under appropriate cyclization conditions to yield a compound of formula (29A), which is then treated under appropriate General Procedure E conditions to yield a compound of formula (29B), which is then treated under appropriate General Procedure F conditions to yield a compound of formula (29C), which is then treated under appropriate General Procedure G conditions to yield a compound of formula (I-29).

Embodiments of General Reaction Scheme 29 are described in more detail below in Synthetic Examples 37 and 39.

General Reaction Scheme 30

Compounds of formula (I-30) are compounds of formula (I), as described above in the Summary of the Invention, and may be prepared according the following General Reaction Scheme 30 wherein $R^1$, $R^{4a}$, $R^{4b}$ and $R^5$ are as described above in the Summary of the Invention, $R^{11}$ is hydrogen, alkyl or $-N(R^8)_2$ where each $R^8$ is as described above in the Summary of the Invention and $Pg^2$ is an oxygen protecting group such as tert-butyldimethylsilyl or tert-butyldiphenylsilyl:

GENERAL REACTION SCHEME 30

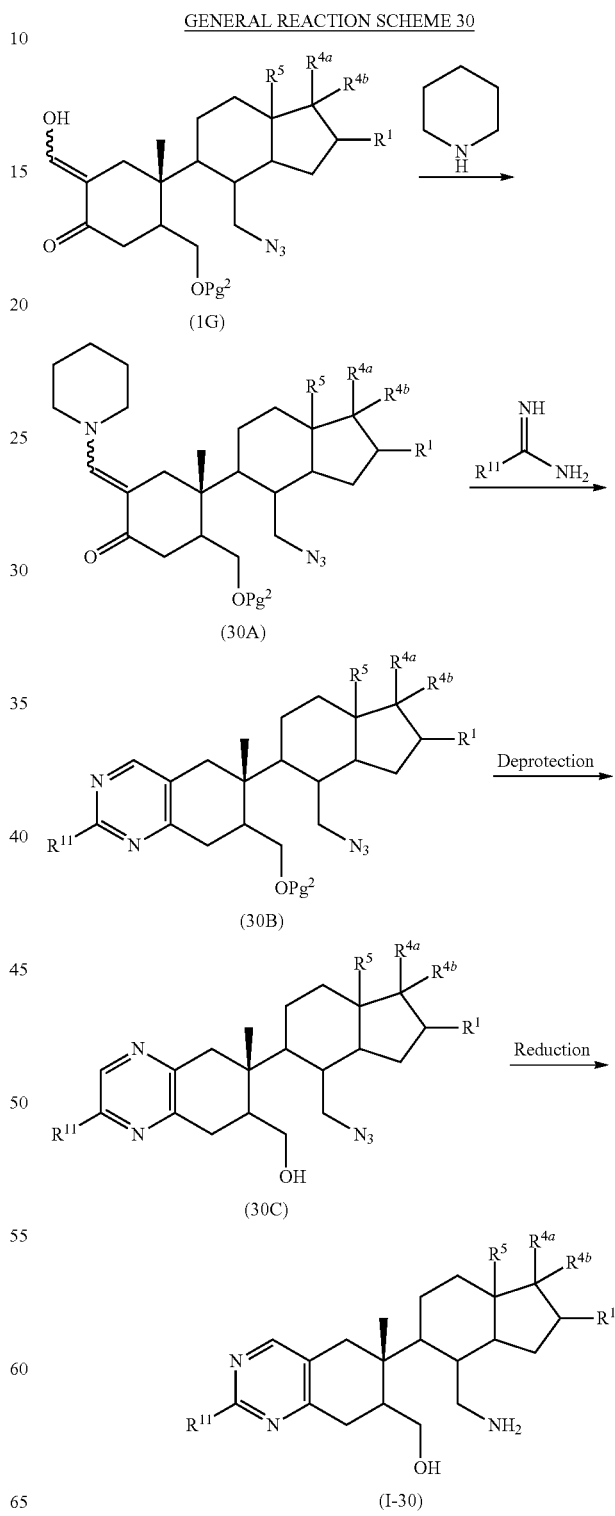

(1G)

(30A)

(30B)

(30C)

(I-30)

Compounds of formula (1G) are prepared as disclosed herein or by methods known to one skilled in the art.

In general, compounds of formula (I-30) are prepared by first treating a compound of formula (1G) with piperidine under appropriate enamine formation conditions to yield a compound of formula (30A), which is then treated with the appropriate optionally substituted guanidine under appropriate condensation/cyclization conditions to yield a compound of formula (30B), which is then treated under the appropriate General Procedure Q conditions to yield a compound of formula (30C), which is then treated under the appropriate General Procedure R conditions or the appropriate General Procedure S conditions to yield a compound of formula (I-30).

An embodiment of General Reaction Scheme 30 is described in more detail below in Synthetic Example 41.

General Reaction Scheme 31

Compounds of formula (I-31) are compounds of formula (I), as described above in the Summary of the Invention, and may be prepared according the following General Reaction Scheme 31 wherein $R^1$, $R^{4a}$, $R^{4b}$ and $R^5$ are as described above in the Summary of the Invention and $R^{11}$ is hydrogen, alkyl or $-N(R^8)_2$ where each $R^8$ is as described above in the Summary of the Invention:

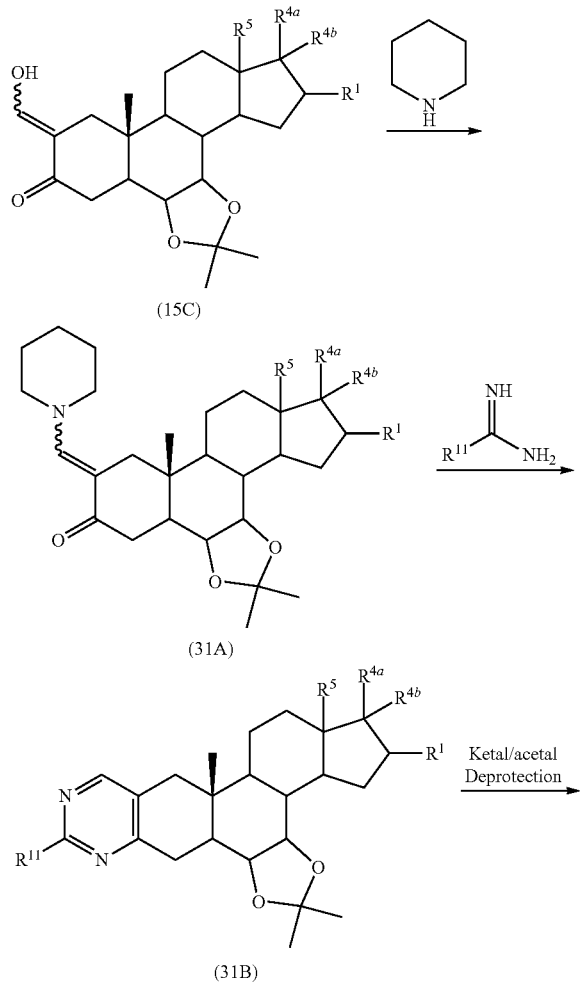

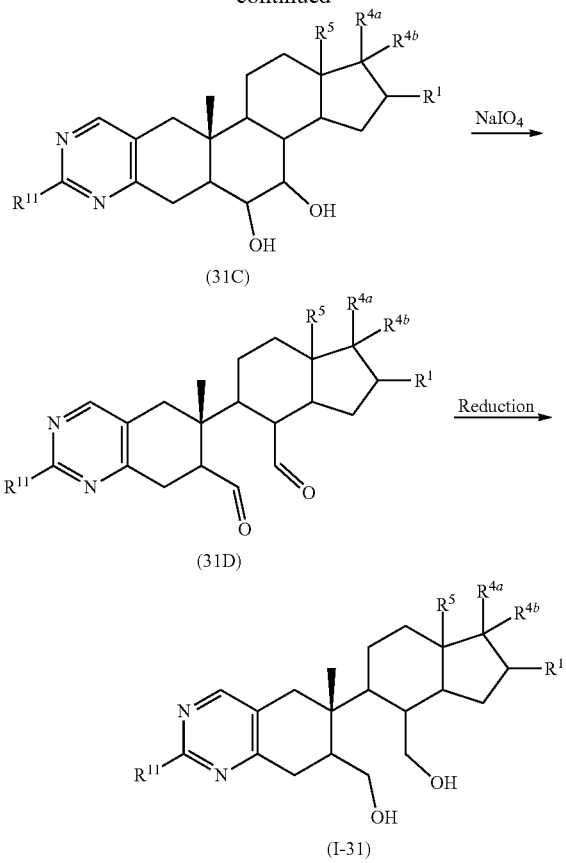

Compounds of formula (15D) may be prepared by method disclosed herein or by methods known to one skilled in the art.

In general, compounds of formula (I-31) are prepared by first treating a compound of formula (15D) with piperidine under appropriate enamine formation conditions to yield a compound of formula (31A), which is then treated with the appropriate optionally substituted acetamidine under appropriate condensation/cyclization conditions to yield a compound of formula (31B), which is then treated under the appropriate General Procedure E conditions to yield a compound of formula (31C), which is then treated under the appropriate General Procedure F conditions to yield a compound of formula (31D), which is then treated under the appropriate General Procedure G conditions to yield a compound of formula (I-31).

An embodiment of General Reaction Scheme 31 is described in more detail below in Synthetic Example 42.

General Reaction Scheme 32

Compounds of formula (I-32) are compounds of formula (I), as described above in the Summary of the Invention, and may be prepared according the following General Reaction Scheme 31 wherein $R^1$, $R^4$, $R^{4b}$ and $R^5$ are as described above in the Summary of the Invention, $R^{11}$ is hydrogen, alkyl or $-N(R^8)_2$ where each $R^8$ is as described above in the Summary of the Invention and each $Pg^1$ is an oxygen protecting group such as tert-butyldimethylsilyl or tert-butyldiphenylsilyl:

GENERAL REACTION SCHEME 32

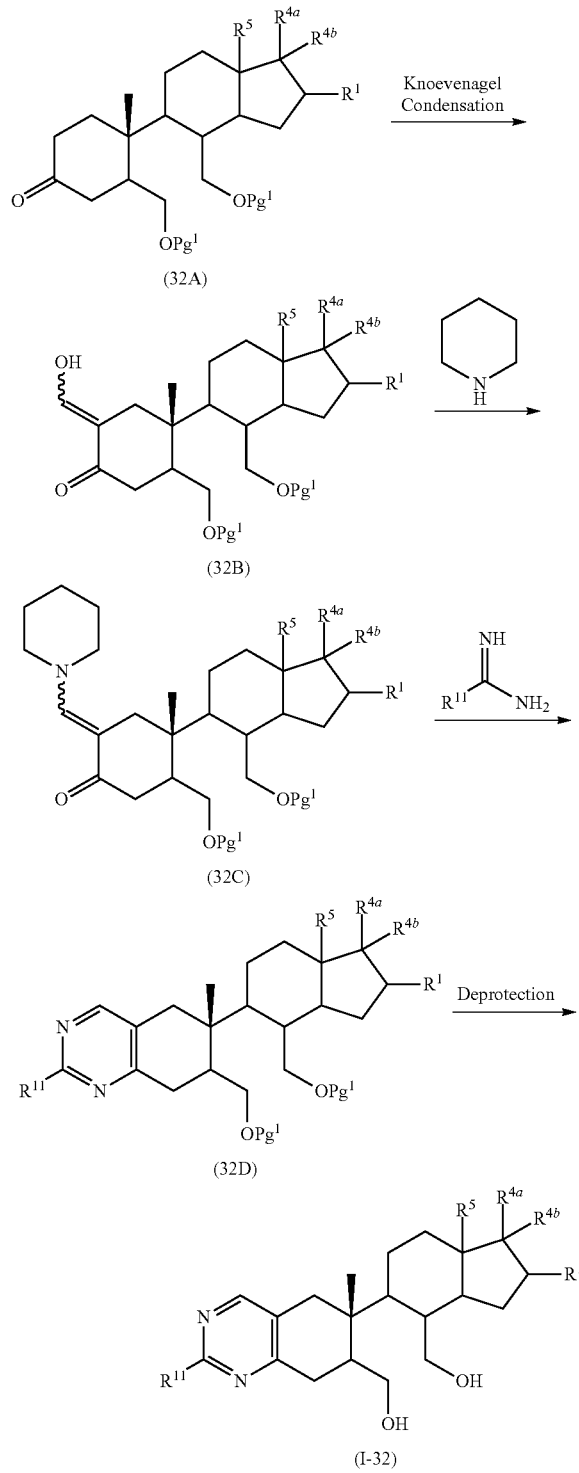

Compounds of formula (32A) may be prepared by methods disclosed herein or by methods known to one skilled in the art.

In general, compounds of formula (I-32) are prepared by first treating a compound of formula (32A) under the appropriate General Procedure O conditions to yield a compound of formula (32B), which is then treated under appropriate enamine formation conditions to yield a compound of formula (32C), which is then treated with the appropriate optionally substituted guanidine under appropriate condensation/cyclization conditions to yield a compound of formula (32D), which is then treated under the appropriate General Procedure Q conditions to yield a compound of formula (I-32).

An embodiment of General Reaction Scheme 32 is described in more detail below in Synthetic Example 43.

General Reaction Scheme 33

Compounds of formula (I-33) are compounds of formula (I), as described above in the Summary of the Invention, and may be prepared according the following General Reaction Scheme 33 wherein $R^1$, $R^4$, $R^{4b}$ and $R^5$ are as described above in the Summary of the Invention and $Pg^2$ is an oxygen protecting group such as ter-butyldimethylsilyl or tert-butyl-diphenylsilyl:

GENERAL REACTION SCHEME 33

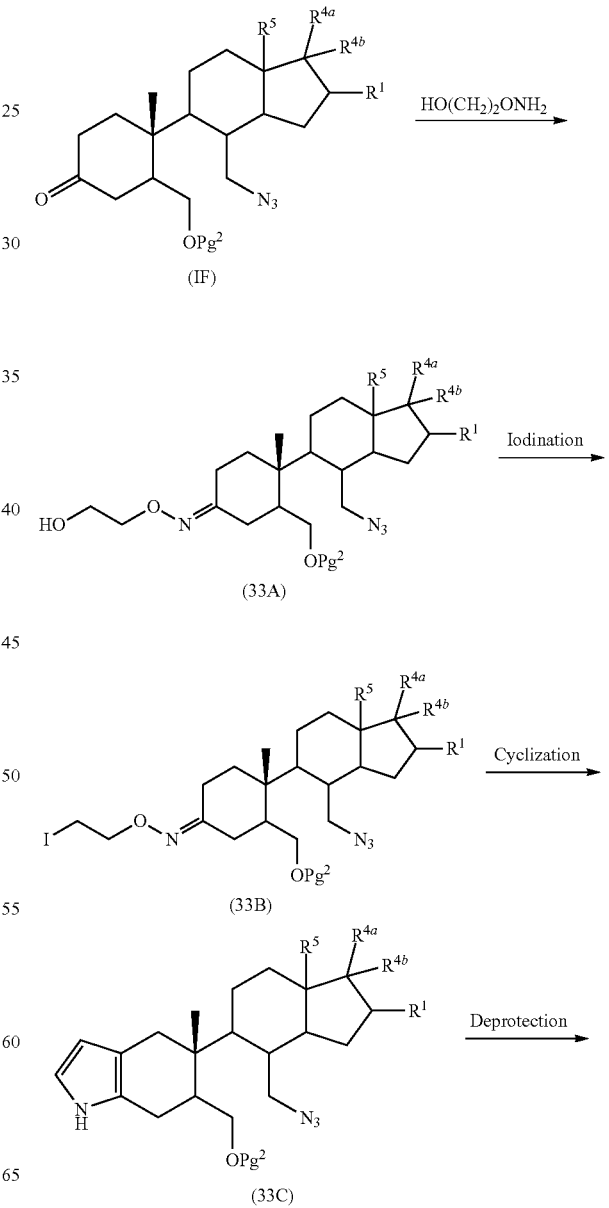

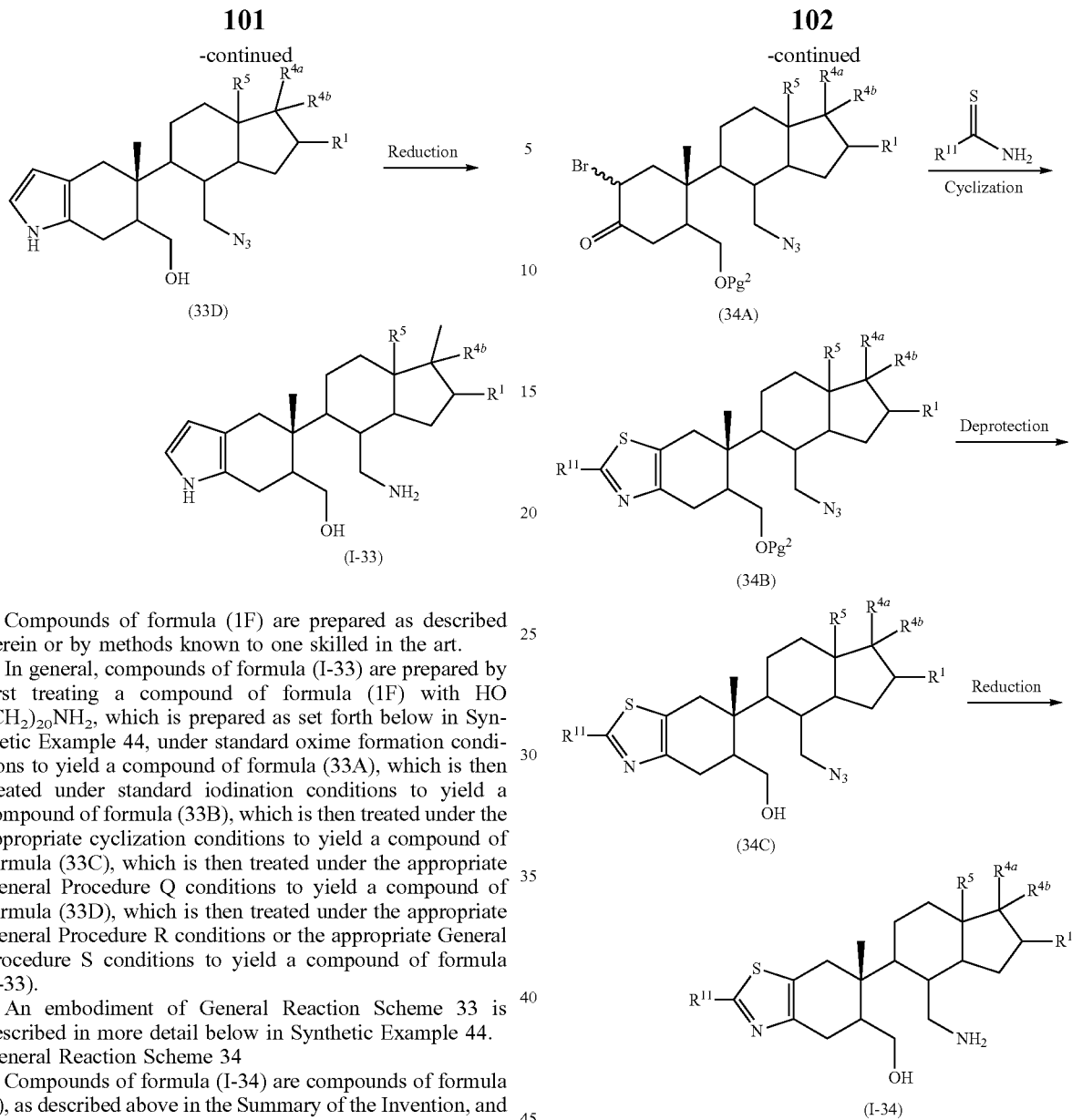

Compounds of formula (1F) are prepared as described herein or by methods known to one skilled in the art.

In general, compounds of formula (I-33) are prepared by first treating a compound of formula (1F) with HO(CH$_2$)$_{20}$NH$_2$, which is prepared as set forth below in Synthetic Example 44, under standard oxime formation conditions to yield a compound of formula (33A), which is then treated under standard iodination conditions to yield a compound of formula (33B), which is then treated under the appropriate cyclization conditions to yield a compound of formula (33C), which is then treated under the appropriate General Procedure Q conditions to yield a compound of formula (33D), which is then treated under the appropriate General Procedure R conditions or the appropriate General Procedure S conditions to yield a compound of formula (I-33).

An embodiment of General Reaction Scheme 33 is described in more detail below in Synthetic Example 44.

General Reaction Scheme 34

Compounds of formula (I-34) are compounds of formula (I), as described above in the Summary of the Invention, and may be prepared according the following General Reaction Scheme 34 wherein R$^1$, R$^4$, R$^{4b}$ and R$^5$ are as described above in the Summary of the Invention, R$^{11}$ is hydrogen, alkyl or —N(R$^8$)$_2$ where each R$^8$ is as described above in the Summary of the Invention and Pg$^2$ is an oxygen protecting group such as tert-butyldimethylsilyl or tert-butyldiphenylsilyl:

GENERAL REACTION SCHEME 34

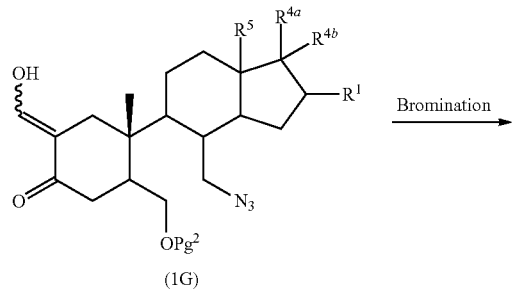

Compounds of formula (IG) are prepared as described herein or by methods known to one skilled in the art.

In general, compounds of formula (I-34) are prepared by first treating a compound of formula (1G) under the appropriate bromination conditions to yield a compound of formula (34A), which is then treated under the appropriate cyclization conditions with the appropriate optionally substituted thioacetamide to yield a compound of formula (34B), which is then treated under the appropriate General Procedure Q conditions to yield a compound of formula (34C), which is then treated under the appropriate General Procedure R conditions or the appropriate General Procedure S conditions to yield a compound of formula (I-34).

An embodiment of General Reaction Scheme 34 is described in more detail below in Synthetic Example 45.

General Reaction Scheme 35

Compounds of formula (I-35) are compounds of formula (I), as described above in the Summary of the Invention, and may be prepared according the following General Reaction Scheme 35 wherein R$^1$, R$^{4a}$, R$^{4b}$ and R$^5$ are as described above in the Summary of the Invention, and $R^{11}$ is hydrogen, alkyl or $—N(R^8)_2$ where each $R^8$ is as described above in the Summary of the Invention and;

GENERAL REACTION SCHEME 35

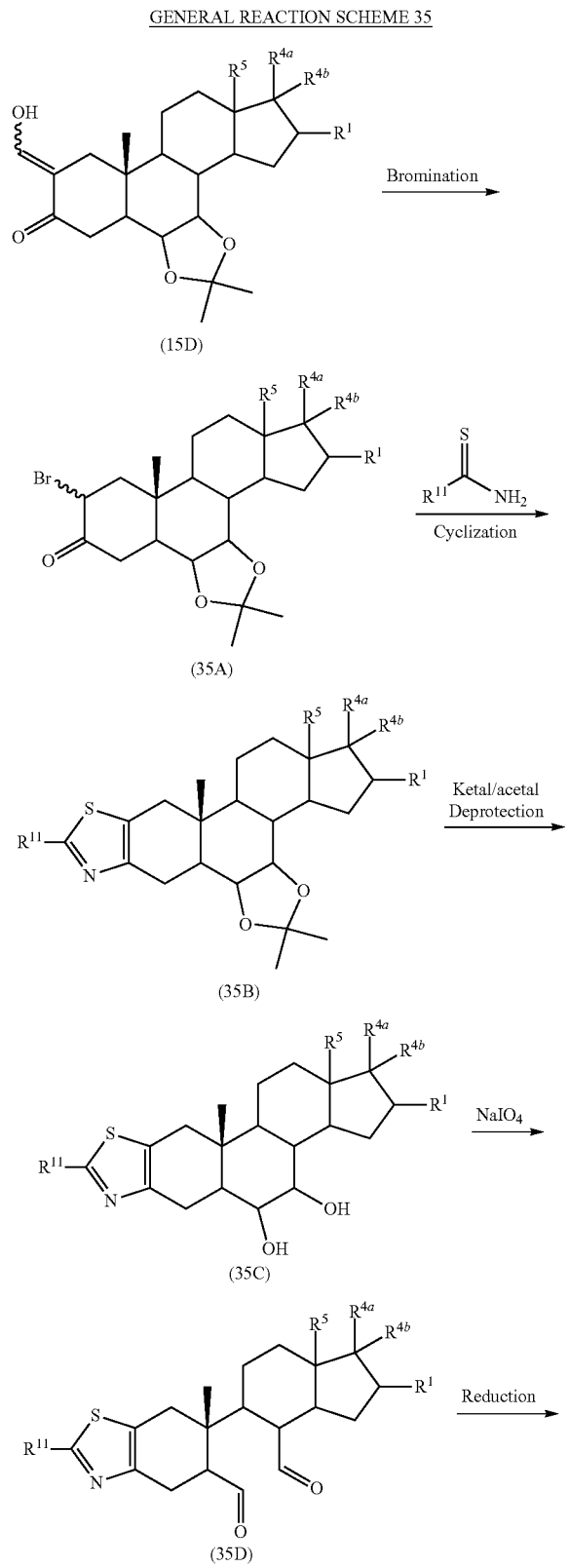

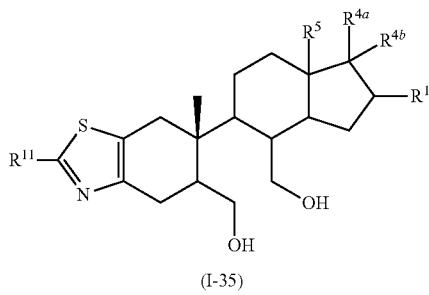

(I-35)

Compounds of formula (15D) are prepared as disclosed herein or by methods known to one skilled in the art.

In general, compounds of formula (I-35) are prepared by first treating a compound of formula (15D) under the appropriate bromination conditions to yield a compound of formula (35A), which is then treated under the appropriate cyclization conditions with the appropriate optionally substituted thiourea to yield a compound of formula (35B), which is then treated under the appropriate General Procedure E conditions to yield a compound of formula (35C), which is then treated under the appropriate General Procedure F conditions to yield a compound of formula (35D), which is then treated under the appropriate General Procedure G conditions to yield a compound of formula (I-35).

An embodiment of General Reaction Scheme 35 is described in more detail below in Synthetic Example 46.

General Reaction Scheme 36

Compounds of formula (I-36) are compounds of formula (I), as described above in the Summary of the Invention, and may be prepared according the following General Reaction Scheme 36 wherein $R^1$, $R^{4a}$, $R^{4b}$ and $R^5$ are as described above in the Summary of the Invention:

GENERAL REACTION SCHEME 36

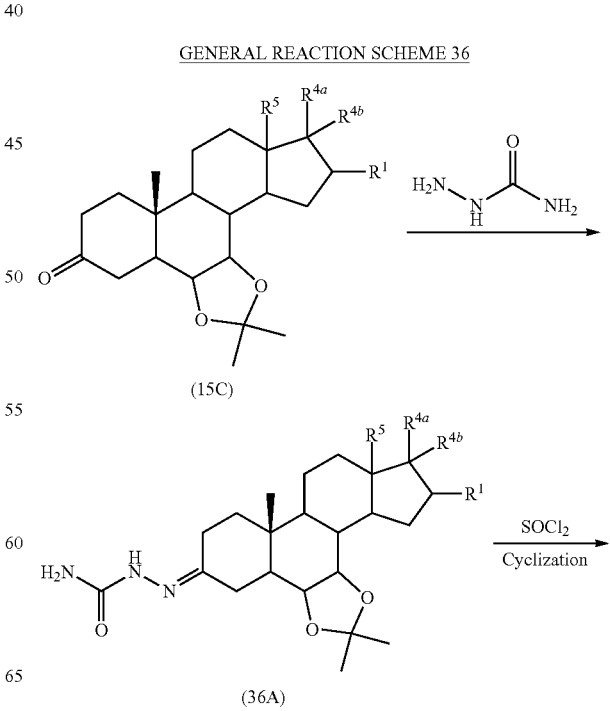

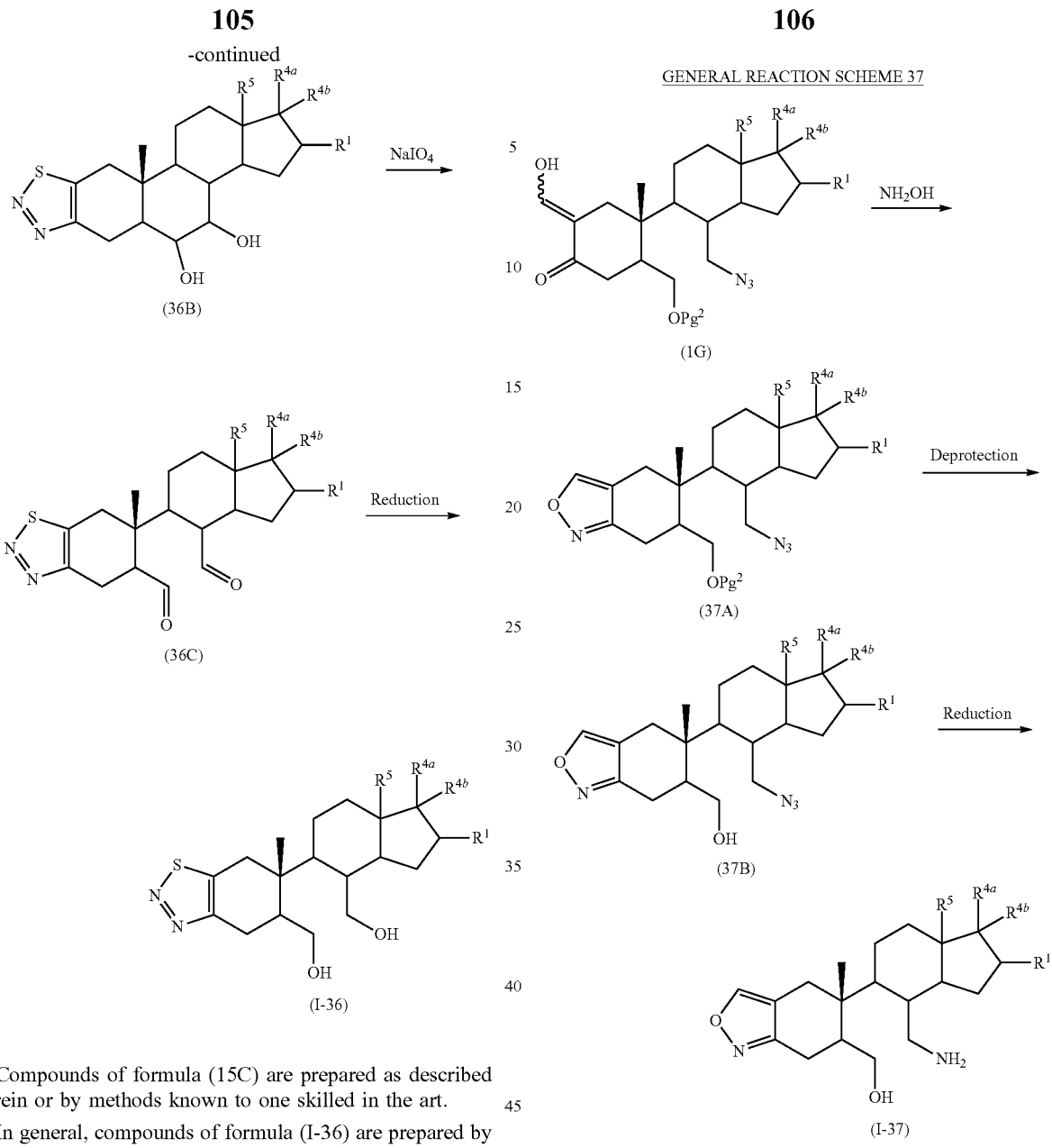

Compounds of formula (15C) are prepared as described herein or by methods known to one skilled in the art.

In general, compounds of formula (I-36) are prepared by first treating a compound of formula (15C) with semicarbazide under appropriate condensation conditions to yield a compound of formula (36A), which is then treated with sulfonyl chloride under appropriate cyclization conditions to yield a compound of formula (36B), which is then treated under the appropriate General Procedure F conditions to yield a compound of formula (36C), which is then treated under the appropriate General Procedure G conditions to yield a compound of formula (I-36).

An embodiment of General Reaction Scheme 36 is described in more detail below in Synthetic Example 47.

General Reaction Scheme 37

Compounds of formula (I-37) are compounds of formula (I), as described above in the Summary of the Invention, and may be prepared according the following General Reaction Scheme 37 wherein $R^1$, $R^{4a}$, $R^{4b}$ and $R^5$ are as described above in the Summary of the Invention and $Pg^2$ is an oxygen protecting group such as tert-butyldimethylsilyl or tert-butyldiphenylsilyl:

Compounds of formula (1G) are prepared by methods disclosed herein or by methods known to one skilled in the art.

In general, compounds of formula (I-37) are prepared by first treating a compound of formula (1G) with hydroxylamine under appropriate condensation/cyclization conditions to yield a compound of formula (37A), which is then treated under the appropriate General Procedure Q conditions to yield a compound of formula (37B), which is then treated under the appropriate General Procedure R conditions or the appropriate General Procedure S conditions to yield a compound of formula (I-37).

An embodiment of General Reaction Scheme 37 is described in more detail below in Synthetic Example 48.

General Reaction Scheme 38

Compounds of formula (I-38) are compounds of formula (I), as described above in the Summary of the Invention, and may be prepared according the following General Reaction Scheme 38 wherein $R^1$, $R^{4a}$, $R^{4b}$ and $R^5$ are as described above in the Summary of the Invention:

GENERAL REACTION SCHEME 38

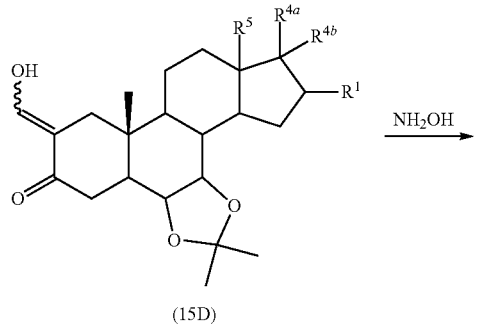

(15D)

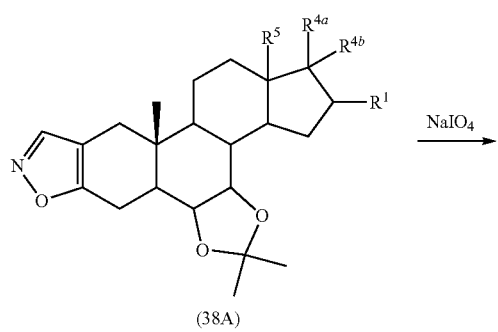

(38A)

-continued (38B)

(I-38)

Compounds of formula (15D) are prepared buy methods disclosed herein or by methods known to one skilled in the art.

In general, compounds of formula (I-38) are prepared by first treating a compound of formula (15D) with hydroxylamine under appropriate condensation/cyclization conditions to yield a compound of formula (38A), which is then treated under the appropriate General Procedure F conditions to yield a compound of formula (38B), which is then treated under the appropriate General Procedure G conditions to yield a compound of formula (I-38).

An embodiment of General Reaction Scheme 38 is described in more detail below in Synthetic Example 49.

General Reaction Scheme 39

Compounds of formula (I-39a) and formula (I-39b) are compounds of formula (I), as described above in the Summary of the Invention, and may be prepared according the following General Reaction Scheme 39 wherein $R^1$ and $R^5$ are each methyl and $R^{4a}$ and $R^{4b}$ are as described above in the Summary of the Invention:

GENERAL REACTION SCHEME 39

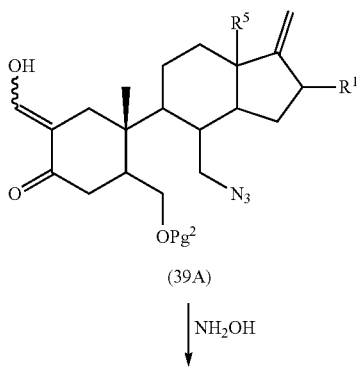

(39A)

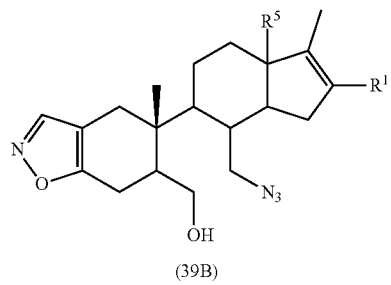 (39B)

and

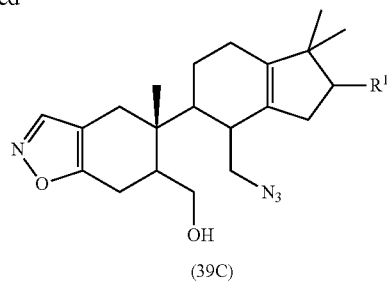 (39C)

Reduction

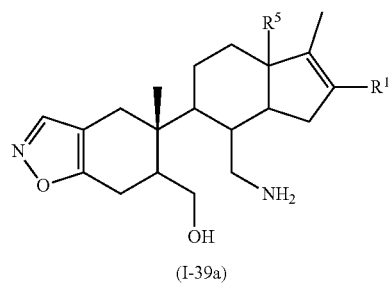 (I-39a)

and

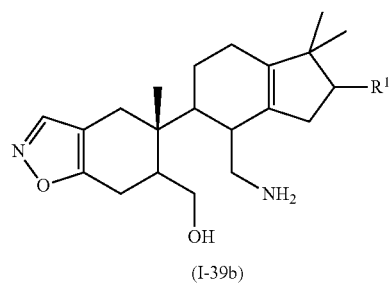 (I-39b)

Compounds of formula (39A) may be prepared by methods disclosed herein or by methods known to one skilled in the art.

In general, compounds of formula (I-39a) and formula (I-39b) are prepared by first treating a compound of formula (39A) with hydroxylamine under the appropriate condensation/cyclization conditions to yield a mixture of a compound of formula (39B) and a compound of formula (39C), which is then treated under the appropriate General Procedure R conditions or the appropriate General Procedure S conditions to yield a mixture of a compound of formula (I-39a) and a compound of formula (I-39b). The individual compounds may be isolated by standard techniques.

An embodiment of General Reaction Scheme 39 is described in more detail below in Synthetic Example 50.

General Reaction Scheme 40

Compounds of formula (I-40) are compounds of formula (I), as described above in the Summary of the Invention, and may be prepared according the following General Reaction Scheme 40 wherein $R^1$, $R^{4a}$, $R^{4b}$ and $R^5$ are as described above in the Summary of the Invention:

GENERAL REACTION SCHEME 40

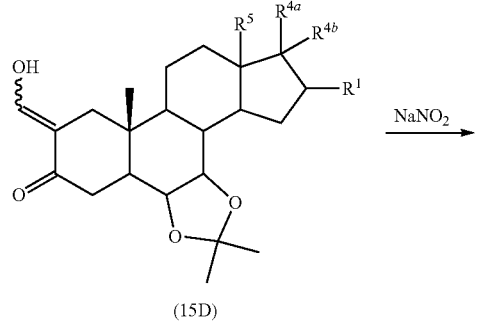 (15D)

$\xrightarrow{NaNO_2}$

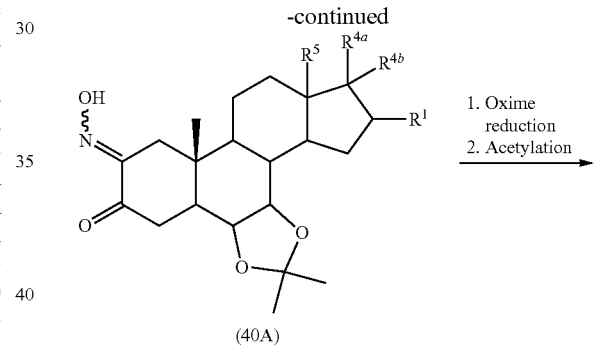 (40A)

1. Oxime reduction
2. Acetylation
$\longrightarrow$

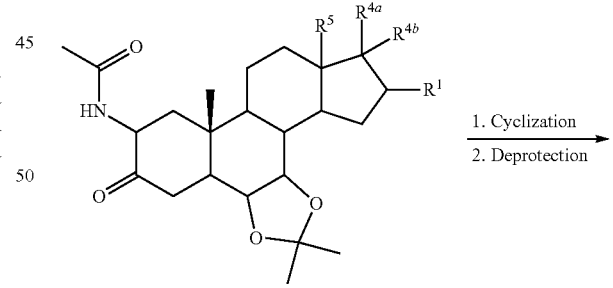 (40B)

1. Cyclization
2. Deprotection
$\longrightarrow$

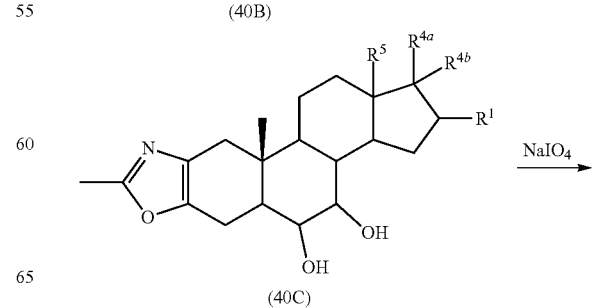 (40C)

$\xrightarrow{NaIO_4}$

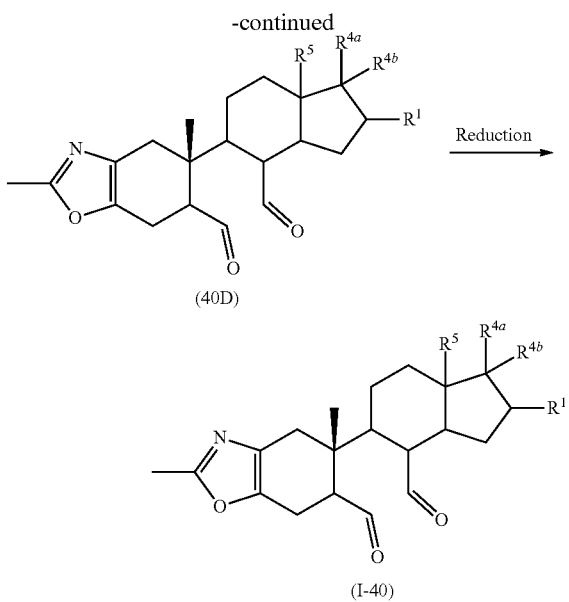

(40D)

(I-40)

Compounds of formula (15D) are prepared by methods disclosed herein or by methods known to one skilled in the art.

In general, compounds of formula (I-40) are prepared by first treating a compound of formula (15D) with sodium nitrite under oxime formation conditions to yield a compound of formula (40A), which is then treated under appropriate oxime reduction followed by acetylation conditions to yield a compound of formula (40B), which is then treated under appropriate cyclization conditions, followed by the appropriate General Procedure E conditions to yield a compound of formula (40C), which is then treated under the appropriate General Procedure F conditions to yield a compound of formula (40D), which is then treated under the appropriate General Procedure G conditions to yield a compound of formula (I-40).

An embodiment of General Reaction Scheme 40 is described in more detail below in Synthetic Example 51.

The compounds of formula (I) wherein Ⓐ is unsubstituted can be treated with an heteroaryl halide under the appropriate basic conditions, such as in the presence of sodium hydride in an aprotic solvent, such as DMF, to form compounds of formula (I) wherein Ⓐ is substituted with the heteroaryl.

All of the compounds described herein as being prepared which may exist in free base or acid form may be converted to their pharmaceutically acceptable salts by treatment with the appropriate inorganic or organic base or acid. Salts of the compounds prepared below may be converted to their free base or acid form by standard techniques. Furthermore, all compounds of the invention which contain an acid or an ester group can be converted to the corresponding ester or acid, respectively, by methods known to one skilled in the art or by methods described herein.

Representative compounds of the invention which were prepared by the methods disclosed herein include (but are not limited to) the compounds listed below in Table 1. The compound (Cpd) numbers in this table correspond to the compound numbers in Synthetic Examples 1 to 511 below.

TABLE 1

| Cpd No. | Compound Name |
|---|---|
| Ia-1 | ((5R,6S)-5-((3aS,4R,5S,7aS)-4-(aminomethyl)-7a-methyl-1-methyleneoctahydro-1H-inden-5-yl)-5-methyl-4,5,6,7-tetrahydro-1H-indazol-6-yl)methanol |
| Ia-2 | ((5R,6S)-5-((4R,5S)-4-(aminomethyl)-1,1-dimethyl-2,3,4,5,6,7-hexahydro-1H-inden-5-yl)-5-methyl-4,5,6,7-tetrahydro-1H-indazol-6-yl)methanol |
| Ia-3 | ((5R,6S)-5-((3aS,4R,5S,7aS)-4-((((2,2-difluorobenzo[d][1,3]dioxol-5-yl)methyl)amino)methyl)-7a-methyl-1-methyleneoctahydro-1H-inden-5-yl)-5-methyl-4,5,6,7-tetrahydro-1H-indazol-6-yl)methanol |
| Ia-4 | ((5R,6S)-5-((4R,5S)-4-(hydroxymethyl)-1,1-dimethyl-2,3,4,5,6,7-hexahydro-1H-inden-5-yl)-5-methyl-4,5,6,7-tetrahydro-1H-indazol-6-yl)methanol |
| Ia-5 | ((5R,6S)-5-((1S,3aS,4S,5S,7aR)-4-(hydroxymethyl)-1,7a-dimethyloctahydro-1H-inden-5-yl)-5-methyl-4,5,6,7-tetrahydro-1H-indazol-6-yl)methanol |
| Ia-6 | ((5R,6S)-5-((1R,3aS,4S,5S,7aR)-4-(aminomethyl)-7a-methyl-1-((R)-6-methylheptan-2-yl)octahydro-1H-inden-5-yl)-5-methyl-4,5,6,7-tetrahydro-1H-indazol-6-yl)methanol |
| Ia-7 | ((5R,6S)-5-((1R,3aS,4S,5S,7aR)-4-((((2,2-difluorobenzo[d][1,3]dioxol-5-yl)methyl)amino)methyl)-7a-methyl-1-((R)-6-methylheptan-2-yl)octahydro-1H-inden-5-yl)-5-methyl-4,5,6,7-tetrahydro-1H-indazol-6-yl)methanol |
| Ia-8 | ((5R,6S)-5-((3aS,4R,5S,7aS)-4-(aminomethyl)-7a-methyl-1-methyleneoctahydro-1H-inden-5-yl)-5-methyl-1-phenyl-4,5,6,7-tetrahydro-1H-indazol-6-yl)methanol |
| Ia-9 | ((5R,6S)-5-((3aS,4R,5S,7aS)-4-(aminomethyl)-7a-methyl-1-methyleneoctahydro-1H-inden-5-yl)-5-methyl-2-phenyl-4,5,6,7-tetrahydro-2H-indazol-6-yl)methanol |
| Ia-10 | ((5R,6S)-5-((3aS,4R,5S,7aS)-4-(aminomethyl)-7a-methyl-1-methyleneoctahydro-1H-inden-5-yl)-5-methyl-1-(pyridin-2-yl)-4,5,6,7-tetrahydro-1H-indazol-6-yl)methanol |
| Ia-11 | ((5R,6S)-5-((3aS,4R,5S,7aS)-4-(aminomethyl)-7a-methyl-1-methyleneoctahydro-1H-inden-5-yl)-5-methyl-2-(pyridin-2-yl)-4,5,6,7-tetrahydro-2H-indazol-6-yl)methanol |

TABLE 1-continued

| Cpd No. | Compound Name |
| --- | --- |
| Ia-12 | ((5R,6S)-5-((3aS,4R,5S,7aS)-4-(aminomethyl)-7a-methyl-1-methyleneoctahydro-1H-inden-5-yl)-1-(tert-butyl)-5-methyl-4,5,6,7-tetrahydro-1H-indazol-6-yl)methanol |
| Ia-13 | ((5R,6S)-5-((3aS,4R,5S,7aS)-4-(aminomethyl)-7a-methyl-1-methyleneoctahydro-1H-inden-5-yl)-2-(tert-butyl)-5-methyl-4,5,6,7-tetrahydro-2H-indazol-6-yl)methanol |
| Ia-14 | ((5R,6S)-5-((3aS,4R,5S,7aS)-4-(aminomethyl)-7a-methyl-1-methyleneoctahydro-1H-inden-5-yl)-1,5-dimethyl-4,5,6,7-tetrahydro-1H-indazol-6-yl)methanol |
| Ia-15 | ((5R,6S)-5-((3aS,4R,5S,7aS)-4-(aminomethyl)-7a-methyl-1-methyleneoctahydro-1H-inden-5-yl)-2,5-dimethyl-4,5,6,7-tetrahydro-2H-indazol-6-yl)methanol |
| Ia-16 | ((5R,6S)-5-((3aS,4R,5S,7aS)-4-(aminomethyl)-7a-methyl-1-methyleneoctahydro-1H-inden-5-yl)-1-cyclohexyl-5-methyl-4,5,6,7-tetrahydro-1H-indazol-6-yl)methanol |
| Ia-17 | ((5R,6S)-5-((3aS,4R,5S,7aS)-4-(aminomethyl)-7a-methyl-1-methyleneoctahydro-1H-inden-5-yl)-2-cyclohexyl-5-methyl-4,5,6,7-tetrahydro-2H-indazol-6-yl)methanol |
| Ia-18 | (((5R,6S)-5-((3aS,4R,5S,7aS)-4-(aminomethyl)-7a-methyl-1-methyleneoctahydro-1H-inden-5-yl)-1-benzyl-5-methyl-4,5,6,7-tetrahydro-1H-indazol-6-yl)methanol |
| Ia-19 | ((5R,6S)-5-((3aS,4R,5S,7aS)-4-(aminomethyl)-7a-methyl-1-methyleneoctahydro-1H-inden-5-yl)-2-benzyl-5-methyl-4,5,6,7-tetrahydro-2H-indazol-6-yl)methanol |
| Ia-20 | ((5R,6S)-5-((3aS,4R,5S,7aS)-4-(aminomethyl)-7a-methyl-1-methyleneoctahydro-1H-inden-5-yl)-5-methyl-1-(pyridin-3-yl)-4,5,6,7-tetrahydro-1H-indazol-6-yl)methanol |
| Ia-21 | ((5R,6S)-5-((3aS,4R,5S,7aS)-4-(aminomethyl)-7a-methyl-1-methyleneoctahydro-1H-inden-5-yl)-5-methyl-2-(pyridin-3-yl)-4,5,6,7-tetrahydro-2H-indazol-6-yl)methanol |
| Ia-22 | ((5R,6S)-5-((3aS,4R,5S,7aS)-4-(aminomethyl)-7a-methyl-1-methyleneoctahydro-1H-inden-5-yl)-5-methyl-1-neopentyl-4,5,6,7-tetrahydro-1H-indazol-6-yl)methanol |
| Ia-23 | ((5R,6S)-5-((3aS,4R,5S,7aS)-4-(aminomethyl)-7a-methyl-1-methyleneoctahydro-1H-inden-5-yl)-5-methyl-2-neopentyl-4,5,6,7-tetrahydro-2H-indazol-6-yl)methanol |
| Ia-26 | ((5R6S)-5-((3aR,6S,7R,7aS)-7-(hydroxymethyl-3a-methyl-3a,4,5,6,7,7a-hexahydro-1H-inden-6-yl)-5-methyl-4,5,6,7-tetrahydro-1H-indazol-6-yl)methanol |
| Ia-27 | ((3aS,4S,5S,7aS)-5-((5R,6S)-6-(hydroxymethyl)-5-methyl-4,5,6,7-tetrahydro-1H-indazol-5-yl)-7a-methyloctahydro-1H-inden-4-yl)methanol |
| Ia-28 | ((5R,6S)-5-((3aR,6S,7R,7aS)-7-(aminomethyl)-3a-methyl-3a,4,5,6,7,7a-hexahydro-1H-inden-6-yl)-5-methyl-4,5,6,7-tetrahydro-1H-indazol-6-yl)methanol |
| Ia-29 | ((5R,6S)-5-((1S,3aS,4S,5S,7aR)-4-(aminomethyl)-1-ethyl-7a-methyloctahydro-1H-inden-5-yl)-5-methyl-4,5,6,7-tetrahydro-1H-indazol-6-yl)methanol |
| Ia-30 | ((5R,6S)-5-((3aS,4R,5S,7aS)-4-(aminomethyl)-7a-methyl-1-methyleneoctahydro-1H-inden-5-yl)-3-(difluoromethyl)-5-methyl-4,5,6,7-tetrahydro-1H-indazol-6-yl)methanol |
| Ia-31 | ((5R,6S)-5-((3aS,4R,5S,7aS)-4-(aminomethyl)-7a-methyl-1-methyleneoctahydro-1H-inden-5-yl)-5-methyl-3-(trifluoromethyl)-4,5,6,7-tetrahydro-1H-indazol-6-yl)methanol |
| Ia-32 | ((5R,6S)-5-((3aS,4R,5S,7aS)-4-(aminomethyl)-7a-methyl-1-methyleneoctahydro-1H-inden-5-yl)-3,5-dimethyl-4,5,6,7-tetrahydro-1H-indazol-6-yl)methanol |
| Ia-33 | ((5R,6S)-5-((3aS,4S,5S,7aS)-4-(aminomethyl)-7a-methyloctahydro-1H-inden-5-yl)-5-methyl-4,5,6,7-tetrahydro-1H-indazol-6-yl)methanol |
| Ia-34 | ((5R,6S)-5-((1S,3aS,4S,5S,7aR)-4-(aminomethyl)-1,7a-dimethyloctahydro-1H-inden-5-yl)-5-methyl-4,5,6,7-tetrahydro-1H-indazol-6-yl)methanol |
| Ia-35 | ((5R,6S)-5-((1S,3aS,4S,5S,7aR)-4-(aminomethyl)-1,7a-dimethyloctahydro-1H-inden-5-yl)-5-methyl-1-phenyl-4,5,6,7-tetrahydro-1H-indazol-6-yl)methanol |
| Ia-36 | ((5R,6S)-5-((1S,3aS,4S,5S,7aR)-4-(aminomethyl)-1,7a-dimethyloctahydro-1H-inden-5-yl)-5-methyl-2-phenyl-4,5,6,7-tetrahydro-2H-indazol-6-yl)methanol |
| Ia-37 | ((5R,6S)-5-((1S,3aS,4S,5S,7aR)-4-(aminomethyl)-1,7a-dimethyloctahydro-1H-inden-5-yl)-1-cyclohexyl-5-methyl-4,5,6,7-tetrahydro-1H-indazol-6-yl)methanol |
| Ia-38 | ((5R,6S)-5-((1S,3aS,4S,5S,7aR)-4-(aminomethyl)-1,7a-dimethyloctahydro-1H-inden-5-yl)-5-methyl-1-neopentyl-4,5,6,7-tetrahydro-1H-indazol-6-yl)methanol |
| Ia-39 | ((5R,6S)-5-((1S,3aS,4S,5S,7aR)-4-(aminomethyl)-1,7a-dimethyloctahydro-1H-inden-5-yl)-5-methyl-2-neopentyl-4,5,6,7-tetrahydro-2H-indazol-6-yl)methanol |

TABLE 1-continued

| Cpd No. | Compound Name |
|---|---|
| Ia-40 | ((5R,6S)-5-((1S,3aS,4S,5S,7aR)-4-(aminomethyl)-1,7a-dimethyloctahydro-1H-inden-5-yl)-1-(tert-butyl)-5-methyl-4,5,6,7-tetrahydro-1H-indazol-6-yl)methanol |
| Ia-41 | ((5R,6S)-5-((1S,3aS,4S,5S,7aR)-4-(aminomethyl)-1,7a-dimethyloctahydro-1H-inden-5-yl)-2-(tert-butyl)-5-methyl-4,5,6,7-tetrahydro-2H-indazol-6-yl)methanol |
| Ia-42 | ((5R,6S)-5-((1S,3aS,4S,5S,7aR)-4-(aminomethyl)-1,7a-dimethyloctahydro-1H-inden-5-yl)-5-methyl-1-(pyridin-2-yl)-4,5,6,7-tetrahydro-1H-indazol-6-yl)methanol |
| Ia-43 | ((5R,6S)-5-((1S,3aS,4S,5S,7aR)-4-(aminomethyl)-1,7a-dimethyloctahydro-1H-inden-5-yl)-5-methyl-2-(pyridin-2-yl)-4,5,6,7-tetrahydro-2H-indazol-6-yl)methanol |
| Ia-44 | (5R,6S)-6-(hydroxymethyl)-5-((3aS,4R,5S,7aS)-4-(hydroxymethyl)-7a-methyl-1-methyleneoctahydro-1H-inden-5-yl)-5-methyl-4,5,6,7-tetrahydro-1H-indazole-3-carboxylic acid |
| Ia-45 | ((5R,6S)-6-(hydroxymethyl)-5-((3aS,4R,5S,7aS)-4-(hydroxymethyl)-7a-methyl-1-methyleneoctahydro-1H-inden-5-yl)-5-methyl-4,5,6,7-tetrahydro-1H-indazol-3-yl)(piperidin-1-yl)methanone |
| Ia-46 | ((5R,6S)-6-(hydroxymethyl)-5-((3aS,4R,5S,7aS)-4-(hydroxymethyl)-7a-methyl-1-methyleneoctahydro-1H-inden-5-yl)-5-methyl-4,5,6,7-tetrahydro-1H-indazol-3-yl)(morpholino)methanone |
| Ia-47 | ((5R,6S)-5-methyl-5-((3aS,4R,5S,7aS)-7a-methyl-1-methylene-4-(piperidin-1-ylmethyl)octahydro-1H-inden-5-yl)-4,5,6,7-tetrahydro-1H-indazol-6-yl)methanol |
| Ia-48 | ((5R,6S)-5-methyl-5-((3aS,4R,5S,7aS)-7a-methyl-1-methylene-4-((4-methylpiperazin-1-yl)methyl)octahydro-1H-inden-5-yl)-4,5,6,7-tetrahydro-1H-indazol-6-yl)methanol |
| Ia-49 | ((5R,6S)-5-methyl-5-((3aS,4R,5S,7aS)-7a-methyl-1-methylene-4-(thiomorpholinomethyl)octahydro-1H-inden-5-yl)-4,5,6,7-tetrahydro-1H-indazol-6-yl)methanol |
| Ia-50 | ((5R,6S)-5-methyl-5-((3aS,4R,5S,7aS)-7a-methyl-1-methylene-4-(morpholinomethyl)octahydro-1H-inden-5-yl)-4,5,6,7-tetrahydro-1H-indazol-6-yl)methanol |
| Ia-51 | ((5R,6S)-5-((3aS,4R,5S,7aS)-4-((1H-imidazol-1-yl)methyl)-7a-methyl-1-methyleneoctahydro-1H-inden-5-yl)-5-methyl-4,5,6,7-tetrahydro-1H-indazol-6-yl)methanol |
| Ia-52 | ((5R,6S)-5-((3aS,4R,5S,7aS)-4-((1H-pyrazol-1-yl)methyl)-7a-methyl-1-methyleneoctahydro-1H-inden-5-yl)-5-methyl-4,5,6,7-tetrahydro-1H-indazol-6-yl)methanol |
| Ia-53 | ((5R,6S)-5-((3aS,4R,5S,7aS)-4-((1H-indol-1-yl)methyl)-7a-methyl-1-methyleneoctahydro-1H-inden-5-yl)-5-methyl-4,5,6,7-tetrahydro-1H-indazol-6-yl)methanol |
| Ia-54 | ((5R,6S)-5-((3aS,4R,5S,7aS)-4-((1H-benzo[d]imidazol-1-yl)methyl)-7a-methyl-1-methyleneoctahydro-1H-inden-5-yl)-5-methyl-4,5,6,7-tetrahydro-1H-indazol-6-yl)methanol |
| Ia-55 | ((5R,6S)-5-((3aS,4R,5S,7aS)-4-((6-amino-9H-purin-9-yl)methyl)-7a-methyl-1-methyleneoctahydro-1H-inden-5-yl)-5-methyl-4,5,6,7-tetrahydro-1H-indazol-6-yl)methanol |
| Ia-56 | ((1R,3aS,4S,5S,7aR)-5-((5R,6S)-6-(hydroxymethyl)-5-methyl-4,5,6,7-tetrahydro-1H-indazol-5-yl)-7a-methyl-1-((R)-6-methylheptan-2-yl)octahydro-1H-inden-4-yl)methanol |
| Ia-57 | ((1R,3aS,4S,5S,7aR)-5-((5R,6S)-6-(aminomethyl)-5-methyl-4,5,6,7-tetrahydro-1H-indazol-5-yl)-7a-methyl-1-((R)-6-methylheptan-2-yl)octahydro-1H-inden-4-yl)methanamine |
| Ia-58 | ((3aS,4R,5S,7aS)-5-((5R,6S)-6-(aminomethyl)-5-methyl-4,5,6,7-tetrahydro-1H-indazol-5-yl)-7a-methyl-1-methyleneoctahydro-1H-inden-4-yl)methanamine |
| Ia-59 | (5R,6S)-6-(hydroxymethyl)-5-((3aS,4R,5S,7aS)-4-(hydroxymethyl)-7a-methyl-1-methyleneoctahydro-1H-inden-5-yl)-5-methyl-4,5,6,7-tetrahydro-1H-indazole-3-carboxamide |
| Ia-60 | (2R,3aS,4R,5S,7aS)-4-(hydroxymethyl)-5-((5R,6S)-6-(hydroxymethyl)-5-methyl-4,5,6,7-tetrahydro-1H-indazol-5-yl)-7a-methyl-1-methyleneoctahydro-1H-inden-2-ol |
| Ia-61 | (2R,4R,5S)-4-(hydroxymethyl)-5-((5R,6S)-6-(hydroxymethyl)-5-methyl-4,5,6,7-tetrahydro-1H-indazol-5-yl)-1,1-dimethyl-2,3,4,5,6,7-hexahydro-1H-inden-2-ol |
| Ia-62 | ((1R,3aS,4S,5S,7aS)-5-((5R,6S)-6-(hydroxymethyl)-5-methyl-4,5,6,7-tetrahydro-1H-indazol-5-yl)-7a-methyl-1-(prop-1-en-2-yl)octahydro-1H-inden-4-yl)methanol |
| Ia-63 | ((5R,6S)-5-((1R,3aS,4S,5S,7aS)-4-(aminomethyl)-7a-methyl-1-(prop-1-en-2-yl)octahydro-1H-inden-5-yl)-5-methyl-4,5,6,7-tetrahydro-1H-indazol-6-yl)methanol |
| Ia-64 | ((5R,6S)-5-((3aS,4R,5S,7aS,E)-1-ethylidene-4-(hydroxymethyl)-7a-methyloctahydro-1H-inden-5-yl)-5-methyl-4,5,6,7-tetrahydro-1H-indazol-6-yl)methanol |
| Ia-65 | ((5R,6S)-5-((3aS,4R,5S,7aS)-4-(aminomethyl)-1-ethylidene-7a-methyloctahydro-1H-inden-5-yl)-5-methyl-4,5,6,7-tetrahydro-1H-indazol-6-yl)methanol |

TABLE 1-continued

| Cpd No. | Compound Name |
|---|---|
| Ia-66 | (2S,3aS,4R,5S,7aS)-4-(hydroxymethyl)-5-((5R,6S)-6-(hydroxymethyl)-5-methyl-4,5,6,7-tetrahydro-1H-indazol-5-yl)-7a-methyl-1-methyleneoctahydro-1H-inden-2-ol |
| Ia-67 | ((5R,6S)-5-((3aS,6S,7R,7aS)-7-(aminomethyl)-3,3a-dimethyl-3a,4,5,6,7,7a-hexahydro-1H-inden-6-yl)-5-methyl-4,5,6,7-tetrahydro-1H-indazol-6-yl)methanol |
| Ia-68 | ((5R,6S)-5-methyl-5-((3aS,4R,5S,7aS)-7a-methyl-4-((methylamino)methyl)-1-methyleneoctahydro-1H-inden-5-yl)-4,5,6,7-tetrahydro-1H-indazol-6-yl)methanol |
| Ia-69 | ((5R,6S)-5-((1S,3aS,4S,5S,7aR)-1,7a-dimethyl-4-((methylamino)methyl)octahydro-1H-inden-5-yl)-5-methyl-4,5,6,7-tetrahydro-1H-indazol-6-yl)methanol |
| Ia-70 | ((5R,6S)-5-((3aS,4R,5S,7aS)-4-((dimethylamino)methyl)-7a-methyl-1-methyleneoctahydro-1H-inden-5-yl)-5-methyl-4,5,6,7-tetrahydro-1H-indazol-6-yl)methanol |
| Ia-71 | ((5R,6S)-5-((1S,3aS,4S,5S,7aR)-4-((dimethylamino)methyl)-1,7a-dimethyloctahydro-1H-inden-5-yl)-5-methyl-4,5,6,7-tetrahydro-1H-indazol-6-yl)methanol |
| Ia-72 | ((3aS,4R,5S,7aS)-7a-methyl-5-((5R,6S)-5-methyl-6-(morpholinomethyl)-4,5,6,7-tetrahydro-1H-indazol-5-yl)-1-methyleneoctahydro-1H-inden-4-yl)methanol |
| Ia-73 | ((3aS,4R,5S,7aS)-7a-methyl-5-((5R,6S)-5-methyl-6-((4-methylpiperazin-1-yl)methyl)-4,5,6,7-tetrahydro-1H-indazol-5-yl)-1-methyleneoctahydro-1H-inden-4-yl)methanol |
| Ia-74 | ((3aS,4R,5S,7aS)-7a-methyl-5-((5R,6S)-5-methyl-6-(piperidin-1-ylmethyl)-4,5,6,7-tetrahydro-1H-indazol-5-yl)-1-methyleneoctahydro-1H-inden-4-yl)methanol |
| Ia-75 | ((3aS,4R,5S,7aS)-7a-methyl-5-((5R,6S)-5-methyl-6-(thiomorpholinomethyl)-4,5,6,7-tetrahydro-1H-indazol-5-yl)-1-methyleneoctahydro-1H-inden-4-yl)methanol |
| Ia-76 | ((3aS,4R,5S,7aS)-7a-methyl-5-((5R,6S)-5-methyl-6-(morpholinomethyl)-4,5,6,7-tetrahydro-1H-indazo1-5-yl)-1-methyleneoctahydro-1H-inden-4-yl)methanamine |
| Ia-77 | ((3aS,4R,5S,7aS)-7a-methyl-5-((5R,6S)-5-methyl-6-((4-methylpiperazin-1-yl)methyl)-4,5,6,7-tetrahydro-1H-indazol-5-yl)-1-methyleneoctahydro-1H-inden-4-yl)methanamine |
| Ia-78 | ((3aS,4R,5S,7aS)-7a-methyl-5-((5R,6S)-5-methyl-6-(piperidin-1-ylmethyl)-4,5,6,7-tetrahydro-1H-indazo1-5-yl)-1-methyleneoctahydro-1H-inden-4-yl)methanamine |
| Ia-79 | ((3aS,4R,5S,7aS)-7a-methyl-5-((5R,6S)-5-methyl-6-(thiomorpholinomethyl)-4,5,6,7-tetrahydro-1H-indazol-5-yl)-1-methyleneoctahydro-1H-inden-4-yl)methanamine |
| Ia-80 | (3aR,4R,5R,7aS)-7a-methyl-5-((5S,6S)-5-methyl-6-(morpholinomethyl)-4,5,6,7-tetrahydro-1H-indazol-5-yl)-1-methyleneoctahydro-1H-inden-4-ol |
| Ia-81 | (3aR,4R,5R,7aS)-7a-methyl-5-((5S,6S)-5-methyl-6-((4-methylpiperazin-1-yl)methyl)-4,5,6,7-tetrahydro-1H-indazol-5-yl)-1-methyleneoctahydro-1H-inden-4-ol |
| Ia-82 | ((3aS,4R,5S,7aS)-5-((5R,6S)-6-(aminomethyl)-5-methyl-4,5,6,7-tetrahydro-1H-indazol-5-yl)-7a-methyl-1-methyleneoctahydro-1H-inden-4-yl)methanol |
| Ia-83 | (3aR,4R,5R,7aS)-5-((5S,6S)-6-(hydroxymethyl)-5-methyl-2-(pyridin-2-yl)-4,5,6,7-tetrahydro-2H-indazol-5-yl)-7a-methyl-1-methyleneoctahydro-1H-inden-4-ol |
| Ia-84 | (3aR,4R,5R,7aS)-5-((5S,6S)-6-(hydroxymethyl)-5-methyl-2-(pyrazin-2-yl)-4,5,6,7-tetrahydro-2H-indazol-5-yl)-7a-methyl-1-methyleneoctahydro-1H-inden-4-ol |
| Ia-85 | (3aR,4R,5R,7aS)-5-((5S,6S)-6-(hydroxymethyl)-5-methyl-2-(pyrimidin-2-yl)-4,5,6,7-tetrahydro-2H-indazol-5-yl)-7a-methyl-1-methyleneoctahydro-1H-inden-4-ol |
| Ib-1 | ((3aS,4R,5S,7aS)-5-((6R,7S)-7-(hydroxymethyl)-6-methyl-5,6,7,8-tetrahydroquinoxalin-6-yl)-7a-methyl-1-methyleneoctahydro-1H-inden-4-yl)methanol |
| Ib-2 | ((6S,7R)-7-((3aS,4R,5S,7aS)-4-(aminomethyl)-7a-methyl-1-methyleneoctahydro-1H-inden-5-yl)-7-methyl-5,6,7,8-tetrahydroquinoxalin-6-yl)methanol |
| Ib-3 | ((1R,3aS,4S,5S,7aR)-5-((6R,7S)-7-(hydroxymethyl)-6-methyl-5,6,7,8-tetrahydroquinoxalin-6-yl)-7a-methyl-1-((R)-6-methylheptan-2-yl)octahydro-1H-inden-4-yl)methanol |
| Ib-4 | ((6S,7R)-7-((1R,3aS,4S,5S,7aR)-4-(aminomethyl)-7a-methyl-1-((R)-6-methylheptan-2-yl)octahydro-1H-inden-5-yl)-7-methyl-5,6,7,8-tetrahydroquinoxalin-6-yl)methanol |
| Ic-1 | ((6R,7S)-2-amino-6-((3aS,4R,5S,7aS)-4-(aminomethyl)-7a-methyl-1-methyleneoctahydro-1H-inden-5-yl)-6-methyl-5,6,7,8-tetrahydroquinazolin-7-yl)methanol |
| Ic-2 | ((6R,7S)-6-((3aS,4R,5S,7aS)-4-(aminomethyl)-7a-methyl-1-methyleneoctahydro-1H-inden-5-yl)-2,6-dimethyl-5,6,7,8-tetrahydroquinazolin-7-yl)methanol |

TABLE 1-continued

| Cpd No. | Compound Name |
|---|---|
| Ic-3 | ((6R,7S)-6-((3aS,4R,5S,7aS)-4-(aminomethyl)-7a-methyl-1-methyleneoctahydro-1H-inden-5-yl)-6-methyl-5,6,7,8-tetrahydroquinazolin-7-yl)methanol |
| Ic-4 | ((1R,3aS,4S,5S,7aR)-5-((6R,7S)-7-(hydroxymethyl)-2,6-dimethyl-5,6,7,8-tetrahydroquinazolin-6-yl)-7a-methyl-1-((R)-6-methylheptan-2-yl)octahydro-1H-inden-4-yl)methanol |
| Ic-5 | ((6R,7S)-6-((1R,3aS,4S,5S,7aR)-4-(aminomethyl)-7a-methyl-1-((R)-6-methylheptan-2-yl)octahydro-1H-inden-5-yl)-2,6-dimethyl-5,6,7,8-tetrahydroquinazolin-7-yl)methanol |
| Ic-6 | ((6R,7S)-2-amino-6-((1R,3aS,4S,5S,7aR)-4-(hydroxymethyl)-7a-methyl-1-((R)-6-methylheptan-2-yl)octahydro-1H-inden-5-yl)-6-methyl-5,6,7,8-tetrahydroquinazolin-7-yl)methanol |
| Ic-7 | ((6R,7S)-2-amino-6-((1R,3aS,4S,5S,7aR)-4-(aminomethyl)-7a-methyl-1-((R)-6-methylheptan-2-yl)octahydro-1H-inden-5-yl)-6-methyl-5,6,7,8-tetrahydroquinazolin-7-yl)methanol |
| Ic-8 | ((1R,3aS,4S,5S,7aR)-5-((6R,7S)-7-(hydroxymethyl)-6-methyl-5,6,7,8-tetrahydroquinazolin-6-yl)-7a-methyl-1-((R)-6-methylheptan-2-yl)octahydro-1H-inden-4-yl)methanol |
| Ic-9 | ((6R,7S)-6-((1R,3aS,4S,5S,7aR)-4-(aminomethyl)-7a-methyl-1-((R)-6-methylheptan-2-yl)octahydro-1H-inden-5-yl)-6-methyl-5,6,7,8-tetrahydroquinazolin-7-yl)methanol |
| Ic-10 | ((6R,7S)-2-amino-6-((3aS,4R,5S,7aS)-4-(hydroxymethyl)-7a-methyl-1-methyleneoctahydro-1H-inden-5-yl)-6-methyl-5,6,7,8-tetrahydroquinazolin-7-yl)methanol |
| Ic-11 | ((3aS,4R,5S,7aS)-5-((6R,7S)-7-(hydroxymethyl)-6-methyl-5,6,7,8-tetrahydroquinazolin-6-yl)-7a-methyl-1-methyleneoctahydro-1H-inden-4-yl)methanol |
| Ic-12 | ((3aS,4R,5S,7aS)-5-((6R,7S)-7-(hydroxymethyl)-2,6-dimethyl-5,6,7,8-tetrahydroquinazolin-6-yl)-7a-methyl-1-methyleneoctahydro-1H-inden-4-yl)methanol |
| Ic-13 | ((3aS,4R,5S,7aS)-5-((2R,3S)-3-(hydroxymethyl)-2-methyl-1,2,3,4-tetrahydrobenzo[4,5]imidazo[2,1-b]quinazolin-2-yl)-7a-methyl-1-methyleneoctahydro-1H-inden-4-yl)methanol |
| Ic-14 | ((2R,3S)-2-((3aS,4R,5S,7aS)-4-(aminomethyl)-7a-methyl-1-methyleneoctahydro-1H-inden-5-yl)-2-methyl-1,2,3,4-tetrahydrobenzo[4,5]imidazo[2,1-b]quinazolin-3-yl)methanol |
| Id-1 | ((5R,6S)-5-((3aS,4R,5S,7aS)-4-(aminomethyl)-7a-methyl-1-methyleneoctahydro-1H-inden-5-yl)-5-methyl-4,5,6,7-tetrahydro-1H-indol-6-yl)methanol |
| Ie-1 | ((5S,6R)-6-((3aS,4R,5S,7aS)-4-(aminomethyl)-7a-methyl-1-methyleneoctahydro-1H-inden-5-yl)-2,6-dimethyl-4,5,6,7-tetrahydrobenzo[d]thiazol-5-yl)methanol |
| Ie-2 | ((5S,6R)-2-amino-6-((3aS,4R,5S,7aS)-4-(aminomethyl)-7a-methyl-1-methyleneoctahydro-1H-inden-5-yl)-6-methyl-4,5,6,7-tetrahydrobenzo[d]thiazol-5-yl)methanol |
| Ie-3 | ((1R,3aS,4S,5S,7aR)-5-((5S,6R)-2-amino-5-(hydroxymethyl)-6-methyl-4,5,6,7-tetrahydrobenzo[d]thiazol-6-yl)-7a-methyl-1-((R)-6-methylheptan-2-yl)octahydro-1H-inden-4-yl)methanol |
| Ie-4 | ((5S,6R)-2-amino-6-((1R,3aS,4S,5S,7aR)-4-(aminomethyl)-7a-methyl-1-((R)-6-methylheptan-2-yl)octahydro-1H-inden-5-yl)-6-methyl-4,5,6,7-tetrahydrobenzo[d]thiazol-5-yl)methanol |
| If-1 | ((1R,3aS,4S,5S,7aR)-5-((5S,6R)-5-(hydroxymethyl)-6-methyl-4,5,6,7-tetrahydrobenzo[d][1,2,3]thiadiazol-6-yl)-7a-methyl-1-((R)-6-methylheptan-2-yl)octahydro-1H-inden-4-yl)methanol |
| If-2 | ((5S,6R)-6-((1R,3aS,4S,5S,7aR)-4-(aminomethyl)-7a-methyl-1-((R)-6-methylheptan-2-yl)octahydro-1H-inden-5-yl)-6-methyl-4,5,6,7-tetrahydrobenzo[d][1,2,3]thiadiazol-5-yl)methanol |
| Ig-1 | ((5R,6S)-5-((3aS,4R,5S,7aS)-4-(aminomethyl)-7a-methyl-1-methyleneoctahydro-1H-inden-5-yl)-5-methyl-4,5,6,7-tetrahydrobenzo[c]isoxazol-6-yl)methanol |
| Ih-1 | ((1R,3aS,4S,5S,7aR)-5-((5R,6S)-6-(hydroxymethyl)-5-methyl-4,5,6,7-tetrahydrobenzo[d]isoxazol-5-yl)-7a-methyl-1-((R)-6-methylheptan-2-yl)octahydro-1H-inden-4-yl)methanol |
| Ih-2 | ((5R,6S)-5-((3aS,6S,7R,7aS)-7-(aminomethyl)-3,3a-dimethyl-3a,4,5,6,7,7a-hexahydro-1H-inden-6-yl)-5-methyl-4,5,6,7-tetrahydrobenzo[d]isoxazol-6-yl)methanol |
| Ih-3 | ((5R,6S)-5-((4R,5S)-4-(aminomethyl)-1,1-dimethyl-2,3,4,5,6,7-hexahydro-1H-inden-5-yl)-5-methyl-4,5,6,7-tetrahydrobenzo[d]isoxazol-6-yl)methanol |
| Ii-1 | ((3aS,4R,5S,7aS)-5-((5R,6S)-6-(hydroxymethyl)-2,5-dimethyl-4,5,6,7-tetrahydrobenzo[d]oxazol-5-yl)-7a-methyl-1-methyleneoctahydro-1H-inden-4-yl)methanol |
| Ii-2 | ((5R,6S)-5-((3aS,4R,5S,7aS)-4-(aminomethyl)-7a-methyl-1-methyleneoctahydro-1H-inden-5-yl)-2,5-dimethyl-4,5,6,7-tetrahydrobenzo[d]oxazol-6-yl)methanol |

The following Synthetic Examples, which are directed to the synthesis of the compounds of the invention; and the following Biological Examples, which are directed to representative biological assays for the compounds of the invention, are provided as a guide to assist in the practice of the invention, and are not intended as a limitation on the scope of the invention.

Synthetic Example 1

Synthesis of ((5R,6S)-5-((3aS,4R,5S,7aS)-4-(aminomethyl)-7a-methyl-1-methyleneoctahydro-1H-inden-5-yl)-5-methyl-4,5,6,7-tetrahydro-1H-indazol-6-yl)methanol (Compound Ia-1)

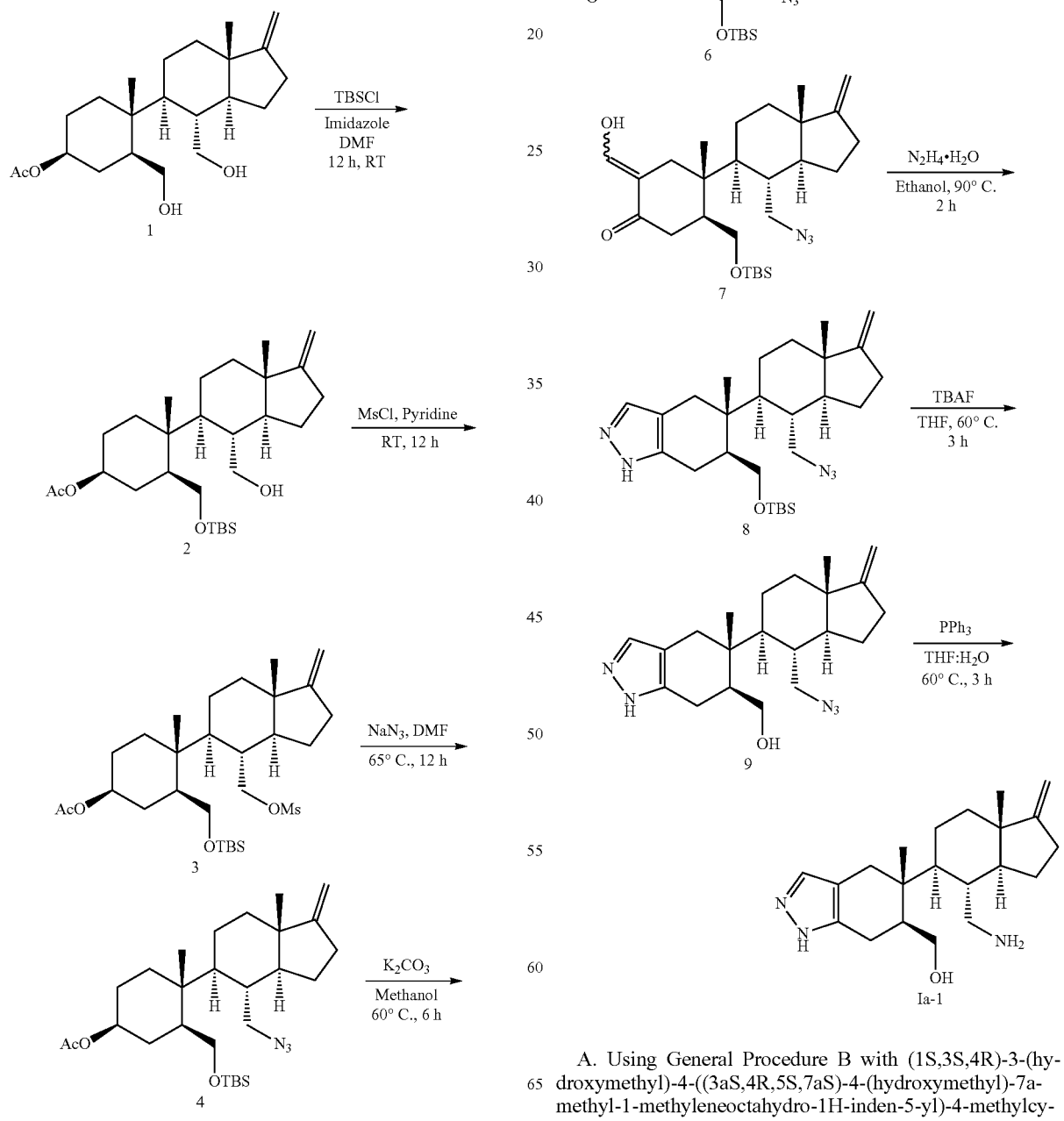

A. Using General Procedure B with (1S,3S,4R)-3-(hydroxymethyl)-4-((3aS,4R,5S,7aS)-4-(hydroxymethyl)-7a-methyl-1-methyleneoctahydro-1H-inden-5-yl)-4-methylcyclohexyl acetate (Compound 1, as prepared in U.S. Pat. No.

7,601,874, 5.0 g, 13.72 mmol imidazole (1.40 g, 20.58 mmol), tert-butyldimethylsilyl chloride (2.26 g, 15.09 mmol) and DMF (50 mL) gave the desired alcohol, (1S,3S,4R)-3-(((tert-butyldimethylsilyl)oxy)methyl)-4-((3aS,4R,5S,7aS)-4-(hydroxymethyl)-7a-methyl-1-methyleneoctahydro-1H-inden-5-yl)-4-methylcyclohexyl acetate (Compound 2, 3.45 g, 53%), as a white foam after purification by column chromatography (230-400 mesh silica gel, eluted with 0-40% pet ether/ethyl acetate).

B. Using General Procedure J with Compound 2 (3.45 g, 7.21 mmol), MsCl (1.12 mL, 14.41 mmol) and pyridine (30 mL) gave the desired mesylate, (1S,3S,4R)-3-(((tert-butyldimethylsilyl)oxy)methyl)-4-methyl-4-((3aS,4R,5S,7aS)-7a-methyl-1-methylene-4-(((methylsulfonyl)oxy)methyl)octahydro-1H-inden-5-yl)cyclohexyl acetate (Compound 3, 3.5 g, 87%), as a white solid which was used as is for the next step without any further purification.

C. Using General Procedure K with Compound 3 (3.5 g, 6.29 mmol), sodium azide (0.82 g, 12.58 mmol) and DMF (35 mL) gave the desired azide, (1S,3S,4R)-4-((3aS,4R,5S,7aS)-4-(azidomethyl)-7a-methyl-1-methyleneoctahydro-1H-inden-5-yl)-3-(((tert-butyldimethylsilyl)oxy)methyl)-4-methylcyclohexyl acetate (Compound 4, 2.8 g, 88%), as an off-white solid which was used as is for the next step without any further purification.

D. Using General Procedure L with Compound 4 (2.8 g, 5.56 mmol), potassium carbonate (anhydrous, 1.54 g, 11.13 mmol) and methanol (30 mL) gave the desired azide, (1S,3S,4R)-4-((3aS,4R,5S,7aS)-4-(azidomethyl)-7a-methyl-1-methyleneoctahydro-1H-inden-5-yl)-3-(((tert-butyldimethylsilyl)oxy)methyl)-4-methylcyclohexan-1-ol (Compound 5, 2.2 g, 86%), as a white solid after purification by column chromatography (230-400 mesh silica gel, eluted with 0-10% pet ether/ethyl acetate).

E. Using General Procedure M with Compound 5 (2.2 g, 4.77 mmol), molecular sieves (4 Å, 2.2 g), NMO-$H_2O$ (1.12 g, 9.54 mmol), TPAP (0.17 g, 0.47 mmol) and dichloromethane (20 mL) gave the desired ketone, (3S,4R)-4-((3aS,4R,5S,7aS)-4-(azidomethyl)-7a-methyl-1-methyleneoctahydro-1H-inden-5-yl)-3-(((tert-butyldimethylsilyl)oxy)methyl)-4-methylcyclohexan-1-one (Compound 6, 1.5 g, 68%), as a white solid after purification by column chromatography (230-400 mesh silica gel, eluted with 0-5% pet ether/ethyl acetate).

F. Using General Procedure O with Compound 6 (1.5 g, 3.27 mmol), sodium hydride (60% in paraffin oil, 0.52 g, 13.06 mmol), ethyl formate (1.6 mL, 19.59 mmol) and THF (15 mL) gave the desired ketone, (4R,5S)-4-((3aS,4R,5S,7aS)-4-(azidomethyl)-7a-methyl-1-methyleneoctahydro-1H-inden-5-yl)-5-(((tert-butyldimethylsilyl)oxy)methyl)-2-(hydroxymethylene)-4-methylcyclohexan-1-one (Compound 7, 1.4 g, 88%), as a pale brown solid after purification by column chromatography (230-400 mesh silica gel, eluted with 0-5% pet ether/ethyl acetate).

G. Using General Procedure P with Compound 7 (1.4 g, 2.87 mmol), hydrazine hydrate (0.21 ml, 4.31 mmol), and ethanol (15 mL) gave the desired pyrazole, (5R,6S)-5-((3aS,4R,5S,7aS)-4-(azidomethyl)-7a-methyl-1-methyleneoctahydro-1H-inden-5-yl)-6-(((tert-butyldimethylsilyl)oxy)methyl)-5-methyl-4,5,6,7-tetrahydro-1H-indazole (Compound 8, 1.2 g, 86%), as a brown foam after purification by column chromatography (230-400 mesh silica gel, eluted with 0-30% pet ether/ethyl acetate).

H. Using General Procedure Q with Compound 8 (1.2 g, 2.48 mmol), TBAF solution (1M in THF, 4.96 mL, 4.96 mmol), and THF (10 mL) gave the desired alcohol, ((5R,6S)-5-((3aS,4R,5S,7aS)-4-(azidomethyl)-7a-methyl-1-methyleneoctahydro-1H-inden-5-yl)-5-methyl-4,5,6,7-tetrahydro-1H-indazol-6-yl)methanol (Compound 9, 0.80 g, 87%), as a yellow solid after purification by column chromatography (230-400 mesh silica gel, eluted with 0-60% pet ether/ethyl acetate).

I. Following the General Procedure R with Compound 9 (0.8 g, 1.65 mmol) and triphenylphosphine (0.87 g, 3.31 mmol) in THF and water (9:1, 10 mL) gave the desired alcohol, ((5R,6S)-5-((3aS,4R,5S,7aS)-4-(aminomethyl)-7a-methyl-1-methyleneoctahydro-1H-inden-5-yl)-5-methyl-4,5,6,7-tetrahydro-1H-indazol-6-yl)methanol (Compound Ia-1, 0.44 g, 59%), as an off white solid after purification by column chromatography (neutral alumina, eluted with 0-5% dichloromethane/methanol).

LCMS: (Method 1b) MS m/z: 344.2 (M+1), $t_R$: 2.504 min, Purity: 90.96% (max).

HPLC: (Method 2a), $t_R$: 2.421 min, Purity: 89.14% (max).

$^1$H-NMR (400 MHz, $CD_3OD$): δ 7.31 (s, 1H), 4.66 (s, 2H), 3.96 (dd, J=2.4, 10.8 Hz, 1H), 3.43-3.38 (m, 1H), 3.27-3.23 (m, 1H), 3.16-3.10 (m, 1H), 2.90-2.86 (m, 1H), 2.70-2.67 (m, 1H), 2.57-2.52 (m, 2H), 2.41-2.37 (m, 2H), 2.17-2.15 (m, 1H), 1.92-1.79 (m, 4H), 1.65-1.58 (m, 2H), 1.46-1.27 (m, 3H), 1.07 (s, 3H), 0.88 (s, 3H).

J. Alternatively, the conversion of Compound 9 to Compound Ia-1 could be performed using General Procedure S with Compound 8 (0.8 g, 1.65 mmol), LAH solution (1 M in THF, 3.31 mL, 3.31 mmol), and tetrahydrofuran (10 mL) gave the desired alcohol, ((5R,6S)-5-((3aS,4R,5S,7aS)-4-(aminomethyl)-7a-methyl-1-methyleneoctahydro-1H-inden-5-yl)-5-methyl-4,5,6,7-tetrahydro-1H-indazol-6-yl)methanol (Compound Ia-1, 0.44 g, 59%), as an off white solid after purification by column chromatography (neutral alumina, eluted with 0-5% dichloromethane/methanol).

Synthetic Example 2

Synthesis of ((5R,6S)-5-((4R,5S)-4-(aminomethyl)-1,1-dimethyl-2,3,4,5,6,7-hexahydro-1H-inden-5-yl)-5-methyl-4,5,6,7-tetrahydro-1H-indazol-6-yl)methanol (Compound Ia-2)

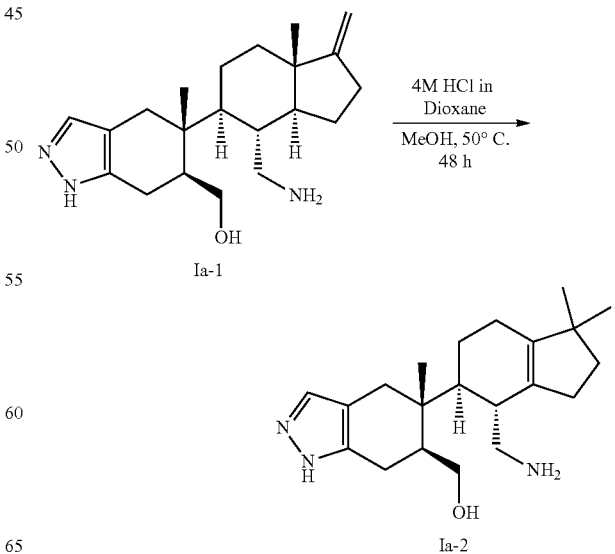

Using General Procedure W with Compound Ia-1 (from Example 1, 350 mg, 1 mmol, 1 eq), 4 M HC in dioxane (1 mL), and methanol (10 mL) gave the desired alcohol, ((5R,6S)-5-((4R,5S)-4-(aminomethyl)-1,1-dimethyl-2,3,4,5,6,7-hexahydro-1H-inden-5-yl)-5-methyl-4,5,6,7-tetrahydro-1H-indazol-6-yl)methanol (Compound Ia-2, 200 mg, 57%), as a white solid after purification by preparative HPLC (Method 3a).

LCMS: (Method 1b) MS m/z: 344.5 (M+1), $t_R$: 2.636 min, Purity: 97.47% (max), 9516% (220 nm).

HPLC: (Method 2a) $t_R$: 2.695 min, Purity: 98.27% (max), 97.66% (220 nm).

$^1$H-NMR (400 MHz, CD$_3$OD): δ 7.29 (s, 1H), 4.03 (dd, J=2.8, 10.8 Hz, 1H), 3.48-3.43 (m, 1H), 3.37-3.33 (m, 1H), 3.12-3.07 (m, 2H), 2.89 (dd, J=9.7, 12.8 Hz, 1H), 2.57-2.50 (m, 4H), 2.47-2.03 (m, 6H), 1.83-1.70 (m, 3H), 1.05 (s, 3H), 0.99 (s, 3H), 0.88 (s, 3H).

Synthetic Example 3

Synthesis of ((5R,6S)-5-((3aS,4R,5S,7aS)-4-((((2,2-difluorobenzo[d][1,3]dioxo-5-yl)methyl)amino)methyl)-7a-methyl-1-methyleneoctahydro-1H-inden-5-yl)-5-methyl-4,5,6,7-tetrahydro-1H-indazol-6-yl)methanol (Compound Ia-3)

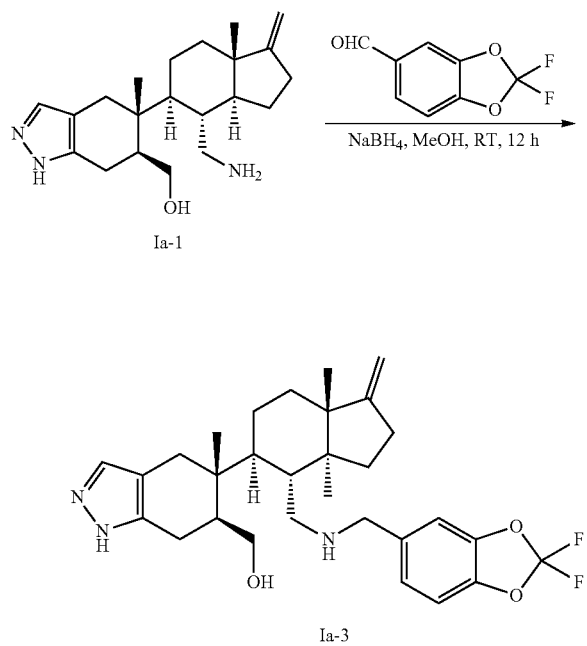

Using General Procedure U with Compound Ia-1 (from Example 1, 0.2 g, 0.582 mmol, 1 eq), 2,2-difluorobenzo[d][1,3]dioxole-5-carbaldehyde (0105 g, 0.582 mmol, 1 eq), sodium borohydride (24 mg, 0.643 mmol, 1.1 eq) and methanol (10 mL) gave the desired amine, ((5R,6S)-5-((3aS,4R,5S,7aS)-4-((((2,2-difluorobenzo[d][1,3]dioxol-5-yl)methyl)amino)methyl)-7a-methyl-1-methyleneoctahydro-1H-inden-5-yl)-5-methyl-4,5,6,7-tetrahydro-1H-indazol-6-yl)methanol (Compound Ia-3, 0.13 g, 44%), as a white solid after purification flash column chromatography (Neutral alumina, eluted with 0-5% dichloromethane/methanol).

LCMS: (Method 1b) MS m/z: 514.2 (M+1), $t_R$: 3.63 min, Purity: 92.65% (max), 92.32% (220 nm).

HPLC: (Method 2a) $t_R$: 3.61 min, Purity: 91.15% (max), 90.88% (220 nm).

$^1$H-NMR (400 MHz, CD$_3$OD): δ 7.27-7.23 (m, 2H), 7.12-7.10 (m, 2H), 4.62-4.57 (s, 2H), 3.95-3.92 (m, 1H), 3.75 (d, J=13.3 Hz, 1H), 367 (d, J=13.3 Hz, 1H), 3.39-3.37 (m, 1H), 3.22-3.16 (m, 1H), 2.96-2.93 (m, 1H), 2.67-2.45 (m, 4H), 2.30-2.19 (m, 3H), 1.80-1.64 (m, 5H), 1.51-1.32 (m, 3H), 1.21-1.17 (m, 1H), 1.04 (s, 3H), 0.83 (s, 3H).

Synthetic Example 4

Synthesis of ((5R,6S)-5-((4R,5S)-4-(hydroxylethyl)-1,1-dimethyl-2,3,4,5,6,7-hexahydro-1H-inden-5-yl)-5-methyl-4,5,6,7-tetrahydro-1H-indazol-6-yl)methanol (Compound Ia-4)

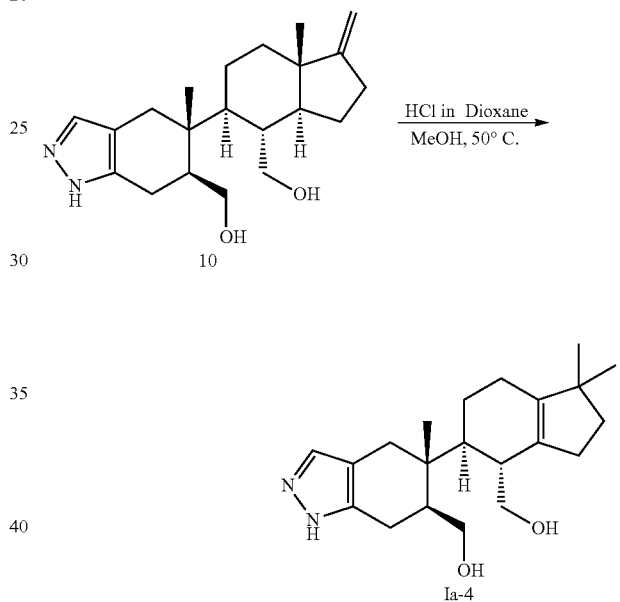

Using General Procedure W with ((3aS,4R,5S,7aS)-5-((5R,6S)-6-(hydroxymethyl)-5-methyl-4,5,6,7-tetrahydro-1H-indazol-5-yl)-7a-methyl-1-methyleneoctahydro-1H-inden-4-yl)methanol (Compound 10, as prepared in U.S. Pat. No. 9,765,085, 0.3 g, 0.87 mmol, 1 eq), HCl in dioxane (6 mL), and methanol (3 mL) gave the desired alcohol, ((5R,6S)-5-((4R,5S)-4-(hydroxymethyl)-1,1-dim ethyl-2,3,4,5,6,7-hexahydro-1H-inden-5-yl)-5-methyl-4,5,6,7-tetrahydro-1H-indazol-6-yl)methanol (Compound Ia-4, 0.07 g, 23%), as a white solid after purification by flash column chromatography (230-400 mesh silica gel, eluted with 0-10% dichloromethane/methanol).

LCMS: (Method 1a) MS n/z: 345.2 (M+1), $t_R$: 2.438 min, Purity: 98.25% (ELSD), 89.89% (220 nm).

HPLC: (Method 2a) $t_R$: 3.504 min, Purity: 98.52% (ELSD), 85.94% (220 nm).

$^1$H-NMR (400 MHz, CD$_3$OD): δ 7.99 (s, 1H), 3.99 (dd, J=3.2, 10.6 Hz, 1H), 3.67 (dd, J=4.0, 10.8 Hz, 1H), 339-3.26 (m, 2H), 2.82-2.65 (m, 2H), 2.40-2.30 (m, 1H), 2.31-2.21 (m, 3H), 1.97-1.95 (m, 4H), 1.70-1.63 (m, 3H), 1.00 (s, 3H), 0.95 (s, 3H), 0.87 (s, 3H).

Synthetic Example 5

Synthesis of ((5R,6S)-5-((1S,3aS,4S,5S,7aR)-4-(hydroxymethyl)-1,7a-dimethyloctahydro-1H-inden-5-yl)-5-methyl-4,5,6,7-tetrahydro-1H-indazol-6-yl)methanol (Compound Ia-5)

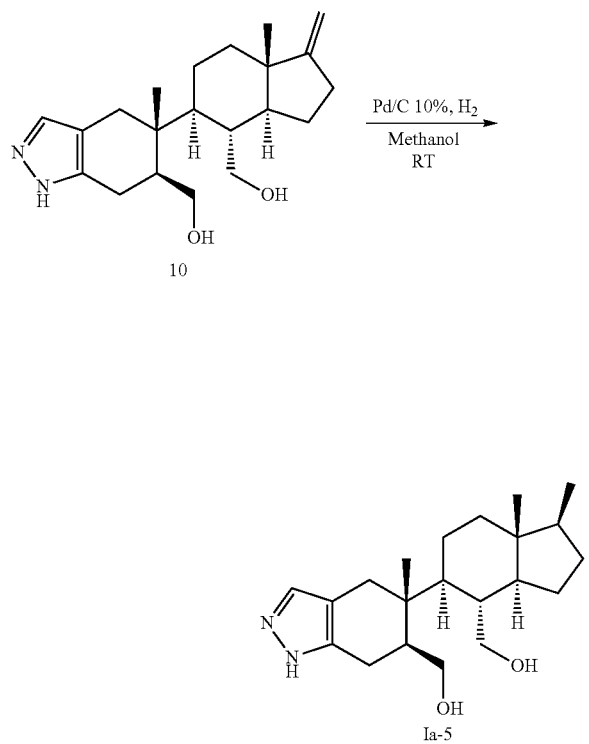

Using General Procedure T with ((3aS,4R,5S,7aS)-5-((5R,6S)-6-(hydroxymethyl)-5-methyl-4,5,6,7-tetrahydro-1H-indazol-5-yl)-7a-methyl-1-methyleneoctahydro-1H-inden-4-yl)methanol (Compound 10, as prepared in U.S. Pat. No. 9,765,085, 0.3 g, 0.87 mol, 1 eq), palladium on carbon (10%, 0.06 g), methanol (7.5 mL) and ethyl acetate (2.5 mL) gave the desired alcohol, ((5R,6S)-5-((1,S,aS, 4S,5S,7aR)-4-(hydroxymethyl)-1,7a-dimethyloctahydro-1H-inden-5-yl)-5-methyl-4,5,6,7-tetrahydro-1H-indazol-6-yl)methanol (Compound Ia-5, 0.16 g, 53%), as a white solid after purification by flash column chromatography (230-400 mesh silica gel, eluted with 0-10% dichloromethane/methanol).

LCMS: (Method 1a) MS m/z: 347.2 (M+1), $t_R$: 2.496 min, Purity: 96.15% (ELSD).

HPLC: (Method 2a) $t_R$: 3.635 min, Purity: 95.50% (UV), 90.40% (220 nm).

$^1$H-NMR (400 MHz, DMSO-$d_6$): δ 12.22 (s, 1H), 7.33 (s, 1H), 4.41 (s, 1H), 4.20 (m, 1H), 3.80 (dd, J=4.4, 10.6 Hz, 1H), 3.71 (d, J=10.4 Hz, 1H), 3.44 (dd, J=3, 6, 10.8 Hz, 1H), 3.18-3.12 (m, 1H), 2.99 (dd, J=5.6, 16.8 Hz, 1H), 2.51-2.08 (m, 4H), 1.75-1.56 (m, 5H), 1.42-1.31 (m, 4H), 1.16-1.12 (m, 2H), 0.97 (s, 3H), 0.80 (d, J=6.8 Hz, 3H) 0.81-0.73 (m, 1H), 0.53 (s, 3H).

Synthetic Example 6

Synthesis of ((5R,6S)-5-((1R,3aS,4S,5S,7aR)-4-(aminomethyl)-7a-methyl-1-((R)-6-methylheptan-2-yl)octahydro-1H-inden-5-yl)-5-methyl-4,5,6,7-tetrahydro-1H-indazol-6-yl)methanol (Compound Ia-6)

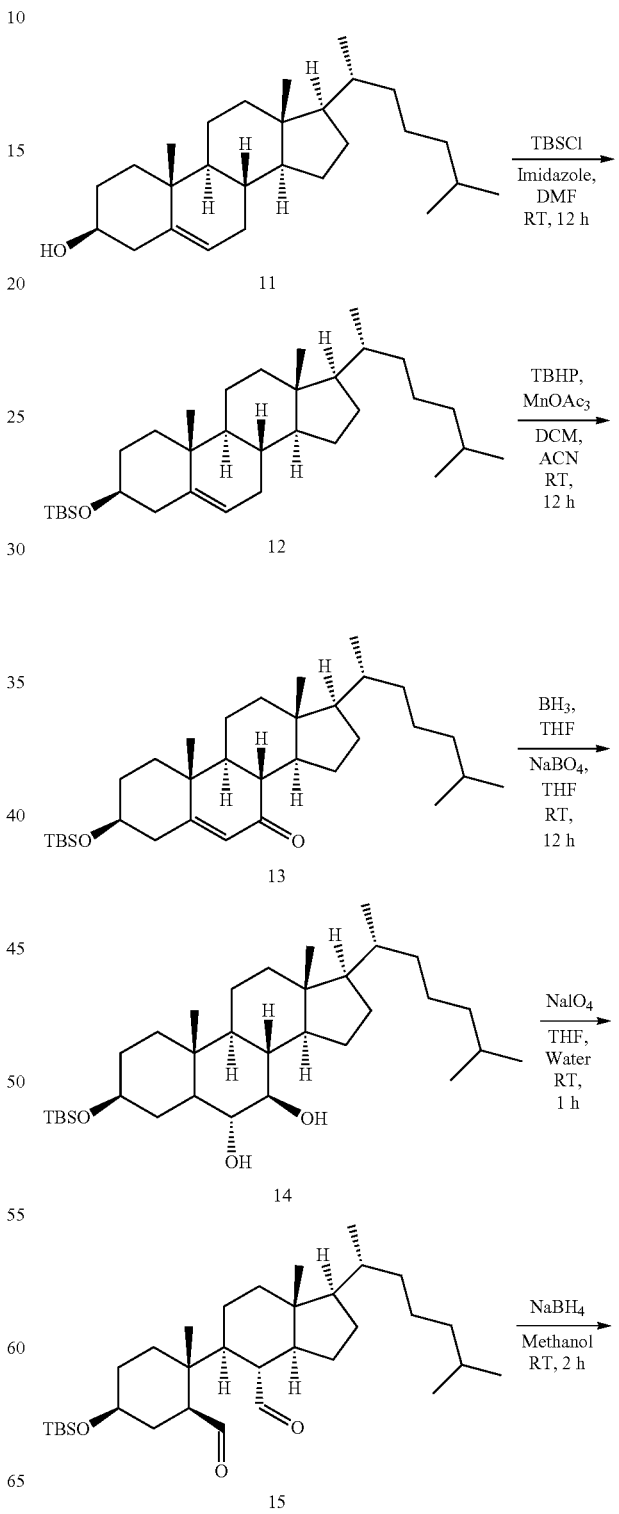

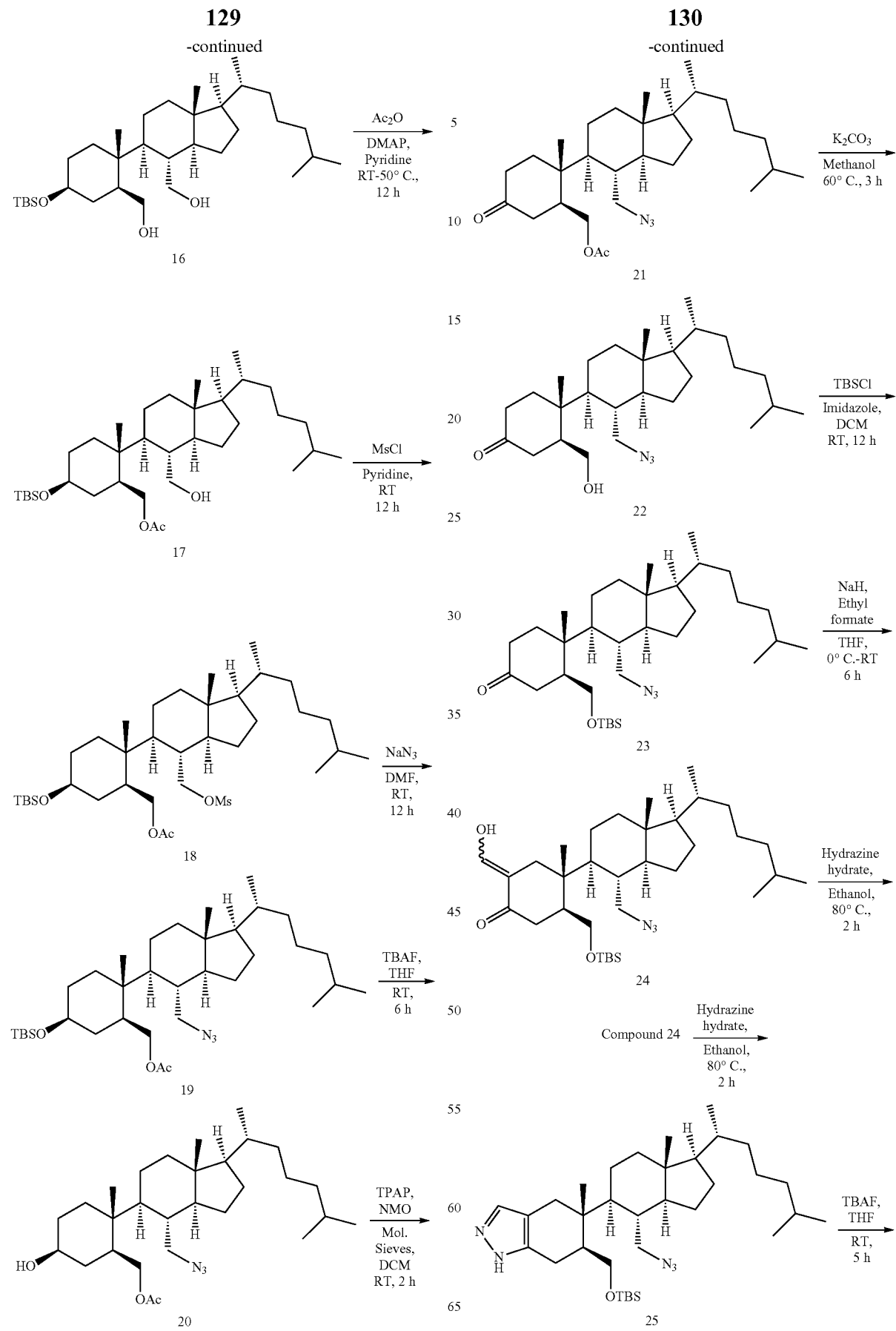

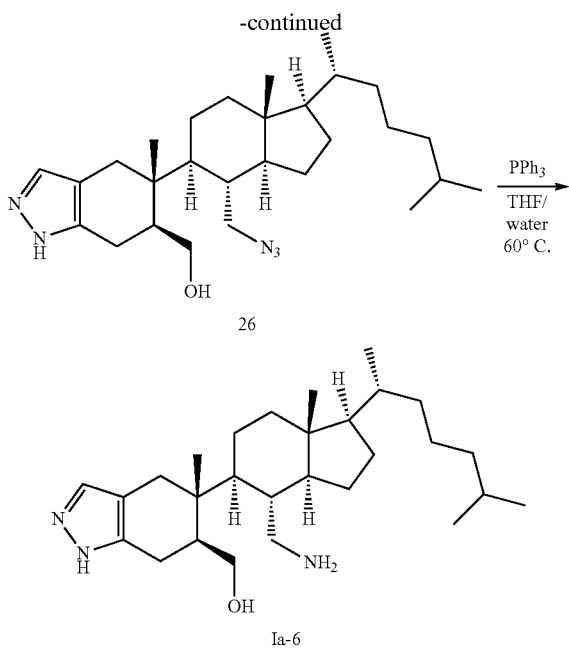

A. Using General Procedure B with cholesterol (Compound 11, 25 g, 64 mmol, 1 eq), imidazole (6.61 g, 97 mmol, 1.5 eq), TBSCl (10 g, 71 mmol, 1.1 eq) and N,N-dimethylformamide (200 mL) gave the desired silyl ether, tert-butyl(((3S,8S,9S,10R,13R,14S,17R)-10,13-dimethyl-17-((R)-6-methylheptan-2-yl)-2,3,4,7,8,9,10,11,12,13,14,15,16,17-tetradecahydro-1H-cyclopenta[a]phenanthren-3-yl)oxy)dimethylsilane (Compound 12, 27 g, 84%), as an off-white solid after purification by flash column chromatography (60-120 mesh silica gel, eluted with 0-40% pet ether/ethyl acetate).

B. Using General Procedure C with Compound 12 (20 g, 40 mmol, 1 eq), imidazole (6.61 g, 97 mmol, 1.5 eq), TBHP in decane (36 mL, 20 mol, 5 eq), manganese (III) acetate dihydrate (1.0 g, 4 mmol, 0.1 eq), molecular sieves (4 Å, 6 g), acetonitrle (100 mL) and dichloromethane (100 mL) gave the desired enone, (3S,8S,9S,10R,13R,14S,17R)-3-((tert-butyldimethylsilyl)oxy)-10,13-dimethyl-17-((R)-6-methylheptan-2-yl)-1,2,3,4,8,9,10,11,12,13,14,15,16,17-tetradecahydro-7H-cyclopenta[a]phenanthren-7-one (Compound 13, 16 g, 78%), as an off-white solid after purification by flash column chromatography (230-400 mesh silica gel, eluted at 0-50% pet ether/ethyl acetate).

C. Using General Procedure D with Compound 13 (16 g, 31.1 mmol, 1 eq), Borane in THF (1 M, 5.3 g, 62 ml, 62 mmol, 2 eq), sodium perborate tetrahydrate (14 g, 93 mmol, 3 eq) and THF (150 mL) gave the desired enone, (3S,6R,7R,8S,9S,10R,13R,14S,17R)-3-((tert-butyldimethylsilyl)oxy)-10,13-dimethyl-17-((R)-6-methylheptan-2-yl)hexadecahydro-1H-cyclopenta[a]phenanthrene-6,7-diol (Compound 14, 14 g, 84%), as an off-white solid after purification by flash column chromatography (230-400 mesh silica gel, eluted with 0-50% pet ether/ethyl acetate).

D. Using General Procedure F with Compound 14 (16 g, 31.1 mmol, 1 eq), sodium metaperiodate (11.2 g, 52 mmol, 2 eq), THF (60 mL) and water (40 mL) gave the desired dialdehyde, (1R,3aS,4S,5S,7aR)-5-((1R,2S,4S)-4-((tert-butyldimethylsilyl)oxy)-2-formyl-1-methylcyclohexyl)-7a-methyl-1-((R)-6-methylheptan-2-yl)octahydro-1H-inden-4-carbaldehyde (Compound 15, 12 g, yield: 86%), as a white solid after purification by flash column chromatography (230-400 mesh silica gel, eluted at 0-50% pet ether/ethyl acetate).

E. Using General Procedure G with Compound 15 (12 g, 22 mmol, 1 eq), sodium borohydride (1.7 g, 45 mmol, 2 eq) and methanol (100 mL) gave the desired diol, ((1S,2R,5S)-5-((tert-butyldimethylsilyl)oxy)-2-((1R,3aS,4S,5S,7aR)-4-(hydroxymethyl)-7a-methyl-1-((R)-6-methylheptan-2-yl)octahydro-H-inden-5-yl)-2-methylcyclohexyl)methanol (Compound 16, 10 g, 83%), as a white solid after purification by flash column chromatography (60-120 mesh silica gel, eluted with 0-50% pet ether/ethyl acetate).

F. Using General Procedure A with Compound 16 (10 g, 18.6 mmol), Ac$_2$O (1.9 g, 18.6 mmol, 1 eq), DMAP (0.22 g, 1.8 mmol, 0.1 eq) and pyridine (50 mL) gave the desired acetate, ((1S,2R,5S)-5-((tert-butyldimethylsilyl)oxy)-2-((1R,3aS,4S,5S,7aR)-4-(hydroxymethyl)-7a-methyl-1-((R)-6-methylheptan-2-yl)octahydro-1H-inden-5-yl)-2-methylcyclohexyl)methyl acetate (Compound 17, 8 g, 74%), as a white solid after purification by flash column chromatography (60-120 mesh silica gel, eluted with 0-40% pet ether/ethyl acetate).

G. Using General Procedure J with Compound 17 (10 g, 18.6 mmol), MsCl (3.17 g, 2.15 ml, 27 mmol, 2 eq) and pyridine (40 mL) gave the desired mesylate, ((1S,2R,5S)-5-((tert-butyldimethylsilyl)oxy)-2-methyl-2-((1R,3aS,4S,5S,7aR)-7a-methyl-1-((R)-6-methylheptan-2-yl)-4-(((methylsulfonyl)oxy)methyl)octahydro-1H-inden-5-yl)cyclohexyl)methyl acetate (Compound 18, 8 g), as a white solid which was used as such for next step without any further purification.

H. Using General Procedure K with Compound 18 (8 g, 12.2 mmol), sodium azide (1.58 g, 24.3 mmol, 2 eq) and DMF (80 mL) gave the desired azide, ((1S,2R,5S)-2-((1R,3aS,4S,5S,7aR)-4-(azidomethyl)-7a-methyl-1-((R)-6-methylheptan-2-yl)octahydro-1H-inden-5-yl)-5-((tert-butyldimethylsilyl)oxy)-2-methylcyclohexyl)methyl acetate (Compound 19, 6.8 g, 81%), as a white solid after purification by flash column chromatography (60-120 mesh silica gel, eluted with 0-60% pet ether/ethyl acetate).

I. Using General Procedure Q with Compound 19 (6.8 g 11.2 mmol), TBAF solution (1M in THF, 5.89 g, 22 mL, 22.5 mmol, 2 eq) and THF (60 mL) gave the desired alcohol, ((1S,2R,5S)-2-((1R,3aS,4S,5S,7aR)-4-(azidomethyl)-7a-methyl-1-((R)-6-methylheptan-2-yl)octahydro-1H-inden-5-yl)-5-hydroxy-2-methylcyclohexyl)methyl acetate (Compound 20, 4.2 g, 74%), as a white solid after purification by flash column chromatography (60-120 mesh silica gel, eluted with 0-50% pet ether/ethyl acetate).

J. Using General Procedure M with Compound 20 (4.2 g, 8.58 mmol, 1 eq), NMO.H$_2$O (13 g, 11 mmol, 1.3 eq), TPAP (0.3 g, 2.5 mmol, 0.3 eq), molecular sieves 4 Å (1 g) and dichloromethane (40 mL) gave the desired ketone, ((1S,2R)-2-((1R,3aS,4S,5S,7aR)-4-(azidomethyl)-7a-methyl-1-((R)-6-methylheptan-2-yl)octahydro-1H-inden-5-yl)-2-methyl-5-oxocyclohexyl)methyl acetate as a white solid (Compound 21, 3.6 g, 87%), as a white solid after purification by flash column chromatography (60-120 mesh silica gel, eluted with 0-40% pet ether/ethyl acetate).

K. Using General Procedure L with Compound 21 (3.6 g, 7.3 mmol, 1 eq), potassium carbonate (anhydrous, 2.03 g, 14.7 mmol, 2 eq) and methanol (36 mL) gave the desired alcohol, (3S,4R)-4-((1R,3aS,4S,5S,7aR)-4-(azidomethyl)-7a-methyl-1-((R)-6-methylheptan-2-yl)octahydro-1H-inden-5-yl)-3-(hydroxymethyl)-4-methylcyclohexan-1-one as a white solid (Compound 22, 27, 84%), as a white solid after purification by flash column chromatography (230-400 mesh silica gel, eluted with 0-50% pet ether/ethyl acetate).

L. Using General Procedure B with Compound 22 (2.7 g, 6.06 mmol, 1 eq), imidazole (0.62 g, 9.9 mmol, 1.5 eq), TBSCl (1.8 g, 12.1 mmol, 2 eq) and DMF (30 mL) gave the desired silyl ether, (3S,4R)-4-((1R,3aS,4S,5S,7aR)-4-(azidomethyl)-7a-methyl-1-((R)-6-methylheptan-2-yl)octahydro-1H-inden-5-yl)-3-(((tert-butyldimethylsilyl)oxy)methyl)-4-methylcyclohexan-1-one (Compound 23, 3 g, 90%), as an off-white solid after purification by flash column chromatography (60-120 mesh silica gel, eluted with 0-20% pet ether/ethyl acetate).

M. Using General Procedure O with Compound 23 (3 g, 5.3 mmol, 1 eq), sodium hydride (60% in paraffin oil, 0.820 g, 21 mmol, 4 eq), ethyl formate (2.6 mL, 32 mmol, 6 eq) and THF (30 mL) gave the desired ketone, (4R,5S)-4-((1R,3aS,4S,5S,7aR)-4-(azidomethyl)-7a-methyl-1-((R)-6-methylheptan-2-yl)octahydro-1H-inden-5-yl)-5-(((tert-butyldimethylsilyl)oxy)methyl)-2-(hydroxymethylene)-4-methylcyclohexan-1-one (Compound 24, 3 g, 96%), as a pale brown solid after purification by flash column chromatography (60-120 mesh silica gel, eluted with 0-40% pet ether/ethyl acetate).

N. Using General Procedure P with Compound 24 (2.9 g, 4.9 mmol, 1 eq), hydrazine hydrate (0.493 g, 9.8 mmol, 2 eq) and ethanol (30 mL) gave the desired pyrazole, (5R,6S)-5-((1R,3aS,4S,5S,7aR)-4-(azidomethyl)-7a-methyl-1-((R)-6-methylheptan-2-yl)octahydro-1H-inden-5-yl)-6-(((tert-butyldimethylsilyl)oxy)methyl)-5-methyl-4,5,6,7-tetrahydro-1H-indazole (Compound 25, 2.7 g, 82%), as a white solid after purification by flash column chromatography (60-120 mesh silica gel, eluted with 0-40% pet ether/ethyl acetate).

O. Using General Procedure Q with Compound 25 (2.7 g, 4.6 mmol, 1 eq), TBAF solution (M in THF, 9.2 mL, 9.2 mmol, 2 eq) and THF (27 mL) gave the desired alcohol, ((5R,6S)-5-((1R,3aS,4S,5S,7aR)-4-(azidomethyl)-7a-methyl-1-((R)-6-methylheptan-2-yl)octahydro-1H-inden-5-yl)-5-methyl-4,5,6,7-tetrahydro-1H-indazol-6-yl)methanol (Compound 26, 2 g, 86%), as a white solid after purification by flash column chromatography (60-120 mesh silica gel, eluted with 0-60% pet ether/ethyl acetate).

P. Using General Procedure R with Compound 26 (1 g, 2.13 mmol, 1 eq), triphenylphosphine (1.1 g, 4.2 mmol, 2 eq), water (1 mL) and THF (10 mL) gave the desired amine, ((5R,6S)-5-((1R,3aS,4S,5S,7aR)-4-(aminomethyl)-7a-methyl-1-((R)-6-methylheptan-2-yl)octahydro-1H-inden-5-yl)-5-methyl-4,5,6,7-tetrahydro-1H-indazol-6-yl)methanol (Compound Ia-6, 0.4 g, 44%), as a white solid after purification by flash column chromatography (Neutral alumina, eluted with 0-5% dichloromethane/methanol).

LCMS: (Method 1b) MS m/z: 444.2 (M+1), $t_R$: 4.358 min, Purity: 97.14% (max), 96.31% (220 nm).

HPLC: (Method 2a) $t_R$: 4.31 min, Purity: 96.30% (max), 95.28% (220 nm).

$^1$H-NMR (400 MHz, CD$_3$OD): δ 7.32 (s, 1H), 3.95 (d, J=10.2 Hz, 1H), 3.43-3.38 (m, 1H), 3.14 (d, J=5.4 Hz, 1H), 2.96-2.92 (m, 1H), 2.69-2.41 (m, 3H), 2.15-2.13 (m, 2H), 2.04-1.96 (m, 1H), 1.95-1.54 (m, 6H), 1.45-1.17 (m, 12H), 1.15-1.05 (m, 3H), 0.98-0.80 (m, 12H).

Synthetic Example 7

Synthesis of ((5R,6S)-5-((1R,3aS,4S,5S,7aR)-4-((((2,2-difluorobenzo[d][1,3]dioxol-5-yl)methyl)amino)methyl)-7a-methyl-1-((R)-6-methylheptan-2-yl)octahydro-1H-inden-5-yl)-5-methyl-4,5,6,7-tetrahydro-1H-indazol-6-yl)methanol (Compound Ia-7)

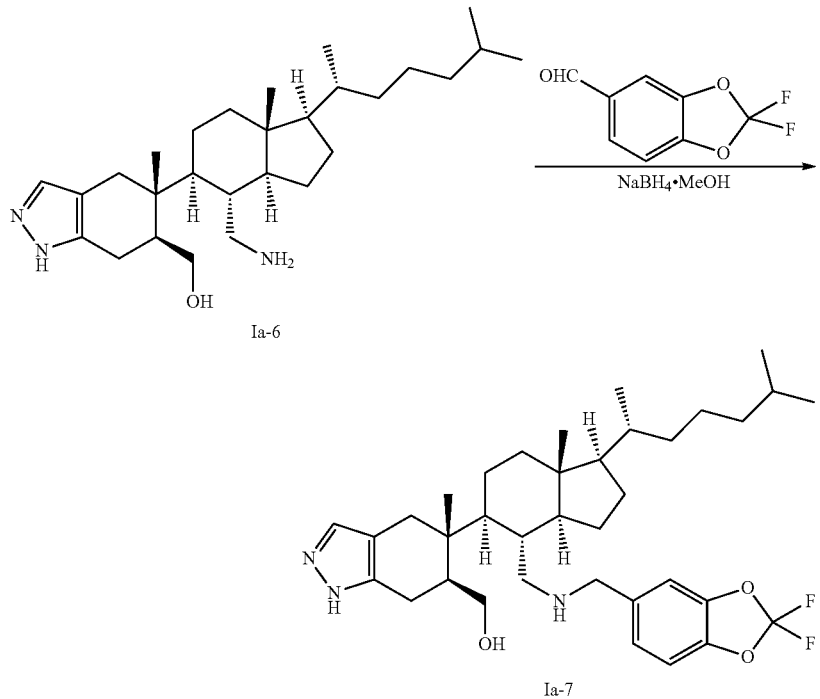

Using General Procedure U with Compound Ia-6 (from Example 6, 0.3 g, 0.67 mmol, 1 eq), 2,2-difluorobenzo[d][1,3]dioxole-5-carbaldehyde (0.125 g, 0.67 mmol, 1 eq), sodium borohydride (28 mg, 0.74 mmol) and methanol (10 mL) gave the desired amine, ((5R,6S)-5-((1R,3aS,4S,5S,7aR)-4-((((2,2-difluorobenzo[d][1,3]dioxol-5-yl)methyl)

amino)methyl)-7a-methyl-1-((R)-6-methylheptan-2-yl)octahydro-1H-inden-5-yl)-5-methyl-4,5,6,7-tetrahydro-1H-indazol-6-yl)methanol (Compound Ia-7, 0.12 g, 29%), as a white solid after purification by flash column chromatography (Neutral alumina, eluted with 0-5% dichloromethane/methanol).

LCMS: (Method 1b) MS m/z: 614.2 (M+1), $t_R$: 5.16 min, Purity: 95.44% (max), 95.32% (220 nm).

HPLC: (Method 2a) $t_R$: 5.102 min, Purity: 94.7% (max), 94.58% (220 nm).

$^1$H-NMR (400 MHz, CD$_3$OD): δ 7.25-7.11 (m, 4H), 3.93 (d, J=9.6 Hz, 1H), 3.75-3.64 (m, 2H), 3.20-3.13 (m, 1H), 2.92-2.89 (m, 1H), 2.61-2.58 (m, 3H), 2.28-2.17 (m, 2H), 1.98-1.86 (m, 2H), 1.65-1.51 (m, 5H), 1.46-1.39 (m, 5H), 1.38-1.23 (m, 8H), 1.15-1.02 (m, 4H), 0.94-0.83 (m, 9H), 0.73 (s, 3H).

Synthetic Example 8

Synthesis of ((5R,6S)-5-((3aS,4R,5S,7aS)-4-(aminomethyl)-7a-methyl-1-methyleneoctahydro-1H-inden-5-yl)-5-methyl-1-phenyl-4,5,6,7-tetrahydro-1H-indazol-6-yl)methanol (Compound Ia-8) and ((5R,6S)-5-((3aS,4R,5S,7aS)-4-(aminomethyl)-7a-methyl-1-methyleneoctahydro-1H-inden-5-yl)-5-methyl-2-phenyl-4,5,6,7-tetrahydro-2H-indazol-6-yl)methanol (Ia-9)

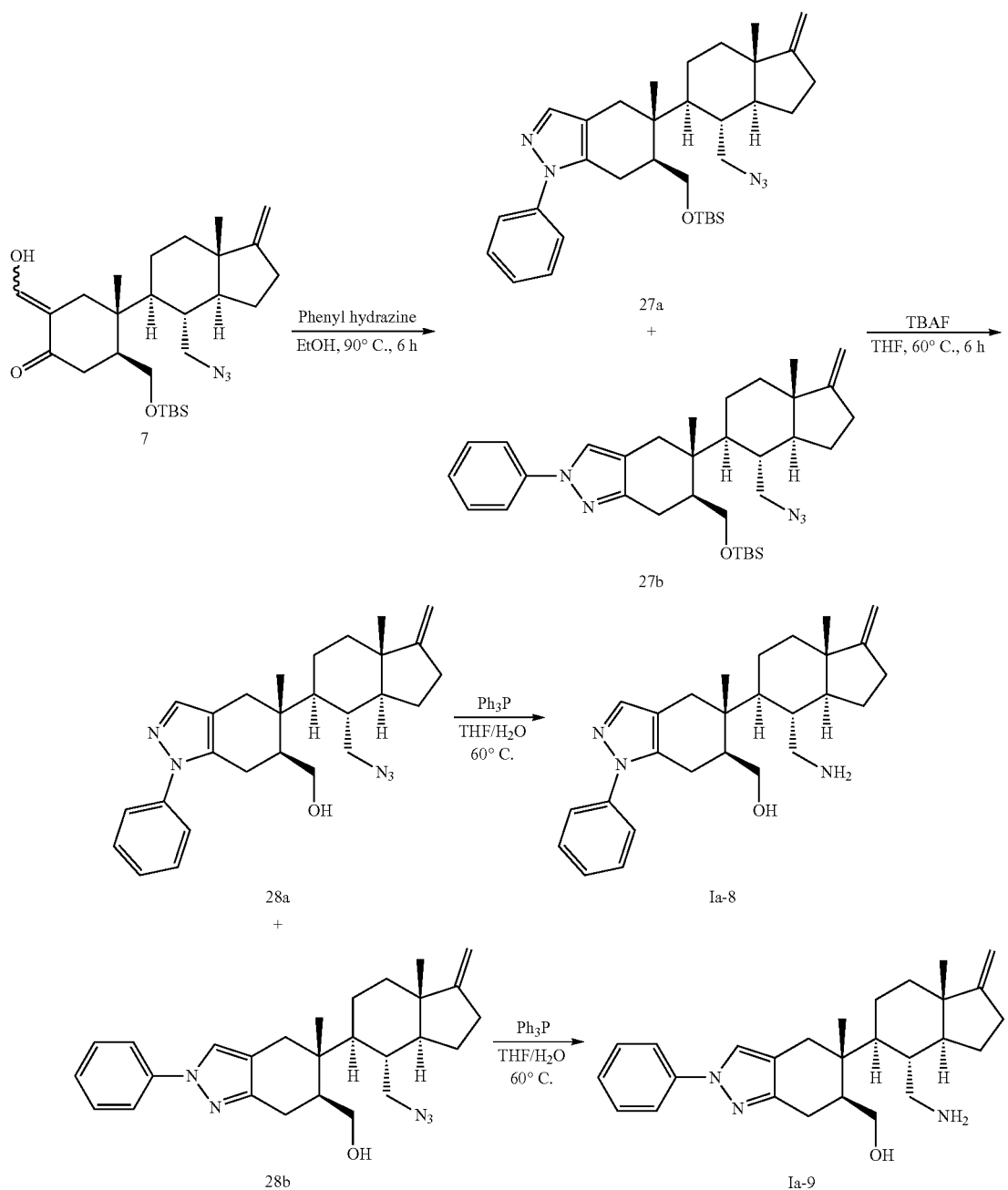

A. Using General Procedure P with Compound 7 (from Example 1, 0.8 g, 1.64 mmol, 1 eq), phenylhydrazine (0.44 g, 4.10 mmol, 2.5 eq) and ethanol (15 mL) gave a mixture of the desired pyrazoles, (5R,6S)-5-((3aS,4R,5S,7aS)-4-(azidomethyl)-7a-methyl-1-methyleneoctahydro-1H-inden-5-yl)-6-(((tert-butyldimethylsilyl)oxy)methyl)-5-methyl-1-phenyl-4,5,6,7-tetrahydro-1H-indazole (Compound 27a) and (5R,6S)-5-((3aS,4R,5S,7aS)-4-(azidomethyl)-7a-methyl-1-methyleneoctahydro-1H-inden-5-yl)-6-(((tert-butyldimethylsilyl)oxy)methyl)-5-methyl-2-phenyl-4,5,6,7-tetrahydro-2H-indazole (Compound 27b, 0.5 g, 55%), as a pale brown gum after purification by flash column chromatography (230-400 mesh silica gel, eluted with 0-30% pet ether/ethyl acetate).

B. Using General Procedure Q with Compounds 27a and Compound 27b, 0.5 g, 0.89 mmol, 1 eq), TBAF solution (1M in THF, 1.78 mL, 1.78 mmol, 2 eq) and THF (15 mL) gave the desired alcohol, ((5R,6S)-5-((3aS,4R,5S,7aS)-4-(azidomethyl)-7a-methyl-1-methyleneoctahydro-1H-inden-5-yl)-5-methyl-1-phenyl-4,5,6,7-tetrahydro-1H-indazol-6-yl)methanol (Compound 28a, 0.23 g, 59%) and ((5R,6S)-5-((3a5,4R,5S,7aS)-4-(azidomethyl)-7a-methyl-1-methyleneoctahydro-1H-inden-5-yl)-5-methyl-2-phenyl-4,5,6,7-tetrahydro-2H-indazol-6-yl)methanol (Compound 28b), as a pale yellow foam after purification by flash column chromatography (230-400 mesh silica gel, eluted with 0-40% pet ether/ethyl acetate).

C. Using General Procedure R with Compound 28a (0.230 g, 0.516 mmol, 1 eq), triphenylphosphine (0.274 g, 1.03 mmol, 2 eq) water (1 mL) and THF (10 mL) gave the desired amine, ((5R,6S)-5-((3aS,4R,5S,7aS)-4-(aminomethyl)-7a-methyl-1-methyleneoctahydro-1H-inden-5-yl)-5-methyl-1-phenyl-4,5,6,7-tetrahydro-1H-indazol-6-yl)methanol as an off-white solid (Compound Ia-8, 13 mg, 6%), as an off-white solid after purification by preparative HPLC (method 3a). Similarly, ((5R,6S)-5-((3aS,4R,5S,7aS)-4-(aminomethyl)-7a-methyl-1-methyleneoctahydro-1H-inden-5-yl)-5-methyl-2-phenyl-4,5,6,7-tetrahydro-2H-indazol-6-yl)methanol (Compound Ia-9) was obtained using the procedure above, making non-critical variations LCMS: (Method 1b) MS m/z: 420.2 (M+1), $t_R$: 3.75 min, Purity: 93.2% (UV).

HPLC: (Method 2a) $t_R$: 3.741 min, Purity: 94.57% (UV).

$^1$H-NMR (400 MHz, DMSO-$d_6$): δ 7.61-7.59 (m, 2H), 7.53-7.49 (m, 2H), 7.45 (s, 1H), 7.37-7.33 (m, 1H), 4.59-4.58 (m, 2H), 4.47-4.46 (m, 1H), 3.74-3.72 (m, 1H), 3.28-3.20 (m, 2H), 3.18-3.05 (m, 2H), 2.74-2.64 (m, 2H), 2.28-2.15 (m, 2H), 2.09-2.00 (m, 2H), 1.80-1.72 (m, 5H), 1.64-1.52 (m, 2H), 1.41-1.36 (m, 2H), 1.34-1.31 (m, 2H), 1.1 (s, 3H), 0.8 (s, 3H).

Synthetic Example 8.1

Synthesis of ((5R,6S)-5-((3aS,4R,5S,7aS)-4-(aminomethyl)-7a-methyl-1-methyleneoctahydro-1H-inden-5-yl)-5-methyl-1-(pyridin-2-yl)-4,5,6,7-tetrahydro-1H-indazol-6-yl)methanol (Compound Ia-10) and ((5R,6S)-5-((3aS,4R,5S,7aS)-4-(aminomethyl)-7a-methyl-1-methyleneoctahydro-1H-inden-5-yl)-5-methyl-2-(pyridin-2-yl)-4,5,6,7-tetrahydro-2H-indazol-6-yl)methanol (Compound Ia-11)

Following the procedure as described in Synthetic Example 8 and making non-critical variations using (2-pyridyl)hydrazine to replace phenyl hydrazine, the title compounds, ((5R,6S)-5-((3aS,4R,5S,7aS)-4-(aminomethyl)-7a-methyl-1-methyleneoctahydro-1H-inden-5-yl)-5-methyl-1-(pyridin-2-yl)-4,5,6,7-tetrahydro-1H-indazol-6-yl)methanol (Compound Ia-10) and ((5R,6S)-5-((3aS,4R,5S,7aS)-4-(aminomethyl)-7a-methyl-1-methyleneoctahydro-1H-inden-5-yl)-5-methyl-2-(pyridin-2-yl)-4,5,6,7-tetrahydro-2H-indazol-6-yl)methanol (Ia-11), were obtained after purification by preparative HPLC.

Compound Ia-11: LCMS: (Method 1c) MS m/z: 421.3 (M+1), $t_R$: 2.984 min, Purity: 96.42% (UV).

Synthetic Example 8.2

Synthesis of ((5R,6S)-5-((3aS,4R,5S,7aS)-4-(aminomethyl)-7a-methyl-1-methyleneoctahydro-1H-inden-5-yl)-1-(tert-butyl)-5-methyl-4,5,6,7-tetrahydro-H-indazol-6-yl)methanol (Compound Ia-12) and ((5R,6S)-5-((3aS,4R,5S,7aS)-4-(aminomethyl)-7a-methyl-1-methyleneoctahydro-1H-inden-5-yl)-2-(tert-butyl)-5-methyl-4,5,6,7-tetrahydro-2H-indazol-6-yl)methanol (Compound Ia-13)

Following the procedure as described in Synthetic Example 8 and making non-critical variations using tert-butylhydrazine to replace phenyl hydrazine, the title compounds, ((5R,6S)-5-((3aS,4R,5S,7aS)-4-(aminomethyl)-7a-methyl-1-methyleneoctahydro-1H-inden-5-yl)-1-(tert-butyl)-5-methyl-4,5,6,7-tetrahydro-1H-indazol-6-yl)methanol (Compound Ia-12) and ((5R,6S)-5-((3aS,4R,5S,7aS)-4-(aminomethyl)-7a-methyl-1-methyleneoctahydro-H-inden-5-yl)-2-(tert-butyl)-5-methyl-4,5,6,7-tetrahydro-2H-indazol-6-yl)methanol (Compound Ia-13), were obtained after purification by preparative HPLC.

Compound Ia-12: LCMS: (Method 1d) MS m/z: 400.4 (M+1), $t_R$: 1.403 min, Purity: 98.76% (UV).

Compound Ia-13: LCMS: (Method 1c) MS m/z: 400.3 (M+1), $t_R$: 144 min, Purity: 98.03% (UV)

Synthetic Example 8.3

Synthesis of ((5R,6S)-5-((3aS,4R,5S,7aS)-4-(aminomethyl)-7a-methyl-1-methyleneoctahydro-1H-inden-5-yl)-1,5-dimethyl-4,5,6,7-tetrahydro-H-indazol-6-yl)methanol (Compound Ia-14) and ((5R,6S)-5-((3aS,4R,5S,7aS)-4-(aminomethyl)-7a-methyl-1-methyleneoctahydro-1H-inden-5-yl)-2,5-dimethyl-4,5,6,7-tetrahydro-2H-indazol-6-yl)methanol (Compound Ia-15)

Following the procedure as described in Synthetic Example 8 and making non-critical variations using methylhydrazine to replace phenyl hydrazine, the title compounds, ((5R,6S)-5-((3aS,4R,5S,7aS)-4-(aminomethyl)-7a-methyl-1-methyleneoctahydro-1H-inden-5-yl)-1,5-dimethyl-4,5,6,7-tetrahydro-1H-indazol-6-yl)methanol (Compound Ia-14) and ((5R,6S)-5-((3aS,4R,5S,7aS)-4-(aminomethyl)-7a-methyl-1-methyleneoctahydro-1H-inden-5-yl)-2,5-dimethyl-4,5,6,7-tetrahydro-2H-indazol-6-yl)methanol (Compound Ia-15), were obtained after purification by preparative HPLC.

Compound Ia-15: LCMS: (Method 1c) MS m/z: 358.3 (M+1), $t_R$: 1.375 min, Purity: 94.05% (UV).

Synthetic Example 8.4

Synthesis of ((5R,6S)-5-((3aS,4R,5S,7aS)-4-(aminomethyl)-7a-methyl-1-methyleneoctahydro-1H-inden-5-yl)-1-cyclohexyl-5-methyl-4,5,6,7-tetrahydro-1H-indazol-6-yl)methanol (Compound Ia-16) and ((5R,6S)-5-((3aS,4R,5S,7aS)-4-(aminomethyl)-7a-methyl-1-methyleneoctahydro-1H-inden-5-yl)-2-cyclohexyl-5-methyl-4,5,6,7-tetrahydro-2H-indazol-6-yl)methanol (Compound Ia-17)

Following the procedure as described in Synthetic Example 8 and making non-critical variations using cyclohexylhydrazine to replace phenyl hydrazine, the title compounds, ((5R,6S)-5-((3aS,4R,5S,7aS)-4-(aminomethyl)-7a-methyl-1-methyleneoctahydro-1H-inden-5-yl)-1-cyclohexyl-5-methyl-4,5,6,7-tetrahydro-1H-indazol-6-yl)methanol (Compound Ia-16) and ((5R,6S)-5-((3aS,4R,5S,7aS)-4-(aminomethyl)-7a-methyl-1-methyleneoctahydro-H-inden-5-yl)-2-cyclohexyl-5-methyl-4,5,6,7-tetrahydro-2H-indazol-6-yl)methanol (Compound Ia-17), were obtained after purification by preparative HPLC.

Compound Ia-16: LCMS: (Method 1d) MS m/z: 426.3 (M+1), $t_R$: 1.589 min, Purity: 99.02% (ELSD).

Synthetic Example 8.5

Synthesis of ((5R,6S)-5-((3aS,4R,5S,7aS)-4-(aminomethyl)-7a-methyl-1-methyleneoctahydro-1H-inden-5-yl)-1-benzyl-5-methyl-4,5,6,7-tetrahydro-1H-indazol-6-yl)methanol (Compound Ia-18) and ((5R,6S)-5-((3aS,4R,5S,7aS)-4-(aminomethyl)-7a-methyl-1-methyleneoctahydro-1H-inden-5-yl)-2-benzyl-5-methyl-4,5,6,7-tetrahydro-2H-indazol-6-yl)methanol (Compound Ia-19)

Following the procedure as described in Synthetic Example 8 and making non-critical variations using benzylhydrazine to replace phenyl hydrazine, the title compounds, ((5R,6S)-5-((3aS,4R,5S,7aS)-4-(aminomethyl)-7a-methyl-1-methyleneoctahydro-1H-inden-5-yl)-1-benzyl-5-methyl-4,5,6,7-tetrahydro-1H-indazol-6-yl)methanol (Compound Ia-18) and ((5R,6S)-5-((3aS,4R,5S,7aS)-4-(aminomethyl)-7a-methyl-1-methyleneoctahydro-1H-inden-5-yl)-2-benzyl-5-methyl-4,5,6,7-tetrahydro-2H-indazol-6-yl)methanol (Compound Ia-19), were obtained after purification by preparative HPLC.

Compound Ia-19: LCMS: (Method 1d) MS m/z: 434.3 (M+1), $t_R$: 1.444 min, Purity: 99.60% (UV).

Synthetic Example 8.6

Synthesis of ((5R,6S)-5-((3aS,4R,5S,7aS)-4-(aminomethyl)-7a-methyl-1-methyleneoctahydro-1H-inden-5-yl)-5-methyl-1-(pyridin-3-yl)-4,5,6,7-tetrahydro-1H-indazol-6-yl)methanol (Compound Ia-20) and ((5R,6S)-5-((3aS,4R,5S,7aS)-4-(aminomethyl)-7a-methyl-1-methyleneoctahydro-1H-inden-5-yl)-5-methyl-2-(pyridin-3-yl)-4,5,6,7-tetrahydro-2H-indazol-6-yl)methanol (Ia-21)

Following the procedure as described in Synthetic Example 8 and making non-critical variations using (3-pyridyl)hydrazine to replace phenyl hydrazine, the title compounds, ((5R,6S)-5-((3aS,4R,5S,7aS)-4-(aminomethyl)-7a-methyl-1-methyleneoctahydro-1H-inden-5-yl)-5-methyl-1-(pyridin-3-yl)-4,5,6,7-tetrahydro-1H-indazol-6-yl)methanol (Compound Ia-20) and ((5R,6S)-5-((3aS,4R,5S,7aS)-4-(aminomethyl)-7a-methyl-1-methyleneoctahydro-H-inden-5-yl)-5-methyl-2-(pyridin-3-yl)-4,5,6,7-tetrahydro-2H-indazol-6-yl)methanol (Compound Ia-21), were obtained after purification by preparative HPLC.

Compound Ia-20: LCMS: (Method 1d) MS m/z: 4213 (M+1), $t_R$: 1.351 min, Purity: 97.66% (UV).

Synthetic Example 8.7

Synthesis of ((5R,6S)-5-((3aS,4R,5S,7aS)-4-(aminomethyl)-7a-methyl-1-methyleneoctahydro-1H-inden-5-yl)-5-methyl-1-neopentyl-4,5,6,7-tetrahydro-1H-indazol-6-yl)methanol (Compound Ia-22) and ((5R,6S)-5-((3aS,4R,5S,7aS)-4-(aminomethyl)-7a-methyl-1-methyleneoctahydro-1H-inden-5-yl)-5-methyl-2-neopentyl-4,5,6,7-tetrahydro-2H-indazol-6-yl)methanol (Compound Ia-23)

Following the procedure as described in Synthetic Example 8 and making non-critical variations using (2,2-dimethylpropyl)hydrazine to replace phenyl hydrazine, the title compounds, ((5R,6S)-5-((3aS,4R,5S,7aS)-4-(aminomethyl)-7a-methyl-1-methyleneoctahydro-1H-inden-5-yl)-5-methyl-1-neopentyl-4,5,6,7-tetrahydro-1H-indazol-6-yl)methanol (Compound Ia-22) and ((5R,6S)-5-((3aS,4R,5S,7aS)-4-(aminomethyl)-7a-methyl-1-methyleneoctahydro-1H-inden-5-yl)-5-methyl-2-neopentyl-4,5,6,7-tetrahydro-2H-indazol-6-yl)methanol (Compound Ia-23), were obtained after purification by preparative HPLC.

Compound Ia-22: LCMS: (Method 1d) MS m/z: 414.3 (M+1), $t_R$: 1.501 min, Purity: 94.89% (UV).

Compound Ia-23: LCMS: (Method 1d) MS m/z: 414.3 (M+1), $t_R$: 1.500 min, Purity: 96.91% (UV).

Synthetic Example 9

Synthesis of (5R,6S)-5-((3aR,6S,7R,7aS)-7-(hydroxymethyl)-3a-methyl-3a,4,5,6,7,7a-hexahydro-1H-inden-6-yl)-5-methyl-4,5,6,7-tetrahydro-1H-indazol-6-yl)methanol (Compound Ia-26)

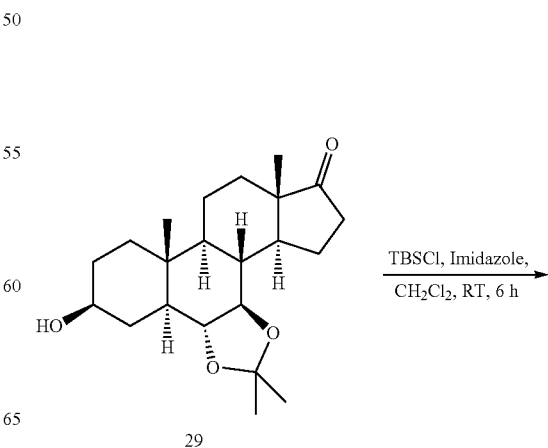

29

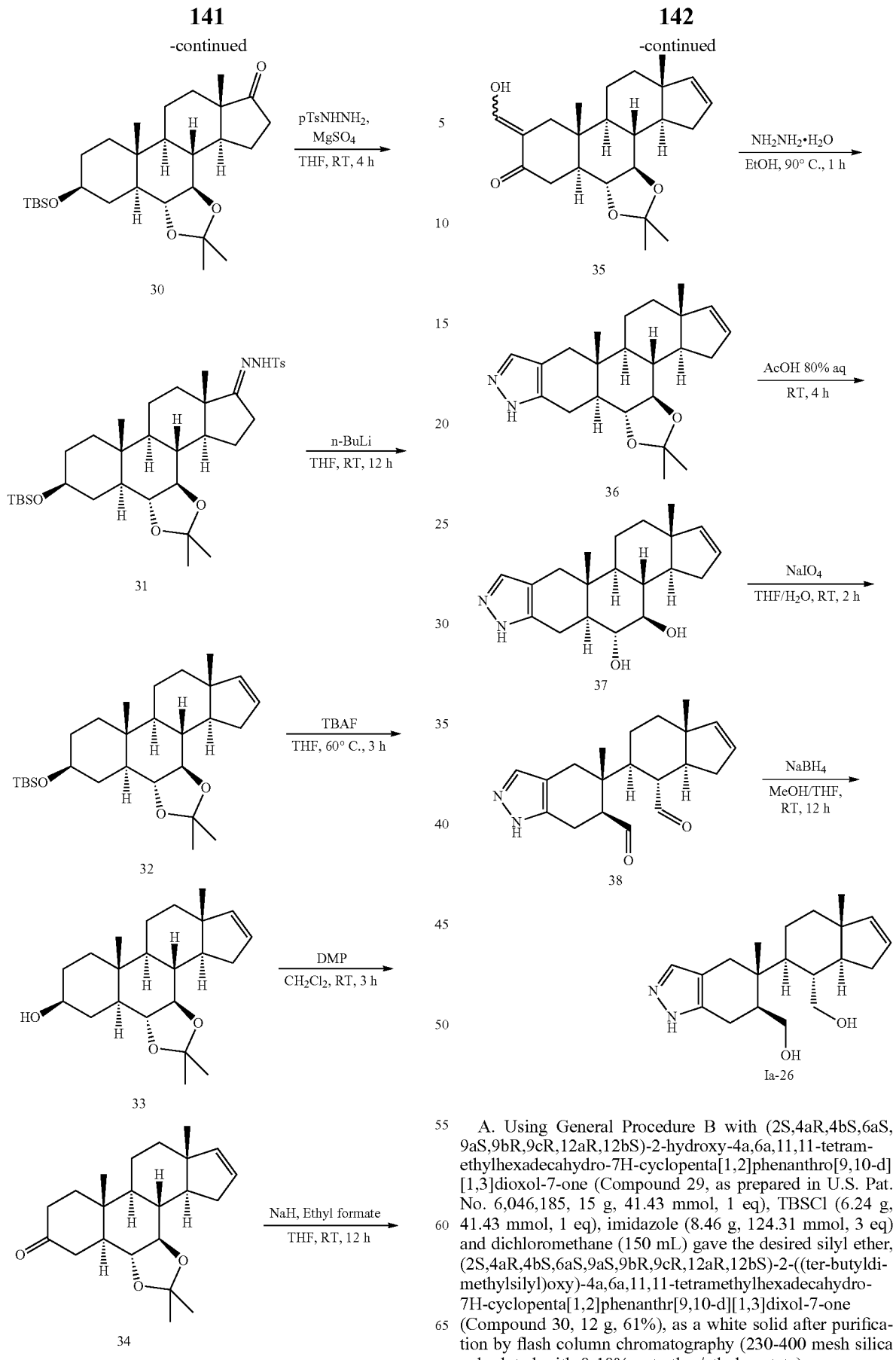

A. Using General Procedure B with (2S,4aR,4bS,6aS,9aS,9bR,9cR,12aR,12bS)-2-hydroxy-4a,6a,11,11-tetramethylhexadecahydro-7H-cyclopenta[1,2]phenanthro[9,10-d][1,3]dioxol-7-one (Compound 29, as prepared in U.S. Pat. No. 6,046,185, 15 g, 41.43 mmol, 1 eq), TBSCl (6.24 g, 41.43 mmol, 1 eq), imidazole (8.46 g, 124.31 mmol, 3 eq) and dichloromethane (150 mL) gave the desired silyl ether, (2S,4aR,4bS,6aS,9aS,9bR,9cR,12aR,12bS)-2-((ter-butyldimethylsilyl)oxy)-4a,6a,11,11-tetramethylhexadecahydro-7H-cyclopenta[1,2]phenanthr[9,10-d][1,3]dixol-7-one (Compound 30, 12 g, 61%), as a white solid after purification by flash column chromatography (230-400 mesh silica gel, eluted with 0-10% pet ether/ethyl acetate).

B. To a solution of Compound 30 (12 g, 25.19 mmol, 1 eq) in THF (100 mL) taken in a 500 mL three-necked RB flask was added magnesium sulphate (7.57 g, 62.98 mmol, 2.5 eq) and p-toluenesulfonyl hydrazide (7.03 g, 37.78 mmol, 1.5 eq). Reaction mass was stirred with the help of a magnetic stirrer and the reaction was carried out under a nitrogen atmosphere. The reaction mass was stirred for 4 h at room temperature. Completion of the reaction was monitored by TLC analysis. The reaction mass was cooled and quenched with ice cold water (100 mL) then extracted with ethyl acetate (2×100 mL). The organic phase was washed with brine solution (2×100 mL), dried over anhydrous sodium sulphate and concentrated on a rotary evaporator at 45° C. to get a crude colorless gum. It was further purified by column chromatography (230-400 mesh silica gel, eluted with 0-40% pet ether/ethyl acetate) to afford N'-((2S,4aR,4bS,6aS,9aS,9bR,9cR,12aR,12bS)-2-((tert-butyldimethylsilyl)oxy)-4a,6a,11,11-tetramethylhexadecahydro-7H-cyclopenta[1,2]phenanthro[9,10-d][1,3]dioxo-7-ylidene)-4-methylbenzenesulfonhydrazide (Compound 31, 12 g, 74%) as a white solid.

C. To a solution of Compound 31 (12 g, 18.63 mmol, 1 eq) in THF (100 mL) taken in a 500 mL three-necked RB flask was added n-butyl lithium (2 M in hexane, 93.2 mL, 186.3 mmol, 10 eq) slowly dropwise at −78° C. Reaction mass was externally cooled with the help of dry ice bath. Reaction mass was stirred with the help of a magnetic stirrer and the reaction was carried out under a nitrogen atmosphere. The reaction mass was slowly warmed to room temperature and stirred for 12 h. Completion of the reaction was monitored by TLC analysis. The reaction mass was cooled to −78° C. quenched with saturated aqueous NH$_4$Cl solution (150 mL) and extracted with ethyl acetate (2×200 mL). The organic phase was washed with brine solution (2×200 mL), dried over anhydrous sodium sulphate and concentrated on a rotary evaporator at 45° C. to get a crude colorless gum. It was further purified by column chromatography (230-400 mesh silica gel, eluted with 0-30% pet ether/ethyl acetate) to afford tert-butyldimethyl(((2S,4aR,4bS,6aR,9aS,9bR,9cR,12aR,12bS)-4a,6a,11,11-tetramethyl-2,3,4,4a,4b,5,6,6a,9,9a,9b,9c,12a,12b-tetradecahydro-1H-cyclopenta[1,2]phenanthro[9,10-d][1,3]dioxol-2-yl)oxy)silane (Compound 32, 5 g, 58%) as a white solid.

D. Using General Procedure Q with Compound 32 (5 g, 10.86 mmol, 1 eq), TBAF solution (1M in THF, 21.7 mL, 21.72 mmol, 2 eq) and THF (50 mL) gave the desired alcohol, (2S,4aR,4bS,6aR,9aS,9bR,9cR,12aR,12bS)-4a,6a,11,11-tetramethyl-2,3,4,4a,4b,566a,9,9a,9b,9c,12a,12b-tetradecahydro-1H-cyclopenta[1,2]phenanthr[9,10-d][1,3]dioxl-2-ol (Compound 33, 3.2 g, 85%), as a pale yellow solid after purification by flash column chromatography (230-400 mesh silica gel, eluted with 0-60% pet ether/ethyl acetate).

E. Using General Procedure N with Compound 33 (3.2 g, 9.24 mmol, 1 eq), Dess-Martin periodinane (4.74 g, 11.09 mmol, 1.2 eq) and dichloromethane (32 mL) gave the desired ketone, (4aR,4bS,6aR,9aS,9bR,9cR,12aR,12bS)-4a,6a,11,11-tetramethyl-1,3,4,4a,4b,5,6,6a,99a,9b,9c,12a,12b-tetradecahydro-2H-cyclopenta[1,2]phenanthr[9,10-d][1,3]dioxol-2-ne (Compound 34, 2.3 g, 72%), as a white solid after purification by flash column chromatography (230-400 mesh silica gel, eluted with 0-30% pet ether/ethyl acetate).

F. Using General Procedure O with Compound 34 (4 g, 6.68 mmol, 1 eq), sodium hydride (60% in paraffin oil, 1.1 g, 26.74 mmol, 4 eq), ethyl formate (3.26 mL, 40.11 mmol, 6 eq) and THF (30 mL) gave the desired ketone, (4aR,4bS,6aR,9aS,9bR,9cR,12aR,12bS)-3-(hydroxymethylene)-4a,6a,11,11-tetramethyl-1,3,4,4a,4b,5,6,6a,9,9a,9b,9c,12a,12b-tetradecahydro-2H-cyclopenta[1,2]phenanthro[9,10-d][1,3]dioxol-2-one (Compound 35, 2 g, 81%), as a yellow solid after purification by flash column chromatography (230-400 mesh silica gel, eluted with 0-15% pet ether/ethyl acetate).

G. Using General Procedure P with Compound 35 (2 g, 5.37 mmol, 1 eq), hydrazine hydrate (0.4 g, 8.06 mmol, 1.5 eq) and ethanol (20 mL) gave the desired pyrazole, (3aS,3bR,3cR,6aR,6bS,11aR,11bS,13aR)-5,5,11a,13a-tetramethyl-3,3a,3b,3c,6a,6b,7,8,11,11a,11b,12,13,13a-tetradecahydrocyclopenta[5,6][1,3]dioxolo[4',5':3,4]naphtho[1,2-f]indazole (Compound 36, 1.8 g, 92%), as a pale yellow solid after purification by flash column chromatography (230-400 mesh silica gel, eluted with 0-60% pet ether/ethyl acetate).

H. Using General Procedure E with Compound 36 (1.8 g, 4.89 mmol, 1 eq), and acetic acid solution (80% aqueous, 20 mL) gave the desired diol, (3aS,3bR,4R,5R,5aS,10aR,10bS,12aR)-10a,12a-dimethyl-3,3a,3b,4,5,5a,6,7,10,10a,10b,11,12,12a-tetradecahydrocyclopenta[5,6]naphtho[1,2-f]indazole-4,5-diol (Compound 37, 1.5 g, 89%), as a pale yellow solid after purification by flash column chromatography (230-400 mesh silica gel, eluted with 0-10% dichloromethane/methanol).

LCMS: (Method 1a) MS m/z: 329.2 (M+1), $t_R$: 2.351 min, Purity: 99.87% (ELSD).

$^1$H-NMR (400 MHz, DMSO-d$_6$): δ 12.21 (s, 1H), 7.21 (s, 1H), 578 (d, J=6.0 Hz, 1H), 5.71 (d, J=5.6 Hz, 1H), 4.55 (s, 1H), 4.25 (d, J=5.2 Hz, 1H), 4.09 (d, J=5.2 Hz, 1H), 3.17-3.09 (m, 2H), 2.99-2.92 (m, 2H), 2.44-2.32 (m, 1H), 2.23-2.02 (m, 3H), 1.75-1.72 (m, 1H), 1.62-1.23 (m, 5H), 1.02-1.01 (m, 1H), 0.74 (s, 3H), 0.71 (s, 3H).

I. Using General Procedure F with Compound 37 (1.5 g, 4.57 mmol, 1 eq), sodium metaperiodate (1.95 g, 9.14 mmol, 2 eq), THF (15 mL) and water (7 mL) gave the desired dialdehyde, (5R,6S)-5-((3aR,6S,7R,7aS)-7-formyl-3a-methyl-3a,4,5,6,7,7a-hexahydro-1H-inden-6-yl)-5-methyl-4,5,6,7-tetrahydro-1H-indazole-6-carbaldehyde (Compound 38, 1.25 g, 83%), as a white solid after purification by flash column chromatography (230-400 mesh silica gel, eluted with 0-1% dichloromethane/methanol).

J. Using General Procedure G with Compound 38 (1.25 g, 3.81 mmol, 1 eq), sodium borohydride (0.289 g, 7.62 mmol, 2 eq), THF (10 mL) and methanol (10 mL) gave the desired diol, (5R,6S)-5-((3aR,6S,7R,7aS)-7-(hydroxymethyl)-3a-methyl-3a,4,5,6,7,7a-hexahydro-1H-inden-6-yl)-5-methyl-4,5,6,7-tetrahydro-1H-indazol-6-yl)methanol (Compound Ia-26, 1 g, 80%), as an off-white solid after purification by flash column chromatography (230-400 mesh silica gel, eluted with 0-20% dichloromethane/methanol).

LCMS: (Method 1b) MS m/z: 331.2 (M+1), $t_R$: 2.29 min, Purity: 99.41% (UV).

HPLC: (Method 2a) $t_R$: 3.25 min, Purity: 99.16% (UV).

$^1$H-NMR (400 MHz, DMSO-d$_6$): δ 12.20 (bs, 1H), 7.33-7.08 (m, 1H), 5.82-5.81 (m, 1H), 5.68-5.67 (m, 1H), 4.41-4.38 (m, 1H), 4.25-4.21 (m, 1H), 3.85-3.83 (m, 1H), 3.72-3.70 (m, 1H), 3.61-3.60 (m, 1H), 3.25-3.09 (m, 2H), 3.02-2.96 (m, 1H), 2.25-2.17 (m, 1H), 2.16-2.06 (m, 1H), 1.93-1.87 (m, 1H), 1.77-1.74 (m, 5H), 1.43-1.40 (m, 2H), 1.23-1.20 (m, 1H), 0.98-093 (s, 3H), 0.74-0.71 (s, 3H).

Synthetic Example 10

Synthesis of ((3aS,4S,5S,7aS)-5-((5R,6S)-6-(hydroxymethyl)-5-methyl-4,5,6,7-tetrahydro-1H-indazol-5-yl)-7a-methyloctahydro-1H-inden-4-yl)methanol (Compound Ia-27)

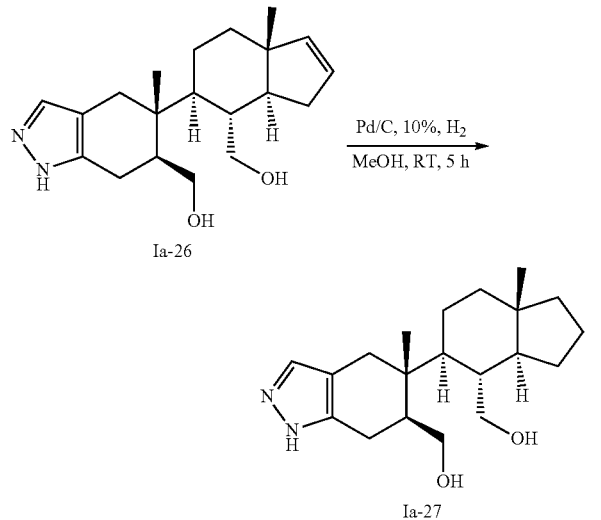

Using General Procedure T with Compound Ia-26 (from Example 9, 0.1 g, 0.302 mmol, 1 eq), Pd/C (10%, 30 mg), a hydrogen atmosphere using a bladder and methanol (10 mL) afforded ((3aS,4S,5S,7aS)-5-((5R,6S)-6-(hydroxynethyl)-5-methyl-4,5,6,7-tetrahydro-1H-indazol-5-yl)-7a-methyloctahydro-1H-inden-4-yl)methanol (Compound Ia-27, 60 mg, 60%) as a white solid after purification by trituration using diethyl ether.

LCMS: (Method 1b) MS m/z: 333.3 (M+1), $t_R$: 3.44 min, Purity: 99.86% (ELSD), 90.27% (220 nm).

HPLC: (Method 2a) $t_R$: 3.42 min, Purity: 92.97% (ELSD), 89.58% (220 nm).

$^1$H-NMR (400 MHz, DMSO-$d_6$): δ 12.16 (bs, 1H), 7.18-7.15 (m, 1H), 4.45-4.40 (m, 1H), 4.22-4.19 (m, 1H), 3.82-3.68 (m, 2H), 3.47-3.37 (m, 2H), 3.16-3.11 (m, 2H), 3.00-2.96 (m, 1H), 2.12-2.04 (m, 2H), 1.78-1.74 (m, 1H), 1.62-1.54 (m, 5H), 1.43-1.30 (m, 5H), 1.17-1.07 (m, 4H), 1.06-0.95 (s, 3H), 0.68-0.63 (s, 3H).

Synthetic Example 11

Synthesis of ((5R,6S)-5-((3aR,6S,7R,7aS)-7-(aminomethyl)-3a-methyl-3a,4,5,6,7,7a-hexahydro-1H-inden-6-yl)-5-methyl-4,5,6,7-tetrahydro-1H-indazol-6-yl)methanol (Compound Ia-28)

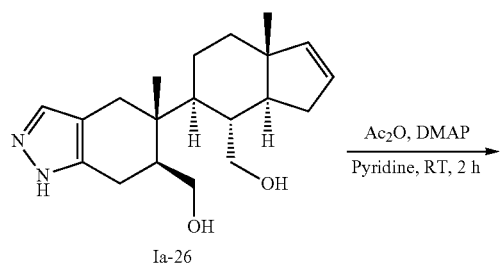

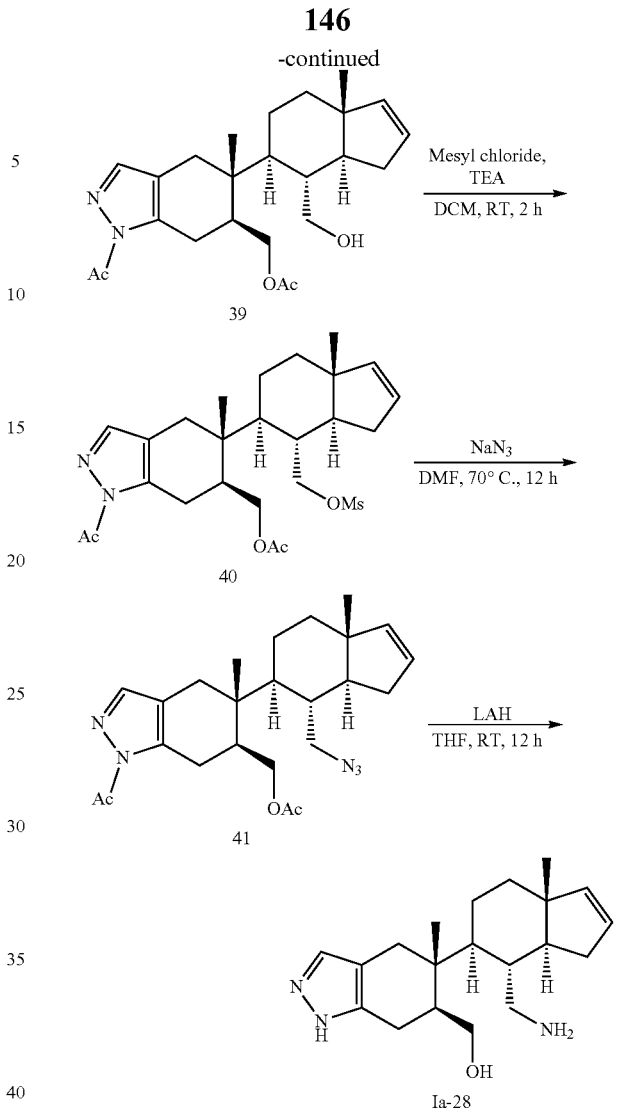

A. Using General Procedure A with Compound Ia-26 (from Example 9, 0.260 g, 0.605 mmol, 1 eq), Ac$_2$O (0.12 g, 1.21 mmol, 2 eq), DMAP (7 mg, 0.0605 mmol, 0.1 eq) and pyridine (10 mL), gave the desired acetate, ((5R,6S)-1-acetyl-5-((3aR,6S,7R,7aS)-7-(hydroxymethyl)-3a-methyl-3a,4,5,6,7,7a-hexahydro-1H-inden-6-yl)-5-methyl-4,5,6,7-tetrahydro-1H-indazol-6-yl)methyl acetate (Compound 39, 0.230 g, 92%), as a white foam after purification by flash column chromatography (230-400 mesh silica gel, eluted with 0-4% dichloromethane/methanol).

B. Using General Procedure J with Compound 39 (0.230 g, 0.627 mmol, 1 eq), triethylamine (0.13 mL, 0.94 mmol, 1.5 eq), MsCl (0.053 mL, 0.69 mmol, 1.1 eq) and dichloromethane (12 mL) gave the desired mesylate, ((5R,6S)-1-acetyl-5-methyl-5-((3aR,6S,7R,7aS)-3a-methyl-7-(((methylsulfonyl)oxy)methyl)-3a,4,5,6,7,7a-hexahydro-1H-inden-6-yl)-4,5,6,7-tetrahydro-1H-indazol-6-yl)methyl acetate (Compound 40, 0.3 g), as a pale yellow foam which was used as is for the next step without any further purification.

C. Using General Procedure K with Compound 40 (0.3 g, 0.609 mmol, 1 eq), sodium azide (0.595 g, 9.14 mmol, 15 eq) and DMF (5 mL) afforded ((5R,6S)-1-acetyl-5-((3aR, 6S,7R,7aS)-7-(azidomethyl)-3a-methyl-3a,4,5,6,7,7a-hexahydro-1H-inden-6-yl)-5-methyl-4,5,6,7-tetrahydro-1H-indazol-6-yl)methyl acetate (Compound 41, 0.130 g, 50%) as an off-white foam after purification by flash column chromatography (230-400 mesh silica gel, eluted with 0-15% pet ether/ethyl acetate).

D. Using General Procedure S with Compound 41 (0.13 g, 0.295 mmol, 1 eq), LAH (1 M in THF solution, 0.88 mL, 0.887 mmol, 3 eq) and THF (10 mL), gave the desired amine, ((5R,6S)-5-((3aR,6S,7R,7aS)-7-(aminomethyl)-3a-methyl-3a,4,5,6,7,7a-hexahydro-1H-inden-6-yl)-5-methyl-4,5,6,7-tetrahydro-1H-indazol-6-yl)methanol (Compound Ia-28, 29 mg, 29%), as a white solid after purification by preparative HPLC (Method 3b).

LCMS: (Method 1b) MS m/z: 330.2 (M+1), $t_R$: 2.291 min, Purity: 97.99% (max), 97.46% (220 nm).

HPLC: (Method 2b) $t_R$: 2.298 min, Purity: 97.90% (max), 97.12% (220 nm).

$^1$H-NMR (400 MHz, DMSO-$d_6$): δ 7.64 (bs, 3H), 7.25 (bs, 1H), 5.87 (d, J=5.6 Hz, 1H), 5.72 (d, J=4.4 Hz, 1H), 4.48 (s, 1H), 3.73-3.71 (m, 1H), 3.17 (t, J=10.0 Hz, 1H), 3.01-2.92 (m, 2H), 2.36-2.26 (m, 3H), 2.07-1.94 (m, 3H), 1.78-1.70 (m, 3H), 1.52-1.47 (m, 2H), 1.29-1.23 (m, 1H), 0.93 (s, 3H), 0.77 (s, 3H).

Synthetic Example 12

Synthesis of ((5R,6S)-5-((1S,3aS,4S,5S,7aR)-4-(aminomethyl)-1-ethyl-7a-methyloctahydro-1H-inden-5-yl)-5-methyl-4,5,6,7-tetrahydro-1H-indazol-6-yl)methanol (Compound Ia-29)

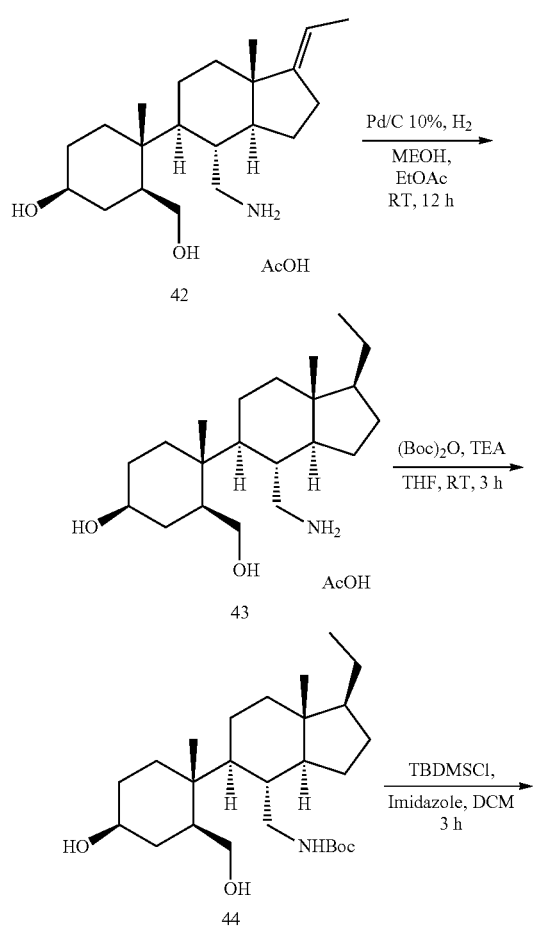

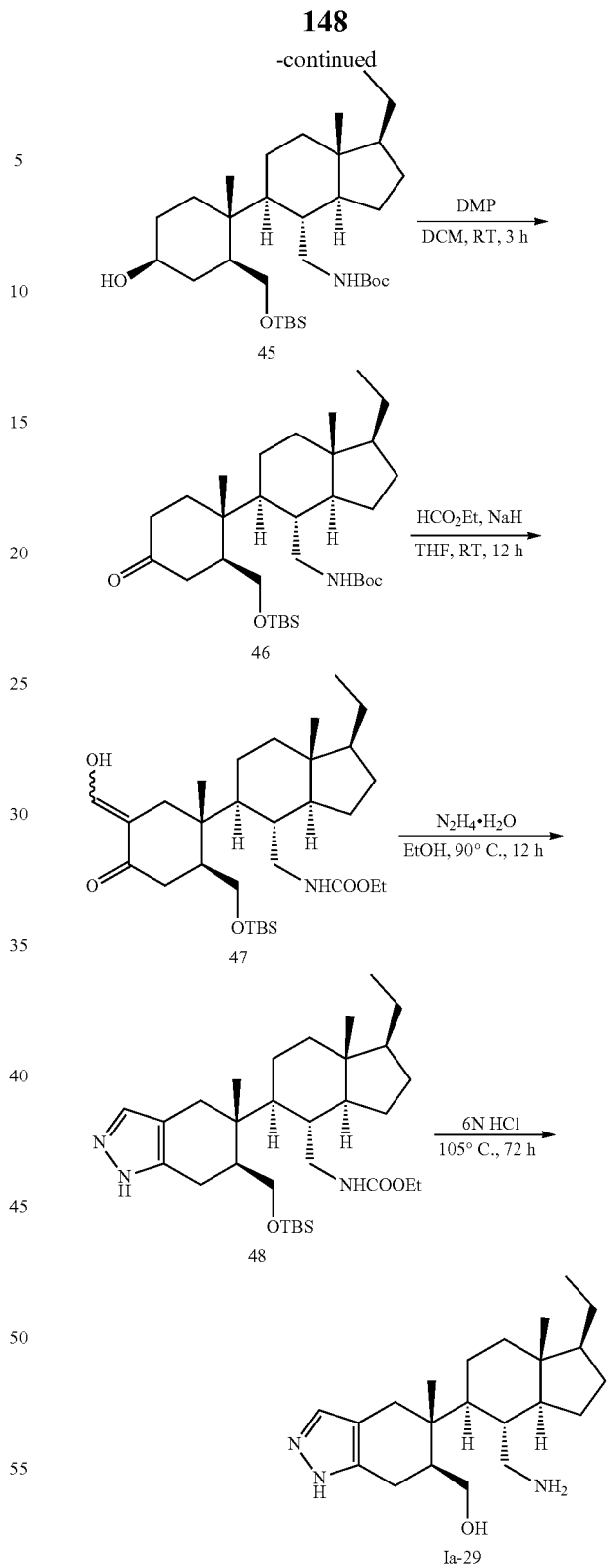

A. Using General Procedure T with (1S,3S,4R)-4-((3aS,4R,5S,7aS,E)-4-(aminomethyl)-1-ethylidene-7a-methyloctahydro-1H-inden-5-yl)-3-(hydroxymethyl)-4-methylcyclohexan-1-ol acetate (Compound 42, as prepared in U.S. Pat. No. 7,601,874, 2 g, 3.57 mmol, 1 eq), Pd/C (10%, 150 mg), methanol (20 mL) and ethyl acetate (8 mL) under 1 hydrogen atmosphere using a balloon gave the desired amine, (1S,3S,4R)-4-(((1S,3aS,4S,5S,7aR)-4-(aminomethyl)-1-ethyl-7a-methyloctahydro-1H-inden-5-yl)-3-(hydroxymethyl)-4-methylcyclohexan-1-ol acetate (Compound 43, 1.9 g, 90%), as a white solid after trituration using diethyl ether.

B. To a solution Compound 43 (1.9 g, 5.6 mmol, 1 eq) in THF (36 mL) and water (4 mL) taken in a 3 necked RB flask (250 mL) was added triethylamine (2.2 mL, 16.88 mol, 3 eq) and di-tert-butyl dicarbonate (1.33 mL, 61.92 mmol, 1.1 eq) dropwise over 2 minutes at 0° C. The reaction mass was stirred for 3 h at room temperature with the help of a magnetic stirrer and the reaction was carried out under a nitrogen atmosphere. Completion of the reaction was monitored by TLC. Reaction mass was concentrated on a rotary evaporator at 45° C. and the crude colorless gum mass obtained was dissolved in ethyl acetate (40 mL) and washed with water (2×30 mL) followed by brine (1×30 mL). Organic phase was dried over anhydrous sodium sulphate and concentrated to get a crude off white solid. Further purification was performed by flash column chromatography (230-400 mesh silica gel, eluted with 0-5% dichloromethane/methanol) to afford tert-butyl (((1S,3aS,4S,5S,7aR)-1-ethyl-5-((1R,2S,4S)-4-hydroxy-2-(hydroxymethyl)-1-methylcyclohexyl)-7a-methyloctahydro-1H-inden-4-yl)methyl)carbamate (Compound 44, 1.8 g, 73%) as a white solid.

C. Using General Procedure B with Compound 44 (1.8 g, 4.11 mmol, 1 eq), imidazole (0.560 g, 8.22 mmol, 2 eq), TBSCl (0.618 g, 4.11 mmol, 1 eq) and dichloromethane (30 mL) gave the desired silyl ether, tert-butyl (((1S,3aS,4S,5S,7aR)-5-((1R,2S,4S)-2-(((tert-butyldimethylsilyl)oxy)methyl)-4-hydroxy-1-methylcyclohexyl)-1-ethyl-7a-methyloctahydro-1H-inden-4-yl)methyl)carbamate (Compound 45, 1.3 g, 58%), as a white solid after purification by column chromatography (230-400 mesh silica gel, eluted with 0-1% dichloromethane/methanol).

D. Using General Procedure N with Compound 44 (13 g, 23.5 mmol, 1 eq), DMP (1.5 g, 35.3 mmol, 1.5 eq) and dichloromethane (20 mL) gave the desired ketone, tert-butyl (((1S,3aS,4S,5S,7aR)-5-((R,2S)-2-(((tert-butyldimethylsilyl)oxy)methyl)-1-methyl-4-oxocyclohexyl)-1-ethyl-7a-methyloctahydro-1H-inden-4-yl)methyl)carbamate (Compound 46, 1 g, 77%), as a white solid after purification by column chromatography (230-400 mesh silica gel, eluted with 0-30% pet ether/ethyl acetate).

E. Using General Procedure O with Compound 46 (1 g, 1.81 mmol, 1 eq), sodium hydride (60% in paraffin oil, 0.290 g, 7.27 mmol, 4 eq), ethyl formate (0.89 mL, 10.9 mmol, 6 eq) and THF (30 mL) gave the desired enone, ethyl (((1S,3aS,4S,5S,7aR)-5-((1R,2S)-2-(((tert-butyldimethylsilyl)oxy)methyl)-5-(hydroxymethylene)-1-methyl-4-oxocyclohexyl)-1-ethyl-7a-methyloctahydro-1H-inden-4-yl)methyl)carbamate (Compound 47, 0.650 g, 65%), as a colorless gummy solid after purification by column chromatography (230-400 mesh silica gel, eluted with 0-20% pet ether/ethyl acetate).

F. Using General Procedure P with Compound 47 (0.650 g, 1.18 mmol, 1 eq), hydrazine hydrate (0.147 g, 2.95 mmol) and ethanol (20 mL) gave the desired pyrazole, ethyl (((1S,3aS,4S,5S,7aR)-5-((5R,6S)-6-(((tert-butyldimethylsilyl)oxy)methyl)-5-methyl-4,5,6,7-tetrahydro-1H-indazol-5-yl)-1-ethyl-7a-methyloctahydro-1H-inden-4-yl)methyl)carbamate (Compound 48, 0.4 g, 63%), as an off-white solid after purification by column chromatography (230-400 mesh silica gel, eluted with 0-60% pet ether/ethyl acetate).

G. To a solution of Compound 48 (0.400 g, 0.732 mmol, 1 eq.) in water (5 mL) in a 25 mL three-necked RB flask was added 6 N HCl (10 mL) at 0° C. The reaction mass was stirred with the help of a magnetic stirrer and the reaction was carried out under a nitrogen atmosphere. The stirring was continued for 12 h at reflux. The completion of the reaction was monitored by TLC. The reaction mass was concentrated on a rotary evaporator at 45° C. and the crude mass obtained was dissolved in dichloromethane (15 mL) and washed with 10% aqueous NaHCO$_3$ solution (2×10 mL). Organic phase was dried over anhydrous sodium sulphate and concentrated to get a crude yellow solid. Further purification was performed by preparative HPLC (Method 3a) to afford ((5R,6S)-5-((1S,3aS,4S,5S,7aR)-4-(aminomethyl)-1-ethyl-7a-methyloctahydro-1H-inden-5-yl)-5-methyl-4,5,6,7-tetrahydro-1H-indazol-6-yl)methanol (Compound Ia-29, 0.1 g, yield: 40%) as a white solid.

LCMS: (Method 1b) MS m/z: 360.3 (M+1), $t_R$: 3.036 min, Purity: 97.56% (ELSD).

HPLC: (Method 2a) $t_R$: 3.008 min, Purity: 97.65% (ELSD), 96.82% (220 nm).

$^1$H-NMR (400 MHz, DMSO-d$_6$): δ 12.19 (s, 1H), 7.60-7.57 (m, 3H), 7.24-7.21 (m, 1H), 4.49-4.46 (m, 1H), 3.72-3.70 (m, 1H), 3.35-3.28 (m, 1H), 3.29-3.17 (m, 1H), 2.99-2.89 (m, 2H), 2.33-2.26 (m, 2H), 1.93-1.94 (m, 1H), 1.82-1.63 (m, 6H), 1.40-1.34 (m, 2H), 1.24-1.08 (m, 5H), 0.98-0.88 (m, 7H), 0.63-0.58 (m, 3H).

Synthetic Example 13

Synthesis of ((5R,6S)-5-((3aS,4R,5S,7aS)-4-(aminomethyl)-7a-methyl-1-methyleneoctahydro-1H-inden-5-yl)-3-(difluoromethyl)-5-methyl-4,5,6,7-tetrahydro-1H-indazol-6-yl)methanol (Compound Ia-30)

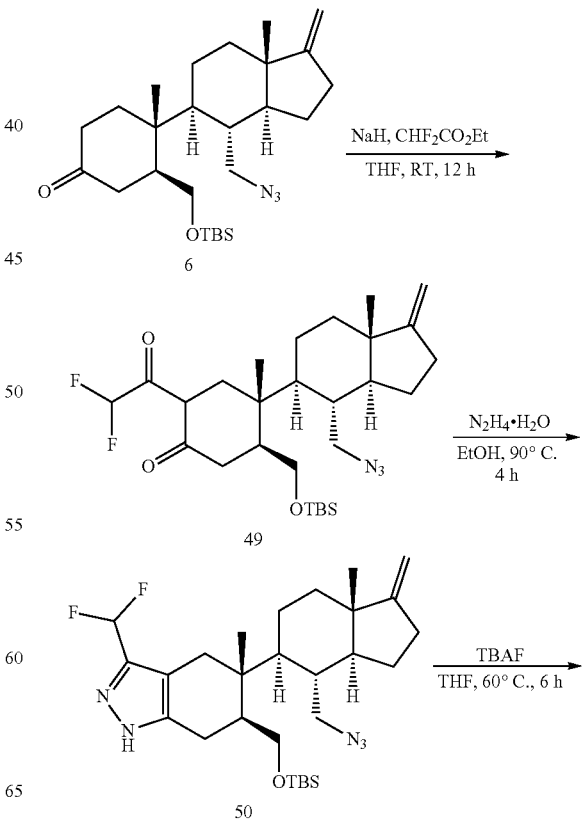

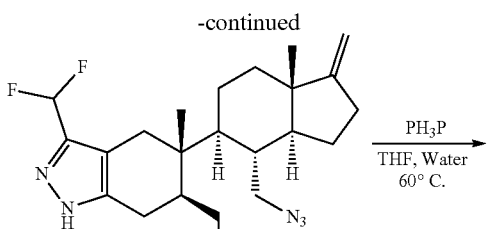

A. Using General Procedure O with Compound 6 (from Example 1, 0.85 g, 1.85 mmol), sodium hydride (60% in paraffin oil, 0.36 g, 7.4 mmol, 4 eq), ethyl difluoroacetate (1.14 mL, 1.11 mmol, 6 eq) and THF (15 mL) gave the desired dione, (4R,5S)-4-((3aS,4R,5S,7aS)-4-(azidomethyl)-7a-methyl-1-methyleneoctahydro-1H-inden-5-yl)-5-(((tert-butyldimethylsilyl)oxy)methyl)-2-(2,2-difluoroacetyl)-4-methylcyclohexan-1-one (Compound 49, 0.8 g, 80%), as an off-white solid after purification by column chromatography (60-120 mesh silica gel, eluted with 0-20% pet ether/ethyl acetate).

B. Using General Procedure P with Compound 49 (0.8 g, 1.85 mmol), hydrazine hydrate (0.2 g, 3.72 mmol) and ethanol (15 mL) gave the desired pyrazole, (5R,6S)-5-((3aS,4R,5S,7aS)-4-(azidomethyl)-7a-methyl-1-methyleneoctahydro-1H-inden-5-yl)-6-(((tert-butyldimethylsilyl)oxy)methyl)-3-(difluoromethyl)-5-methyl-4,5,6,7-tetrahydro-1H-indazole (Compound 50, 0.3 g, 38%), as a white solid after purification by column chromatography (60-120 mesh silica gel, eluted with 0-50% pet ether/ethyl acetate).

C. Using General Procedure Q with Compound 50 (03 g, 0.56 mmol), TBAF solution (1M in THF, 1.1 mL, 1.12 mmol) and THF (15 mL) gave the desired alcohol, ((5R,6S)-5-((3aS,4R,5S,7aS)-4-(azidomethyl)-7a-methyl-1-methyleneoctahydro-1H-inden-5-yl)-3-(difluoromethyl)-5-methyl-4,5,6,7-tetrahydro-1H-indazol-6-yl)methanol (Compound 51a, 0.1 g, 43%), as a white solid after purification by column chromatography (60-120 mesh silica gel, eluted with 0-60% pet ether/ethyl acetate).

D. Using General Procedure R with Compound 51 (0.1 g, 0.24 mmol), triphenylphosphine (0.13 g, 0.48 mmol), THF (10 mL) and water (5 mL) gave the desired amine, ((5R,6S)-5-((3aS,4R,5S,7aS)-4-(aminomethyl)-7a-methyl-1-methyleneoctahydro-1H-inden-5-yl)-3-(difluoromethyl)-5-methyl-4,5,6,7-tetrahydro-1H-indazol-6-yl)methanol (Compound Ia-30, 0.044 g, 47%), as a white solid after purification by column chromatography (Neutral alumina, eluted with 0-10% dichloromethane/methanol).

LCMS: (Method 1b) MS m/z: 394.0 (M+1), $t_R$: 3366 min, Purity: 92.39% (max), 91.69% (220 nm).

HPLC: (Method 2a) $t_R$:3.306 min, Purity: 95.03% (max), 94.11% (220 nm).

$^1$H-NMR (400 MHz, CD$_3$OD): δ 6.84-6.57 (t, $J_{HF}$=54.7 Hz, 1H), 4.68-4.66 (m, 2H), 3.96 (dd, J=2.8, 10.8 Hz, 1H), 3.70-3.68 (m, 1H), 3.59-3.56 (m, 1H), 3.42-3.32 (m, 2H), 3.17-3.11 (m, 2H), 3.03-2.91 (m, 1H), 2.76-2.49 (m, 3H), 2.40-2.26 (m, 1H), 2.24-2.13 (m, 1H), 1.89-1.28 (m, 10H), 1.09 (s, 3H), 0.86 (s, 3H).

Synthetic Example 13.1

Synthesis of ((5R,6S)-5-((3aS,4R,5S,7aS)-4-(aminomethyl)-7a-methyl-1-methyleneoctahydro-1H-inden-5-yl)-5-methyl-3-(trifluoromethyl)-4,5,6,7-tetrahydro-1H-indazol-6-yl)methanol (Compound Ia-31)

Following the procedure as described in Synthetic Example 13 and making non-critical variations using ethyl trifluoroacetate to replace ethyl difluoroacetate in the conversion of Compound 6 to Compound 49, the title compound, ((5R,6S)-5-((3aS,4R,5S,7aS)-4-(aminomethyl)-7a-methyl-1-methyleneoctahydro-1H-inden-5-yl)-5-methyl-3-(trifluromethyl)-4,5,6,7-tetrahydro-1H-indazol-6-yl)methanol (Compound Ia-31, 50 mg, 34%), was obtained as a white solid after purification by column chromatography (Neutral alumina, eluted with 0-20% dichloromethane/methanol).

LCMS: (Method 1b) MS m/z: 358.2 (M+1), $t_R$: 2.591 min, Purity: 94.95% (max), 93.8% (220 nm).

HPLC: (Method 2a) $t_R$: 2.430 min, Purity: 95.64% (max), 93.82% (220 nm).

$^1$H-NMR (400 MHz, CD$_3$OD): δ 4.65 (s, 2H), 3.96 (dd, J=2.4, 10.8 Hz, 1H), 3.34-3.04 (m, 3H), 2.85-2.81 (m, 1H), 2.57-2.11 (m, 9H), 1.89-1.26 (m, 9H), 1.07 (s, 3H), 0.88 (s, 3H).

Synthetic Example 13.2

Synthesis of ((5R,6S)-5-((3aS,4R,5S,7aS)-4-(aminomethyl)-7a-methyl-1-methyleneoctahydro-1H-inden-5-yl)-3,5-dimethyl-4,5,6,7-tetrahydro-1H-indazol-6-yl)methanol (Compound Ia-32)

Following the procedure as described in Synthetic Example 13 and making non-critical variations using ethyl acetate to replace ethyl difluoroacetate in the conversion of Compound 6 to Compound 49, the title compound, ((5R,6S)-5-((3aS,4R,5S,7aS)-4-(aminomethyl)-7a-methyl-1-methyleneoctahydro-1H-inden-5-yl)-3,5-dimethyl-4,5,6,7-tetrahydro-1H-indazol-6-yl)methanol (Compound Ia-32, 17 mg, 30%), was obtained as a white solid after purification by column chromatography (Neutral alumina, eluted with 0-5% dichloromethane/methanol).

LCMS: (Method 1b) MS m/z: 412.0 (M+1), $t_R$: 3.693 min, Purity: 95.26% (max).

HPLC: (Method 1a) $t_R$: 3.454 min, Purity: 95.11% (max).

$^1$H-NMR (400 MHz, CD$_3$OD): δ 64.67 (s, 2H), 3.97 (d, J=10.6 Hz, 1H), 3.42-3.33 (m, 1H), 3.19-3.14 (m, 1H), 2.94-2.86 (m, 1H), 2.75-2.65 (m, 1H), 2.64-2.50 (m, 2H), 2.43-2.17 (m, 3H), 1.88-1.24 (m, 10H), 1.10 (s, 3H), 0.85 (s, 3H).

Synthetic Example 14
Synthesis of ((5R,6S)-5-((3aS,4S,5S,7aS)-4-(aminomethyl)-7a-methyloctahydro-1H-inden-5-yl)-5-methyl-4,5,6,7-tetrahydro-1H-indazol-6-yl)methanol (Compound Ia-33)
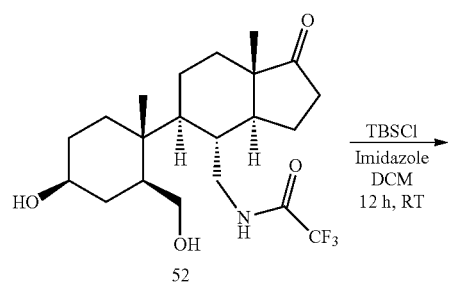
52
TBSCl
Imidazole
DCM
12 h, RT
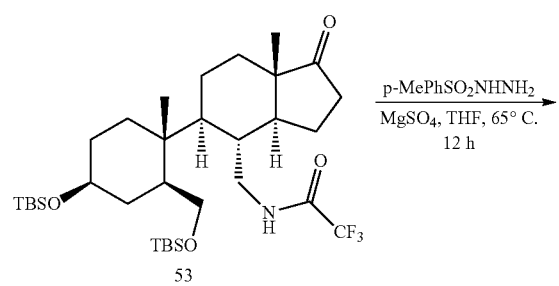
53
p-MePhSO₂NHNH₂
MgSO₄, THF, 65° C.
12 h
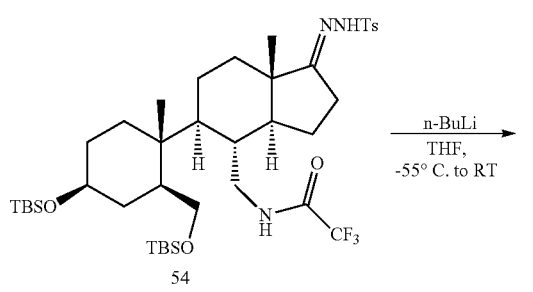
54
n-BuLi
THF,
−55° C. to RT
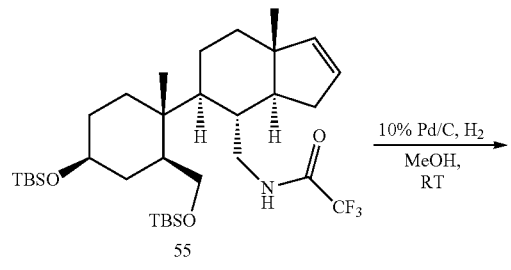
55
10% Pd/C, H₂
MeOH,
RT
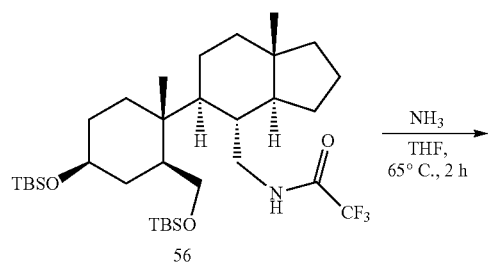
56
NH₃
THF,
65° C., 2 h
-continued
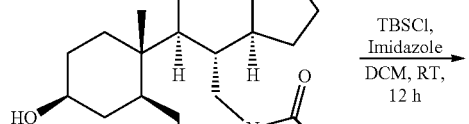
TBSCl,
Imidazole
DCM, RT,
12 h
57
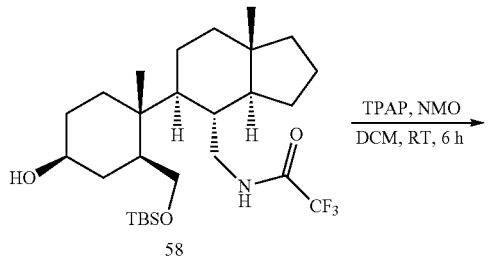
58
TPAP, NMO
DCM, RT, 6 h
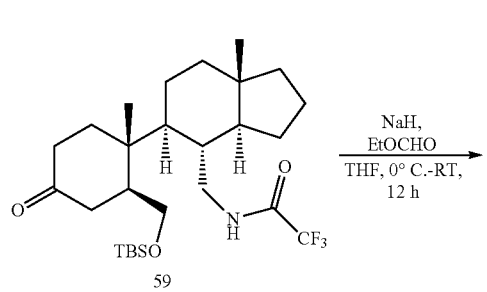
59
NaH,
EtOCHO
THF, 0° C.-RT,
12 h
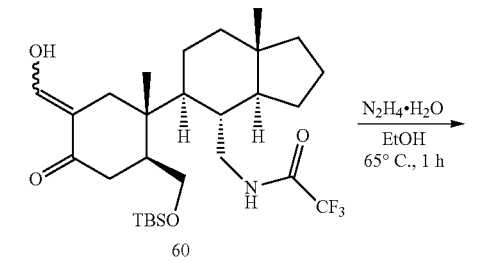
60
N₂H₄·H₂O
EtOH
65° C., 1 h
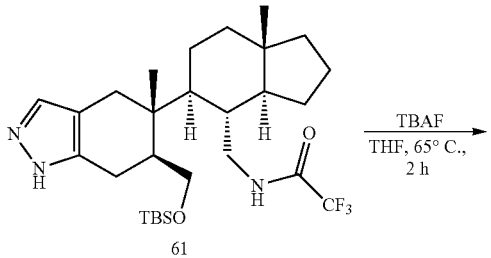
61
TBAF
THF, 65° C.,
2 h
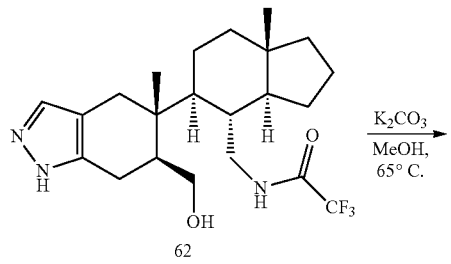
62
K₂CO₃
MeOH,
65° C.

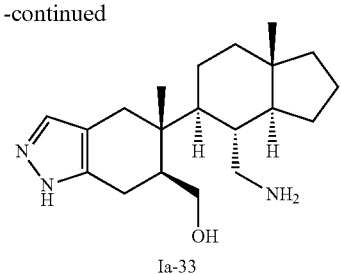

Ia-33

A. Using General Procedure B with 2,2,2-trifluoro-N-(((3aS,4R,5S,7aS)-5-((1R,2S,4S)-4-hydroxy-2-(hydroxymethyl)-1-methylcyclohexyl)-7a-methyl-1-oxooctahydro-1H-inden-4-yl)methyl)acetamide (Compound 52, 8.8 g, 21.0 mmol, 1 eq) imidazole (7.1 g, 105.2 mmol, 5 eq), TBSCl (6.3 g, 42.009 mmol, 2 eq) and dichloromethane (100 mL) gave the desired silyl ether, N-(((3aS,4R,5S,7aS)-5-((1R,2S,4S)-4-((tert-butyldimethylsilyl)oxy)-2-(((tert-butyldimethylsilyl)oxy)methyl)-1-methylcyclohexyl)-7a-methyl-1-oxooctahydro-1H-inden-4-yl)methyl)-2,2,2-trifluoroacetamide (Compound 53, 13 g, 96%), as an off-white solid after purification by column chromatography (60-120 mesh silica gel, eluted with 0-20% pet ether/ethyl acetate).

B. To a solution Compound 53 (13 g, 20.08 mmol, 1 eq) in THF (100 mL) and magnesium sulphate (6.04 g, 50.20 mmol, 2.5 eq) taken in a 3-necked RB flask (250 mL) was added p-toluenesulphonyl hydrazide (11 g, 60.65 mol, 3 eq). The reaction mass was stirred for 12 h with the help of a magnetic stirrer and the reaction was carried out under a nitrogen atmosphere. Completion of the reaction was monitored by TLC. Reaction mass was diluted with ethyl acetate (100 mL), washed with water (2×25 mL) followed by brine wash (1×25 mL). The organic layer was dried over sodium sulphate and concentrated on a rotary evaporator. The crude residue was purified by column chromatography (60-120 mesh silica gel, eluted with 0-20%) pet ether/ethyl acetate to afford N-(((3aS,4R,5S,7aS)-5-((1R,2S,4S)-4-((tert-butyldimethylsilyl)oxy)-2-(((tert-butyldimethylsilyl)oxy)methyl)-1-methylcyclohexyl)-7a-methyl-1-(2-tosylhydrazineylidene)octahydro-1H-inden-4-yl)methyl)-2,2,2-trifluoroacetamide as an off-white solid (Compound 54, 11.5 g, 95%).

C. To a solution Compound 54 (11.5 g, 14.5 mmol, 1 eq) in THF (150 mL) taken in a 3-necked RB flask (500 mL) was added n-BuLi (70 ml, 70 mmol, 5 eq) dropwise at −55° C. After addition, the reaction mixture was allowed to warm to RT. Reaction mass was stirred at RT for 10 h with a magnetic stirrer under a nitrogen atmosphere. Completion of the reaction was monitored by TLC. Reaction mass was quenched with a cold saturated aqueous solution of ammonium chloride at 0° C. and stirred for 5 min at RT. The solid precipitated was washed with water (150 mL), followed by brine wash (25 mL). The organic layer was dried over sodium sulphate and concentrated on a rotary evaporator. The crude residue was purified by column chromatography (60-120 mesh silica gel, eluted with 0-10% pet ether/ethyl acetate) to afford N-(((3aR,6S,7R,7aS)-6-((1R,2S,4S)-4-((tert-butyldimethylsilyl)oxy)-2-(((tert-butyldimethylsilyl)oxy)methyl)-1-methylcyclohexyl)-3a-methyl-3a,4,5,6,7,7a-hexahydro-1H-inden-7-yl)methyl)-2,2,2-trifluoroacetamide as an off-white solid (Compound 55, 2.4 g, yield: 27%).

D. Using General Procedure T with Compound 55 (2.4 g, 3.8 mmol, 1 eq), palladium on carbon (10%, 0.24 g) and methanol (10 mL) under a hydrogen atmosphere gave the desired alkane, N-(((3aS,4S,5S,7aS)-5-((R,2S,4S)-4-((tert-butyldimethylsilyl)oxy)-2-(((tert-butyldimethylsilyl)oxy)methyl)-1-methylcyclohexyl)-7a-methyloctahydro-1H-inden-4-yl)methyl)-2,2,2-trifluoroacetamide (Compound 56, 2.3 g, 95%), as a white solid after purification by column chromatography (230-400 mesh silica gel, eluted with 0-50% pet ether/ethyl acetate).

E. Using General Procedure Q with Compound 56 (2.3 g, 3.6 mmol, 1 eq), TBAF (1M THF, 1.89 g, 7.2 mmol, 2 eq) and THF (35 mL) gave the desired diol, 2,2,2-trifluoro-N-(((3aS,4S,5S,7aS)-5-((1R,2S,4S)-4-hydroxy-2-(hydroxymethyl)-1-methylcyclohexyl)-7a-methyloctahydro-1H-inden-4-yl)methyl)acetamide (Compound 57, 1.4 g, 95%), as a white solid after purification by column chromatography (60-120 mesh silica gel, eluted with 0-50% pet ether/ethyl acetate).

F. Using General Procedure B with Compound 57 (1.4 g, 3.5 mmol, 1 eq), imidazole (0.578 g, 3.8 mmol, 1.1 eq), TBSCl (0.358 g, 5.259 mmol, 1.5 eq) and dichloromethane (20 mL) gave the desired silyl ether, N-(((3aS,4S,5S,7aS)-5-((1R,2S,4S)-2-(((tert-butyldimethylsilyl)oxy)methyl)-4-hydroxy-1-methylcyclohexyl)-7a-methyloctahydro-1H-inden-4-yl)methyl)-2,2,2-trifluoroacetamide (Compound 58, 1 g, 58%), as a white solid after purification by column chromatography (60-120 mesh silica gel, eluted with 0-40% pet ether/ethyl acetate).

G. Using General Procedure M with Compound 58 (1 g, 1.9 mmol, 1 eq) NMO.H$_2$O (0.34 g, 2.89 mmol, 1.5 eq), TPAP (0.07 g, 0.192 mmol, 0.1 eq), molecular sieves (4 Å, 300 mg) and dichloromethane (15 mL) gave the desired ketone, N-(((3aS,4S,5S,7aS)-5-((1R,2S)-2-(((tert-butyldimethylsilyl)oxy)methyl)-1-methyl-4-oxocyclohexyl)-7a-methyloctahydro-1H-inden-4-yl)methyl)-2,2,2-trifluoroacetamide (Compound 59, 0.840 g, 84%), as a white solid after purification by column chromatography (60-120 mesh silica gel, eluted with 0-40% pet ether/ethyl acetate).

H. Using General Procedure O with Compound 59 (0.84 g, 1.6 mmol), sodium hydride (0.175 g, 7.3 mmol, 4.5 eq) in THF (20 mL) and ethyl formate (1.203 g, 1.3 mL, 16 mmol, 10 eq) gave the desired enone, N-(((3aS,4S,5S,7aS)-5-((1R,2S)-2-(((tert-butyldimethylsilyl)oxy)methyl)-5-(hydroxymethylene)-1-methyl-4-oxocyclohexyl)-7a-methyloctahydro-1H-inden-4-yl)methyl)-2,2,2-trifluoroacetamide (Compound 60, 0.80 g, 90%), as a white solid after purification by column chromatography (60-120 mesh silica gel, eluted with 0-30% pet ether/ethyl acetate).

I. Using General Procedure P with Compound 60 (0.8 g, 1.46 mmol, 1 eq), hydrazine hydrate (0.36 g, 7.33 mmol, 5 eq) and ethanol (15 mL) gave the desired pyrazole, N-(((3aS,4S,5S,7aS)-5-((5R,6S)-6-(((tert-butyldimethylsilyl)oxy)methyl)-5-methyl-4,5,6,7-tetrahydro-1H-indazol-5-yl)-7a-methyloctahydro-1H-inden-4-yl)methyl)-2,2,2-trifluoroacetamide (Compound 61, 0.7 g, 88%), as a white solid after purification by column chromatography (60-120 mesh silica gel, eluted with 0-50% pet ether/ethyl acetate).

J. Using General Procedure Q with Compound 61 (0.7 g, 1.29 mmol, 1 eq), TBAF (1M in THF, 0.502 g, 2 ml, 1.9 mmol, 1.5 eq) and THF (15 mL) gave the desired alcohol, 2,2,2-trifluoro-N-(((3aS,4S,5S,7aS)-5-((5R,6S)-6-(hydroxymethyl)-5-methyl-4,5,6,7-tetrahydro-1H-indazol-5-yl)-7a-methyloctahydro-1H-inden-4-yl)methyl)acetamide (Compound 62, 0.4 g, 72%), as a white solid after purification by column chromatography (60-120 mesh silica gel, eluted with 0-10% methanol/dichloromethane).

K. Using General Procedure L with Compound 62 (0.4 g, 0.936 mmol, 1 eq), potassium carbonate (0.647 g, 4.68 mmol, 5 eq) and methanol (10 mL) gave the desired amine, ((5R,6S)-5-((3aS,4S,5S,7aS)-4-(aminomethyl)-7a-methyl-octahydro-1H-inden-5-yl)-5-methyl-4,5,6,7-tetrahydro-1H-indazol-6-yl)methanol (Compound Ia-33, 0.106 g, 35%), as a white solid after purification by column chromatography (60-120 mesh silica gel, eluted with 0-50% methanol/dichloromethane).

LCMS: (Method 1b) MS m/z: 332.5 (M+1), $t_R$: 2.546 min, Purity: 99.32% (ELSD), 90.14% (220 nm).

HPLC: (Method 2a) $t_R$: 2.39 min, Purity: 95.0% (ELSD), 93.20% (220 nm).

$^1$H-NMR (400 MHz, CD$_3$OD): δ 7.29 (s, 1H), 3.97-3.94 (m, 1H), 3.41-3.36 (m, 1H), 3.20-3.09 (m, 2H), 2.81-2.52 (m, 3H), 2.38-2.34 (m, 1H), 2.15-2.13 (m, 1H), 1.83-1.49 (m, 10H), 1.40-1.18 (m, 5H), 1.06 (s, 3H), 0.81 (s, 3H).

Synthetic Example 15

Synthesis of ((5R,6S)-5-((1S,3aS,4S,5S,7aR)-4-(aminomethyl)-1,7a-dimethyloctahydro-1H-inden-5-yl)-5-methyl-4,5,6,7-tetrahydro-1H-indazol-6-yl)methanol (Compound Ia-34)

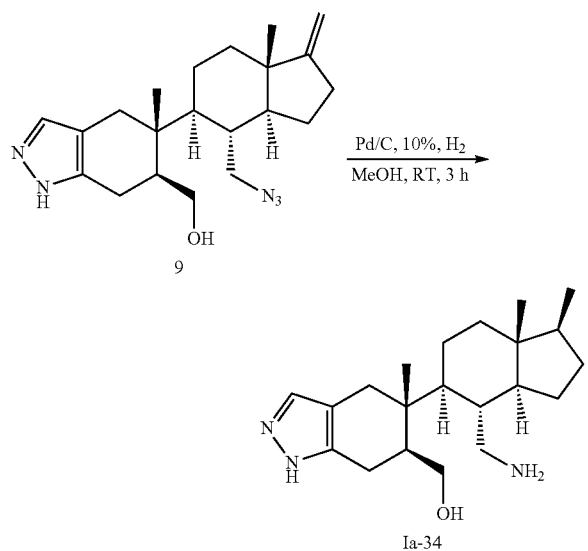

Using General Procedure T with Compound 9 (from Example 1, 0.2 g, 0.504 mmol, 1 eq), Pd/C (10%, 30 mg) and methanol (10 mL) under 1 hydrogen atmosphere using a balloon gave the desired alkane, ((5R,6S)-5-((1S,3aS,5S,7aR)-4-(aminomethyl)-1,7a-dimethyloctahydro-1H-inden-5-yl)-5-methyl-4,5,6,7-tetrahydro-1H-indazol-6-yl)methanol (Compound Ia-34, 80 mg, 49%), as a white solid after purification by column chromatography (neutral alumina, eluted with 0-10% dichloromethane/methanol).

LCMS: (Method 1b) MS m/z: 346.3 (M+1), $t_R$: 2.54 min, Purity: 93.32% (max), 91.86% (220 nm).

HPLC: (Method 2a) $t_R$: 2.71 min, Purity: 90.10% (max), 89.25% (220 nm).

$^1$H-NMR (400 MHz, CD$_3$OD): δ 7.37-7.33 (m, 1H), 3.96-3.94 (m, 1H), 3.42-3.40 (m, 2H), 3.12 (dd, J=5.6, 17.2 Hz, 1H), 2.92-2.89 (m, 1H), 2.69-2.66 (m, 1H), 2.53-2.49 (m, 1H), 2.41-2.37 (m, 1H), 2.16-2.14 (m, 1H), 1.92-1.73 (m, 5H), 1.68-1.61 (m, 2H), 1.54-1.48 (m, 2H), 1.40-1.28 (m, 3H), 1.06-1.01 (s, 3H), 0.90-0.86 (m, 3H), 0.67-0.65 (s, 3H).

Synthetic Example 15.1

Synthesis of ((5R,6S)-5-((1S,3aS,4S,5S,7aR)-4-(aminomethyl)-1,7a-dimethyloctahydro-1H-inden-5-yl)-5-methyl-1-phenyl-4,5,6,7-tetrahydro-1H-indazol-6-yl)methanol (Compound Ia-35) and ((5R,6S)-5-((1S,3aS,4S,5S,7aR)-4-(aminomethyl)-1,7a-dimethyloctahydro-1H-inden-5-yl)-5-methyl-2-phenyl-4,5,6,7-tetrahydro-2H-indazol-6-yl)methanol (Compound Ia-36)

Following the procedure as described in Synthetic Example 15 and making non-critical variations using Compound Ia-8 or Compound Ia-9 (from Example 8) separately in place of Compound 9, the respective title compounds, ((5R,6S)-5-((1S,3aS,4S,5S,7aR)-4-(aminomethyl)-1,7a-dimethyloctahydro-1H-inden-5-yl)-5-methyl-1-phenyl-4,5,6,7-tetrahydro-1H-indazol-6-yl)methanol (Compound Ia-35) and ((5R,6S)-5-((1S,3aS,4S,5S,7aR)-4-(aminomethyl)-1,7a-dimethyloctahydro-1H-inden-5-yl)-5-methyl-2-phenyl-4,5,6,7-tetrahydro-2H-indazol-6-yl)methanol (Compound Ia-36), were obtained.

Compound Ia-35: LCMS: (Method 1f) MS m/z: 422.2 (M+1), $t_R$: 1.782 min, Purity: 91.72% (UV).

Compound Ia-36: LCMS: (Method 1f) MS m/z: 422.2 (M+1), $t_R$: 1.851 min, Purity: 93.39% (UV).

Synthetic Example 15.2

Synthesis ((5R,6S)-5-((1S,3aS,4S,5S,7aR)-4-(aminomethyl)-1,7a-dimethyloctahydro-1H-inden-5-yl)-1-cyclohexyl-5-methyl-4,5,6,7-tetrahydro-1H-indazol-6-yl)methanol (Compound Ia-37)

Following the procedure as described in Synthetic Example 15 and making non-critical variations using Compound Ia-16 (from Example 8.4) in place of Compound 9, the title compound, ((5R,6S)-5-((1S,3aS,4S,5S,7aR)-4-(aminomethyl)-1,7a-dimethyloctahydro-1H-inden-5-yl)-1-cyclohexyl-5-methyl-4,5,6,7-tetrahydro-1H-indazol-6-yl)methanol (Compound Ia-37), was obtained.

LCMS: (Method 1d) MS m/z: 428.1 (M+1), $t_R$: 1.579 min, Purity: 99.64% (UV).

Synthetic Example 15.3

Synthesis of ((5R,6S)-5-((1S,3aS,4S,5S,7aR)-4-(aminomethyl)-1,7a-dimethyloctahydro-1H-inden-5-yl)-5-methyl-1-neopentyl-4,5,6,7-tetrahydro-1H-indazol-6-yl)methanol (Compound Ia-38) and ((5R,6S)-5-((1S,3aS,4S,5S,7aR)-4-(aminomethyl)-1,7a-dimethyloctahydro-1H-inden-5-yl)-5-methyl-2-neopentyl-4,5,6,7-tetrahydro-2H-indazol-6-yl)methanol (Compound Ia-39)

Following the procedure as described in Synthetic Example 15 and making non-critical variations using Compound Ia-22 or Compound Ia-23 (from Example 8.7) separately in place of Compound 9, the respective title compounds, ((5R,6S)-5-((1S,3aS,4S,5S,7aR)-4-(aminomethyl)-1,7a-dimethyloctahydro-1H-inden-5-yl)-5-methyl-1-neopentyl-4,5,6,7-tetrahydro-1H-indazol-6-yl)methanol (Compound Ia-38) and ((5R,6S)-5-((1S,3aS,4S,5S,7aR)-4-(aminomethyl)-1,7a-dimethyloctahydro-1H-inden-5-yl)-5-methyl-2-neopentyl-4,5,6,7-tetrahydro-2H-indazol-6-yl)methanol (Compound Ia-39), were obtained.

Compound Ia-38: LCMS: (Method 1c) MS m/z: 416.4 (M+1), $t_R$: 2.267 min, Purity: 97.95% (UV).

Synthetic Example 15.4

Synthesis of ((5R,6S)-5-((1S,3aS,4S,5S,7aR)-4-(aminomethyl)-1,7a-dimethyloctahydro-1H-inden-5-yl)-1-(tert-butyl)-5-methyl-4,5,6,7-tetrahydro-H-indazol-6-yl) (Compound Ia-40) and ((5R,6S)-5-((1S,3aS,4S,5S,7aR)-4-(aminomethyl)-1,7a-dimethyloctahydro-1H-inden-5-yl)-2-(tert-butyl)-5-methyl-4,5,6,7-tetrahydro-2H-indazol-6-yl)methanol (Compound Ia-41)

Following the procedure as described in Synthetic Example 15 and making non-critical variations using Compound Ia-12 or Compound Ia-13 (from Example 8.2) separately in place of Compound 9, the respective title compounds, ((5R,6S)-5-((1S,3aS,4S,5S,7aR)-4-(aminomethyl)-1,7a-dimethyloctahydro-1H-inden-5-yl)-1-(tert-butyl)-5-methyl-4,5,6,7-tetrahydro-1H-indazol-6-yl) (Compound Ia-40) and ((5R,6S)-5-((1S,3aS,4S,5S,7aR)-4-(aminomethyl)-1,7a-dimethyloctahydro-1H-inden-5-yl)-2-(tert-butyl)-5-methyl-4,5,6,7-tetrahydro-2H-indazol-6-yl)methanol (Compound Ia-41), were obtained.

Compound Ia-40: LCMS: (Method 1h) MS m/z: 402.3 (M+1), $t_R$: 3.177 min, Purity: 93.758% (UV).

Compound Ia-41: LCMS: (Method 1h) MS m/z: 402.4 (M+1), $t_R$: 3.299 min, Purity: 97.930% (UV).

Synthetic Example 15.5

Synthesis of ((5R,6S)-5-((1S,3aS,4S,5S,7aR)-4-(aminomethyl)-1,7a-dimethyloctahydro-1H-inden-5-yl)-5-methyl-1-(pyridin-2-yl)-4,5,6,7-tetrahydro-1H-indazol-6-yl)methanol (Compound Ia-42) and ((5R,6S)-5-((1S,3aS,4S,5S,7aR)-4-(aminomethyl)-1,7a-dimethyloctahydro-1H-inden-5-yl)-5-methyl-2-(pyridin-2-yl)-4,5,6,7-tetrahydro-2H-indazol-6-yl)methanol (Compound Ia-43)

Following the procedure as described in Synthetic Example 15 and making non-critical variations using Compound Ia-10 or Compound Ia-11 (from Example 8.1) separately in place of Compound 9, the respective title compounds, ((5R,6S)-5-((1S,3aS,4S,5S,7aR)-4-(aminomethyl)-1,7a-dimethyloctahydro-1H-inden-5-yl)-5-methyl-1-(pyridin-2-yl)-4,5,6,7-tetrahydro-1H-indazol-6-yl)methanol (Compound Ia-42) and ((5R,6S)-5-((1S,3aS,4S,5S,7aR)-4-(aminomethyl)-1,7a-dimethyloctahydro-1H-inden-5-yl)-5-methyl-2-(pyridin-2-yl)-4,5,6,7-tetrahydro-2H-indazol-6-yl)methanol (Compound Ia-43), were obtained.

Compound Ia-42: LCMS: (Method 1c) MS m/z: 423.3 (M+1), $t_R$: 2.407 min, Purity: 91.87% (UV).

Compound Ia-43: LCMS: (Method 1c) MS m/z: 423.3 (M+1), $t_R$: 2423 min, Purity: 9126% (UV).

Synthetic Example 16

Synthesis of (5R,6S)-6-(hydroxymethyl)-5-((3aS,4R,5S,7aS)-4-(hydroxymethyl)-7a-methyl-1-methyleneoctahydro-1H-inden-5-yl)-5-methyl-4,5,6,7-tetrahydro-1H-indazole-3-carboxylic acid (Compound Ia-44)

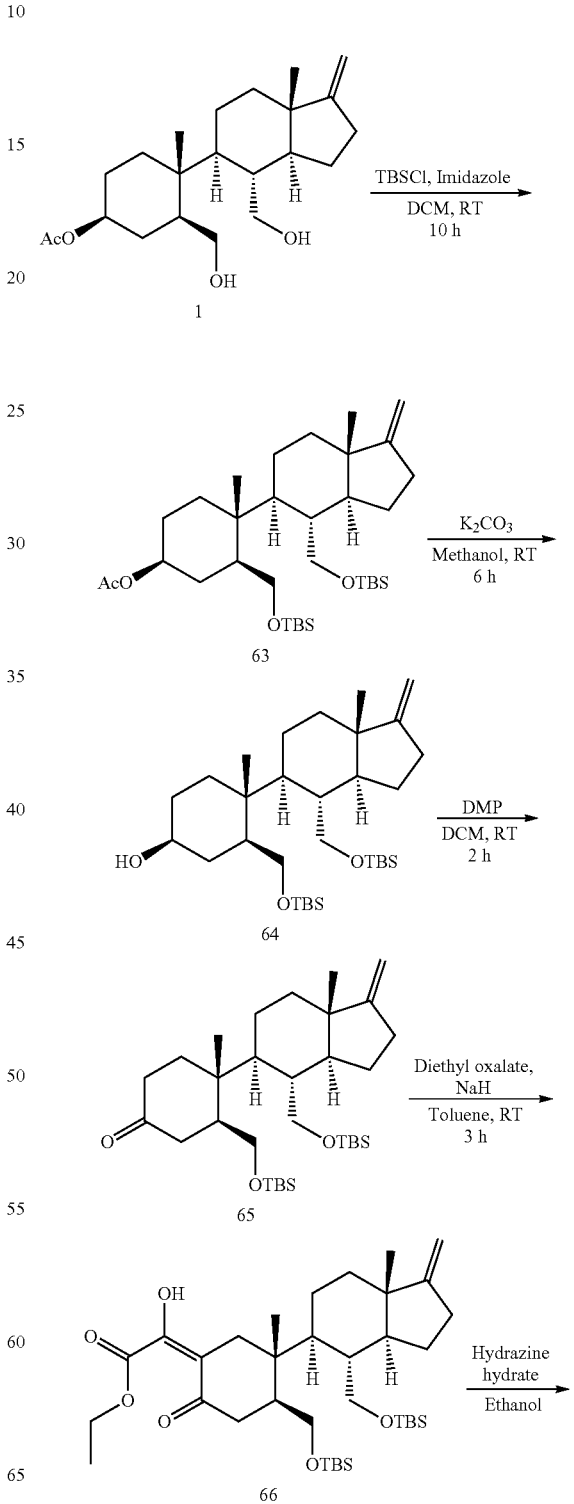

-continued

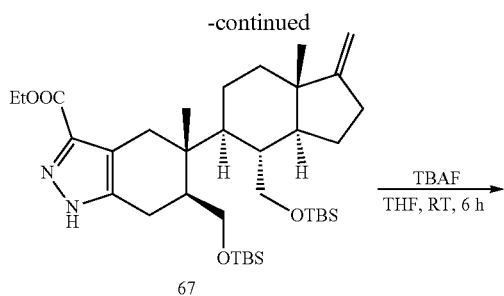

67

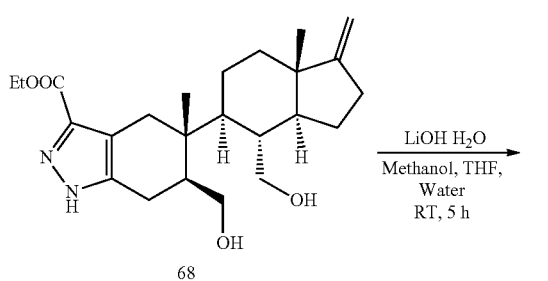

68

HOOC structure

Ia-44

A. Using General Procedure B with Compound 1 (from Example 1, 15.0 g, 41.15 mmol), imidazole (11.21 g, 164.60 mmol) and TBSCl (18.61 g, 123.45 mmol) in DCM (150 mL), followed by purification by column chromatography on silica gel (60-120 mesh, 0-10% EtOAc/pet ether) afforded (1S,3S,4R)-3-(((tert-butyldimethylsilyl)oxy) methyl)-4-((3aS,4R,5S,7aS)-4-(((tert-butyldimethylsilyl) oxy)methyl)-7a-methyl-1-methyleneoctahydro-1H-inden-5-yl)-4-methylcyclohexyl acetate (Compound 63, 16.5 g, 68%) as a white solid.

B. Following the General Procedure L with Compound 63 (16.5 g, 27.85 mmol) and $K_2CO_3$ (7.7 g, 55.64 mmol) in MeOH (170 mL), followed by purification by column chromatography on silica gel (30-40% EtOAc/pet ether) afforded (1S,3S,4R)-3-(((tert-butyldimethylsilyl)oxy) methyl)-4-((3aS,4R,5S,7aS)-4-(((tert-butyldimethylsilyl)oxy)methyl)-7a-methyl-1-methyleneoctahydro-1H-inden-5-yl)-4-methylcyclohexan-1-ol (Compound 64, 14.0 g, 91%) as a white solid.

C. Following the General Procedure N with Compound 64 (14.0 g, 25.41 mmol) and DMP (16.16 g, 38.11 mmol) in DCM (140 mL), followed by purification by column chromatography on silica gel (60-120 mesh, 20-30% EtOAc/pet ether) afforded (3S,4R)-3-(((tert-butyldimethylsilyl)oxy) methyl)-4-((3aS,4R,5S,7aS)-4-(((tert-butyldimethylsilyl) oxy)methyl)-7a-methyl-1-methyleneoctahydro-1H-inden-5-yl)-4-methylcyclohexan-1-one (Compound 65, 10.5 g, 75%) as a white solid.

D. To a stirred solution of the sodium hydride (60%, 2.30 g, 57.38 mmol) in toluene (30 mL) at 0° C. was added Compound 65 (10.5 g, 19.13 mmol) in toluene (80 mL) dropwise. The mixture was stirred at same temperature for 2 hours. To the resulting mixture was added diethyl oxalate (1129 g, 77.25 mmol) at 0° C. and stirred at room temperature for 3 hours. The mixture was quenched with a saturated aqueous solution of $NH_4Cl$ (50 g dissolved in 100 mL water) and the aqueous was extracted with EtOAc (2×100 mL). The combined organic extracts were washed with brine (1×100 mL), dried over $Na_2SO_4$, filtered and concentrated under reduced pressure. The residue was purified by column chromatography on silica gel (230-400 mesh, 20-25% EtOAc/pet ether) to afford ethyl (E)-2-((4S,5R)-4-(((tert-butyldimethylsilyl)oxy)methyl)-5-((3aS,4R,5S,7aS)-4-(((tert-butyldimethylsilyl)oxy)methyl)-7a-methyl-1-methyleneoctahydro-1H-inden-5-yl)-5-methyl-2-oxocyclohexylidene)-2-hydroxyacetate (Compound 66, 6.5 g, 52%) as a pale yellow solid.

E. Following the General Procedure P with Compound 66 (6.5 g, 10.01 mmol) and hydrazine hydrate (0.73 mL, 15.02 mmol) in EtOH (60 mL), followed by purification by column chromatography on silica gel (230-400 mesh, 50-60% EtOAc/pet ether) afforded ethyl (5R,6S)-6-(((tert-butyldimethylsilyl)oxy)methyl)-5-((3aS,4R,5S,7aS)-4-(((tert-butyldimethylsilyl)oxy)methyl)-7a-methyl-1-methyleneoctahydro-1H-inden-5-yl)-5-methyl-4,5,6,7-tetrahydro-1H-indazole-3-carboxylate (Compound 67, 3.4 g, 52%) as an off white solid.

F. Following the General Procedure Q with Compound 67 (3.4 g, 5.27 mmol) and TBAF (1M in THF, 10.54 mL, 10.54 mmol) in THF (30 mL), followed by purification by column chromatography on silica gel (5-10% $MeOH/CH_2Cl_2$) afforded ethyl (5R,6S)-6-(hydroxymethyl)-5-((3aS,4R,5S,7aS)-4-(hydroxymethyl)-7a-methyl-1-methyleneoctahydro-1H-inden-5-yl)-5-methyl-4,5,6,7-tetrahydro-1H-indazole-3-carboxylate (Compound 68, 1.6 g, 73%) as an off white solid.

G. To a stirred solution of ethyl Compound 68 (1.6 g, 3.84 mmol) in THF:MeOH:water (6:4:1, 10 mL) was added lithium hydroxide monohydrate (0.48 g, 11.52 mmol) at room temperature and the reaction mixture was stirred for 5 hours. The reaction mixture was concentrated under reduced pressure and diluted with EtOAc (2×10 mL) then washed consecutively with water (1×10 mL) and brine (1×10 mL). The organic layer was dried over $Na_2SO_4$, filtered and concentrated. The residue was purified by preparative HPLC (Method 3a) to afford (5R,6S)-6-(hydroxymethyl)-5-((3aS, 4R,5S,7aS)-4-(hydroxymethyl)-7a-methyl-1-methyleneoctahydro-1H-inden-5-yl)-5-methyl-4,5,6,7-tetrahydro-1H-indazole-3-carboxylic acid (Compound Ia-44, 1.3 g, 87%) as a white solid.

LCMS: (Method 1b) MS m/z: 389.2 (M+1), $t_R$: 3.503 min, Purity: 98.18% (UV).

HPLC: (Method 2a) $t_R$: 3.458 min, Purity: 96.91% (UV).

$^1$H-NMR (400 MHz, DMSO-$d_6$): δ 12.88 (s, 2H), 4.57 (s, 2H), 4.28 (s, 1H), 3.83 (d, J=10.6 Hz, 1H), 3.71 (d, J=9.0 Hz, 1H), 3.53-3.40 (m, 2H), 3.38-2.51 (m, 4H), 2.44-2.14 (m, 4H), 1.83-1.29 (m, 8H), 1.11-1.08 (m, 1H), 0.99 (s, 3H), 0.76 (s, 3H).

Synthetic Example 17

Synthesis of ((5R,6S)-6-(hydroxymethyl)-5-((3aS,4R,5S,7aS)-4-(hydroxymethyl)-7a-methyl-1-methyleneoctahydro-1H-inden-5-yl)-5-methyl-4,5,6,7-tetrahydro-1H-indazol-3-yl)(piperidin-1-yl)methanone (Compound Ia-45)

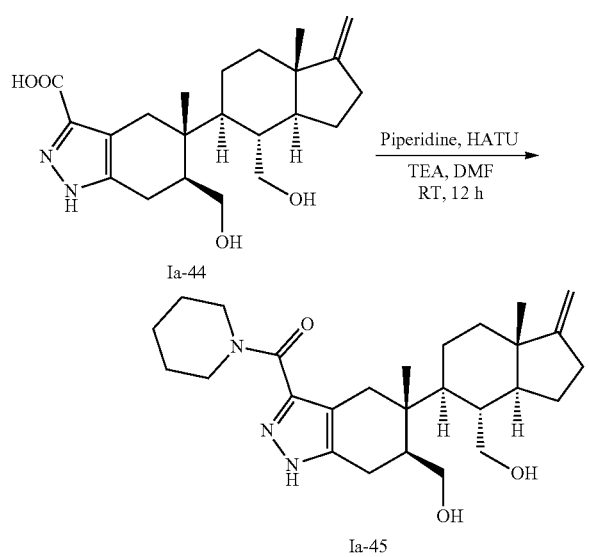

To a solution of Compound Ia-44 (from Example 16, 200 mg, 0.515 mmol, 1 eq) in DMF (10 mL) taken in a 2-necked RB flask (50 mL) was added piperidine (0.1 mL, 1.03 mmol 2 eq) and triethylamine (0.21 mL, 1.5 mmol, 3 eq). Reaction mass was cooled to 0° C. and HATU (0.293 g, 0.0.722 mmol, 1.5 eq) was added in one lot. Reaction mass was stirred at room temperature for 12 h with the help of a magnetic stirrer under a nitrogen atmosphere. Completion of the reaction was monitored by TLC. Reaction mass was concentrated on a rotary evaporator at 50° C. and the crude mass obtained was further purified by column chromatography (60-120 mesh silica gel, eluted with 0-10% dichloromethane/methanol to afford ((5R,6S)-6-(hydroxymethyl)-5-((3a5,4R,5S,7aS)-4-(hydroxymethyl)-7a-methyl-1-methyleneoctahydro-1H-inden-5-yl)-5-methyl-4,5,6,7-tetrahydro-1H-indazol-3-yl)(piperidin-1-yl)methanone (Compound Ia-45, 30 mg, 13%) as an off-white solid.

LCMS: (Method 1a) MS m/z: 456.2 (M+1), $t_R$: 2.601 min, Purity: 97.44% (max).

HPLC: (Method 2a) $t_R$:4.15 min, Purity: 95.14% (max).

$^1$H-NMR (400 MHz, CD$_3$OD): δ4.62 (s, 2H), 4.05 (d, J=11.4 Hz, 1H), 3.94 (m, 1H), 3.83-3.52 (m, 5H), 3.35-3.33 (m, 1H), 3.32-3.17 (m, 1H), 2.74-2.45 (m, 3H), 2.32-2.26 (m, 3H), 2.03-1.91 (m, 1H), 1.82-1.50 (m, 12H), 1.49-1.18 (m, 5H), 0.85 (s, 3H).

Synthetic Example 17.1

Synthesis of ((5R,6S)-6-(hydroxymethyl)-5-((3aS,4R,5S,7aS)-4-(hydroxymethyl)-7a-methyl-1-methyleneoctahydro-1H-inden-5-yl)-5-methyl-4,5,6,7-tetrahydro-H-indazol-3-yl)(morpholino)methanone (Compound Ia-46)

Following the procedure as described in Synthetic Example 17 and making non-critical variations using morpholine to replace piperidine, the title compound, ((5R,6S)-6-(hydroxymethyl)-5-((3aS,4R,5S,7aS)-4-(hydroxymethyl)-7a-methyl-1-methyleneoctahydro-1H-inden-5-yl)-5-methyl-4,5,6,7-tetrahydro-1H-indazol-3-yl)(morpholino) methanone as (Compound Ia-46, 30 mg, yield: 13%), was obtained as an off-white solid.

LCMS: (Method 1a) MS m/z: 458.3 (M+1), $t_R$:2.370 min, Purity: 96.05% (max).

HPLC: (Method 2a) $t_R$:3.603 min, Purity: 94.25% (max).

$^1$H-NMR (400 MHz, CD$_3$OD): δ4.63 (s, 2H), 4.05 (d, J=11.3 Hz, 1H), 3.94 (m, 1H), 3.89-3.60 (m, 9H), 3.38-3.33 (m, 1H), 3.20-3.15 (m, 1H), 2.75-2.24 (m, 6H), 1.93-1.82 (m, 1H), 1.79-1.57 (m, 6H), 1.55-1.43 (m, 2H), 1.40-1.11 (m, 4H), 0.85 (s, 3H).

Synthetic Example 18

Synthesis of ((5R,6S)-5-methyl-5-((3aS,4R,5S,7aS)-7a-methyl-1-methylene-4-(piperidin-1-ylmethyl) octahydro-1H-inden-5-yl)-4,5,6,7-tetrahydro-1H-indazol-6-yl)methanol (Compound Ia-47)

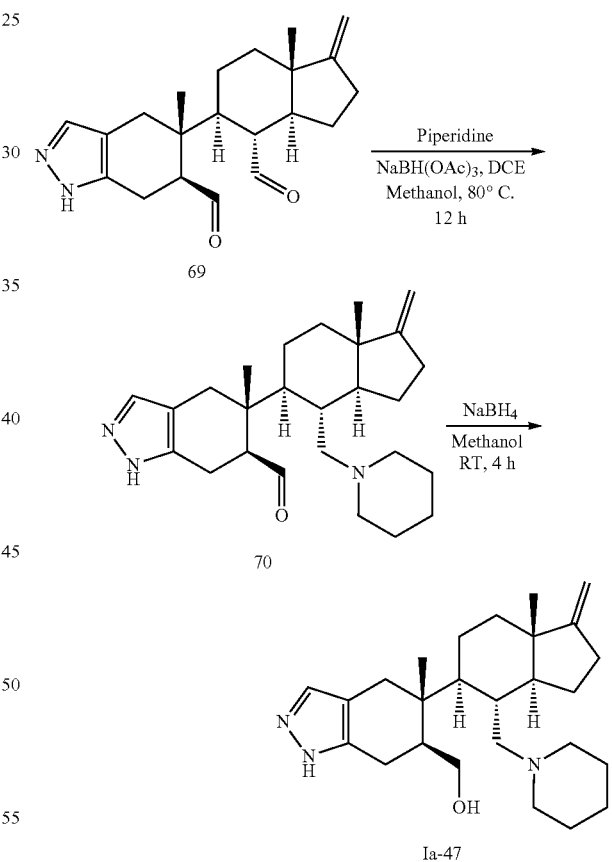

A. Using General Procedure V with (5R,6S)-5-((3aS,4R,5S,7aS)-4-formyl-7a-methyl-1-methyleneoctahydro-1H-inden-5-yl)-5-methyl-4,5,6,7-tetrahydro-1H-indazole-6-carbaldehyde (Compound 69, as prepared in U.S. Pat. No. 9,765,085, 0.25 g, 0.73 mmol), piperidine (0.36 mL, 3.67 mmol), 4 Å molecular sieves (0.25 g) and NaBH(OAc)$_3$ (0.31 g, 1.47 mmol) in DCE/MeOH (8 mL, 3:1) gave the desired aldehyde, (5R,6S)-5-methyl-5-((3aS,4R,5S,7aS)-7a-methyl-1-methylene-4-(piperidin-1-ylmethyl)octahydro- 1H-inden-5-yl)-4,5,6,7-tetrahydro-1H-indazole-6-carbaldehyde (Compound 70a, 0.2 g, 66%), as a pale yellow solid, which was used in next step without purification.

B. Using General Procedure G with (5R,6S)-5-methyl-5-((3aS,4R,5S,7aS)-7a-methyl-1-methylene-4-(piperidin-1-ylmethyl)octahydro-1H-inden-5-yl)-4,5,6,7-tetrahydro-1H-indazole-6-carbaldehyde (Compound 70a, 0.2 g, 0.49 mmol) and sodium borohydride (0.04 g, 0.98 mmol), followed by purification by preparatory HPLC (Method 3a) to afford ((5R,6S)-5-methyl-5-((3aS,4R,5S,7aS)-7a-methyl-1-methylene-4-(piperidin-1-ylmethyl)octahydro-1H-inden-5-yl)-4,5,6,7-tetrahydro-1H-indazol-6-yl)methanol (Compound Ia-47, 22 mg, 11%) as an off white solid.

LCMS: (Method 1d) MS m/z: 412.3 (M+1), $t_R$: 2.190 min, Purity: 80.49% (UV).

HPLC: (Method 2a) $t_R$: 3.405 min, Purity: 92.69% (UV).

$^1$H-NMR (400 MHz, CD$_3$OD): δ 7.68 (s, 1H), 4.62 (s, 2H), 4.01 (d, J=12 Hz 1H), 3.74 (d, J=12 Hz, 1H), 3.32-3.19 (m, 1H), 2.88-2.49 (m, 8H), 2.31-2.23 (m, 3H), 2.03-1.91 (m, 2H), 1.88-1.31 (m, 14H), 1.10 (s, 3H), 0.82 (s, 3H).

Synthetic Example 18.1

Synthesis of ((5R,6S)-5-methyl-5-((3aS,4R,5S,7aS)-7a-methyl-1-methylene-4-((4-methylpiperazin-1-yl)methyl)octahydro-1H-inden-5-yl)-4,5,6,7-tetrahydro-1H-indazol-6-yl)methanol (Compound Ia-48)

Following the procedure as described in Synthetic Example 18 and making non-critical variations using 1-methylpiperazine to replace piperidine, the title compound, ((5R,6S)-5-methyl-5-((3aS,4R,5S,7aS)-7a-methyl-1-methylene-4-((4-methylpiperazin-1-yl)methyl)octahydro-1H-inden-5-yl)-4,5,6,7-tetrahydro-1H-indazol-6-yl)methanol (Compound Ia-48, 150 mg, 60%), was obtained following purification by preparative HPLC (Method 3a), as an off white solid.

LCMS: (Method 1a) MS m/z: 427.3 (M+1), $t_R$: 2.091 min, Purity: 87.12% (UV).

HPLC: (Method 2a) $t_R$: 3.009 min, Purity: 85.93% (UV).

$^1$H-NMR (400 MHz, CD$_3$OD): δ 7.55 (s, 1H), 4.62 (d, J=8.0 Hz, 2H), 4.01 (d, J=11.6 Hz, 1H), 3.74 (d, J=11.2 Hz, 1H), 3.34-3.32 (m, 3H), 2.91 (s, 3H), 2.77-2.66 (m, 4H), 2.55-2.41 (m, 4H), 2.32-2.26 (m, 3H), 1.92-1.77 (m, 2H), 1.67-1.49 (m, 7H), 1.42-1.31 (m, 1H), 1.18 (s, 3H), 1.16-1.01 (m, 2H), 1.0 (s, 3H).

Synthetic Example 18.2

Synthesis of ((5R,6S)-5-methyl-5-((3aS,4R,5S,7aS)-7a-methyl-1-methylene-4-(thiomorpholinomethyl)octahydro-1H-inden-5-yl)-4,5,6,7-tetrahydro-1H-indazol-6-yl)methanol (Compound Ia-49)

Following the procedure as described in Synthetic Example 18 and making non-critical variations using thiomorpholine to replace piperidine, the title compound, ((5R,6S)-5-methyl-5-((3a5,4R,5S,7aS)-7a-methyl-1-methylene-4-(thiomorpholinomethyl)octahydro-1H-inden-5-yl)-4,5,6,7-tetrahydro-1H-indazol-6-yl)methanol (Compound Ia-49, 60 mg, 30%), was obtained following purification by preparative HPLC (Method 3a), as an off white solid.

LCMS: (Method 1d) MS/z: 430.2 (M+1), $t_R$: 1.470 min, Purity: 99.66% (UV).

HPLC: (Method 2a) $t_R$: 3.459 min, Purity: 93.95% (UV).

$^1$H-NMR (400 MHz, CD$_3$OD): δ 7.28 (s, 1H), 4.62 (s, 2H), 4.02 (d, J=11.6 Hz, 1H), 3.73 (d, J=11.2 Hz, 1H), 3.18-3.00 (m, 3H), 2.74-2.68 (m, 8H), 2.55-2.44 (m, 2H), 2.35-2.25 (m, 3H), 1.92-1.76 (m, 2H), 1.68-1.50 (m, 6H), 1.42-1.31 (m, 2H), 1.13 (s, 3H), 0.84 (s, 3H).

Synthetic Example 18.3

Synthesis of ((5R,6S)-5-methyl-5-((3aS,4R,5S,7aS)-7a-methyl-1-methylene-4-(morpholinomethyl)octahydro-1H-inden-5-yl)-4,5,6,7-tetrahydro-1H-indazol-6-yl)methanol (Compound Ia-5)

Following the procedure as described in Synthetic Example 18 and making non-critical variations using morpholine to replace piperidine, the title compound, ((5R,6S)-5-methyl-5-((3aS,4R,5S,7aS)-7a-methyl-1-methylene-4-(morpholinomethyl)octahydro-1H-inden-5-yl)-4,5,6,7-tetrahydro-1H-indazol-6-yl)methanol (Compound Ia-50, 70 mg, 43%), was obtained following purification by preparative HPLC (Method 3a), as an off white solid.

LCMS: (Method 1a) MS m/z: 414.2 (M+1), $t_R$: 2.212 min, Purity: 94.09% (UV).

HPLC: (Method 2a) $t_R$: 3.243 min, Purity: 96.39% (UV).

$^1$H-NMR (400 MHz, CD$_3$OD): δ 7.26 (s, 1H), 4.62 (s, 2H), 4.05-4.02 (m, 1H), 3.76-3.67 (m, 5H), 3.16-3.12 (m, 1H), 2.71-2.48 (m, 6H), 2.32-2.25 (m, 6H), 1.93-1.31 (m, 9H), 1.12 (s, 3H), 0.84 (s, 3H).

Synthetic Example 19

Synthesis of ((5R,6S)-5-((3aS,4R,5S,7aS)-4-((1H-imidazol-1-yl)methyl)-7a-methyl-1-methyleneoctahydro-1H-inden-5-yl)-5-methyl-4,5,6,7-tetrahydro-1H-indazol-6-yl)methanol (Compound Ia-51)

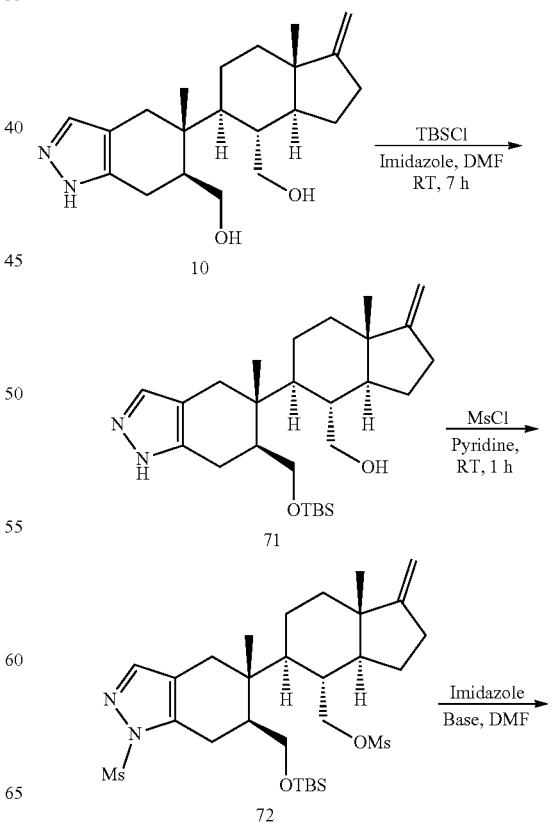

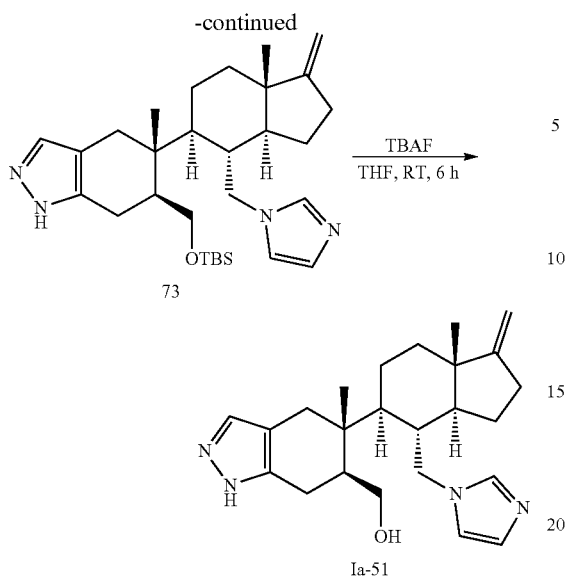

73

Ia-51

A. Using General Procedure B with ((3aS,4R,5S,7aS)-5-((5R,6S)-6-(hydroxymethyl)-5-methyl-4,5,6,7-tetrahydro-1H-indazol-5-yl)-7a-methyl-1-methyleneoctahydro-1H-inden-4-yl)methanol (Compound 10, as prepared in U.S. Pat. No. 9,765,085 2.0 g, 5.80 mmol), imidazole (1.20 g, 17.42 mmol) and TBSCl (0.96 g, 6.38 mmol) in DMF (20 mL) gave the desired TBS-protected alcohol, ((3aS,4R,5S,7aS)-5-((5R,6S)-6-(((tert-butyldimethylsilyl)oxy)methyl)-5-methyl-4,5,6,7-tetrahydro-1H-indazol-5-yl)-7a-methyl-1-methyleneoctahydro-1H-inden-4-yl)methanol (Compound 71, 2.6 g, 97.7%), as a white gummy solid, which was used in next step without purification.

B. Using General Procedure J with Compound 71 (2.6 g, 5.67 mmol) and MsCl (1.44 mL, 14.17 mmol) in pyridine (20 mL) gave the desired mesylated compound, ((3aS,4R,5S,7aS)-5-((5R,6S)-6-(((tert-butyldimethylsilyl)oxy)methyl)-5-methyl-1-(methylsulfonyl)-4,5,6,7-tetrahydro-1H-indazol-5-yl)-7a-methyl-1-methyleneoctahydro-1H-inden-4-yl)methyl methanesulfonate (Compound 72, 3.0 g, 86%), as a brown solid, which was used in next step without purification.

C. To a stirred solution of imidazole (0.38 g, 5.53 mmol) in DMF (7 mL) was added sodium hydride (60% dispersion in oil, 0.23 g, 5.80 mmol) at 0° C. The reaction mixture was stirred at 0° C. for 1 hour. To the resultant solution was added Compound 72 (1.7 g, 2.76 mmol) in DMF (10 mL) dropwise at 0° C. The reaction mixture was stirred at room temperature for 18 hours. It was quenched with saturated aqueous solution of NaHCO$_3$ (5 g dissolved in 10 mL of water) and the aqueous was extracted with EtOAc (2×10 mL) and washed consecutively with water (1×10 mL) and brine (1×10 mL). The organic layer was dried over Na$_2$SO$_4$, filtered and concentrated to afford (5R,6S)-5-((3aS,4R,5S,7aS)-4-((H-imidazol-1-yl)methyl)-7a-methyl-1-methyleneoctahydro-H-inden-5-yl)-6-(((tert-butyldimethylsilyl)oxy)methyl)-5-methyl-4,5,6,7-tetrahydro-1H-indazole (Compound 73, 1.6 g) as a yellow gummy solid, which was used in the next step without purification.

D. Following the General Procedure Q with Compound 73 (1.6 g, 3.14 mmol) and TBAF (1 M in THF, 6.29 mL, 6.29 mmol) in THF (15 mL), the reaction was stirred at room temperature for 6 hours, followed by purification by preparative HPLC (Method 3e) to afford ((5R,6S)-5-((3aS,4R, 5S,7aS)-4-((1H-imidazol-1-yl)methyl)-7a-methyl-1-methyleneoctahydro-H-inden-5-yl)-5-methyl-4,5,6,7-tetrahydro-1H-indazol-6-yl)methanol (Compound Ia-51, 200 mg, 16%) as a white solid.

LCMS: (Method 1a) MS m/z: 395.2 (M+1), t$_R$: 1.998 min, Purity: 97.89% (UV).
HPLC: (Method 2d) t$_R$: 8.988 min, Purity: 84.80% (UV).
$^1$H-NMR (400 MHz, DMSO): δ 8.31 (broad s, 1H), 7.67 (s, 1H), 7.24 (d, J=14.4 Hz, 2H), 6.90 (s, 1H), 4.58 (d, J=8.4 Hz, 2H), 4.35 (d, J=12.4 Hz, 1H), 4.10-4.04 (m, 1H), 3.75 (d, J=8.4 Hz, 1H), 3.21-3.16 (m, 1H), 2.89-2.83 (m, 1H), 2.67-2.63 (m, 2H), 2.44-2.40 (m, 1H), 2.38-2.31 (m, 2H), 2.27-2.03 (m, 3H), 1.77-1.74 (m, 2H), 1.51-1.37 (m, 3H), 1.27-1.22 (m, 1H), 1.12-0.94 (m, 5H), 0.8 (s, 3H).

Synthetic Example 19.1

Synthesis of ((5R,6S)-5-((3aS,4R,5S,7aS)-4-((1H-pyrazol-1-yl)methyl)-7a-methyl-1-methyleneoctahydro-1H-inden-5-yl)-5-methyl-4,5,6,7-tetrahydro-H-indazol-6-yl)methanol (Compound Ia-52)

Following the procedure as described in Synthetic Example 19 and making non-critical variations using pyrazole to replace imidazole, the title compound, ((5R,6S)-5-((3aS,4R,5S,7aS)-4-((1H-pyrazol-1-yl)methyl)-7a-methyl-1-methyleneoctahydro-1H-inden-5-yl)-5-methyl-4,5,6,7-tetrahydro-1H-indazol-6-yl)methanol (Compound Ia-52, 44 mg, 9%), was obtained by purification by preparative HPLC (Method 3e), as a white solid.

LCMS: (Method 1a) MS m/z: 395.3 (M+1), t$_R$: 2.469 min, Purity: 92.71% (UV).
HPLC: (Method 2d) t$_R$: 11.789 min, Purity: 99.38% (ELSD).
$^1$H-NMR (400 MHz, CD$_3$OD): δ 7.66-7.64 (m, 1H), 7.49-7.48 (m, 1H), 7.37 (s, 1H), 6.29-6.27 (m, 1H), 4.65-4.60 (m, 2H), 4.25-3.95 (m, 2H), 3.32-3.31 (m, 1H), 282-2.78 (m, 2H), 2.53-2.25 (m, 6H), 1.87-1.82 (m, 2H), 1.73-1.61 (m, 3H), 1.43-1.38 (m, 2H), 1.30-1.14 (m, 4H), 1.04-0.96 (m, 1H), 0.8 (s, 3H).

Synthetic Example 19.2

Synthesis of ((5R,6S)-5-((3aS,4R,5S,7aS)-4-((1H-indol-1-yl)methyl)-7a-methyl-1-methyleneoctahydro-1H-inden-5-yl)-5-methyl-4,5,6,7-tetrahydro-1H-indazol-6-yl)methanol (Compound Ia-53)

Following the procedure as described in Synthetic Example 19 and making non-critical variations using indole to replace imidazole, the title compound, ((5R,6S)-5-((3aS, 4R,5S,7aS)-4-((1H-indol-1-yl)methyl)-7a-methyl-1-methyleneoctahydro-1H-inden-5-yl)-5-methyl-4,5,6,7-tetrahydro-1H-indazol-6-yl)methanol (Compound Ia-53, 30 mg, 13%), was obtained by purification by preparative HPLC (Method 3e), as a white solid.

LCMS: (Method 1c) MS m/z: 444.2 (M+1), t$_R$: 2.876 min, Purity: 98.64% (ELSD).
HPLC: (Method 2d) t$_R$: 12.208 min, Purity: 97.15% (UV).
$^1$H-NMR (400 MHz, CD$_3$OD): δ 7.55 (d, J=8.0 Hz, 1H), 7.42 (d, J=8.4 Hz, 1H), 7.37-7.34 (m, 2H), 7.19-7.15 (m, 1H), 7.04-7.01 (m, 1H), 6.49 (d, J=3.2 Hz, 1H), 4.70-4.57 (m, 3H), 4.17-3.99 (m, 2H), 3.33-3.32 (m, 1H), 3.19-3.09 (m, 2H), 2.91-2.87 (m, 1H), 2.62-2.33 (m, 3H), 2.19-2.17 (m, 2H), 1.97-1.85 (m, 3H), 1.7 (d, J=8.8 Hz, 2H), 1.45-1.39 (m, 1H), 131-1.17 (m, 3H), 1.0 (d, J=6.4 Hz, 1H), 0.92-0.79 (m, 4H).

Synthetic Example 19.3

Synthesis of ((5R,6S)-5-((3aS,4R,5S,7aS)-4-((1H-benzo[d]imidazol-1-yl)methyl)-7a-methyl-1-methyleneoctahydro-1H-inden-5-yl)-5-methyl-4,5,6,7-tetrahydro-1H-indazol-6-yl)methanol (Compound Ia-54)

Following the procedure as described in Synthetic Example 19 and making non-critical variations using benzimidazole to replace imidazole, the title compound, ((5R,6S)-5-((3aS,4R,5S,7aS)-4-((1H-benzo[d]imidazol-1-yl)methyl)-7a-methyl-1-methyleneoctahydro-1H-inden-5-yl)-5-methyl-4,5,6,7-tetrahydro-1H-indazol-6-yl)methanol (Compound Ia-54, 30 mg, 27%), was obtained by purification by preparative HPLC (Method 3e), as a white solid.

LCMS: (Method 1c) MS m/z: 445.3 (M+1), $t_R$: 2.232 min, Purity: 82.93% (UV).

HPLC: (Method 2d) $t_R$: 7.152 min, Purity: 79.90% (UV).

$^1$H-NMR (400 MHz, CD$_3$OD): δ 8.34 (s, 1H), 7.71-7.62 (m, 2H), 7.40-7.29 (m, 3H), 4.63-4.58 (m, 2H), 4.34-4.31 (m, 1H), 4.03-3.99 (m, 1H), 3.44-339 (m, 1H), 3.18-3.09 (m, 2H), 2.92-2.88 (m, 1H), 2.66-2.20 (m, 5H), 2.02-1.72 (m, 5H), 1.55-1.313 (m, 3H), 1.23 (s, 3H), 1.18-0.92 (m, 1H), 0.84 (s, 3H).

Synthetic Example 19.4

Synthesis of ((5R,6S)-5-((3aS,4R,5S,7aS)-4-((6-amino-9H-purin-9-yl)methyl)-7a-methyl-1-methyleneoctahydro-1H-inden-5-yl)-5-methyl-4,5,6,7-tetrahydro-1H-indazol-6-yl)methanol (Compound Ia-55)

Following the procedure as described in Synthetic Example 19 and making non-critical variations using adenine to replace imidazole, the title compound, ((5R,6S)-5-((3aS,4R,5S,7aS)-4-((6-amino-9H-purin-9-yl)methyl)-7a-methyl-1-methyleneoctahydro-1H-inden-5-yl)-5-methyl-4,5,6,7-tetrahydro-1H-indazol-6-yl)methanol (Compound Ia-55, 44 mg, 34%), was obtained by purification by preparative HPLC (Method 3e), as a white solid.

LCMS: (Method 1c) MS m/z: 462.3 (M+1), $t_R$: 2.037 min, Purity: 77.25% (UV).

HPLC: (Method 2d) $t_R$: 6.026 min, Purity: 75.41% (UV).

$^1$H-NMR (400 MHz, CD$_3$OD): δ 8.27-8.24 (m, 2H), 7.35 (s, 1H), 4.75 (d, J=2.4 Hz, 1H), 4.63-4.60 (m, 1H), 4.32-4.26 (m, 1H), 4.02-3.99 (m, 1H), 3.45-3.33 (m, 1H), 3.14-3.08 (m, 1H), 2.87-2.62 (m, 4H), 2.32-2.29 (m, 2H), 2.08-1.85 (m, 3H), 1.71-1.41 (m, 4H), 1.31-1.06 (m, 6H), 0.83 (s, 3H).

Synthetic Example 20

Synthesis of ((1R,3aS,4S,5S,7aR)-5-((5R,6S)-6-(hydroxymethyl)-5-methyl-4,5,6,7-tetrahydro-1H-indazol-5-yl)-7a-methyl-1-((R)-6-methylheptan-2-yl)octahydro-1H-inden-4-yl)methanol (Compound Ia-56) and ((1R,3aS,4S,6,7aR)-5-((5R,6S)-6-(aminomethyl)-5-methyl-4,5,6,7-tetrahydro-1H-indazol-5-yl)-7a-methyl-1-((R)-6-methylheptan-2-yl)octahydro-1H-inden-4-yl)methanamine (Compound Ia-57)

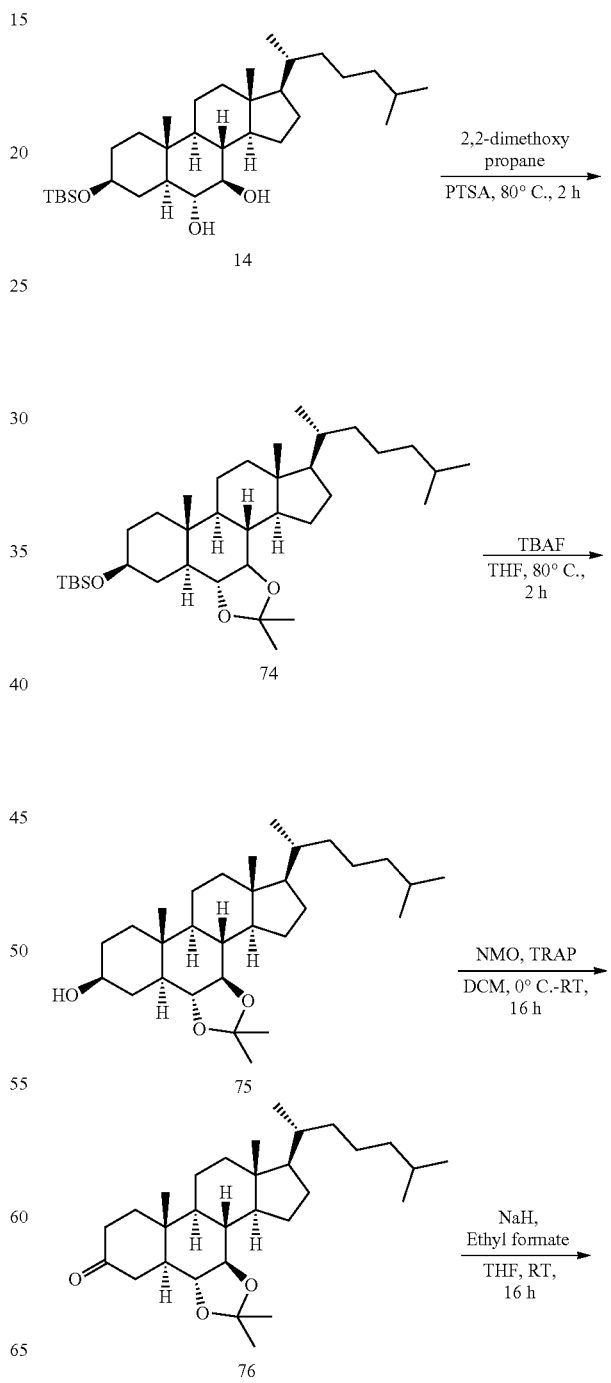

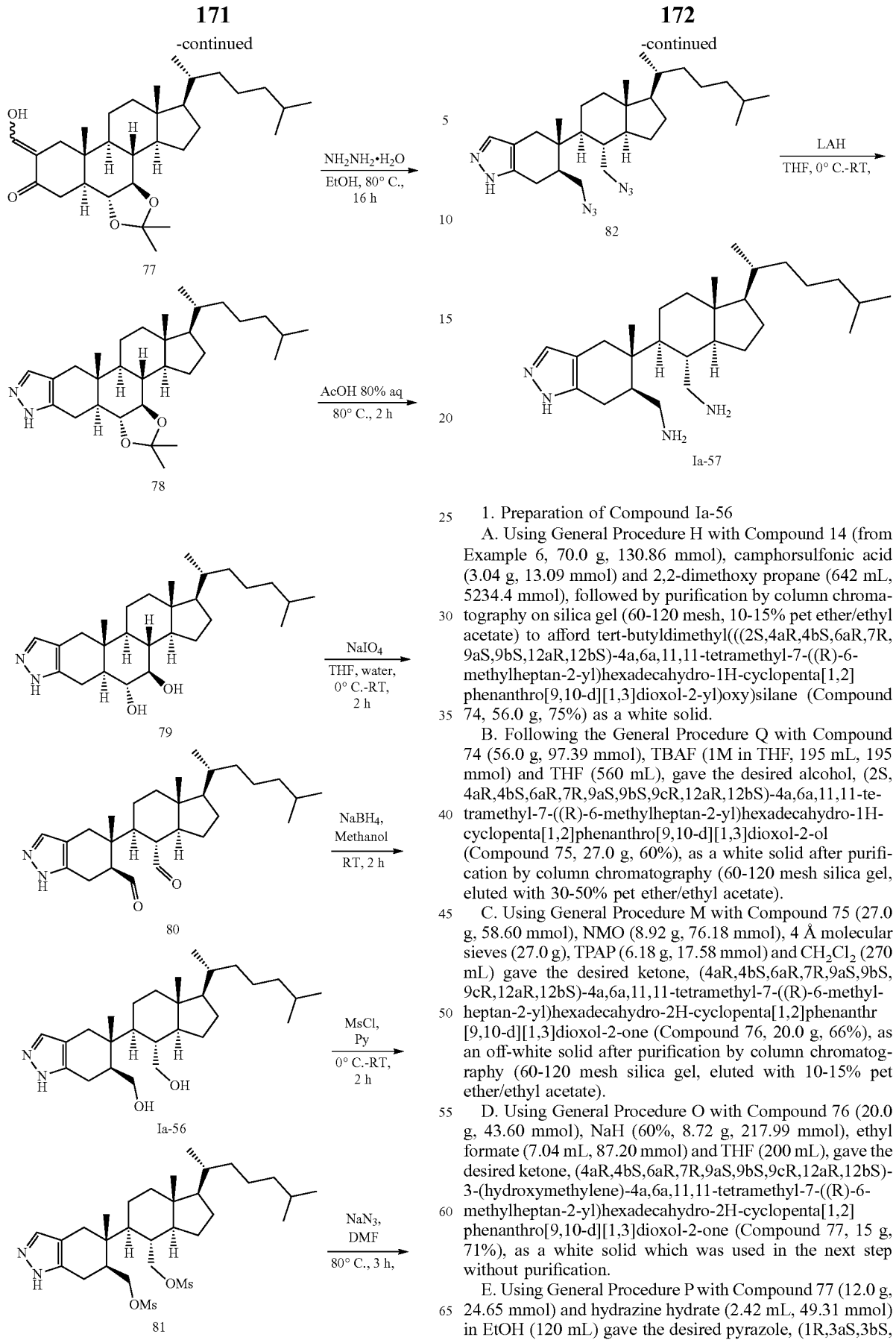

1. Preparation of Compound Ia-56

A. Using General Procedure H with Compound 14 (from Example 6, 70.0 g, 130.86 mmol), camphorsulfonic acid (3.04 g, 13.09 mmol) and 2,2-dimethoxy propane (642 mL, 5234.4 mmol), followed by purification by column chromatography on silica gel (60-120 mesh, 10-15% pet ether/ethyl acetate) to afford tert-butyldimethyl(((2S,4aR,4bS,6aR,7R,9aS,9bS,12aR,12bS)-4a,6a,11,11-tetramethyl-7-((R)-6-methylheptan-2-yl)hexadecahydro-1H-cyclopenta[1,2]phenanthro[9,10-d][1,3]dioxol-2-yl)oxy)silane (Compound 74, 56.0 g, 75%) as a white solid.

B. Following the General Procedure Q with Compound 74 (56.0 g, 97.39 mmol), TBAF (1M in THF, 195 mL, 195 mmol) and THF (560 mL), gave the desired alcohol, (2S,4aR,4bS,6aR,7R,9aS,9bS,9cR,12aR,12bS)-4a,6a,11,11-tetramethyl-7-((R)-6-methylheptan-2-yl)hexadecahydro-1H-cyclopenta[1,2]phenanthro[9,10-d][1,3]dioxol-2-ol (Compound 75, 27.0 g, 60%), as a white solid after purification by column chromatography (60-120 mesh silica gel, eluted with 30-50% pet ether/ethyl acetate).

C. Using General Procedure M with Compound 75 (27.0 g, 58.60 mmol), NMO (8.92 g, 76.18 mmol), 4 Å molecular sieves (27.0 g), TPAP (6.18 g, 17.58 mmol) and CH$_2$Cl$_2$ (270 mL) gave the desired ketone, (4aR,4bS,6aR,7R,9aS,9bS,9cR,12aR,12bS)-4a,6a,11,11-tetramethyl-7-((R)-6-methylheptan-2-yl)hexadecahydro-2H-cyclopenta[1,2]phenanthr[9,10-d][1,3]dioxol-2-one (Compound 76, 20.0 g, 66%), as an off-white solid after purification by column chromatography (60-120 mesh silica gel, eluted with 10-15% pet ether/ethyl acetate).

D. Using General Procedure O with Compound 76 (20.0 g, 43.60 mmol), NaH (60%, 8.72 g, 217.99 mmol), ethyl formate (7.04 mL, 87.20 mmol) and THF (200 mL), gave the desired ketone, (4aR,4bS,6aR,7R,9aS,9bS,9cR,12aR,12bS)-3-(hydroxymethylene)-4a,6a,11,11-tetramethyl-7-((R)-6-methylheptan-2-yl)hexadecahydro-2H-cyclopenta[1,2]phenanthro[9,10-d][1,3]dioxol-2-one (Compound 77, 15 g, 71%), as a white solid which was used in the next step without purification.

E. Using General Procedure P with Compound 77 (12.0 g, 24.65 mmol) and hydrazine hydrate (2.42 mL, 49.31 mmol) in EtOH (120 mL) gave the desired pyrazole, (1R,3aS,3bS,3cR,6aR,6bS,11aR,11bS,13aR)-5,5,11a,13a-tetramethyl-1-

((R)-6-methylheptan-2-yl)-1,2,3,3a,3b,3c,6a,6b,7,8,11,11a,11b,12,13,13a-hexadecahydrocyclopenta[5,6][1,3]dioxolo[4',5':3,4]naphtho[1,2-f]indazole (Compound 78, 6.0 g, 52%), as an off white solid after purification by column chromatography (230-400 mesh silica gel, eluted with 50-60% pet ether/ethyl acetate).

F. Using General Procedure E with Compound 78 (6.0 g, 12.43 mmol) in 80% AcOH (60 mL) gave the desired dialcohol, (1R,3aS,3bS,4R,5R,5aS,10aR,10bS,12aR)-10a,12a-dimethyl-1-((R)-6-methylheptan-2-yl)-1,2,3,3a,3b,4,5,5a,6,7,10,10a,10b,11,12,12a-hexadecahydrocyclopenta[5,6]naphtho[1,2-f]indazole-4,5-diol (Compound 79, 6.0 g), as a yellow gummy solid which was used in the next step without purification.

G. Using General Procedure F with Compound 79 (6.0 g, 13.55 mmol) and sodium metaperiodate (5.80 g, 27.11 mmol) in THF:water (4:1, 60 mL) gave the desired dialdehyde, (5R,6S)-5-((1R,3aS,4S,5S,7aR)-4-formyl-7a-methyl-1-((R)-6-methylheptan-2-yl)octahydro-1H-inden-5-yl)-5-methyl-4,5,6,7-tetrahydro-1H-indazole-6-carbaldehyde (Compound 80, 4.0 g, 67%), as a white solid after purification by column chromatography (230-400 mesh silica gel, eluted with 60-80% pet ether/ethyl acetate).

H. Using General Procedure G with Compound 80 (4.0 g, 9.08 mmol) and sodium borohydride (0.69 g, 18.15 mmol) in THF:MeOH (1:1, 40 mL) gave the desired dialcohol, ((1R,3aS,4S,5S,7aR)-5-((5R,6S)-6-(hydroxymethyl)-5-methyl-4,5,6,7-tetrahydro-1H-indazol-5-yl)-7a-methyl-1-((R)-6-methylheptan-2-yl)octahydro-1H-inden-4-yl)methanol (Compound Ia-56, 4.0 g, 99%), as a white solid which was used in the next step without purification.

LCMS: (Method 1f) MS m/z: 445.5 (M+1), $t_R$: 3.911 min, Purity: 94.3% (ELSD).

$^1$H-NMR (400 MHz, DMSO-$d_6$): δ 12.28 (s, 1H), 7.18 (s, 1H), 4.53-4.42 (m, 1H), 4.18 (s, 1H), 3.79 (d, J=10.6 Hz, 1H), 3.70 (d, J=8.9 Hz, 1H), 3.43 (d, J=10.2 Hz, 1H) 3.14-3.10 (m, 1H), 2.98 (dd, J=5.3, 16.6 Hz, 1H), 2.44-2.33 (m, 1H), 2.15-2.09 (m, 2H), 1.86-1.81 (m, 1H), 1.73-1.66 (m, 2H), 1.53-1.30 (m, 11H), 1.16-1.00 (m, 6H), 0.98-0.91 (m, 4H), 0.88-0.84 (m, 9H), 0.64 (s, 3H).

2. Preparation of Compound Ia-57

A. Using General Procedure J with Compound Ia-56 (2.0 g, 4.49 mmol) and MsCl (1.74 mL, 22.49 mmol) in pyridine (40 mL) gave the desired mesylate, ((5R,6S)-5-methyl-5-((1R,3aS,4S,5S,7aR)-7a-methyl-1-((R)-6-methylheptan-2-yl)-4-(((methylsulfonyl)oxy)methyl)octahydro-1H-inden-5-yl)-4,5,6,7-tetrahydro-1H-indazol-6-yl)methyl methanesulfonate (Compound 81, 1.7 g, 52%), as an off-white solid after purification by column chromatography (230-400 mesh silica gel, eluted with 40-50% pet ether/ethyl acetate).

B. Using General Procedure K with Compound 81 (1.7 g, 2.83n mol) and sodium azide (0.92 g, 14.15 mmol) in DMF (20 mL), gave the desired azide, (5R,6S)-6-(azidomethyl)-5-((1R,3aS,4S,5S,7aR)-4-(azidomethyl)-7a-methyl-1-((R)-6-methylheptan-2-yl)octahydro-1H-inden-5-yl)-5-methyl-4,5,6,7-tetrahydro-1H-indazole (Compound 82, 0.60 g, 50%), as a white solid after purification by column chromatography (230-400 mesh silica gel, eluted with 30-40% pet ether/ethyl acetate).

C. Using General Procedure S with Compound 82 (0.25 g, 0.51 mmol) and LAH (1 M in THF) (2.02 mL, 2.02 mmol) in THF (5 mL), gave the desired amine, ((1R,3aS,4S,5S,7aR)-5-((5R,6S)-6-(aminomethyl)-5-methyl-4,5,6,7-tetrahydro-1H-indazol-5-yl)-7a-methyl-1-((R)-6-methylheptan-2-yl)octahydro-1H-inden-4-yl)methanamine (Compound Ia-57, 80 mg, 36%), as an off white solid after purification by preparative HPLC (Method 3e).

LCMS: (Method 1d) MS m/z: 443.4 (M+1), $t_R$: 1.483 min, Purity: 97.53% (ELSD).

HPLC: (Method 2d) $t_R$: 8.820 min, Purity: 98.87% (ELSD).

$^1$H-NMR (400 MHz, CD$_3$OD): δ 7.33 (s, 1H), 3.32-3.00 (m, 3H), 2.87-2.39 (m, 4H), 2.05-1.90 (m, 4H), 1.74-1.51 (m, 5H), 1.49-1.30 (m, 12H), 1.21-1.14 (m, 4H), 1.06-0.88 (m, 9H), 0.77 (s, 3H).

Synthetic Example 21

Synthesis of ((3aS,4R,5S,7aS)-5-((5R,6S)-6-(aminomethyl)-5-methyl-4,5,6,7-tetrahydro-1H-indazol-5-yl)-7a-methyl-1-methyleneoctahydro-1H-inden-4-yl)methanamine (Compound Ia-58)

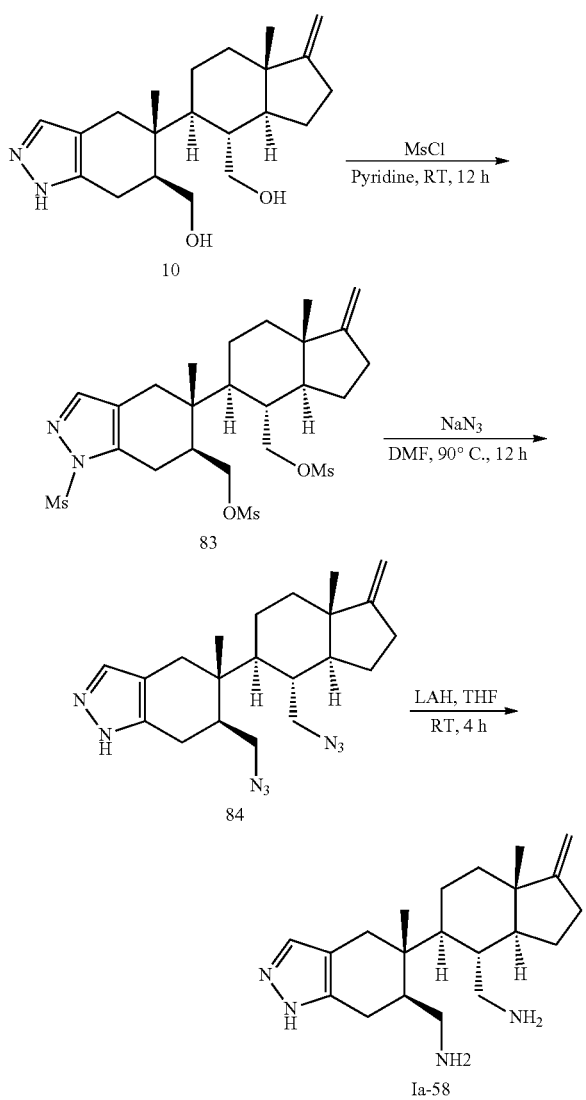

A. Using General Procedure J with Compound 10 (from Example 4, 0.7 g, 2.03 mmol) and MsCl (0.63 mL, 8.13 mmol) in pyridine (7 mL), followed by purification by column chromatography on silica gel (230-400 mesh, 20-30% EtOAc/pet ether) afforded ((5R,6S)-5-methyl-5-((3aS,4R,5S,7aS)-7a-methyl-1-methylene-4-(((methylsulfonyl)oxy)methyl)octahydro-1H-inden-5-yl)-1-(methylsulfonyl)-4,5,6,7-tetrahydro-1H-indazol-6-yl)methyl methanesulfonate (Compound 83, 0.9 g, 77%) as a yellow solid.

B. Using General Procedure K with Compound 83 (0.9 g, 1.56 mmol) and sodium azide (1.01 g, 15.60 mmol) in DMF (10 mL), followed by purification by column chromatography on silica gel (230-400 mesh, 15-25% EtOAc/pet ether) afforded (5R,6S)-6-(azidomethyl)-5-((3aS,4R,5S,7aS)-4-(azidomethyl)-7a-methyl-1-methyleneoctahydro-1H-inden-5-yl)-5-methyl-4,5,6,7-tetrahydro-1H-indazole (Compound 84, 0.6 g, 98%) as an off white solid.

C. Using General Procedure S with Compound 84 (0.1 g, 0.25 mmol) and LAH (2 M in THF) (0.38 mL, 0.76 mmol) in THF (5 mL), followed by purification by preparative HPLC (Method 3e) to afford ((3aS,4R,5S,7aS)-5-((5R,6S)-6-(aminomethyl)-5-methyl-4,5,6,7-tetrahydro-1H-indazol-5-yl)-7a-methyl-1-methyleneoctahydro-1H-inden-4-yl)methanamine (Compound Ia-58, 30 mg, 35%) as an off white solid.

LCMS: (Method 1d) MS m/z: 343.2 (M+1), $t_R$: 0.425 min, Purity: 81.20% (UV).

HPLC: (Method 2d) $t_R$: 7.743 min, Purity: 95.11% (ELSD).

$^1$H-NMR (400 MHz, DMSO-$d_6$): δ 12.23 (s, 1H), 7.19 (s, 1H), 4.59 (s, 2H), 3.04-2.91 (m, 3H), 2.33-2.21 (m, 4H), 1.79-1.71 (m, 5H), 1.56-1.38 (m, 6H), 1.29-1.11 (m, 4H), 1.01 (s, 2H), 0.90 (s, 3H), 0.86 (s, 3H).

Synthetic Example 22

Synthesis of (5R,6S)-6-(hydroxymethyl)-5-((3aS,4R,5S,7aS)-4-(hydroxymethyl)-7a-methyl-1-methyleneoctahydro-1H-inden-5-yl)-5-methyl-4,5,6,7-tetrahydro-1H-indazole-3-carboxamide (Compound Ia-59)

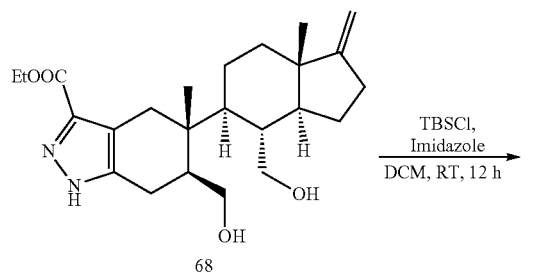

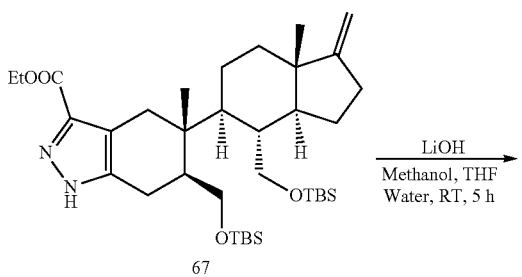

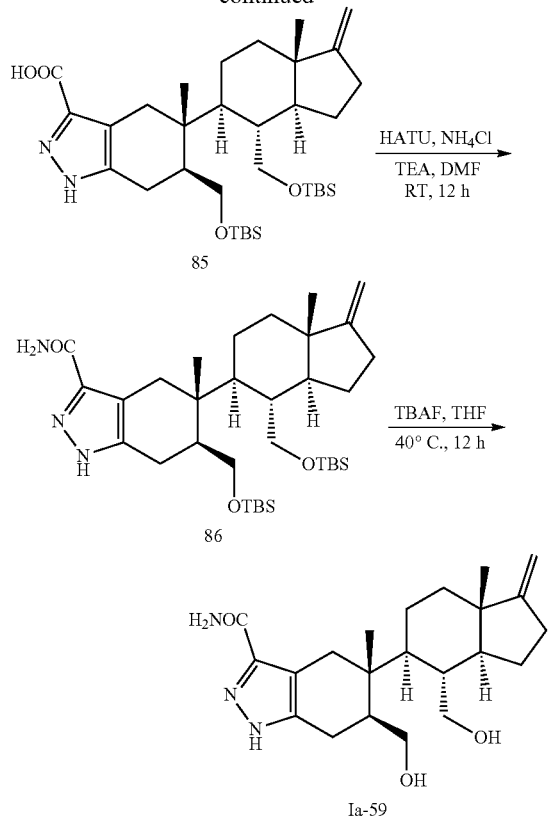

A. Using General Procedure B with Compound 68 (from Example 16, 0.15 g, 0.36 mmol), imidazole (0.1 g, 1.44 mmol) and TBSCl (0.16 g, 1.08 mmol) in DCM (5 mL), followed by purification by column chromatography on silica gel (230-400 mesh, 10-15% EtOAc/pet ether) afforded ethyl (5R,6S)-6-(((tert-butyldimethylsilyl)oxy)methyl)-5-((3aS,4R,5S,7aS)-4-(((tert-butyldimethylsilyl)oxy)methyl)-7a-methyl-1-methyleneoctahydro-1H-inden-5-yl)-5-methyl-4,5,6,7-tetrahydro-1H-indazole-3-carboxylate (Compound 67, 0.17 g, 73%) as a white foam.

B. To a stirred solution of Compound 67 (0.17 g, 0.26 mmol) in THF:MeOH:water (6:4:1.10 mL) was added lithium hydroxide monohydrate (0.033 g, 0.79 mmol) at room temperature and the reaction mixture was stirred for 5 hours. The reaction mixture was concentrated under reduced pressure and diluted with EtOAc (2×10 mL) then washed consecutively with water (1×10 mL) and brine (1×10 mL). The organic layer was dried over $Na_2SO_4$, filtered and concentrated. The residue was purified by column chromatography on silica gel (230-400 mesh, 50-55% EtOAc/pet ether) to afford (5R,6S)-6-(((tert-butyldimethylsilyl)oxy)methyl)-5-((3aS,4R,5S,7aS)-4-(((tert-butyldimethylsilyl)oxy)methyl)-7a-methyl-1-methyleneoctahydro-1H-inden-5-yl)-5-methyl-4,5,6,7-tetrahydro-1H-indazole-3-carboxylic acid (Compound 85, 0.13 g, 81%) as a white solid.

C. To a stirred solution of Compound 85 (0.13 g, 0.21 mmol) in DMF (5 mL) were added triethylamine (0.08 mL, 0.57 mmol), ammonium chloride (0.11 g, 2.11 mmol) followed by portion wise addition of HATU (0.12 g, 0.32 mmol) at 0° C. The reaction mixture was stirred at room temperature for 12 hours. The reaction mixture was diluted with ice cold water (10 mL) and the aqueous was extracted with EtOAc (2×10 mL) and washed with brine (10 mL). The organic layer was dried over Na$_2$SO$_4$, filtered and concentrated. The residue was purified by column chromatography on silica gel (230-400 mesh, 40-50% EtOAc/pet ether) to afford (5R,6S)-6-(((tert-butyldimethylsilyl)oxy)methyl)-5-((3aS,4R,5S,7aS)-4-(((tert-butyldimethylsilyl)oxy)methyl)-7a-methyl-1-methyleneoctahydro-1H-inden-5-yl)-5-methyl-4,5,6,7-tetrahydro-1H-indazole-3-carboxamide (Compound 86, 0.12 g, 92%) as a white solid.

D. Following the General Procedure Q with Compound 86 (0.12 g, 0.19 mmol) and TBAF (1M in THF) (0.6 mL, 0.58 mmol) in THF (5 mL), followed by purification by preparative HPLC (Method 3a) afforded (5R,6S)-6-(hydroxymethyl)-5-((3aS,4R,5S,7aS)-4-(hydroxymethyl)-7a-methyl-1-methyleneoctahydro-1H-inden-5-yl)-5-methyl-4,5,6,7-tetrahydro-1H-indazole-3-carboxamide (Compound Ia-59, 22 mg, 30%) as an off white solid.

LCMS: (Method 1a) MS m/z: 388.3 (M+1), $t_R$: 2.325 min, Purity: 94.63% (UV).

HPLC: (Method 2a) $t_R$: 3.312 min, Purity: 93.23% (UV).

$^1$H-NMR (400 MHz, CD$_3$OD): δ 4.62 (s, 2H), 4.07 (d, J=11.6 Hz, 1H), 3.95 (dd, J=2.8, 10.6 Hz, 1H), 3.72 (d, J=11.2 Hz, 1H), 3.20-3.15 (m, 1H), 2.91-2.87 (m, 1H), 2.55-2.49 (m, 3H), 2.30-2.05 (m, 2H), 1.94-1.78 (m, 1H), 1.70-1.52 (m, 4H), 1.42-1.18 (m, 4H), 1.11 (s, 3H), 0.86 (s, 3H).

Synthetic Example 23

Synthesis of (2R,3aS,4R,5S,7aS)-4-(hydroxymethyl)-5-((5R,6S)-6-(hydroxylmethyl)-5-methyl-4,5,6,7-tetrahydro-1H-indazol-5-yl)-7a-methyl-1-methyleneoctahydro-1H-inden-2-ol (Compound Ia-60)

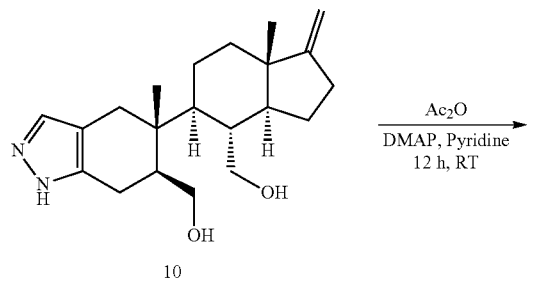
10

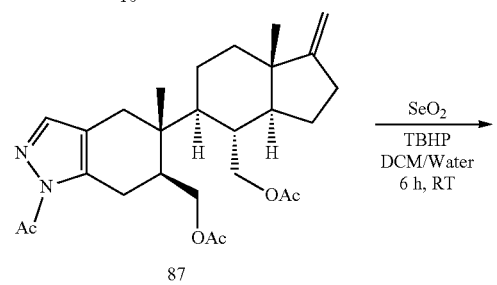
87

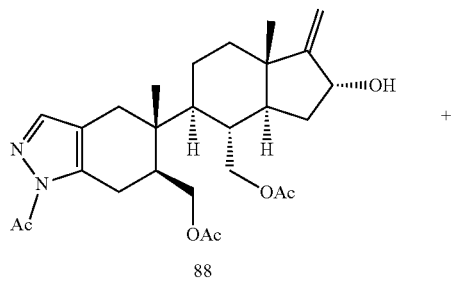
88

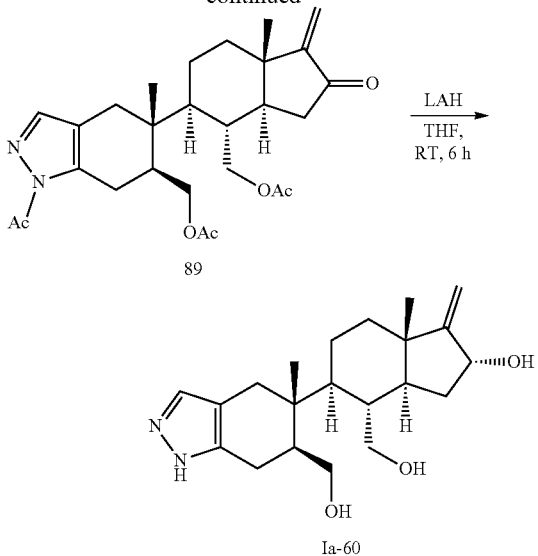
89

Ia-60

A. Using General Procedure A with Compound 10 (from Example 4, 0.10 g, 0.29 mmol), DMAP (4 mg, 0.03 mmol) and Ac$_2$O (0.06 mL, 0.64 mmol) in Pyridine (5 mL), followed by purification by column chromatography on silica gel (230-400 mesh, 10-20% EtOAc/pet ether) afforded ((3aS,4R,5S,7aS)-5-((5R,6S)-6-(acetoxymethyl)-1-acetyl-5-methyl-4,5,6,7-tetrahydro-1H-indazol-5-yl)-7a-methyl-1-methyleneoctahydro-1H-inden-4-yl)methyl acetate (Compound 87, 0.13 g, 95%) as a white foam.

B. To a stirred solution of selenium dioxide (0.061 g, 0.55 mmol) and TBHP (70% in water, 0.07 mL, 0.55 mmol) in DCM (5 mL) at 0° C. was added Compound 87 (0.13 g, 0.28 mmol) in DCM (10 mL) dropwise. The resultant solution was stirred at room temperature for 6 hours. The mixture was concentrated under reduced pressure and the residue was diluted with saturated solution of NaHCO$_3$ (5 g dissolved in 10 mL water). The aqueous layer was extracted with EtOAc (2×10 mL). The combined organic extracts were washed with brine (1×10 mL), dried over Na$_2$SO$_4$, filtered and concentrated under reduced pressure. The residue was a mixture of two compounds, ((2R,3aS,4R,5S,7aS)-5-((5R,6S)-6-(acetoxymethyl)-1-acetyl-5-methyl-4,5,6,7-tetrahydro-1H-indazol-5-yl)-2-hydroxy-7a-methyl-1-methyleneoctahydro-1H-inden-4-yl)methyl acetate (Compound 88) and ((3aS,4R,5S,7aS)-5-((5R,6S)-6-(acetoxymethyl)-1-acetyl-5-methyl-4,5,6,7-tetrahydro-1H-indazol-5-yl)-7a-methyl-1-methylene-2-oxooctahydro-1H-inden-4-yl)methyl acetate (Compound 89), which was used in the next step without purification (Mixture of Compounds 88 and 89, 0.11 g) as a white solid.

C. Using General Procedure S with the mixture of Compounds 88 and 89 (0.11 g, 0.25 mmol) and LAH (1M in THF, 0.50 mL, 0.49 mmol) in THF (10 mL), followed by purification by column chromatography using neutral alumina (10-20% MeOH/CH$_2$Cl$_2$) afforded (2R,3aS,4R,5S,7aS)-4-(hydroxymethyl)-5-((5R,6S)-6-(hydroxylmethyl)-5-methyl-4,5,6,7-tetrahydro-1H-indazol-5-yl)-7a-methyl-1-methyleneoctahydro-1H-inden-2-ol (Compound Ia-60, 29 mg, 33%) as a white solid.

LCMS: (Method 1b) MS m/z: 361.2 (M+1), $t_R$: 2.601 min, Purity: 94.80% (UV).

HPLC: (Method 1a) $t_R$: 2.721 min, Purity: 93.10% (UV).

¹H-NMR (400 MHz, CD₃OD): δ 7.30 (s, 1H), 5.01 (s, 1H), 4.83-4.62 (m, 2H), 4.02 (dd, J=2.0, 11.4 Hz, 1H), 394 (dd, J=2.8, 10.8 Hz, 1H), 3.68-3.66 (m, 1H), 320-315 (m, 1H), 2.70-2.60 (m, 2H), 2.30-2.26 (m, 2H), 1.87-1.70 (m, 6H), 1.63-1.48 (m, 2H), 1.30-1.17 (m, 2H), 1.10 (s, 3H), 0.91 (s, 3H).
Synthetic Example 24
Synthesis of (2R,4R,5S)-4-(hydroxymethyl)-5-((5R, 6S)-6-(hydroxymethyl)-5-methyl-4,5,6,7-tetrahydro-1H-indazol-5-yl)-1,1-dimethyl-2,3,4,5,6,7-hexahydro-1H-inden-2-ol (Compound Ia-61)
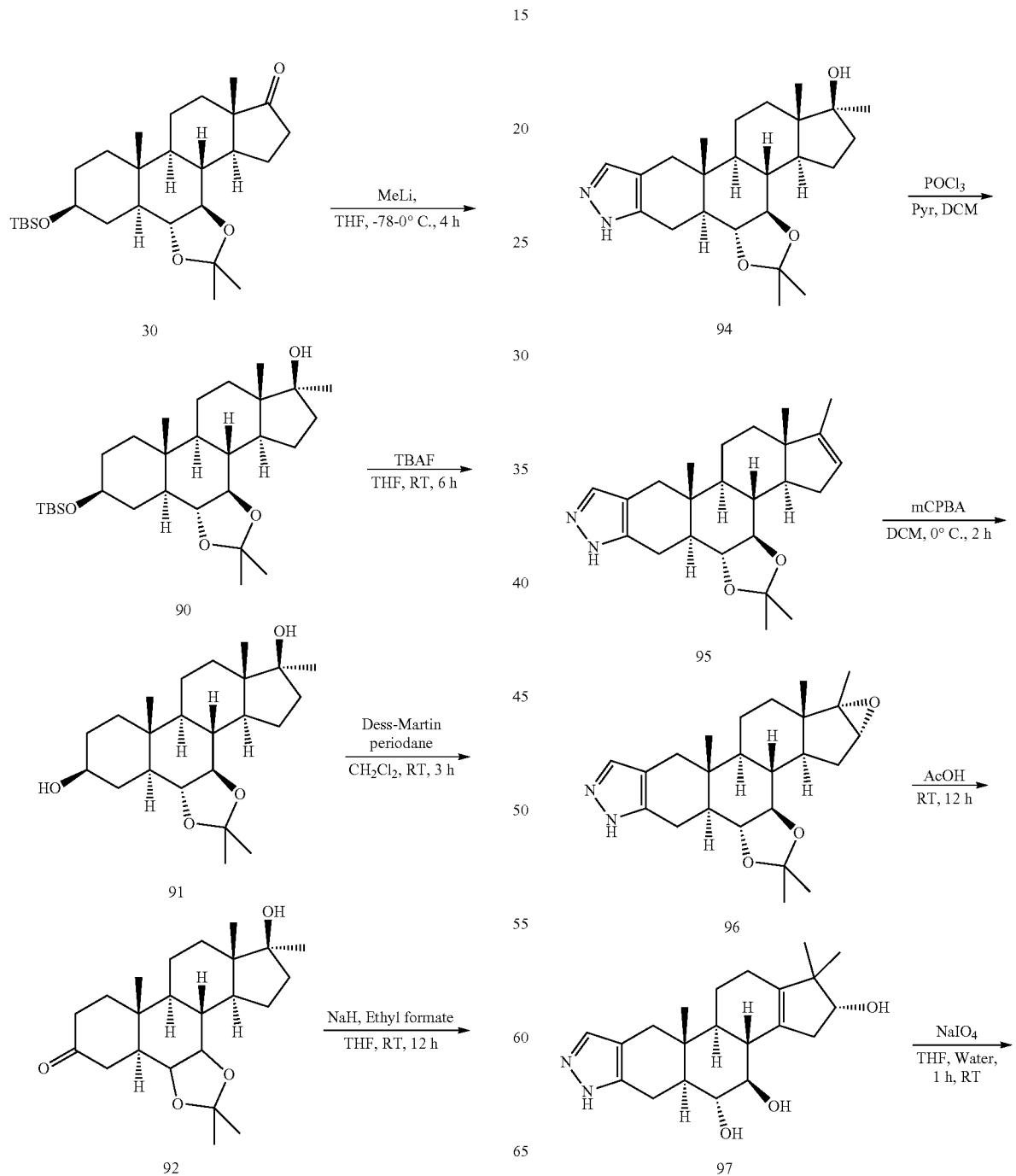

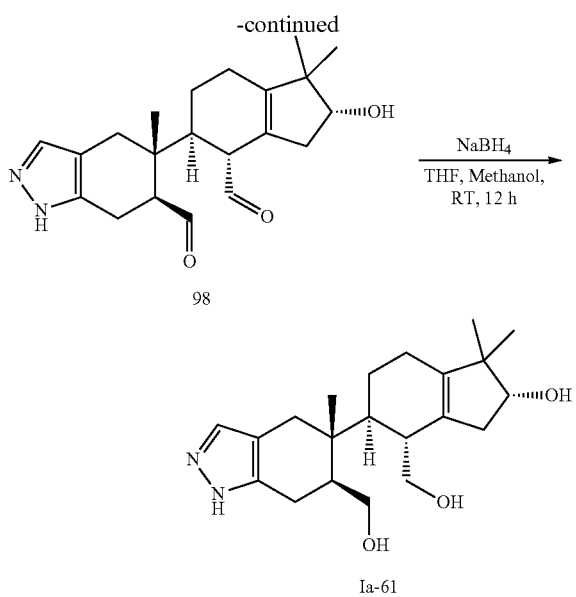

A. To a stirred solution of Compound 30 (from Example 9, 10.0 g, 21.0 mmol) in THF (100 mL) was added methyllithium (1.6 M in ether, 39.33 mL, 62.92 mmol) dropwise at −78° C. The reaction mixture was stirred at 0° C. for 4 hours. The reaction mixture was diluted with saturated aqueous solution of Na₂SO₄ (50 g dissolved in 100 mL of water) and the aqueous layer was extracted with EtOAc (2×100 mL) then washed consecutively with water (1×100 mL) and brine (1×100 mL). The organic layer was dried over Na₂SO₄, filtered and concentrated. The residue was purified by column chromatography on silica gel (230-400 mesh, 30-40% EtOAc/pet ether) to afford (2S,4aR,4bS,6aS,7S,9aS,9bR,9cR,12aR,12bS)-2-((tert-butyldimethylsilyl)oxy)-4a,6a,7,11,11-pentamethylhexadecahydro-1H-cyclopenta[1,2]phenanthro[9,10-d][1,3]dioxol-7-ol (Compound 90, 8.0 g, 77%) as a white solid.

B. Following the General Procedure Q with Compound 90 (8.0 g, 16.23 mmol), TBAF (M in THF, 32.47 mL, 32.47 mmol) and THF (80 mL) afforded (2S,4aR,4bS,6aS,7S,9aS,9bR,9cR,12aR,12bS)-4a,6a,7,11,11-pentamethylhexadecahydro-1H-cyclopenta[1,2]phenanthro[9,10-d][1,3]dioxole-2,7-diol (Compound 91, 4.9 g, 79%) as a white solid following purification by column chromatography on silica gel (230-400 mesh, 70-80% EtOAc/pet ether).

C. Following the General Procedure N with Compound 91 (4.9 g, 12.94 mmol), Dess-Martin periodane (8.24 g, 19.42 mmol) and DCM (50 mL) afforded (4aR,4bS,6aS,7S,9aS,9bR,12bS)-7-hydroxy-4a,6a,7,11,11-pentamethylhexadecahydro-2H-cyclopenta[1,2]phenanthro[9,10-d][1,3]dioxol-2-one (Compound 92, 3.3 g, 67%) as a white solid following purification by column chromatography on silica gel (230-400 mesh, 20-30% EtOAc/pet ether).

D. Following the General Procedure O with Compound 92 (3.3 g, 8.76 mmol), NaH (60% in paraffin oil, 1.4 g, 35.06 mmol), ethyl formate (4.25 mL, 52.58 mmol) and THF (30 mL) afforded (4aR,4bS,6aS,7S,9aS,9bR,9cR,12aR,12bS)-7-hydroxy-3-(hydroxymethylene)-4a,6a,7,11,11-pentamethylhexadecahydro-2H-cyclopenta[1,2]phenanthro[9,10-d][1,3]dioxol-2-one (Compound 93, 3.1 g, 88%) as a white solid following purification by column chromatography on silica gel (230-400 mesh, 20-30% EtOAc/pet ether).

E. Following the General Procedure P with Compound 93 (3.1 g, 7.66 mmol), hydrazine hydrate (0.56 mL, 11.49 mmol) and ethanol (30 mL) afforded (1S,3aS,3bR,3cR,6aR,6bS,11aR,11bS,13aS)-1,5,5,11a,13a-pentamethyl-1,2,3,3a,3b,3c,6a,6b,7,8,11,11a,11b,12,13,13a-hexadecahydrocyclopenta[5,6][1,3]dioxolo[4',5':3,4]naphtho[1,2-f]indazol-1-ol (Compound 94, 2.8 g, 91%) as a white solid following purification by column chromatography on silica gel (230-400 mesh, 0-5% MeOH/CH₂Cl₂).

F. To a stirred solution of Compound 94 (2.8 g, 6.99 mmol) in pyridine:DCM (1:1, 30 mL) was added POCl₃ (1.96 mL, 20.97 mmol) dropwise at 0° C. The resultant solution was stirred at room temperature for 12 hours. The reaction mixture was evaporated under reduced pressure and residue was diluted with saturated solution of NaHCO₃ (15 g dissolved in 30 mL water). The aqueous was extracted with EtOAc (2×30 mL) then washed consecutively with water (1×30 mL) and brine (1×30 mL). The organic layer was dried over Na₂SO₄, filtered and concentrated. The residue was purified by column chromatography on silica gel (230-400 mesh, 0-5% MeOH/CH₂Cl₂) to afford (3aS,3bR,3cR,6aR,6bS,11aR,11bS,13aS)-1,5,5,11a,13a-pentamethyl-3,3a,3b,3c,6a,6b,7,8,11,11a,11b,12,13,13a-tetradecahydrocyclopenta[5,6][1,3]dioxolo[4',5':3,4]naphtho[1,2-f]indazole (Compound 95, 0.85 g, 32%) as an off white solid.

G. To a stirred solution of Compound 95 (0.85 g, 2.22 mmol) in CH₂Cl₂ (10 mL) was added meta-chloroperoxybenzoic acid (1.15 g, 6.67 mmol) portion wise at 0° C. The resultant mixture was stirred at room temperature for 2 hours. The reaction mixture was evaporated under reduced pressure and residue was diluted with saturated solution of NaHCO₃ (5 g dissolved in 10 mL water). The aqueous layer was extracted with CH₂Cl₂ (2×10 mL) then washed consecutively with water (1×10 mL) and brine (1×10 mL). The organic layer was dried over Na₂SO₄, filtered and concentrated. The residue was purified by column chromatography on silica gel (230-400 mesh, 5-10% MeOH/CH₂Cl₂) to afford (3aR,3bS,8aR,8bS,10aS,10bS,11aR,12aS,12bR,12cR)-2,2,8a,10a,10b-pentamethyl-3a,3b,4,5,8,8a,8b,9,10,10a,10b,11a,12,12a,12b,12c-hexadecahydro-[1,3]dioxolo[4',5':3,4]oxireno[2'',3'':3',4']cyclopenta[1',2':5,6]naphtho[1,2-f]indazole (Compound 96, 0.5 g, 57%) as a white solid.

H. Following the General Procedure E with Compound 96 (0.5 g, 1.25 mmol) and 80% AcOH (5 mL) afforded (2R,3bR,4R,5R,5aS,10aR,10bS)-1,1,10a-trimethyl-1,2,3,3b,4,5,5a,6,7,10,10a,10b,11,12-tetradecahydrocyclopenta[5,6]naphtho[1,2-f]indazole-2,4,5-triol (Compound 97, 0.23 g, 51%) as a white solid following purification by column chromatography on silica gel (230-400 mesh, 10-20% MeOH/CH₂Cl₂).

I. Following the General Procedure F with Compound 97 (0.23 g, 0.64 mmol), sodium metaperiodate (0.27 g, 1.28 mmol) and THF:water (4:1, 5 mL) afforded (5R,6S)-5-((2R,4R,5S)-4-formyl-2-hydroxy-1,1-dimethyl-2,3,4,5,6,7-hexahydro-1H-inden-5-yl)-5-methyl-4,5,6,7-tetrahydro-1H-indazole-6-carbaldehyde (Compound 98, 0.18 g, 79%) as a white solid following purification by column chromatography on silica gel (230-400 mesh, 5-10% MeCOH/CH₂Cl₂).

J. Following the General Procedure G with Compound 98 (0.18 g, 0.50 mmol), sodium borohydride (0.038 g, 1.01 mmol) and THF:MeOH (1:1, 5 mL) afforded (2R,4R,5S)-4-(hydroxymethyl)-5-((5R,6S)-6-(hydroxymethyl)-5-methyl-4,5,6,7-tetrahydro-1H-indazol-5-yl)-1,1-dimethyl-2,3,4,5,6,7-hexahydro-1H-inden-2-ol (Compound Ia-61, 33 mg, 18%) as a white solid following purification by column chromatography on neutral alumina (10-20% MeOH/CH₂Cl₂).

LCMS: (Method 1b) MS m/z: 361.2 (M+1), $t_R$: 2.351 min, Purity: 97.84% (UV).

HPLC: (Method 2a) $t_R$: 2.382 min, Purity: 98.31% (UV).

¹H-NMR (400 MHz, CD₃OD): δ 7.35 (s, 1H), 4.00 (dd, J=2.8, 10.4 Hz, 1H), 3.66 (dd, J=3.8, 11.0 Hz, 1H), 3.46-3.38 (m, 3H), 3.20-3.16 (m, 1H), 2.64-2.49 (m, 3H), 2.33-2.13 (m, 4H), 2.02-1.74 (m, 5H), 1.77-1.74 (m, 2H), 1.60-1.55 (m, 1H), 1.08 (s, 3H), 0.94 (s, 3H).
Synthetic Example 25
Synthesis of ((1R,3aS,4S,5,7a)-5-((5R,3)-6-(hydroxymethyl)-5-methyl-4,5,6,7-tetrahydro-1H-indazol-5-yl)-7a-methyl-1-(prop-1-en-2-yl)octahydro-1H-inden-4-yl)methanol (Compound Ia-62)
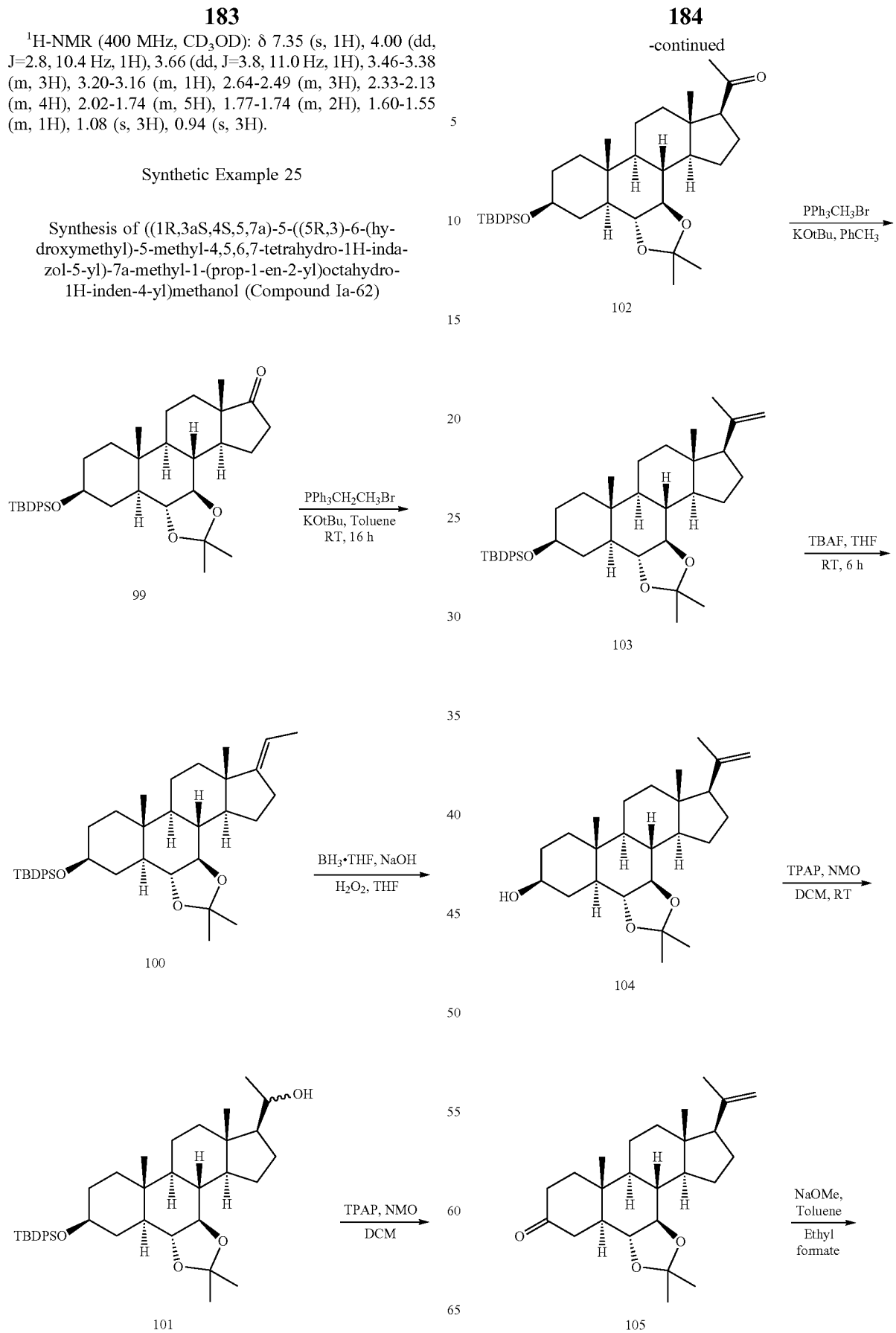

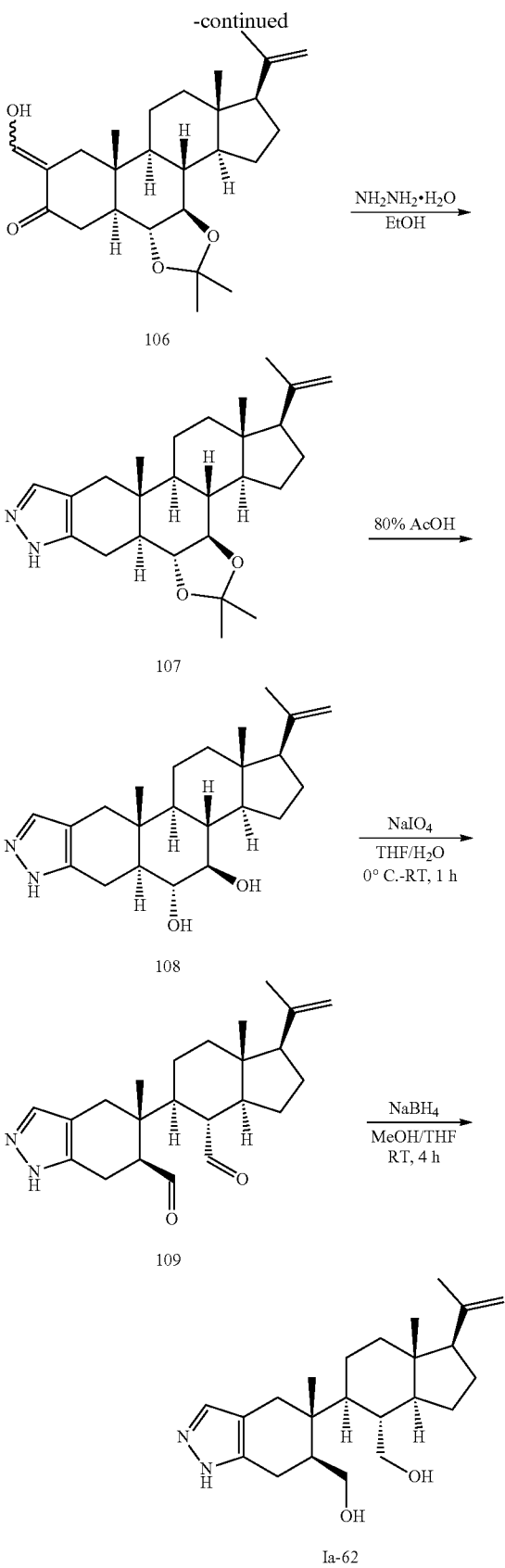

A. Following the General Procedure I with (2S,4aR,4bS, 6aS,9aS,9bR,9cR,12aR,12bS)-2-((tert-butyldiphenylsilyl)

oxy)-4a,6a,11,11-tetramethylhexadecahydro-7H-cyclopenta [1,2]phenanthro[9,10-d][1,3]dioxol-7-one (Compound 99, as prepared in U.S. Pat. No. 9,765,085, 5.0 g, 8.32 mmol), ethyltriphenylphosphonium bromide (15.44 g, 41.60 mmol), potassium-tert-butoxide (4.66 g, 41.60 mmol) and toluene (50 mL) gave the desired alkene tert-butyl(((2,4aR,4bS,6aS, 9aS,9bR,9cR,12aR,12bS,E)-7-ethylidene-4a,6a,11,11-tetramethylhexadecahydro-1H-cyclopenta[1,2]phenanthro[9, 10-d][1,3]dioxol-2-yl)oxy)diphenylsilane (Compound 100, 4.0 g, 79%) as a yellow solid after purification by column chromatography on silica gel (230-400 mesh, 0-20% pet ether/ethyl acetate).

B. To a stirred solution of Compound 100 (4.0 g, 6.53 mmol) in THF (40 mL) at 0° C. was added borane in THF (1 M, 13.05 mL, 13.05 mmol) dropwise. The reaction mixture was stirred at room temperature for 1 hour. The mixture was cooled to 0° C. and added sodium hydroxide solution (10% aqueous, 45.94 mL) followed by hydrogen peroxide (30%, 30.63 mL) dropwise. The resultant solution was stirred at room temperature for 2 hours. The aqueous was extracted with EtOAc (2×40 mL) and washed consecutively with water (1×40 mL) and brine (1×40 mL). The organic layer was dried over Na$_2$SO$_4$, filtered and concentrated. The crude was purified by column chromatography on silica gel (230-400 mesh, 0-30% pet ether/ethyl acetate) to afford 1-((2S,4aR,4bS,6aS,7S,9aS,9bS,9cR,12aR,12bS)-2-((tert-butyldiphenylsilyl)oxy)-4a,6a,11,11-tetramethylhexadecahydro-1H-cyclopenta[1,2]phenanthro[9,10-d][1,3] dioxol-7-yl)ethan-1-ol (Compound 101, 3.3 g, 80%) as an off-white solid.

C. Using General Procedure M with Compound 101 (3.0 g, 4.75 mmol), NMO (1.29 g, 11.01 mmol), 4 Å molecular sieves (3.0 g) and TPAP (0.17 g, 0.48 mmol) in CH$_2$Cl$_2$ (30 mL) gave the desired ketone, 1-((2S,4aR,4bS,6aS,7S,9aS, 9bR,9cR,12aR,12bS)-2-((tert-butyldiphenylsilyl)oxy)-4a, 6a,11,11-tetramethylhexadecahydro-1H-cyclopenta[1,2] phenanthro[9,10-d][1,3]dioxol-7-yl)ethan-1-one (Compound 102, 2.5 g, 36%), as an off-white solid after purification by column chromatography (230-400 mesh silica gel, eluted with 15-20% pet ether/ethyl acetate).

D. Following the General Procedure I with Compound 102 (2.5 g, 3.97 mmol), methyltriphenylphosphonium bromide (7.10 g, 19.87 mmol), potassium-tert-butoxide (2.23 g, 19.87 mmol) and toluene (30 mL) gave the desired alkene, tert-butyldiphenyl(((2,4aR,4bS,6aS,7R,9aS,9bS,9cR,12aR, 12bS)-4a,6a,11,11-tetramethyl-7-(prop-1-en-2-yl)hexadecahydro-1H-cyclopenta[1,2]phenanthro[9,10-d][1,3]dioxol-2-yl)oxy)silane (Compound 103, 2.2 g, 88%), as a pale yellow solid after purification by column chromatography on silica gel (230-400 mesh, 0-10% pet ether/ethyl acetate).

E. Following the General Procedure Q with Compound 103 (2.2 g, 3.51 mmol) and TBAF (1 M in THF, 7.02 mL, 7.02 mmol) in THF (20 mL), gave the desired alcohol, (2S,4aR,4bS,6aS,7R,9aS,9bS,9cR,12aR,12bS)-4a,6a,11,11-tetramethyl-7-(prop-1-en-2-yl)hexadecahydro-1H-cyclopenta[1,2]phenanthro[9,10-d][1,3]dioxol-2-ol (Compound 104, 1.0 g, 73%), as a white solid after purification by column chromatography (230-400 mesh silica gel, eluted with 0-30% pet ether/ethyl acetate).

F. Using General Procedure M with Compound 104 (1.0 g, 2.57 mmol), NMO (0.69 g, 5.15 mmol), 4 Å molecular sieves (1.0 g) and TPAP (0.09 g, 0.26 mmol) in CH$_2$Cl$_2$ (10 mL) gave the desired ketone, (4aR,4bS,6aS,7R,9aS,9bS, 9cR,12aR,12bS)-4a,6a,11,11-tetramethyl-7-(prop-1-en-2-yl)hexadecahydro-2H-cyclopenta[1,2]phenanthro[9,10-d] [1,3]dioxol-2-one (Compound 105, 0.90 g, 91%), as an off-white solid after purification by column chromatography (230-400 mesh silica gel, eluted with 15-25% pet ether/ethyl acetate).

G. To a stirred solution of Compound 105 (0.90 g, 2.33 mmol) in toluene (10 mL) at 0° C. were added sodium methoxide solution (25% wt. in MeOH, 1.51 mL, 6.60 mmol) and ethyl formate (0.94 mL, 11.65 mmol) dropwise. The resultant solution was stirred at room temperature for 16 hours. The mixture was evaporated under reduced pressure and the residue was diluted with ice cold water (1×10 mL). The aqueous was extracted with EtOAc (2×10 mL) and washed with brine (1×10 mL). The organic layer was dried over $Na_2SO_4$, filtered and concentrated to afford (4aR,4bS, 6aS,7R,9aS,9bS,9cR,12aR,12bS)-3-(hydroxymethylene)-4a,6a,11,11-tetramethyl-7-(prop-1-en-2-yl)hexadecahydro-2H-cyclopenta[1,2]phenanthro[9,10-d][1,3]dixol-2-one (Compound 106, 0.9 g, 93%) as a brown gummy solid which was used in the next step without purification.

H. Using General Procedure P with Compound 106 (0.9 g, 2.17 mmol) and hydrazine hydrate (0.53 mL, 10.86 mmol) in EtOH (10 mL) gave the desired pyrazole, (1R,3aS,3bS, 3cR,6aR,6bS,11aR,11bS,13aS)-5,5,11a,13a-tetramethyl-1-(prop-1-en-2-yl)-1,2,3,3a,3b,3c,6a,6b,7,8,11,11a,11b,12,13, 13a-hexadecahydrocyclopenta[5,6][1,3]dioxolo[4',5':3,4] naphtho[1,2-t]indazole (Compound 107, 0.8 g, 90%), as an off-white solid after purification by column chromatography on silica gel (230-400 mesh, 0-10% dichloromethane/methanol).

I. Using General Procedure E with Compound 107 (0.8 g, 1.95 mmol) in 80% AcOH (10 mL) gave the desired dialcohol, (1R,3aS,3bS,4R,5R,5aS,10aR,10bS,12aS)-1a, 12a-dimethyl-1-(prop-1-en-2-yl)-1,2,3,3a,3b,4,5,5a,6,7,10, 10a,10b,11,12,12a-hexadecahydrocyclopenta[5,6]naphtho [1,2-f]indazole-4,5-diol (Compound 108, 0.7 g, 97%), as an off-white solid after purification by column chromatography (230-400 mesh silica gel, eluted with 10-15% methanol/ dichloromethane).

LCMS: (Method 1e) MS m/z: 371.2 (M+1), $t_R$: 3.182 min, Purity: 94.99% (UV).

HPLC: (Method 2e) $t_R$: 6.876 min, Purity: 98.00% (UV).

$^1$H-NMR (400 MHz, $CD_3OD$): δ 7.29 (s, 1H), 4.76 (s, 1H), 3.30-3.27 (m, 1H), 3.16-3.07 (m, 2H), 2.67-2.63 (m, 1H), 2.32-2.04 (m, 4H), 1.93-1.82 (m, 1H), 1.79-1.51 (m, 10H), 1.42-1.05 (m, 4H), 0.82 (s, 3H), 0.66 (s, 3H).

J. Using General Procedure F with Compound 108 (0.70 g, 1.89 mmol), sodium metaperiodate (0.81 g, 3.78 mmol) and THF/water (4:1) (10 mL) gave the desired dialdehyde, (5R,6S)-5-((1R,3aS,4S,5S,7aS)-4-formyl-7a-methyl-1-(prop-1-en-2-yl)octahydro-1H-inden-5-yl)-5-methyl-4,5,6, 7-tetrahydro-1H-indazole-6-carbaldehyde (Compound 109, 0.68 g, 98%), as an off white solid which was used in the next step without purification.

K. Using General Procedure G with Compound 109 (0.68 g, 1.85 mmol), sodium borohydride (0.14 g, 3.69 mmol) and THF/MeOH (1:1, 10 mL) gave the desired dialcohol, ((1R, 3aS,4S,5S,7aS)-5-((5R,6S)-6-(hydroxymethyl)-5-methyl-4, 5,6,7-tetrahydro-1H-indazol-5-yl)-7a-methyl-1-(prop-1-en-2-yl)octahydro-1H-inden-4-yl)methanol (Compound Ia-62, 0.50 g, 73%), as an off white solid after purification by column chromatography (Neutral alumina, eluted with 10% dichloromethane/methanol).

LCMS: (Method 1e) MS m/z: 373.2 (M+1), $t_R$: 3.050 min, Purity: 98.65% (UV).

HPLC: (Method 2e) $t_R$: 6.657 min, Purity: 99.52% (UV).

$^1$H-NMR (400 MHz, $CD_3OD$): δ 7.27 (s, 1H), 4.86-4.73 (m, 2H), 4.05-3.94 (m, 2H), 3.69-3.66 (m, 1H), 3.38-3.36 (m, 1H), 3.20-3.15 (m, 1H), 2.69-2.65 (m, 2H), 2.25-2.08 (m, 3H), 1.88-1.82 (m, 3H), 1.76-1.63 (m, 7H), 1.59-1.45 (m, 2H), 1.33-1.18 (m, 2H), 1.10 (s, 3H), 0.65 (s, 3H).

Synthetic Example 26

Synthesis of ((5R,6S)-5-((1R,3aS,4S,5S,7aS)-4-(aminomethyl)-7a-methyl-1-(prop-1-en-2-yl)octahydro-1H-inden-5-yl)-5-methyl-4,5,6,7-tetrahydro-1H-indazol-6-yl)methanol (Compound Ia-63)

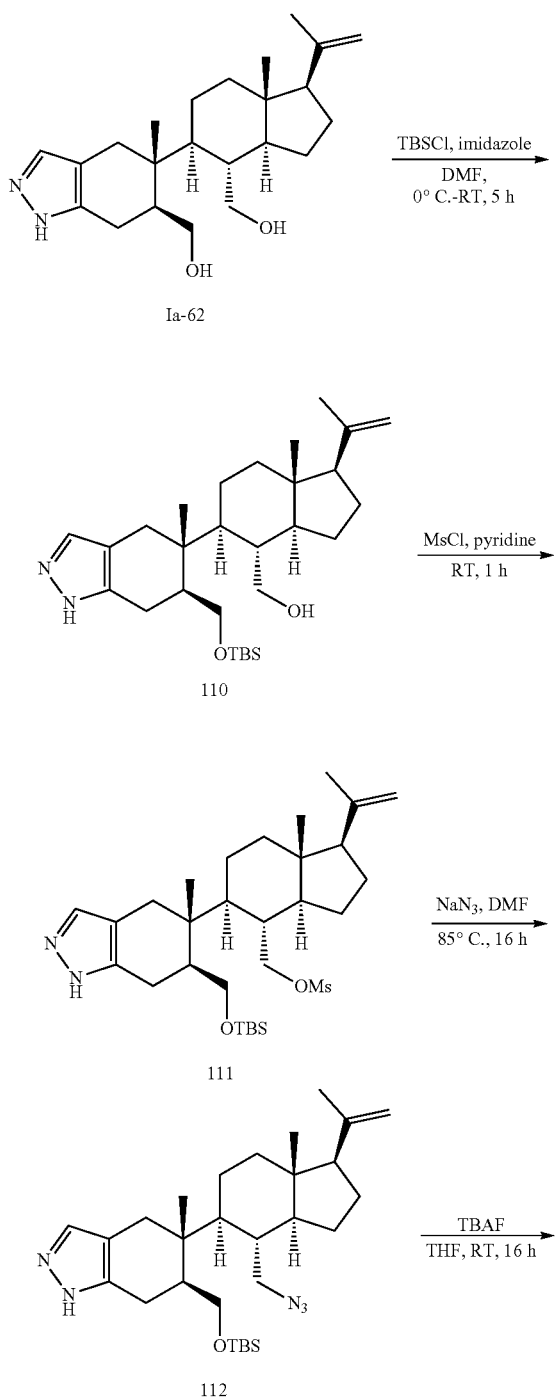

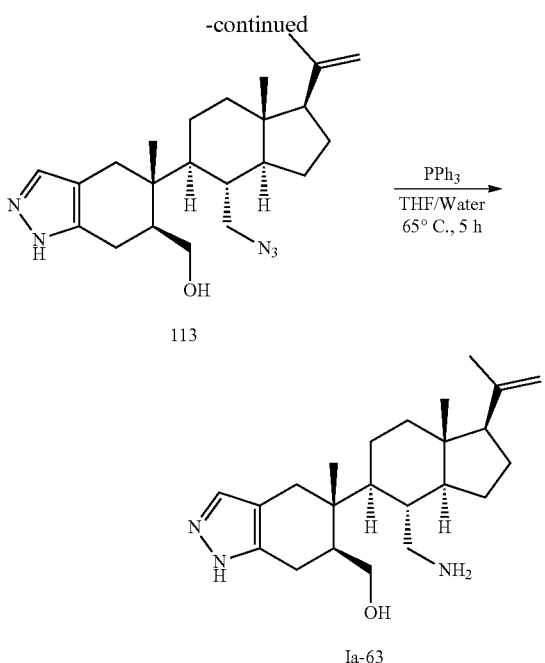

113

Ia-63

A. Using General Procedure B with Compound Ia-62, from Example 25, 0.5 g, 1.34 mmol), imidazole (0.27 g, 3.97 mmol), TBSCl (0.30 g, 2.01 mmol) and DMF (5 mL) gave the desired silyl ether, ((1R,3aS,4S,5S,7aS)-5-((5R,6S)-6-(((tert-butyldimethylsilyl)oxy)methyl)-5-methyl-4,5,6,7-tetrahydro-1H-indazol-5-yl)-7a-methyl-1-(prop-1-en-2-yl)octahydro-1H-inden-4-yl)methanol (Compound 110, 0.5 g, 77%), as a white solid after purification by column chromatography on silica gel (230-400 mesh, 40-50% pet ether/ethyl acetate).

B. Using General Procedure J with Compound 110 (0.5 g, 1.03 mmol), MsCl (0.16 mL, 2.07 mmol) and pyridine (5 mL) gave the desired mesylate, ((1R,3aS,4S,5S,7aS)-5-((5R,6S)-6-(((tert-butyldimethylsilyl)oxy)methyl)-5-methyl-4,5,6,7-tetrahydro-1H-indazol-5-yl)-7a-methyl-1-(prop-1-en-2-yl)octahydro-1H-inden-4-yl)methyl methanesulfonate (Compound 111, 0.55 g, 95%), as a yellow gummy solid which was taken for next step without purification.

C. Using General Procedure K with Compound 111 (0.55 g, 0.97 mmol), sodium azide (0.13 g, 2.00 mmol) and DMF (5 mL), gave the desired azide, (5R,6S)-5-((1R,3aS,4S,5S,7aS)-4-(azidomethyl)-7a-methyl-1-(prop-1-en-2-yl)octahydro-1H-inden-5-yl)-6-(((tert-butyldimethylsilyl)oxy)methyl)-5-methyl-4,5,6,7-tetrahydro-1H-indazole (Compound 112, 0.45 g, 91%), as a white solid after purification by column chromatography (230-400 mesh silica gel, eluted with 25-30% pet ether/ethyl acetate).

D. Following the General Procedure Q with Compound 112 (0.45 g, 0.88 mmol), TBAF (1M in THF, 1.76 mL, 1.76 mmol) and THF (5 mL), gave the desired alcohol, ((5R,6S)-5-((1R,3aS,4S,5S,7aS)-4-(azidomethyl)-7a-methyl-1-(prop-1-en-2-yl)octahydro-1H-inden-5-yl)-5-methyl-4,5,6,7-tetrahydro-1H-indazol-6-yl)methanol (Compound 113, 0.30 g, 86%), as a brown gummy solid which was used in the next step without purification.

E. Using General Procedure R with Compound 113 (0.30 g, 0.76 mmol), triphenylphosphine (0.40 g, 151 mmol) and THF:water (9:1, 5 mL) gave the desired amine, ((5R,6S)-5-((1R,3aS,4S,5S,7aS)-4-(aminomethyl)-7a-methyl-1-(prop-1-en-2-yl)octahydro-1H-inden-5-yl)-5-methyl-4,5,6,7-tetrahydro-1H-indazol-6-yl)methanol (Compound Ia-63, 60 mg, 21%), as an off white solid after purification by preparative HPLC (Method 3a).

LCMS: (Method 1e) MS m/z: 372.2 (M+1), $t_R$: 2.770 min, Purity: 91.42% (UV).

HPLC: (Method 2e) $t_R$: 5.498 min, Purity: 99.13% (UV).

$^1$H-NMR (400 MHz, CD$_3$OD): δ 7.30 (s, 1H), 4.86 (s, 1H), 4.75 (s, 1H), 398-3.95 (m, 1H), 3.42-3.40 (m, 1H), 3.17-3.10 (m, 2H), 2.81-2.78 (m, 1H), 2.68-2.64 (m, 1H), 2.56-2.50 (m, 1H), 2.39-2.35 (m, 1H), 2.18-2.12 (m, 2H), 1.88-1.53 (m, 11H), 1.35-1.27 (m, 3H), 1.05 (s, 3H), 0.67 (s, 3H).

Synthetic Example 27

Synthesis of ((5R,6S)-5-((3aS,4R,5S,7aS,E)-1-ethylidene-4-(hydroxymethyl)-7a-methyloctahydro-1H-inden-5-yl)-5-methyl-4,5,6,7-tetrahydro-1H-indazol-6-yl)methanol (Compound Ia-64)

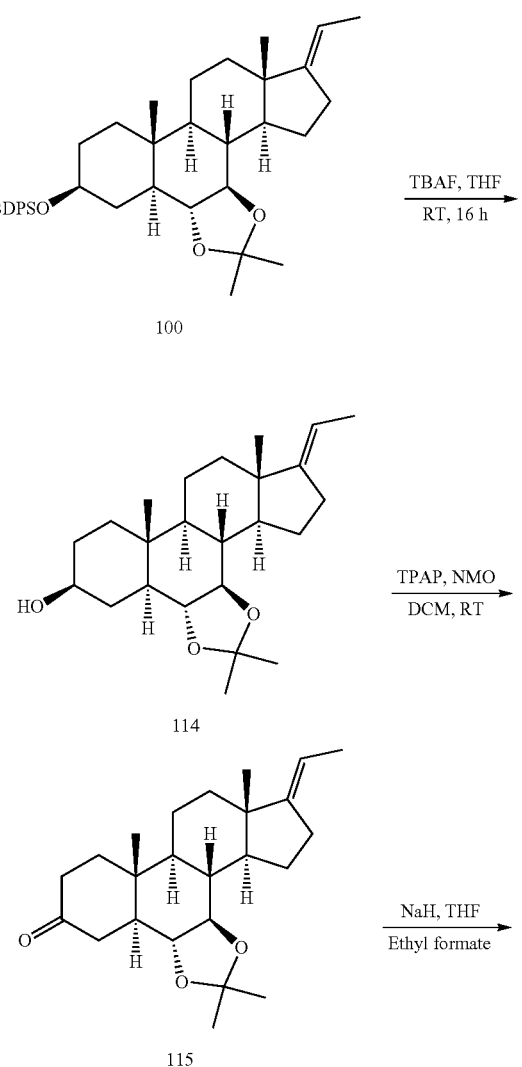

100

114

115

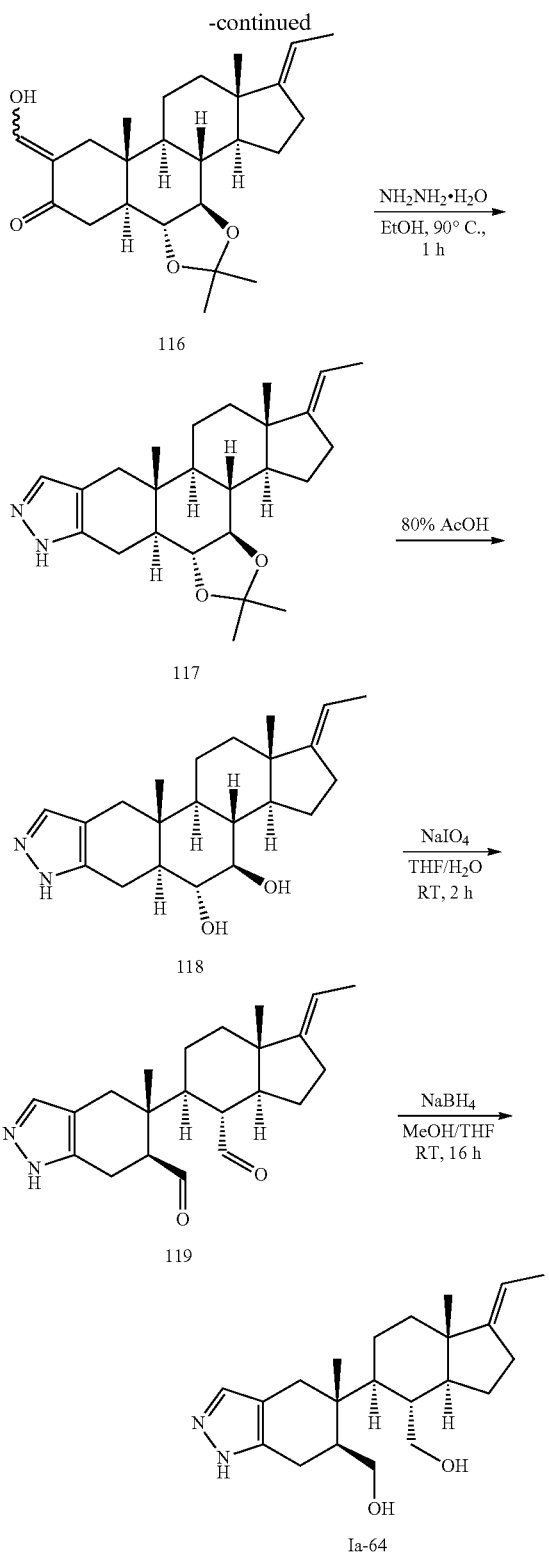

A. Following the General Procedure Q with Compound 100 (from Example 25, 4.0 g, 6.53 mmol) and TBAF (1 M in THF, 13.05 mL, 13.05 mmol) in THF (40 mL) gave the desired alcohol, (2S,4aR,4bS,6aS,9aS,9bR,9cR,12aR,12bS,E)-7-ethylidene-4a,6a,11,11-tetramethylhexadecahydro-1H-cyclopenta[1,2]phenanthro[9,10-d][1,3]dioxol-2-ol (Compound 114, 2.3 g, 94%), as an off-white solid after purification by column chromatography (230-400 mesh silica gel, eluted with 0-30% pet ether/ethyl acetate).

B. Using General Procedure M with Compound 114 (2.3 g, 6.14 mmol), NMO (1.44 g, 10.65 mmol), 4 Å molecular sieves (2.0 g) and TPAP (0.22 g, 0.61 mmol) in $CH_2Cl_2$ (20 mL) gave the desired ketone, (4aR,4bS,6aS,9aS,9bR,9cR,12aR,12bS,E)-7-ethylidene-4a,6a,11,11-tetramethylhexadecahydro-2H-cyclopenta[1,2]phenanthro[9,10-d][1,3]dioxol-2-one (Compound 115, 2.0 g, 88%), as an off-white solid after purification by column chromatography (230-400 mesh silica gel, eluted with 15-25% pet ether/ethyl acetate).

C. Following the General Procedure O with Compound 115 (2.0 g, 5.37 mmol), NaH (60% in paraffin oil, 0.64 g, 16.11 mmol), ethyl formate (2.17 mL, 26.85 mmol) and THF (20 mL) gave the desired ketone, (4aR,4bS,6aS,7E,9aS,9bR,9cR,12aR,12bS)-7-ethylidene-3-(hydroxymethylene)-4a,6a,11,11-tetramethylhexadecahydro-2H-cyclopenta[1,2]phenanthro[9,10-d][1,3]dixol-2-one (Compound 116, 2.0 g, 93%), as a brown gummy which was used in the next step without purification.

D. Using General Procedure P with Compound 116 (2.0 g, 4.99 mmol) and hydrazine hydrate (0.98 mL, 19.97 mmol) in EtOH (20 mL) gave the desired pyrazole, (3aS,3bR,3cR,6aR,6bS,11aR,11bS,13aS,E)-1-ethylidene-5,5,11a,13a-tetramethyl-1,2,3,3a,3b,3c,6a,6b,7,8,11,11a,11b,12,13,13a-hexadecahydrocyclopenta[5,6][1,3]dioxolo[4',5':3,4]naphtho[1,2-f]indazole (Compound 117, 1.5 g, 76%), as an off-white solid after purification by column chromatography (230-400 mesh silica gel, eluted with 30-40% pet ether/ethyl acetate).

E. Using General Procedure E with Compound 117 (1.5 g, 3.78 mmol) in AcOH (80%, 15 mL) gave the desired dialcohol, (3aS,3bR,4R,5R,5aS,10aR,10bS,12aS,E)-1-ethylidene-10a,12a-dimethyl-1,2,3,3a,3b,4,5,5a,6,7,10,10a,10b,11,12,12a-hexadecahydrocyclopenta[5,6]naphtho[1,2-f]indazole-4,5-diol (Compound 118, 1.3 g, 97%), as an off-white solid after purification by column chromatography (230-400 mesh silica gel, eluted with 0-5% methanol/dichloromethane).

LCMS: (Method 1e) MS m/z: 357.2 (M+1), $t_R$: 3.077 min, Purity: 96.18% (UV).

HPLC: (Method 2e) $t_R$: 5.605 min, Purity: 99.61% (UV).

$^1$H-NMR (400 MHz, $CD_3D$): δ 7.29 (s, 1H), 5.18-5.16 (m, 1H), 3.37-3.3 (m 1H), 3.2-3.10 (m, 2H), 2.68-2.64 (m, 1H), 2.39-2.07 (m, 6H), 1.79-1.54 (m, 9H), 1.42-1.31 (m, 1H), 1.11-1.05 (m, 1H), 0.97 (s, 3H), 0.82 (s, 3H).

F. Using General Procedure F with Compound 118 (1.3 g, 3.65 mmol), sodium metaperiodate (1.56 g, 7.29 mmol) and THF:water (4:1, 10 mL) gave the desired dialdehyde, (5R,6S)-5-((3aS,4R,5S,7aS,E)-1-ethylidene-4-formyl-7a-methyloctahydro-1H-inden-5-yl)-5-methyl-4,5,6,7-tetrahydro-1H-indazole-6-carbaldehyde (Compound 119, 1.0 g, 77%), as an off white solid which was used in the next step without purification.

G. Using General Procedure G with Compound 119 (1.0 g, 2.82 mmol), sodium borohydride (0.21 g, 5.55 mmol) and THF:MeOH (1:1, 10 mL) gave the desired dialcohol, ((5R,6S)-5-((3aS,4R,5S,7aS,E)-1-ethylidene-4-(hydroxymethyl)-7a-methyloctahydro-1H-inden-5-yl)-5-methyl-4,5,6,7-tetrahydro-1H-indazol-6-yl)methanol (Compound Ia-64, 0.70 g, 69%), as an off white solid after purification by column chromatography (Neutral alumina, eluted with 10% dichloromethane/methanol).

LCMS: (Method 1e) MS m/z: 359.2 (M+1), $t_R$: 2.964 min, Purity: 92.11% (UV).

HPLC: (Method 2a) $t_R$: 5.430 min, Purity: 97.64% (UV).

$^1$H-NMR (400 MHz, CD$_3$OD): δ 7.28 (s, 1H), 5.12 (m, 1H), 4.05 (d, J=10.8 Hz, 1H), 3.95 (dd, J=2.8, 10.6 Hz, 1H), 3.73-3.70 (m, 1H), 3.39-3.36 (m, 2H), 3.18 (dd, J=5.6, 17.0 Hz, 1H), 2.70-2.66 (m, 2H), 2.38-2.25 (m, 5H), 1.86-1.64 (m, 7H), 1.55-1.30 (m, 3H), 1.10 (s, 3H), 0.95 (s, 3H).

Synthetic Example 28

Synthesis of ((5R,6S)-5-((3aS,4R,5S,7aS)-4-(aminomethyl)-1-ethylidene-7a-methyloctahydro-1H-inden-5-yl)-5-methyl-4,5,6,7-tetrahydro-1H-indazol-6-yl)methanol (Compound Ia-65)

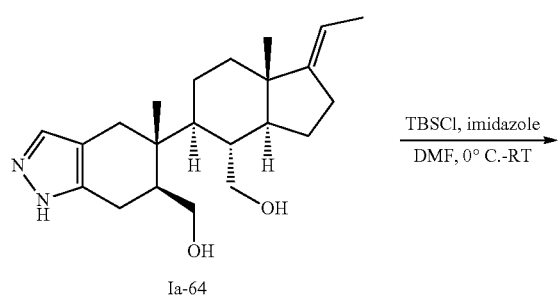

Ia-64

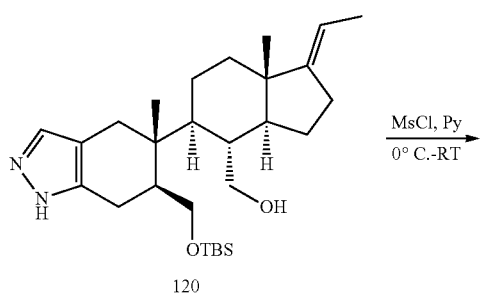

120

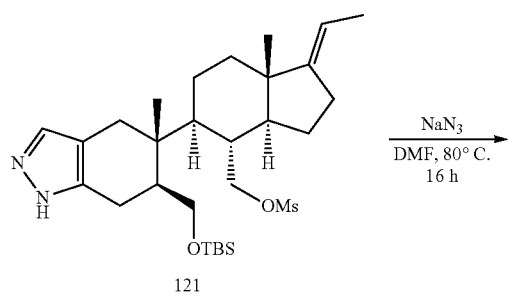

121

122

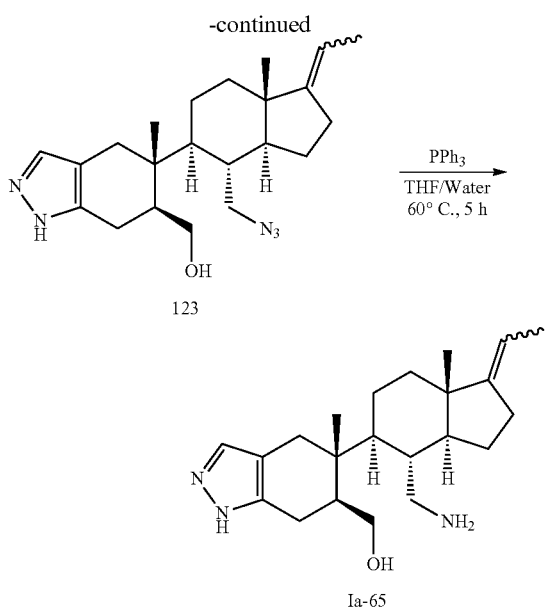

123

Ia-65

A. Using General Procedure B with Compound Ia-64 (from Example 27, 0.70 g, 1.95 mmol), imidazole (0.27 g, 3.97 mmol), TBSCl (0.35 g, 2.34 mmol) and DMF (7 mL) gave the desired silyl ether, ((3aS,4R,5S,7aS,E)-5-((5R,6S)-6-(((tert-butyldimethylsilyl)oxy)methyl)-5-methyl-4,5,6,7-tetrahydro-1H-indazol-5-yl)-1-ethylidene-7a-methyloctahydro-1H-inden-4-yl)methanol (Compound 120, 0.7 g, 76%), as a white solid after purification by column chromatography on silica gel (230-400 mesh, 40-50% pet ether/ethyl acetate).

B. Using General Procedure J with Compound 120 (0.7 g, 1.48 mmol), MsCl (0.23 mL, 2.96 mmol) and pyridine (7 mL) gave the desired mesylate, ((3aS,4R,5S,7aS,E)-5-((5R, 6)-6-(((ter-butyidimethylsilyl)oxy)methyl)-5-methyl-4,5,6, 7-tetrahydro-1H-indazol-5-yl)-1-ethylidene-7a-methyloctahydro-1H-inden-4-yl)methyl methanesulfonate (Compound 121, 0.7 g, 86%), as a yellow gummy solid which was used in the next step without purification.

C. Using General Procedure K with Compound 121 (0.7 g, 1.27 mmol), sodium azide (0.17 g, 2.61 mmol) and DMF (7 mL), gave the desired azide, (5R,6S)-5-((3aS,4R,5S,7aS)-4-(azidomethyl)-1-ethylidene-7a-methyloctahydro-1H-inden-5-yl)-6-(((tert-butyldimethylsilyl)oxy)methyl)-5-methyl-4,5,6,7-tetrahydro-1H-indazole (Compound 122, 0.55 g, 87%), as a white solid after purification by column chromatography (230-400 mesh silica gel, eluted with 20-30% pet ether/ethyl acetate).

D. Following the General Procedure Q with Compound 122 (0.55 g, 1.10 mmol), TBAF (1M in THF, 2.21 mL, 2.21 mmol) and THF (5 mL), gave the desired alcohol, ((5R, 65S)-5-((3aS,4R,5S,7aS)-4-(azidomethyl)-1-ethylidene-7a-methyloctahydro-1H-inden-5-yl)-5-methyl-4,5,6,7-tetrahydro-1H-indazol-6-yl)methanol (123, 0.32 g, 76%), as an off white solid after purification by column chromatography (230-400 mesh silica gel, eluted with 40-50% pet ether/ethyl acetate).

E. Using General Procedure R with Compound 123 (0.15 g, 0.39 mmol), triphenylphosphine (0.21 g, 0.80 mmol) and THF:water (9:1, 5 mL) gave the desired amine, ((5R,6S)-5-((3aS,4R,5S,7aS)-4-(aminomethyl)-1-ethylidene-7a-methyloctahydro-1H-inden-5-yl)-5-methyl-4,5,6,7-tetrahydro-1H-indazol-6-yl)methanol (Compound Ia-65, 20 mg, 14%), as an off white solid after purification by preparative HPLC (Method 3c).

LCMS: (Method 1e) MS m/z: 358.2 (M+1), $t_R$: 2.667 min, Purity: 98.85% (UV).

HPLC: (Method 2e) $t_R$: 4.569 min, Purity: 97.48% (UV).

$^1$H-NMR (400 MHz, CD$_3$OD): δ 7.32 (s, 1H), 5.18-5.09 (m, 1H), 3.94 (d, J=10.84 Hz, 1H), 3.42-3.37 (m, 1H), 3.15-3.09 (m, 1H), 2.71-2.67 (m, 1H), 2.51-2.32 (m, 4H), 2.16-2.14 (m, 1H), 1.97-1.87 (m, 6H), 1.68-1.55 (m, 5H), 1.46-1.30 (m, 3H), 1.05 (s, 3H), 0.85 (s, 3H).

Synthetic Example 29

Synthesis of (2S,3aS,4R,5S,7aS)-4-(hydroxymethyl)-5-((5R,6S)-6-(hydroxymethyl)-5-methyl-4,5,6,7-tetrahydro-1H-indazol-5-yl)-7a-methyl-1-methyleneoctahydro-1H-inden-2-ol (Compound Ia-66)

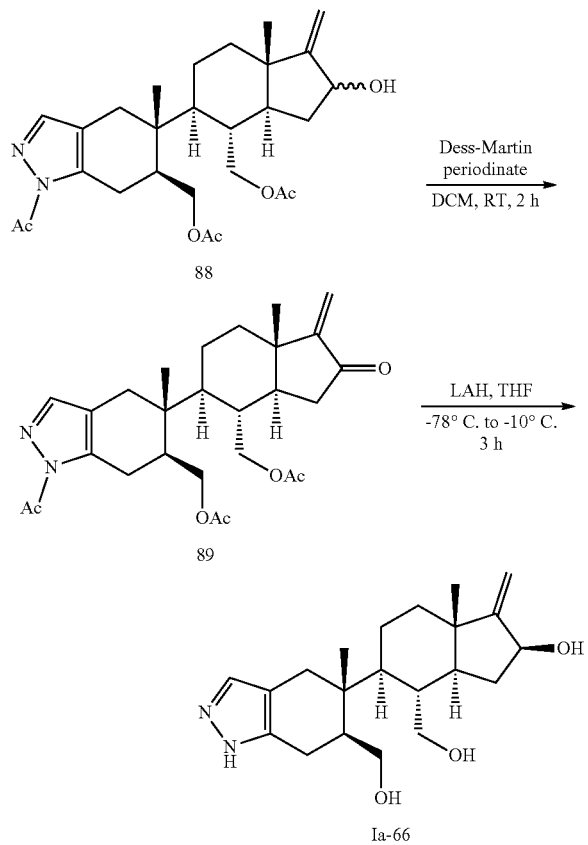

A. The mixture of Compound 88 and Compound 89, as prepared in Example 23, were separated as white solids after purification by column chromatography on silica gel (230-400 mesh, 10-20% pet ether/ethyl acetate). Compound 89 was used in a subsequent step. Compound 88 was converted to Compound 89 as below.

B. Using General Procedure N with Compound 88 (0.40 g, 0.82 mmol), DMP (0.52 g, 1.23 mmol) and dichloromethane (5 mL) afforded the desired ketone, ((3aS,4R,5S,7aS)-5-((5R,6S)-6-(acetoxymethyl)-1-acetyl-5-methyl-4,5,6,7-tetrahydro-1H-indazol-5-yl)-7a-methyl-1-methylene-2-oxooctahydro-1H-inden-4-yl)methyl acetate (Compound 89, 0.38 g, 95%), as a white solid after purification by column chromatography on silica gel (10-15% pet ether/ethyl acetate).

C. Using General Procedure S with Compound 89 (0.5 g, 1.03 mmol), LAH (1 M in THF, 3.10 mL, 3.10 mmol) and THF (5 mL), at −78° C. to −10° C. over 3 h, afforded the desired trialcohol, (2S,3aS,4R,5S,7aS)-4-(hydroxymethyl)-5-((5R,6s)-6-(hydroxymethyl)-5-methyl-4,5,6,7-tetrahydro-1H-indazol-5-yl)-7a-methyl-1-methyleneoctahydro-1H-inden-2-ol (Compound Ia-66, 200 mg, 54%), as an off white solid after purification by preparatory HPLC (Method 3c).

LCMS: (Method 1a) MS m/z: 361.5 (M+1), $t_R$: 1.846 min, Purity: 98.76% (ELSD).

HPLC: (Method 2c) $t_R$ 1.850 min, Purity: 99.73% (ELSD).

$^1$H-NMR (400 MHz, CD$_3$OD): δ 7.32 (s, 1H), 5.03 (s, 1H), 4.87 (s, 1H), 4.48-4.44 (m, 1H), 4.07-4.04 (m, 1H), 3.94 (dd, J=2.4, 10.6 Hz, 1H), 3.70-368 (m, 1H), 3.21-3.15 (m, 1H), 2.72-2.68 (m, 2H), 2.32-2.28 (m, 3H), 1.83-1.69 (m, 4H), 1.46-1.36 (m, 3H), 1.21-1.11 (m, 4H), 1.05-1.00 (m, 4H).

Synthetic Example 30

Synthesis of ((5R,6S)-5-((3aS,6S,7R,7aS)-7-(aminomethyl)-3,3a-dimethyl-3a,4,5,6,7,7a-hexahydro-1H-inden-6-yl)-5-methyl-4,5,6,7-tetrahydro-1H-indazol-6-yl)methanol (Compound Ia-67)

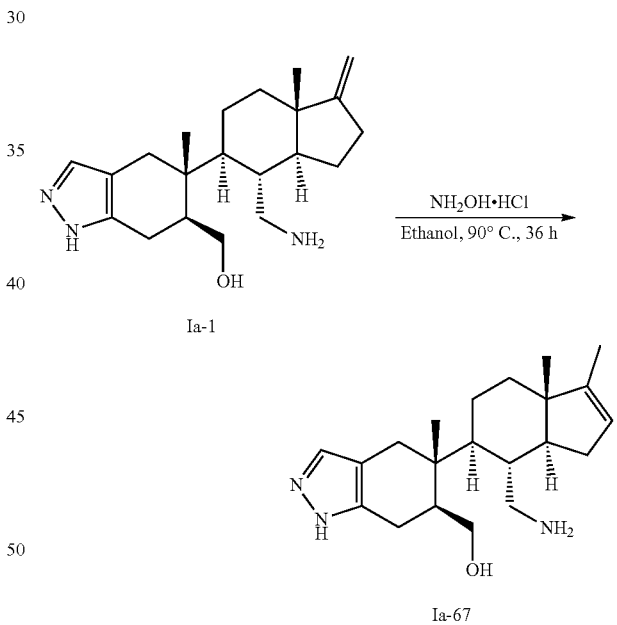

A. To a solution of Compound Ia-1 (as prepared in Example 1, 100 mg, 0.29 mmol) in ethanol (5 mL) was added hydroxylamine hydrochloride (61 mg, 0.87 mmol) and the resultant mixture was stirred at 90° C. for 36 h.

B. The mixture was concentrated on a rotary evaporator to get a pale brown residue which was dissolved in ethyl acetate (20 mL). The organic phase was washed with water (10 mL) followed by brine solution wash (10 mL). The organic phase was dried over anhydrous sodium sulphate (500 mg) and concentrated to afford an inseparable mixture of ((5R,6S)-5-((3aS,6S,7R,7aS)-7-(aminomethyl)-3,3a-dimethyl-3a,4,5,6,7,7a-hexahydro-1H-inden-6-yl)-5-methyl-4,5,6,7-tetrahydro-1H-indazol-6-yl)methanol (Compound Ia-67) in ((5R,6S)-5-((3aS,4R,5S,7aS)-4-(aminomethyl)-7a-methyl-1-methyleneoctahydro-1H-inden-5-yl)-5-methyl-4,5,6,7-tetrahydro-1H-indazol-6-yl)methanol (Compound Ia-1, 85 mg) as an off white solid.

LCMS: (Method 1i) MS m/z: 322.3 (M+1), $t_R$: 6.611 min, Purity: 11.78% (UV).

HPLC: (Method 2b) $t_R$: 7.230 min, Purity: 13.33% (UV).

$^1$H-NMR (400 MHz, CD$_3$OD): Key distinctive NMR signal δ 5.32 (s, 1H).

Synthetic Example 31

Synthesis of ((5R,6S)-5-methyl-5-((3aS,4R,5S,7aS)-7a-methyl-4-((methylamino)methyl)-1-methyleneoctahydro-1H-inden-5-yl)-4,5,6,7-tetrahydro-1H-indazol-6-yl)methanol (Compound Ia-68) and ((5R,6S)-5-((1S,3aS,4S,5S,7aR)-1,7a-dimethyl-4-((methylamino)methyl)octahydro-1H-inden-5-yl)-5-methyl-4,5,6,7-tetrahydro-1H-indazol-6-yl)methanol (Compound Ia-69)

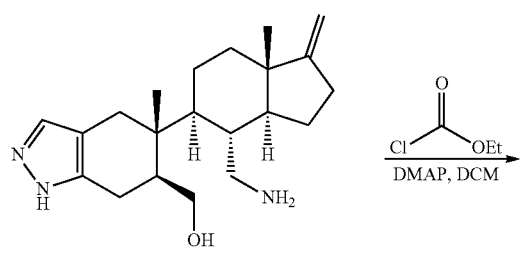

A. Title compound ((5R,6S)-5-methyl-5-((3aS,4R,5S,7aS)-7a-methyl-4-((methylamino)methyl)-1-methyleneoctahydro-1H-inden-5-yl)-4,5,6,7-tetrahydro-1H-indazol-6-yl)methanol (Compound Ia-68) was obtained from the treatment of Compound Ia-1 (from Example 1) with ethyl chloroformate followed by reduction with LAH.

LCMS: (Method 1h) MS m/z: 358.3 (M+1), $t_R$: 2.419 min, Purity: 98.076% (UV).

B. Title compound ((5R,6S)-5-((1S,3aS,4S,5S,7aR)-1,7a-dimethyl-4-((methylamino)methyl)octahydro-1H-inden-5-yl)-5-methyl-4,5,6,7-tetrahydro-1H-indazol-6-yl)methanol (Compound Ia-69) was obtained by reducing Compound Ia-68 under appropriate General Procedure T conditions.

LCMS: (Method 1j) MS m/z: 360.3 (M+1), $t_R$: 1.767 min, Purity: 96.9% (UV).

Synthetic Example 32

Synthesis of ((5R,6S)-5-((3aS,4R,5S,7aS)-4-((dimethylamino)methyl)-7a-methyl-1-methyleneoctahydro-1H-inden-5-yl)-5-methyl-4,5,6,7-tetrahydro-1H-indazol-6-yl)methanol (Compound Ia-70) and ((5R,6S)-5-((1S,3aS,4S,5S,7aR)-4-((dimethylamino)methyl)-1,7a-dimethyloctahydro-1H-inden-5-yl)-5-methyl-4,5,67-tetrahydro-1H-indazol-6-yl)methanol (Compound Ia-71)

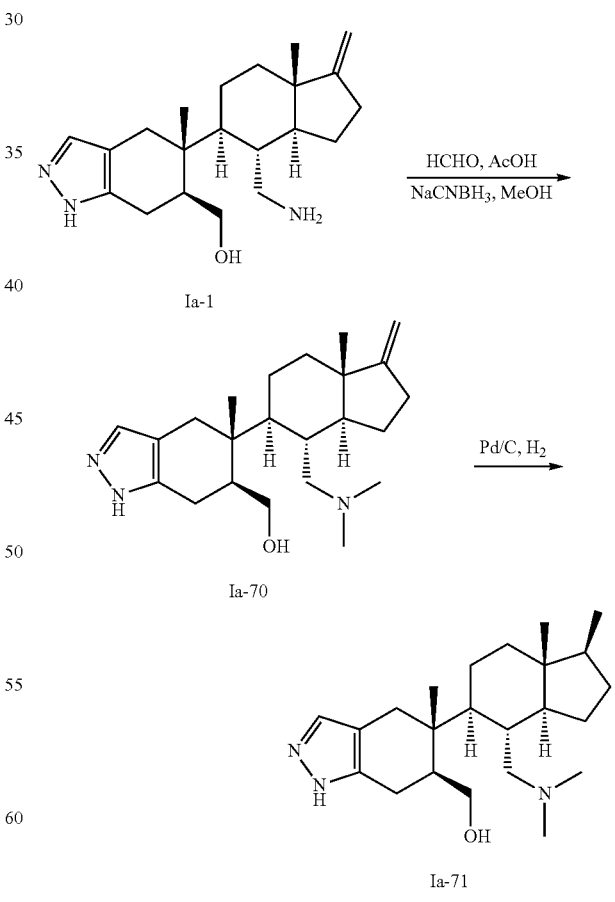

A. Title compound ((5R,6S)-5-((3aS,4R,5S,7aS)-4-((dimethylamino)methyl)-7a-methyl-1-methyleneoctahydro-1H-inden-5-yl)-5-methyl-4,5,6,7-tetrahydro-1H-indazol-6-yl)

methanol (Compound Ia-70) was obtained from Compound Ia-1 (from Example 1) by appropriate General Procedure U conditions.

LCMS: (Method 1h) MS m/z: 358.3 (M+1), $t_R$: 2.419 min, Purity: 98.076% (UV).

B. Title compound ((5R,6S)-5-((1S,3aS,4S,5S,7aR)-4-((dimethylamino)methyl)-1,7a-dimethyloctahydro-1H-inden-5-yl)-5-methyl-4,5,6,7-tetrahydro-1H-indazol-6-yl)methanol (Compound Ia-71) was obtained from Compound Ia-70 by appropriate General Procedure T conditions.

LCMS: (Method 1h) MS m/z: 358.3 (M+1), $t_R$: 2.419 min, Purity: 98.076% (UV).

Synthetic Example 33

Synthesis of ((3aS,4R,5S,7aS)-7a-methyl-5-((5R,6S)-5-methyl-6-(morpholinomethyl)-4,5,6,7-tetrahydro-1H-indazol-5-yl)-1-methyleneoctahydro-1H-inden-4-yl)methanol (Compound Ia-72)

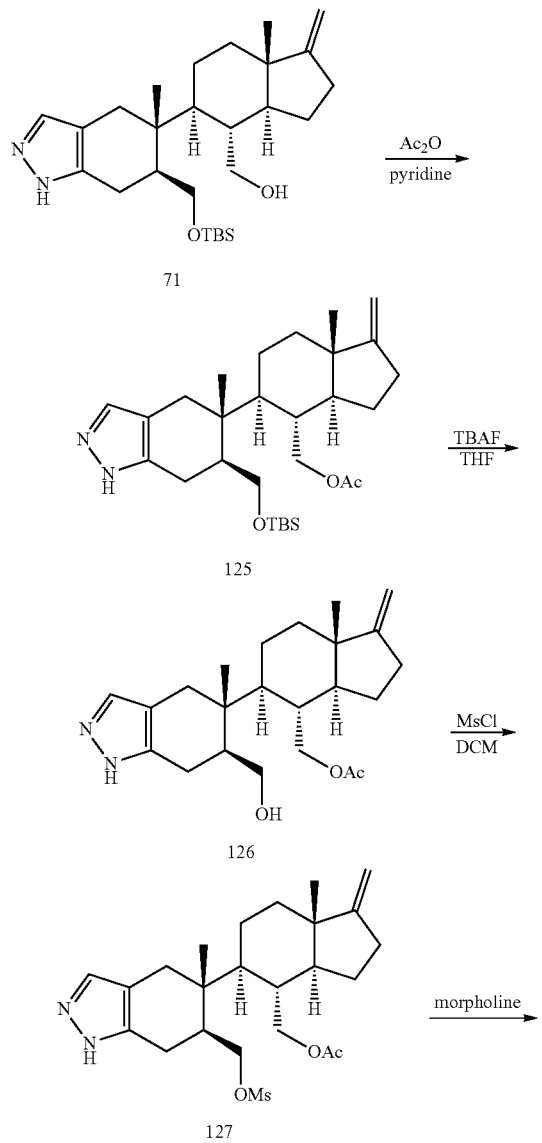

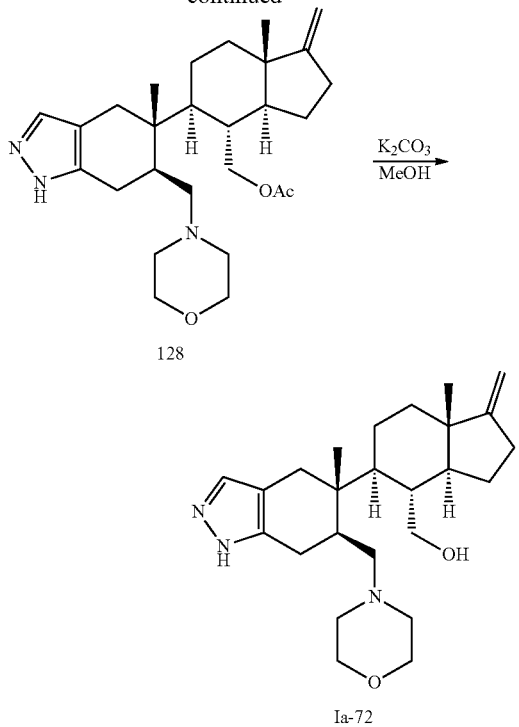

Title compound ((3aS,4R,5S,7aS)-7a-methyl-5-((5R,6S)-5-methyl-6-(morpholinomethyl)-4,5,6,7-tetrahydro-1H-indazol-5-yl)-1-methyleneoctahydro-1H-inden-4-yl)methanol (Compound Ia-72) was obtained from Compound 71 (from Example 19) by protection of the alcohol, removal of the TBS protecting group, mesylation of the alcohol, treatment with morpholine followed by deprotection of the alcohol.

LCMS: (Method 1d) MS m/z: 414.3 (M+1), $t_R$: 1.388 min, Purity: 99.915% (UV).

Synthetic Example 33.1

((3aS,4R,5S,7aS)-7a-methyl-5-((5R,6S)-5-methyl-6-((4-methylpiperazin-1-yl)methyl)-4,5,6,7-tetrahydro-1H-indazol-5-yl)-1-methyleneoctahydro-1H-inden-4-yl)methanol (Compound Ia-73)

Following the procedure as described in Synthetic Example 33 and making non-critical variations using 1-methylpiperazine in place of morpholine, the title compound, ((3aS,4R,5S,7aS)-7a-methyl-5-((5R,6S)-5-methyl-6-((4-methylpiperazin-1-yl)methyl)-4,5,6,7-tetrahydro-1H-indazol-5-yl)-1-methyleneoctahydro-1H-inden-4-yl)methanol (Compound Ia-73), was obtained.

LCMS: (Method 1c) MS m/z: 427.3 (M+1), $t_R$: 2.111 min, Purity: 99.490% (ELSD).

Synthetic Example 33.2

((3aS,4R,5S,7aS)-7a-methyl-5-((5R,6S)-5-methyl-6-(piperidin-1-ylmethyl)-4,5,6,7-tetrahydro-1H-indazol-5-yl)-1-methyleneoctahydro-1H-inden-4-yl)methanol (Compound Ia-74)

Following the procedure as described in Synthetic Example 33 and making non-critical variations using piperidine in place of morpholine, the title compound, ((3aS, 4R,5S,7aS)-7a-methyl-5-((5R,6S)-5-methyl-6-(piperidin-1-ylmethyl)-4,5,6,7-tetrahydro-1H-indazol-5-yl)-1-methyleneoctahydro-1H-inden-4-yl)methanol (Compound Ia-74), was obtained.

LCMS: (Method 1c) MS m/z: 411.3 (M+1), $t_R$: 3.083 min, Purity: 98.296% (ELSD).

Synthetic Example 33.3

((3aS,4R,5S,7aS)-7a-methyl-5-((5R,6S)-5-methyl-6-(thiomorpholinomethyl)-4,5,6,7-tetrahydro-1H-indazol-5-yl)-1-methyleneoctahydro-1H-inden-4-yl)methanol (Compound Ia-75)

Following the procedure as described in Synthetic Example 33 and making non-critical variations using thiomorpholine in place of morpholine, the title compound, ((3aS,4R,5S,7aS)-7a-methyl-5-((5R,6S)-5-methyl-6-(thiomorpholinomethyl)-4,5,6,7-tetrahydro-1H-indazol-5-yl)-1-methyleneoctahydro-1H-inden-4-yl)methanol (Compound Ia-75), was obtained.

LCMS: (Method 1c) MS m/z: 430.2 (M+1), $t_R$: 2.334 min, Purity: 96.496% (ELSD).

Synthetic Example 34

Synthesis of ((3aS,4R,5S,7aS)-7a-methyl-5-((5R,6S)-5-methyl-6-(morpholinomethyl)-4,5,6,7-tetrahydro-1H-indazol-5-yl)-1-methyleneoctahydro-1H-inden-4-yl)methanamine (Compound Ia-76)

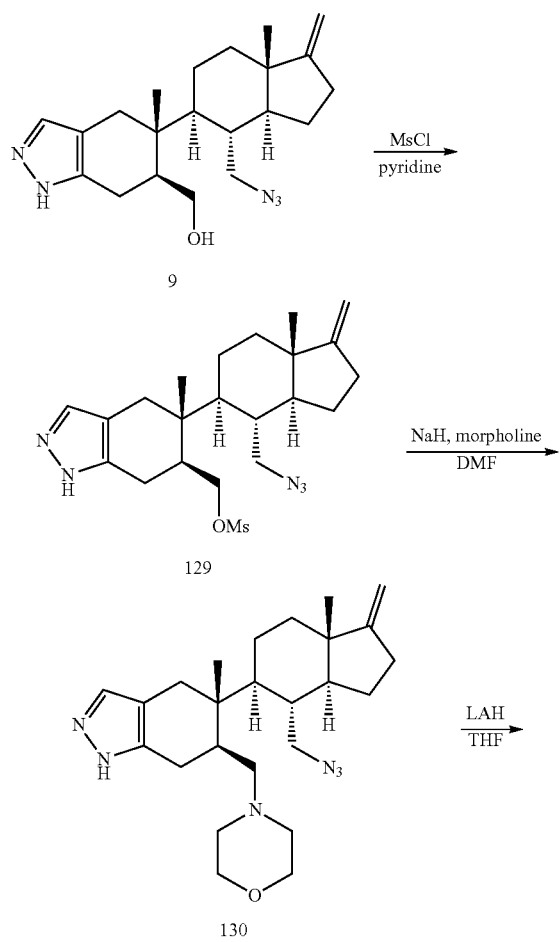

-continued

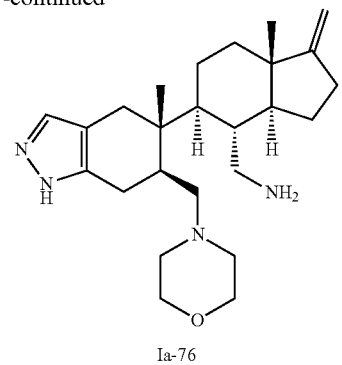

Ia-76

Title compound ((3aS,4R,5S,7aS)-7a-methyl-5-((5R,6S)-5-methyl-6-(morpholinomethyl)-4,5,6,7-tetrahydro-1H-indazol-5-yl)-1-methyleneoctahydro-1H-inden-4-yl)methanamine (Compound Ia-76) was obtained from Compound 9 (from Example 1) by conversion of the alcohol to the mesylate, displacement of the mesylate by morpholine and finally reduction with LAH.

LCMS: (Method 1c) MS m/z: 413.3 (M+1), $t_R$: 1.829 min, Purity: 94.312% (UV).

Synthetic Example 34.1

((3aS,4R,5S,7aS)-7a-methyl-5-((5R,6S)-5-methyl-6-((4-methylpiperazin-1-yl)methyl)-4,5,6,7-tetrahydro-1H-indazol-5-yl)-1-methyleneoctahydro-1H-inden-4-yl)methanamine (Compound Ia-77)

Following the procedure as described in Synthetic Example 34 and making non-critical variations using 1-methylpiperazine in place of morpholine, the title compound, ((3aS,4R,5S,7aS)-7a-methyl-5-((5R,6S)-5-methyl-6-((4-methylpiperazin-1-yl)methyl)-4,5,6,7-tetrahydro-1H-indazol-5-yl)-1-methyleneoctahydro-1H-inden-4-yl)methanamine (Compound Ia-77), was obtained.

LCMS: (Method 1d) MS m/z: 426.3 (M+1), $t_R$: 0.964 min, Purity: 98.639% (ELSD).

Synthetic Example 34.2

((3aS,4R,5S,7aS)-7a-methyl-5-((5R,6S)-5-methyl-6-(piperidin-1-ylmethyl)-4,5,6,7-tetrahydro-1H-indazol-5-yl)-1-methyleneoctahydro-1H-inden-4-yl)methanamine (Compound Ia-78)

Following the procedure as described in Synthetic Example 34 and making non-critical variations using piperidine in place of morpholine, the title compound. ((3aS,4R,5S,7aS)-7a-methyl-5-((5R,6S)-5-methyl-6-(piperidin-1-ylmethyl)-4,5,6,7-tetrahydro-1H-indazol-5-yl)-1-methyleneoctahydro-1H-inden-4-yl)methanamine (Compound Ia-78). was obtained.

LCMS: (Method 1c) MS m/z: 411.3 (M+1), $t_R$: 1.968 min, Purity: 98.238% (ELSD).

Synthetic Example 34.3

((3aS,4R,5S,7aS)-7a-methyl-5-((5R,6S)-5-methyl-6-(thiomorpholinomethyl)-4,5,6,7-tetrahydro-1H-indazol-5-yl)-1-methyleneoctahydro-1H-inden-4-yl)methanamine (Compound Ia-79)

Following the procedure as described in Synthetic Example 34 and making non-critical variations using thiomorpholine in place of morpholine, the title compound. ((3aS,4R,5S,7aS)-7a-methyl-5-((5R,6S)-5-methyl-6-(thiomorpholinomethyl)-4,5,6,7-tetrahydro-1H-indazol-5-yl)-1-methyleneoctahydro-1H-inden-4-yl)methanamine (Compound Ia-79). was obtained.

LCMS: (Method 1c) MS m/z: 429.3 (M+1), $t_R$: 1.949 min, Purity: 97.565% (ELSD).

Synthetic Example 35

Synthesis of (3aR,4R,5R,7aS)-7a-methyl-5-((5S,6S)-5-methyl-6-(morpholinomethyl)-4,5,6,7-tetrahydro-1H-indazol-5-yl)-1-methyleneoctahydro-1H-inden-4-ol (Compound Ia-80)

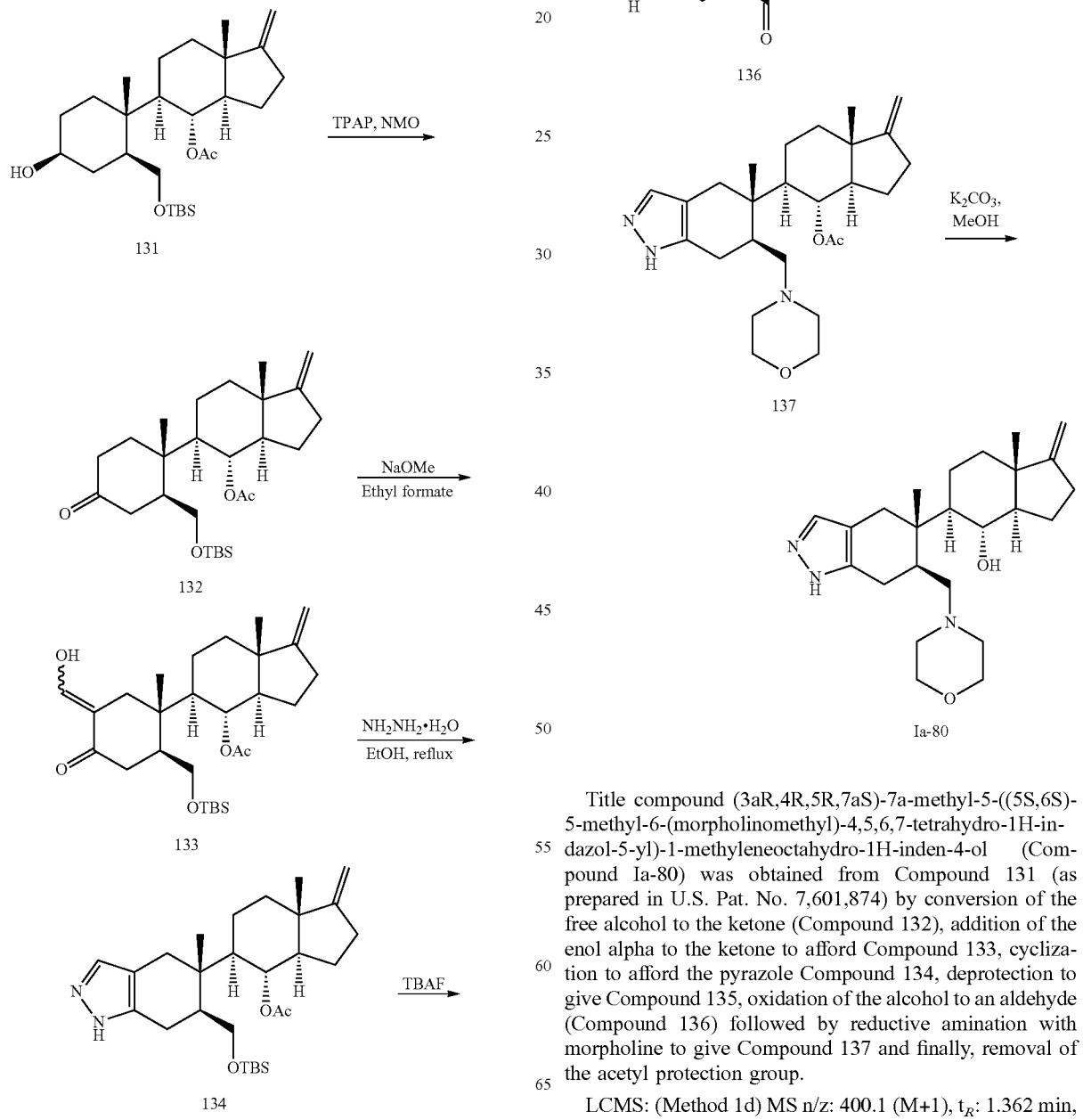

Title compound (3aR,4R,5R,7aS)-7a-methyl-5-((5S,6S)-5-methyl-6-(morpholinomethyl)-4,5,6,7-tetrahydro-1H-indazol-5-yl)-1-methyleneoctahydro-1H-inden-4-ol (Compound Ia-80) was obtained from Compound 131 (as prepared in U.S. Pat. No. 7,601,874) by conversion of the free alcohol to the ketone (Compound 132), addition of the enol alpha to the ketone to afford Compound 133, cyclization to afford the pyrazole Compound 134, deprotection to give Compound 135, oxidation of the alcohol to an aldehyde (Compound 136) followed by reductive amination with morpholine to give Compound 137 and finally, removal of the acetyl protection group.

LCMS: (Method 1d) MS n/z: 400.1 (M+1), $t_R$: 1.362 min, Purity: 99.65% (UV).

Synthetic Example 35.1

Synthesis of (3aR,4R,5R,7aS)-7a-methyl-5-((5S,6S)-5-methyl-6-((4-methylpiperazin-1-yl)methyl)-4,5,6,7-tetrahydro-1H-indazol-5-yl)-1-methyleneoctahydro-1H-inden-4-ol (Compound Ia-81)

Following the procedure as described in Synthetic Example 35 and making non-critical variations using 1-methylpiperazine in place of morpholine, the title compound (3aR,4R,5R,7aS)-7a-methyl-5-((S,6S)-5-methyl-6-((4-methylpiperazin-1-yl)methyl)-4,5,6,7-tetrahydro-1H-indazol-5-yl)-1-methyleneoctahydro-1H-inden-4-ol (Compound Ia-81) was obtained.

LCMS: (Method 1c) MS m/z: 413.3 (M+1), $t_R$: 1.983 min, Purity: 90.84% (UV).

Synthetic Example 36

Synthesis of (3aR,4R,5R,7aS)-5-((5S,6S)-6-(hydroxymethyl)-5-methyl-2-(pyridin-2-yl)-4,5,6,7-tetrahydro-2H-indazol-5-yl)-7a-methyl-1-methyleneoctahydro-1H-inden-4-ol Ia-83, and (3aR,4R,5R,7aS)-5-((5S,6S)-6-(hydroxymethyl)-5-methyl-2-(pyrazin-2-yl)-4,5,6,7-tetrahydro-2H-indazol-5-yl)-7a-methyl-1-methyleneoctahydro-1H-inden-4-ol Ia-84

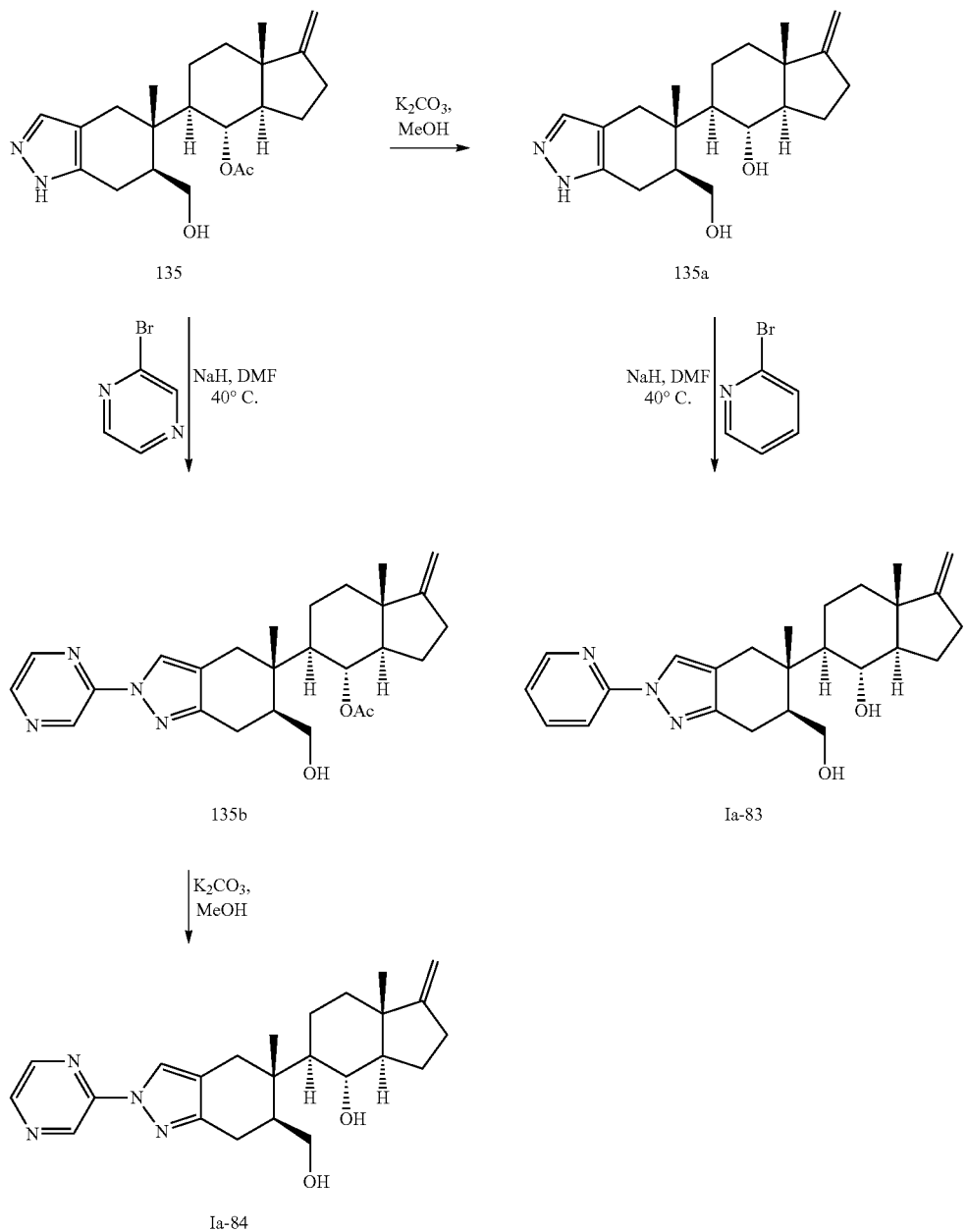

A. Title compound (3aR,4R,5R,7aS)-5-((5S,6S)-6-(hydroxymethyl)-5-methyl-2-(pyridin-2-yl)-4,5,6,7-tetrahydro-2H-indazol-5-yl)-7a-methyl-1-methyleneoctahydro-1H-inden-4-ol (Compound Ia-83) was obtained from Compound 135 (as prepared in Example 35) by deprotection using K₂CO in methanol followed by addition of 2-bromopyridine with sodium hydride in DMF, followed by preparative HPLC (Method 3e).

LCMS: (Method 1f) MS m/z: 408 (M+1), $t_R$: 2.48 min, Purity: 90.0% (UV).

HPLC: (Method 2a) $t_R$: 4.52 min, Purity: 88.9% (UV).

¹H-NMR (400 MHz, CD₃OD): δ 8.41-8.39 (m, 1H), 8.28 (s, 1H), 7.91-7.83 (m, 2H), 7.25 (s, 1H), 4.62 (s, 2H), 3.96 (d, J=10.6 Hz, 1H), 3.36 (t, J=10.2 Hz, 1H), 3.15-3.23 (m, 1H), 2.81-2.77 (m, 2H), 2.61-2.50 (m, 2H), 2.44 (d, J=15.8 Hz, 1H), 2.32-2.20 (m, 1H), 2.11-2.01 (m, 1H), 1.96-1.93 (m, 1H), 1.82-1.76 (m, 2H), 1.66-1.61 (m, 1H), 1.59-1.48 (m, 2H), 1.43-1.17 (m, 2H), 1.22 (s, 3H), 0.86 (s, 3H)

B. Title compound (3aR,4R,5R,7aS)-5-((5S,6S)-6-(hydroxymethyl)-5-methyl-2-(pyrazin-2-yl)-4,5,6,7-tetrahydro-2H-indazol-5-yl)-7a-methyl-1-methyleneoctahydro-1H-inden-4-ol (Compound Ia-84) was obtained from Compound 135 (as prepared in Example 35) by addition of 2-bromopyrazine with sodium hydride in DMF followed by deprotection using K₂CO in methanol, followed by column chromatography (silica gel 230-400 mesh, eluted with EtOAc/pet ether (52%)).

LCMS: (Method 1f) MS m/z: 409 (M+1), $t_R$: 2.32 min, Purity: 95.9% (UV).

HPLC: (Method 2a) $t_R$: 4.29 min, Purity: 94.8% (UV).

¹H-NMR (400 MHz, CD₃OD): δ 9.15 (s, 1H), 8.44 (s, 2H), 8.29 (s, 1H), 4.63 (s, 2H), 3.96 (dd, J=2.8, 10.6 Hz, 1H), 3.75 (t, J=4.8 Hz, 1H), 3.40 (t, J=10.3 Hz, 1H), 3.22 (dd, J=5.8, 17.6 Hz, 1H), 2.83-2.74 (m, 2H), 2.58-2.52 (m, 2H), 2.45 (d, J=16.2 Hz, 1H), 2.31-2.29 (m, 1H), 2.01-1.90 (m, 1H), 1.83-1.76 (m, 2H), 1.56-1.51 (m, 3H), 1.42-1.39 (m, 1H), 1.22 (s, 3H), 1.24-1.11 (m, 1H), 0.86 (s, 3H)

Synthetic Example 36.1

Synthesis of (3aR,4R,5R,7aS)-5-((5S,6S)-6-(hydroxynethyl)-5-methyl-2-(pyrimidin-2-yl)-4,5,6,7-tetrahydro-2H-indazol-5-yl)-7a-methyl-1-methyleneoctahydro-1H-inden-4-ol Ia-85

Following the procedure as described in Synthetic Example 36 for the synthesis of Compound Ia-85 and making non-critical variations using 2-chloropyrimidine in place of 2-bromopyridine, the title compound, (3aR,4R,5R,7aS)-5-((5S,6S)-6-(hydroxymethyl)-5-methyl-2-(pyrimidin-2-yl)-4,5,6,7-tetrahydro-2H-indazol-5-yl)-7a-methyl-1-methyleneoctahydro-1H-inden-4-ol (Compound Ia-85), was obtained.

LCMS: (Method 1f) MS m/z: 409 (M+1), $t_R$: 2.16 min, Purity: 89.5% (UV).

HPLC: (Method 2a) $t_R$: 5.18 min, Purity: 95.4% (UV).

¹H-NMR (400 MHz, CD₃OD): δ 8.76 (d, J=4.9 Hz, 2H), 8.37 (s, 1H), 7.32 (t, J=4.9 Hz, 1H), 4.62 (s, 2H), 3.95 (d, J=10.5 Hz, 1H), 3.75 (t, J=9.6 Hz, 1H), 3.40 (t, J=10.2 Hz, 1H), 3.23 (dd, J=5.9, 17.7 Hz, 1H), 2.78-2.75 (m, 2H), 2.59-2.52 (m, 2H), 2.45 (d, J=15.9 Hz, 1H), 2.33-2.24 (m, 1H), 1.98-1.92 (m, 1H), 1.82-1.76 (m, 2H), 1.59-1.51 (m, 3H), 1.43-1.31 (m, 1H), 1.29 (s, 3H), 1.23-1.11 (m, 1H), 0.85 (s, 3H).

Synthetic Example 37

Synthesis of ((3aS,4R,5S,7aS)-5-((5R,6S)-6-(aminomethyl)-5-methyl-4,5,6,7-tetrahydro-1H-indazol-5-yl)-7a-methyl-1-methyleneoctahydro-1H-inden-4-yl)methanol (Compound Ia-82)

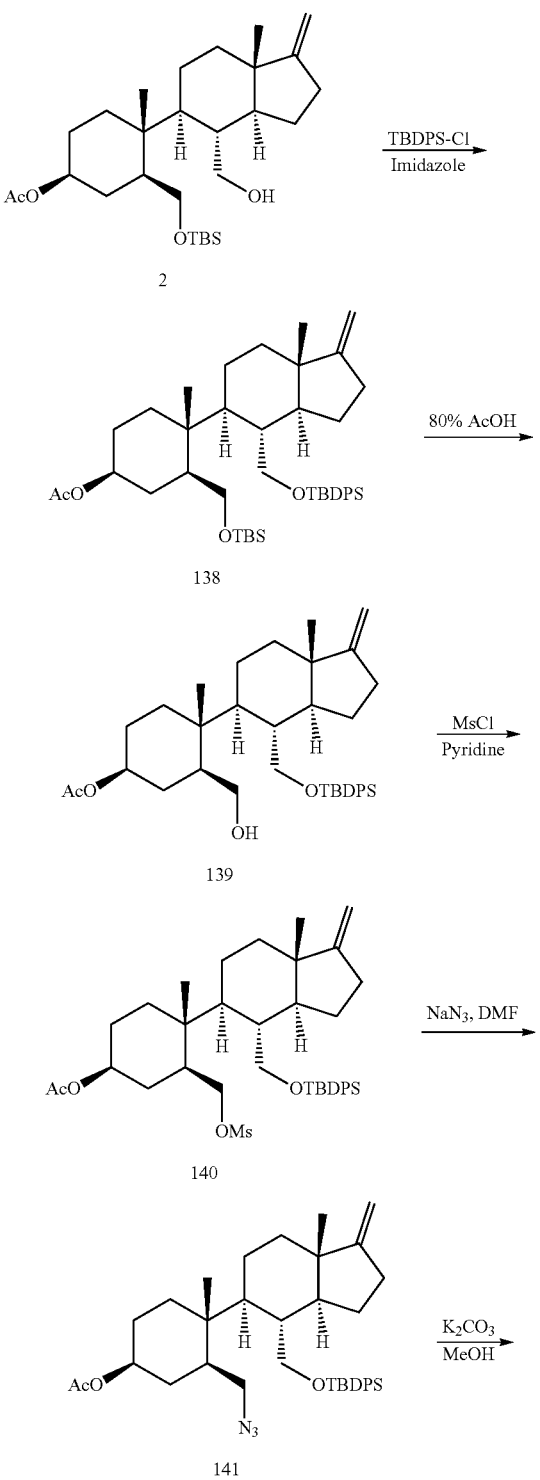

209

-continued

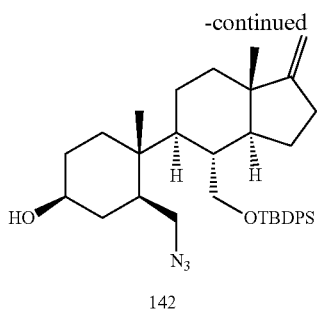

142

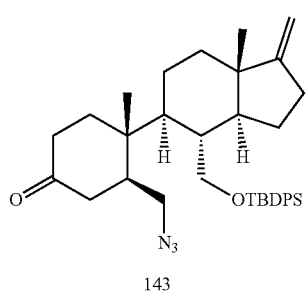

143

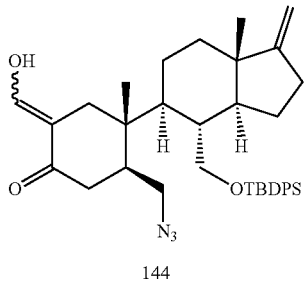

144

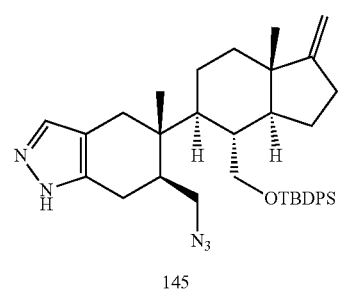

145

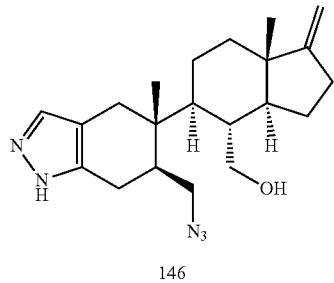

146

210

-continued

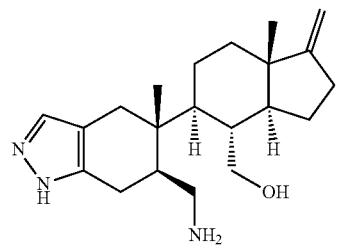

Ia-82

Title compound ((3aS,4R,5S,7aS)-5-((5R,6S)-6-(aminomethyl)-5-methyl-4,5,6,7-tetrahydro-1H-indazol-5-yl)-7a-methyl-1-methyleneoctahydro-1H-inden-4-yl)methanol (Compound Ia-82) was obtained by the scheme above.

LCMS: (Method 1h) MS m/z: 344.3 (M+1), $t_R$: 2.732 min, Purity: 92.409% (UV).

Synthetic Example 38

Synthesis of ((3aS,4R,5S,7aS)-5-((6R,7S)-7-(hydroxymethyl)-6-methyl-5,6,7,8-tetrahydroquinoxalin-6-yl)-7a-methyl-1-methyleneoctahydro-1H-inden-4-yl)methanol (Compound Ib-1)

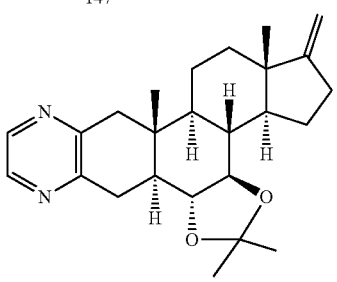

147

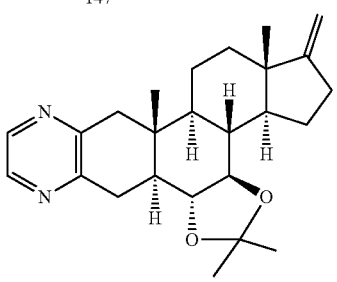

148

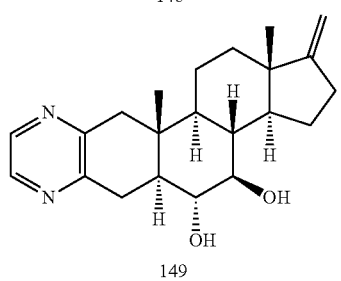

149

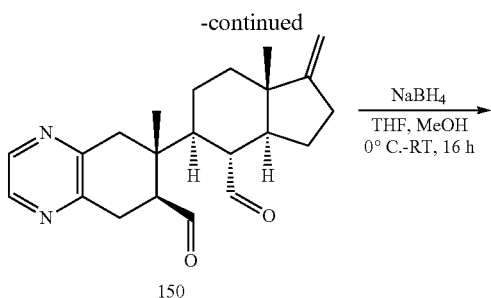

A. To a stirred solution of (4aR,4bS,6aS9aS,9bR,9cR,12aR,12bS)-4a,6a,11,11-tetramethyl-7-methylenehexadecahydro-2H-cyclopenta[1,2]phenanthro[9,10-d][1,3]dioxol-2-one (Compound 147, as prepared in U.S. Pat. No. 9,765,085, 10.0 g, 27.89 mmol) in morpholine (100 mL) were added sulphur (8.93 g, 278.92 mmol) and ethanediamine (16.76 g, 278.92 mmol). The reaction mixture was stirred at 130° C. for 16 hours. The mixture was diluted with ice cold water (1×100 mL) and the aqueous was extracted with EtOAc (2×100 mL) and washed with brine (1×100 mL). The organic layer was dried over Na₂SO₄, filtered and concentrated. The crude was purified by column chromatography on silica gel (60-120 mesh, 0-10% pet ether/ethyl acetate) to afford (3aS,3bR,3cR,6aR,6bS,12aR,12bS,14aS)-5,5,12a,14a-tetramethyl-1-methylene-2,3,3a,3b,3c,6a,6b,7,12,12a,12b,13,14,14a-tetradecahydro-1H-cyclopenta[5,6][1,3]dioxolo[4',5':3,4]naphth[1,2-g]quinoxaline (Compound 148, 4.08 g, 37%) as a yellow solid.

B. Using General Procedure E with Compound 148 (4.0 g, 10.14 mmol) in 80% AcOH (40 mL) gave the desired dialcohol, (3aS,3bR,4R,5R,5aS,11aR,11bS,13aS)-11a,13a-dimethyl-1-methylene-2,3,3a,3b,4,5,5a,6,11,11a,11b,12,13,13a-tetradecahydro-1H-cyclopenta[5,6]naphtho[1,2-g]quinoxaline-4,5-diol (Compound 149, 2.79 g, 78%), as an off-white solid after purification by column chromatography on silica gel (230-400 mesh, 0-5% dichloromethane/methanol).

LCMS: (Method Ie) MS m/z: 355.2 (M+1), $t_R$: 2.749 min, Purity: 96.92% (UV).

HPLC: (Method 2e) $t_R$: 6.616 min, Purity: 95.28% (UV).

¹H-NMR (400 MHz, CD₃OD): δ 8.39 (d, J=2.4 Hz, 2H), 4.69-4.68 (m, 2H), 3.41-3.35 (m, 2H), 3.19-3.14 (m, 1H), 3.02-2.98 (m, 1H), 2.80-2.65 (m, 2H), 2.56-2.49 (m, 1H), 2.31-2.23 (m, 1H), 2.18-2.11 (m, 1H), 1.95-1.60 (m, 6H), 1.33-1.28 (m, 3H), 0.87 (s, 6H).

C. Using General Procedure F with Compound 149 (275 g, 7.76 mmol), sodium metaperiodate (3.48 g, 16.29 mmol) and THF/water (4:1) (30 mL) gave the desired dialdehyde, (6S,7R)-7-((3aS,4R,5S,7aS)-4-formyl-7a-methyl-1-methyleneoctahydro-1H-inden-5-yl)-7-methyl-5,6,7,8-tetrahydroquinoxaline-6-carbaldehyde (Compound 150, 2.59 g, 95%), as a white solid after purification by column chromatography (230-400 silica mesh, eluted with 50-60% pet ether/ethyl acetate).

D. Using General Procedure G with Compound 150 (2.59 g, 7.35 mmol), sodium borohydride (5.84 g, 15.43 mmol) and THF/MeOH (1:1) (30 mL) gave the desired dialcohol, ((3aS,4R,5S,7aS)-5-((6R,7S)-7-(hydroxymethyl)-6-methyl-5,6,7,8-tetrahydroquinoxalin-6-yl)-7a-methyl-1-methyleneoctahydro-1H-inden-4-yl)methanol (Compound Ib-1, 2.18 g, 83%), as a white solid after purification by column chromatography (Neutral alumina, eluted with 0-5% methanol/dichloromethane).

LCMS: (Method Ie) MS m/z: 357.1 (M+1), $t_R$: 2.636 min, Purity: 98.31% (UV).

HPLC: (Method 2e) $t_R$: 5.759 min, Purity: 98.70% (UV).

¹H-NMR (400 MHz, CD₃OD): δ 8.40 (d, J=2.40 Hz, 1H), 8.37 (d, J=2.40 Hz, 1H), 4.63 (d, J=2.00 Hz, 2H), 4.07-4.04 (m, 1H), 4.00-3.97 (m, 1H), 3.76-3.72 (m, 1H), 3.49-3.43 (m, 2H), 3.17-3.08 (m, 3H), 3.00-2.93 (m, 1H), 2.80-2.76 (m, 1H), 2.56-2.50 (m, 1H), 2.45-2.39 (m, 1H), 2.33-2.24 (m, 1H), 1.90-1.36 (m, 7H), 1.17 (s, 3H), 0.87 (s, 3H).

Synthetic Example 39

Synthesis of ((6S,7R)-7-((3aS,4R,5S,7aS)-4-(aminomethyl)-7a-methyl-1-methyleneoctahydro-1H-inden-5-yl)-7-methyl-5,6,7,8-tetrahydroquinoxalin-6-yl)methanol (Compound Ib-2)

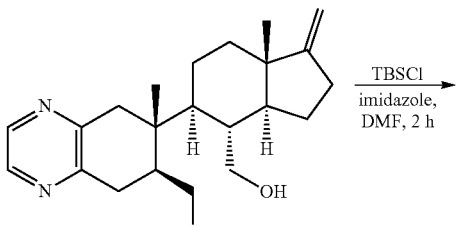

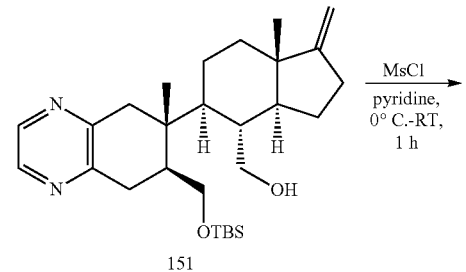

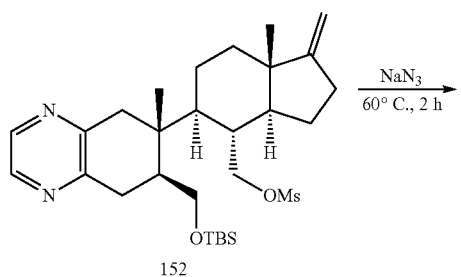

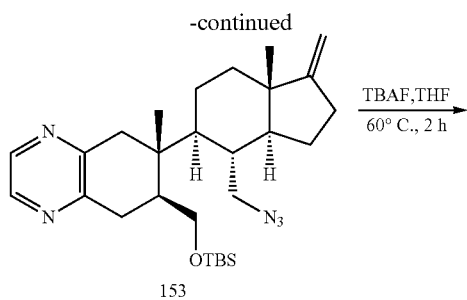

153

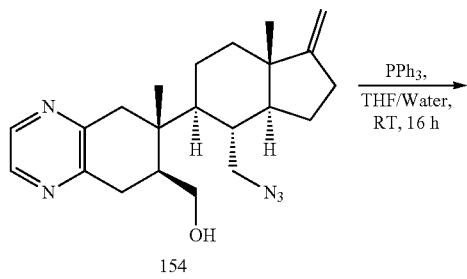

154

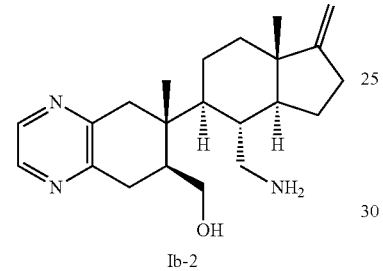

Ib-2

A. Using General Procedure B with Compound Ib-1 (from Example 38, 2.10 g, 5.89 mmol), imidazole (0.60 g, 8.84 mmol), TBSCl (1.07 g, 7.07 mmol) and DMF (20 mL) gave the desired silyl ether, ((3aS,4R,5S,7aS)-5-((6R,7S)-7-(((tert-butyldimethylsilyl)oxy)methyl)-6-methyl-5,6,7,8-tetrahydroquinoxalin-6-yl)-7a-methyl-1-methyleneoctahydro-1H-inden-4-yl)methanol (Compound 151, 2.39 g, 86%), as a white solid after purification by column chromatography on silica gel (230-400 mesh, 40-50% pet ether/ethyl acetate).

B. Using General Procedure J with Compound 151 (2.35 g, 5.00 mmol), MsCl (0.70 mL, 8.98 mmol) and pyridine (20 mL) gave the desired mesylate, ((3aS,4R,5S,7aS)-5-((6R,7S)-7-(((tert-butyldimethylsilyl)oxy)methyl)-6-methyl-5,6,7,8-tetrahydroquinoxalin-6-yl)-7a-methyl-1-methyleneoctahydro-1H-inden-4-yl)methyl methanesulfonate (Compound 152, 2.49 g, 91%), as a yellow gummy solid which was taken for next step without purification.

C. Using General Procedure K with Compound 152, 2.49 g, 4.54 mmol), sodium azide (0.44 g, 6.81 mmol) and DMF (25 mL), gave the desired azide, (6R,7S)-6-((3aS,4R,5S,7aS)-4-(azidomethyl)-7a-methyl-1-methyleneoctahydro-1H-inden-5-yl)-7-(((tert-butyldimethylsilyl)oxy)methyl)-6-methyl-5,6,7,8-tetrahydroquinoxaline (Compound 153, 1.69 g, 75%), as a white solid after purification by column chromatography (230-400 mesh silica gel, eluted with 25-30% pet ether/ethyl acetate).

D. Using General Procedure Q with Compound 153 (1.69 g, 3.41 mmol), TBAF solution (1M in THF, 6.82 mL, 6.82 mmol) and THF (17 mL) gave the desired alcohol, ((6S,7R)-7-((3aS,4R,5S,7aS)-4-(azidomethyl)-7a-methyl-1-methyleneoctahydro-1H-inden-5-yl)-7-methyl-5,6,7,8-tetrahydroquinoxalin-6-yl)methanol (Compound 154, 1.1 g, 85%), as brown gummy solid which was taken for next step without purification.

E. Using General Procedure R with Compound 154 (0.50 g, 1.31 mmol), triphenylphosphine (0.69 g, 2.62 mmol), water (0.5 mL) and THF (4.5 mL) gave the desired amine, ((6S,7R)-7-((3aS,4R,5S,7aS)-4-(aminomethyl)-7a-methyl-1-methyleneoctahydro-1H-inden-5-yl)-7-methyl-5,6,7,8-tetrahydroquinoxalin-6-yl)methanol (Compound Ib-2, 130 mg, 28%), as a white solid after purification by flash column chromatography (Neutral alumina, eluted with 0-10% dichloromethane/methanol).

LCMS: (Method Ie) MS m/z: 356.2 (M+1), $t_R$: 2.350 min, Purity: 91.25% (UV).

HPLC: (Method 2e) $t_R$: 4.827 min, Purity: 94.22% (UV).

$^1$H-NMR (400 MHz, CD$_3$OD): δ 8.40 (d, J=2.40 Hz, 1H), 8.39 (d, J=2.80 Hz, 1H), 4.66 (d, J=2.08 Hz, 2H), 4.00 (dd, J=2.88, 10.86 Hz, 1H), 3.49-3.38 (m, 2H), 3.22-3.08 (m, 2H), 2.96-2.78 (m, 3H), 2.59-2.52 (m, 1H), 2.37-2.30 (m, 2H), 1.95-1.84 (m, 3H), 1.79-1.59 (m, 3H), 1.54-1.41 (m, 2H), 1.31-1.24 (m, 1H), 1.14 (s, 3H), 0.89 (s, 3H).

Synthetic Example 40

Synthesis of ((1R,3aS,4S,5S,7aR)-5-((6R,7S)-7-(hydroxymethyl)-6-methyl-5,6,7,8-tetrahydroquinoxalin-6-yl)-7a-methyl-1-((R)-6-methylheptan-2-yl)octahydro-1H-inden-4-yl)methanol (Compound Ib-3)

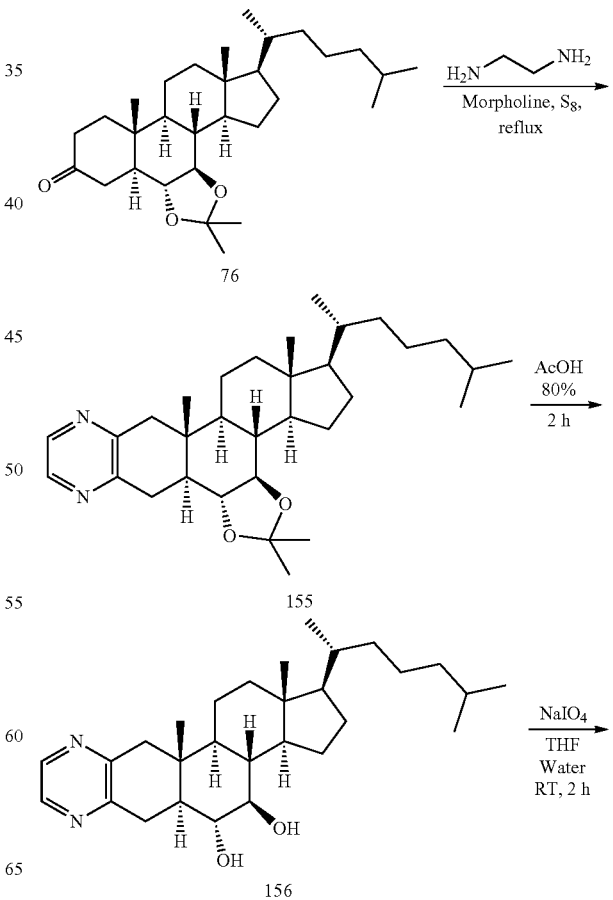

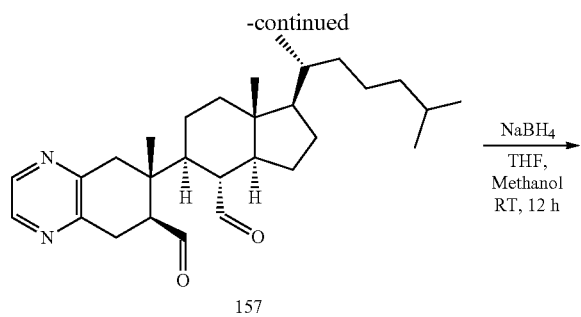

157

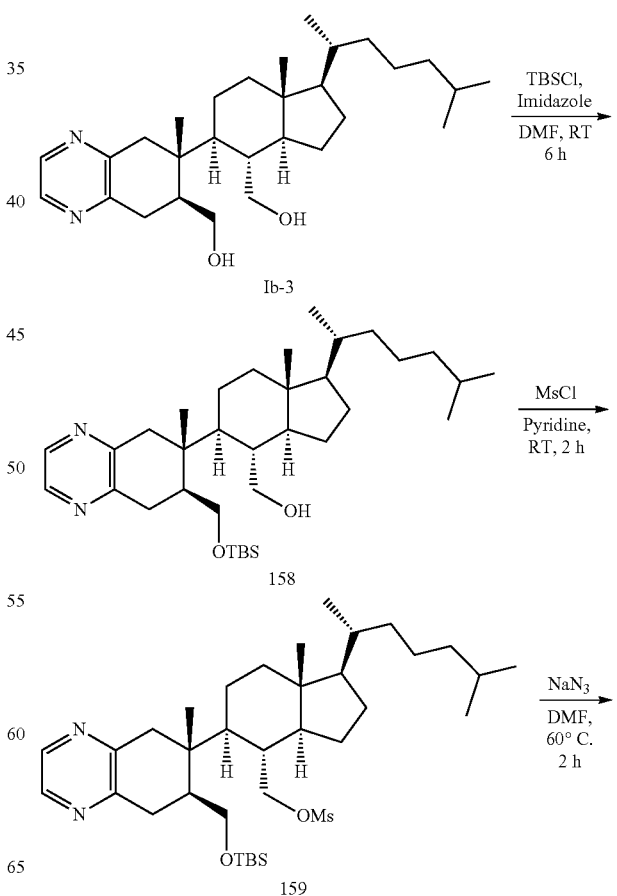

A. To a stirred solution of Compound 76 (from Example 20, 5.0 g, 10.90 mmol) in morpholine (50 mL) were added sulphur (3.49 g, 108.99 mmol) and ethanediamine (1.97 g, 32.70 mmol). The reaction mixture was stirred at 130° C. for 24 hours. The mixture was diluted with ice cold water (1×50 mL) and the aqueous was extracted with EtOAc (2×50 mL) and washed with brine (1×50 mL). The organic layer was dried over $Na_2SO_4$, filtered and concentrated. The crude was purified by column chromatography on silica gel (230-400 mesh, 0-10% pet ether/ethyl acetate) to afford (1R,3aS,3bS,3cR,6aR,6bS,12aR,12bS,14aR)-5,5,12a,14a-tetramethyl-1-((R)-6-methylheptan-2-yl)-2,3,3a,3b,3c,6a,6b,7,12,12a,12b,13,14,14a-tetradecahydro-1H-cyclopenta[5,6][1,3]dioxol[4',5':3,4]naphth[1,2-g]quinoxaline (Compound 155, 2.0 g, 37%) as a yellow solid.

B. Using General Procedure E with Compound 155, 2.0 g, 4.04 mmol) in AcOH (80%, 20 mL) gave the desired dialcohol, (1R,3aS,3bS,4R,5R,5aS,11aR,11b S,13aR)-11a,13a-dimethyl-1-((R)-6-methylheptan-2-yl)-2,3,3a,3b,4,5,5a,6,11,11a,11b,12,13,13a-tetradecahydro-1H-cyclopenta[5,6]naphtho[1,2-g]quinoxaline-4,5-diol (Compound 156, 1.6 g, 88%), as an off-white solid after purification by column chromatography (230-400 mesh silica gel, eluted with 5-10% methanol/dichloromethane).

LCMS: (Method 1f MS m/z: 455.3 (M+1), $t_R$: 2.577 min, Purity: 99.94% (ELSD).

HPLC: (Method 2b) $t_R$: 18.463 min, Purity: 96.86% (UV).

$^1$H-NMR (400 MHz, $CD_3OD$): δ 8.40-8.39 (m, 2H), 3.40-3.39 (m, 1H), 3.15-3.10 (m, 1H), 3.00-2.95 (m, 1H), 2.69-2.64 (m, 2H), 2.15-2.10 (m 1H), 2.09-1.97 (m 1H), 1.93-1.84 (m 1H), 1.77-1.69 (m, 2H), 1.62-1.51 (m, 4H), 1.43-1.41 (m, 3H), 1.32-1.07 (m, 10H), 1.00-0.99 (m, 3H), 0.92-0.88 (m, 9H), 0.78 (s, 3H).

C. Using General Procedure F with Compound 156 (1.6 g, 3.52 mmol), sodium metaperiodate (1.51 g, 7.04 mmol) and THF:water (4:1, 15 mL) gave the desired dialdehyde, (6S,7R)-7-((1R,3aS,4S,5S,7aR)-4-formyl-7a-methyl-1-((R)-6-methylheptan-2-yl)octahydro-1H-inden-5-yl)-7-methyl-5,6,7,8-tetrahydroquinoxaline-6-carbaldehyde (Compound 157, 1.2 g, 75%), as an off white solid after purification by column chromatography (230-400 mesh silica gel, eluted with 50-60% pet ether/ethyl acetate).

D. Using General Procedure G with Compound 157 (1.2 g, 2.65 mmol), sodium borohydride (0.20 g, 5.29 mmol) and THF:MeOH (1:1, 20 mL) gave the desired dialcohol, ((1R,3aS,4S,5S,7aR)-5-((6R,7S)-7-(hydroxymethyl)-6-methyl-5,6,7,8-tetrahydroquinoxalin-6-yl)-7a-methyl-1-((R)-6-methylheptan-2-yl)octahydro-1H-inden-4-yl)methanol (Compound Ib-3, 0.84 g, 69%), as an off white solid after purification by column chromatography (Neutral alumina, eluted with 10% dichloromethane/methanol).

LCMS: (Method 1d) MS m/z: 457.4 (M+1), $t_R$: 2.948 min Purity: 89.11% (UV).

HPLC: (Method 2a) $t_R$: 5.998 min, Purity: 99.79% (UV).

$^1$H-NMR (400 MHz, $CD_3OD$): δ 8.39 (d, J=2.6 Hz, 1H), 8.37 (d, J=2.6 Hz, 1H), 4.03-3.96 (m, 2H), 3.69-3.67 (m, 1H), 3.48-3.42 (m, 2H), 3.10-2.92 (m, 2H), 278-2.74 (m, 1H), 2.43-2.36 (m, 1H), 2.03-1.79 (m, 3H), 1.73-1.63 (m, 2H), 1.60-1.47 (m, 4H), 1.45-1.36 (m, 3H), 1.33-1.28 (m, 1H), 1.26-1.13 (m, 9H), 1.10-1.00 (m, 1H), 095-0.89 (m, 9H), 0.77 (s, 3H).

Synthetic Example 41

Synthesis of ((6S,7R)-7-((1R,3aS,4S,5S,7aR)-4-(aminomethyl)-7a-methyl-1-((R)-6-methylheptan-2-yl)octahydro-1H-inden-5-yl)-7-methyl-5,6,7,8-tetrahydroquinoxalin-6-yl)methanol (Compound Ib-4)

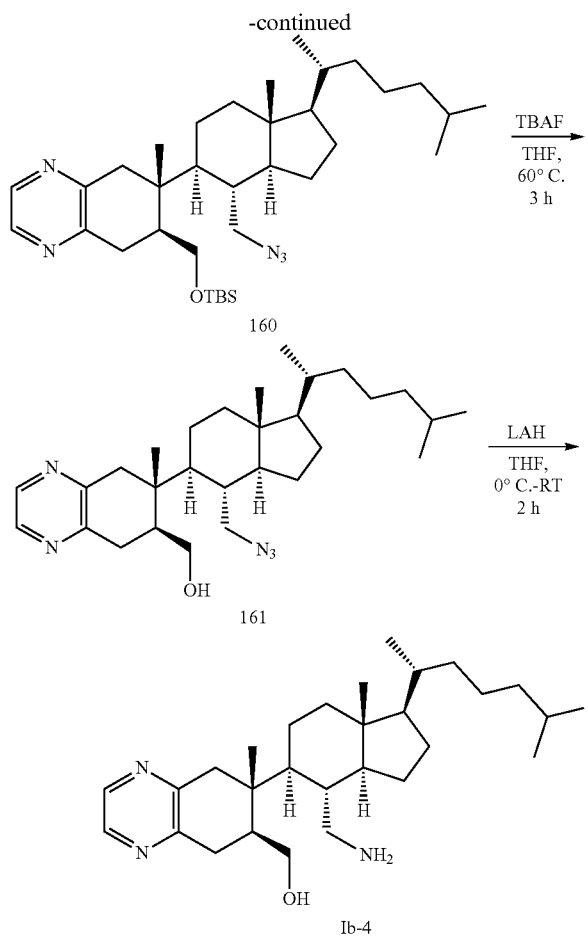

mmol) and THF (6 mL), gave the desired alcohol, ((6S,7R)-7-((1R,3aS,4S,5S,7aR)-4-(azidomethyl)-7a-methyl-1-((R)-6-methylheptan-2-yl)octahydro-1H-inden-5-yl)-7-methyl-5,6,7,8-tetrahydroquinoxalin-6-yl)methanol (Compound 161, 0.31 g, 64%), as an off white solid after purification by column chromatography (230-400 mesh silica gel, eluted with 50-60% pet ether/ethyl acetate).

E. Using General Procedure S with Compound 161, (0.31 g, 0.64 mmol), LAH (2M in THF) (0.64 mL, 1.29 mmol) and THF (5 mL), gave the desired alcohol, ((6S,7R)-7-((1R,3aS,4S,5S,7aR)-4-(aminomethyl)-7a-methyl-1-((R)-6-methylheptan-2-yl)octahydro-1H-inden-5-yl)-7-methyl-5,6,7,8-tetrahydroquinoxalin-6-yl)methanol (Compound Ib-4, 30 mg, 10%), as an off white solid after purification by preparative HPLC (Method 3a).

LCMS: (Method 1h) MS m/z: 456.3 (M+1), $t_R$: 2.079 min, Purity: 90.64% (UV).

HPLC: (Method 2a) $t_R$: 4.742 min, Purity: 97.15% (UV).

$^1$H-NMR (400 MHz, CD$_3$OD): δ 8.38 (m, 2H), 3.97 (m, 1H), 3.47-3.36 (m, 2H), 3.19-3.05 (m, 2H), 2.94-2.87 (m, 1H), 2.81-2.74 (m, 2H), 2.28-2.02 (m, 3H), 1.93-1.67 (m, 5H), 1.56-1.46 (m, 3H), 1.32-1.03 (m, 11H), 0.96-0.89 (m, 11H), 0.78 (s, 3H).

Synthetic Example 42

Synthesis of ((6R,7S)-2-amino-6-((3aS,4R,5S,7aS)-4-(aminomethyl)-7a-methyl-1-methyleneoctahydro-1H-inden-5-yl)-6-methyl-5,6,7,8-tetrahydroquinazolin-7-yl)methanol (Compound Ic-1)

A. Using General Procedure B with Compound Ib-3 (as prepared in Example 40, 0.79 g, 1.73 mmol), imidazole (0.35 g, 5.14 mmol), TBSCl (0.31 g, 2.06 mmol) and DMF (10 mL) gave the desired silyl ether, ((1R,3aS,4S,5S,7aR)-5-((6R,7S)-7-(((tert-butyldimethylsilyl)oxy)methyl)-6-methyl-5,6,7,8-tetrahydroquinoxalin-6-yl)-7a-methyl-1-((R)-6-methylheptan-2-yl)octahydro-1H-inden-4-yl)methanol (Compound 158, 0.65 g, 66%), as a white solid after purification by column chromatography on silica gel (230-400 mesh, 40-50% pet ether/ethyl acetate).

B. Using General Procedure J with Compound 158 (0.65 g, 1.14 mmol), MsCl (0.18 mL, 2.33 mmol) and pyridine (5 mL) gave the desired mesylate, ((1R,3aS,4S,5S,7aR)-5-((6R,7S)-7-(((tert-butyldimethylsilyl)oxy)methyl)-6-methyl-5,6,7,8-tetrahydroquinoxalin-6-yl)-7a-methyl-1-((R)-6-methylheptan-2-yl)octahydro-1H-inden-4-yl)methyl methanesulfonate (Compound 159, 0.70 g, 95%), as an off white solid after purification by column chromatography on silica gel (230-400 mesh, 40-45% pet ether/ethyl acetate).

C. Using General Procedure K with Compound 159 (0.70 g, 1.08 mmol), sodium azide (0.14 g, 2.16 mmol) and DMF (7 mL), gave the desired azide, (6R,7S)-6-((1R,3aS,4S,5S,7aR)-4-(azidomethyl)-7a-methyl-1-((R)-6-methylheptan-2-yl)octahydro-1H-inden-5-yl)-7-(((tert-butyldimethylsilyl)oxy)methyl)-6-methyl-5,6,7,8-tetrahydroquinoxaline (Compound 160, 0.60 g, 93%), as a white solid after purification by column chromatography (230-400 mesh silica gel, eluted with 25-30% pet ether/ethyl acetate).

D. Following the General Procedure Q with Compound 160 (0.60 g, 1.01 mmol), TBAF (1M in THF, 3.12 mL, 3.12

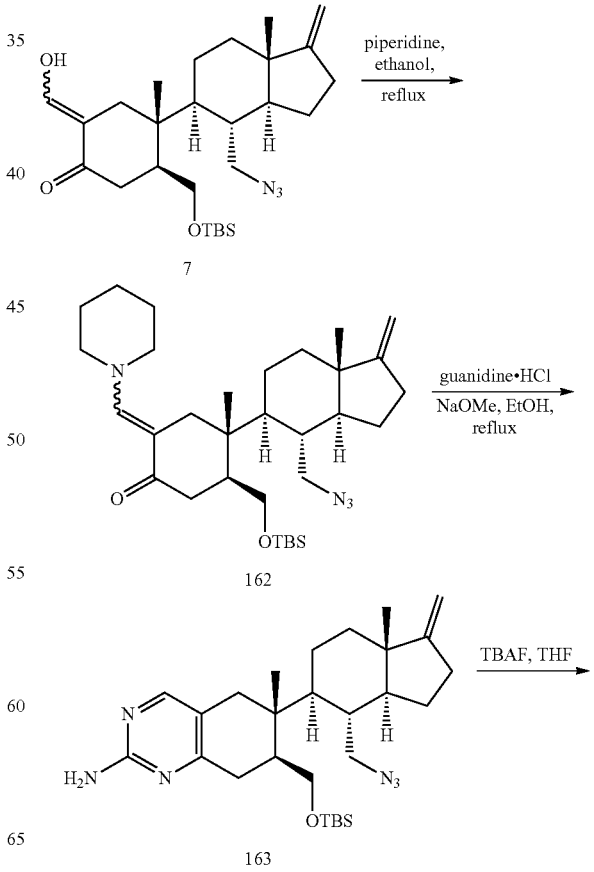

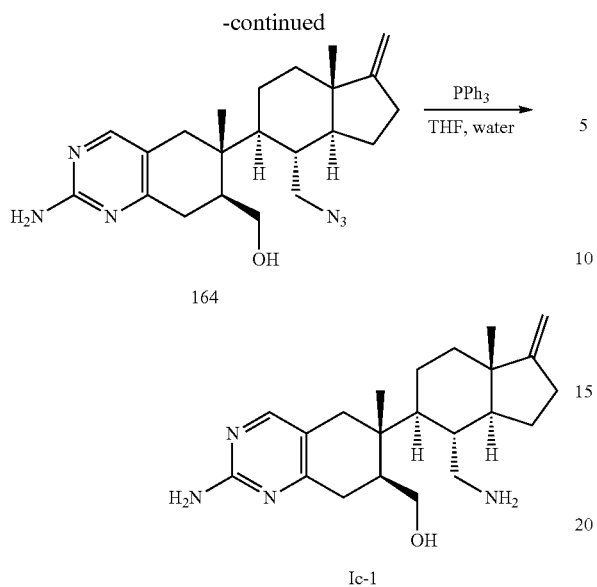

A. To a stirred solution of Compound 7 (from Example 1, 1.3 g, 2.66 mmol) in ethanol (10 mL) was added piperidine (0.3 mL, 2.93 mmol) at room temperature. The resultant solution was stirred at 90° C. for 0.5 hour. The reaction mixture was evaporated under reduced pressure to give the desired ketone, (4R,5S)-4-((3aS,4R,5S,7aS)-4-(azidomethyl)-7a-methyl-1-methyleneoctahydro-1H-inden-5-yl)-5-(((tert-butyldimethylsilyl)oxy)methyl)-4-methyl-2-(piperidin-1-ylmethylene)cyclohexan-1-one (Compound 162, 1.3 g, 88%), as a brown gummy solid which was used in the next step without purification.

B. To a stirred solution of sodium methoxide (0.13 g, 2.34 mmol) and guanidine hydrochloride (0.12 g, 1.29 mmol) in ethanol (5 mL) was added Compound 162 (0.65 g, 1.17 mmol) in ethanol (5 mL) dropwise at room temperature. The resultant solution was stirred at 90° C. for 12 hours. The reaction mixture was evaporated under reduced pressure and the residue was diluted with ethyl acetate (2×10 mL). Organic layer was washed consecutively with water (1×10 mL) and brine (1×10 mL), dried over sodium sulphate, filtered and concentrated to give the desired pyrimidine, (6R,7S)-6-((3aS,4R,5S,7aS)-4-(azidomethyl)-7a-methyl-1-methyleneoctahydro-1H-inden-5-yl)-7-(((tert-butyldimethylsilyl)oxy)methyl)-6-methyl-5,6,7,8-tetrahydroquinazolin-2-amine (Compound 163, 0.59 g, 99%), as a brown gummy solid which was used in the next step without purification.

C. Following the General Procedure Q with Compound 163, 0.60 g, 1.17 mmol), TBAF (1M in THF, 2.35 mL, 2.35 mmol) and THF (10 mL), gave the desired alcohol, ((6R,7S)-2-amino-6-((3aS,4R,5S,7aS)-4-(azidomethyl)-7a-methyl-1-methyleneoctahydro-1H-inden-5-yl)-6-methyl-5,6,7,8-tetrahydroquinazolin-7-yl)methanol (Compound 164, 0.45 g, 97%), as a brown gummy solid which was used in the next step without purification.

D. Using General Procedure R with Compound 164 (0.45 g, 1.13 mmol), triphenyl phosphine (0.59 g, 2.27 mmol) and THF:water (9:1, 5 mL) gave the desired amine, ((6R,7S)-2-amino-6-((3aS,4R,5S,7aS)-4-(aminomethyl)-7a-methyl-1-methyleneoctahydro-1H-inden-5-yl)-6-methyl-5,6,7,8-tetrahydroquinazolin-7-yl)methanol (Compound Ic-1, 150 mg, 36%), as an off white solid after purification by preparative HPLC (Method 3c).

LCMS: (Method Ie) MS m/z: 371.2 (M+1), $t_R$: 2.173 min, Purity: 92.94% (UV).

HPLC: (Method 2b) $t_R$: 4.035 min, Purity: 95.09% (UV).

$^1$H-NMR (400 MHz, CD$_3$OD): δ 8.03 (s, 1H), 4.69 (s, 2H), 3.92 (dd, J=2.68, 10.86 Hz, 1H), 3.46-3.35 (m, 2H), 3.13-3.05 (m, 2H), 2.77-2.73 (m, 1H), 2.63-2.56 (m, 2H), 2.46-2.30 (m, 2H), 2.24-2.18 (m, 1H), 2.02-1.86 (m, 4H), 1.73-1.45 (m, 3H), 1.42-1.22 (m, 2H), 1.04 (s, 3H), 0.90 (s, 3H).

Synthetic Example 42.1

Synthesis of ((6R,7S)-6-((3aS,4R,5S,7aS)-4-(aminomethyl)-7a-methyl-1-methyleneoctahydro-1H-inden-5-yl)-2,6-dimethyl-5,6,7,8-tetrahydroquinazolin-7-yl)methanol (Compound Ic-2)

Following the procedure as described in Synthetic Example 42 and making non-critical variations using acetamidine.HCl to replace guanidine.HCl, the title compound, ((6R,7S)-6-((3aS,4R,5S,7aS)-4-(aminomethyl)-7a-methyl-1-methyleneoctahydro-1H-inden-5-yl)-2,6-dimethyl-5,6,7,8-tetrahydroquinazolin-7-yl)methanol (Compound Ib-2, 70 mg, 26%), was obtained as an off white solid after purification by preparative HPLC (Method 3c).

LCMS: (Method Ie) MS m/z: 370.2 (M+1), $t_R$: 2.262 min, Purity: 97.56% (UV).

HPLC: (Method 2b) $t_R$: 4.143 min, Purity: 99.48% (UV).

$^1$H-NMR (400 MHz, CD$_3$OD): δ 8.41 (s, 1H), 4.66 (s, 2H), 3.98 (dd, J=2.80, 1080 Hz, 1H), 3.45-3.40 (m, 1H), 3.28-3.19 (m, 2H), 2.91-2.80 (m, 3H), 2.64-2.60 (m, 5H), 2.35-2.27 (m, 2H), 1.91-1.85 (m, 3H), 1.78-1.60 (m, 3H), 1.49-1.27 (m, 3H), 1.08 (s, 3H), 0.89 (s, 3H).

Synthetic Example 42.2

Synthesis of ((6R,7S)-6-((3aS,4R,5S,7aS)-4-(aminomethyl)-7a-methyl-1-methyleneoctahydro-1H-inden-5-yl)-6-methyl-5,6,7,8-tetrahydroquinazolin-7-yl)methanol (Compound Ic-3)

Following the procedure as described in Synthetic Example 42 and making non-critical variations using formamidine.HCl to replace guanidine-HCl, the title compound, ((6R,7S)-6-((3aS,4R,5S,7aS)-4-(aminomethyl)-7a-methyl-1-methyleneoctahydro-1H-inden-5-yl)-6-methyl-5,6,7,8-tetrahydroquinazolin-7-yl)methanol (Compound Ic-3, 15 mg, 4%), was obtained as an off white solid after purification by preparative HPLC (Method 3c).

LCMS: (Method Ie) MS m/z: 356.2 (M+1), $t_R$: 2.242 min, Purity: 97.18% (UV).

HPLC: (Method 2e) $t_R$: 4.680 min, Purity: 95.76% (UV).

$^1$H-NMR (400 MHz, CD$_3$OD): δ 8.87 (s, 1H), 8.52 (s, 1H), 4.65 (s, 2H), 3.97 (dd, J=2.96, 10.84 Hz, 1H), 3.45-3.40 (m, 1H), 3.23-3.19 (m, 1H), 2.96-2.84 (m, 3H), 2.69-2.64 (m, 1H), 2.31-2.28 (m, 2H), 1.89-1.84 (m, 3H), 1.70-1.64 (m, 4H), 1.48-1.27 (m, 4H), 1.08 (s, 3H), 0.85 (s, 3H).

Synthetic Example 43

Synthesis of (((1R,3aS,4S,5S,7aR)-5-((6R,7S)-7-(hydroxymethyl)-2,6-dimethyl-5,6,7,8-tetrahydroquinazolin-6-yl)-7a-methyl-1-((R)-6-methylheptan-2-yl)octahydro-1H-inden-4-yl)methanol (Compound Ic-4)

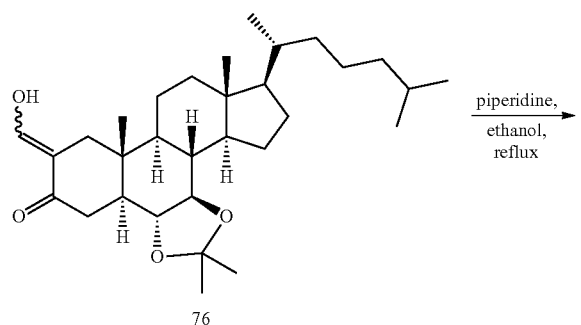

76

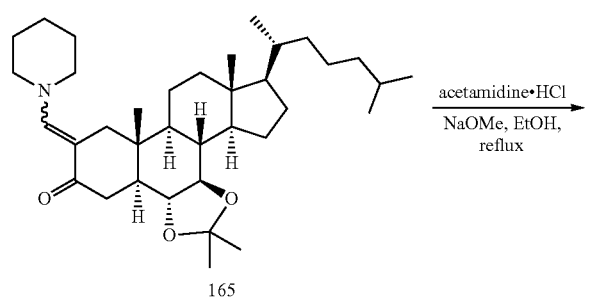

165

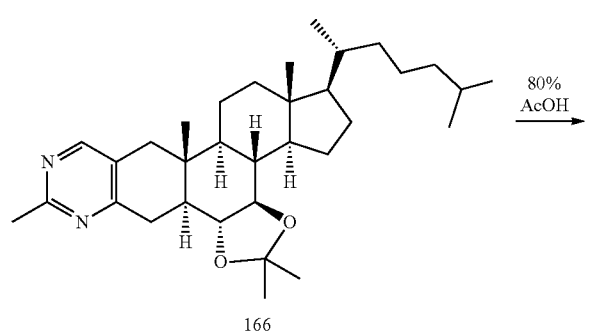

166

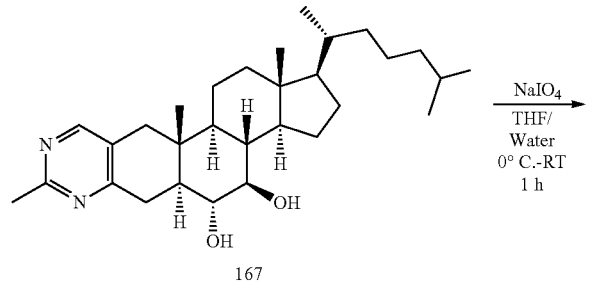

167

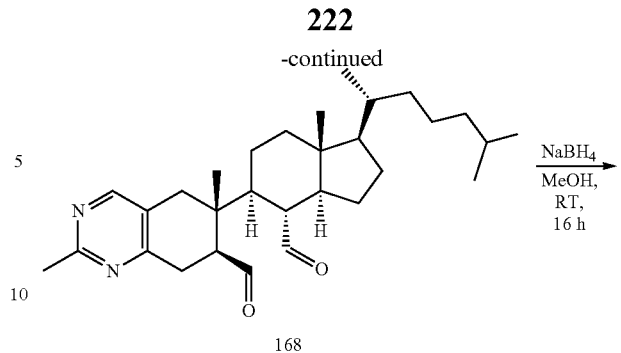

168

Ic-4

A. To a stirred solution of Compound 76 (from Example 20, 6 g, 12.37 mmol) in EtOH (60 mL) was added at room temperature piperidine (1.46 mL, 14.79 mmol) dropwise. The resultant solution was stirred at 90° C. for 2 hours. The mixture was evaporated under reduced pressure to afford the desired ketone, (4aR,4bS,6aR,7R,9aS,9bS,9cR,12aR,12bS)-4a,6a,11,11-tetramethyl-7-((R)-6-methylheptan-2-yl)-3-(piperidin-1-ylmethylene)hexadecahydro-2H-cyclopenta[1,2]phenanthro[9,10-d][1,3]dixol-2-one (Compound 165, 6.1 g, 89%), as a brown gummy solid which was taken for next step without purification.

B. To a stirred solution of sodium methoxide (0.66 g, 12.22 mmol) and acetamidine HCl (0.58 g, 6.14 mmol) in EtOH (10 mL) was added at room temperature Compound 165 (3.4 g, 6.13 mmol) in EtOH (25 mL) dropwise. The reaction mixture was stirred at 90° C. for 12 hours. The mixture was evaporated under reduced pressure and the residue was diluted with EtOAc (2×30 mL) and washed consecutively with water (1×30 mL) and brine (1×30 mL). The organic layer was dried over $Na_2SO_4$, filtered and concentrated. The crude was purified by column chromatography on silica gel (230-400 mesh, 30-40% pet ether/ethyl acetate) to afford (1R,3aS,3bS,3cR,6aR,6bS,12aR,12bS,14aR)-5,5,9,12a,14a-pentamethyl-1-((R)-6-methylheptan-2-yl)-2,3,3a,3b,3c,6a,6b,7,12,12a,12b,13,14,14a-tetradecahydro-1H-cyclopenta[5,6][1,3]dioxolo[4',5':3,4]naphtho[1,2-g]quinazoline (Compound 166, 2.6 g, 83%) as an off-white solid.

C. Using General Procedure E with Compound 166 (2.6 g, 5.11 mmol) in AcOH (80%, 25 mL), gave the desired dialcohol, (1R,3aS,3bS,4R,5R,5aS,11aR,11bS,13aR)-8,11a,13a-trimethyl-1-((R)-6-methylheptan-2-yl)-2,3,3a,3b,4,5,5a,6,11,11a,11b,12,13,13a-tetradecahydro-1H-cyclopenta[5,6]naphtho[1,2-g]quinazoline-4,5-diol (Compound 167, 2.2 g, 92%), as an off-white solid after purification by column chromatography on silica gel (230-400 mesh, 0-10% dichloromethane/methanol).

LCMS: (Method 1d) MS m/z: 469.4 (M+1), $t_R$: 2.584 min, Purity: 97.92% (ELSD).

HPLC: (Method 2a) $t_R$: 5.383 min, Purity: 93.51% (UV).

¹H-NMR (400 MHz, CD₃OD): δ 8.38 (s, 1H), 3.34-3.10 (m, 3H), 2.85-2.81 (m, 1H), 2.63 (s, 3H), 2.44-2.40 (m, 1H), 2.14-1.65 (m, 5H), 1.60-1.41 (m, 7H), 1.31-1.06 (m, 10H), 1.02-0.98 (m, 3H), 0.92-0.90 (m, 6H), 0.82 (s, 3H), 0.77 (s, 3H).

D. Using General Procedure F with Compound 167 (2.0 g, 4.27 mmol), sodium metaperiodate (1.92 g, 8.96 mmol) and THF/water (4:1) (20 mL) gave the desired dialdehyde, (6R,7S)-6-((1R,3aS,4S,5S,7aR)-4-formyl-7a-methyl-1-((R)-6-methylheptan-2-yl)octahydro-1H-inden-5-yl)-2,6-dimethyl-5,6,7,8-tetrahydroquinazoline-7-carbaldehyde (Compound 168, 1.98 g, 99%), as a white solid which was used in the next step without purification.

E. Using General Procedure G with Compound 168 (1.98 g, 4.24 mmol), sodium borohydride (0.66 g, 17.39 mmol) and MeOH (20 mL) gave the desired dialcohol, ((1R,3aS,4S,5S,7aR)-5-((6R,7S)-7-(hydroxymethyl)-2,6-dimethyl-5,6,7,8-tetrahydroquinazolin-6-yl)-7a-methyl-1-((R)-6-methylheptan-2-yl)octahydro-1H-inden-4-yl)methanol (Compound Ic-4, 1.80 g, 90%), as a white solid after purification by column chromatography (Neutral alumina, eluted with 0-10% dichloromethane/methanol).

LCMS: (Method Ie) MS m/z: 471.4 (M+1), $t_R$: 4.139 min, Purity: 92.39% (UV).

HPLC: (Method 2b) $t_R$: 8.411 min, Purity: 98.57% (UV).
¹H-NMR (400 MHz, CD₃OD): δ 8.37 (s, 1H), 4.02-3.95 (m, 2H), 3.68-3.66 (m, 1H), 3.42-3.40 (m, 1H), 2.88-2.83 (m, 1H), 2.63-2.53 (m, 4H), 2.39-2.32 (m, 1H), 2.01-1.91 (m, 3H), 1.65-1.50 (m, 6H), 1.42-1.31 (m, 5H), 1.24-1.02 (m, 10H), 0.95-0.89 (m, 10H), 0.76 (s, 3H).

Synthetic Example 43.0.1

Synthesis of ((6R,7S)-6-((1R,3aS,4S,5S,7aR)-4-(aminomethyl)-7a-methyl-1-((R)-6-methylheptan-2-yl)octahydro-1H-inden-5-yl)-2,6-dimethyl-5,6,7,8-tetrahydroquinazolin-7-yl)methanol (Compound Ic-5)

Following the procedure as described in Synthetic Example 26 and making non-critical variations using Ic-4 to replace Ia-62, the title compound, ((6R,7S)-6-((1R,3aS,4S,5S,7aR)-4-(aminomethyl)-7a-methyl-1-((R)-6-methylheptan-2-yl)octahydro-1H-inden-5-yl)-2,6-dimethyl-5,6,7,8-tetrahydroquinazolin-7-yl)methanol (Compound Ic-5), was obtained.

LCMS: (Method 1d) MS m/z: 470.4 (M+1), $t_R$: 1.848 min, Purity: 98.37% (UV).

Synthetic Example 43.1

Synthesis of ((6R,7S)-2-amino-6-((1R,3aS,4S,5S,7aR)-4-(hydroxymethyl)-7a-methyl-1-((R)-6-methylheptan-2-yl)octahydro-1H-inden-5-yl)-6-methyl-5,6,7,8-tetrahydroquinazolin-7-yl)methanol (Compound 1c-6)

Following the procedure as described in Synthetic Example 43 and making non-critical variations using guanidine HCl to replace acetamidine-HCl, the title compound, ((6R,7S)-2-amino-6-((1R,3aS,4S,5S,7aR)-4-(hydroxymethyl)-7a-methyl-1-((R)-6-methylheptan-2-yl)octahydro-1H-inden-5-yl)-6-methyl-5,6,7,8-tetrahydroquinazolin-7-yl)methanol (Compound Ic-6, 70 mg, 18%), was obtained as an off white solid after purification by preparative HPLC (Method 3a).

LCMS: (Method 1g) MS m/z: 472.4 (M+1), $t_R$: 7.099 min, Purity: 96.35% (UV).

HPLC: (Method 2e) $t_R$: 7.282 min, Purity: 98.25% (UV).
¹H-NMR (400 MHz, CD₃OD): δ 7.97 (s, 1H), 4.00-3.91 (m, 2H), 3.66-3.63 (m, 1H), 3.17-3.12 (m, 2H), 2.69-2.63 (m, 2H), 2.38-2.26 (m, 2H), 2.00-1.77 (m, 3H), 1.68-1.46 (m, 6H), 1.40-1.23 (m, 5H), 1.19-0.99 (m, 9H), 0.94-0.88 (m, 9H), 0.74 (s, 3H).

Synthetic Example 43.1.1

((6R,7S)-2-amino-6-((1R,3aS,4S,5S,7aR)-4-(aminomethyl)-7a-methyl-1-((R)-6-methylheptan-2-yl)octahydro-1H-inden-5-yl)-6-methyl-5,6,7,8-tetrahydroquinazolin-7-yl)methanol (Compound Ic-7)

Following the procedure as described in Synthetic Example 26 and making non-critical variations using Ic-6 to replace Ia-62, the title compound, ((6R,7S)-2-amino-6-((1R,3aS,4S,5S,7aR)-4-(aminomethyl)-7a-methyl-1-((R)-6-methylheptan-2-yl)octahydro-1H-inden-5-yl)-6-methyl-5,6,7,8-tetrahydroquinazolin-7-yl)methanol (Compound Ic-7), was obtained.

LCMS: (Method 1c) MS m/z: 471.4 (M+1), $t_R$: 2.539 min, Purity: 97.65% (UV).

Synthetic Example 43.2

Synthesis of ((1R,3aS,4S,5S,7aR)-5-((6R,7S)-7-(hydroxymethyl)-6-methyl-5,6,7,8-tetrahydroquinazolin-6-yl)-7a-methyl-1-((R)-6-methylheptan-2-yl)octahydro-1H-inden-4-yl)methanol (Compound Ic-8)

Following the procedure as described in Synthetic Example 43 and making non-critical variations using formamidine-HCl to replace acetamidine HCl, the title compound, ((1R,3aS,4S,5S,7aR)-5-((6R,7S)-7-(hydroxymethyl)-6-methyl-5,6,7,8-tetrahydroquinazolin-6-yl)-7a-methyl-1-((R)-6-methylheptan-2-yl)octahydro-1H-inden-4-yl)methanol (Compound Ic-8, 0.71 g, 37%), was obtained as an off white solid after purification by column chromatography (Neutral alumina, eluted with 10% dichloromethane/methanol).

LCMS: (Method 1c) MS m/z: 457.4 (M+1), $t_R$: 3242 min, Purity: 89.23% (UV).

HPLC: (Method 2b) $t_R$: 16.486 min, Purity: 90.99% (UV).
¹H-NMR (400 MHz, CD₃OD): δ 8.88 (s, 1H), 8.50 (s, 1H), 4.02-3.95 (m, 2H), 3.71-3.66 (m, 2H), 3.59-3.57 (m, 1H), 3.44-3.36 (m, 1H), 2.93-2.86 (m, 2H), 2.64-2.60 (m, 1H), 2.38-2.36 (m, 1H), 2.02-1.81 (m, 3H), 1.71-1.50 (m, 6H), 1.41-1.39 (m, 3H), 1.24-1.12 (m, 9H), 0.97-0.89 (m, 9H), 0.77 (s, 3H).

Synthetic Example 43.2.1

Synthesis of ((6R,7S)-6-((1R,3aS,4S,5S,7aR)-4-(aminomethyl)-7a-methyl-1-((R)-6-methylheptan-2-yl)octahydro-1H-inden-5-yl)-6-methyl-5,6,7,8-tetrahydroquinazolin-7-yl)methanol (Compound Ic-9)

Following the procedure as described in Synthetic Example 26 and making non-critical variations using Ic-8 to replace Ia-62, the title compound, ((6R,7S)-6-((1R,3aS,4S,5S,7aR)-4-(aminomethyl)-7a-methyl-1-((R)-6-methylheptan-2-yl)octahydro-1H-inden-5-yl)-6-methyl-5,6,7,8-tetra-hydroquinazolin-7-yl)methanol (Compound Ic-9), was obtained.

LCMS: (Method 1c) MS m/z: 456.4 (M+1), $t_R$: 2.718 min, Purity: 96.77% (UV).

Synthetic Example 44

Synthesis of ((6R,7S)-2-amino-6-((3aS,4R,5S,7aS)-4-(hydroxymethyl)-7a-methyl-1-methyleneoctahydro-1H-inden-5-yl)-6-methyl-5,6,7,8-tetrahydro-quinazolin-7-yl)methanol (Compound Ic-10)

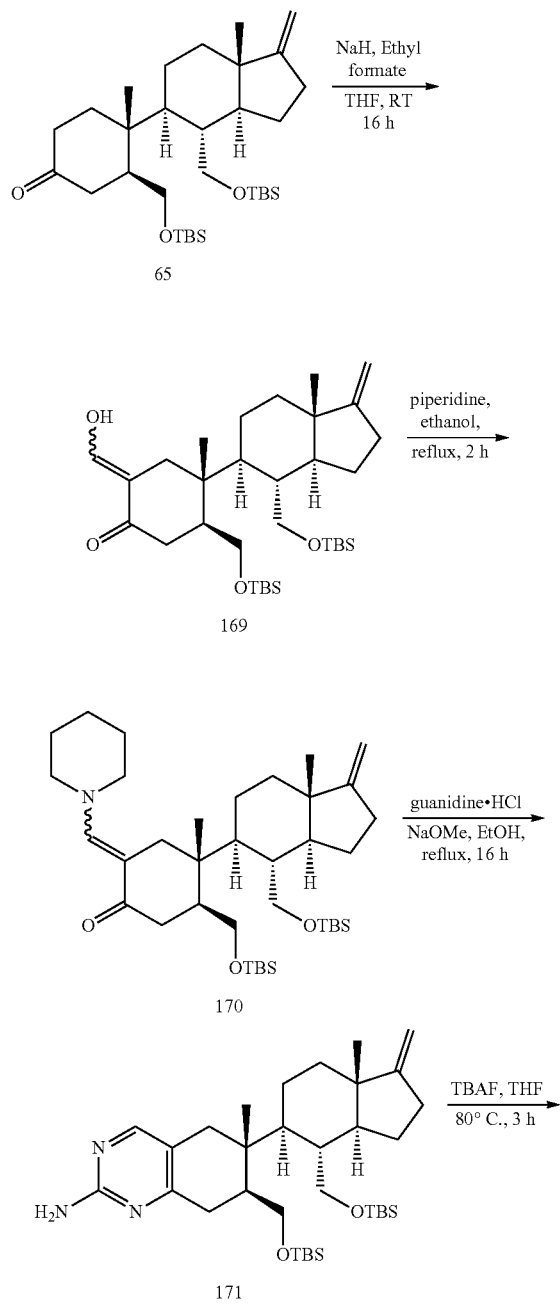

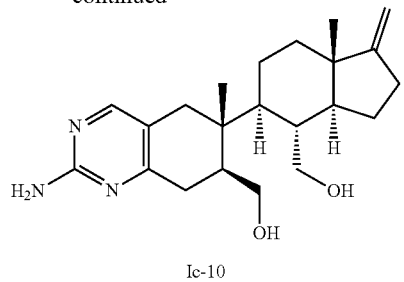

Ic-10

A. Following the General Procedure O with Compound 65 (from Example 16, 2.65 g, 4.83 mmol), NaH (60% in paraffin oil, 0.77 g, 19.31 mmol), ethyl formate (2.35 mL, 28.96 mmol) and THF (30 mL) gave the desired ketone, (4R,5S)-5-(((tert-butyldimethylsilyl)oxy)methyl)-4-((3aS, 4R,5S,7aS)-4-(((tert-butyldimethylsilyl)oxy)methyl)-7a-methyl-1-methyleneoctahydro-1H-inden-5-yl)-2-(hydroxymethylene)-4-methylcyclohexan-1-one (Compound 169, 2.15 g, 77%), as a brown gummy solid which was used in the next step without purification.

B. To a stirred solution of Compound 169 (2.15 g, 3.73 mmol) in ethanol (20 mL) was added piperidine (0.4 mL, 4.05 mmol) at room temperature. The resultant solution was stirred at reflux for 2 hours. The reaction mixture was evaporated under reduced pressure to give the desired ketone, (4R,5S)-5-(((tert-butyldimethylsilyl)oxy)methyl)-4-((3aS,4R,5S,7aS)-4-(((tert-butyldimethylsilyl)oxy)methyl)-7a-methyl-1-methyleneoctahydro-1H-inden-5-yl)-4-methyl-2-(piperidin-1-ylmethylene)cyclohexan-1-one (Compound 170, 2.4 g, 100%), as a brown gummy solid which was used in the next step without purification.

C. To a stirred solution of sodium methoxide (89 mg, 1.64 mmol) and guanidine hydrochloride (0.16 g, 1.64 mmol) in ethanol (5 mL) was added Compound 170 (0.88 g, 1.37 mmol) in ethanol (5 mL) dropwise at room temperature. The resultant solution was stirred at reflux for 16 hours. The reaction mixture was evaporated under reduced pressure and the residue was diluted with ethyl acetate (10 mL). The organic layer was washed consecutively with water (1×10 mL) and brine (1×10 mL), dried over sodium sulphate, filtered and concentrated to give the desired pyrimidine, (6R,7S)-7-(((tert-butyldimethylsilyl)oxy)methyl)-6-((3aS, 4R,5S,7aS)-4-(((tert-butyldimethylsilyl)oxy)methyl)-7a-methyl-1-methyleneoctahydro-1H-inden-5-yl)-6-methyl-5, 6,7,8-tetrahydroquinazolin-2-amine (Compound 171, 0.52 g, 63%), as a pale yellow gummy solid which was used in the next step without purification.

D. Following the General Procedure Q with Compound 171, 0.62 g, 1.03 mmol), TBAF (1M in THF, 2.07 mL, 2.07 mmol) and THF (5 mL), gave the desired alcohol, ((6R,7S)-2-amino-6-((3aS,4R,5S,7aS)-4-(hydroxymethyl)-7a-methyl-1-methyleneoctahydro-1H-inden-5-yl)-6-methyl-5, 6,7,8-tetrahydroquinazolin-7-yl)methanol (Compound Ic-10, 85 mg, 22%), as an off white solid after purification by preparative HPLC (Method 3c).

LCMS: (Method 1e) MS m/z: 372.2 (M+1), $t_R$: 2.577 min, Purity: 96.17% (UV).

HPLC: (Method 2d) $t_R$: 7.387 min, Purity: 98.83% (UV).

$^1$H-NMR (400 MHz, CD$_3$OD): δ 7.99 (s, 1H), 4.63 (s, 2H), 4.04 (d, J=11.2 Hz, 1H), 3.96 (dd, J=10.8, 2.8 Hz, 1H), 3.75-3.62 (m, 2H), 3.34-3.14 (m, 2H), 2.73-2.28 (m, 6H), 1.91-1.19 (m, 9H), 1.07 (s, 3H), 0.86 (s, 3H).

Synthetic Example 44.1

Synthesis of ((3aS,4R,5S,7aS)-5-((6R,7S)-7-(hydroxymethyl)-6-methyl-5,6,7,8-tetrahydroquinazolin-6-yl)-7a-methyl-1-methyleneoctahydro-1H-inden-4-yl)methanol (Compound Ic-11)

Following the procedure as described in Synthetic Example 44 and making non-critical variations using formamidine HCl to replace guanidine-HCl, the title compound, ((3aS,4R,5S,7aS)-5-((6R,7S)-7-(hydroxymethyl)-6-methyl-5,6,7,8-tetrahydroquinazolin-6-yl)-7a-methyl-1-methyleneoctahydro-1H-inden-4-yl)methanol (Compound Ic-11, 30 mg, 6%), was obtained as an off white solid after purification by preparative HPLC (Method 3c).

LCMS: (Method Ie) MS m/z: 357.2 (M+1), $t_R$: 2.614 min, Purity: 91.21% (UV).
HPLC: (Method 2d) $t_R$: 8.611 min, Purity: 97.44% (UV).
$^1$H-NMR (400 MHz, CD$_3$OD): δ 8.87 (s, 1H), 8.49 (s, 1H), 4.65-4.63 (m, 2H), 4.06-3.95 (m, 2H), 3.75-3.72 (m, 1H), 3.45-3.36 (m, 2H), 2.96-2.91 (m, 2H), 2.65-2.29 (m, 5H), 1.93-1.67 (m, 4H), 1.59-1.49 (m, 3H), 1.48-1.30 (m, 1H), 1.14 (s, 3H), 0.87 (s, 3H).

Synthetic Example 44.2

Synthesis of ((3aS,4R,5S,7aS)-5-((6R,7S)-7-(hydroxymethyl)-2,6-dimethyl-5,6,7,8-tetrahydroquinazolin-6-yl)-7a-methyl-1-methyleneoctahydro-1H-inden-4-yl)methanol (Compound Ic-12)

Following the procedure as described in Synthetic Example 44 and making non-critical variations using acetamidine-HCl to replace guanidine-HCl, the title compound, ((3aS,4R,5S,7aS)-5-((6R,7S)-7-(hydroxymethyl)-2,6-dimethyl-5,6,7,8-tetrahydroquinazolin-6-yl)-7a-methyl-1-methyleneoctahydro-1H-inden-4-yl)methanol (Compound Ic-12), was obtained.

LCMS: (Method 1c) MS m/z: 371.3 (M+1), $t_R$: 1.788 min, Purity: 86.00% (UV).

Synthetic Example 44.3

Synthesis of ((3aS,4R,5S,7aS)-5-((2R,3S)-3-(hydroxymethyl)-2-methyl-1,2,3,4-tetrahydrobenzo[4,5]imidazo[2,1-b]quinazolin-2-yl)-7a-methyl-1-methyleneoctahydro-1H-inden-4-yl)methanol (Compound Ic-13)

Following the procedure as described in Synthetic Example 44 and making non-critical variations skipping the formation of Compound 170 and directly treating Compound 169 with 1H-benzoimidazol-2-ylamine HCl (1.5 equivalents) to replace guanidine HCl, in ethanol, for 2 hours, at 90° C., without sodium methoxide, the title compound, ((3aS,4R,5S,7aS)-5-((2R,3S)-3-(hydroxymethyl)-2-methyl-1,2,3,4-tetrahydrobenzo[4,5]imidazo[2,1-b]quinazolin-2-yl)-7a-methyl-1-methyleneoctahydro-1H-inden-4-yl)methanol (Compound Ic-13), was obtained.

LCMS: (Method 1d) MS m/z: 446.3 (M+1), $t_R$: 1.532 min, Purity: 99.87% (UV).

Synthetic Example 44.3.1 ((2R,3S)-2-((3aS,4R,5S,7aS)-4-(aminomethyl)-7a-methyl-1-methyleneoctahydro-1H-inden-5-yl)-2-methyl-1,2,3,4-tetrahydrobenzo[4,5]imidazo[2,1-b]quinazolin-3-yl)methanol (Compound Ic-14)

Following the procedure as described in Synthetic Example 26 and making non-critical variations using Ic-13 to replace Ia-62, and additionally utilizing triphenyl phosphine in THF/water at ambient temperature for 16 hours to replace LAH as the reducing agent, the title compound, ((2R,3S)-2-((3aS,4R,5S,7aS)-4-(aminomethyl)-7a-methyl-1-methyleneoctahydro-1H-inden-5-yl)-2-methyl-1,2,3,4-tetrahydrobenzo[4,5]imidazo[2,1-b]quinazolin-3-yl)methanol (Compound Ic-14), was obtained.

LCMS: (Method 1j) MS m/z: 445.3 (M+1), $t_R$: 1.995 min, Purity: 92.10% (UV).

Synthetic Example 45

Synthesis of ((5R,6S)-5-((3aS,4R,5S,7aS)-4-(aminomethyl)-7a-methyl-1-methyleneoctahydro-1H-inden-5-yl)-5-methyl-4,5,6,7-tetrahydro-1H-indol-6-yl)methanol (Compound Id-1)

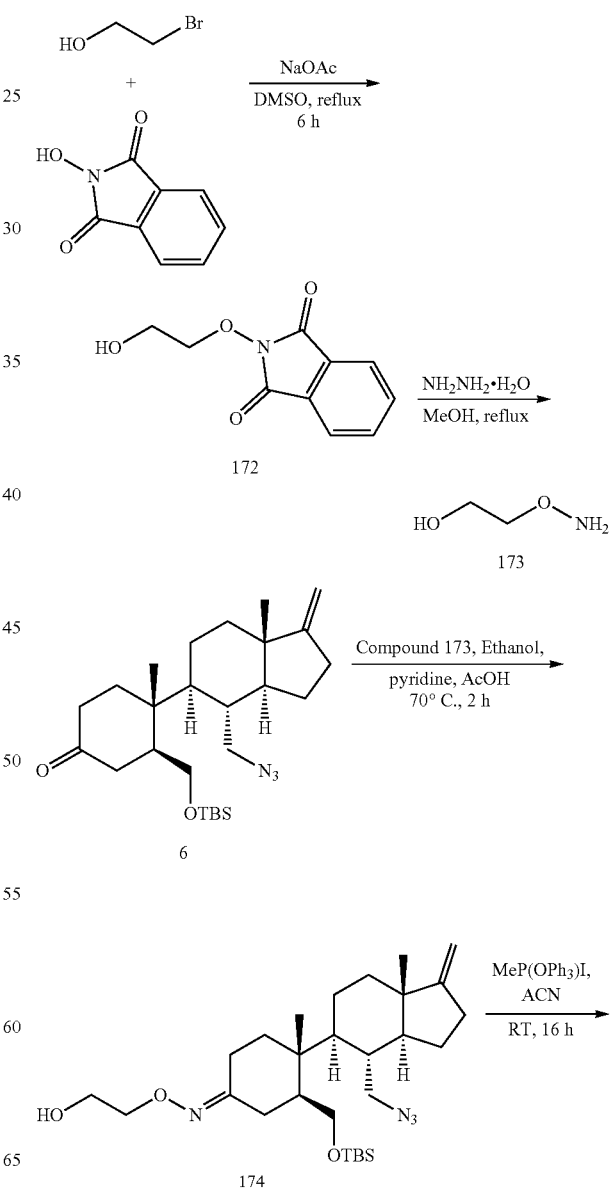

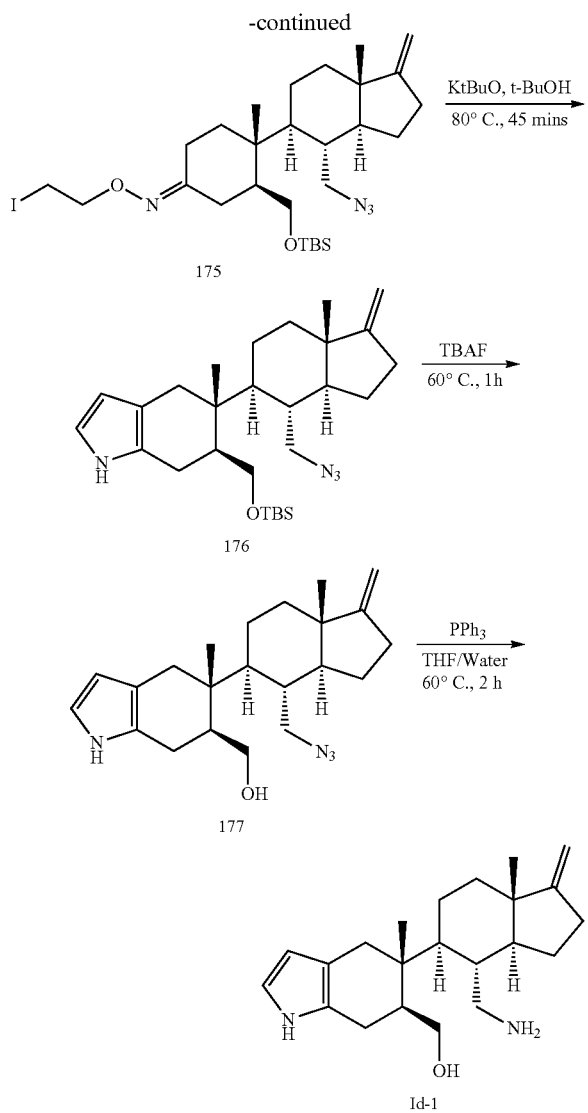

A. To a stirred solution of 2-bromoethanol (50.0 g, 400.10 mmol) in DMSO (500 mL) was added N-hydroxyphthalimide (65.27 g, 400.10 mmol) and sodium acetate (65.64 g, 800.20 mmol) at room temperature. The resultant solution was stirred at 100° C. for 6 hours. The reaction mixture was diluted with water (1×500 mL) and aqueous was extracted with ethyl acetate (2×500 mL). Organic layer was washed with brine (1×500 mL) and dried over sodium sulphate, filtered and concentrated. The residue was purified by flash column chromatography (60-120 mesh silica gel, 40-50% pet ether/ethyl acetate) to give the desired pthalimide, 2-(2-hydroxyethoxy)isoindoline-1,3-dione (Compound 172, 29.0 g, 35%), as a pale yellow solid.

B. To a stirred solution of Compound 172 (29.0 g, 139.97 mmol) in MeOH (300 mL) was added hydrazine hydrate (9.63 mL, 195.96 mmol) at room temperature. The resultant solution was stirred at 70° C. for 1.5 hours. The reaction mixture was cooled to room temperature and diluted with CHCl₃ (1×300 mL). The resultant slurry was filtered through Buchner funnel and washed with CHCl₃ (2×300 mL). The filtrate was concentrated, and the residue was distilled under vacuum (0.025 mmHg) at 75-80° C. to give the desired alcohol, 2-(aminooxy)ethan-1-ol (Compound 173, 3.0 g, 28%), as a colorless oil.

C. To a stirred solution of Compound 6 (from Example 1, 4.0 g, 8.70 mmol) in ethanol (40 mL) were added Compound 173 (2.01 g, 26.10 mmol), pyridine (0.77 mL, 9.57 mmol) and acetic acid (0.55 mL, 9.57 mmol). The resultant solution was heated to 70° C. and stirred for 2 hours. The reaction mixture was evaporated under reduced pressure. The residue was diluted with dichloromethane (2×40 mL) and washed consecutively with water (1×40 mL) and brine (1×40 mL). Organic layer was dried over sodium sulphate, filtered and concentrated to give the desired oxime, (3S,4R)-4-((3aS,4R,5S,7aS)-4-(azidomethyl)-7a-methyl-1-methyleneoctahydro-1H-inden-5-yl)-3-(((tert-butyldimethylsilyl)oxy)methyl)-4-methylcyclohexan-1-one O-(2-hydroxyethyl) oxime (Compound 174, 4.1 g, 91%), as a colourless gummy solid which was used in the next step without purification.

D. To a stirred solution of Compound 174 (4.0 g, 7.71 mmol) in ACN (40 mL) was added methyl(triphenoxy)phosphonium iodide (10.46 g, 23.13 mmol) at 0° C. The reaction mass was stirred at room temperature for 16 hours. The mixture was evaporated under reduced pressure and diluted with ethyl acetate (2×40 mL) and washed consecutively with water (1×40 mL) and brine (1×40 mL). Organic layer was dried over sodium sulphate, filtered and concentrated to give the desired oxime, (3S,4R)-4-((3aS,4R,5S,7aS)-4-(azidomethyl)-7a-methyl-1-methyleneoctahydro-1H-inden-5-yl)-3-(((tert-butyldimethylsilyl)oxy)methyl)-4-methylcyclohexan-1-one O-(2-iodoethyl) oxime (Compound 175, 1.6 g, 33%), as a brown gummy solid after purification by column chromatography (230-400 mesh silica gel, eluted with 0-5% pet ether/ethyl acetate).

E. To a stirred solution of Compound 175 (1.6 g, 2.54 mmol) in tert-butyl alcohol (15 mL) was added potassium-tert-butoxide (1.43 g, 12.72 mmol) at room temperature. The reaction mass was heated to 80° C. for 45 minutes. The mixture was concentrated and residue was diluted with ethyl acetate (2×10 mL) and washed consecutively with water (1×10 mL) and brine (1×10 mL). Organic layer was dried over sodium sulphate, filtered and concentrated to afford the desired indole, (5R,6S)-5-((3aS,4R,5S,7aS)-4-(azidomethyl)-7a-methyl-1-methyleneoctahydro-1H-inden-5-yl)-6-(((tert-butyldimethylsilyl)oxy)methyl)-5-methyl-4,5,6,7-tetrahydro-1H-indole (Compound 176, 1.2 g, 98%), as a brown gummy solid which was used in the next step without purification.

F. Following the General Procedure Q with Compound 176 (1.2 g, 2.49 mmol), TBAF (1M in THF, 7.46 mL, 7.46 mmol) and THF (10 mL), gave the desired alcohol, ((5R,6S)-5-((3aS,4R,5S,7aS)-4-(azidomethyl)-7a-methyl-1-methyleneoctahydro-1H-inden-5-yl)-5-methyl-4,5,6,7-tetrahydro-1H-indol-6-yl)methanol (Compound 177, 0.9 g, 98%), as a brown gummy solid which was used in the next step without purification.

G. Using General Procedure R with Compound 177 (0.8 g, 2.17 mmol), triphenyl phosphine (1.14 g, 4.34 mmol) and THF:water (9:1, 10 mL) gave the desired amine, ((5R,6S)-5-((3aS,4R,5S,7aS)-4-(aminomethyl)-7a-methyl-1-methyleneoctahydro-1H-inden-5-yl)-5-methyl-4,5,6,7-tetrahydro-1H-indol-6-yl)methanol (Compound Id-1, 120 mg, 16%), as a white solid after purification by preparative HPLC (Method 3c).

LCMS: (Method 1d) MS m/z: 343.3 (M+1), $t_R$: 1.450 min, Purity: 98.76% (ELSD).

HPLC: (Method 2e) $t_R$: 4.355 min, Purity: 89.15% (UV); (Method 2d $t_R$: 8.231 min, Purity: 97.32% (ELSD)).

¹H-NMR (400 MHz, CD₃OD): δ 6.59 (d, J=2.8 Hz, 1H), 6.01 (d, J=2.4 Hz, 1H), 4.61 (s, 2H), 3.89 (dd, J=5.2, 10.8 Hz, 1H), 3.59 (dd, J=6.4, 10.8 Hz, 1H), 3.02-2.99 (m, 1H), 2.75-2.52 (m, 4H), 2.30-2.21 (m, 1H), 1.88-1.73 (m, 5H), 1.66-1.52 (m, 3H), 1.35-1.20 (m, 4H), 1.11 (s, 3H), 0.81 (s, 3H).

Synthetic Example 46

Synthesis of ((5S,6R)-6-((3aS,4R,5S,7aS)-4-(aminomethyl)-7a-methyl-1-methyleneoctahydro-1H-inden-5-yl)-2,6-dimethyl-4,5,6,7-tetrahydrobenzo[d]thiazol-5-yl)methanol (Compound Ie-1)

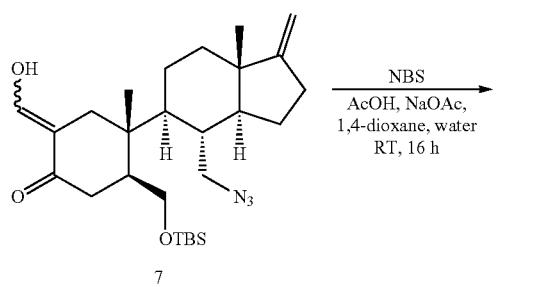

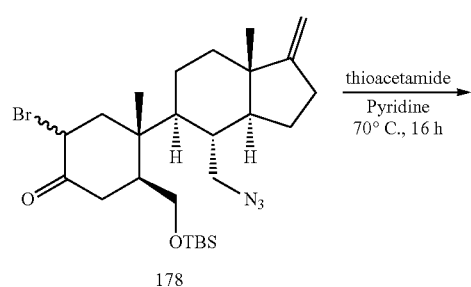

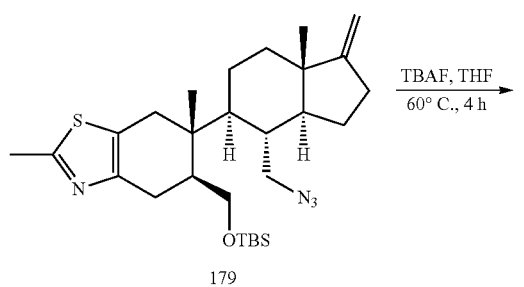

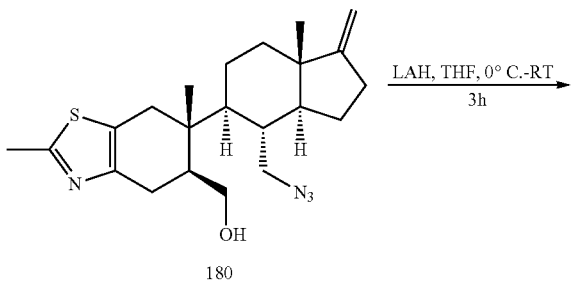

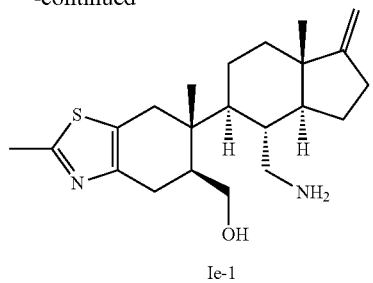

A. To a stirred solution of Compound 7 (from Example 1, 5.0 g, 10.25 mmol) in 1,4 dioxane (50 mL) and water (5 mL) was added sodium acetate (0.92 g, 11.28 mmol), N-bromosuccinimide (0.92 g, 11.28 mmol) and acetic acid (5 mL) at room temperature. The resultant solution was stirred at room temperature for 16 hours. The reaction mixture was evaporated under reduced pressure and diluted with ethyl acetate (2×50 mL). The organic layer was washed consecutively with water (1×10 mL) and brine (1×10 mL), dried over sodium sulphate, filtered and concentrated. The crude was purified by flash column chromatography (230-400 mesh silica gel, eluted with 0-30% pet ether/ethyl acetate) to afford (4R,5S)-4-((3aS,4R,5S,7aS)-4-(azidomethyl)-7a-methyl-1-methyleneoctahydro-1H-inden-5-yl)-2-bromo-5-(((tert-butyldimethylsilyl)oxy)methyl)-4-methylcyclohexan-1-one (Compound 178, 2.6 g, 47%) as a brown solid.

B. To a stirred solution of Compound 178 (1.20 g, 2.23 mmol) in pyridine (10 mL) was added thioacetamide (0.67 g, 8.91 mmol) at room temperature. The resultant solution was stirred at 70° C. for 16 hours. The reaction mixture was evaporated under reduced pressure and residue was diluted with saturated sodium bicarbonate solution (5 g dissolved in 10 mL water). The aqueous solution was extracted with ethyl acetate (2×10 mL), washed consecutively with water (1×10 mL) and brine (1×10 mL). Organic layer was dried over sodium sulphate, filtered and concentrated to give the desired thiazole, (5S,6R)-6-((3aS,4R,5S,7aS)-4-(azidomethyl)-7a-methyl-1-methyleneoctahydro-1H-inden-5-yl)-5-(((tert-butyldimethylsilyl)oxy)methyl)-2,6-dimethyl-4,5,6,7-tetrahydrobenzo[d]thiazole (Compound 179, 0.82 g, 71%), as a brown gummy solid which was used in the next step without purification.

C. Following the General Procedure Q with Compound 179, 0.80 g, 1.55 mmol), TBAF (1M in THF, 3.10 mL, 3.10 mmol) and THF (10 mL), gave the desired alcohol, ((5S,6R)-6-((3aS,4R,5S,7aS)-4-(azidomethyl)-7a-methyl-1-methyleneoctahydro-1H-inden-5-yl)-2,6-dimethyl-4,5,6,7-tetrahydrobenzo[d]thiazol-5-yl)methanol (Compound 180, 0.42 g, 68%), as a brown gummy solid which was used in the next step without purification.

D. Using General Procedure S with Compound 180 (0.20 g, 0.50 mmol), LAH (1 M in THF) (1.00 mL, 1.00 mmol) and THF (5 mL), gave the desired alcohol, ((5S,6R)-6-((3aS,4R,5S,7aS)-4-(aminomethyl)-7a-methyl-1-methyleneoctahydro-1H-inden-5-yl)-2,6-dimethyl-4,5,6,7-tetrahydrobenzo[d]thiazol-5-yl)methanol (Compound Ie-1, 20 mg, 11%), as an off white solid after purification by preparative HPLC (Method 3c).

LCMS: (Method Ie) MS m/z: 375.3 (M+1), $t_R$: 2.798 min, Purity: 78.34% (UV).

HPLC: (Method 2e) $t_R$: 5.232 min, Purity: 82.38% (UV).

$^1$H-NMR (400 MHz, CD$_3$OD): δ 4.69-4.62 (m, 2H), 3.92 (dd, J=2.6, 10.8 Hz, 1H), 3.45-3.39 (m, 1H), 3.28-3.24 (m,

1H), 3.20-3.15 (m, 1H), 3.08-3.04 (m, 1H), 2.93-2.89 (m, 1H), 2.64 (s, 3H), 2.59-2.52 (m, 1H), 2.39-2.31 (m, 1H), 2.21-2.19 (m, 1H), 200-1.85 (m, 3H), 1.72-1.56 (m, 3H), 1.49-1.36 (m, 2H), 1.33-1.27 (m, 1H), 1.11 (s, 3H), 1.07-1.03 (m, 2H), 0.90 (s, 3H).

Synthetic Example 46.1

Synthesis of ((5S,6R)-2-amino-6-((3aS,4R,5S,7aS)-4-(aminomethyl)-7a-methyl-1-methyleneoctahydro-1H-inden-5-yl)-6-methyl-4,5,6,7-tetrahydrobenzo[d]thiazol-5-yl)methanol (Compound Ie-2)

Following the procedure as described in Synthetic Example 46 and making non-critical variations using thiourea to replace thiacetamide and triphenyl phosphine in THF:water (9:1) at 60° C., in place of LAH in THF in the reduction of azide to amine, the title compound, ((5S,6R)-2-amino-6-((3aS,4R,5S,7aS)-4-(aminomethyl)-7a-methy-1-methyleneoctahydro-1H-inden-5-yl)-6-methyl-4,5,6,7-tetrahydrobenzo[d]thiazol-5-yl)methanol (Compound Ie-2, 30 mg, 16%), was obtained as a white solid after purification by preparative HPLC (Method 3c).

LCMS: (Method 1e) MS m/z: 376.2 (M+1), $t_R$: 2.437 min, Purity: 82.88% (UV).

HPLC: (Method 2e) $t_R$: 4.455 min, Purity: 88.64% (UV).

$^1$H-NMR (400 MHz, CD$_3$OD): δ 4.70 (s, 2H), 3.88-3.86 (m, 1H), 3.51-3.47 (m, 1H), 2.90-2.73 (m, 2H), 2.50-2.70 (m, 1H), 2.38-2.37 (m, 3H), 2.34-2.30 (m, 1H), 2.13-1.88 (m, 5H), 1.66-1.47 (3H, m), 1.44-132 (m, 3H), 1.11 (s, 3H), 0.86 (s, 3H).

Synthetic Example 47

Synthesis of ((1R,3aS,4S,5S,7aR)-5-((5S,6R)-2-amino-5-(hydroxymethyl)-6-methyl-4,5,6,7-tetrahydrobenzo[d]thiazol-6-yl)-7a-methyl-1-((R)-6-methylheptan-2-yl)octahydro-1H-inden-4-yl)methanol (Compound Ie-3)

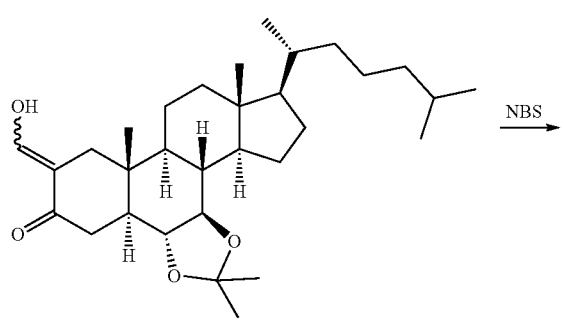

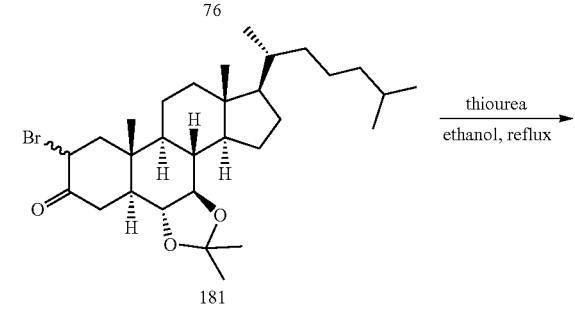

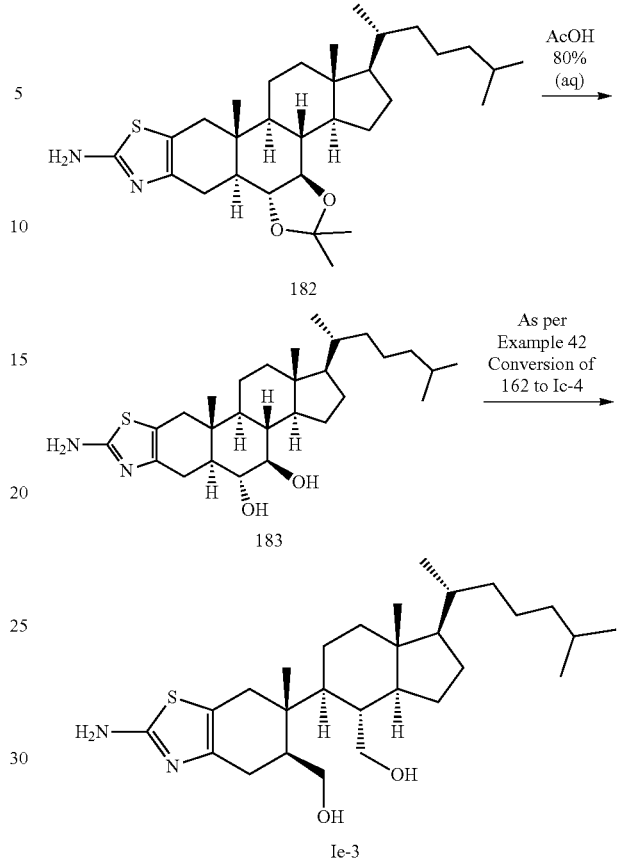

NBS treatment of Compound 76, from Example 20, to provide Compound 181 followed by thiourea addition to provide Compound 182 and cyclization provides Compound 183. Following the procedure as described in Synthetic Example 42, for the conversion of Compound 162 to Compound 10-1 and making non-critical variations using Compound 183 to replace Compound 162, the title compound, ((1R,3aS,4S,5S,7aR)-5-((5S,6R)-2-amino-5-(hydroxymethyl)-6-methyl-4,5,6,7-tetrahydrobenzo[d]thiazol-6-yl)-7a-methyl-1-((R)-6-methylheptan-2-yl)octahydro-1H-inden-4-yl)methanol (Compound Ic-3), was obtained.

LCMS: (Method 1c) MS m/z: 477.4 (M+1), $t_R$: 3.100 min, Purity: 85.75% (UV).

Synthetic Example 47.1

((5S,6R)-2-amino-6-((1R,3aS,4S,5S,7aR)-4-(aminomethyl)-7a-methyl-1-((R)-6-methylheptan-2-yl)octahydro-1H-inden-5-yl)-6-methyl-4,5,6,7-tetrahydrobenzo[d]thiazol-5-yl)methanol (Compound Ie-4)

Following the procedure as described in Synthetic Example 26 and making non-critical variations using Ie-3 to replace Ia-62, the title compound, ((5S,6R)-2-amino-6-((1R,3aS,4S,5S,7aR)-4-(aminomethyl)-7a-methyl-1-((R)-6-methylheptan-2-yl)octahydro-1H-inden-5-yl)-6-methyl-4,5,6,7-tetrahydrobenzo[d]thiazol-5-yl)methanol (Compound Ie-4), was obtained.

LCMS: (Method 1j) MS m/z: 476.4 (M+1), $t_R$: 1.730 min, Purity: 92.90% (UV).

Synthetic Example 48

Synthesis of ((1R,3aS,4S,5S,7aR)-5-((5S,6R)-5-(hydroxymethyl)-6-methyl-4,5,6,7-tetrahydrobenzo[d][1,2,3]thiadiazol-6-yl)-7a-methyl-1-((R)-6-methylheptan-2-yl)octahydro-1H-inden-4-yl)methanol (Compound If-1)

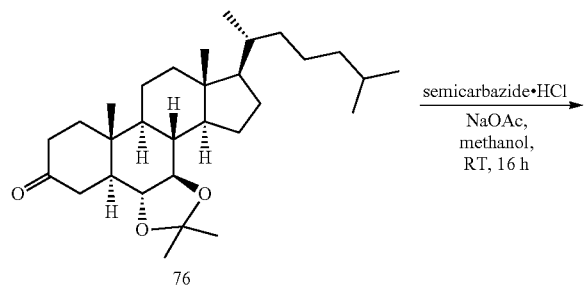

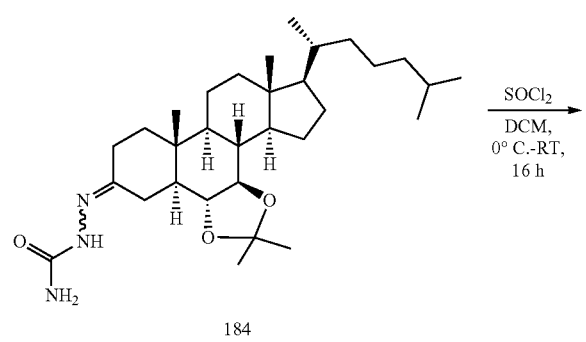

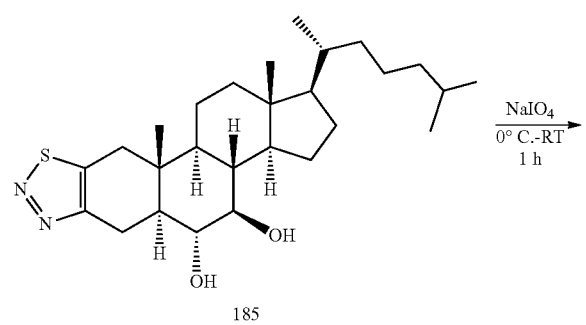

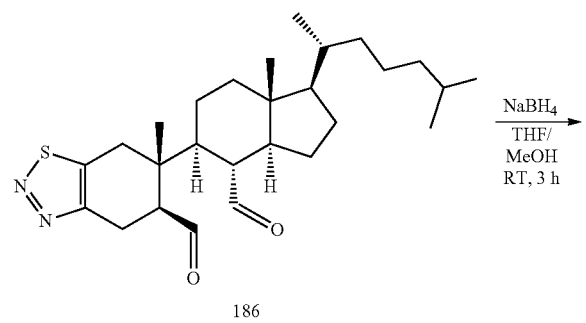

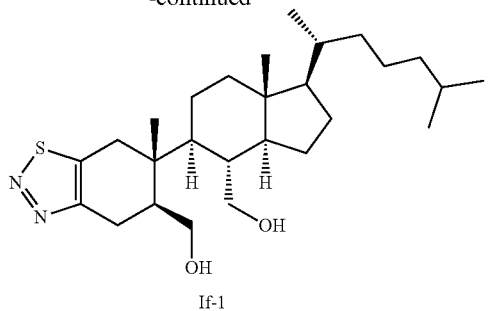

If-1

A. To a stirred solution of sodium acetate (1.61 g, 19.62 mmol) and semicarbazide.HCl (1.75 g, 15.70 mmol) in MeOH (10 mL) was added at room temperature, Compound 76 (from Example 20, 60 g, 13.08 mmol) in MeOH (50 mL) dropwise. The reaction mixture was stirred at room temperature for 16 hours. The mixture was evaporated under reduced pressure and the residue was diluted with EtOAc (2×60 mL) and washed consecutively with water (1×60 mL) and brine (1×60 mL). The organic layer was dried over $Na_2SO_4$, filtered and concentrated. The crude was purified by column chromatography on silica gel (230-400 mesh, 40-50% pet ether/ethyl acetate) to afford 2-((4aR,4bS,6aR,7R,9aS,9bS,9cR,12aR,12bS)-4a,6a,11,11-tetramethyl-7-((R)-6-methylheptan-2-yl)hexadecahydro-2H-cyclopenta[1,2]phenanthro[9,10-d][1,3]dioxol-2-ylidene)hydrazine-1-carboxamide (Compound 184, 6.5 g, 96%) as a white gummy solid.

B. To a stirred solution of Compound 184 (6.5 g, 12.60 mmol) in $CH_2Cl_2$ (60 mL) at 0° C. was added thionyl chloride (18.28 mL, 252.05 mmol) dropwise. The reaction mixture was stirred at room temperature for 16 hours. The mixture was evaporated under reduced pressure and the residue was diluted with a saturated aqueous $NaHCO_3$ solution (1×60 mL), extracted with $CH_2Cl_2$ (2×60 mL) and washed consecutively with water (1×60 mL) and brine (1×60 mL). The organic layer was dried over $Na_2SO_4$, filtered and concentrated. The crude was purified by column chromatography on silica gel (230-400 mesh, 40-50% pet ether/ethyl acetate) to afford (1R,3aS,3bS,4R,5R,5aS,10aR,10bS,12aR)-10a,12a-dimethyl-1-((R)-6-methylheptan-2-yl)-2,3,3a,3b,4,5,5a,6,10,10a,10b,11,12,12a-tetradecahydro-1H-cyclopenta[7,8]phenanthro[2,3-d][1,2,3]thiadiazole-4,5-diol (Compound 185, 4.0 g, 69%) as a white solid.

LCMS: (Method 1f) MS m/z: 461.4 (M+1), $t_R$: 4.567 min, Purity: 98.74% (UV).

HPLC: (Method 2d) $t_R$: 20.953 min, Purity: 95.26% (UV).

$^1$H-NMR (400 MHz, DMSO-d$_6$): δ 3.66 (dd, J=5.0, 17.1 Hz, 1H), 3.38-3.36 (m, 1H), 3.24 (d, J=17.2 Hz, 1H), 3.11 (t, J=9.4 Hz, 1H), 2.76-2.69 (m, 1H), 2.56 (d, J=17.2 Hz, 1H), 2.11 (d, J=12.6 Hz, 1H), 2.02-1.98 (m, 1H), 1.88-1.85 (m, 1H), 1.71-1.62 (m, 2H), 1.60-1.48 (m, 4H), 1.40-1.35 (m, 3H), 1.34-1.06 (m, 9H), 1.03-0.98 (m, 3H), 0.91-0.89 (m, 6H), 0.85 (s, 3H), 0.76 (s, 3H).

C. Using General Procedure F with Compound 185 (0.25 g, 0.54 mmol), sodium metaperiodate (0.23 g, 1.09 mmol) and THF/water (4:1) (5 mL) gave the desired dialdehyde, (5S,6R)-6-((1R,3aS,4S,5S,7aR)-4-formyl-7a-methyl-1-((R)-6-methylheptan-2-yl)octahydro-1H-inden-5-yl)-6-methyl-4,5,6,7-tetrahydrobenzo[d][1,2,3]thiadiazole-5-carbaldehyde (Compound 186, 0.20 g, 80%), as a yellow gummy solid which was used in the next step without purification.

D. Using General Procedure G with Compound 186, 0.20 g, 0.44 mmol), sodium borohydride (33 mg, 0.87 mmol) and THF/MeOH (1:1, 5 mL) gave the desired dialcohol, ((1R,3aS,4S,5S,7aR)-5-((5S,6R)-5-(hydroxynethyl)-6-methyl-4,5,6,7-tetrahydrobenzo[d][1,2,3]thiadiazol-6-yl)-7a-methyl-1-((R)-6-methylheptan-2-yl)octahydro-1H-inden-4-yl)methanol (Compound If-1, 40 mg, 20%), as a white solid after purification by preparative HPLC (Method 3a).

LCMS: (Method 1c) MS m/z: 463.3 (M+1), $t_R$: 3.126 min, Purity: 96.73% (ELSD).

HPLC: (Method 2b) $t_R$: 13.114 min, Purity: 86.21% (UV).

$^1$H-NMR (400 MHz, CD$_3$OD): δ 3.99-3.96 (m, 2H), 3.69-3.63 (m, 1H), 3.49-3.40 (m, 1H), 3.16-3.12 (m, 1H), 3.03-2.97 (m, 1H), 2.89-2.85 (m, 1H), 2.32-2.28 (m, 1H), 201-1.80 (m, 3H), 1.71-1.52 (m, 6H), 1.50-1.23 (m, 7H), 1.20-1.04 (m, 8H), 0.97-0.88 (m, 9H), 0.75 (m, 3H).

Synthetic Example 48.1

Synthesis of ((5S,6R)-6-((1R,3aS,4S,5S,7aR)-4-(aminomethyl)-7a-methyl-1-((R)-6-methylheptan-2-yl)octahydro-1H-inden-5-yl)-6-methyl-4,5,6,7-tetrahydrobenzo[d][1,2,3]thiadiazol-5-yl)methanol (Compound If-2)

Following the procedure as described in Synthetic Example 26 and making non-critical variations using If-1 to replace Ia-62, the title compound, ((5S,6R)-6-((1R,3aS,4S,5S,7aR)-4-(aminomethyl)-7a-methyl-1-((R)-6-methylheptan-2-yl)octahydro-1H-inden-5-yl)-6-methyl-4,5,6,7-tetrahydrobenz[d][1,2,3]thiadiazol-5-yl)methanol (Compound If-2), was obtained.

LCMS: (Method 1c) MS m/z: 462.2 (M+1), $t_R$: 3.028 min, Purity: 99.90% (UV).

Synthetic Example 49

Synthesis of ((5R,6S)-5-((3aS,4R,5S,7aS)-4-(aminomethyl)-7a-methyl-1-methyleneoctahydro-1H-inden-5-yl)-5-methyl-4,5,6,7-tetrahydrobenzo[c]isoxazol-6-yl)methanol (Compound Ig-1)

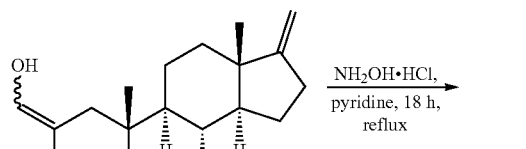

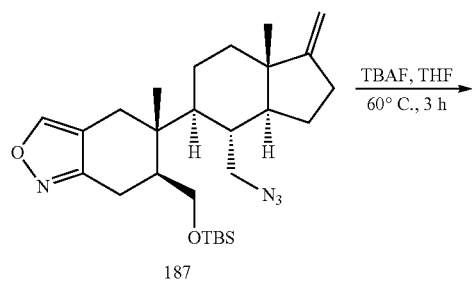

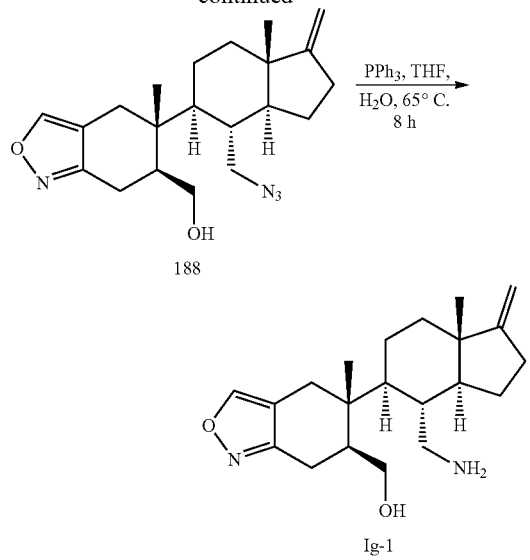

A. To a stirred solution of hydroxylamine hydrochloride (0.43 g, 6.15 mmol) in pyridine (10 mL) was added Compound 7 (from Example 1, 1.0 g, 2.05 mmol) portionwise at room temperature. The resultant solution was heated to reflux for 18 hours. The reaction mixture was evaporated under reduced pressure. The residue was diluted with EtOAc (2×10 mL) and washed consecutively with water (1×10 mL) and brine (1×10 mL). The organic layer was dried over Na$_2$SO$_4$, filtered and concentrated to give the desired isoxazole, (5R,6S)-5-((3aS,4R,5S,7aS)-4-(azidomethyl)-7a-methyl-1-methyleneoctahydro-1H-inden-5-yl)-6-(((tert-butyldimethylsilyl)oxy)methyl)-5-methyl-4,5,6,7-tetrahydrobenzo[c]isoxazole (Compound 187, 0.80 g, 81%), as a brown gummy solid which was used in the next step without purification.

B. Following the General Procedure Q with Compound 187 (0.80 g, 1.65 mmol), TBAF (1M in THF, 3.30 mL, 3.30 mmol) and THF (10 mL), gave the desired alcohol, ((5R,6S)-5-((3aS,4R,5S,7aS)-4-(azidomethyl)-7a-methyl-1-methyleneoctahydro-1H-inden-5-yl)-5-methyl-4,5,6,7-tetrahydrobenz[c]isoxazol-6-yl)methanol (Compound 188, 0.6 g, 98%), as a brown gummy solid which was used in the next step without purification.

C. Using General Procedure R with Compound 188, 0.60 g, 1.62 mmol), triphenyl phosphine (0.85 g, 3.24 mmol) and THF:water (9:1, 10 mL) gave the desired amine, ((5R,6S)-5-((3aS,4R,5S,7aS)-4-(aminomethyl)-7a-methyl-1-methyleneoctahydro-1H-inden-5-yl)-5-methyl-4,5,6,7-tetrahydrobenzo[c]isoxazol-6-yl)methanol (Compound Ig-1, 90 mg, 16%), as an off white solid after purification by preparative HPLC (Method 3c).

LCMS: (Method 1e) MS m/z: 345.2 (M+1), $t_R$: 2.717 min, Purity: 97.29% (UV).

HPLC: (Method 2e) $t_R$: 4.654 min, Purity: 98.54% (UV).

$^1$H-NMR (400 MHz, CD$_3$OD): δ 8.37 (s, 1H), 4.70 (s, 2H), 3.96-3.93 (m, 1H), 3.47-3.40 (m, 2H), 3.26-3.20 (m, 1H), 3.15-3.11 (m, 1H), 2.70-2.52 (m, 4H), 2.39-2.31 (m, 1H), 2.19-2.18 (m, 1H), 2.02-1.96 (m, 2H), 1.92-1.86 (m, 2H), 1.73-1.57 (m, 2H), 1.50-1.42 (m, 1H), 1.38-1.27 (m, 2H), 1.06 (s, 3H), 0.90 (s, 3H).

Synthetic Example 50

Synthesis of ((1R,3aS,4S,5S,7aR)-5-((5R,6S)-6-(hydroxymethyl)-5-methyl-4,5,6,7-tetrahydrobenzo[d]isoxazol-5-yl)-7a-methyl-1-((R)-6-methylheptan-2-yl)octahydro-1H-inden-4-yl)methanol (Compound Ih-1)

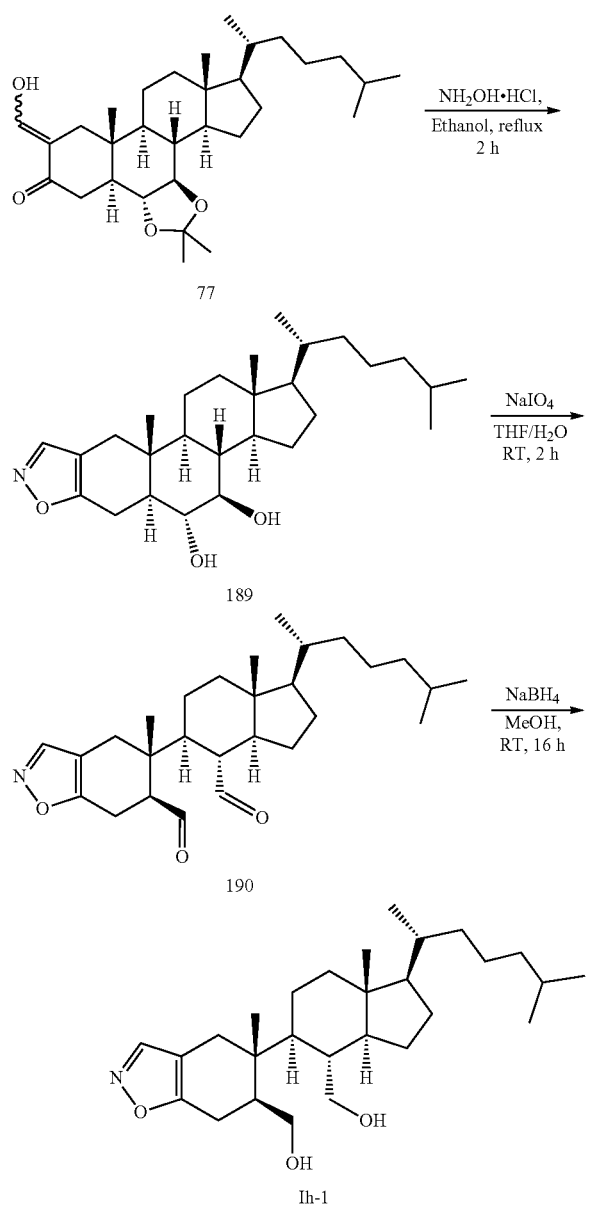

A. To a stirred solution of Compound 77 (from Example 20, 2.0 g, 4.10 mmol) in ethanol (20 mL) was added hydroxylamine hydrochloride (0.42 g, 6.04 mmol) at room temperature. The resultant solution was heated to reflux for 2 hours. The reaction mixture was evaporated under reduced pressure. The residue was diluted with EtOAc (40 mL) and washed consecutively with water (1×20 mL) and brine (1×20 mL). The organic layer was dried over $Na_2SO_4$, filtered and concentrated to give the desired isoxazole, (1R,3aS,3bS,4R,5R,5aS,10aR,10bS,12aR)-10a,12a-dimethyl-1-((R)-6-methylheptan-2-yl)-2,3,3a,3b,4,5,5a,6,10,10a,10b,11,12,12a-tetradecahydro-1H-cyclopenta[7,8]phenanthro[3,2-d]isoxazole-4,5-diol (Compound 189, 0.88 g, 48%), as a pale yellow liquid after purification by column chromatography (230-400 mesh silica gel, eluted with 80-95% pet ether/ethyl acetate).

B. Using General Procedure F with Compound 189 (088 g, 1.98 mmol), sodium metaperiodate (0.85 g, 3.97 mmol) and THF:water (4:1, 10 mL) gave the desired dialdehyde, (5R,6S)-5-((1R,3aS,4S,5S,7aR)-4-formyl-7a-methyl-1-((R)-6-methylheptan-2-yl)octahydro-1H-inden-5-yl)-5-methyl-4,5,6,7-tetrahydrobenz[d]isoxazole-6-carbaldehyde (Compound 190, 0.87 g, 99%), as a pale yellow solid which was used in the next step without purification.

C. Using General Procedure G with Compound 190 (0.87 g, 1.97 mmol), sodium borohydride (0.15 g, 3.97 mmol) and MeOH (10 mL) gave the desired dialcohol, ((1R,3aS,4S,5S,7aR)-5-((5R,6S)-6-(hydroxymethyl)-5-methyl-4,5,6,7-tetrahydrobenzo[d]isoxazol-5-yl)-7a-methyl-1-((R)-6-methylheptan-2-yl)octahydro-1H-inden-4-yl)methanol (Compound Ih-1, 57 mg, 6%), as an off white solid after purification by preparative HPLC (Method 3a).

LCMS: (Method 1c) MS m/z: 446.4 (M+1), $t_R$: 3.738 min, Purity: 94.02% (UV).

HPLC: (Method 2d) $t_R$: 15.566 min, Purity: 93.79% (UV).

$^1$H-NMR (400 MHz, $CD_3OD$): δ 8.16 (s, 1H), 3.99-3.91 (m, 2H), 3.64 (d, J=11.3 Hz, 1H), 3.39-3.36 (m, 1H), 3.16-3.15 (m, 1H), 2.65-2.61 (m, 2H), 2.24-2.20 (m, 2H), 2.02-1.80 (m, 5H), 1.63-1.38 (m, 9H), 1.31-1.13 (m, 9H), 1.09-0.88 (m, 9H), 0.74 (s, 3H).

Synthetic Example 51

Synthesis of ((5R,6S)-5-((3aS,6S,7R,7aS)-7-(aminomethyl)-3,3a-dimethyl-3a,4,5,6,7,7a-hexahydro-1H-inden-6-yl)-5-methyl-4,5,6,7-tetrahydrobenzo[d]isoxazol-6-yl)methanol (Compound Ih-2) and ((5R,6S)-5-((4R,5S)-4-(aminomethyl)-1,1-dimethyl-2,3,4,5,6,7-hexahydro-1H-inden-5-yl)-5-methyl-4,5,6,7-tetrahydrobenzo[d]isoxazol-6-yl)methanol (Compound Ih-3)

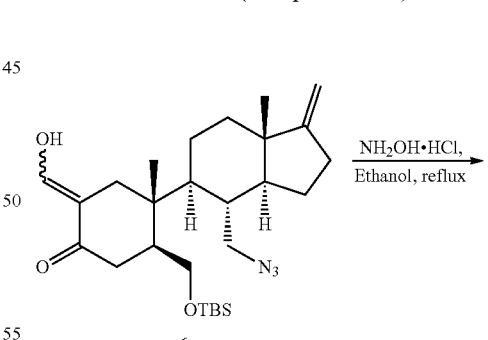

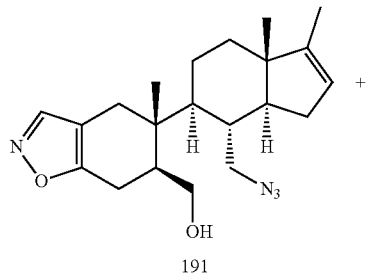

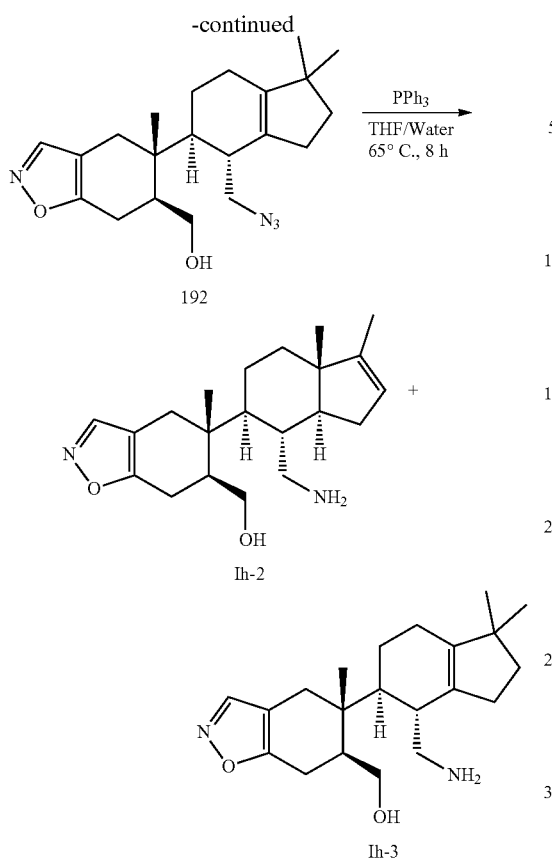

A. To a stirred solution of Compound 6, from Example 1 (2.5 g, 5.13 mmol) in ethanol (25 mL) was added hydroxylamine hydrochloride (1.07 g, 15.38 mmol) at room temperature. The resultant solution was heated to reflux for 8 hours. The reaction mixture was evaporated under reduced pressure. The residue was diluted with EtOAc (20 mL) and washed consecutively with water (1×10 mL) and brine (1×10 mL). The organic layer was dried over Na$_2$SO$_4$, filtered and concentrated to give the desired isoxazole as a mixture of two isomers, ((5R,6S)-5-((3aS,6S,7R,7aS)-7-(azidomethyl)-3,3a-dimethyl-3a,4,5,6,7,7a-hexahydro-1H-inden-6-yl)-5-methyl-4,5,6,7-tetrahydrobenzo[d]isoxazol-6-yl)methanol (Compound 191, minor) and ((5R,6S)-5-((4R,5S)-4-(azidomethyl)-1,1-dimethyl-2,3,4,5,6,7-hexahydro-1H-inden-5-yl)-5-methyl-4,5,6,7-tetrahydrobenzo[d]isoxazol-6-yl)methanol (Compound 192, major) (1.9 g total), as a brown gummy solid which was used in the next step without purification.

B. Using General Procedure R with the mixture of Compound 191 and Compound 192 (2.2 g, 5.94 mmol), triphenyl phosphine (3.1 g, 11.88 mmol) and THF:water (9:1, 20 mL) gave the desired amine, ((5R,6S)-5-((3aS,6S,7R,7aS)-7-(aminomethyl)-3,3a-dimethyl-3a,4,5,6,7,7a-hexahydro-1H-inden-6-yl)-5-methyl-4,5,6,7-tetrahydrobenzo[d]isoxazol-6-yl)methanol (Compound Ih-2, 70 mg, 3% over 3 steps) and ((5R,6S)-5-((4R,5S)-4-(aminomethyl)-1,1-dimethyl-2,3,4,5,6,7-hexahydro-1H-inden-5-yl)-5-methyl-4,5,6,7-tetrahydrobenzo[d]isoxazol-6-yl)methanol (Compound Ih-3, 110 mg, 5% over 3 steps), as off white solids after purification and separation by preparative HPLC (Method 3c).

Compound Ih-2:

LCMS: (Method 1e) MS m/z: 345.2 (M+1), t$_R$: 2.801 min, Purity: 93.06% (UV).

HPLC: (Method 2e) t$_R$: 4.743 min, Purity: 88.58% (UV).

$^1$H-NMR (400 MHz, CD$_3$OD): δ 8.14 (s, 1H), 4.01 (dd, J=3.2, 10.8 Hz, 1H), 3.51-3.45 (m, 1H), 3.17 (dd, J=5.7, 17.8 Hz, 1H), 3.03 (dd, J=3.2, 13.0 Hz, 1H), 280 (dd, J=9.2, 13.0 Hz, 1H), 2.62-2.55 (m, 1H), 2.50-2.41 (m, 3H), 2.31-2.18 (m, 2H), 2.10-1.90 (m, 4H), 1.84-1.83 (m, 1H), 1.80-1.67 (m, 3H), 1.04 (s, 3H), 0.98 (s, 3H), 0.89 (s, 3H).

Compound Ih-3:

LCMS: (Method 1e) MS m/z: 345.2 (M+1), t$_R$: 2.723 min, Purity: 88.43% (UV).

HPLC: (Method 2b) t$_R$: 4.712 min, Purity: 88.03% (UV).

$^1$H-NMR (400 MHz, CD$_3$OD): δ 8.22 (s, 1H), 5.35 (s, 1H), 3.94 (dd, J=2.8, 10.8 Hz, 1H), 3.47-3.42 (m, 2H), 3.19-3.14 (m, 2H), 2.73-2.57 (m, 2H), 2.40-2.36 (m, 1H), 2.26-2.23 (m, 3H), 2.22-1.97 (m, 2H), 1.80-1.61 (m, 7H), 1.35-1.31 (m, 1H), 1.05 (s, 3H), 0.86 (s, 3H).

Synthetic Example 52

Synthesis of ((3aS,4R,5S,7aS)-5-((5R,6S)-6-(hydroxymethyl)-2,5-dimethyl-4,5,6,7-tetrahydrobenzo[d]oxazol-5-yl)-7a-methyl-1-methyleneoctahydro-1H-inden-4-yl)methanol (Compound Ii-1)

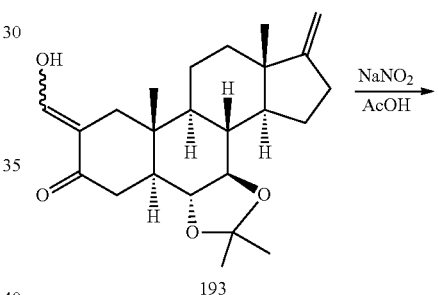

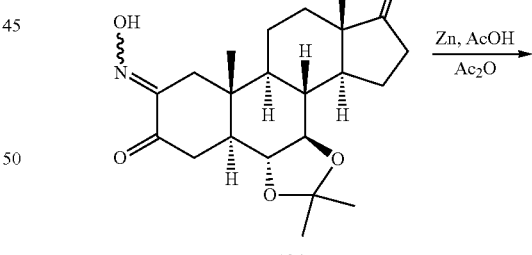

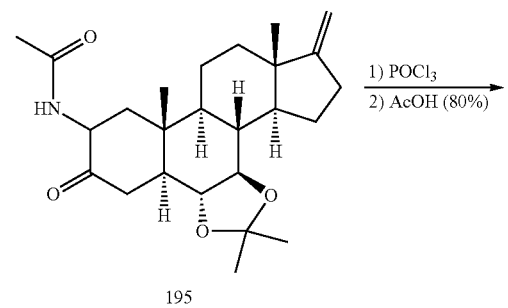

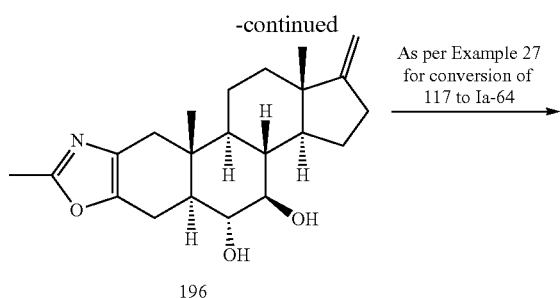

As per Example 27 for conversion of 117 to Ia-64

196

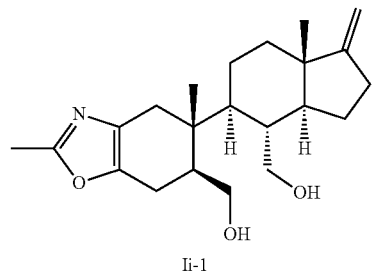

Ii-1

Oxime formation of (4aR,4bS,6aS,9aS,9bR,9cR,12aR,12bS)-3-(hydroxymethyl ene)-4a,6a,11,11-tetra methyl-7-methylenehexadecahydro-2H-cyclopenta[1,2]phenanthro[9,10-d][1,3]dioxol-2-one (Compound 19, as prepared in U.S. Pat. No. 9,765,085), followed by oxime formation to obtain Compound 194, Beckmann rearrangement to obtain Compound 195, and cyclization followed by deprotection provided Compound 196. Following the procedure as described in Synthetic Example 27, for the conversion of Compound 117 to Compound Ia-64 and making non-critical variations using Compound 196 to replace Compound 117, the title compound, ((3aS,4R,5S,7aS)-5-((5R,6S)-6-(hydroxymethyl)-2,5-dimethyl-4,5,67-tetrahydrobenze[d]oxazol-5-yl)-7a-methyl-1-methyleneoctahydro-1H-inden-4-yl)methanol (Compound Ii-1), was obtained.

LCMS: (Method 1h) MS m/z: 360.2 (M+1), $t_R$: 2.806 min, Purity: 85.42% (UV).

Synthetic Example 52.1

((5R,6S)-5-((3aS,4R,5S,7aS)-4-(aminomethyl)-7a-methyl-1-methyleneoctahydro-1H-inden-5-yl)-2,5-dimethyl-4,5,6,7-tetrahydrobenzo[d]oxazol-6-yl)methanol (Compound Ii-2)

Following the procedure as described in Synthetic Example 26 and making non-critical variations using Ii-1 (from Example 51) to replace Ia-62, the title compound, ((5R,6S)-5-((3aS,4R,5S,7aS)-4-(aminomethyl)-7a-methyl-1-methyleneoctahydro-1H-inden-5-yl)-2,5-dimethyl-4,5,6,7-tetrahydrobenzo[d]oxazol-6-yl)methanol (Compound Ii-2), was obtained.

LCMS: (Method 1h) MS m/z: 359.3 (M+1), $t_R$: 2.533 min, Purity: 82.04% (UV).

Biological Example 1

Rat Dorsal Root Ganglion Excitability Response of Representative Compounds

Dorsal root ganglions (DRGs) were dissected from adult rats. The tissue was processed, and cells were seeded into call culture plates (48 center wells of one quadrant in 384-well plates) and cultured for 2 days prior to Electrical field stimulation (EFS). To visualize the neuronal excitability response, intracellular $Ca^{+2}$ transients were monitored using the $Ca^{+2}$ indicator, Ca5. Ca5 was added to the cultures 1 h prior to EFS. Representative test compounds of the invention (i.e., test compounds) and reference compound, tetracaine, were added in concentration-response format encompassing six concentrations, performed in duplicate. The highest concentration tested was typically 30 μM with 1 in 3 dilutions generating the subsequent concentrations.

Effects on DRG excitability by the test compounds and standard were evaluated using four EFS protocols as disclosed in Table 2.

TABLE 2

EFS PROTOCOL PARAMETERS

| Protocol # | Voltage (V) | Frequency (Hz) | Pulse duration (ms) | # of pulses |
|---|---|---|---|---|
| 1 | 20 | 5 | 0.3 | 25 |
| 2 | 20 | 30 | 0.3 | 150 |
| 3 | 30 | 5 | 0.3 | 25 |
| 4 | 30 | 30 | 0.3 | 150 |

Experimental results were performed using two separate sets of plates using separate test compound and standard dilutions, to provide n=2. In the first set of experiments, compounds were added 24 h prior to EFS to increase the possibility to also detect more long-term compound effects. In the second set of experiments the compounds were added directly prior to EFS. Excitability response to EFS was analyzed as the average fluorescence ratio (peak/baseline) change per well. All plates were evaluated using high content imaging equipment post-EFS, imaging the Ca5 background staining to detect any possible compound-related toxic effects.

According to the above assay, the test compounds listed in Table 3 below were found to modulate Rat DRG excitability at the concentrations shown. Average response by the standard compound, tetracaine, was 4.05 μM. Scoring for the test compounds was as follows: "A" represents an $EC_{50}$ below 2 M, "B" represents an $EC_{50}$ between 2 and 6 μM, "C" represents an $EC_{50}$ between 6 and 15 μM and "D" represents an $EC_{50}$ above 15 μM.

TABLE 3

| Cpd. No. | Scoring |
|---|---|
| Ia-1 | C |
| Ia-2 | D |
| Ia-3 | B |
| Ia-6 | C |
| Ia-8 | B |
| Ia-11 | B |
| Ia-12 | B |
| Ia-13 | B |
| Ia-16 | B |
| Ia-19 | B |
| Ia-20 | C |
| Ia-22 | B |
| Ia-23 | B |
| Ia-27 | C |
| Ia-29 | C |
| Ia-32 | D |
| Ia-33 | C |
| Ia-34 | C |
| Ia-35 | A |
| Ia-36 | B |
| Ia-37 | A |
| Ia-38 | A |

TABLE 3-continued

| Cpd. No. | Scoring |
|---|---|
| Ia-40 | B |
| Ia-41 | A |
| Ia-42 | A |
| Ia-43 | A |
| Ia-47 | C |
| Ia-48 | C |
| Ia-65 | C |
| Ia-66 | D |
| Ia-72 | D |
| Ia-76 | C |
| Ia-82 | C |
| Ib-2 | D |
| Ic-1 | D |
| Ic-3 | D |
| Id-1 | C |
| Ig-1 | C |

Biological Example 2

T Cell Proliferation and Cytokine Release Activity of Representative Compounds

Spleens were obtained from six male, CD-1 outbred mice, approximately 8 weeks old. Cells were harvested under sterile conditions by forcing each spleen though a cell filter (pore size 100 µm diameter). A homogenous cell suspension was obtained by washing the cells in fresh medium and passing cells through a smaller cell filter (pore size 70 µm).

Untouched T cells were isolated using the Pan T cell isolation kit (Miltenyi Biotech). Briefly, cells were counted and incubated with the required volume of antibody cocktail for 5 minutes at 4° C. before addition of microbeads and incubation for 10 minutes at 4° C. Labeled cells were retained in a magnetic column while unlabeled cells (T cells) passed through the column and were retained for use in the assay.

Cell viability was assessed by Trypan Blue exclusion and found to be >99% prior to transfer to plates. Isolated T cells were seeded out in 96 well plates at a density of 50,000 cells per well and allowed to incubate for 60 minutes in a humidified cell culture (37° C., 5% $CO_2$) incubator prior to compound treatment. The media used for this assay (Tex-MACS, Miltenyi Biotech) was previously optimized for proliferation of T cells in serum free conditions.

Representative compounds of the invention (i.e., test compounds) were prepared as 30 mM stocks in 100% DMSO. Test compounds were initially diluted in media to yield 3 mM stocks before an additional 1:10 dilution in media was performed to yield working stocks of 300 µM (1% DMSO). Subsequent dilutions were performed in media (supplemented with 1% DMSO). When added to the assay plates (1:10 dilution), these yielded final concentrations in the assay plates of in 0.1% DMSO. The reference compound, Cyclosporin A, was prepared in an identical manner as above.

Unstimulated and Stimulated Control wells received an identical volume of TexMACS media/1% DMSO at this time, resulting in a final concentration of 0.1% DMSO across the plate. Mouse anti-CD3/anti-CD28 dynabeads were prepared (following the manufacturers' instructions) in TexMACS media and added to appropriate wells to achieve a final concentration of 1 bead per cell. Unstimulated Control wells then received an identical volume of Tex-MACS. Plates were centrifuged 72 hours after addition of dynabeads, (300×g for 3 minutes) to pellet the cells and 60% of the supernatant was removed to a fresh plate for analysis by ELISA. After removal of 60% of the supernatant for subsequent ELISA, cell proliferation was assessed using the CCK-8 assay.

According to the above assay, the test compounds listed in Table 4 below were found to modulate cell proliferation at the concentrations shown. Average response by the standard compound, cyclosporin A, was 1 uM. Scoring for the representative compounds was as follows: "A" represents an $IC_{50}$ below 2 µM, "B" represents an $IC_{50}$ between 2 and 6 µM, "C" represents an $IC_{50}$ between 6 and 15 and "D" represents an $IC_{50}$ above 15 µM.

TABLE 4

| Cpd. No. | Scoring |
|---|---|
| Ia-1 | C |
| Ia-3 | A |
| Ia-6 | A |
| Ia-7 | A |
| Ia-30 | C |
| Ia-31 | B |
| Ia-32 | C |

Biological Example 3

Human Dorsal Root Ganglion (DRG) Excitability Response of Representative Compounds Human DRGs are transferred into a dissection vessel containing a cold (4° C.), fresh proprietary dissection solution. DRGs are maintained completely submerged in dissection solution followed by dissection by an appropriate method.

Cells are plated into a 96 well plate. Calcium dye (Fluo 8-AM) is loaded in each well for a period of 20 to 25 min, maintaining temperature at ambient. The baseline excitability profile (ability of firing action potentials) of the cells is assessed at both low and high threshold stimulations using optical EFS. Following baseline profiling, cells are subjected to test compounds.

Representative compounds of the invention (i.e., test compounds) are added to cells and the cells are stimulated (using EFS) to induce action potentials at regular intervals, according to the parameters outlined in Table 5. Four concentrations of each compound are utilized and directly injected into separate wells to allow for determination of a dose response ($IC_{50}$). At the end of the protocol, the nociceptor positive control compound (capsaicin) is perfused into the cells at 200 nM and signal recorded. TTX (300 nM) is also examined using this protocol in a separate well.

TABLE 5

| EFS PROTOCOL AND RECORDING SEQUENCE | |
|---|---|
| Action | Parameter/Detail |
| Baseline Low Voltage | 2 s recording with stimulation (5 Hz) |
| Rest | 3 min |
| Baseline High Voltage | 2 s recording with stimulation (5 Hz) |
| Preincubation of Test compounds | 5 min |
| Test Compound Low Votage Signal | 2 s recording with stimulation (5 Hz) |
| Rest | 3 min |

TABLE 5-continued

EFS PROTOCOL AND RECORDING SEQUENCE

| Action | Parameter/Detail |
| --- | --- |
| Test Compound High Votage Signal | 2 s recording with stimulation (5 Hz) |
| Washout | 5 min |
| Capsaicin | 20 s (recording 3 min) |

Recordings are performed in stream mode at 100 Hz for the EFS portion of the above protocol and in time lapse model at 0.2 Hz for the final step utilizing capsaicin. For each concentration tested, the number of cells blocked vs baseline will be counted at different thresholds.

Compounds of the invention may be tested in this assay to determine their ability to modulate human DRG excitability.

According to the above assay, the test compounds listed in Table 6 below were found to modulate cell proliferation at the concentrations shown. Average response by the standard compound, cyclosporin A, was 1 μM. Scoring for the representative compounds was as follows: "A" represents an $IC_{50}$ below 2 μM, "B" represents an $IC_{50}$ between 2 and 6 μM, "C" represents an $IC_{50}$ between 6 and 15 and "D" represents an $IC_{50}$ above 15 μM.

TABLE 6

| Cpd. No. | Scoring |
| --- | --- |
| Ia-1 | A |

Biological Example 4

Pulmonary LPS Challenge Assay of Representative Compounds in Mice

Mice (male, C57Bl/6) were acclimatized for a period of about 7 days before initiation of the experiment and randomized on the day prior to treatment. Mice received vehicle or representative test compounds of the invention (i.e., test compounds) once daily for three days by oral gavage on Day −2, Day −1 and on Day 0 (the last dose being 1 h prior to LPS administration). One group of mice received the reference standard, dexamethasone, once, IP on Day 0 at 1 h prior to LPS administration. Pulmonary inflammation was induced in all animals except the sham control animals by intratracheal instillation of 20 μg LPS per animal in 50 μl saline. Sham control animals received 50 μl saline alone.

Twenty-four hours post LPS administration, animals were euthanized and the trachea was cannulated. Cold Hanks Balanced Salt Solution (HBSS) (SIGMA; Catalogue number: H1387), pH 7.2, was infused into the lungs and bronchoalveolar lavage fluid (BALF) was collected.

Total leukocyte counts were performed from the collected BALF using a mini flow-cytometer and differential counts were performed in cytospin smears stained with Leishman's staining manually. ELISA kits were used for quantification of cytokines in the BALF (TNFα, IL-1β, IL-6 and KC). Reagents, samples and standards were prepared as per kit manual. Total protein analysis in BALF samples were performed using the Biorad protein assay reagent.

According to the above assay, test compounds were found to modulate inflammatory markers in BALF, indicating efficacy against LPS-induced inflammation. In particular, Compound Ia-1 induced 44% protection from neutrophilia at 30 mg/kg. This was the same % protection as the reference compound, dexamethasone, at 3.0 mg/kg.

Other compounds of the invention tested in this assay were Compounds Ia-29, Ia-44 and Ia-66.

Biological Example 5

Formalin Pain Assay of Representative Compounds in Mice

Mice (male, C57BL/6) were placed singly in a Perspex chamber for approximately 30 min on three successive days to acclimate and thereby reduce stress-induced behaviors. On the fourth day, the experimental animals received a 25 μl injection of 2.5% formalin beneath the left plantar skin using a 29-gauge syringe. Animals were administered vehicle, reference standard Tramadol or representative compounds of the invention (i.e., test compounds) prior to formalin injection. The total time spent on flinches/licking/biting of the hind paw was recorded by visual observation for every 5 min period/interval for total observation duration of 60 min in two phases, the early phase (0-5 min) and the late phase (15-40 min). Observers were blinded to the treatment group allocation.

According to the above assay, the test compounds listed in Table 7 below were active in the formalin pain assay in mice at concentrations disclosed. Average AUC % Inhibition by the reference compound, tramadol was 59%. For test compounds, the % protection from 0-60 min was used to assess activity. Scoring for the test compounds was as follows: "A" represents a % protection of 81 to 100%, "B" represents a % protection of 61 to 80%, "C" represents a % protection of 31 to 60% and "D" represents a % protection of 0 to 30%.

TABLE 7

| Cpd. No. | Scoring |
| --- | --- |
| Ia-1 | B |
| Ia-6 | C |
| Ia-8 | D |
| Ia-27 | D |
| Ia-29 | D |
| Ia-32 | C |
| Ia-33 | C |
| Ia-34 | C |
| Ia-66 | D |
| Ig-1 | C |

In particular, during the early phase, which measures neurogenic pain, Compound Ia-1 demonstrated a 59% inhibition at a 30 mg/kg dose as compared to 51% inhibition by the reference compound, tramadol, at a 10 mg/kg dose. During the late phase, which measures inflammatory pain, Compound Ia-1 demonstrated a 52% inhibition at a 30 mg/kg dose as compared to 62% inhibition at a 10 mg/kg dose by the reference compound, tramadol.

Biological Example 6

TNBS Colitis Assay of Representative Compounds in Rats Rats (male, Sprague-Dawley) were anaesthetized and a solution of TNBS (48 mg/kg) in ethanol, was instilled intra-rectally to induce colitis, 1 h after oral dosing of representative compounds of the invention (i.e., test compounds). Test compounds were dosed PO, QD for 7 days, using prednisolone as a reference standard. Rats were observed for body weight loss and fecal output. On Day 7, rats were euthanized and the colon was evaluated for length, weight, wall thickness, ulcer number and length and for the presence of adhesions and strictures. A colonic score was calculated based on the severity of the colonic parameters.

According to the above assay, Compound Ia-1, when tested in this assay, demonstrated 36% inhibition of the colonic score at 30 mg/kg dose as compared to 68% reduction at a 10 mg/kg dose of the reference standard, prednisolone.

Biological Example 7

Cyclophosphamide-Induced Cystitis in Rats (Visceral Pain)

Representative compounds of the invention (i.e., test compounds) were administered to female Sprague-Dawley rats, for four days by oral gavage in 0.9% saline. Two hours after the fourth dose, the rats were challenged by intraperitoneal administration of cyclophosphamide (150 mg/kg). Referred mechanical sensitivity was measured four hours later by applying a series of eight von Frey filaments to the lower abdomen, three times each for 1-2 seconds with a 5 second interval between applications. Responses were scored (zero-no response; one-response, two-response and change of position, and three-response, change of position and licking the site or vocalization), totaled and the percent of maximal possible nociceptive score calculated. Ibuprofen was used as a reference standard.

According to the above assay, Compound Ia-1, when tested in this assay, increased the nociceptive threshold of 70-91% of baseline (pre-challenge) levels at 0.3 to 1.0 mg/kg dose as compared to the reference standard's, ibuprofen, demonstration of 123% of baseline levels at 300 mg/kg dose.

Biological Example 8

Rat Ketamine Cystitis (Visceral Pain)

Rats (female, Sprague-Dawley) received daily intraperitoneal injections of saline (sham control) or ketamine (50 mg/kg) for 14 days. Representative compounds of the invention (i.e., test compounds) were administered PO, QD starting on Day 0 at doses of 10, 3 or 1 mg/kg and Tramadol was used as a reference control compound at 10 mg/kg. Referred mechanical sensitivity was assessed on Day 7 and Day 14 by application of a series of von Frey filaments to the lower abdomen and the nociceptive threshold was scored.

According to the above assay, Compound Ia-1 demonstrated an increase of 61% (relative to unchallenged) in the nociceptive threshold at 1.0 mg/kg dose, an increase of 69% (relative to unchallenged) at 3.0 mg/kg dose and an increase of 85% (relative to unchallenged) at 10 mg/kg dose. The reference compounds, tramadol, demonstrated an increase of 85% (relative to unchallenged) at 10 mg/kg dose.

Biological Example 9

Rat Chronic Prostatitis/Chronic Pelvic Pain (Pelvic Pain)

Representative compounds of the invention (i.e., test compounds) were administered for 11 days by oral gavage in 0.9% saline (3, 10 or 30 mg/kg QD; 5 mL/kg dose volume) to male Sprague-Dawley rats. Carrageenan-mediated chronic prostatitis/chronic pelvic pain (CP/CPPS) established in rats (10 per group) by administration of an intraprostatic injection of carrageenan (~12.5 µL/lobe of a 30 mg/mL solution) into both ventral prostate lobes, on Day 0. Referred mechanical sensitivity was measured on Days 0, 1, 3 and 7, 2 hours after test compound, or vehicle (saline) administration, by applying 6 von Frey filaments with increasing forces of 0.16-2 g to the scrotal skin area, 3 times each for 1-2 seconds, with a 5-second interval between applications. Responses were scored (zero-no response; one-reaction of the animal, two-jump, and three-licking the site) and expressed as the nociceptive threshold for each day of assessment. Ibuprofen was used as a reference standard.

According to the above assay, Compound Ia-1 restored nociceptive threshold to 65% of baseline on Day 3 at the 30 mg/kg dose as compared to the reference standard, ibuprofen (300 mg/kg), which restored the threshold to 120% of the baseline.

Biological Example 10

Rat Monosodium Iodoacetate-Induced Osteoarthritis (Osteoarthritis/Inflammatory Pain)

Representative compounds of the invention (i.e., test compounds) were administered to rats (male, Wistar) PO, QD, at 3 or 30 mg/kg, starting on Day 0 through to Day 21 of the study. Osteoarthritis was modeled by intra-articular injection of 3 mg of monosodium iodoacetate (MIA) in the right knee. Knee swelling, paw withdrawal threshold (mechanical allodynia) and the difference in weight bearing were measured on Day 0 (pre-induction) and on Days 3, 7, 14 and 21 post-MIA injection. Tramadol was used as a reference standard.

According to the above assay, Compound Ia-1 demonstrated a 50% reduction difference in weight bearing at 3.0 mg/kg dose as compared to the vehicle and a 57% reduction at 30 mg/kg as compared to the vehicle. The reference compound, tramadol, demonstrated a 79% reduction at 10 mg/kg as compared to the vehicle.

On Day 3, Compound Ia-1 demonstrated a reduction in knee diameter as compared to the vehicle of 23% at 3.0 mg/kg and a 43% reduction at 30 mg/kg. The reference compound demonstrated a 11% reduction at 30 mg/kg.

Biological Example 11

Complete Freund's Adjuvant (CFA) Model of Inflammatory Pain in Rats (Inflammatory Pain)

Representative compounds of the invention (i.e., test compounds) were tested in this model of inflammatory pain. The rats (male, Wistar) were acclimatized to the instruments (plantar test surface and dynamic plantar aesthesiometer) on two consecutive days prior to the initiation of the study. On Day 0, basal paw withdrawal latency and paw withdrawal threshold were taken and animals were randomized to different groups. Complete Freund's Adjuvant (CFA) at 1 mg/mL (0.1 mL) was injected into the plantar surface of right hind paw. Test compounds (3 or 30 mg/kg) were administered PO, twice (Day 0 and Day 1) or once, on Day 1 (24 h after CFA). Thermal hyperalgesia and mechanical allodynia were assessed at 0 (baseline), 1, 3 and 6 h after administration of the test compound on Day 1. Diclofenac was used as a reference compound, given once on Day 1.

According to the above assay, Compound Ia-1 demonstrated an increase in the paw withdrawal threshold of 31% at a 30 mg/kg dose as compared to 62% by the reference compound, diclofenac (30 mg/kg).

Biological Example 12

Rat Carrageenan-Induced Hyperalgesia and Paw Edema (Inflammatory Pain)

Representative compounds of the invention (i.e., test compounds) were administered PO, QD for 3 days prior to carrageenan injection, once at 1 h prior to carrageen, or at 5 min or 1 h post-challenge to rats (male, Sprague-Dawley). Rats received either an intraplantar injection of saline (sham) or carrageen (0.1 mL of a 2% solution [w/v]) in the right hind paw. Mechanical hyperalgesia (using an analgesymeter) and paw volume (using a digital plethysmometer) were measured at baseline (0 hr), 2, 4 and 6 h post carrageenan injection for all the animals. Celecoxib, given 1 h prior to carrageen challenge, was used as a reference standard.

According to the above assay, Compound Ia-1, at 30 mg/kg, demonstrated an average increase of 41% in the paw withdrawal threshold as compared to the vehicle when administered at the time of, or 1 h after challenge. The reference compound, celecoxib, demonstrated a 59% increase at 10 mg/kg.

Biological Example 13

Spinal Nerve Ligation (Neuropathic Pain)

Rats (male, Sprague-Dawley) were anaesthetized and placed in a prone position and the left paraspinal muscles were separated from the spinous processes at the L6-S2 levels. The L6 transverse process was carefully removed to visually identify the L4-L6 spinal nerves. The left L5 spinal nerves were isolated and tightly ligated with 6-0 silk thread. The skin was sutured to close the open tissue and animals were allowed to recover for 1 week before pain assessment. Basal readings for mechanical allodynia and thermal hyperalgesia were performed using a dynamic plantar aesthesiometer and plantar test surface, respectively, before surgery. On Day 7 following surgery, mechanical allodynia and thermal hyperalgesia were assessed and animals were randomized into treatment groups based on these baseline readings. From Day 7 to Day 14, the rats either received vehicle, tramadol (reference standard) or representative compounds of the invention (i.e., test compounds). Thermal hyperalgesia and mechanical allodynia were tested at 0, 60 and 120 minutes post administration of compounds on Days 7 and 14.

According to the above assay, Compound Ia-1 demonstrated an overall 82% increase in paw withdrawal threshold at 30 mg/kg, 62% at 10 mg/kg and 48% at 3 mg/kg, as compared to the vehicle. The reference compound demonstrated a 77% increase at 10 mg/kg.

Biological Example 14

Bleomycin Lung Fibrosis

Mice (male, C57BL/6) were randomized into treatment groups and fibrosis was induced by intratracheal administration of bleomycin. Treatment with representative compounds of the invention (i.e., test compounds) or reference standard (pirfenidone) was initiated on Day −1 and administered daily unto Day 7 or Day 21. For groups undergoing bronchoalveolar lavage (BAL), the trachea was cannulated and infused with ice cold Hank's Balanced Salt Solution (HBSS, pH 7.2). The collected lavage fluid was analyzed for cell numbers (total and differential counts) and levels of soluble TGFβ and collagen. For other groups, the lungs were either snap-frozen or formalin-fixed for further analyses.

According to the above assay, Compound Ia-1 demonstrated a reduction in BAL macrophages at Day 7 as compared to the vehicle of 35% at 30 mg/kg dose and of 41% at 3.0 mg/kg dose. The reference standard, pirfenidone, demonstrated a 30% reduction at 100 mg/kg dose.

In addition, Compound Ia-1 demonstrated a 31% reduction in fibrosis at Day 14 at 30 mg/kg dose and a 34% reduction at 30 mg/kg dose. The reference compound demonstrated a 46% reduction at 100 mg/kg dose.

Biological Example 15

Metabolism by Human Liver Microsomes

Representative compounds of the invention (i.e., test compounds) and the positive control, 7-ethoxycoumarin, were prepared as stock solutions at 10 mM in DMSO and eventually diluted to 10 μM in the test plate, with an appropriate amount of acetonitrle and tris HCl buffer. Final DMSO and acetonitrile concentrations were 0.01% and 0.5% respectively. NADPH was prepared in tris HCl buffer to a stock of 10 mM. A frozen aliquot of live microsomes was retrieved from the freezer (−80° C.) and thawed by placing the tube on wet ice. After thawing, the tubes were gently mixed and the required amount, transferred to tris HCl buffer. Test compounds or positive control were preincubated, separately, for 10 minutes, with liver microsomes (1 mg/mL protein), at 37° C., in 100 mM Tris HCl at pH 7.5. After preincubation the reaction was started by adding 1 mM NADPH (pre-equilibrated to 30° C.) and the reaction allowed to proceed for 60 minutes. At 60 minutes, a 50 μL aliquot was removed and quenched with 200 uL of acetonitrile containing a mixture of internal standards (Tolbutamide (500 ng/mL) and Telmistartan (500 ng/mL)) and vortexed then centrifuged at 4000 rmp for 10 minutes (Eppendorf 5810R). The supernatant was transferred to a 96 well plate for LC-MS/MS analysis.

An LC-MS/MS method was devised for the test compounds and the control, using a AB Sciex API 4000 system coupled to a NEXAR™ UHPLC (Shimadzu) system. Analytes were separated on a Phenomenex Kinetex C18 column (50×2.1 mm, 5 μm) using a gradient that was appropriate for each compound, at a flow rate of 1 ml/minute, utilizing a mobile phase of 0.1% formic acid in MILLI-Q™ water (A) and 0.1% formic acid in acetonitrile (B). The MS instrument was operated in positive mode (ESI+)/negative (ESI−). The multiple reaction monitoring (MRM) transition for test and control compounds was used for the LC-MS/MS analysis. MRM transitions for control compound 7-ethoxycoumarinm were Quadropole 1: 191.0, Quadropole 3: 163.0, dwell time: 75 msec, using curtain gas settings of 5 V, ion-spray voltage of 5500 V, temperature of 50° C. and gas settings for nebulizer and auxiliary set to 30 and 40 psi, respectively. The interface heater was kept on. Entrance potential and collision cell exit potential were varied to tune for a specific compound.

Using a suitable LC-MS/MS method, the percentage of drug remaining at 60 minutes (PCR60) was assessed by comparing the average analyte to internal standard area ratio at 60 minutes to the average analyte to internal standard area ratio at 0 time control, as a percentage, from a 5 to 10 μL sample injection.

According to the above assay, the representative compounds listed in Table 8 below were active in the Human liver microsome assay at 10 M and the % of drug remaining after 60 minutes (PDR60), in the presence of NADPH, was assessed by LC-MS/MS. Average PDR60 for the standard compound, 7-ethoxycoumarin was <=65% in the presence of NADPH. Scoring for the test compounds, in the presence of NADPH, was as follows: "A" represents a PDR$^{60}$ of 81 to 100%, "B" represents a PDR$^{60}$ of 61 to 80%, "C" represents a PDR$^{60}$ of 31 to 60% and "D" represents a PDR$^{60}$ of 0 to 30%.

TABLE 8

| Cpd. No. | Scoring |
|---|---|
| Ia-1 | B |
| Ia-2 | B |
| Ia-3 | D |
| Ia-5 | D |
| Ia-6 | A |
| Ia-8 | D |
| Ia-11 | B |
| Ia-12 | D |
| Ia-13 | A |
| Ia-16 | B |
| Ia-19 | B |
| Ia-20 | D |
| Ia-22 | D |
| Ia-28 | A |
| Ia-29 | C |
| Ia-32 | B |
| Ia-33 | B |
| Ia-34 | B |
| Ia-36 | A |
| Ia-41 | A |
| Ia-47 | D |
| Ia-48 | D |
| Ia-57 | A |
| Ia-58 | A |
| Ia-65 | A |
| Ia-66 | A |
| Ia-72 | D |
| Ia-76 | D |
| Ia-82 | B |
| Ib-2 | B |
| Ic-1 | A |
| Ic-3 | A |
| Id-1 | C |
| Ig-1 | A |

All of the U.S. patents, U.S. patent application publications, U.S. patent applications, foreign patents, foreign patent applications and non-patent publications referred to in this specification are incorporated herein by reference in their entireties.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

What is claimed is:
1. A compound of formula (I):

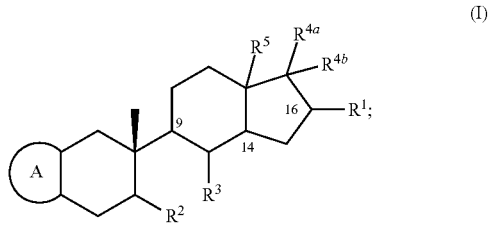

wherein:
(A) is an optionally substituted 5 to 14 membered fused N-heteroaryl, wherein the N-heteroaryl contains 1 to 13 carbon atoms and 1 to 6 nitrogen, oxygen or sulfur atoms; is fused to the cyclohexane; and optionally substituted by one or more substituents selected from the group consisting of alkyl, alkenyl, halo, haloalkyl, cyano, oxo, thioxo, nitro, thioxo, aryl, aralkyl, cycloalkyl, cycloalkylalkyl, heterocyclyl, heterocyclylalkyl, heteroaryl, heteroarylalkyl, —R$^{21}$—OR$^{20}$, —R$^{21}$—OC(O)—R$^{20}$, —R$^{21}$—N(R$^{20}$)$_2$, —R$^{21}$—C(O)R$^{20}$, —R$^{21}$—C(O)OR$^{20}$, —R$^{21}$—C(O)N(R$^{20}$)$_2$, —R$^{21}$—N(R$^{20}$)C(O)OR$^{22}$, —R$^{21}$—N(R$^{20}$)C(O)R$^{22}$, —R$^{21}$—N(R$^{20}$)S(O)$_p$R$^{22}$ where p is 1 to 2, —R$^{21}$—N=C(OR$^{20}$)R$^{20}$, —R$^{20}$, —R$^{21}$—S(O)$_p$OR$^{22}$ where p is 1 to 2, —R$^{21}$—S(O)$_t$R$^{22}$ where t is 0 to 2, and —R$^{21}$—S(O)$_p$N(R$^{20}$)$_2$ where p is 1 to 2; where each R$^{20}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each R$^{21}$ is independently a direct bond or a straight or branched alkylene chain; and each R$^{22}$ is alkyl, alkenyl, haloalkyl, cycloalkyl, cycloalkylalkyl, aryl, aralkyl, heterocyclyl, heterocyclylalkyl, heteroaryl or heteroarylalkyl;
R$^1$ is hydrogen or —R$^6$—OR$^7$;
R$^2$ is —R$^6$—OR$^7$ or —R$^6$—N(R$^8$)$_2$;
R$^3$ is —R$^6$—OR$^7$ or —R$^6$—N(R$^8$)$_2$;
R$^{4a}$ and R$^{4b}$ are each independently selected from hydrogen, alkyl or alkenyl;
or R$^{4a}$ is hydrogen, alkyl or alkenyl and R$^{4b}$ is a direct bond to the carbon to which R$^1$ is attached;
or R$^{4a}$ and R$^{4b}$ together form alkylidene;
R$^5$ is alkyl or R$^5$ is a direct bond to the carbon at C14;
each R$^6$ is independently selected from a direct bond or a straight or branched alkylene chain;
each R$^7$ is independently selected from hydrogen or alkyl; and
each R$^8$ is independently selected from hydrogen, alkyl or optionally substituted heteroarylalkyl,
wherein the heteroarylalkyl has a formula —R$_b$R$_i$,
wherein R$_b$ is an alkylene chain containing 1 to 12 carbon atoms and is optionally substituted by one selected from the group consisting of alkyl, alkenyl, halo, cyano, nitro, aryl, cycloalkyl, heterocyclyl, heteroaryl, oxo, trimethylsilanyl, —OR$^{20}$, —OC(O)—R$^{20}$, —N(R$^{20}$)$_2$, —C(O)R$^{20}$, —C(O)OR$^{20}$, —C(O)N(R$^{20}$)$_2$, —N(R$^{20}$)C(O)OR$^{22}$, —N(R$^{20}$)C(O)R$^{22}$, —N(R$^{20}$)S(O)$_p$R$^{22}$ where p is 1 to 2, —S(O)$_p$OR$^{22}$ where p is 1 to 2, —S(O)$_t$R$^{22}$ where t is 0 to 2, and —S(O)$_p$N(R$^{20}$)$_2$ where p is 1 to 2; where each R$^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each R$^{22}$ is alkyl, haloalkyl, cycloalkyl, cycloalkylalkyl, aryl, aralkyl, heterocyclyl, heterocylylalkyl, heteroaryl or heteroarylalkyl; and $R_i$ is a heteroaryl radical containing 1 to 13 carbon atoms and 1 to 6 nitrogen, oxygen or sulfur atoms; and optionally substituted by one or more substituents selected from the group consisting of alkyl, alkenyl, halo, haloalkyl, cyano, oxo, thioxo, nitro, thioxo, aryl, aralkyl, cycloalkyl, cycloalkylalkyl, heterocyclyl, heterocyclylalkyl, heteroaryl, heteroarylalkyl, —$R^{21}$—$OR^{20}$, —$R^{21}$—OC(O)—$R^{20}$, —$R^{21}$—N($R^{20}$)$_2$, —$R^{21}$—C(O)$R^{20}$, —$R^{21}$—C(O)$OR^{20}$, —$R^{21}$—C(O)N($R^{20}$)$_2$, —$R^{21}$—N($R^{20}$)C(O)$OR^{22}$, —$R^{21}$—N($R^{20}$)C(O)$R^{22}$, —$R^{21}$—N($R^{20}$)S(O)$_p R^{22}$ where p is 1 to 2, —$R^{21}$—N=C($OR^{20}$)$R^{20}$, —$R^{21}$—S(O)$_p OR^{22}$ where p is 1 to 2, —$R^{21}$—S(O)$_t R^{22}$ where t is 0 to 2, and —$R^{21}$—S(O)$_p$N($R^{20}$)$_2$ where p is 1 to 2; where each $R^{20}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; and each $R^{22}$ is alkyl, alkenyl, haloalkyl, cycloalkyl, cycloalkylalkyl, aryl, aralkyl, heterocyclyl, heterocyclylalkyl, heteroaryl or heteroarylalkyl;

or two $R^8$'s, together with the nitrogen to which they are attached, form an optionally substituted N-heterocyclyl or an optionally substituted N-heteroaryl, wherein the N-heterocyclyl contains 2 to 12 carbon atoms and from 1 to 6 heteroatoms selected from the group consisting of nitrogen, oxygen and sulfur; and optionally substituted by one or more substituents selected from the group consisting of alkyl, alkenyl, halo, haloalkyl, cyano, oxo, thioxo, nitro, aryl, aralkyl, cycloalkyl, cycloalkylalkyl, optionally substituted heterocyclyl, optionally substituted heterocyclylalkyl, optionally substituted heteroaryl, optionally substituted heteroarylalkyl, —$R^{21}$—$OR^{20}$, —$R^{21}$—OC(O)—$R^{20}$, —$R^{21}$—N($R^{20}$)$_2$, —$R^{21}$—C(O)$R^{20}$, —$R^{21}$—C(O)$OR^{20}$, —$R^{21}$—C(O)N($R^{20}$)$_2$, —$R^{21}$—N($R^{20}$)C(O)$OR^{22}$, —$R^{21}$—N($R^{20}$)C(O)$R^{22}$, —$R^{21}$—N($R^{20}$)S(O)$_p R^{22}$ (where p is 1 to 2), —$R^{21}$—N=C($OR^{20}$)$R^{20}$, —$R^{21}$—S(O)$_p OR^{22}$ (where p is 1 to 2), —$R^{21}$—S(O)$_t R^{22}$ (where t is 0 to 2), and —$R^{21}$—S(O)$_p$N($R^{20}$)$_2$ (where p is 1 to 2) where each $R^{20}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; and each $R^{22}$ is alkyl, alkenyl, haloalkyl, cycloalkyl, cycloalkylalkyl, aryl, aralkyl, heterocyclyl, heterocyclylalkyl, heteroaryl or heteroarylalkyl, and where the optional substituents on the heterocyclyl, heterocyclylalkyl, heteroaryl and heteroarylalkyl substitutents are selected from alkyl, halo or haloalkyl;

and wherein the N-heteroaryl contains 1 to 13 carbon atoms and 1 to 6 nitrogen, oxygen or sulfur atoms; and optionally substituted by one or more substituents selected from the group consisting of alkyl, alkenyl, halo, haloalkyl, cyano, oxo, thioxo, nitro, thioxo, aryl, aralkyl, cycloalkyl, cycloalkylalkyl, heterocyclyl, heterocyclylalkyl, heteroaryl, heteroarylalkyl, —$R^{21}$—$OR^{20}$, —$R^{21}$—OC(O)—$R^{20}$, —$R^{21}$—N($R^{20}$)$_2$, —$R^{21}$—C(O)$R^{20}$, —$R^{21}$—C(O)$OR^{20}$, —$R^{21}$—C(O)N($R^{20}$)$_2$, —$R^{21}$—N($R^{20}$)C(O)$OR^{22}$, —$R^{21}$—N($R^{20}$)C(O)$R^{22}$, —$R^{21}$—N($R^{20}$)S(O)$_p R^{22}$ where p is 1 to 2, —$R^{21}$—N=C($OR^{20}$)$R^{20}$, —$R^{21}$—S(O)$_p OR^{22}$ where p is 1 to 2, —$R^{21}$—S(O)$_t R^{22}$ where t is 0 to 2, and —$R^{21}$—S(O)$_p$N($R^{20}$)$_2$ where p is 1 to 2; where each $R^{20}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; and each $R^{22}$ is alkyl, alkenyl, haloalkyl, cycloalkyl, cycloalkylalkyl, aryl, aralkyl, heterocyclyl, heterocyclylalkyl, heteroaryl or heteroarylalkyl;

or a stereoisomer, enantiomer or tautomer thereof or mixtures thereof, or a pharmaceutically acceptable salt thereof.

2. The compound of claim 1 wherein:

Ⓐ is a fused 5-membered N-heteroaryl optionally substituted by one or more substituents selected from alkyl, haloalkyl, —C(O)$OR^7$, —N($R^8$)$_2$, —C(O)N($R^8$)$_2$, cycloalkyl, aryl, aralkyl or heteroaryl;

$R^1$ is hydrogen or —$R^6$—$OR^7$;

$R^2$ is —$R^6$—$OR^7$ or —$R^6$—N($R^8$)$_2$;

$R^3$ is —$R^6$—$OR^7$ or —$R^6$—N($R^8$)$_2$;

$R^{4a}$ and $R^{4b}$ are each independently selected from hydrogen, alkyl or alkenyl;

or $R^{4a}$ is hydrogen, alkyl or alkenyl and $R^{4b}$ is a direct bond to the carbon to which $R^1$ is attached;

or $R^{4a}$ and $R^{4b}$ together form alkylidene;

$R^5$ is alkyl or $R^5$ is a direct bond to the carbon at C14;

each $R^6$ is independently selected from a direct bond or a straight or branched alkylene chain;

each $R^7$ is independently selected from hydrogen or alkyl; and each $R^8$ is independently selected from hydrogen, alkyl or optionally substituted heteroarylalkyl, or two $R^8$'s, together with the nitrogen to which they are attached, form an optionally substituted N-heterocyclyl or an optionally substituted N-heteroaryl.

3. The compound of claim 2 wherein:

Ⓐ is selected from optionally substituted pyrazolyl, optionally substituted oxazolyl, optionally substituted isoxazolyl, optionally substituted pyrrolyl, optionally substituted thiazolyl, or optionally substituted thiadiazolyl;

$R^1$ is hydrogen or —$R^6$—$OR^7$;

$R^2$ is —$R^6$—$OR^7$ or —$R^6$—N($R^8$)$_2$;

$R^3$ is —$R^6$—$OR^7$ or —$R^6$—N($R^8$)$_2$;

$R^{4a}$ and $R^{4b}$ are each independently selected from hydrogen, alkyl or alkenyl;

or $R^{4a}$ is hydrogen, alkyl or alkenyl and $R^{4b}$ is a direct bond to the carbon to which $R^1$ is attached;

or $R^{4a}$ and $R^{4b}$ together form alkylidene;

$R^5$ is alkyl or $R^5$ is a direct bond to the carbon at C14;

each $R^6$ is independently selected from a direct bond or a straight or branched alkylene chain;

each $R^7$ is independently selected from hydrogen or alkyl; and each $R^8$ is independently selected from hydrogen, alkyl or optionally substituted heteroarylalkyl, or two $R^8$'s, together with the nitrogen to which they are attached, form an optionally substituted N-heterocyclyl or an optionally substituted N-heteroaryl.

4. The compound of claim 3 wherein:
Ⓐ is optionally substituted pyrazolyl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ and $R^{4b}$ are each independently selected from hydrogen, alkyl or alkenyl;
or $R^{4a}$ is hydrogen, alkyl or alkenyl and $R^{4b}$ is a direct bond to the carbon to which $R^1$ is attached;
or $R^{4a}$ and $R^{4b}$ together form alkylidene;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl, or two $R^8$'s, together with the nitrogen to which they are attached, form an optionally substituted N-heterocyclyl or an optionally substituted N-heteroaryl.

5. The compound of claim 4 wherein:
Ⓐ is optionally substituted pyrazolyl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ and $R^{4b}$ are each independently selected from hydrogen, alkyl or alkenyl;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two $R^8$'s, together with the nitrogen to which they are attached, form an optionally substituted N-heterocyclyl or an optionally substituted N-heteroaryl.

6. The compound of claim 5 selected from:
((5R,6S)-5-((1S,3aS,4S,5S,7aR)-4-(aminomethyl)-1-ethyl-7a-methyloctahydro-1H-inden-5-yl)-5-methyl-4,5,6,7-tetrahydro-1H-indazol-6-yl)methanol;
((5R,6S)-5-((4R,5S)-4-(hydroxymethyl)-1,1-dimethyl-2,3,4,5,6,7-hexahydro-1H-inden-5-yl)-5-methyl-4,5,6,7-tetrahydro-1H-indazol-6-yl)methanol;
((5R,6S)-5-((1S,3aS,4S,5S,7aR)-4-(hydroxymethyl)-1,7a-dimethyloctahydro-1H-inden-5-yl)-5-methyl-4,5,6,7-tetrahydro-1H-indazol-6-yl)methanol;
((5R,6S)-5-((4R,5S)-4-(aminomethyl)-1,1-dimethyl-2,3,4,5,6,7-hexahydro-1H-inden-5-yl)-5-methyl-4,5,6,7-tetrahydro-1H-indazol-6-yl)methanol;
((5R,6S)-5-((1S,3aS,4S,5S,7aR)-4-(aminomethyl)-1,7a-dimethyloctahydro-1H-inden-5-yl)-5-methyl-4,5,6,7-tetrahydro-1H-indazol-6-yl)methanol;
((3aS,4S,5S,7aS)-5-((5R,6S)-6-(hydroxymethyl)-5-methyl-4,5,6,7-tetrahydro-1H-indazol-5-yl)-7a-methyloctahydro-1H-inden-4-yl)methanol;
(2R,4R,5S)-4-(hydroxymethyl)-5-((5R,6S)-6-(hydroxymethyl)-5-methyl-4,5,6,7-tetrahydro-1H-indazol-5-yl)-1,1-dimethyl-2,3,4,5,6,7-hexahydro-1H-inden-2-ol;
((5R,6S)-5-((3aS,4S,5S,7aS)-4-(aminomethyl)-7a-methyloctahydro-1H-inden-5-yl)-5-methyl-4,5,6,7-tetrahydro-1H-indazol-6-yl)methanol;
((5R,6S)-5-((1R,3aS,4S,5S,7aR)-4-(aminomethyl)-7a-methyl-1-((R)-6-methylheptan-2-yl)octahydro-1H-inden-5-yl)-5-methyl-4,5,6,7-tetrahydro-1H-indazol-6-yl)methanol;
((5R,6S)-5-((1R,3aS,4S,5S,7aR)-4-((((2,2-difluorobenzo[d][1,3]dioxol-5-yl)methyl)amino)methyl)-7a-methyl-1-((R)-6-methylheptan-2-yl)octahydro-1H-inden-5-yl)-5-methyl-4,5,6,7-tetrahydro-1H-indazol-6-yl)methanol;
((5R,6S)-5-((1R,3aS,4S,5S,7aS)-4-(aminomethyl)-7a-methyl-1-(prop-1-en-2-yl)octahydro-1H-inden-5-yl)-5-methyl-4,5,6,7-tetrahydro-1H-indazol-6-yl)methanol;
((1R,3aS,4S,5S,7aR)-5-((5R,6S)-6-(aminomethyl)-5-methyl-4,5,6,7-tetrahydro-1H-indazol-5-yl)-7a-methyl-1-((R)-6-methylheptan-2-yl)octahydro-1H-inden-4-yl)methanamine;
((1R,3aS,4S,5S,7aR)-5-((5R,6S)-6-(hydroxymethyl)-5-methyl-4,5,6,7-tetrahydro-1H-indazol-5-yl)-7a-methyl-1-((R)-6-methylheptan-2-yl)octahydro-1H-inden-4-yl)methanol;
((1R,3aS,4S,5S,7aS)-5-((5R,6S)-6-(hydroxymethyl)-5-methyl-4,5,6,7-tetrahydro-1H-indazol-5-yl)-7a-methyl-1-(prop-1-en-2-yl)octahydro-1H-inden-4-yl)methanol;
((5R,6S)-5-((1S,3aS,4S,5S,7aR)-1,7a-dimethyl-4-((methylamino)methyl)octahydro-1H-inden-5-yl)-5-methyl-4,5,6,7-tetrahydro-1H-indazol-6-yl)methanol;
((5R,6S)-5-((1S,3aS,4S,5S,7aR)-4-(aminomethyl)-1,7a-dimethyloctahydro-1H-inden-5-yl)-5-methyl-2-phenyl-4,5,6,7-tetrahydro-2H-indazol-6-yl)methanol;
((5R,6S)-5-((1S,3aS,4S,5S,7aR)-4-(aminomethyl)-1,7a-dimethyloctahydro-1H-inden-5-yl)-5-methyl-1-phenyl-4,5,6,7-tetrahydro-1H-indazol-6-yl)methanol;
((5R,6S)-5-((1S,3aS,4S,5S,7aR)-4-(aminomethyl)-1,7a-dimethyloctahydro-1H-inden-5-yl)-1-cyclohexyl-5-methyl-4,5,6,7-tetrahydro-1H-indazol-6-yl)methanol;
((5R,6S)-5-((1S,3aS,4S,5S,7aR)-4-(aminomethyl)-1,7a-dimethyloctahydro-1H-inden-5-yl)-5-methyl-1-(pyridin-2-yl)-4,5,6,7-tetrahydro-1H-indazol-6-yl)methanol;
((5R,6S)-5-((1S,3aS,4S,5S,7aR)-4-(aminomethyl)-1,7a-dimethyloctahydro-1H-inden-5-yl)-5-methyl-2-(pyridin-2-yl)-4,5,6,7-tetrahydro-2H-indazol-6-yl)methanol;
((5R,6S)-5-((1S,3aS,4S,5S,7aR)-4-(aminomethyl)-1,7a-dimethyloctahydro-1H-inden-5-yl)-2-(tert-butyl)-5-methyl-4,5,6,7-tetrahydro-2H-indazol-6-yl)methanol;
((5R,6S)-5-((1S,3aS,4S,5S,7aR)-4-(aminomethyl)-1,7a-dimethyloctahydro-1H-inden-5-yl)-1-(tert-butyl)-5-methyl-4,5,6,7-tetrahydro-1H-indazol-6-yl)methanol;
((5R,6S)-5-((1S,3aS,4S,5S,7aR)-4-(aminomethyl)-1,7a-dimethyloctahydro-1H-inden-5-yl)-5-methyl-1-neopentyl-4,5,6,7-tetrahydro-1H-indazol-6-yl)methanol; or
((5R,6S)-5-((1S,3aS,4S,5S,7aR)-4-(aminomethyl)-1,7a-dimethyloctahydro-1H-inden-5-yl)-5-methyl-2-neopentyl-4,5,6,7-tetrahydro-2H-indazol-6-yl)methanol.

7. The compound of claim 4 wherein:
Ⓐ is optionally substituted pyrazolyl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;

$R^{4a}$ is hydrogen, alkyl or alkenyl and $R^{4b}$ is a direct bond to the carbon to which $R^1$ is attached;

$R^5$ is alkyl or $R^5$ is a direct bond to the carbon at C14;

each $R^6$ is independently selected from a direct bond or a straight or branched alkylene chain;

each $R^7$ is independently selected from hydrogen or alkyl; and each $R^8$ is independently selected from hydrogen, alkyl or optionally substituted heteroarylalkyl, or two $R^8$'s, together with the nitrogen to which they are attached, form an optionally substituted N-heterocyclyl or an optionally substituted N-heteroaryl.

8. The compound of claim 7 selected from:
((5R,6S)-5-((3aR,6S,7R,7aS)-7-(hydroxymethyl)-3a-methyl-3a,4,5,6,7,7a-hexahydro-1H-inden-6-yl)-5-methyl-4,5,6,7-tetrahydro-1H-indazol-6-yl)methanol;
((5R,6S)-5-((3aR,6S,7R,7aS)-7-(aminomethyl)-3a-methyl-3a,4,5,6,7,7a-hexahydro-1H-inden-6-yl)-5-methyl-4,5,6,7-tetrahydro-1H-indazol-6-yl)methanol; or
((5R,6S)-5-((3aS,6S,7R,7aS)-7-(aminomethyl)-3,3a-dimethyl-3a,4,5,6,7,7a-hexahydro-1H-inden-6-yl)-5-methyl-4,5,6,7-tetrahydro-1H-indazol-6-yl)methanol.

9. The compound of claim 4 wherein:
Ⓐ is optionally substituted pyrazolyl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ and $R^{4b}$ together form alkylidene;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two $R^8$'s, together with the nitrogen to which they are attached, form an optionally substituted N-heterocyclyl or an optionally substituted N-heteroaryl.

10. The compound of claim 9 selected from:
((5R,6S)-5-((3aS,4R,5S,7aS)-4-(aminomethyl)-7a-methyl-1-methyleneoctahydro-1H-inden-5-yl)-5-methyl-4,5,6,7-tetrahydro-1H-indazol-6-yl)methanol;
((5R,6S)-5-((3aS,4R,5S,7aS)-4-(aminomethyl)-7a-methyl-1-methyleneoctahydro-1H-inden-5-yl)-5-methyl-1-phenyl-4,5,6,7-tetrahydro-1H-indazol-6-yl)methanol;
(5R,6S)-6-(hydroxymethyl)-5-((3aS,4R,5S,7aS)-4-(hydroxymethyl)-7a-methyl-1-methyleneoctahydro-1H-inden-5-yl)-5-methyl-4,5,6,7-tetrahydro-1H-indazole-3-carboxylic acid;
(5R,6S)-6-(hydroxymethyl)-5-((3aS,4R,5S,7aS)-4-(hydroxymethyl)-7a-methyl-1-methyleneoctahydro-1H-inden-5-yl)-5-methyl-4,5,6,7-tetrahydro-1H-indazole-3-carboxamide;
((5R,6S)-6-(hydroxymethyl)-5-((3aS,4R,5S,7aS)-4-(hydroxymethyl)-7a-methyl-1-methyleneoctahydro-1H-inden-5-yl)-5-methyl-4,5,6,7-tetrahydro-1H-indazol-3-yl)(piperidin-1-yl)methanone;
((5R,6S)-6-(hydroxymethyl)-5-((3aS,4R,5S,7aS)-4-(hydroxymethyl)-7a-methyl-1-methyleneoctahydro-1H-inden-5-yl)-5-methyl-4,5,6,7-tetrahydro-1H-indazol-3-yl)(morpholino)methanone;
(2R,3aS,4R,5S,7aS)-4-(hydroxymethyl)-5-((5R,6S)-6-(hydroxymethyl)-5-methyl-4,5,6,7-tetrahydro-1H-indazol-5-yl)-7a-methyl-1-methyleneoctahydro-1H-inden-2-ol;
(2S,3aS,4R,5S,7aS)-4-(hydroxymethyl)-5-((5R,6S)-6-(hydroxymethyl)-5-methyl-4,5,6,7-tetrahydro-1H-indazol-5-yl)-7a-methyl-1-methyleneoctahydro-1H-inden-2-ol;
((5R,6S)-5-((3aS,4R,5S,7aS)-4-((((2,2-difluorobenzo[d][1,3]dioxol-5-yl)methyl)amino)methyl)-7a-methyl-1-methyleneoctahydro-1H-inden-5-yl)-5-methyl-4,5,6,7-tetrahydro-1H-indazol-6-yl)methanol;
((5R,6S)-5-((3aS,4R,5S,7aS)-4-(aminomethyl)-7a-methyl-1-methyleneoctahydro-1H-inden-5-yl)-3,5-dimethyl-4,5,6,7-tetrahydro-1H-indazol-6-yl)methanol;
((5R,6S)-5-((3aS,4R,5S,7aS)-4-(aminomethyl)-7a-methyl-1-methyleneoctahydro-1H-inden-5-yl)-5-methyl-3-(trifluoromethyl)-4,5,6,7-tetrahydro-1H-indazol-6-yl)methanol;
((5R,6S)-5-((3aS,4R,5S,7aS)-4-(aminomethyl)-7a-methyl-1-methyleneoctahydro-1H-inden-5-yl)-3-(difluoromethyl)-5-methyl-4,5,6,7-tetrahydro-1H-indazol-6-yl)methanol;
((5R,6S)-5-methyl-5-((3aS,4R,5S,7aS)-7a-methyl-1-methylene-4-(morpholinomethyl)octahydro-1H-inden-5-yl)-4,5,6,7-tetrahydro-1H-indazol-6-yl)methanol;
((5R,6S)-5-methyl-5-((3aS,4R,5S,7aS)-7a-methyl-1-methylene-4-((4-methylpiperazin-1-yl)methyl)octahydro-1H-inden-5-yl)-4,5,6,7-tetrahydro-1H-indazol-6-yl)methanol;
((5R,6S)-5-((3aS,4R,5S,7aS)-4-((1H-imidazol-1-yl)methyl)-7a-methyl-1-methyleneoctahydro-1H-inden-5-yl)-5-methyl-4,5,6,7-tetrahydro-1H-indazol-6-yl)methanol;
((5R,6S)-5-((3aS,4R,5S,7aS)-4-((1H-pyrazol-1-yl)methyl)-7a-methyl-1-methyleneoctahydro-1H-inden-5-yl)-5-methyl-4,5,6,7-tetrahydro-1H-indazol-6-yl)methanol;
((3aS,4R,5S,7aS)-5-((5R,6S)-6-(aminomethyl)-5-methyl-4,5,6,7-tetrahydro-1H-indazol-5-yl)-7a-methyl-1-methyleneoctahydro-1H-inden-4-yl)methanamine;
((5R,6S)-5-((3aS,4R,5S,7aS)-4-((1H-indol-1-yl)methyl)-7a-methyl-1-methyleneoctahydro-1H-inden-5-yl)-5-methyl-4,5,6,7-tetrahydro-1H-indazol-6-yl)methanol;
((5R,6S)-5-((3aS,4R,5S,7aS)-4-((6-amino-9H-purin-9-yl)methyl)-7a-methyl-1-methyleneoctahydro-1H-inden-5-yl)-5-methyl-4,5,6,7-tetrahydro-1H-indazol-6-yl)methanol;
((5R,6S)-5-((3aS,4R,5S,7aS)-4-((1H-benzo[d]imidazol-1-yl)methyl)-7a-methyl-1-methyleneoctahydro-1H-inden-5-yl)-5-methyl-4,5,6,7-tetrahydro-1H-indazol-6-yl)methanol;
((5R,6S)-5-methyl-5-((3aS,4R,5S,7aS)-7a-methyl-1-methylene-4-(thiomorpholinomethyl)octahydro-1H-inden-5-yl)-4,5,6,7-tetrahydro-1H-indazol-6-yl)methanol;
((5R,6S)-5-methyl-5-((3aS,4R,5S,7aS)-7a-methyl-1-methylene-4-(piperidin-1-ylmethyl)octahydro-1H-inden-5-yl)-4,5,6,7-tetrahydro-1H-indazol-6-yl)methanol;
(3aR,4R,5R,7aS)-7a-methyl-5-((5S,6S)-5-methyl-6-(morpholinomethyl)-4,5,6,7-tetrahydro-1H-indazol-5-yl)-1-methyleneoctahydro-1H-inden-4-ol;
((5R,6S)-5-((3aS,4R,5S,7aS)-4-(aminomethyl)-1-ethylidene-7a-methyloctahydro-1H-inden-5-yl)-5-methyl-4,5,6,7-tetrahydro-1H-indazol-6-yl)methanol;
((5R,6S)-5-((3aS,4R,5S,7aS,E)-1-ethylidene-4-(hydroxymethyl)-7a-methyloctahydro-1H-inden-5-yl)-5-methyl-4,5,6,7-tetrahydro-1H-indazol-6-yl)methanol;

((5R,6S)-5-methyl-5-((3aS,4R,5S,7aS)-7a-methyl-4-((methylamino)methyl)-1-methyleneoctahydro-1H-inden-5-yl)-4,5,6,7-tetrahydro-1H-indazol-6-yl)methanol;

((5R,6S)-5-((3aS,4R,5S,7aS)-4-((dimethylamino)methyl)-7a-methyl-1-methyleneoctahydro-1H-inden-5-yl)-5-methyl-4,5,6,7-tetrahydro-1H-indazol-6-yl)methanol;

((3aS,4R,5S,7aS)-7a-methyl-5-((5R,6S)-5-methyl-6-(piperidin-1-ylmethyl)-4,5,6,7-tetrahydro-1H-indazol-5-yl)-1-methyleneoctahydro-1H-inden-4-yl)methanol;

((3aS,4R,5S,7aS)-7a-methyl-5-((5R,6S)-5-methyl-6-(morpholinomethyl)-4,5,6,7-tetrahydro-1H-indazol-5-yl)-1-methyleneoctahydro-1H-inden-4-yl)methanol;

((3aS,4R,5S,7aS)-7a-methyl-5-((5R,6S)-5-methyl-6-(thiomorpholinomethyl)-4,5,6,7-tetrahydro-1H-indazol-5-yl)-1-methyleneoctahydro-1H-inden-4-yl)methanol;

((3aS,4R,5S,7aS)-7a-methyl-5-((5R,6S)-5-methyl-6-((4-methylpiperazin-1-yl)methyl)-4,5,6,7-tetrahydro-1H-indazol-5-yl)-1-methyleneoctahydro-1H-inden-4-yl)methanol;

((3aS,4R,5S,7aS)-7a-methyl-5-((5R,6S)-5-methyl-6-(piperidin-1-ylmethyl)-4,5,6,7-tetrahydro-1H-indazol-5-yl)-1-methyleneoctahydro-1H-inden-4-yl)methanamine;

((3aS,4R,5S,7aS)-7a-methyl-5-((5R,6S)-5-methyl-6-(morpholinomethyl)-4,5,6,7-tetrahydro-1H-indazol-5-yl)-1-methyleneoctahydro-1H-inden-4-yl)methanamine;

((3aS,4R,5S,7aS)-7a-methyl-5-((5R,6S)-5-methyl-6-(thiomorpholinomethyl)-4,5,6,7-tetrahydro-1H-indazol-5-yl)-1-methyleneoctahydro-1H-inden-4-yl)methanamine;

((3aS,4R,5S,7aS)-7a-methyl-5-((5R,6S)-5-methyl-6-((4-methylpiperazin-1-yl)methyl)-4,5,6,7-tetrahydro-1H-indazol-5-yl)-1-methyleneoctahydro-1H-inden-4-yl)methanamine;

((5R,6S)-5-((3aS,4R,5S,7aS)-4-(aminomethyl)-7a-methyl-1-methyleneoctahydro-1H-inden-5-yl)-2-(tert-butyl)-5-methyl-4,5,6,7-tetrahydro-2H-indazol-6-yl)methanol;

((5R,6S)-5-((3aS,4R,5S,7aS)-4-(aminomethyl)-7a-methyl-1-methyleneoctahydro-1H-inden-5-yl)-1-(tert-butyl)-5-methyl-4,5,6,7-tetrahydro-1H-indazol-6-yl)methanol;

((5R,6S)-5-((3aS,4R,5S,7aS)-4-(aminomethyl)-7a-methyl-1-methyleneoctahydro-1H-inden-5-yl)-2,5-dimethyl-4,5,6,7-tetrahydro-2H-indazol-6-yl)methanol;

((5R,6S)-5-((3aS,4R,5S,7aS)-4-(aminomethyl)-7a-methyl-1-methyleneoctahydro-1H-inden-5-yl)-1-cyclohexyl-5-methyl-4,5,6,7-tetrahydro-1H-indazol-6-yl)methanol;

((5R,6S)-5-((3aS,4R,5S,7aS)-4-(aminomethyl)-7a-methyl-1-methyleneoctahydro-1H-inden-5-yl)-5-methyl-2-(pyridin-2-yl)-4,5,6,7-tetrahydro-2H-indazol-6-yl)methanol;

((5R,6S)-5-((3aS,4R,5S,7aS)-4-(aminomethyl)-7a-methyl-1-methyleneoctahydro-1H-inden-5-yl)-2-benzyl-5-methyl-4,5,6,7-tetrahydro-2H-indazol-6-yl)methanol;

((5R,6S)-5-((3aS,4R,5S,7aS)-4-(aminomethyl)-7a-methyl-1-methyleneoctahydro-1H-inden-5-yl)-5-methyl-1-(pyridin-3-yl)-4,5,6,7-tetrahydro-1H-indazol-6-yl)methanol;

((5R,6S)-5-((3aS,4R,5S,7aS)-4-(aminomethyl)-7a-methyl-1-methyleneoctahydro-1H-inden-5-yl)-5-methyl-1-neopentyl-4,5,6,7-tetrahydro-1H-indazol-6-yl)methanol;

((5R,6S)-5-((3aS,4R,5S,7aS)-4-(aminomethyl)-7a-methyl-1-methyleneoctahydro-1H-inden-5-yl)-5-methyl-2-neopentyl-4,5,6,7-tetrahydro-2H-indazol-6-yl)methanol;

((3aS,4R,5S,7aS)-5-((5R,6S)-6-(aminomethyl)-5-methyl-4,5,6,7-tetrahydro-1H-indazol-5-yl)-7a-methyl-1-methyleneoctahydro-1H-inden-4-yl)methanol;

(3aR,4R,5R,7aS)-7a-methyl-5-((5S,6S)-5-methyl-6-((4-methylpiperazin-1-yl)methyl)-4,5,6,7-tetrahydro-1H-indazol-5-yl)-1-methyleneoctahydro-1H-inden-4-ol;

((5R,6S)-5-((3aS,4R,5S,7aS)-4-(aminomethyl)-7a-methyl-1-methyleneoctahydro-1H-inden-5-yl)-5-methyl-2-phenyl-4,5,6,7-tetrahydro-2H-indazol-6-yl)methanol;

((5R,6S)-5-((3aS,4R,5S,7aS)-4-(aminomethyl)-7a-methyl-1-methyleneoctahydro-1H-inden-5-yl)-5-methyl-1-(pyridin-2-yl)-4,5,6,7-tetrahydro-1H-indazol-6-yl)methanol;

((5R,6S)-5-((3aS,4R,5S,7aS)-4-(aminomethyl)-7a-methyl-1-methyleneoctahydro-1H-inden-5-yl)-1,5-dimethyl-4,5,6,7-tetrahydro-1H-indazol-6-yl)methanol;

((5R,6S)-5-((3aS,4R,5S,7aS)-4-(aminomethyl)-7a-methyl-1-methyleneoctahydro-1H-inden-5-yl)-2-cyclohexyl-5-methyl-4,5,6,7-tetrahydro-2H-indazol-6-yl)methanol;

((5R,6S)-5-((3aS,4R,5S,7aS)-4-(aminomethyl)-7a-methyl-1-methyleneoctahydro-1H-inden-5-yl)-1-benzyl-5-methyl-4,5,6,7-tetrahydro-1H-indazol-6-yl)methanol;

((5R,6S)-5-((3aS,4R,5S,7aS)-4-(aminomethyl)-7a-methyl-1-methyleneoctahydro-1H-inden-5-yl)-5-methyl-2-(pyridin-3-yl)-4,5,6,7-tetrahydro-2H-indazol-6-yl)methanol;

(3aR,4R,5R,7aS)-5-((5S,6S)-6-(hydroxymethyl)-5-methyl-2-(pyridin-2-yl)-4,5,6,7-tetrahydro-2H-indazol-5-yl)-7a-methyl-1-methyleneoctahydro-1H-inden-4-ol;

(3aR,4R,5R,7aS)-5-((5S,6S)-6-(hydroxymethyl)-5-methyl-2-(pyrazin-2-yl)-4,5,6,7-tetrahydro-2H-indazol-5-yl)-7a-methyl-1-methyleneoctahydro-1H-inden-4-ol; or (3aR,4R,5R,7aS)-5-((5S,6S)-6-(hydroxymethyl)-5-methyl-2-(pyrimidin-2-yl)-4,5,6,7-tetrahydro-2H-indazol-5-yl)-7a-methyl-1-methyleneoctahydro-1H-inden-4-ol.

11. The compound of claim 3 wherein:
Ⓐ is optionally substituted isoxazolyl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ and $R^{4b}$ are each independently selected from hydrogen, alkyl or alkenyl;
or $R^{4a}$ is hydrogen, alkyl or alkenyl and $R^{4b}$ is a direct bond to the carbon to which $R^1$ is attached;
or $R^{4a}$ and $R^{4b}$ together form alkylidene;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl, or two R⁸'s, together with the nitrogen to which they are attached, form an optionally substituted N-heterocyclyl or an optionally substituted N-heteroaryl.

12. The compound of claim 11 wherein:
Ⓐ is optionally substituted isoxazolyl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ and $R^{4b}$ are each independently selected from hydrogen, alkyl or alkenyl;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two R⁸'s, together with the nitrogen to which they are attached, form an optionally substituted N-heterocyclyl or an optionally substituted N-heteroaryl.

13. The compound of claim 12 selected from:
((5R,6S)-5-((4R,5S)-4-(aminomethyl)-1,1-dimethyl-2,3,4,5,6,7-hexahydro-1H-inden-5-yl)-5-methyl-4,5,6,7-tetrahydrobenzo[d]isoxazol-6-yl)methanol; or
((1R,3aS,4S,5S,7aR)-5-((5R,6S)-6-(hydroxymethyl)-5-methyl-4,5,6,7-tetrahydrobenzo[d]isoxazol-5-yl)-7a-methyl-1-((R)-6-methylheptan-2-yl)octahydro-1H-inden-4-yl)methanol.

14. The compound of claim 11 wherein:
Ⓐ is optionally substituted isoxazolyl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ is hydrogen, alkyl or alkenyl and $R^{4b}$ is a direct bond to the carbon to which $R^1$ is attached;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two R⁸'s, together with the nitrogen to which they are attached, form an optionally substituted N-heterocyclyl or an optionally substituted N-heteroaryl.

15. The compound of claim 14 selected from:
((5R,6S)-5-((3aS,6S,7R,7aS)-7-(aminomethyl)-3,3a-dimethyl-3a,4,5,6,7,7a-hexahydro-1H-inden-6-yl)-5-methyl-4,5,6,7-tetrahydrobenzo[d]isoxazol-6-yl)methanol.

16. The compound of claim 11 wherein:
Ⓐ is optionally substituted isoxazolyl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ and $R^{4b}$ together form alkylidene;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two R⁸'s, together with the nitrogen to which they are attached, form an optionally substituted N-heterocyclyl or an optionally substituted N-heteroaryl.

17. The compound of claim 16 selected from:
((5R,6S)-5-((3aS,4R,5S,7aS)-4-(aminomethyl)-7a-methyl-1-methyleneoctahydro-1H-inden-5-yl)-5-methyl-4,5,6,7-tetrahydrobenzo[c]isoxazol-6-yl)methanol.

18. The compound of claim 3 wherein:
Ⓐ is optionally substituted pyrrolyl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ and $R^{4b}$ are each independently selected from hydrogen, alkyl or alkenyl;
or $R^{4a}$ is hydrogen, alkyl or alkenyl and $R^{4b}$ is a direct bond to the carbon to which $R^1$ is attached;
or $R^{4a}$ and $R^{4b}$ together form alkylidene;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two R⁸'s, together with the nitrogen to which they are attached, form an optionally substituted N-heterocyclyl or an optionally substituted N-heteroaryl.

19. The compound of claim 18 wherein:
Ⓐ is optionally substituted pyrrolyl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ and $R^{4b}$ are each independently selected from hydrogen, alkyl or alkenyl;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two R⁸'s, together with the nitrogen to which they are attached, form an optionally substituted N-heterocyclyl or an optionally substituted N-heteroaryl.

20. The compound of claim 18 wherein:
Ⓐ is optionally substituted pyrrolyl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ is hydrogen, alkyl or alkenyl and $R^{4b}$ is a direct bond to the carbon to which $R^1$ is attached;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two R⁸'s, together with the nitrogen to which they are attached, form an optionally substituted N-heterocyclyl or an optionally substituted N-heteroaryl.

21. The compound of claim 18 wherein:
Ⓐ is optionally substituted pyrrolyl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ and $R^{4b}$ together form alkylidene;
$R^5$ is alkyl or $R^5$ is a direct bond to the carbon at C14;
each $R^6$ is independently selected from a direct bond or a straight or branched alkylene chain;

each R⁷ is independently selected from hydrogen or alkyl; and each R⁸ is independently selected from hydrogen, alkyl or optionally substituted heteroarylalkyl, or two R⁸'s, together with the nitrogen to which they are attached, form an optionally substituted N-heterocyclyl or an optionally substituted N-heteroaryl.

22. The compound of claim 21 selected from:
((5R,6S)-5-((3aS,4R,5S,7aS)-4-(aminomethyl)-7a-methyl-1-methyleneoctahydro-1H-inden-5-yl)-5-methyl-4,5,6,7-tetrahydro-1H-indol-6-yl)methanol.

23. The compound of claim 3 wherein:
Ⓐ is optionally substituted thiazolyl;
R¹ is hydrogen or —R⁶—OR⁷;
R² is —R⁶—OR⁷ or —R⁶—N(R⁸)₂;
R³ is —R⁶—OR⁷ or —R⁶—N(R⁸)₂;
R⁴ᵃ and R⁴ᵇ are each independently selected from hydrogen, alkyl or alkenyl;
or R⁴ᵃ is hydrogen, alkyl or alkenyl and R⁴ᵇ is a direct bond to the carbon to which R¹ is attached;
or R⁴ᵃ and R⁴ᵇ together form alkylidene;
R⁵ is alkyl or R⁵ is a direct bond to the carbon at C14;
each R⁶ is independently selected from a direct bond or a straight or branched alkylene chain;
each R⁷ is independently selected from hydrogen or alkyl; and
each R⁸ is independently selected from hydrogen, alkyl or optionally substituted heteroarylalkyl,
or two R⁸'s, together with the nitrogen to which they are attached, form an optionally substituted N-heterocyclyl or an optionally substituted N-heteroaryl.

24. The compound of claim 23 wherein:
Ⓐ is optionally substituted thiazolyl;
R¹ is hydrogen or —R⁶—OR⁷;
R² is —R⁶—OR⁷ or —R⁶—N(R⁸)₂;
R³ is —R⁶—OR⁷ or —R⁶—N(R⁸)₂;
R⁴ᵃ and R⁴ᵇ are each independently selected from hydrogen, alkyl or alkenyl;
R⁵ is alkyl or R⁵ is a direct bond to the carbon at C14;
each R⁶ is independently selected from a direct bond or a straight or branched alkylene chain;
each R⁷ is independently selected from hydrogen or alkyl; and
each R⁸ is independently selected from hydrogen, alkyl or optionally substituted heteroarylalkyl,
or two R⁸'s, together with the nitrogen to which they are attached, form an optionally substituted N-heterocyclyl or an optionally substituted N-heteroaryl.

25. The compound of claim 24 selected from:
((1R,3aS,4S,5S,7aR)-5-((5S,6R)-2-amino-5-(hydroxymethyl)-6-methyl-4,5,6,7-tetrahydrobenzo[d]thiazol-6-yl)-7a-methyl-1-((R)-6-methylheptan-2-yl)octahydro-1H-inden-4-yl)methanol; or
((5S,6R)-2-amino-6-((1R,3aS,4S,5S,7aR)-4-(aminomethyl)-7a-methyl-1-((R)-6-methylheptan-2-yl)octahydro-1H-inden-5-yl)-6-methyl-4,5,6,7-tetrahydrobenzo[d]thiazol-5-yl)methanol.

26. The compound of claim 23 wherein:
Ⓐ is optionally substituted thiazolyl;
R¹ is hydrogen or —R⁶—OR⁷;
R² is —R⁶—OR⁷ or —R⁶—N(R⁸)₂;
R³ is —R⁶—OR⁷ or —R⁶—N(R⁸)₂;
R⁴ᵃ is hydrogen, alkyl or alkenyl and R⁴ᵇ is a direct bond to the carbon to which R¹ is attached;
R⁵ is alkyl or R⁵ is a direct bond to the carbon at C14;
each R⁶ is independently selected from a direct bond or a straight or branched alkylene chain;

each R⁷ is independently selected from hydrogen or alkyl; and each R⁸ is independently selected from hydrogen, alkyl or optionally substituted heteroarylalkyl, or two R⁸'s, together with the nitrogen to which they are attached, form an optionally substituted N-heterocyclyl or an optionally substituted N-heteroaryl.

27. The compound of claim 23 wherein:
Ⓐ is optionally substituted thiazolyl;
R¹ is hydrogen or —R⁶—OR⁷;
R² is —R⁶—OR⁷ or —R⁶—N(R⁸)₂;
R³ is —R⁶—OR⁷ or —R⁶—N(R⁸)₂;
R⁴ᵃ and R⁴ᵇ together form alkylidene;
R⁵ is alkyl or R⁵ is a direct bond to the carbon at C14;
each R⁶ is independently selected from a direct bond or a straight or branched alkylene chain;
each R⁷ is independently selected from hydrogen or alkyl; and
each R⁸ is independently selected from hydrogen, alkyl or optionally substituted heteroarylalkyl,
or two R⁸'s, together with the nitrogen to which they are attached, form an optionally substituted N-heterocyclyl or an optionally substituted N-heteroaryl.

28. The compound of claim 27 selected from:
((5S,6R)-6-((3aS,4R,5S,7aS)-4-(aminomethyl)-7a-methyl-1-methyleneoctahydro-1H-inden-5-yl)-2,6-dimethyl-4,5,6,7-tetrahydrobenzo[d]thiazol-5-yl)methanol; or
((5S,6R)-2-amino-6-((3aS,4R,5S,7aS)-4-(aminomethyl)-7a-methyl-1-methyleneoctahydro-1H-inden-5-yl)-6-methyl-4,5,6,7-tetrahydrobenzo[d]thiazol-6-yl)methanol.

29. The compound of claim 3 wherein:
Ⓐ is optionally substituted thiadiazolyl;
R¹ is hydrogen or —R⁶—OR⁷;
R² is —R⁶—OR⁷ or —R⁶—N(R⁸)₂;
R³ is —R⁶—OR⁷ or —R⁶—N(R⁸)₂;
R⁴ᵃ and R⁴ᵇ are each independently selected from hydrogen, alkyl or alkenyl;
or R⁴ᵃ is hydrogen, alkyl or alkenyl and R⁴ᵇ is a direct bond to the carbon to which R¹ is attached;
or R⁴ᵃ and R⁴ᵇ together form alkylidene;
R⁵ is alkyl or R⁵ is a direct bond to the carbon at C14;
each R⁶ is independently selected from a direct bond or a straight or branched alkylene chain;
each R⁷ is independently selected from hydrogen or alkyl; and
each R⁸ is independently selected from hydrogen, alkyl or optionally substituted heteroarylalkyl,
or two R⁸'s, together with the nitrogen to which they are attached, form an optionally substituted N-heterocyclyl or an optionally substituted N-heteroaryl.

30. The compound of claim 29 wherein:
Ⓐ is optionally substituted thiadiazolyl;
R¹ is hydrogen or —R⁶—OR⁷;
R² is —R⁶—OR⁷ or —R⁶—N(R⁸)₂;
R³ is —R⁶—OR⁷ or —R⁶—N(R⁸)₂;
R⁴ᵃ and R⁴ᵇ are each independently selected from hydrogen, alkyl or alkenyl;
R⁵ is alkyl or R⁵ is a direct bond to the carbon at C14;
each R⁶ is independently selected from a direct bond or a straight or branched alkylene chain;
each R⁷ is independently selected from hydrogen or alkyl; and
each R⁸ is independently selected from hydrogen, alkyl or optionally substituted heteroarylalkyl, or two $R^8$'s, together with the nitrogen to which they are attached, form an optionally substituted N-heterocyclyl or an optionally substituted N-heteroaryl.

31. The compound of claim 30 selected from:
((1R,3aS,4S,5S,7aR)-5-((5S,6R)-5-(hydroxymethyl)-6-methyl-4,5,6,7-tetrahydrobenzo[d][1,2,3]thiadiazol-6-yl)-7a-methyl-1-((R)-6-methylheptan-2-yl)octahydro-1H-inden-4-yl)methanol; or
((5S,6R)-6-((1R,3aS,4S,5S,7aR)-4-(aminomethyl)-7a-methyl-1-((R)-6-methylheptan-2-yl)octahydro-1H-inden-5-yl)-6-methyl-4,5,6,7-tetrahydrobenzo[d][1,2,3]thiadiazol-5-yl)methanol.

32. The compound of claim 29 wherein:
Ⓐ is optionally substituted thiadiazolyl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ is hydrogen, alkyl or alkenyl and $R^{4b}$ is a direct bond to the carbon to which $R^1$ is attached;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two $R^8$'s, together with the nitrogen to which they are attached, form an optionally substituted N-heterocyclyl or an optionally substituted N-heteroaryl.

33. The compound of claim 29 wherein:
Ⓐ is optionally substituted thiadiazolyl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ and $R^{4b}$ together form alkylidene;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two $R^8$'s, together with the nitrogen to which they are attached, form an optionally substituted N-heterocyclyl or an optionally substituted N-heteroaryl.

34. The compound of claim 3 wherein:
Ⓐ is optionally substituted oxazolyl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ and $R^{4b}$ are each independently selected from hydrogen, alkyl or alkenyl;
or $R^{4a}$ is hydrogen, alkyl or alkenyl and $R^{4b}$ is a direct bond to the carbon to which $R^1$ is attached;
or $R^{4a}$ and $R^{4b}$ together form alkylidene;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two $R^8$'s, together with the nitrogen to which they are attached, form an optionally substituted N-heterocyclyl or an optionally substituted N-heteroaryl.

35. The compound of claim 34 wherein:
Ⓐ is optionally substituted oxazolyl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ and $R^{4b}$ are each independently selected from hydrogen, alkyl or alkenyl;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two $R^8$'s, together with the nitrogen to which they are attached, form an optionally substituted N-heterocyclyl or an optionally substituted N-heteroaryl.

36. The compound of claim 34 wherein:
Ⓐ is optionally substituted oxazolyl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ is hydrogen, alkyl or alkenyl and $R^{4b}$ is a direct bond to the carbon to which $R^1$ is attached;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two $R^8$'s, together with the nitrogen to which they are attached, form an optionally substituted N-heterocyclyl or an optionally substituted N-heteroaryl.

37. The compound of claim 34 wherein:
Ⓐ is optionally substituted oxazolyl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ and $R^{4b}$ together form alkylidene;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two $R^8$'s, together with the nitrogen to which they are attached, form an optionally substituted N-heterocyclyl or an optionally substituted N-heteroaryl.

38. The compound of claim 37 selected from:
((3aS,4R,5S,7aS)-5-((5R,6S)-6-(hydroxymethyl)-2,5-dimethyl-4,5,6,7-tetrahydrobenzo[d]oxazol-5-yl)-7a-methyl-1-methyleneoctahydro-1H-inden-4-yl)methanol; or
((5R,6S)-5-((3aS,4R,5S,7aS)-4-(aminomethyl)-7a-methyl-1-methyleneoctahydro-1H-inden-5-yl)-2,5-dimethyl-4,5,6,7-tetrahydrobenzo[d]oxazol-6-yl)methanol.

39. The compound of claim 1 wherein:
Ⓐ is fused 6-membered N-heteroaryl optionally substituted by one or more substitutents selected from alkyl, haloalkyl, —$C(O)OR^7$, —$N(R^8)_2$, —$C(O)N(R^8)_2$, cycloalkyl, aryl, aralkyl or heteroaryl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ and $R^{4b}$ are each independently selected from hydrogen, alkyl or alkenyl;

or $R^{4a}$ is hydrogen, alkyl or alkenyl and $R^{4b}$ is a direct bond to the carbon to which $R^1$ is attached;

or $R^{4a}$ and $R^{4b}$ together form alkylidene;

$R^5$ is alkyl or $R^5$ is a direct bond to the carbon at C14;

each $R^6$ is independently selected from a direct bond or a straight or branched alkylene chain;

each $R^7$ is independently selected from hydrogen or alkyl; and each $R^8$ is independently selected from hydrogen, alkyl or optionally substituted heteroarylalkyl, or two $R^8$'s, together with the nitrogen to which they are attached, form an optionally substituted N-heterocyclyl or an optionally substituted N-heteroaryl.

40. The compound of claim 39 wherein:

Ⓐ is selected from optionally substituted pyrazinyl or optionally substituted pyrimidinyl;

$R^1$ is hydrogen or —$R^6$—$OR^7$;

$R^2$ is —$R^6$—$OR^7$ or —$R^6$—$N(R^8)_2$;

$R^3$ is —$R^6$—$OR^7$ or —$R^6$—$N(R^8)_2$;

$R^{4a}$ and $R^{4b}$ are each independently selected from hydrogen, alkyl or alkenyl;

or $R^{4a}$ is hydrogen, alkyl or alkenyl and $R^{4b}$ is a direct bond to the carbon to which $R^1$ is attached;

or $R^{4a}$ and $R^{4b}$ together form alkylidene;

$R^5$ is alkyl or $R^5$ is a direct bond to the carbon at C14;

each $R^6$ is independently selected from a direct bond or a straight or branched alkylene chain;

each $R^7$ is independently selected from hydrogen or alkyl; and each $R^8$ is independently selected from hydrogen, alkyl or optionally substituted heteroarylalkyl, or two $R^8$'s, together with the nitrogen to which they are attached, form an optionally substituted N-heterocyclyl or an optionally substituted N-heteroaryl.

41. The compound of claim 40 wherein:

Ⓐ is optionally substituted pyrazinyl;

$R^1$ is hydrogen or —$R^6$—$OR^7$;

$R^2$ is —$R^6$—$OR^7$ or —$R^6$—$N(R^8)_2$;

$R^3$ is —$R^6$—$OR^7$ or —$R^6$—$N(R^8)_2$;

$R^{4a}$ and $R^{4b}$ are each independently selected from hydrogen, alkyl or alkenyl;

or $R^{4a}$ is hydrogen, alkyl or alkenyl and $R^{4b}$ is a direct bond to the carbon to which $R^1$ is attached;

or $R^{4a}$ and $R^{4b}$ together form alkylidene;

$R^5$ is alkyl or $R^5$ is a direct bond to the carbon at C14;

each $R^6$ is independently selected from a direct bond or a straight or branched alkylene chain;

each $R^7$ is independently selected from hydrogen or alkyl; and each $R^8$ is independently selected from hydrogen, alkyl or optionally substituted heteroarylalkyl, or two $R^8$'s, together with the nitrogen to which they are attached, form an optionally substituted N-heterocyclyl or an optionally substituted N-heteroaryl.

42. The compound of claim 41 wherein:

Ⓐ is optionally substituted pyrazinyl;

$R^1$ is hydrogen or —$R^6$—$OR^7$;

$R^2$ is —$R^6$—$OR^7$ or —$R^6$—$N(R^8)_2$;

$R^3$ is —$R^6$—$OR^7$ or —$R^6$—$N(R^8)_2$;

$R^{4a}$ and $R^{4b}$ are each independently selected from hydrogen, alkyl or alkenyl;

$R^5$ is alkyl or $R^5$ is a direct bond to the carbon at C14;

each $R^6$ is independently selected from a direct bond or a straight or branched alkylene chain;

each $R^7$ is independently selected from hydrogen or alkyl; and each $R^8$ is independently selected from hydrogen, alkyl or optionally substituted heteroarylalkyl, or two $R^8$'s, together with the nitrogen to which they are attached, form an optionally substituted N-heterocyclyl or an optionally substituted N-heteroaryl.

43. The compound of claim 42 selected from:

((1R,3aS,4S,5S,7aR)-5-((6R,7S)-7-(hydroxymethyl)-6-methyl-5,6,7,8-tetrahydroquinoxalin-6-yl)-7a-methyl-1-((R)-6-methylheptan-2-yl)octahydro-1H-inden-4-yl)methanol; or ((6S,7R)-7-((1R,3aS,4S,5S,7aR)-4-(aminomethyl)-7a-methyl-1-((R)-6-methylheptan-2-yl)octahydro-1H-inden-5-yl)-7-methyl-5,6,7,8-tetrahydroquinoxalin-6-yl)methanol.

44. The compound of claim 41 wherein:

Ⓐ is optionally substituted pyrazinyl;

$R^1$ is hydrogen or —$R^6$—$OR^7$;

$R^2$ is —$R^6$—$OR^7$ or —$R^6$—$N(R^8)_2$;

$R^3$ is —$R^6$—$OR^7$ or —$R^6$—$N(R^8)_2$;

$R^{4a}$ is hydrogen, alkyl or alkenyl and $R^{4b}$ is a direct bond to the carbon to which $R^1$ is attached;

$R^5$ is alkyl or $R^5$ is a direct bond to the carbon at C14;

each $R^6$ is independently selected from a direct bond or a straight or branched alkylene chain;

each $R^7$ is independently selected from hydrogen or alkyl; and each $R^8$ is independently selected from hydrogen, alkyl or optionally substituted heteroarylalkyl, or two $R^8$'s, together with the nitrogen to which they are attached, form an optionally substituted N-heterocyclyl or an optionally substituted N-heteroaryl.

45. The compound of claim 41 wherein:

Ⓐ is optionally substituted pyrazinyl;

$R^1$ is hydrogen or —$R^6$—$OR^7$;

$R^2$ is —$R^6$—$OR^7$ or —$R^6$—$N(R^8)_2$;

$R^3$ is —$R^6$—$OR^7$ or —$R^6$—$N(R^8)_2$;

$R^{4a}$ and $R^{4b}$ together form alkylidene;

$R^5$ is alkyl or $R^5$ is a direct bond to the carbon at C14;

each $R^6$ is independently selected from a direct bond or a straight or branched alkylene chain;

each $R^7$ is independently selected from hydrogen or alkyl; and each $R^8$ is independently selected from hydrogen, alkyl or optionally substituted heteroarylalkyl, or two $R^8$'s, together with the nitrogen to which they are attached, form an optionally substituted N-heterocyclyl or an optionally substituted N-heteroaryl.

46. The compound of claim 45 selected from:

((3aS,4R,5S,7aS)-5-((6R,7S)-7-(hydroxymethyl)-6-methyl-5,6,7,8-tetrahydroquinoxalin-6-yl)-7a-methyl-1-methyleneoctahydro-1H-inden-4-yl)methanol; or ((6S,7R)-7-((3aS,4R,5S,7aS)-4-(aminomethyl)-7a-methyl-1-methyleneoctahydro-1H-inden-5-yl)-7-methyl-5,6,7,8-tetrahydroquinoxalin-6-yl)methanol.

47. The compound of claim 40 wherein:

Ⓐ is optionally substituted pyrimidinyl;

$R^1$ is hydrogen or —$R^6$—$OR^7$;

$R^2$ is —$R^6$—$OR^7$ or —$R^6$—$N(R^8)_2$;

$R^3$ is —$R^6$—$OR^7$ or —$R^6$—$N(R^8)_2$;

$R^{4a}$ and $R^{4b}$ are each independently selected from hydrogen, alkyl or alkenyl;

or $R^{4a}$ is hydrogen, alkyl or alkenyl and $R^{4b}$ is a direct bond to the carbon to which $R^1$ is attached;

or $R^{4a}$ and $R^{4b}$ together form alkylidene;

$R^5$ is alkyl or $R^5$ is a direct bond to the carbon at C14;

each $R^6$ is independently selected from a direct bond or a straight or branched alkylene chain;

each $R^7$ is independently selected from hydrogen or alkyl; and each $R^8$ is independently selected from hydrogen, alkyl or optionally substituted heteroarylalkyl, or two $R^8$'s, together with the nitrogen to which they are attached, form an optionally substituted N-heterocyclyl or an optionally substituted N-heteroaryl.

48. The compound of claim 47 wherein:

(A) is optionally substituted pyrimidinyl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ and $R^{4b}$ are each independently selected from hydrogen, alkyl or alkenyl;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two $R^8$'s, together with the nitrogen to which they are attached, form an optionally substituted N-heterocyclyl or an optionally substituted N-heteroaryl.

49. The compound of claim 48 selected from:
((6R,7S)-2-amino-6-((1R,3aS,4S,5S,7aR)-4-(hydroxymethyl)-7a-methyl-1-((R)-6-methylheptan-2-yl)octahydro-1H-inden-5-yl)-6-methyl-5,6,7,8-tetrahydroquinazolin-7-yl)methanol;
((6R,7S)-2-amino-6-((1R,3aS,4S,5S,7aR)-4-(aminomethyl)-7a-methyl-1-((R)-6-methylheptan-2-yl)octahydro-1H-inden-5-yl)-6-methyl-5,6,7,8-tetrahydroquinazolin-7-yl)methanol;
((1R,3aS,4S,5S,7aR)-5-((6R,7S)-7-(hydroxymethyl)-2,6-dimethyl-5,6,7,8-tetrahydroquinazolin-6-yl)-7a-methyl-1-((R)-6-methylheptan-2-yl)octahydro-1H-inden-4-yl)methanol;
((6R,7S)-6-((1R,3aS,4S,5S,7aR)-4-(aminomethyl)-7a-methyl-1-((R)-6-methylheptan-2-yl)octahydro-1H-inden-5-yl)-2,6-dimethyl-5,6,7,8-tetrahydroquinazolin-7-yl)methanol;
((1R,3aS,4S,5S,7aR)-5-((6R,7S)-7-(hydroxymethyl)-6-methyl-5,6,7,8-tetrahydroquinazolin-6-yl)-7a-methyl-1-((R)-6-methylheptan-2-yl)octahydro-1H-inden-4-yl)methanol; or
((6R,7S)-6-((1R,3aS,4S,5S,7aR)-4-(aminomethyl)-7a-methyl-1-((R)-6-methylheptan-2-yl)octahydro-1H-inden-5-yl)-6-methyl-5,6,7,8-tetrahydroquinazolin-7-yl)methanol.

50. The compound of claim 47 wherein:

(A) is optionally substituted pyrimidinyl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ is hydrogen, alkyl or alkenyl and $R^{4b}$ is a direct bond to the carbon to which $R^1$ is attached;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two $R^8$'s, together with the nitrogen to which they are attached, form an optionally substituted N-heterocyclyl or an optionally substituted N-heteroaryl.

51. The compound of claim 47 wherein:

(A) is optionally substituted pyrimidinyl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ and $R^{4b}$ together form alkylidene;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two $R^8$'s, together with the nitrogen to which they are attached, form an optionally substituted N-heterocyclyl or an optionally substituted N-heteroaryl.

52. The compound of claim 51 selected from:
((6R,7S)-2-amino-6-((3aS,4R,5S,7aS)-4-(aminomethyl)-7a-methyl-1-methyleneoctahydro-1H-inden-5-yl)-6-methyl-5,6,7,8-tetrahydroquinazolin-7-yl)methanol;
((6R,7S)-6-((3aS,4R,5S,7aS)-4-(aminomethyl)-7a-methyl-1-methyleneoctahydro-1H-inden-5-yl)-2,6-dimethyl-5,6,7,8-tetrahydroquinazolin-7-yl)methanol;
((6R,7S)-6-((3aS,4R,5S,7aS)-4-(aminomethyl)-7a-methyl-1-methyleneoctahydro-1H-inden-5-yl)-6-methyl-5,6,7,8-tetrahydroquinazolin-7-yl)methanol;
((6R,7S)-2-amino-6-((3aS,4R,5S,7aS)-4-(hydroxymethyl)-7a-methyl-1-methyleneoctahydro-1H-inden-5-yl)-6-methyl-5,6,7,8-tetrahydroquinazolin-7-yl)methanol;
((3aS,4R,5S,7aS)-5-((6R,7S)-7-(hydroxymethyl)-2,6-dimethyl-5,6,7,8-tetrahydroquinazolin-6-yl)-7a-methyl-1-methyleneoctahydro-1H-inden-4-yl)methanol; or
((3aS,4R,5S,7aS)-5-((6R,7S)-7-(hydroxymethyl)-6-methyl-5,6,7,8-tetrahydroquinazolin-6-yl)-7a-methyl-1-methyleneoctahydro-1H-inden-4-yl)methanol.

53. The compound of claim 1 wherein:

(A) is an optionally substituted fused 13-membered N-heteroaryl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ and $R^{4b}$ are each independently selected from hydrogen, alkyl or alkenyl;
or $R^{4a}$ is hydrogen, alkyl or alkenyl and $R^{4b}$ is a direct bond to the carbon to which $R^1$ is attached;
or $R^{4a}$ and $R^{4b}$ together form alkylidene;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two $R^8$'s, together with the nitrogen to which they are attached, form an optionally substituted N-heterocyclyl or an optionally substituted N-heteroaryl.

54. The compound of claim 53 wherein:

(A) is optionally substituted benzo[4,5]imidazo[1,2-a]pyrimidinyl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ and $R^{4b}$ are each independently selected from hydrogen, alkyl or alkenyl;
or $R^{4a}$ is hydrogen, alkyl or alkenyl and $R^{4b}$ is a direct bond to the carbon to which $R^1$ is attached;
or $R^{4a}$ and $R^{4b}$ together form alkylidene;

$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two $R^8$'s, together with the nitrogen to which they are attached, form an optionally substituted N-heterocyclyl or an optionally substituted N-heteroaryl.

55. The compound of claim 54 wherein:
Ⓐ is optionally substituted benzo[4,5]imidazo[1,2-a]pyrimidinyl;
$R^1$ is hydrogen or —$R^6$—$OR^7$;
$R^2$ is —$R^6$—$OR^7$ or —$R^6$—$N(R^8)_2$;
$R^3$ is —$R^6$—$OR^7$ or —$R^6$—$N(R^8)_2$;
$R^{4a}$ and $R^{4b}$ together form alkylidene;
$R^5$ is alkyl or $R^5$ is a direct bond to the carbon at C14;
each $R^6$ is independently selected from a direct bond or a straight or branched alkylene chain;
each $R^7$ is independently selected from hydrogen or alkyl; and
each $R^8$ is independently selected from hydrogen, alkyl or optionally substituted heteroarylalkyl,
or two $R^8$'s, together with the nitrogen to which they are attached, form an optionally substituted N-heterocyclyl or an optionally substituted N-heteroaryl.

56. The compound of claim 55 selected from:
((3aS,4R,5S,7aS)-5-((2R,3S)-3-(hydroxymethyl)-2-methyl-1,2,3,4-tetrahydrobenzo[4,5]imidazo[2,1-b]quinazolin-2-yl)-7a-methyl-1-methyleneoctahydro-1H-inden-4-yl)methanol; or
((2R,3S)-2-((3aS,4R,5S,7aS)-4-(aminomethyl)-7a-methyl-1-methyleneoctahydro-1H-inden-5-yl)-2-methyl-1,2,3,4-tetrahydrobenzo[4,5]imidazo[2,1-b]quinazolin-3-yl)methanol.

57. A pharmaceutical composition comprising a compound of claim 1, or a stereoisomer, enantiomer or tautomer thereof or mixtures thereof, or a pharmaceutically acceptable salt thereof, and a pharmaceutically acceptable excipient.

58. A method for treating pain comprising administering an effective amount of a compound of claim 1, or a stereoisomer, enantiomer or tautomer thereof or mixtures thereof, or a pharmaceutically acceptable salt thereof, or a composition of claim 57 to a mammal in need thereof.

* * * * *